US010702601B2

(12) United States Patent
Hernandez et al.

(10) Patent No.: US 10,702,601 B2
(45) Date of Patent: Jul. 7, 2020

(54) PORCINE EPIDEMIC DIARRHEA VIRUS VACCINE

(71) Applicant: Boehringer Ingelheim Animal Health USA Inc., Duluth, GA (US)

(72) Inventors: Luis Alejandro Hernandez, Story City, IA (US); Arun V. Iyer, Ames, IA (US); Dianna M. Murphy Jordan, Ames, IA (US); Abby Rae Patterson, Story City, IA (US); Michael B. Roof, Ames, IA (US); Eric Martin Vaughn, Ames, IA (US); Joseph Gilbert Victoria, Ames, IA (US)

( * ) Notice: Subject to any disclaimer, the term of this patent is extended or adjusted under 35 U.S.C. 154(b) by 0 days.

(21) Appl. No.: 15/920,565

(22) Filed: Mar. 14, 2018

(65) Prior Publication Data

US 2018/0207260 A1 Jul. 26, 2018

Related U.S. Application Data

(63) Continuation of application No. 14/672,631, filed on Mar. 30, 2015, now Pat. No. 9,950,061.

(60) Provisional application No. 61/974,722, filed on Apr. 3, 2014.

(51) Int. Cl.

| | |
|---|---|
| ***A61K 39/215*** | (2006.01) |
| ***C07K 14/165*** | (2006.01) |
| ***C07K 14/005*** | (2006.01) |
| ***C07K 16/10*** | (2006.01) |
| ***A61K 45/06*** | (2006.01) |
| ***C12N 7/00*** | (2006.01) |
| *A61K 39/00* | (2006.01) |

(52) U.S. Cl.

CPC ............ *A61K 39/215* (2013.01); *A61K 45/06* (2013.01); *C07K 14/005* (2013.01); *C07K 14/165* (2013.01); *C07K 16/10* (2013.01); *C12N 7/00* (2013.01); *A61K 2039/5252* (2013.01); *A61K 2039/552* (2013.01); *C07K 2317/76* (2013.01); *C12N 2710/14043* (2013.01); *C12N 2710/14143* (2013.01); *C12N 2770/20021* (2013.01); *C12N 2770/20022* (2013.01); *C12N 2770/20034* (2013.01); *C12N 2770/20063* (2013.01)

(58) Field of Classification Search

None

See application file for complete search history.

(56) References Cited

U.S. PATENT DOCUMENTS

| | | | |
|---|---|---|---|
| 7,452,542 B2 | 11/2008 | Denison | |
| 7,527,967 B2 | 5/2009 | Chao et al. | |
| 7,906,311 B2 | 3/2011 | David et al. | |
| 2003/0157135 A1 | 8/2003 | Tsuji et al. | |
| 2006/0039926 A1 | 2/2006 | Denison | |
| 2007/0286872 A1 | 12/2007 | Denison | |
| 2015/0283229 A1 | 10/2015 | Hernandez et al. | |
| 2017/0080083 A1* | 3/2017 | Marthaler | A61K 39/215 |

FOREIGN PATENT DOCUMENTS

| | | | |
|---|---|---|---|
| CN | 1827172 | A | 9/2006 |
| CN | 1323718 | C | 7/2007 |
| CN | 101117627 | A | 2/2008 |
| CN | 1011176271 | | 2/2008 |
| CN | 101491673 | A | 7/2009 |
| CN | 102399806 | A | 4/2012 |
| CN | 102949718 | A | 3/2013 |
| CN | 103041385 | A | 4/2013 |
| CN | 103194472 | A | 7/2013 |
| CN | 103585625 | A | 2/2014 |
| CN | 103992989 | A | 8/2014 |
| EP | 1071407 | A1 | 1/2001 |
| JP | H1084951 | A | 4/1998 |
| JP | 3812814 | B2 | 8/2006 |
| JP | 2007522127 | A | 8/2007 |
| KR | 100143239 | | 4/1998 |
| KR | 100179947 | B1 | 11/1998 |
| KR | 100267745 | B1 | 11/2000 |
| KR | 20030082098 | A | 10/2003 |
| KR | 100432977 | B1 | 5/2004 |
| KR | 100502008 | B1 | 7/2005 |
| KR | 100737434 | B1 | 7/2007 |
| KR | 100773141 | B1 | 11/2007 |
| KR | 100773241 | | 11/2007 |
| KR | 20120066555 | A | 6/2012 |
| KR | 20120066556 | A | 6/2012 |
| KR | 20120066559 | A | 6/2012 |
| KR | 101442493 | B1 | 9/2014 |
| RU | 2357755 | C2 | 6/2009 |
| WO | 2005072214 | A2 | 8/2005 |
| WO | 2015153425 | A1 | 10/2015 |

OTHER PUBLICATIONS

Meng et al., Factsheet Pork Information Gateway, Aug. 29, 2013. (Year: 2013).*

Marthaler et al., Genome Announcements, Aug. 2013, 1(4): e00555-13. (Year: 2013).*

GenBank Accession No. KJ645666.1, GI: 658130455 , Porcine epidemic diarrhea virus strain USA/Iowa70/2013, complete genome, Jul. 17, 2014, pp. 1-10.

GenBank Accession No. KJ645688.1, GI: 658130609, Porcine epidemic diarrhea virus strain USA/Iowa96/2013, complete genome, Jul. 17, 2014, pp. 1-10.

GenBank Accession No. KJ645694.1, GI: 658130651 , Porcine epidemic diarrhea virus strain USA/Iowa103/2013, complete genome, Jul. 17, 2014, pp. 1-10.

GenBank Accession No. KJ645695.1, GI: 658130658 , Porcine epidemic diarrhea virus strain USA/Iowa106/2013, complete genome, Jul. 17, 2014, pp. 1-10.

(Continued)

*Primary Examiner* — Nicole Kinsey White

(57) ABSTRACT

The present invention relates to immunogenic compositions, wherein the immunogenic compositions include a recombinant spike antigen porcine epidemic diarrhea virus (PEDV). The immunogenic compositions commonly include an oil-in-water emulsion as an adjuvant. Methods for producing the immunogenic compositions and the recombinant PEDV spike antigen are also provided.

16 Claims, 66 Drawing Sheets

Specification includes a Sequence Listing.

(56) References Cited

OTHER PUBLICATIONS

GenBank Accession No. KJ645696.1, GI: 658130665 , Porcine epidemic diarrhea virus strain USA/Iowa107/2013, complete genome, Jul. 17, 2014, pp. 1-10.
GenBank Accession No. Z25483.1, GI: 410505 , Porcine epidemic diarrhea virus spike protein mRNA, complete CDS, Nov. 14, 2005, pp. 1-3.
Hoang et al., "Full-Length Genome Sequence of a Plaque-Cloned Virulent Porcine Epidemic Diarrhea Virus Isolate (USA/Iowa/18984/2013) from a Midwestern U.S. Swine Herd". Genome Announcements, vol. 1, No. 6, Nov./Dec. 2013, ppe01049-12-e01049-13.
Huang et al., "Origin, Evolution, and Genotyping of Emergent Porcine Epidemic Diarrhea Virus Strains in the United States". mBio, vol. 4, No. 5, Sep./Oct. 2013, pp. 1-8.
International Search Report and Written Opinion for PCT/US2015/023284 dated Jul. 1, 2015.
Kweon et al., "Derivation of attenuated porcine epidemic diarrhea virus (PEDV) as vaccine candidate". Vaccine, vol. 17, 1999, pp. 2546-2553.
Li et al., "Molecular characterization and phylogenetic analysis of porcine epidemic diarrhea virus (PEDV) field strains in south China". Virus Genes, vol. 45, 2012, pp. 181-185.
Li et al., "New Variants of Porcine Epidemic Diarrhea Virus, China, 2011." Emerging Infectious Diseases, vol. 18, No. 8, Aug. 2012, pp. 1350-1353.
Li et al., "Phylogenetic analysis of porcine epidemic diarrhea virus (PEDV) field strains in central China based on the ORF3 gene and the main neutralization epitopes". Archives of Virology, vol. 159, 2014,pp. 1057-1065.
Marthaler et al., "Complete Genome Sequence of Porcine Epidemic Diarrhea Virus Strain USA/Colorado/2013 from the United States". Genome Announcements, vol. 1, No. 4, Jul./Aug 2013, pp. 1-2.
Meng et al., "Evaluation on the Efficacy and Immunogenicity of Recombinant DNA Plasmids Expressing Spike Genese from Porcine Transmissible Gastroenteritis Virus and Porcine Epidemic Diarrhea Virus." PLOS One, vol. 8, No. 3, Mar. 2013, e57468, pp. 1-14.
Mole, Beth, "Deadly pig virus slips through US borders". Nature, vol. 499, Jul. 25, 2013, p. 388.
NCBI Reference Sequence: NC_003436.1, GI 19387576, Porcine epidemic diarrhea virus, complete genome, Feb. 10, 2015, pp. 1-11.
Nuntawan et al., "One World—One Health: The Threat of Emerging Swine Diseases. An Asian Perspective". Transboundary and Emerging Diseases, vol. 59, Supp. 1, 2012, pp. 9-17.
Pan et al., "Isolation and characterization of a variant porcine epidemic diarrhea virus in China". Virology Journal, vol. 9, 2012, pp. 195-203.
Park et al., "Molecular characterization and phylogenetic analysis of porcine epidemic diarrhea virus (PEDV) field solates in Korea". Archives of Virology, vol. 156, 2011, pp. 577-584.
Park et al., "Molecular epidemiology and phylogenetic analysis of porcine epidemic diarrhea virus (PEDV) field isolates in Korea". Archives of Virology, vol. 158, 2013, pp. 1533-1541.
Sato et al., "Mutations in the spike gene of porcine epidemic diarrhea virus associated with growth adaptation in vitro and attenuation of virulence in vivo". Virus Genes, vol. 43, 2011, pp. 72-78.
Sofer, G. "Virus Inactivation in the 1990s- and into the 21st Century." BioPharm International, Part 4, Culture Media, Biotechnology Products, and Vaccines, Jan. 2003, pp. 50-57.
Song et al., "Oral efficacy of Vero cell attenuated porcine epidemic diarrhea virus DR13 strain". Research in Veterinary Science, vol. 82, 2007, pp. 134-140.
Song et al., "Porcine epidemic diarrhoea virus: a comprehensive review of molecular epidemiology, diagnosis, and vaccines". Virus Genes, vol. 44, 2012, pp. 167-175.
Stevenson et al., "Emergence of Porcine epidemic diarrhea virus in the United States: clinical signs, lesions, and viral genomic sequences". Journal of Veterinary Diagnostic Investigation, vol. 25, No. 5, Sep. 2013, pp. 649-654.
Tian et al., "Molecular Characterization and Phylogenetic Analysis of New Variants of the Porcine Epidemic Diarrhea Virus in Gansu, China in 2012a". Viruses, vol. 5, 2013, pp. 1991-2004.
United States Department of Agriculture, "Technical Note: Porcine Epidemic Diarrhea (PED)", pp. 1-5. [Accessed at https://www.aasv.org/aasv%20website/Resources/Diseases/PED/usda_ped_tech_note.pdf on May 27, 2015].
Vanac, Mary, "Ohio scientists map genes of pig virus". The Columbus Dispatch, Columbus, Ohio, Mar. 17, 2014, pp. 1-2.
Vogel, F.R., "Improving Vaccine Performance with Adjuvants." Clinical Infectious Diseases, vol. 30, Suppl. 3, 2000, pp. S266-S270.
Wang et al., Figure: New variant of Porcine Epidemic Diarrhea Virus, Centers for Disease Control and Prevention, vol. 20, No. 5, May 2014, pp. 1-3. [Accessed at: http://wwwnc.cdc.gov/eid/article/20/5/14-0195-f1.htm on Mar. 17, 2014].
Wang et al., "New Variant of Porcine Epidemic Diarrhea Virus, United States, 2014". Emerging Infectious Diseases, vol. 20, No. 5, May 2014, pp. 917-919.
Yang et al., "Genetic variation analysis of reemerging porcine epidemic diarrhea virus prevailing in central China from 2010 to 2011". Virus Genes, vol. 2013, pp. 337-344.
Zhang et al., "Occurrence and investigation of enteric viral infections in pigs with diarrhea in China". Archives of Virology, vol. 158, 2013, pp. 1631-1636.
"More Tools to Help Fight PEDV". Pork Checkoff Report Newsletter, vol. 10, No. 1, National Pork Board, Des Moines, IA, USA, Jan. 2014, pp. 1-4.
Abstract in English of CN101117627, 2008.
Abstract in English of CN101491673, 2009.
Abstract in English of CN102399806, 2012.
Abstract in English of CN102949718, 2013.
Abstract in English of CN103041385, 2013.
Abstract in English of CN103194472, 2013.
Abstract in English of CN103585625, Feb. 19, 2014.
Abstract in English of CN1323718, 2007.
Abstract in English of CN1827172, 2006.
Abstract in English of JP3812814, 2006.
Abstract in English of JPH1084951, 1998.
Abstract in English of KR100143239, 1998.
Abstract in English of KR10019947, 1998.
Abstract in English of KR100267745, 2000.
Abstract in English of KR100432977, 2004.
Abstract in English of KR100502008, 2005.
Abstract in English of KR100737434, 2007.
Abstract in English of KR100773141, 2007.
Abstract in English of KR20030082098, 2003.
Abstract in English of KR20120066555, 2012.
Abstract in English of KR20120066556, 2012.
Abstract in English of KR20120066559, 2012.
Abstract in English of RU2357755, 2009.
Ackerman, Matthew A., "Acute cases of Porcine Epidemic Diarrhea Virus in a sow farm and nursery". Pig to Pork, pig333.com, Oct. 4, 2013, [accessed at: https://www.pig333.com/clinical-case-of-the-world/acute-cases-of-porcine-epidemic-diarrhea-virus-in-a-sow-farm-and-nurse_7587/ on Apr. 30, 2015], pp. 1-6.
Bi et al., "Complete Genome Sequence of Porcine Epidemic Diarrhea Virus Strain AJ1102 Isolated from a Suckling Piglet with Acute Diarrhea in China". Journal of Virology, vol. 86, No. 19, Oct. 2012, pp. 10910-10911.
Chen et al., "Complete Genome Sequence of a Porcine Epidemic Diarrhea Virus Variant". Journal of Virology, vol. 86, No. 6, 2012, p. 3408.
Chen et al., "Isolation and Characterization of Porcine Epidemic Diarrhea Viruses Associated with the 2013 Disease Outbreak among Swine in the United States". Journal of Clinical Microbiology, vol. 52, No. 1, Jan. 2014, pp. 234-243.

(56) References Cited

OTHER PUBLICATIONS

Chen et al., "Molecular characterization and phylogenetic analysis of porcine epidemic diarrhea virus (PEDV) samples from field cases in Fujian, China". Virus Genes, vol. 45, 2012, pp. 499-507.
Fan et al., "Complete Genome Sequence of a Novel Porcine Epidemic Diarrhea Virus in South China". Journal of Virology, vol. 86, No. 18, Sep. 2012, pp. 10248-10249.
Feng et al., "Baculovirus Surface Display of Sars Coronavirus (SARS-CoV) Spike Protein and Immunogenicity of the Displayed Protein in Mice Models". DNA and Cell Biology, vol. 25, No. 12, 2006, pp. 668-673.
Gao et al., "Phylogenetic analysis of porcine epidemic diarrhea virus field strains prevailing recently in China". Archives of Virology, vol. 158, 2013, pp. 711-715.
GenBank Accession No. JQ023161.1, GI: 280851043, Porcine epidemic diarrhea virus strain virulent DR13, complete genome, May 5, 2012, pp. 1-9.
GenBank Accession No. AF298212.1, GI: 22478818 , Porcine epidemic diarrhea virus nonfunctional spike protein mRNA, partial sequence, Aug. 26, 2002, p. 1.
GenBank Accession No. JQ023162.1, GI: 380851050, Porcine epidemic diarrhea virus strain attenuated DR13, complete genome, May 5, 2012, pp. 1-9.
GenBank Accession No. JQ282909.1, GI: 377824029 , Porcine epidemic diarrhea virus strain CH/FJND-Mar. 2011, complete genome, Feb. 28, 2012, pp. 1-9.
GenBank Accession No. JX088695.1, GI: 399227061, Porcine epidemic diarrhea virus strain GD-B, complete genome, Aug. 13, 2012, pp. 1-9.
GenBank Accession No. KC210145.1, GI: 459357901, Porcine epidemic diarrhea virus isolate AH2012, complete genome, Mar. 11, 2012, pp. 1-9.
GenBank Accession No. KF6503701, GI: 557844660, Porcine epidemic diarrhea virus isolate ISU13-19338E-IN-homogenate, complete genome, Dec. 20, 2013, pp. 1-11.
GenBank Accession No. KF650371.1, GI: 557844677, Porcine epidemic diarrhea virus isolate ISU13-19338E-IN-passage3, complete genome, Dec. 20, 2013, pp. 1-11.
GenBank Accession No. KF650372.1, GI: 557844691, Porcine epidemic diarrhea virus isolate ISU13-19338E-IN-passage9, complete genome, Dec. 20, 2013, pp. 1-11.
GenBank Accession No. KF650373.1, GI: 557844705, Porcine epidemic diarrhea virus isolate ISU13-22038-IA-homogenate, complete genome, Dec. 20, 2013, pp. 1-11.
GenBank Accession No. KF650374.1, GI: 557844721, Porcine epidemic diarrhea virus isolate ISU13-22038-IA-passage3, complete genome, Dec. 20, 2013, pp. 1-11.
GenBank Accession No. KF650375.1, GI: 557844737, Porcine epidemic diarrhea virus isolate ISU13-22038-IA-passage9, complete genome, Dec. 20, 2013, pp. 1-11.
GenBank Accession No. KF804028.1, GI: 557844763, Porcine epidemic diarrhea virus isolate USA/Iowa/18984/2013, complete genome, Dec. 26, 2013, pp. 1-9.
GenBank Accession No. KJ399978.1, GI: 591400267 , Porcine epidemic diarrhea virus strain OH851, complete genome, Mar. 12, 2014, pp. 1-9.
GenBank Accession No. KJ645635.1, GI: 658130238 , Porcine epidemic diarrhea virus strain USA/Indiana12.83/2013, complete genome, Jul. 17, 2014, pp. 1-10.
GenBank Accession No. KJ645636.1, GI: 658130245 , Porcine epidemic diarrhea virus strain USA/Iowa28/2013, complete genome, Jul. 17, 2014, pp. 1-10.
GenBank Accession No. KJ645641.1, GI: 658130280 , Porcine epidemic diarrhea virus strain USA/Indiana34/2013, complete genome, Jul. 17, 2014, pp. 1-10.
GenBank Accession No. KJ645649.1, GI: 658130336 , Porcine epidemic diarrhea virus strain USA/Iowa23.57/2013, complete genome, Jul. 17, 2014, pp. 1-10.

* cited by examiner

FIG. 1

PEDV 1251-125-10 (125-10) near-complete genome (SEQ ID NO:1) aligned to closest Chinese PEDV G2a strain: AH2012 (GenBank Accn #: KC210145) (nucleotides 45-28031 of SEQ ID NO:10).

```
125_10  1     GACTCTTGTCTACTCAATTCAACTAAACGAAATTCCTTGTCCTTCCGGCCGCATGTCCAT  60
              ||||||||||||||||||||||||||||||||||  ||||||||||||||||||||||||
AH2012  45    GACTCTTGTCTACTCAATTCAACTAAACGAAATT--TTGTCCTTCCGGCCGCATGTCCAT  102

125_10  61    GCTGCTGGAAGCTGACGTGGAATTTCATTAGGTTTGCTTAAGTAGCCATCGCAAGTGCTG  120
              ||||||||||||||||||||||||||||||||||||||||||||||||||||||||||||
AH2012  103   GCTGCTGGAAGCTGACGTGGAATTTCATTAGGTTTGCTTAAGTAGCCATCGCAAGTGCTG  162

125_10  121   TGCTGTCCTCTAGTTCCTGGTTGGCGTTCCGTCGCCTTCTACATACTAGACAAACAGCCT  180
              ||||||||||||||||||||||||||||||||||||||||||||||||||||||||||||
AH2012  163   TGCTGTCCTCTAGTTCCTGGTTGGCGTTCCGTCGCCTTCTACATACTAGACAAACAGCCT  222

125_10  181   TCCTCCGGTTCCGTCTGGGGGTTGTGTGGATAACTAGTTCCGTCTAGTTTGAAACCAGTA  240
              |||||||||||||||||||||||| |||||||||||||||||||||||||||||||||||
AH2012  223   TCCTCCGGTTCCGTCTGGGGGTTGCGTGGATAACTAGTTCCGTCTAGTTTGAAACCAGTA  282

125_10  241   ACTGTCGGCTATGGCTAGCAACCATGTTACATTGGCTTTTGCCAATGATGCAGAAATTTC  300
              |||||||||||||||||||||||| || ||||||||||||||||||||||||||||||||
AH2012  283   ACTGTCGGCTATGGCTAGCAACCAAGTCACATTGGCTTTTGCCAATGATGCAGAAATTTC  342

125_10  301   AGCTTTTGGCTTTTGCACTGCTAGTGAAGCCGTCTCATACTATTCTGAGGCCGCCGCTAG  360
              ||||||||||||||||||||||||||||||||||||||||||||||||||||||||||||
AH2012  343   AGCTTTTGGCTTTTGCACTGCTAGTGAAGCCGTCTCATACTATTCTGAGGCCGCCGCTAG  402

125_10  361   TGGATTTATGCAATGCCGTTTCGTGTCCTTCGATCTCGCTGACACTGTTGAGGGATTGCT  420
              ||||||||||||||||||||||||||||||||||||||||||||||||||||||||||||
AH2012  403   TGGATTTATGCAATGCCGTTTCGTGTCCTTCGATCTCGCTGACACTGTTGAGGGATTGCT  462

125_10  421   TCCCGAAGACTATGTCATGGTGGTGGTCGGCACTACCAAGCTTAGTGCGTATGTGGACAC  480
              ||||||||||||||||||||||||||||||||||||||||||||||||||||||||||||
AH2012  463   TCCCGAAGACTATGTCATGGTGGTGGTCGGCACTACCAAGCTTAGTGCGTATGTGGACAC  522

125_10  481   TTTTGGTAGCCGCCCCAAAAACATTTGTGGTTGGCTGTTATTTTCTAACTGTAATTACTT  540
              ||||||||||||||||| ||||||||||||||||||||||||||||||||||||||||||
AH2012  523   TTTTGGTAGCCGCCCCAGAAACATTTGTGGTTGGCTGTTATTTTCTAACTGTAATTACTT  582

125_10  541   CCTCGAAGAGTTAGAGCTTACTTTTGGTCGTCGTGGTGGTAACATCGTGCCAGTTGACCA  600
              |||||||||||||||||| |||||||||||||||||||||||||||||||||||||||||
AH2012  583   CCTCGAAGAGTTAGAGCTCACTTTTGGTCGTCGTGGTGGTAACATCGTGCCAGTTGACCA  642

125_10  601   ATACATGTGTGGCGCTGACGGTAAACCTGTTCTTCAGGAATCCGAATGGGAGTATACAGA  660
              ||||||||||||||||||||| ||||||||||||||||||||||| ||||||||||||||
AH2012  643   ATACATGTGTGGCGCTGACGGGAAACCTGTTCTTCAGGAATCCGAGTGGGAGTATACAGA  702

125_10  661   TTTCTTTGCTGACTCCGAAGACGGTCAACTCAACATTGCTGGTATCACTTATGTGAAGGC  720
               || |||||||||||||||||||||||||||||||||||||| |||||||||||||||||
AH2012  703   CTTTTTTGCTGACTCCGAAGACGGTCAACTCAACATTGCTGGGATCACTTATGTGAAGGC  762

125_10  721   CTGGATTGTAGAGCGATCGGATGTCTCTTATGCGAGTCAGAATTTAACATCTATTAAGTC  780
              ||||||||||||||||||||| ||||||||||||||||||||||||||||||||||||||
AH2012  763   CTGGATTGTAGAGCGATCGGACGTCTCTTATGCGAGTCAGAATTTAACATCTATTAAGTC  822

125_10  781   TATTACTTACTGTTCAACCTATGAGCATACTTTTCCTGATGGTACTGCCATGAAGGTTGC  840
              ||||||||||||||||||||||||||||||||||||||||||||||||||||||||||||
AH2012  823   TATTACTTACTGTTCAACCTATGAGCATACTTTTCCTGATGGTACTGCCATGAAGGTTGC  882

125_10  841   ACGTACTCCAAAGATTAAGAAGACTGTTGTCTTGTCTGAGCCACTTGCTACTATCTACAG  900
              ||||||||||||||||||||||||||||||||||||||||||||||||||||||||||||
AH2012  883   ACGTACTCCAAAGATTAAGAAGACTGTTGTCTTGTCTGAGCCACTTGCTACTATCTACAG  942
```

FIG. 1 (cont'd)

```
125_10  901   GGAAATTGGTTCTCCTTTTGTGGATAATGGGAGCGATGCTCGTTCTATCATTAAGAGACC  960
              ||||||||||||||||||||||||||||||||||||||||||||||||||||||||||||
AH2012  943   GGAAATTGGTTCTCCTTTTGTGGATAATGGGAGCGATGCTCGTTCTATCATTAAGAGACC  1002

125_10  961   AGTGTTCCTCCACGCTTTTGTTAAGTGTAAGTGTGGTAGTTATCATTGGACTGTTGGTGA  1020
              ||||||||||||||||||||||||||||||||||||||||||||||||||||||||||||
AH2012  1003  AGTGTTCCTCCACGCTTTTGTTAAGTGTAAGTGTGGTAGTTATCATTGGACTGTTGGTGA  1062

125_10  1021  TTGGACTTCCTATGTCTCCACTTGCTGTGGCTTTAAGTGTAAGCCAGTCCTTGTGGCTTC  1080
              ||||||||||||||||||||||||||||||||||||||||||||||||||||||||||||
AH2012  1063  TTGGACTTCCTATGTCTCCACTTGCTGTGGCTTTAAGTGTAAGCCAGTCCTTGTGGCTTC  1122

125_10  1081  ATGCTCTGCTACGCCTGGTTCTGTTGTGGTTACGCGCGCTGGTGCTGGCACTGGTGTTAA  1140
              ||||||||||||||||||||||||||||||||||||||||||||||||||||||||||||
AH2012  1123  ATGCTCTGCTACGCCTGGTTCTGTTGTGGTTACGCGCGCTGGTGCTGGCACTGGTGTTAA  1182

125_10  1141  GTATTACAACAACATGTTCCTGCGCCATGTGGCAGACATTGATGGGTTGGCATTCTGGCG  1200
              ||||||||||||||||||||||||||||||||||||||||||||||||||||||||||||
AH2012  1183  GTATTACAACAACATGTTCCTGCGCCATGTGGCAGACATTGATGGGTTGGCATTCTGGCG  1242

125_10  1201  AATTCTCAAGGTGCAGTCCAAAGACGACCTCGCTTGCTCTGGTAAATTCCTTGAACACCA  1260
              |||||| |||||||||||||||||||||||||||||||||||||||||||||||||||||
AH2012  1243  AATTCTTAAGGTGCAGTCCAAAGACGACCTCGCTTGCTCTGGTAAATTCCTTGAACACCA  1302

125_10  1261  TGAGGAAGGTTTCACAGATCCTTGCTACTTTTTGAATGACTCGAGCATTGCTACTAAGCT  1320
              ||||||||||||||||||||||||||||||||||||||||||||||||||||||||||||
AH2012  1303  TGAGGAAGGTTTCACAGATCCTTGCTACTTTTTGAATGACTCGAGCATTGCTACTAAGCT  1362

125_10  1321  CAAGTTTGACATCCTTAGTGGCAAGTTTTCTGATGAAGTCAAACAAGCTATCTTTGCTGG  1380
              ||||||||||||||||||||||||||||||||||||||||||||||||||||||||||||
AH2012  1363  CAAGTTTGACATCCTTAGTGGCAAGTTTTCTGATGAAGTCAAACAAGCTATCTTTGCTGG  1422

125_10  1381  TCATGTTGTTGTTGGCAGCGCGMTCGTTGACATTGTTGACGATGCACTGGGACAGCCTTG  1440
              |||||||||||||||||| ||| |||||||||||||||||||||||||||||||||||||
AH2012  1423  TCATGTTGTTGTTGGCAGTGCGCTCGTTGACATTGTTGACGATGCACTGGGACAGCCTTG  1482

125_10  1441  GTTTATACGTAAGCTTGGTGACCTTGCAAGTGCAGCTTGGGAGCAGCTTAAGGCTGTCGT  1500
              ||||||||||||||||||||||||||||||||||||||||||||||||||||||||||||
AH2012  1483  GTTTATACGTAAGCTTGGTGACCTTGCAAGTGCAGCTTGGGAGCAGCTTAAGGCTGTCGT  1542

125_10  1501  TAGAGGCCTTAACCTCCTGTCTGATGAGGTCGTGCTCTTTGGCAAAAGACTTAGCTGTGC  1560
              ||||||||||||||||||||||||||||||||||||||||||||||||||||||||||||
AH2012  1543  TAGAGGCCTTAACCTCCTGTCTGATGAGGTCGTGCTCTTTGGCAAAAGACTTAGCTGTGC  1602

125_10  1561  CACTCTTAGTATCGTTAACGGTGTTTTTGAGTTCATCGCCGAAGTGCCTGAGAAGTTGGC  1620
              ||||||||||||||||||||||||||||||||| |||||||||||||| |||||||||||
AH2012  1603  CACTCTTAGTATCGTTAACGGTGTTTTTGAGTTTATCGCCGAAGTGCCAGAGAAGTTGGC  1662

125_10  1621  TGCGGCTGTTACAGTTTTTGTCAACTTCTTGAATGAGCTTTTTGAGTCTGCCTGTGACTG  1680
              ||||||||||||||||||||||||||||||||||||||||||||||||||||||||||||
AH2012  1663  TGCGGCTGTTACAGTTTTTGTCAACTTCTTGAATGAGCTTTTTGAGTCTGCCTGTGACTG  1722

125_10  1681  CTTAAAGGTCGGAGGTAAAACCTTTAACAAGGTTGGCTCTTATGTTCTTTTTGACAACGC  1740
              ||||||||||||||||||||||||||||||||||||||| ||||| ||||||||||||||
AH2012  1723  CTTAAAGGTCGGAGGTAAAACCTTTAACAAGGTTGGCTCCTATGTCCTTTTTGACAACGC  1782

125_10  1741  ATTGGTTAAGCTTGTCAAGGCAAAAGTTCGCGGCCCACGACAGGCAGGTGTTTGTGAAGT  1800
              ||||||||||||||||||||||||||||||||||||||||||||||||||||||||||||
AH2012  1783  ATTGGTTAAGCTTGTCAAGGCAAAAGTTCGCGGCCCACGACAGGCAGGTGTTTGTGAAGT  1842

125_10  1801  TCGTTACACAAGCCTTGTTATTGGGAGTACTACCAAGGTGGTTTCCAAGCGCGTTGAAAA  1860
              ||||||||||||||||||||||||||||||||||||||||||||||||||||||||||||
```

FIG. 1 (cont'd)

```
AH2012  1843   TCGTTACACAAGCCTTGTTATTGGGAGTACTACCAAGGTGGTTTCCAAGCGCGTTGAAAA  1902

125_10  1861   TGCCAATGTGAATCTCGTCGTCGTTGACGAGGATGTGACCCTCAACACCACTGGTCGTAC  1660
               |||||||||||||||||||||||||||||||||||||||||||||||||||||||| |||
AH2012  1903   TGCCAATGTGAATCTCGTCGTCGTTGACGAGGATGTGACCCTCAACACCACTGGTCATAC  1962

125_10  1661   AGTTGTTGTTGACGGACTTGCATTCTTCGAGAGTGACGGGTTTTACAGACATCTTGCTGA  1980
               ||||||||||||||||||||||||||||||||||||||||||||||||||||||||||||
AH2012  1963   AGTTGTTGTTGACGGACTTGCATTCTTCGAGAGTGACGGGTTTTACAGACATCTTGCTGA  2022

125_10  1981   TGCTGACGTTGTCATTGAACATCCTGTTTATAAGTCTGCTTGTGAGCTCAAGCCAGTTTT  2040
               ||||||||||||||||||||||||||||||||||||||||||||||||||||||||||||
AH2012  2023   TGCTGACGTTGTCATTGAACATCCTGTTTATAAGTCTGCTTGTGAGCTCAAGCCAGTTTT  2082

125_10  2041   TGAGTGTGACCCAATACCTGATTTTCCTATGCCTGTGGCCGCTAGTGTTGCAGAGCTTTG  2100
               ||||||||| |||||||||| |||||||||||||||||||||||||||||||||||||||
AH2012  2083   TGAGTGTGATCCAATACCTGGTTTTCCTATGCCTGTGGCCGCTAGTGTTGCAGAGCTTTG  2142

125_10  2101   TGTGCAAACTGATCTGTTGCTTAAAAATTACAACACTCCTTATAAAACTTACAGCTGCGT  2160
               ||||||||||||||||||||||||||||||||||||||||||||||||||||||||||||
AH2012  2143   TGTGCAAACTGATCTGTTGCTTAAAAATTACAACACTCCTTATAAAACTTACAGCTGCGT  2202

125_10  2161   TGTGAGAGGTGATAAGTGTTGTATCACTTGCACCTTACATTTCACAGCACCAAGTTATAT  2220
               ||||||||||||||||||||| |||||||||||||||||| |||||||||||||||||||
AH2012  2203   TGTGAGAGGTGATAAGTGTTGCATCACTTGCACCTTACATATCACAGCACCAAGTTATAT  2262

125_10  2221   GGAGGCTGCTGCTAATTTTGTAGACCTCTGTACCAAGAACATTGGTACTGCTGGTTTTCA  2280
               ||||| ||||||||||||||||||||||||||||||||||||||||||||||||||||||
AH2012  2263   GGAGGATGCTGCTAATTTTGTAGACCTCTGTACCAAGAACATTGGTACTGCTGGTTTTCA  2322

125_10  2281   TGAGTTTTACATTACGGCCCATGAACAACAGGATCTGCAAGGGTTCGTAACCACTTGTTG  2340
               ||||||||||||||||||||||||||||||||||||||||||||||||||||||||||||
AH2012  2323   TGAGTTTTACATTACGGCCCATGAACAACAGGATCTGCAAGGGTTCGTAACCACTTGTTG  2382

125_10  2341   CACGATGTCAGGTTTTGAGTGTTTTATGCCTATAATCCCACAGTGTCCAGCAGTGCTTGA  2400
               ||||||||||||||||||||||||||||||||||||||||||||||||||||||||||||
AH2012  2383   CACGATGTCAGGTTTTGAGTGTTTTATGCCTATAATCCCACAGTGTCCAGCAGTGCTTGA  2442

125_10  2401   AGAGATTGATGGTGGTAGCATCTGGCGGTCTTTTATCACTGGTCTTAATACAATGTGGGA  2460
               ||||||||||||||||||||||||||||||||||||||||||||||||||||||||||||
AH2012  2443   AGAGATTGATGGTGGTAGCATCTGGCGGTCTTTTATCACTGGTCTTAATACAATGTGGGA  2502

125_10  2461   TTTTTGCAAGCATCTTAAAGTCAGCTTTGGACTAGATGGCATTGTTGTCACTGTAGCACG  2520
               ||||||||||||||||||||||||||||||||||||||||||||||||||||||||||||
AH2012  2503   TTTTTGCAAGCATCTTAAAGTCAGCTTTGGACTAGATGGCATTGTTGTCACTGTAGCACG  2562

125_10  2521   CAAATTTAAACGACTTGGTGCTCTCTTGGCAGAAATGTATAACACTTACCTTTCAACTGT  2580
               ||||||||||||||||||||||||||||||||||||||||||||||||||||||||||||
AH2012  2563   CAAATTTAAACGACTTGGTGCTCTCTTGGCAGAAATGTATAACACTTACCTTTCAACTGT  2622

125_10  2581   GGTGGAAAACTTGGTACTGGCCGGTGTTAGCTTCAAGTATTATGCCACCAGTGTCCCAAA  2640
               ||||||||||||||||||||||||||||||||||||||||||||||||||||||||||||
AH2012  2623   GGTGGAAAACTTGGTACTGGCCGGTGTTAGCTTCAAGTATTATGCCACCAGTGTCCCAAA  2682

125_10  2641   AATTGTTTTGGGCTGTTGTTTTCACAGTGTTAAAAGTGTTCTTGCAAGTGCCTTCCAGAT  2700
               ||||||||||||||||||||||||||||||||||||||||||||||||||||||||||||
AH2012  2683   AATTGTTTTGGGCTGTTGTTTTCACAGTGTTAAAAGTGTTCTTGCAAGTGCCTTCCAGAT  2742

125_10  2701   TCCTGTCCAGGCAGGCGTTGAGAAGTTTAAAGTCTTCCTTAACTGTGTTCACCCTGTTGT  2760
               |||||||||||||||| |||||||||||||||||||||||||||||||||||||||||||
AH2012  2743   TCCTGTCCAGGCAGGCATTGAGAAGTTTAAAGTCTTCCTTAACTGTGTTCACCCTGTTGT  2802
```

FIG. 1 (cont'd)

```
125_10  2761  ACCACGTGTCATTGAAACTTCTTTTGTGGAATTAGAAGAGACGACATTTAAACCACCAGC  2820
              |||||| |||||||||||||||||||||||||||||||||||||||||||||||||||||
AH2012  2803  ACCACGCGTCATTGAAACTTCTTTTGTGGAATTAGAAGAGACGACATTTAAACCACCAGC  2862

125_10  2821  ACTCAATGGTAGTATTGCTATTGTTGATGGCTTTGCTTTCTATTATGATGGAACACTATA  2880
              ||||||||||||||||||||||||||||||||||||||||||||||||||||||||||||
AH2012  2863  ACTCAATGGTAGTATTGCTATTGTTGATGGCTTTGCTTTCTATTATGATGGAACACTATA  2662

125_10  2881  CTATCCCACCGATGGTAATAGCGTTGTTCCTATCTGCTTTAAGAAGAAAGGTGGTGGTGA  2940
              ||||||||||||||||||||| ||||| ||||| || ||||||||||| |||||||||||
AH2012  2663  CTATCCCACCGATGGTAATAGTGTTGTGCCTATTTGTTTTAAGAAGAAGGGTGGTGGTGA  2982

125_10  2941  TGTCAAATTCTCTGATGAAGTCTCTGTTAAAACCATTGACCCAGTTTATAAGGTCTCCCT  3000
              ||||||||||||||||||||||||||||| ||||||||||||||||||||||||||||||
AH2012  2983  TGTCAAATTCTCTGATGAAGTCTCTGTTAGAACCATTGACCCAGTTTATAAGGTCTCCCT  3042


125_10  3001  TGAATTTGAGTTCGAGTCTGAGACTATTATGGCTGTGCTTAATAAGGCTGTTGGTAATTG  3060
              |||||||||||||||||||||||||||||||||||||||||||||||||||||||||| |
AH2012  3043  TGAATTTGAGTTCGAGTCTGAGACTATTATGGCTGTGCTTAATAAGGCTGTTGGTAATCG  3102

125_10  3061  TATCAAGGTTACAGGTGGTTGGGACGATGTTGTTGAGTATATCAATGTTGCCATTGAGGT  3120
              ||||||||||||||||||||||||||||||||||||||||||||| ||||||||||||||
AH2012  3103  TATCAAGGTTACAGGTGGTTGGGACGATGTTGTTGAGTATATCAACGTTGCCATTGAGGT  3162

125_10  3121  TCTTAAAGATCACATCGATGTGCCTAAGTACTACATCTATGATGAGGAAGGTGGCACCGA  3180
              |||||||||||| |||||||||||||||||||||||||||||||||||||||||||||||
AH2012  3163  TCTTAAAGATCATATCGATGTGCCTAAGTACTACATCTATGATGAGGAAGGTGGCACCGA  3222

125_10  3181  TCCTAATCTGCCCGTAATGGTTTCTCAGTGGCCGTTGAATGATGACACGATCTCACAGGA  3240
              ||||||||| ||||||||||||||||||||||||||||||||||||||||||||||||||
AH2012  3223  TCCTAATCTTCCCGTAATGGTTTCTCAGTGGCCGTTGAATGATGACACGATCTCACAGGA  3282

125_10  3241  TCTGCTTGATGTTGAAGTTGTTACTGATGCGCCAGTTGATTTCGAGGGTGATGAAGTAGA  3300
              |||||||||||| ||||||||||||||||| ||| |||||||||||||||||||||||||
AH2012  3283  TCTGCTTGATGTGGAAGTTGTTACTGATGCACCAATTGATTTCGAGGGTGATGAAGTAGA  3342

125_10  3301  CTCCTCTGACCCTGWTAAGGTGGCAGACGTGGCTAACTCTGAGCCTGAGGATGACGGTCT  3360
              |||||||||||||| |||||||||||| |||||||||||||||||||||||||| |||| 
AH2012  3343  CTCCTCTGACCCTGATAAGGTGGCAGATGTGGCTAACTCTGAGCCTGAGGATGATGGTCC  3402

125_10  3361  TAATGTAGCTCCTGAAACAAATGTAGAGTCTGAAGTTGAGGAAGTTGCCGCAACCTTGTC  3420
              ||||||||||||||||||||||||||||||||||||||||||||||||||||||||||||
AH2012  3403  TAATGTAGCTCCTGAAACAAATGTAGAGTCTGAAGTTGAGGAAGTTGCCGCAACCTTGTC  3462

125_10  3421  CTTTA---AAGATACACCTTCCACAGTTACTAAGGATCCTTTTGCTTTTGACTTTGCAAG  3477
               ||||   ||||||||||||||||||||||||||||||||||||||||||||||||||||
AH2012  3463  TTTTATTAAAGATACACCTTCCACAGTTACTAAGGATCCTTTTGCTTTTGACTTTGCAAG  3522

125_10  3478  CTATGGAGGACTTAAGGTTTTAAGACAATCTCATAACAACTGCTGGGTTACTTCTACCTT  3537
              ||||||||||||||||||||||||||||||||||||||||||||||||||||||||||||
AH2012  3523  CTATGGAGGACTTAAGGTTTTAAGACAATCTCATAACAACTGCTGGGTTACTTCTACCTT  3582

125_10  3538  GGTGCAGCTACAATTGCTTGGCATCGTTGATGACCCTGCAATGGAGCTTTTTAGTGCTGG  3597
              ||||||||||||||||||||||||||||||||||||||||||||||||||||||||||||
AH2012  3583  GGTGCAGCTACAATTGCTTGGCATCGTTGATGACCCTGCAATGGAGCTTTTTAGTGCTGG  3642

125_10  3598  TAGAGTTGGTCCAATGGTTCGCAAATGCTATGAGTCACAAAAGGCTATCTTGGGATCTTT  3657
              ||||||||||||||||||||||||||||||||||||||||||||||||||||||||||||
AH2012  3643  TAGAGTTGGTCCAATGGTTCGCAAATGCTATGAGTCACAAAAGGCTATCTTGGGATCTTT  3702

125_10  3658  GGGTGATGTGTCGGCTTGCCTAGAGTCTCTGACTAAGGACCTACACACACTTAAGATTAC  3717
```

FIG. 1 (cont'd)

```
                    ||||||||||||||||||||||||||||||||||||||||||||||||||||||||||||
AH2012  3703        GGGTGATGTGTCGGCTTGCCTAGAGTCTCTGACTAAGGACCTACACACACTTAAGATTAC  3762

125_10  3718        CTGTTCTGTAGTCTGTGGTTGTGGTACTGGTGAACGTATCTATGATGGTTGTGCTTTTCG  3777
                    ||||||||||||||||||||||||||||||||||||||||||||| ||||||||||||||
AH2012  3763        CTGTTCTGTAGTCTGTGGTTGTGGTACTGGTGAACGTATCTATGAGGGTTGTGCTTTTCG  3822

125_10  3778        TATGACGCCAACTTTGGAACCGTTCCCATATGGTGCTTGTGCTCAGTGTGCTCAAGTTTT  3837
                    ||||||||||||||||||||||||||||||||||||||||||||||||||||||||||||
AH2012  3823        TATGACGCCAACTTTGGAACCGTTCCCATATGGTGCTTGTGCTCAGTGTGCTCAAGTTTT  3882

125_10  3838        GATGCACACTTTTAAAAGTATTGTTGGCACCGGCATCTTTTGTCGAGATACTACTGCTCT  3897
                    ||||||||||||||||||||||||||||||||||||||||||||||||||||||||||||
AH2012  3883        GATGCACACTTTTAAAAGTATTGTTGGCACCGGCATCTTTTGTCGAGATACTACTGCTCT  3942

125_10  3898        CTCCTTGGATTCTTTGGTTGTAAAACCTCTTTGTGCGGCTGCTTTTATAGGCAAGGATAG  3957
                    ||||||||||||||||||||||||||||||||||||||||||||||||||||||||||||
AH2012  3943        CTCCTTGGATTCTTTGGTTGTAAAACCTCTTTGTGCGGCTGCTTTTATAGGCAAGGATAG  4002

125_10  3958        TGGTCATTATGTCACTAACTTTTATGATGCTGCTATGGCTATTGATGGTTATGGTCGTCA  4017
                    ||||||||||||||||||||||||||||||||||||||||||||||||||||||||||||
AH2012  4003        TGGTCATTATGTCACTAACTTTTATGATGCTGCTATGGCTATTGATGGTTATGGTCGTCA  4062


125_10  4018        TCAGATAAAGTATGACACACTGAACACTATTTGTGTTAAAGACGTTAATTGGACAGCACC  4077
                    ||||||||||||||||||||||||||||||||||||||||||||||||||||||||||||
AH2012  4063        TCAGATAAAGTATGACACACTGAACACTATTTGTGTTAAAGACGTTAATTGGACAGCACC  4122

125_10  4078        TTTTGTCCCAGACGTTGAGCCTGTATTGGAGCCTGTTGTCAAACCTTTCTATTCTTATAA  4137
                    ||||||||||||||||||||||||||||||||||||||||||||||||||||||||||||
AH2012  4123        TTTTGTCCCAGACGTTGAGCCTGTATTGGAGCCTGTTGTCAAACCTTTCTATTCTTATAA  4182

125_10  4138        GAATGTTGATTTTTACCAAGGAGATTTTAGTGACCTTGTTAAACTTCCATGTGATTTTGT  4197
                    ||||||||||||||||||||||||||||||||||||||||||||||||||||||||||||
AH2012  4183        GAATGTTGATTTTTACCAAGGAGATTTTAGTGACCTTGTTAAACTTCCATGTGATTTTGT  4242

125_10  4198        TGTTAATGCTGCAAATGAGAATTTGTCTCACGGTGGCGGCATAGCAAAGGCCATTGATGT  4257
                    ||||||||||||||||||||||||||||||||||||||||||||||||||||||||||||
AH2012  4243        TGTTAATGCTGCAAATGAGAATTTGTCTCACGGTGGCGGCATAGCAAAGGCCATTGATGT  4302

125_10  4258        TTATACCAAGGGCATGTTGCAGAAGTGCTCGAATGATTACATTAAAGCACACGGTCCCAT  4317
                    ||||||||||||||||||||||||||||||||||||||||||||||||||||||||||||
AH2012  4303        TTATACCAAGGGCATGTTGCAGAAGTGCTCGAATGATTACATTAAAGCACACGGTCCCAT  4362

125_10  4318        TAAAGTTGGACGTGGTGTCATGTTGGAGGCATTAGGTCTTAAGGTCTTTAATGTTGTTGG  4377
                    ||||||||||||||||||||||||||||||||||||||||||||||||||||||||||||
AH2012  4363        TAAAGTTGGACGTGGTGTCATGTTGGAGGCATTAGGTCTTAAGGTCTTTAATGTTGTTGG  4422

125_10  4378        TCCACGTAAGGGTAAGCATGCACCTGAGCTTCTTGTTAAGGCTTATAAGTCCGTTTTTGC  4437
                    ||||||||||||||||||||||||||||||||||||||||||||||||||||||||||||
AH2012  4423        TCCACGTAAGGGTAAGCATGCACCTGAGCTTCTTGTTAAGGCTTATAAGTCCGTTTTTGC  4482

125_10  4438        TAATTCAGGTGTTGCTCTTACACCTTTGATTAGTGTTGGAATTTTTAGTGTTCCTTTGGA  4497
                    ||||||||||||||||||||||||||||||||||||||||||||||||||||||||||||
AH2012  4483        TAATTCAGGTGTTGCTCTTACACCTTTGATTAGTGTTGGAATTTTTAGTGTTCCTTTGGA  4542

125_10  4498        AGAATCTTTATCTGCTTTTCTTGCATGTGTTGGTGATCGCCACTGTAAGTGCTTTTGTTA  4557
                    ||||||||||||||||||||||||||||||||||||||||||||||||||||||||||||
AH2012  4543        AGAATCTTTATCTGCTTTTCTTGCATGTGTTGGTGATCGCCACTGTAAGTGCTTTTGTTA  4602

125_10  4558        TAGTGACAAAGAGCGCGAGGCGATCATTAATTACATGGATGGCTTGGTAGATGCTATTTT  4617
                    ||||||||||||||||||||||||||||||||||||||||||||||||||||||||||||
```

FIG. 1 (cont'd)

```
AH2012  4603   TAGTGACAAAGAGCGCGAGGCGATCATTAATTACATGGATGGCTTGGTAGATGCTATTTT  4662

125_10  4618   CAAAGATGCACTTGTTGATACTACTCCTGTCCAGGAAGATGTTCAACAAGTTTCACAAAA  4677
               ||||||||| ||||||||||||||||||||||||||||||||||||||||||||||||||
AH2012  4663   CAAAGATGCGCTTGTTGATACTACTCCTGTCCAGGAAGATGTTCAACAAGTTTCACAAAA  4722

125_10  4678   ACCAGTTTTGCCTAATTTTGAACCTTTCAGGATTGAAGGTGCTCATGCTTTCTATGAGTG  4737
               ||||||||||||||||||||||||||||||||||||||||||||||||||||||||||||
AH2012  4723   ACCAGTTTTGCCTAATTTTGAACCTTTCAGGATTGAAGGTGCTCATGCTTTCTATGAGTG  4782

125_10  4738   CAACCCTGAAGGTTTGATGTCATTAGGTGCTGACAAGCTGGTGTTGTTTACAAATTCCAA  4797
               ||||||||||||||||||||||||||||||||||||||||||||||||||||||||||||
AH2012  4783   CAACCCTGAAGGTTTGATGTCATTAGGTGCTGACAAGCTGGTGTTGTTTACAAATTCCAA  4842

125_10  4798   TTTGGATTTTTGTAGCGTTGGTAAGTGTCTTAACAATGTGACTGGCGGTGCATTGCTTGA  4857
               |||||||||||||||||||||||||||||||||||||||||| |||||||||||||||||
AH2012  4843   TTTGGATTTTTGTAGCGTTGGTAAGTGTCTTAACAATGTGACCGGCGGTGCATTGCTTGA  4902

125_10  4858   AGCCATAAATGTATTTAAAAAGAGTAACAAAACAGTGCCTGCTGGCAACTGTGTTACTTT  4917
               ||||||||||||||||||||||||||||||||||||||||||||||||||||||||||||
AH2012  4903   AGCCATAAATGTATTTAAAAAGAGTAACAAAACAGTGCCTGCTGGCAACTGTGTTACTTT  4962

125_10  4918   TGAGTGTGCAGATATGATTTCTATTACTATGGTAGTATTGCCATCTGACGGTGATGCTAA  4977
               |||||||||||| ||||||||||||||||||||||||||||||||||| |||||||||||
AH2012  4963   TGAGTGTGCAGACATGATTTCTATTACTATGGTAGTATTGCCATCTGATGGTGATGCTAA  5022

125_10  4978   TTATGACAAAAATTATGCACGCGCCGTCGTCAAGGTATCTAAGCTTAAAGGCAAGTTATT  5037
               ||||||||||||||||||||||||||||||||||||||||||||||||||||||||||||
AH2012  5023   TTATGACAAAAATTATGCACGCGCCGTCGTCAAGGTATCTAAGCTTAAAGGCAAGTTATT  5082


125_10  5038   GCTTGCTGTTGGTGATGCCATGTTGTATTCCAAGTTGTCCCACCTCAGCGTGTTAGGTTT  5097
               |||||||||||||||||||| ||||||||||||||||||||||||||||||| |||||||
AH2012  5083   GCTTGCTGTTGGTGATGCCACGTTGTATTCCAAGTTGTCCCACCTCAGCGTGGTAGGTTT  5142

125_10  5098   CGTATCCACACCTGATGATGTGGAGCGTTTCTACGCAAATAAGAGTGTGGTTATTAAAGT  5157
               ||||||||||||||||||||||||||||||||||||||||||||||||||||||||||||
AH2012  5143   CGTATCCACACCTGATGATGTGGAGCGTTTCTACGCAAATAAGAGTGTGGTTATTAAAGT  5202

125_10  5158   TACTGAGGATACACGTAGTGTTAAGACTGTTAAAGTAGAATCCACTGTTACTTATGGACA  5217
                |||||||||||||||||||||||| ||||||||||||||||||||||||||||||||||
AH2012  5203   CACTGAGGATACACGTAGTGTTAAGGCTGTTAAAGTAGAATCCACTGTTACTTATGGACA  5262

125_10  5218   ACAAATTGGACCTTGTCTTGTTAATGACACCGTTGTCACAGACAACAAACCTGTTGTTGC  5277
               ||||||||||||||||||||||||||||||||||||||||||||||||||||||||||||
AH2012  5263   ACAAATTGGACCTTGTCTTGTTAATGACACCGTTGTCACAGACAACAAACCTGTTGTTGC  5322

125_10  5278   TGATGTTGTAGCTAAGGTTGTACCAAGTGCTAATTGGGATTCACATTATGGTTTTGATAA  5337
               ||||||||||||||||||||||||||||||||||||||||||||||||||||||||||||
AH2012  5323   TGATGTTGTAGCTAAGGTTGTACCAAGTGCTAATTGGGATTCACATTATGGTTTTGATAA  5382

125_10  5338   GGCTGGTGAGTTCCACATGCTAGACCATACTGGGTTTGCCTTTCCTAGTGAAGTTGTTAA  5397
               ||||||||||||||||||||||||||||||||||||||||||||||||||||||||||||
AH2012  5383   GGCTGGTGAGTTCCACATGCTAGACCATACTGGGTTTGCCTTTCCTAGTGAAGTTGTTAA  5442

125_10  5398   CGGTAGGCGTGTGCTTAAAACCACAGATAATAACTGTTGGGTTAATGTTACATGTTTACA  5457
               ||||||||||||||||||||||||||||||||||||||||||||||||||||||||||||
AH2012  5443   CGGTAGGCGTGTGCTTAAAACCACAGATAATAACTGTTGGGTTAATGTTACATGTTTACA  5502

125_10  5458   ATTACAGTTTGCTAGATTTAGGTTCAAGTCAGCAGGTCTACAGGCTATGTGGGAGTCCTA  5517
               ||||||||||||||||||||||||||||||||||||||||||||||||||||||||||||
AH2012  5503   ATTACAGTTTGCTAGATTTAGGTTCAAGTCAGCAGGTCTACAGGCTATGTGGGAGTCCTA  5562
```

FIG. 1 (cont'd)

```
125_10  5518  TTGTACTGGTGATGTTGCTATGTTTGTGCATTGGTTGTACTGGCTTACTGGTGTTGACAA  5577
              ||||||||||||||||||||||||||||||||||||||||||||||||||||||||||||
AH2012  5563  TTGTACTGGTGATGTTGCTATGTTTGTGCATTGGTTGTACTGGCTTACTGGTGTTGACAA  5622

125_10  5578  AGGTCAGCCTAGTGATTCAGAAAATGCACTTAACATGTTGTCTAAGTACATTGTTCCTGC  5637
              |||||||||||||||||||||||||||||||||||||||||| |||||||||||| ||||
AH2012  5623  AGGTCAGCCTAGTGATTCAGAAAATGCACTTAACATGTTGTCCAAGTACATTGTTTCTGC  5682

125_10  5638  TGGTTCTGTCACTATTGAACGTGTCACGCATGACGGTTGTTGTTGTAGTAAGCGTGTTGT  5697
              |||||||||||||||||||||||||||||||||||| |||||||||||||||||||||||
AH2012  5683  TGGTTCTGTCACTATTGAACGTGTCACGCATGACGGCTGTTGTTGTAGTAAGCGTGTTGT  5742

125_10  5698  CACTGCACCAGTTGTGAATGCTAGCGTGTTGAAGCTTGGCGTCGAGGATGGTCTTTGTCC  5757
              ||||||||||||||||||||||||||| ||||||||||||||||||||||||||||||||
AH2012  5743  CACTGCACCAGTTGTGAATGCTAGCGTATTGAAGCTTGGCGTCGAGGATGGTCTTTGTCC  5802

125_10  5758  ACATGGTCTTAACTACATTGACAAAGTTGTTGTAGTTAAAGGTACTACAATTGTTGTCAA  5817
              |||||||||||||||||||||||||||||||||||| |||||||||||||||||||||||
AH2012  5803  ACATGGTCTTAACTACATTGACAAAGTTGTTGTAGTCAAAGGTACTACAATTGTTGTCAA  5862

125_10  5818  TGTTGGAAAACCTGTAGTGGCACCATCGCACCTCTTTCTTAAGGGTGTTTCCTACACAAC  5877
              ||||||||||||||||||||||||||| |||||||||||||||||||||||| |||||||
AH2012  5863  TGTTGGAAAACCTGTAGTGGCACCATCACACCTCTTTCTTAAGGGTGTTTCTTACACAAC  5662

125_10  5878  ATTCCTAGATAATGGTAACGGTGTTGCCGGCCATTATACTGTTTTTGATCATGACACTGG  5937
              |||||||||||||||||||||||||| |||||||||||||||||||||||||||||||||
AH2012  5663  ATTCCTAGATAATGGTAACGGTGTTGTCGGCCATTATACTGTTTTTGATCATGACACTGG  5982

125_10  5938  TATGGTGCATGATGGAGATGTTTTTGTACCAGGTGATCTCAATGTGTCTCCTGTTACAAA  5997
              |||||||||||||||||||| ||||||||| |||||||||||||| ||||||||||||||
AH2012  5983  TATGGTGCATGATGGAGATGCTTTTGTACCGGGTGATCTCAATGTATCTCCTGTTACAAA  6042

125_10  5998  TGTTGTCGTCTCAGAGCAGACGGCTGTTGTGATTAAAGACCCTGTGAAGAAAGTAGAGTT  6057
              ||||||||||||||||||||||||||||||||||||||||||||||||||||||||||||
AH2012  6043  TGTTGTCGTCTCAGAGCAGACGGCTGTTGTGATTAAAGACCCTGTGAAGAAAGTAGAGTT  6102


125_10  6058  AGACGCTACAAAGCTGTTAGACACTATGAATTATGCATCGGAAAGATTCTTTTCCTTTGG  6117
              ||||||||||||||||||||||||||||||||||||||||||||||||||||||||||||
AH2012  6103  AGACGCTACAAAGCTGTTAGACACTATGAATTATGCATCGGAAAGATTCTTTTCCTTTGG  6162

125_10  6118  TGATTTTATGTCACGTAATTTAATTACAGTGTTTTTGTACATCCTTAGTATTTTGGGTCT  6177
              ||||||||||||||||||||||||||||||||||||||||||||||||||||||||||||
AH2012  6163  TGATTTTATGTCACGTAATTTAATTACAGTGTTTTTGTACATCCTTAGTATTTTGGGTCT  6222

125_10  6178  CTGTTTTAGGGCCTTTCGTAAGAGGGATGTTAAAGTTCTAGCTGGTGTACCCCAACGTAC  6237
              ||||||||||||||||||||||||||||||||||||||||||||||||||||||||||||
AH2012  6223  CTGTTTTAGGGCCTTTCGTAAGAGGGATGTTAAAGTTCTAGCTGGTGTACCCCAACGTAC  6282

125_10  6238  TGGTATTATATTGCGTAAAAGTGTGCGCTATAATGCAAAGGCTTTGGGTGTCTTCTTCAA  6297
              ||||||||||||||||||||||||||||||||||||||||||||||||||||||||||||
AH2012  6283  TGGTATTATATTGCGTAAAAGTGTGCGCTATAATGCAAAGGCTTTGGGTGTCTTCTTCAA  6342

125_10  6298  GCTAAAACTTTATTGGTTCAAAGTTCTTGGTAAGTTTAGTTTGGGTATTTATGCATTGTA  6357
              ||||||||||||||||||||||||||||||||||||||||||||||||||||||||||||
AH2012  6343  GCTAAAACTTTATTGGTTCAAAGTTCTTGGTAAGTTTAGTTTGGGTATTTATGCATTGTA  6402

125_10  6358  TGCATTACTATTCATGACAATACGCTTTACACCTATAGGTGGCCCTGTTTGTGATGATGT  6417
              ||||||||||||||||||||||||||||||||||||||||||||||||||||||||||||
AH2012  6403  TGCATTACTATTCATGACAATACGCTTTACACCTATAGGTGGCCCTGTTTGTGATGATGT  6462

125_10  6418  TGTTGCTGGTTATGCTAATTCTAGTTTTGACAAGAATGAGTATTGCAACAGTGTTATTTG  6477
```

FIG. 1 (cont'd)

```
                      ||||||||||||||||||||||||||||||||||||||||||||||||||||||||||||
AH2012  6463   TGTTGCTGGTTATGCTAATTCTAGTTTTGACAAGAATGAGTATTGCAACAGTGTTATTTG  6522

125_10  6478   TAAGGTCTGTCTCTATGGGTACCAGGAACTTTCGGACTTCTCTCACACACAGGTAGTATG  6537
               ||||||||||||||||||||||||||||||||||||||||||||||||||||||||||||
AH2012  6523   TAAGGTCTGTCTCTATGGGTACCAGGAACTTTCGGACTTCTCTCACACACAGGTAGTATG  6582

125_10  6538   GCAACACCTTAGAGACCCATTAATTGGTAATGTGATGCCTTTCTTTTATTTGGCATTTCT  6597
               ||||||||||||||||||||||||||||||||||||||||||||||||||||||||||||
AH2012  6583   GCAACACCTTAGAGACCCATTAATTGGTAATGTGATGCCTTTCTTTTATTTGGCATTTCT  6642

125_10  6598   GGCAATTTTTGGGGGTGTTTATGTAAAGGCTATTACTCTCTATTTTATTTTCCAGTATCT  6657
               ||||||||||||||||||||||||||||||||||||||||||||||||||||||||||||
AH2012  6643   GGCAATTTTTGGGGGTGTTTATGTAAAGGCTATTACTCTCTATTTTATTTTCCAGTATCT  6702

125_10  6658   TAACATACTTGGTGTGTTTTTGGGCCTACAACAGTCCATTTGGTTTTTGCAGCTTGTGCC  6717
               |||||| |||||||||||||||||||||||||||||||||||||||||||||||||||||
AH2012  6703   TAACATTCTTGGTGTGTTTTTGGGCCTACAACAGTCCATTTGGTTTTTGCAGCTTGTGCC  6762

125_10  6718   TTTTGATGTCTTTGGTGACGAGATCGTCGTCTTTTTCATCGTTACACGCGTATTGATGTT  6777
               ||||||||||||||||||||||||||||||||||||||||||||||||||||||||||||
AH2012  6763   TTTTGATGTCTTTGGTGACGAGATCGTCGTCTTTTTCATCGTTACACGCGTATTGATGTT  6822

125_10  6778   CCTTAAGCATGTTTTCCTTGGCTGCGATAAGGCATCTTGTGTGGCTTGCTCTAAGAGTGC  6837
               ||||||||||||||||||||||||||||||||||||||||||||||||||||||||||||
AH2012  6823   CCTTAAGCATGTTTTCCTTGGCTGCGATAAGGCATCTTGTGTGGCTTGCTCTAAGAGTGC  6882

125_10  6838   TCGCCTTAAGCGCGTTCCTGTCCAGACTATTTTTCAGGGTACTAGCAAATCCTTCTACGT  6897
               ||||||||||||||||||||||||||||||||||||||||||||||||||||||||||||
AH2012  6883   TCGCCTTAAGCGCGTTCCTGTCCAGACTATTTTTCAGGGTACTAGCAAATCCTTCTACGT  6942

125_10  6898   ACATGCCAATGGTGGTTCTAAGTTCTGTAAGAAGCACAATTTCTTTTGTTTAAATTGTGA  6957
               ||||||||||||||||||||||||||||||||||||||||||||||||||||||||||||
AH2012  6943   ACATGCCAATGGTGGTTCTAAGTTCTGTAAGAAGCACAATTTCTTTTGTTTAAATTGTGA  7002

125_10  6958   TTCTTATGGTCCAGGCTGCACTTTTATTAATGACGTCATTGCAACTGAAGTTGGTAATGT  7017
               ||||||||||||||||||||||||||||||||||||||||||||||||||||||||||||
AH2012  7003   TTCTTATGGTCCAGGCTGCACTTTTATTAATGACGTCATTGCAACTGAAGTTGGTAATGT  7062

125_10  7018   TGTCAAACTTAATGTGCAACCGACAGGTCCTGCCACTATTCTTATTGACAAGGTTGAATT  7077
               ||||||||||||||||||||||||||||||||||||||||||||||||||||||||||||
AH2012  7063   TGTCAAACTTAATGTGCAACCGACAGGTCCTGCCACTATTCTTATTGACAAGGTTGAATT  7122


125_10  7078   CAGTAATGGTTTTTACTATCTTTATAGTGGTGACACATTTTGGAAGTACAACTTTGACAT  7137
               ||||||||||||||||||||||||||||||||||||||||||||||||||||||||||||
AH2012  7123   CAGTAATGGTTTTTACTATCTTTATAGTGGTGACACATTTTGGAAGTACAACTTTGACAT  7182

125_10  7138   AACAGATAACAAATACACTTGCAAAGAGTCACTTAAAAATTGTAGCATAATCACAGACTT  7197
               ||||||||||||||||||||||||||||||||||||||||||||||||||||||||||||
AH2012  7183   AACAGATAACAAATACACTTGCAAAGAGTCACTTAAAAATTGTAGCATAATCACAGACTT  7242

125_10  7198   TATTGTTTTTAACAATAATGGTTCCAATGTAAATCAGGTTAAGAATGCATGTGTGTATTT  7257
               ||||||||||||||||||||||||||||||||||||||||||||||||||||||||||||
AH2012  7243   TATTGTTTTTAACAATAATGGTTCCAATGTAAATCAGGTTAAGAATGCATGTGTGTATTT  7302

125_10  7258   TTCACAGATGCTTTGTAAACCTGTTAAGTTAGTGGACTCAGCGTTGTTGGCCAGTTTGTC  7317
               ||||||||||||||||||||||||||||||||||||||||||||||||||||||||||||
AH2012  7303   TTCACAGATGCTTTGTAAACCTGTTAAGTTAGTGGACTCAGCGTTGTTGGCCAGTTTGTC  7362

125_10  7318   TGTTGATTTTGGTGCAAGCTTACATAGTGCTTTTGTTAGTGTGTTGTCGAATAGTTTTGG  7377
               ||||||||||||||||||||||||||||||||||||||||||||||||||||||||||||
AH2012  7363   TGTTGATTTTGGTGCAAGCTTACATAGTGCTTTTGTTAGTGTGTTGTCGAATAGTTTTGG  7422
```

FIG. 1 (cont'd)

```
125_10  7378  CAAAGACCTGTCAAGTTGTAATGACATGCAGGATTGCAAGAGCACATTGGGTTTTGATGA  7437
              ||||||||||||||||||||||||||||||||||||||||||||||||||||||||||||
AH2012  7423  CAAAGACCTGTCAAGTTGTAATGACATGCAGGATTGCAAGAGCACATTGGGTTTTGATGA  7482

125_10  7438  TGTACCATTGGATACCTTTAATGCTGCTGTTGCTGAGGCTCATCGTTACGATGTCCTCTT  7497
              ||||||||||||||||||||||||||||||||||||||||||||||||||||||||||||
AH2012  7483  TGTACCATTGGATACCTTTAATGCTGCTGTTGCTGAGGCTCATCGTTACGATGTCCTCTT  7542

125_10  7498  GACTGACATGTCGTTCAACAATTTTACCACCAGTTATGCAAAACCAGAGGAAAAACTTCC  7557
              ||||||||||||||||||||||||||||||||||||||||||||||||||||||||||||
AH2012  7543  GACTGACATGTCGTTCAACAATTTTACCACCAGTTATGCAAAACCAGAGGAAAAACTTCC  7602

125_10  7558  CGTCCATGACATTGCCACGTGTATGCGTGTAGGTGCCAAGATTGTTAATCATAACGTTCT  7617
              ||||||||||||||||||||||||||||||||||||||||||||||||||||||||||||
AH2012  7603  CGTCCATGACATTGCCACGTGTATGCGTGTAGGTGCCAAGATTGTTAATCATAACGTTCT  7662

125_10  7618  TGTCAAGGATAGTATACCTGTGGTGTGGCTTGTACGTGATTTCATTGCCCTTTCTGAAGA  7677
              |||||||||||||||||||||||||||||||||||||||||||||||||||||| |||||
AH2012  7663  TGTCAAGGATAGTATACCTGTGGTGTGGCTTGTACGTGATTTCATTGCCCTTTCGGAAGA  7722

125_10  7678  AACTAGGAAGTACATTATTCGTACGACTAAAGTTAAGGGTATAACCTTCATGTTGACCTT  7737
              ||||||||||||||||||||||||||||||||||||||||||||||||||||||||||||
AH2012  7723  AACTAGGAAGTACATTATTCGTACGACTAAAGTTAAGGGTATAACCTTCATGTTGACCTT  7782

125_10  7738  TAATGATTGTCGTATGCATACTACCATACCTACTGTTTGCATTGCAAATAAGAAGGGTGC  7797
              ||||||||||||||||||||||||||||||||||||||||||||||||||||||||||||
AH2012  7783  TAATGATTGTCGTATGCATACTACCATACCTACTGTTTGCATTGCAAATAAGAAGGGTGC  7842

125_10  7798  AGGTCTTCCTAGTTTTTCAAAGGTTAAGAAATTCTTCTGGTTTTTGTGTCTGTTCATAGT  7857
              ||||||||||||||||||||||||||||||||||||||||||||||||||||||||||||
AH2012  7843  AGGTCTTCCTAGTTTTTCAAAGGTTAAGAAATTCTTCTGGTTTTTGTGTCTGTTCATAGT  7902

125_10  7858  TGCTGTTTTCTTTGCACTAAGCTTTTTTGATTTTAGTACTCAGGTTAGCAGTGATAGTGA  7917
              ||||||||||||||||||||||||||||||||| ||||||||||||||||||||||| ||
AH2012  7903  TGCTGTTTTCTTTGCACTAAGCTTTCTTGATTTTAGTACTCAGGTTAGCAGTGATAGCGA  7962

125_10  7918  TTATGACTTCAAGTATATTGAGAGTGGCCAGTTGAAGACTTTTGACAATCCACTTAGTTG  7977
              ||||||||||||||||||||||||||||||||||||||||||||||||||||||||||||
AH2012  7963  TTATGACTTCAAGTATATTGAGAGTGGCCAGTTGAAGACTTTTGACAATCCACTTAGTTG  8022

125_10  7978  TGTGCATAATGTCTTTAGTAACTTCGACCAGTGGCATGATGCCAAGTTTGGTTTCACCCC  8037
              ||||||||||||||||||||||||||||||||||||||||||||||||||||||||||||
AH2012  8023  TGTGCATAATGTCTTTAGTAACTTCGACCAGTGGCATGATGCCAAGTTTGGTTTCACCCC  8082

125_10  8038  CGTCAACAATCCTAGTTGTCCTATAGTCGTTGGTGTATCAGACGAAGCGCGCACTGTTCC  8097
              |||||||||||||||||||||||||||||||||||||| |||||||||||||||||||||
AH2012  8083  CGTCAACAATCCTAGTTGTCCTATAGTCGTTGGTGTGTCAGACGAAGCGCGCACTGTTCC  8142

125_10  8098  AGGTATCCCAGCAGGTGTTTATTTAGCTGGTAAAACACTTGTTTTTGCTATTAACACCAT  8157
              ||||||||||||||||||||||||||||||||||||||||||||||||||||||||||||
AH2012  8143  AGGTATCCCAGCAGGTGTTTATTTAGCTGGTAAAACACTTGTTTTTGCTATTAACACCAT  8202

125_10  8158  TTTTGGTACATCTGGTTTGTGCTTTGATGCTAGTGGCGTTGCTGATAAGGGCGCTTGCAT  8217
              ||||||||||||||||||||||||||||||||||||||||||||||||||||||||||||
AH2012  8203  TTTTGGTACATCTGGTTTGTGCTTTGATGCTAGTGGCGTTGCTGATAAGGGCGCTTGCAT  8262

125_10  8218  TTTTAATTCGGCTTGCACCACATTATCTGGTTTGGGTGGAACTGCTGTCTACTGTTATAA  8277
              ||||||||||||||||||||||||||||||||||||||||||||||||||||||||||||
AH2012  8263  TTTTAATTCGGCTTGCACCACATTATCTGGTTTGGGTGGAACTGCTGTCTACTGTTATAA  8322
```

FIG. 1 (cont'd)

```
125_10  8278  GAATGGTCTAGTTGAAGGTGCTAAACTTTATAGTGAGTTGGCACCTCATAGCTACTATAA  8337
              ||||||||||||||||||||||||||||||||||||||||||||||||||||||||||||
AH2012  8323  GAATGGTCTAGTTGAAGGTGCTAAACTTTATAGTGAGTTGGCACCTCATAGCTACTATAA  8382

125_10  8338  AATGGTAGATGGTAATGCTGTGTCTTTACCTGAAATTATCTCACGCGGCTTTGGCATCCG  8397
              ||||||||||||||||||||||||||||||||||||||||||||||||||||||||||||
AH2012  8383  AATGGTAGATGGTAATGCTGTGTCTTTACCTGAAATTATCTCACGCGGCTTTGGCATCCG  8442

125_10  8398  TACTATCCGTACAAAGGCTATGACCTACTGTCGCGTTGGCCAGTGTGTGCAATCTGCAGA  8457
              ||||||||||||||||||||||||||||||||||||||||||||||||||||||||||||
AH2012  8443  TACTATCCGTACAAAGGCTATGACCTACTGTCGCGTTGGCCAGTGTGTGCAATCTGCAGA  8502

125_10  8458  AGGTGTTTGTTTTGGCGCCGATAGATTCTTTGTCTATAATGCAGAATCTGGTTCTGACTT  8517
              ||||||||||||||||||||||||||||||||||||||||||||||||||||||||||||
AH2012  8503  AGGTGTTTGTTTTGGCGCCGATAGATTCTTTGTCTATAATGCAGAATCTGGTTCTGACTT  8562

125_10  8518  TGTTTGTGGCACAGGGCTCTTTACATTGTTGATGAACGTTATTAGTGTTTTTTCCAAGAC  8577
              ||||||||||||||||||||||||||||||||||||||||||||||||||||||||||||
AH2012  8563  TGTTTGTGGCACAGGGCTCTTTACATTGTTGATGAACGTTATTAGTGTTTTTTCCAAGAC  8622

125_10  8578  AGTACCAGTAACTGTGTTGTCTGGTCAAATACTTTTTAATTGCATTATTGCTTTTGCTGC  8637
              ||||||||||||||||||||||||||||||||||||||||||||||||||||||||||||
AH2012  8623  AGTACCAGTAACTGTGTTGTCTGGTCAAATACTTTTTAATTGCATTATTGCTTTTGCTGC  8682

125_10  8638  TGTTGCGGTGTGTTTCTTATTTACAAAGTTTAAGCGCATGTTCGGTGATATGTCTGTTGG  8697
              ||||||||||||||||||||||||||||||||||||||||||||||||||||||||||||
AH2012  8683  TGTTGCGGTGTGTTTCTTATTTACAAAGTTTAAGCGCATGTTCGGTGATATGTCTGTTGG  8742

125_10  8698  CGTTTTCACTGTCGGTGCTTGTACTTTGTTGAACAATGTTTCCTACATTGTAACACAGAA  8757
              ||||||||||||||||||||||||||||||||||||||||||||||||||||||||||||
AH2012  8743  CGTTTTCACTGTCGGTGCTTGTACTTTGTTGAACAATGTTTCCTACATTGTAACACAGAA  8802

125_10  8758  CACACTTGGCATGTTGGGCTATGCAACTTTGTACTTTTTGTGCACTAAAGGTGTTAGATA  8817
              ||||||||||||||||||||||||||||||||||||||||||||||||||||||||||||
AH2012  8803  CACACTTGGCATGTTGGGCTATGCAACTTTGTACTTTTTGTGCACTAAAGGTGTTAGATA  8862

125_10  8818  TATGTGGATTTGGCATTTGGGATTTTTGATCTCATATATACTTATTGCACCATGGTGGGT  8877
              ||||||||||||||||||||||||||||||||||||||||||||||||||||||||||||
AH2012  8863  TATGTGGATTTGGCATTTGGGATTTTTGATCTCATATATACTTATTGCACCATGGTGGGT  8662

125_10  8878  TTTGATGGTTTATGCCTTTTCAGCCATTTTTGAGTTTATGCCTAACCTTTTTAAGCTTAA  8937
              ||||||||||||||||||||||||||||||||||||||||||||||||||||||||||||
AH2012  8663  TTTGATGGTTTATGCCTTTTCAGCCATTTTTGAGTTTATGCCTAACCTTTTTAAGCTTAA  8982

125_10  8938  GGTTTCAACACAACTTTTTGAGGGTGACAAGTTCGTAGGCTCTTTTGAAAATGCTGCAGC  8997
              ||||||||||||||||||||||||||||||||||||||||||||||||||||||||||||
AH2012  8983  GGTTTCAACACAACTTTTTGAGGGTGACAAGTTCGTAGGCTCTTTTGAAAATGCTGCAGC  9042

125_10  8998  AGGTACATTTGTGCTTGATATGCATGCCTATGAGAGACTTGCCAACTCTATCTCAACTGA  9057
              ||||||||||||||||||||||||||||||||||||||||||||||||||||||||||||
AH2012  9043  AGGTACATTTGTGCTTGATATGCATGCCTATGAGAGACTTGCCAACTCTATCTCAACTGA  9102

125_10  9058  AAAACTGCGTCAGTATGCTAGTACTTACAATAAGTACAAGTATTATTCAGGCAGTGCTTC  9117
              ||||||||||||||||||||||||||||||||||||||||||||||||||||||||||||
AH2012  9103  AAAACTGCGTCAGTATGCTAGTACTTACAATAAGTACAAGTATTATTCAGGCAGTGCTTC  9162

125_10  9118  AGAGGCTGATTACAGGCTTGCTTGTTTTGCCCATTTGGCCAAGGCTATGATGGATTATGC  9177
              ||||||||||||||||||||||||||||||||||||||||||||||||||||||||||||
AH2012  9163  AGAGGCTGATTACAGGCTTGCTTGTTTTGCCCATTTGGCCAAGGCTATGATGGATTATGC  6622

125_10  9178  TTCTAATCACAACGACACGTTATACACACCACCCACTGTGAGTTACAATTCAACTCTACA  6637
              ||||||||||||||||||||||||||||||||||||||||||||||||||||||||||||
AH2012  6623  TTCTAATCACAACGACACGTTATACACACCACCCACTGTGAGTTACAATTCAACTCTACA  6682
```

FIG. 1 (cont'd)

```
125_10  6638   GGCTGGCTTGCGTAAGATGGCACAACCATCTGGTGTTGTTGAGAAGTGCATAGTTCGTGT  6697
               ||||||||||||||||||||||||||||||||||||||||||||||||||||||||||||
AH2012  6683   GGCTGGCTTGCGTAAGATGGCACAACCATCTGGTGTTGTTGAGAAGTGCATAGTTCGTGT  9342

125_10  6698   TTGCTATGGTAATATGGCTCTTAATGGCCTATGGCTTGGTGATACTGTTATCTGCCCACG  9357
               ||||||||||||||||||||||||||||||||||||||||||||||||||||||||||||
AH2012  9343   TTGCTATGGTAATATGGCTCTTAATGGCCTATGGCTTGGTGATACTGTTATCTGCCCACG  9402

125_10  9358   CCATGTTATAGCGTCTAGTACTACTAGCACTATAGATTATGACTATGCCCTTTCTGTTTT  9417
               ||||||||||||||||||||||||||||||||||||||||||||||||||||||||||||
AH2012  9403   CCATGTTATAGCGTCTAGTACTACTAGCACTATAGATTATGACTATGCCCTTTCTGTTTT  9462

125_10  9418   ACGCCTCYACAACTTCTCCATTTCATCTGGTAATGTTTTCCTAGGTGTTGTGGGTGTAAC  9477
               ||||||| ||||||||||||||||||||||||||||||||||||||||||||||||||||
AH2012  9463   ACGCCTCCACAACTTCTCCATTTCATCTGGTAATGTTTTCCTAGGTGTTGTGGGTGTAAC  9522

125_10  9478   CATGCGAGGTGCTTTGTTGCAGATAAAGGTTAATCAAAACAATGTCCACACGCCTAAGTA  9537
               ||||||||||||||||||||||||||||||||||||||||||||||||||||||||||||
AH2012  9523   CATGCGAGGTGCTTTGTTGCAGATAAAGGTTAATCAAAACAATGTCCACACGCCTAAGTA  9582

125_10  9538   CACCTATCGCACAGTTAGACCGGGTGAATCTTTTAATATCTTGGCGTGCTATGATGGTTC  9597
               ||||||||||||||||||||||||||||||||||||||||||||||||||||||||||||
AH2012  9583   CACCTATCGCACAGTTAGACCGGGTGAATCTTTTAATATCTTGGCGTGCTATGATGGTTC  9642

125_10  9598   TGCAGCTGGTGTTTACGGCGTTAACATGCGCTCTAATTACACTATTAGAGGCTCGTTCAT  9657
               ||||||||||||||||||||||||||||||||||||||||||||||||||||||||||||
AH2012  9643   TGCAGCTGGTGTTTACGGCGTTAACATGCGCTCTAATTACACTATTAGAGGCTCGTTCAT  9702

125_10  9658   TAATGGCGCTTGTGGTTCACCTGGTTATAACATTAACAATGGTACCGTTGAGTTTTGCTA  9717
               ||||||||||||||||||||||||||||||||||||||||||||||||||||||||||||
AH2012  9703   TAATGGCGCTTGTGGTTCACCTGGTTATAACATTAACAATGGTACCGTTGAGTTTTGCTA  9762

125_10  9718   TTTACACCAGCTTGAACTTGGTTCAGGCTGTCATGTTGGTAGCGACTTAGATGGTGTTAT  9777
               ||||||||||||||||||||||||||||||||||||||||||||||||||||||||||||
AH2012  9763   TTTACACCAGCTTGAACTTGGTTCAGGCTGTCATGTTGGTAGCGACTTAGATGGTGTTAT  9822

125_10  9778   GTATGGTGGTTATGAGGACCAACCTACTTTGCAAGTTGAAGGCGCTAGTAGTCTGTTTAC  9837
               ||||||||||||||||||||||||||||||||||||||||||||||||||||||||||||
AH2012  9823   GTATGGTGGTTATGAGGACCAACCTACTTTGCAAGTTGAAGGCGCTAGTAGTCTGTTTAC  9882

125_10  9838   AGAGAATGTGTTGGCATTTCTTTATGCAGCACTCATTAATGGTTCTACCTGGTGGCTTAG  9897
               ||||||||||||||||||||||||||||||||||||||||||||||||||||||||||||
AH2012  9883   AGAGAATGTGTTGGCATTTCTTTATGCAGCACTCATTAATGGTTCTACCTGGTGGCTTAG  9942

125_10  9898   TTCTTCTAGGATTGCTGTAGACAGGTTTAATGAGTGGGCTGTTCATAATGGTATGACAAC  9957
               ||||||||||||||||||||||||||||||||||||||||||||||||||||||||||||
AH2012  9943   TTCTTCTAGGATTGCTGTAGACAGGTTTAATGAGTGGGCTGTTCATAATGGTATGACAAC  10002

125_10  9958   AGTAGTTAATACTGATTGCTTTTCTATTCTTGCTGCTAAGACTGGTGTTGATGTACAACG  10017
               ||||||||||||||||||||||||||||||||||||||||||||||||||||||||||||
AH2012  10003  AGTAGTTAATACTGATTGCTTTTCTATTCTTGCTGCTAAGACTGGTGTTGATGTACAACG  10062

125_10  10018  TTTGTTGGCCTCAATCCAGTCTCTGCATAAGAATTTTGGTGGAAAGCAAATTCTTGGCTA  10077
               ||||||||||||||||||||||||||||||||||||||||||||||||||||||||||||
AH2012  10063  TTTGTTGGCCTCAATCCAGTCTCTGCATAAGAATTTTGGTGGAAAGCAAATTCTTGGCTA  10122

125_10  10078  TACCTCGTTGACAGATGAGTTTACTACAGGTGAAGTTATACGTCAAATGTATGGCGTTWA  10137
               |||||||||||||||||||||||||||||||||||||||||||||||||||||||||| |
AH2012  10123  TACCTCGTTGACAGATGAGTTTACTACAGGTGAAGTTATACGTCAAATGTATGGCGTTAA  10182

125_10  10138  TCTTCAGAGTGGTTATGTTTCACGCGCCTGTAGAAATGTCTTGCTGGTTGGTTCTTTTCT  10197
               ||||||||||||||||||||||||||||||||||||||||||||||||||||||||||||
AH2012  10183  TCTTCAGAGTGGTTATGTTTCACGCGCCTGTAGAAATGTCTTGCTGGTTGGTTCTTTTCT  10242
```

FIG. 1 (cont'd)

```
125_10  10198  GACTTTCTTTTGGTCAGAATTAGTTTCCTACACTAAGTTCTTTTGGGTAAATCCTGGTTA  10257
               ||||||||||||||||||||||||||||||||||||||||||||||||||||||||||||
AH2012  10243  GACTTTCTTTTGGTCAGAATTAGTTTCCTACACTAAGTTCTTTTGGGTAAATCCTGGTTA  10302

125_10  10258  TGTCACACCTATGTTTGCGTGTTTGTCATTGCTGTCCTCACTTTTGATGTTCACACTCAA  10317
               ||||||||||||||||||||||||||||||||||||||||||||||||||||||||||||
AH2012  10303  TGTCACACCTATGTTTGCGTGTTTGTCATTGCTGTCCTCACTTTTGATGTTCACACTCAA  10362

125_10  10318  GCATAAGACATTGTTTTTCCAGGTCTTTCTAATACCTGCTCTGATTGTTACATCTTGCAT  10377
               ||||||||||||||||||||||||||||||||||||||||||||||||||||||||||||
AH2012  10363  GCATAAGACATTGTTTTTCCAGGTCTTTCTAATACCTGCTCTGATTGTTACATCTTGCAT  6622

125_10  10378  TAATTTGGCATTTGATGTTGAAGTCTACAACTATTTGGCAGAGCATTTTGATTACCATGT  6637
               ||||||||||||||||||||||||||||||||||||||||||||||||||||||||||||
AH2012  6623  TAATTTGGCATTTGATGTTGAAGTCTACAACTATTTGGCAGAGCATTTTGATTACCATGT  6682

125_10  6638  TTCTCTCATGGGTTTTAATGCACAAGGTCTTGTTAACATCTTTGTCTGCTTTGTTGTTAC  6697
               ||||||||||||||||||||||||||||||||||||||||||||||||||||||||||||
AH2012  6683  TTCTCTCATGGGTTTTAATGCACAAGGTCTTGTTAACATCTTTGTCTGCTTTGTTGTTAC  10542

125_10  6698  CATTTTACACGGCACATACACATGGCGCTTTTTTAACACACCTGTGAGTTCTGTCACTTA  10557
               ||||||||||||||||||||||||||||||||||||||||||||||||||||||||||||
AH2012  10543  CATTTTACACGGCACATACACATGGCGCTTTTTTAACACACCTGTGAGTTCTGTCACTTA  10602

125_10  10558  TGTGGTAGCTTTGCTGACTGCGGCATATAACTATTTTTACGCTAGTGACATTCTTAGTTG  10617
               ||||||||||||||||||||||||||||||||||||||||||||||||||||||||||||
AH2012  10603  TGTGGTAGCTTTGCTGACTGCGGCATATAACTATTTTTACGCTAGTGACATTCTTAGTTG  10662

125_10  10618  TGCTATGACACTATTTGCTAGTGTGACTGGCAACTGGTTCGTTGGTGCTGTTTGTTATAA  10677
               ||||||||||||||||||||||||||||||||||||||||||||||||||||||||||||
AH2012  10663  TGCTATGACACTATTTGCTAGTGTGACTGGCAACTGGTTCGTTGGTGCTGTTTGTTATAA  10722

125_10  10678  AGCTGCTGTTTATATGGCCTTGAGATTTCCTACTTTTGTGGCTATTTTTGGTGATATTAA  10737
               ||||||||||||||||||||||||||||||||||||||||||||||||||||||||||||
AH2012  10723  AGCTGCTGTTTATATGGCCTTGAGATTTCCTACTTTTGTGGCTATTTTTGGTGATATTAA  10782

125_10  10738  GAGTGTTATGTTCTGTTACCTTGTGTTGGGTTATTTTACCTGTTGCTTCTACGGTATTCT  10797
               ||||||||||||||||||||||||||||||||||||||||||||||||||||||||||||
AH2012  10783  GAGTGTTATGTTCTGTTACCTTGTGTTGGGTTATTTTACCTGTTGCTTCTACGGTATTCT  10842

125_10  10798  CTACTGGTTCAACAGGTTTTTTAAGGTTAGTGTAGGTGTCTATGACTATACTGTTAGTGC  10857
               ||||||||||||||||||||||||||||||||||||||||||||||||||||||||||||
AH2012  10843  CTACTGGTTCAACAGGTTTTTTAAGGTTAGTGTAGGTGTCTATGACTATACTGTTAGTGC  10902

125_10  10858  TGCTGAGTTTAAGTATATGGTTGCTAACGGCCTACGTGCACCAACTGGAACACTTGATTC  10917
               ||||||||||||||||||||||||||||||||||||||||||||||||||||||||||||
AH2012  10903  TGCTGAGTTTAAGTATATGGTTGCTAACGGCCTACGTGCACCAACTGGAACACTTGATTC  10962

125_10  10918  ACTACTTCTGTCTGCCAAATTGATTGGTATTGGTGGTGAGCGGAATATTAAGATTTCTTC  10977
               ||||||||||||||||||||||||||||||||||||||||||||||||||||||||||||
AH2012  10963  ACTACTTCTGTCTGCCAAATTGATTGGTATTGGTGGTGAGCGGAATATTAAGATTTCTTC  11022

125_10  10978  CGTTCAGTCTAAACTGACTGATATTAAGTGTAGTAACGTTGTGCTTTTAGGCTGTCTCTC  11037
               ||||||||||||||||||||||||||||||||||||||||||||||||||||||||||||
AH2012  11023  CGTTCAGTCTAAACTGACTGATATTAAGTGTAGTAACGTTGTGCTTTTAGGCTGTCTCTC  11082

125_10  11038  TAGCATGAATGTCTCAGCAAATTCAACAGAATGGGCCTATTGTGTTGACTTGCATAACAA  11097
               ||||||||||||||||||||||||||||||||||||||||||||||||||||||||||||
AH2012  11083  TAGCATGAATGTCTCAGCAAATTCAACAGAATGGGCCTATTGTGTTGACTTGCATAACAA  11142
```

FIG. 1 (cont'd)

```
125_10  11098  GATCAACTTGTGTAATGACCCAGAAAAAGCGCAGGAAATGCTACTTGCTTTGTTGGCATT  11157
               ||||||||||||||||||||||||||||||||||||||||||||||||||||||||||||
AH2012  11143  GATCAACTTGTGTAATGACCCAGAAAAAGCGCAGGAAATGCTACTTGCTTTGTTGGCATT  11202

125_10  11158  TTTCCTTAGTAAGAATAGTGCTTTTGGTTTAGATGACTTATTGGAATCCTATTTTAATGA  11217
               ||||||||||||||||||||||||||||||||||||||||||||||||||||||||||||
AH2012  11203  TTTCCTTAGTAAGAATAGTGCTTTTGGTTTAGATGACTTATTGGAATCCTATTTTAATGA  11262

125_10  11218  CAATAGTATGTTGCAGAGTGTTGCATCTACTTATGTCGGTTTGCCTTCTTATGTCATTTA  11277
               ||||||||||||||||||||||||||||||||||||||||||||||||||||||||||||
AH2012  11263  CAATAGTATGTTGCAGAGTGTTGCATCTACTTATGTCGGTTTGCCTTCTTATGTCATTTA  11322

125_10  11278  TGAAAATGCACGCCAACAGTATGAAGATGCTGTTAATAATGGTTCTCCACCTCAGTTGGT  11337
               ||||||||||||||||||||||||||||||||||||||||||||||||||||||||||||
AH2012  11323  TGAAAATGCACGCCAACAGTATGAAGATGCTGTTAATAATGGTTCTCCACCTCAGTTGGT  11382

125_10  11338  TAAGCAATTGCGCCATGCCATGAATGTAGCAAAGAGCGAATTTGACCGTGAGGCTTCTAC  11397
               ||||||||||||||||||||||||||||||||||||||||||||||||||||||||||||
AH2012  11383  TAAGCAATTGCGCCATGCCATGAATGTAGCAAAGAGCGAATTTGACCGTGAGGCTTCTAC  11442

125_10  11398  TCAGCGTAAGCTTGATAGAATGGCGGAACAGGCTGCAGCACAGATGTACAAAGAGGCACG  11457
               ||||||||||||||||||||||||||||||||||||||||||||||||||||||||| |
AH2012  11443  TCAGCGTAAGCTTGATAGAATGGCGGAACAGGCTGCAGCACAGATGTACAAAGAGGCAAG  11502

125_10  11458  AGCAGTTAATAGGAAGTCCAAAGTTGTAAGTGCTATGCATTCACTGCTTTTTGGTATGTT  11517
               ||||||||||||||||||||||||||||||||||||||||||||||||||||||||||||
AH2012  11503  AGCAGTTAATAGGAAGTCCAAAGTTGTAAGTGCTATGCATTCACTGCTTTTTGGTATGTT  11562

125_10  11518  GAGACGTTTGGACATGTCTTCTGTAGACACCATTCTCAACTTGGCAAAGGATGGGGTTGT  11577
               ||||||||||||||||||||||||||||||||||||||||||||||||||||||||||||
AH2012  11563  GAGACGTTTGGACATGTCTTCTGTAGACACCATTCTCAACTTGGCAAAGGATGGGGTTGT  11622

125_10  11578  ACCTCTGTCTGTCATACCGGCAGTCAGTGCTACTAAGCTTAACATTGTTACTTCTGATAT  11637
               ||||||||||||||||||||||||||||||||||||||||||||||||||||||||||||
AH2012  11623  ACCTCTGTCTGTCATACCGGCAGTCAGTGCTACTAAGCTTAACATTGTTACTTCTGATAT  11682

125_10  11638  CGATTCTTATAATCGTATCCAGCGTGAGGGATGTGTCCACTACGCTGGTACCATTTGGAA  11697
               ||||||||||||||||||||||||||||||||||||||||||||||||||||||||||||
AH2012  11683  CGATTCTTATAATCGTATCCAGCGTGAGGGATGTGTCCACTACGCTGGTACCATTTGGAA  11742

125_10  11698  TATAATTGATATCAAGGACAATGATGGCAAGGTGGTACACGTTAAGGAGGTAACCGCACA  11757
               ||||||||||||||||||||||||||||||||||||||||||||||||||||||||||||
AH2012  11743  TATAATTGATATCAAGGACAATGATGGCAAGGTGGTACACGTTAAGGAGGTAACCGCACA  11802

125_10  11758  GAATGCTGAGTCCCTGTCATGGCCCCTGGTCCTTGGGTGTGAGCGTATTGTCAAGCTCCA  11817
               ||||||||||||||||||||||||||||||||||||||||||||||||||||||||||||
AH2012  11803  GAATGCTGAGTCCCTGTCATGGCCCCTGGTCCTTGGGTGTGAGCGTATTGTCAAGCTCCA  11862

125_10  11818  GAATAATGAAATTATTCCTGGTAAGCTGAAGCAGCGCTCCATTAAGGCAGAAGGAGATGG  11877
               ||||||||||||||||||||||||||||||||||||||||||||||||||||||||||||
AH2012  11863  GAATAATGAAATTATTCCTGGTAAGCTGAAGCAGCGCTCCATTAAGGCAGAAGGAGATGG  11662

125_10  11878  CATAGTTGGAGAAGGTAAGGCACTTTACAATAATGAGGGTGGACGTACTTTTATGTATGC  11937
               ||||||||||||||||||||||||||||||||||||||||||||||||||||||||||||
AH2012  11663  CATAGTTGGAGAAGGTAAGGCACTTTACAATAATGAGGGTGGACGTACTTTTATGTATGC  11982

125_10  11938  TTTCATCTCGGACAAACCGGACCTGCGTGTAGTCAAGTGGGAGTTCGATGGTGGTTGTAA  11997
               ||||||||||||||||||||||||||||||||||||||||||||||||||||||||||||
AH2012  11983  TTTCATCTCGGACAAACCGGACCTGCGTGTAGTCAAGTGGGAGTTCGATGGTGGTTGTAA  12042

125_10  11998  CACTATTGAGCTAGAACCACCACGTAAGTTCTTGGTGGATTCTCCTAATGGTGCACAGAT  12057
               ||||||||||||||||||||||||||||||||||||||||||||||||||||||||||||
AH2012  12043  CACTATTGAGCTAGAACCACCACGTAAGTTCTTGGTGGATTCTCCTAATGGTGCACAGAT  12102
```

FIG. 1 (cont'd)

```
125_10  12058  CAAGTATCTCTACTTTGTTCGTAACCTTAACACGTTACGTAGGGGTGCTGTTCTCGGCTA  12117
               ||||||||||||||||||||||||||||||||||||||||||||||||||||||||||||
AH2012  12103  CAAGTATCTCTACTTTGTTCGTAACCTTAACACGTTACGTAGGGGTGCTGTTCTCGGCTA  12162

125_10  12118  CATAGGTGCCACTGTACGCTTGCAGGCTGGTAAACAAACAGAACAGGCTATTAACTCTTC  12177
               ||||||||||||||||||||||||||||||||||||||||||||||||||||||||||||
AH2012  12163  CATAGGTGCCACTGTACGCTTGCAGGCTGGTAAACAAACAGAACAGGCTATTAACTCTTC  12222

125_10  12178  ATTGTTGACACTTTGCGCTTTCGCTGTGGATCCTGCTAAGACCTACATCGATGCTGTCAA  12237
               ||||||||||||||||||||||||||||||||||||||||||||||||||||||||||||
AH2012  12223  ATTGTTGACACTTTGCGCTTTCGCTGTGGATCCTGCTAAGACCTACATCGATGCTGTCAA  12282

125_10  12238  AAGTGGTCACAAACCAGTAGGTAACTGTGTTAAGATGTTGGCCAATGGTTCTGGTAATGG  12297
               ||||||||||||||||||||||||||||||||||||||||||||||||||||||||||||
AH2012  12283  AAGTGGTCACAAACCAGTAGGTAACTGTGTTAAGATGTTGGCCAATGGTTCTGGTAATGG  12342

125_10  12298  ACAAGCTGTTACTAATGGTGTGGAGGCTAGTACTAACCAGGATTCATACGGTGGTGCGTC  12357
               ||||||||||||||||||||||||||||||||||||||||||||||||||||||||||||
AH2012  12343  ACAAGCTGTTACTAATGGTGTGGAGGCTAGTACTAACCAGGATTCATACGGTGGTGCGTC  12402

125_10  12358  CGTGTGTCTATATTGTAGAGCACATGTTGAGCATCCATCTATGGATGGTTTTTGCAGACT  12417
               ||||||||||||||||||||||||||||||||||||||||||||||||||||||||||||
AH2012  12403  CGTGTGTCTATATTGTAGAGCACATGTTGAGCATCCATCTATGGATGGTTTTTGCAGACT  12462

125_10  12418  GAAAGGCAAGTACGTACAGGTTCCACTAGGTACAGTGGATCCTATACGTTTTGTACTTGA  12477
               ||||||||||||||||||||||||||||||||||||||||||||||||||||||||||||
AH2012  12463  GAAAGGCAAGTACGTACAGGTTCCACTAGGTACAGTGGATCCTATACGTTTTGTACTTGA  12522

125_10  12478  GAATGACGTTTGCAAGGTTTGTGGTTGTTGGCTGGCTAATGGCTGCACTTGTGACAGATC  12537
               ||||||||||||||||||||||||||||||||||||||||||||||||||||||||||||
AH2012  12523  GAATGACGTTTGCAAGGTTTGTGGTTGTTGGCTGGCTAATGGCTGCACTTGTGACAGATC  12582

125_10  12538  CATTATGCAAAGCACTGATATGGCTTATTTAAACGAGTACGGGGCTCTAGTGCAGCTCGA  12597
               ||||||||||||||||||||||||||||||||||||||||||||||||||||||||||||
AH2012  12583  CATTATGCAAAGCACTGATATGGCTTATTTAAACGAGTACGGGGCTCTAGTGCAGCTCGA  12642

125_10  12598  CTAGAGCCCTGTAACGGTACTGATACACAACATGTGTATCGTGCTTTTGACATCTACAAC  12657
               ||||||||||||||||||||||||||||||||||||||||||||||||||||||||||||
AH2012  12643  CTAGAGCCCTGTAACGGTACTGATACACAACATGTGTATCGTGCTTTTGACATCTACAAC  12702

125_10  12658  AAGGATGTTGCTTGTCTAGGTAAATTCCTCAAGGTGAACTGTGTTCGCCTGAAGAATTTG  12717
               ||||||||||||||||||||||||||||||||||||||||||||||||||||||||||||
AH2012  12703  AAGGATGTTGCTTGTCTAGGTAAATTCCTCAAGGTGAACTGTGTTCGCCTGAAGAATTTG  12762

125_10  12718  GATAAGCATGATGCATTCTATGTTGTCAAAAGATGTACCAAGTCTGCGATGGAACACGAG  12777
               ||||||||||||||||||||||||||||||||||||||||||||||||||||||||||||
AH2012  12763  GATAAGCATGATGCATTCTATGTTGTCAAAAGATGTACCAAGTCTGCGATGGAACACGAG  12822

125_10  12778  CAATCCATCTATAGCAGACTTGAAAAGTGTGGAGCCGTAGCCGAACACGATTTCTTCACT  12837
               ||||||||||||||||||||||||||||||||||||||||||||||||||||||||||||
AH2012  12823  CAATCCATCTATAGCAGACTTGAAAAGTGTGGAGCCGTAGCCGAACACGATTTCTTCACT  12882

125_10  12838  TGGAAGGATGGTCGTGCCATCTATGGTAACGTTTGTAGAAAGGATCTTACCGAGTATACT  12897
               ||||||||||||||||||||||||||||||||||||||||||||||||||||||||||||
AH2012  12883  TGGAAGGATGGTCGTGCCATCTATGGTAACGTTTGTAGAAAGGATCTTACCGAGTATACT  12942

125_10  12898  ATGATGGATTTGTGTTACGCTTTACGTAACTTTGATGAAAACAATTGCGATGTTCTTAAG  12957
               ||||||||||||||||||||||||||||||||||||||||||||||||||||||||||||
AH2012  12943  ATGATGGATTTGTGTTACGCTTTACGTAACTTTGATGAAAACAATTGCGATGTTCTTAAG  13002
```

FIG. 1 (cont'd)

```
125_10  12958  AGCATTTTAATTAAGGTAGGCGCTTGTGAGGAGTCCTACTTCAATAATAAAGTCTGGTTT  13017
               ||||||||||||||||||||||||||||||||||||||||||||||||||||||||||||
AH2012  13003  AGCATTTTAATTAAGGTAGGCGCTTGTGAGGAGTCCTACTTCAATAATAAAGTCTGGTTT  13062

125_10  13018  GACCCTGTTGAAAATGAAGACATTCATCGTGTCTATGCATTGTTAGGTACCATTGTTTCA  13077
               ||||||||||||||||||||||||||||||||||||||||||||||||||||||||||||
AH2012  13063  GACCCTGTTGAAAATGAAGACATTCATCGTGTCTATGCATTGTTAGGTACCATTGTTTCA  13122

125_10  13078  CGTGCTATGCTTAAATGCGTTAAGTTCTGTGATGCAATGGTTGAACAAGGTATAGTTGGT  13137
               ||||||||||||||||||||||||||||||||||||||||||||||||||||||||||||
AH2012  13123  CGTGCTATGCTTAAATGCGTTAAGTTCTGTGATGCAATGGTTGAACAAGGTATAGTTGGT  13182

125_10  13138  GTTGTCACATTAGATAATCAGGATCTTAATGGTGATTTTTATGATTTTGGTGATTTTACT  13197
               |||||||| |||||||||||||||||||||||||||||||||||||||||||||||||||
AH2012  13183  GTTGTCACTTTAGATAATCAGGATCTTAATGGTGATTTTTATGATTTTGGTGATTTTACT  13242

125_10  13198  TGTAGCATCAAGGGAATGGGTATACCCATTTGCACATCATATTACTCTTATATGATGCCT  13257
               ||||||||||||||||||||||||||||||||||||||||||||||||||||||||||||
AH2012  13243  TGTAGCATCAAGGGAATGGGTATACCCATTTGCACATCATATTACTCTTATATGATGCCT  13302

125_10  13258  GTTATGGGTATGACTAATTGCCTTGCTAGTGAGTGTTTTGTTAAGAGTGATATATTTGGT  13317
               ||||||||||||||||||||||||||||||||||||||||||||||||||||||||||||
AH2012  13303  GTTATGGGTATGACTAATTGCCTTGCTAGTGAGTGTTTTGTTAAGAGTGATATATTTGGT  13362

125_10  13318  GAGGATTTCAAGTCATATGACCTGCTGGAATATGATTTCACGGAGCATAAGACAGCACTC  13377
               ||||||||||||||||||||||||||||||||||||||||||||||||||||||||||||
AH2012  13363  GAGGATTTCAAGTCATATGACCTGCTGGAATATGATTTCACGGAGCATAAGACAGCACTC  13422

125_10  13378  TTCAACAAGTATTTCAAGTATTGGGGACTGCAATACCACCCTAACTGTGTGGACTGCAGT  13437
               ||||||||||||||||||||||||||||||||||||||||||||||||||||||||||||
AH2012  13423  TTCAACAAGTATTTCAAGTATTGGGGACTGCAATACCACCCTAACTGTGTGGACTGCAGT  13482

125_10  13438  GATGAGCAGTGCATAGTTCACTGTGCCAACTTCAATACGTTGTTTTCCACTACTATACCT  13497
               ||||||||||||||||||||||||||||||||||||||||||||||||||||||||||||
AH2012  13483  GATGAGCAGTGCATAGTTCACTGTGCCAACTTCAATACGTTGTTTTCCACTACTATACCT  13542

125_10  13498  ATTACGGCATTTGGACCTTTGTGTCGCAAGTGTTGGATTGATGGTGTTCCACTGGTAACT  13557
               ||||||||||||||||||||||||||||||||||||||||||||||||||||||||||||
AH2012  13543  ATTACGGCATTTGGACCTTTGTGTCGCAAGTGTTGGATTGATGGTGTTCCACTGGTAACT  13602

125_10  13558  ACAGCTGGTTATCATTTTAAACAGTTAGGTATAGTTTGGAACAATGACCTCAACTTACAC  13617
               ||||||||||||||||||||||||||||||||||||||||||||||||||||||||||||
AH2012  13603  ACAGCTGGTTATCATTTTAAACAGTTAGGTATAGTTTGGAACAATGACCTCAACTTACAC  13662

125_10  13618  TCTAGCAGGCTCTCTATTAACGAATTACTCCAGTTTTGTAGTGATCCTGCATTGCTTATA  13677
               ||||||||||||||||||||||||||||||||||||||||||||||||||||||||||||
AH2012  13663  TCTAGCAGGCTCTCTATTAACGAATTACTCCAGTTTTGTAGTGATCCTGCATTGCTTATA  13722

125_10  13678  GCATCATCACCAGCCCTTGTTGATCAGCGTACTGTTTGCTTTTCAGTTGCAGCGCTAGGT  13737
               ||||||||||||||||||||||||||||||||||||||||||||||||||||||||||||
AH2012  13723  GCATCATCACCAGCCCTTGTTGATCAGCGTACTGTTTGCTTTTCAGTTGCAGCGCTAGGT  13782

125_10  13738  ACAGGTATGACTAACCAGACTGTTAAACCTGGCCATTTCAATAAGGAGTTTTATGACTTC  13797
               ||||||||||||||||||||||||||||||||||||||||||||||||||||||||||||
AH2012  13783  ACAGGTATGACTAACCAGACTGTTAAACCTGGCCATTTCAATAAGGAGTTTTATGACTTC  13842

125_10  13798  TTACTTGAGCAAGGTTTCTTTTCTGAGGGCTCTGAGCTTACTTTAAAGCACTTCTTCTTT  13857
               ||||||||||||||||||||||||||||||||||||||||||||||||||||||||||||
AH2012  13843  TTACTTGAGCAAGGTTTCTTTTCTGAGGGCTCTGAGCTTACTTTAAAGCACTTCTTCTTT  13902

125_10  13858  GCACAGAAGGGTGATGCAGCTGTTAAGGATTTTGACTACTATAGGTATAATAGACCTACT  13917
               ||||||||||||||||||||||||||||||||||||||||||||||||||||||||||||
AH2012  13903  GCACAGAAGGGTGATGCAGCTGTTAAGGATTTTGACTACTATAGGTATAATAGACCTACT  13962
```

FIG. 1 (cont'd)

```
125_10  13918  GTTCTGGACATTTGCCAAGCTCGCGTCGTGTATCAAATAGTGCAACGCTATTTTGATATT  13977
               ||||||||||||||||||||||||||||||||||||||||||||||||||||||||||||
AH2012  13963  GTTCTGGACATTTGCCAAGCTCGCGTCGTGTATCAAATAGTGCAACGCTATTTTGATATT  14022

125_10  13978  TACGAAGGTGGTTGTATCACTGCTAAAGAGGTGGTTGTTACAAACCTTAACAAGAGCGCA  14037
               ||||||||||||||||||||||||||||||||||||||||||||||||||||||||||||
AH2012  14023  TACGAAGGTGGTTGTATCACTGCTAAAGAGGTGGTTGTTACAAACCTTAACAAGAGCGCA  14082

125_10  14038  GGTTATCCTTTGAACAAGTTTGGTAAAGCTGGTCTTTACTATGAGTCTTTATCCTATGAG  14097
               ||||||||||||||||||||||||||||||||||||||||||||||||||||||||||||
AH2012  14083  GGTTATCCTTTGAACAAGTTTGGTAAAGCTGGTCTTTACTATGAGTCTTTATCCTATGAG  14142

125_10  14098  GAACAGGATGAACTTTATGCTTATACTAAGCGTAACATCCTGCCCACTATGACACAGCTC  14157
               ||||||||||||||||||||||||||||||||||||||||||||||||||||||||||||
AH2012  14143  GAACAGGATGAACTTTATGCTTATACTAAGCGTAACATCCTGCCCACTATGACACAGCTC  14202

125_10  14158  AACCTTAAATATGCTATAAGTGGCAAAGAACGTGCACGCACAGTGGGTGGTGTTTCGCTT  14217
               ||||||||||||||||||||||||||||||||||||||||||||||||||||||||||||
AH2012  14203  AACCTTAAATATGCTATAAGTGGCAAAGAACGTGCACGCACAGTGGGTGGTGTTTCGCTT  14262

125_10  14218  TTGTCAACCATGACTACTCGGCAGTATCATCAGAAACACCTTAAGTCCATAGTTAATACT  14277
               ||||||||||||||||||||||||||||||||||||||||||||||||||||||||||||
AH2012  14263  TTGTCAACCATGACTACTCGGCAGTATCATCAGAAACACCTTAAGTCCATAGTTAATACT  14322

125_10  14278  AGGGGCGCTTCGGTTGTTATTGGTACTACTAAGTTTTATGGTGGTTGGGACAATATGCTT  14337
               ||||||||||||||||||||||||||||||||||||||||||||||||||||||||||||
AH2012  14323  AGGGGCGCTTCGGTTGTTATTGGTACTACTAAGTTTTATGGTGGTTGGGACAATATGCTT  14382

125_10  14338  AAGAACCTTATTGATGGTGTTGAAAATCCGTGTCTTATGGGTTGGGACTACCCAAAGTGC  14397
               ||||||||||||||||||||||||||||||||||||||||||||||||||||||||||||
AH2012  14383  AAGAACCTTATTGATGGTGTTGAAAATCCGTGTCTTATGGGTTGGGACTACCCAAAGTGC  14442

125_10  14398  GACAGAGCACTGCCCAATRTGATACGTATGATTTCAGCCATGATTTTAGGCTCTAAGCAC  14457
               |||||||||||||||||| |||||||||||||||||||||||||||||||||||||||||
AH2012  14443  GACAGAGCACTGCCCAATATGATACGTATGATTTCAGCCATGATTTTAGGCTCTAAGCAC  14502

125_10  14458  ACCACATGCTGCAGTTCCACTGACCGCTTTTTCAGGTTGTGCAATGAATTGGCTCAAGTC  14517
               ||||||||||||||||||||||||||||||||||||||||||||||||||||||||||||
AH2012  14503  ACCACATGCTGCAGTTCCACTGACCGCTTTTTCAGGTTGTGCAATGAATTGGCTCAAGTC  14562

125_10  14518  CTTACTGAGGTTGTTTATTCTAATGGAGGTTTTTATTTGAAGCCAGGTGGTACTACCTCT  14577
               ||||||||||||||||||||||||||||||||||||||||||||||||||||||||||||
AH2012  14563  CTTACTGAGGTTGTTTATTCTAATGGAGGTTTTTATTTGAAGCCAGGTGGTACTACCTCT  14622

125_10  14578  GGTGATGCAACCACCGCATATGCAAACTCAGTTTTTAATATCTTCCAAGCAGTAAGTGCC  14637
               ||||||||||||||||||||||||||||||||||||||||||||||||||||||||||||
AH2012  14623  GGTGATGCAACCACCGCATATGCAAACTCAGTTTTTAATATCTTCCAAGCAGTAAGTGCC  14682

125_10  14638  AATGTTAACAAACTTCTTAGTGTTGACAGCAATGTCTGTCATAATTTAGAAGTTAAGCAA  14697
               ||||||||||||||||||||||||||||||||||||||||||||||||||||||||||||
AH2012  14683  AATGTTAACAAACTTCTTAGTGTTGACAGCAATGTCTGTCATAATTTAGAAGTTAAGCAA  14742

125_10  14698  TTGCAGCGTAAGCTTTATGAGTGCTGTTATAGATCAACTACCGTCGATGACCAGTTCGTC  14757
               ||||||||||||||||||||||||||||||||||||||||||||||||||||||||||||
AH2012  14743  TTGCAGCGTAAGCTTTATGAGTGCTGTTATAGATCAACTACCGTCGATGACCAGTTCGTC  14802

125_10  14758  GTTGAGTATTATGGTTACTTGCGTAAACATTTTTCAATGATGATTCTTTCTGATGATGGC  14817
               ||||||||||||||||||||||||||||||||||||||||||||||||||||||||||||
AH2012  14803  GTTGAGTATTATGGTTACTTGCGTAAACATTTTTCAATGATGATTCTTTCTGATGATGGC  14862
```

FIG. 1 (cont'd)

```
125_10  14818  GTTGTTTGTTATAACAATGACTATGCATCACTTGGTTATGTCGCTGATCTTAACGCATTC  14877
               ||||||||||||||||||||||||||||||||||||||||||||||||||||||||||||
AH2012  14863  GTTGTTTGTTATAACAATGACTATGCATCACTTGGTTATGTCGCTGATCTTAACGCATTC  14662

125_10  14878  AAGGCTGTTTTGTATTACCAGAACAATGTCTTCATGAGCGCCTCTAAATGTTGGATCGAG  14937
               ||||||||||||||||||||||||||||||||||||||||||||||||||||||||||||
AH2012  14663  AAGGCTGTTTTGTATTACCAGAACAATGTCTTCATGAGCGCCTCTAAATGTTGGATCGAG  14982

125_10  14938  CCTGACATTAATAAAGGTCCTCATGAATTTTGCTCGCAGCATACTATGCAGATTGTCGAT  14997
               ||||||||||||||||||||||||||||||||||||||||||||||| ||||||||||||
AH2012  14983  CCTGACATTAATAAAGGTCCTCATGAATTTTGCTCGCAGCATACTATACAGATTGTCGAT  15042

125_10  14998  AAAGATGGTACTTATTACCTTCCTTACCCTGATCCTTCAAGAATTCTCTCTGCAGGTGTG  15057
               |||||||||||||||||||||||||||||||||||||||||||| |||||||||||||||
AH2012  15043  AAAGATGGTACTTATTACCTTCCTTACCCTGATCCTTCAAGAATCCTCTCTGCAGGTGTG  15102

125_10  15058  TTTGTTGATGACGTTGTTAAAACTGATGCAGTTGTATTGCTTGAACGTTATGTGTCATTG  15117
               |||||||||||||||||||||||||||||| |||||||||||||||||||||||||||||
AH2012  15103  TTTGTTGATGACGTTGTTAAAACTGATGCACTTGTATTGCTTGAACGTTATGTGTCATTG  15162

125_10  15118  GCTATAGATGCCTACCCGTTATCTAAGCATGAAAACCCTGAATATAAGAAGGTGTTTTAT  15177
               ||||||||||||||||||||||||||||||||||||||||||||||||||||||||||||
AH2012  15163  GCTATAGATGCCTACCCGTTATCTAAGCATGAAAACCCTGAATATAAGAAGGTGTTTTAT  15222

125_10  15178  GTGCTTTTGGATTGGGTTAAGCATCTGTACAAAACTCTTAATGCTGGTGTGTTAGAGTCT  15237
               ||||||||||||||||||||||||||||||||||||||||||||||||||||||||||||
AH2012  15223  GTGCTTTTGGATTGGGTTAAGCATCTGTACAAAACTCTTAATGCTGGTGTGTTAGAGTCT  15282

125_10  15238  TTTTCTGTCACACTTTTGGAAGATTCTACTGCTAAATTCTGGGATGAGAGCTTTTATGCC  15297
               ||||||||||||||||||||||||||||||||||||||||||||||||||||||||||||
AH2012  15283  TTTTCTGTCACACTTTTGGAAGATTCTACTGCTAAATTCTGGGATGAGAGCTTTTATGCC  15342

125_10  15298  AACATGTATGAGAAATCTGCAGTTTTACAATCTGCAGGGCTTTGTGTTGTTTGTGGCTCT  15357
               ||||||||||||||||||||||||||||||||||||||||||||||||||||||||||||
AH2012  15343  AACATGTATGAGAAATCTGCAGTTTTACAATCTGCAGGGCTTTGTGTTGTTTGTGGCTCT  15402

125_10  15358  CAAACTGTTTTACGTTGTGGTGATTGTCTACGGCGTCCTATGCTTTGTACTAAGTGTGCT  15417
               ||||||||||||||||||||||||||||||||||||||||||||||||||||||||||||
AH2012  15403  CAAACTGTTTTACGTTGTGGTGATTGTCTACGGCGTCCTATGCTTTGTACTAAGTGTGCT  15462

125_10  15418  TATGATCATGTCATTGGAACAACTCACAAGTTCATTTTGGCCATCACTCCATATGTGTGT  15477
               ||||||||||||||||||||||||||||||||||||||||||||||||||||||||||||
AH2012  15463  TATGATCATGTCATTGGAACAACTCACAAGTTCATTTTGGCCATCACTCCATATGTGTGT  15522

125_10  15478  TGTGCTTCAGATTGTGGTGTCAATGATGTAACTAAGCTCTACTTAGGTGGTCTTAGTTAT  15537
               ||||||||||||||||||||||||||||||||||||||||||||||||||||||||||||
AH2012  15523  TGTGCTTCAGATTGTGGTGTCAATGATGTAACTAAGCTCTACTTAGGTGGTCTTAGTTAT  15582

125_10  15538  TGGTGTCATGACCACAAGCCACGTCTTGCATTCCCGTTGTGCTCTGCTGGTAATGTTTTT  15597
               ||||||||||||||||||||||||||||||||||||||||||||||||||||||||||||
AH2012  15583  TGGTGTCATGACCACAAGCCACGTCTTGCATTCCCGTTGTGCTCTGCTGGTAATGTTTTT  15642

125_10  15598  GGCTTGTACAAAAATTCTGCTACCGGCTCACCCGATGTTGAAGACTTTAATCGCATTGCT  15657
               ||||||||||||||||||||||||||||||||||||||||||||||||||||||||||||
AH2012  15643  GGCTTGTACAAAAATTCTGCTACCGGCTCACCCGATGTTGAAGACTTTAATCGCATTGCT  15702

125_10  15658  ACATCCGATTGGACTGATGTTTCTGACTACAGGTTGGCAAATGATGTCAAGGACTCATTG  15717
               ||||||||||||||||||||||||||||||||||||||||||||||||||||||||||||
AH2012  15703  ACATCCGATTGGACTGATGTTTCTGACTACAGGTTGGCAAATGATGTCAAGGACTCATTG  15762

125_10  15718  CGTCTGTTTGCAGCGGAAACTATCAAGGCCAAGGAGGAGAGCGTTAAGTCATCCTATGCT  15777
               ||||||||||||||||||||||||||||||||||||||||||||||||||||||||||||
AH2012  15763  CGTCTGTTTGCAGCGGAAACTATCAAGGCCAAGGAGGAGAGCGTTAAGTCATCCTATGCT  15822
```

FIG. 1 (cont'd)

```
125_10  15778  TGTGCAACACTACATGAGGTTGTAGGACCTAAAGAGTTGTTGCTCAAATGGGAAGTCGGC  15837
               ||||||||||||||||| ||||||||||||||||||||||||||||||||||||||||||
AH2012  15823  TGTGCAACACTACATGATGTTGTAGGACCTAAAGAGTTGTTGCTCAAATGGGAAGTCGGC  15882

125_10  15838  AGACCCAAACCACCCCTTAATAGAAATTCGGTTTTCACTTGTTATCATATAACGAAGAAC  15897
               ||||||||||||||||||||||||||||||||||||||||||||||||||||||||||||
AH2012  15883  AGACCCAAACCACCCCTTAATAGAAATTCGGTTTTCACTTGTTATCATATAACGAAGAAC  15942

125_10  15898  ACCAAATTTCAAATCGGTGAGTTTGTGTTTGAGAAGGCAGAATATGATAATGATGCTGTA  15957
               ||||||||||||||||||||||||||||||||||||||||||||||||||||||||||||
AH2012  15943  ACCAAATTTCAAATCGGTGAGTTTGTGTTTGAGAAGGCAGAATATGATAATGATGCTGTA  16002

125_10  15958  ACATATAAAACTACCGCCACAACAAAACTTGTTCCTGGCATGGTTTTTGTGCTTACCTCA  16017
               ||||||||||||||||||||||||||||||||||||||||||||||||||||||||||||
AH2012  16003  ACATATAAAACTACCGCCACAACAAAACTTGTTCCTGGCATGGTTTTTGTGCTTACCTCA  16062

125_10  16018  CATAATGTTCAGCCATTGCGCGCACCGACCATTGCTAATCAAGAACGTTATTCCACTATA  16077
               ||||||||||||||||||||||||||||||||||||||||||||||||||||||||||||
AH2012  16063  CATAATGTTCAGCCATTGCGCGCACCGACCATTGCTAATCAAGAACGTTATTCCACTATA  16122

125_10  16078  CATAAGTTGCATCCTGCTTTTAACATACCTGAAGCTTATTCTAGCTTAGTGCCCTATTAC  16137
               ||||||||||||||||||||||||||||||||||||||||||||||||||||||||||||
AH2012  16123  CATAAGTTGCATCCTGCTTTTAACATACCTGAAGCTTATTCTAGCTTAGTGCCCTATTAC  16182

125_10  16138  CAATTGATTGGTAAGCAGAAGATTACAACTATTCAGGGACCTCCCGGTAGTGGTAAATCT  16197
               ||||||||||||||||||||||||||||||||||||||||||||||||||||||||||||
AH2012  16183  CAATTGATTGGTAAGCAGAAGATTACAACTATTCAGGGACCTCCCGGTAGTGGTAAATCT  16242

125_10  16198  CACTGTGTTATAGGGCTAGGTTTGTACTATCCAGGTGCACGTATAGTGTTTACAGCTTGT  16257
               ||||||||||||||||||||||||||||||||||||||||||||||||||||||||||||
AH2012  16243  CACTGTGTTATAGGGCTAGGTTTGTACTATCCAGGTGCACGTATAGTGTTTACAGCTTGT  16302

125_10  16258  TCTCATGCAGCGGTCGATTCACTTTGTGTGAAAGCTTCCACTGCTTATAGCAATGACAAA  16317
               ||||||||||||||||||||||||||||||||||| ||||||||||||||||||||||||
AH2012  16303  TCTCATGCAGCGGTCGATTCACTTTGTGTGAAAGCCTCCACTGCTTATAGCAATGACAAA  16362

125_10  16318  TGTTCACGCATCATACCACAGCGCGCTCGTGTTGAGTGTTATGATGGTTTCAAGTCTAAT  16377
               ||||||||||||||||||||||||||||||||||||||||||||||||||||||||||||
AH2012  16363  TGTTCACGCATCATACCACAGCGCGCTCGTGTTGAGTGTTATGATGGTTTCAAGTCTAAT  16422

125_10  16378  AATACTAGTGCTCAGTACCTTTTCTCTACTGTCAATGCTTTGCCAGAGTGCAATGCGGAC  16437
               ||||||||||||||||||||||||||||||||||||||||||||||||||||||||||||
AH2012  16423  AATACTAGTGCTCAGTACCTTTTCTCTACTGTCAATGCTTTGCCAGAGTGCAATGCGGAC  16482

125_10  16438  ATTGTTGTGGTGGATGAGGTCTCTATGTGCACTAATTATGACTTGTCTGTCATAAATCAG  16497
               ||||||||||||||||||||||||||||||||||||||||||||||||||||||||||||
AH2012  16483  ATTGTTGTGGTGGATGAGGTCTCTATGTGCACTAATTATGACTTGTCTGTCATAAATCAG  16542

125_10  16498  CGCATCAGCTATAGGCATGTAGTCTATGTTGGTGACCCTCAACAGCTGCCTGCACCACGT  16557
               ||||||||||||||||||||||||||||||||||||||||||||||||||||||||||||
AH2012  16543  CGCATCAGCTATAGGCATGTAGTCTATGTTGGTGACCCTCAACAGCTGCCTGCACCACGT  16602

125_10  16558  GTTATGATTTCACGTGGTACTTTGGAACCAAAGGACTACAACGTTGTCACTCAACGCATG  16617
               ||||||||||||||||||||||||||||||||||||||||||||||||||||||||||||
AH2012  16603  GTTATGATTTCACGTGGTACTTTGGAACCAAAGGACTACAACGTTGTCACTCAACGCATG  16662

125_10  16618  TGTGCCCTTAAGCCTGATGTTTTCTTGCACAAGTGTTATCGCTGTCCTGCTGAGATAGTG  16677
               ||||||||||||||||||||||||||||||||||||||||||||||||||||||||||||
AH2012  16663  TGTGCCCTTAAGCCTGATGTTTTCTTGCACAAGTGTTATCGCTGTCCTGCTGAGATAGTG  16722
```

FIG. 1 (cont'd)

```
125_10  16678  CGTACTGTGTCTGAGATGGTCTATGAAAACCAATTCATTCCTGTGCACCCAGATAGCAAG  16737
               ||||||||||||||||||||||||||||||||||||||||||||||||||||||||||||
AH2012  16723  CGTACTGTGTCTGAGATGGTCTATGAAAACCAATTCATTCCTGTGCACCCAGATAGCAAG  16782

125_10  16738  CAGTGTTTTAAAATCTTTTGCAAGGGTAATGTTCAGGTTGATAATGGTTCAAGCATTAAT  16797
               ||||||||||||||||||||||||||||||||||||||||||||||||||||||||||||
AH2012  16783  CAGTGTTTTAAAATCTTTTGCAAGGGTAATGTTCAGGTTGATAATGGTTCAAGCATTAAT  16842

125_10  16798  CGCAGGCAATTGGATGTTGTGCGTATGTTTTTGGCTAAAAATCCTAGGTGGTCAAAGGCT  16857
               ||||||||||||||||||||||||||||||||||||||||||||||||||||||||||||
AH2012  16843  CGCAGGCAATTGGATGTTGTGCGTATGTTTTTGGCTAAAAATCCTAGGTGGTCAAAGGCT  16902

125_10  16858  GTTTTTATTTCTCCTTATAACAGCCAGAATTATGTTGCCAGCCGCATGCTAGGTCTACAA  16917
               ||||||||||||||||||||||||||||||||||||||||||||||||||||||||||||
AH2012  16903  GTTTTTATTTCTCCTTATAACAGCCAGAATTATGTTGCCAGCCGCATGCTAGGTCTACAA  16962

125_10  16918  ATTCAGACAGTTGACTCATCCCAGGGTAGTGAGTATGACTATGTCATTTACACACAAACT  16977
               ||||||||||||||||||||||||||||||||||||||||||||||||||||||||||||
AH2012  16963  ATTCAGACAGTTGACTCATCCCAGGGTAGTGAGTATGACTATGTCATTTACACACAAACT  17022

125_10  16978  TCAGATACTGCCCATGCCTGTAATGTTAACAGGTTTAATGTTGCCATCACAAGGGCCAAG  17037
               ||||||||||||||||||||||||||||||||||||||||||||||||||||||||||||
AH2012  17023  TCAGATACTGCCCATGCCTGTAATGTTAACAGGTTTAATGTTGCCATCACAAGGGCCAAG  17082

125_10  17038  AAAGGCATATTATGTATAATGTGCGATAGGTCCCTTTTTGATGTGCTTAAATTCTTTGAG  17097
               ||||||||||||||||||||||||||||||||||||||||||||||||||||||||||||
AH2012  17083  AAAGGCATATTATGTATAATGTGCGATAGGTCCCTTTTTGATGTGCTTAAATTCTTTGAG  17142

125_10  17098  CTTAAATTGTCTGATTTGCAGGCTAATGAGGGTTGTGGTCTTTTTAAAGACTGTAGCAGA  17157
               ||||||||||||||||||||||||||||||||||||||||||||||||||||||||||||
AH2012  17143  CTTAAATTGTCTGATTTGCAGGCTAATGAGGGTTGTGGTCTTTTTAAAGACTGTAGCAGA  17202

125_10  17158  GGTGATGATCTGTTGCCACCATCTCACGCTAACACCTTCATGTCTTTAGCGGACAATTTT  17217
               ||||||||||||||||||||||||||||||||||||||||||||||||||||||||||||
AH2012  17203  GGTGATGATCTGTTGCCACCATCTCACGCTAACACCTTCATGTCTTTAGCGGACAATTTT  17262

125_10  17218  AAGACTGATCAAGATCTTGCTGTTCAAATAGGTGTTAATGGACCCATTAAATATGAGCAT  17277
               ||||||||||||||||||||||||||||||||||||||||||||||||||||||||||||
AH2012  17263  AAGACTGATCAAGATCTTGCTGTTCAAATAGGTGTTAATGGACCCATTAAATATGAGCAT  17322

125_10  17278  GTTATCTCGTTTATGGGTTTCCGTTTTGATATCAACATACCCAACCATCATACTCTCTTT  17337
               ||||||||||||||||||||||||||||||||||||||||||||||||||||||||||||
AH2012  17323  GTTATCTCGTTTATGGGTTTCCGTTTTGATATCAACATACCCAACCATCATACTCTCTTT  17382

125_10  17338  TGCACACGCGACTTTGCCATGCGCAATGTTAGAGGTTGGTTAGGCTTTGACGTTGAAGGA  17397
               ||||||||||||||||||||||||||||||||||||||||||||||||||||||||||||
AH2012  17383  TGCACACGCGACTTTGCCATGCGCAATGTTAGAGGTTGGTTAGGCTTTGACGTTGAAGGA  17442

125_10  17398  GCACATGTTGTTGGCTCTAACGTCGGTACAAATGTCCCATTGCAATTAGGGTTTTCTAAC  17457
               ||||||||||||||||||||||||||||||||||||||||||||||||||||||||||||
AH2012  17443  GCACATGTTGTTGGCTCTAACGTCGGTACAAATGTCCCATTGCAATTAGGGTTTTCTAAC  17502

125_10  17458  GGTGTTGATTTTGTTGTCAGACCTGAAGGTTGCGTTGTAACAGAGTCTGGTGACTACATT  17517
               ||||||||||||||||||||||||||||||||||||||||||||||||||||||||||||
AH2012  17503  GGTGTTGATTTTGTTGTCAGACCTGAAGGTTGCGTTGTAACAGAGTCTGGTGACTACATT  17562

125_10  17518  AAACCCGTCAGAGCTCGTGCTCCACCAGGGGAACAATTCGCACACCTTTTGCCTTTACTT  17577
               ||||||||||||||||||||||||||||||||||||||||||||||||||||||||||||
AH2012  17563  AAACCCGTCAGAGCTCGTGCTCCACCAGGGGAACAATTCGCACACCTTTTGCCTTTACTT  17622

125_10  17578  AAACGCGGCCAACCATGGGATGTTGTCCGCAAACGTATAGTGCAGATGTGTAGTGACTAC  17637
               ||||||||||||||||||||||||||||||||||||||||||||||||||||||||||||
AH2012  17623  AAACGCGGCCAACCATGGGATGTTGTCCGCAAACGTATAGTGCAGATGTGTAGTGACTAC  17682
```

FIG. 1 (cont'd)

```
125_10  17638  CTGGCCAACCTATCAGACATACTAATTTTTGTGTTGTGGGCTGGTGGTTTGGAGTTGACA  17697
               ||||||||||||||||||||||||||||||||||||||||||||||||||||||||||||
AH2012  17683  CTGGCCAACCTATCAGACATACTAATTTTTGTGTTGTGGGCTGGTGGTTTGGAGTTGACA  17742

125_10  17698  ACTATGCGTTATTTTGTCAAGATTGGACCAAGTAAGAGTTGTGATTGTGGTAAGGTTGCT  17757
               ||||||||||||||||||||||||||||||||||||||||||||||||||||||||||||
AH2012  17743  ACTATGCGTTATTTTGTCAAGATTGGACCAAGTAAGAGTTGTGATTGTGGTAAGGTTGCT  17802

125_10  17758  ACTTGTTACAATAGTGCGCTGCATACGTACTGTTGTTTCAAACATGCCCTTGGTTGTGAT  17817
               ||||||||||||||||||||||||||||||||||||||||||||||||||||||||||||
AH2012  17803  ACTTGTTACAATAGTGCGCTGCATACGTACTGTTGTTTCAAACATGCCCTTGGTTGTGAT  17862

125_10  17818  TATCTGTATAACCCATACTGTATTGATATACAGCAGTGGGGATACAAGGGATCACTTAGC  17877
               ||||||||||||||||||||||||||||||||||||||||||||||||||||||||||||
AH2012  17863  TATCTGTATAACCCATACTGTATTGATATACAGCAGTGGGGATACAAGGGATCACTTAGC  17662

125_10  17878  CTTAACCACCATGAGCATTGTAATGTACATAGAAACGAGCATGTGGCTTCTGGTGATGCC  17937
               ||||||||||||||||||||||||||||||||||||||||||||||||||||||||||||
AH2012  17663  CTTAACCACCATGAGCATTGTAATGTACATAGAAACGAGCATGTGGCTTCTGGTGATGCC  17982

125_10  17938  ATAATGACTCGCTGTCTGGCCATACATGATTGCTTTGTCAAGAACGTTGACTGGTCCATC  17997
               ||||||||||||||||||||||||||||||||||||||||||||||||||||||||||||
AH2012  17983  ATAATGACTCGCTGTCTGGCCATACATGATTGCTTTGTCAAGAACGTTGACTGGTCCATC  18042

125_10  17998  ACATACCCATTTATTGGTAATGAGGCTGTTATTAATAAGAGCGGCCGAATTGTGCAATCA  18057
               ||||||||||||||||||||||||||||||||||||||||||||||||||||||||||||
AH2012  18043  ACATACCCATTTATTGGTAATGAGGCTGTTATTAATAAGAGCGGCCGAATTGTGCAATCA  18102

125_10  18058  CACACTATGCGGTCAGTTCTTAAGTTATACAATCCGAAAGCCATATATGATATTGGCAAT  18117
               ||||||||||||||||||||||||||||||||||||||||||||||||||||||||||||
AH2012  18103  CACACTATGCGGTCAGTTCTTAAGTTATACAATCCGAAAGCCATATATGATATTGGCAAT  18162

125_10  18118  CCTAAGGGCATTAGATGTGCCGTAACGGATGCTAAGTGGTTTTGCTTTGACAAGAATCCT  18177
               ||||||||||||||||||||||||||||||||||||||||||||||||||||||||||||
AH2012  18163  CCTAAGGGCATTAGATGTGCCGTAACGGATGCTAAGTGGTTTTGCTTTGACAAGAATCCT  18222

125_10  18178  AYTAATTCTAATGTCAAGACATTGGAGTATGACTATATAACACATGGCCAATTTGATGGG  18237
               | ||||||||||||||||||||||||||||||||||||||||||||||||||||||||||
AH2012  18223  ACTAATTCTAATGTCAAGACATTGGAGTATGACTATATAACACATGGCCAATTTGATGGG  18282

125_10  18238  TTGTGCTTGTTTTGGAATTGCAATGTAGACATGTATCCAGAATTTTCTGTGGTCTGTCGT  18297
               ||||||||||||||||||||||||||||||||||||||||||||||||||||||||||||
AH2012  18283  TTGTGCTTGTTTTGGAATTGCAATGTAGACATGTATCCAGAATTTTCTGTGGTCTGTCGT  18342

125_10  18298  TTTGATACTCGCTGTAGGTCACCACTCAACTTGGAGGGTTGTAATGGTGGTTCACTGTAT  18357
               ||||||||||||||||||||||||||||||||||||||||||||||||||||||||||||
AH2012  18343  TTTGATACTCGCTGTAGGTCACCACTCAACTTGGAGGGTTGTAATGGTGGTTCACTGTAT  18402

125_10  18358  GTTAATAATCATGCATTCCATACACCGGCTTTTGACAAGCGTGCTTTTGCTAAGTTGAAG  18417
               ||||||||||||||||||||||||||||||||||||||||||||||||||||||||||||
AH2012  18403  GTTAATAATCATGCATTCCATACACCGGCTTTTGACAAGCGTGCTTTTGCTAAGTTGAAG  18462

125_10  18418  CCAATGCCATTTTTCTTTTATGATGATACTGAGTGTGACAAGTTACAGGACTCCATAAAC  18477
               ||||||||||||||||||||||||||||||||||||||||||||||||||||||||||||
AH2012  18463  CCAATGCCATTTTTCTTTTATGATGATACTGAGTGTGACAAGTTACAGGACTCCATAAAC  18522

125_10  18478  TATGTTCCTCTTAGGGCTAGTAACTGCATTACTAAATGTAATGTTGGTGGTGCTGTCTGT  18537
               ||||||||||||||||||||||||||||||||||||||||||||||||||||||||||||
AH2012  18523  TATGTTCCTCTTAGGGCTAGTAACTGCATTACTAAATGTAATGTTGGTGGTGCTGTCTGT  18582
```

FIG. 1 (cont'd)

```
125_10  18538  AGTAAGCATTGTGCTATGTATCATAGCTATGTTAATGCTTACAACACTTTTACGTCGGCG  18597
               ||||||||||||||||||||||||||||||||||||||||||||||||||||||||||||
AH2012  18583  AGTAAGCATTGTGCTATGTATCATAGCTATGTTAATGCTTACAACACTTTTACGTCGGCG  18642

125_10  18598  GGCTTTACTATTTGGGTGCCTACTTCGTTTGACACCTATAATCTGTGGCAGACATTTAGT  18657
               ||||||||||||||||||||||||||||||||||||||||||||||||||||||||||||
AH2012  18643  GGCTTTACTATTTGGGTGCCTACTTCGTTTGACACCTATAATCTGTGGCAGACATTTAGT  18702

125_10  18658  AACAATTTGCAAGGTCTTGAGAACATTGCTTTCAATGTCGTAAAGAAAGGATCTTTTGTT  18717
               ||||||||||||||||||||||||||||||||||||||||||||||||||||||||||||
AH2012  18703  AACAATTTGCAAGGTCTTGAGAACATTGCTTTCAATGTCGTAAAGAAAGGATCTTTTGTT  18762

125_10  18718  GGTGCCGAAGGTGAACTTCCTGTAGCTGTGGTTAATGACAAAGTGCTCGTTAGAGATGGT  18777
               ||||||||||||||||||||||||||||||||||||||||||||||||||||||||||||
AH2012  18763  GGTGCCGAAGGTGAACTTCCTGTAGCTGTGGTTAATGACAAAGTGCTCGTTAGAGATGGT  18822

125_10  18778  ACTGTTGATACTCTTGTTTTTACAAACAAGACATCACTACCCACTAACGTAGCTTTTGAG  18837
               ||||||||||||||||||||||||||||||||||||||||||||||||||||||||||||
AH2012  18823  ACTGTTGATACTCTTGTTTTTACAAACAAGACATCACTACCCACTAACGTAGCTTTTGAG  18882

125_10  18838  TTGTATGCCAAGCGTAAGGTAGGACTCACCCCACCCATTACGATCCTACGTAACTTGGGT  18897
               ||||||||||||||||||||||||||||||||||||||||||||||||||||||||||||
AH2012  18883  TTGTATGCCAAGCGTAAGGTAGGACTCACCCCACCCATTACGATCCTACGTAACTTGGGT  18942

125_10  18898  GTAGTTTGTACATCTAAGTGTGTCATTTGGGACTATGAAGCCGAACGTCCACTTACTACT  18957
               ||||||||||||||||||||||||||||||||||||||||||||||||||||||||||||
AH2012  18943  GTAGTTTGTACATCTAAGTGTGTCATTTGGGACTATGAAGCCGAACGTCCACTTACTACT  19002

125_10  18958  TTTACAAAGGATGTTTGTAAATATACCGACTTTGAGGGTGACGTCTGTACACTCTTTGAT  19017
               ||||||||||||||||||||||||||||||||||||||||||||||||||||||||||||
AH2012  19003  TTTACAAAGGATGTTTGTAAATATACCGACTTTGAGGGTGACGTCTGTACACTCTTTGAT  19062

125_10  19018  AACAGCATTGTTGGTTCATTAGAGCGATTCTCCATGACCCAAAATGCTGTGCTTATGTCA  19077
               ||||||||||||||||||||||||||||||||||||||||||||||||||||||||||||
AH2012  19063  AACAGCATTGTTGGTTCATTAGAGCGATTCTCCATGACCCAAAATGCTGTGCTTATGTCA  19122

125_10  19078  CTTACAGCTGTTAAAAAGCTTAYTGGCATAAAGTTAACTTATGGTTATCTTAATGGTGTC  19137
               |||||||||||||||||||||| |||||||||||||||||||||||||||||||||||||
AH2012  19123  CTTACAGCTGTTAAAAAGCTTACTGGCATAAAGTTAACTTATGGTTATCTTAATGGTGTC  19182

125_10  19138  CCAGTTAACACACATGAAGATAAACCTTTTACTTGGTATATTTACACTAGGAAGAACGGC  19197
               ||||||||||||||||||||||||||||||||||||||||||||||||||||||||||||
AH2012  19183  CCAGTTAACACACATGAAGATAAACCTTTTACTTGGTATATTTACACTAGGAAGAACGGC  16642

125_10  19198  AAGTTCGAGGACCATCCTGATGGCTATTTTACCCAAGGTAGAACAACCGCTGATTTTAGC  16657
               ||||||||||||||||||||||||||||||||||||||||||||||||||||||||||||
AH2012  16643  AAGTTCGAGGACCATCCTGATGGCTATTTTACCCAAGGTAGAACAACCGCTGATTTTAGC  19302

125_10  16658  CCTCGTAGCGACATGGAAAAGGACTTCCTAAGTATGGATATGGGTCTGTTTATTAACAAG  19317
               ||||||||||||||||||||||||||||||||||||||||||||||||||||||||||||
AH2012  19303  CCTCGTAGCGACATGGAAAAGGACTTCCTAAGTATGGATATGGGTCTGTTTATTAACAAG  19362

125_10  19318  TACGGACTTGAAGATTACGGCTTTGAGCACGTTGTGTATGGTGATGTTTCAAAAACCACC  19377
               ||||||||||||||||||||||||||||||||||||||||||||||||||||||||||||
AH2012  19363  TACGGACTTGAAGATTACGGCTTTGAGCACGTTGTGTATGGTGATGTTTCAAAAACCACC  19422

125_10  19378  CTTGGTGGTTTGCATCTACTAATTTCGCAGGTGCGTCTGGCCTGTATGGGTGTGCTCAAA  19437
               ||||||||||||||||||||||||||||||||||||||||||||||||||||||||||||
AH2012  19423  CTTGGTGGTTTGCATCTACTAATTTCGCAGGTGCGTCTGGCCTGTATGGGTGTGCTCAAA  19482

125_10  19438  ATAGACGAGTTTGTGTCTAGTAATGATAGCACGTTAAAGTCTTGTACTGTTACATATGCT  19497
               ||||||||||||||||||||||||||||||||||||||||||||||||||||||||||||
AH2012  19483  ATAGACGAGTTTGTGTCTAGTAATGATAGCACGTTAAAGTCTTGTACTGTTACATATGCT  19542
```

FIG. 1 (cont'd)

```
125_10  19498  GATAACCCTAGTAGTAAGATGGTTTGTACGTATATGGATCTCCTGCTTGACGATTTTGTC  19557
               ||||||||||||||||||||||||||||||||||||||||||||||||||||||||||||
AH2012  19543  GATAACCCTAGTAGTAAGATGGTTTGTACGTATATGGATCTCCTGCTTGACGATTTTGTC  19602

125_10  19558  AGCATTCTTAAATCTTTGGATTTGGGCGTTGTATCTAAAGTTCATGAAGTTATGGTCGAT  19617
               ||||||||||||||||||||||||||||||||||||||||||||||||||||||||||||
AH2012  19603  AGCATTCTTAAATCTTTGGATTTGGGCGTTGTATCTAAAGTTCATGAAGTTATGGTCGAT  19662

125_10  19618  TGTAAAATGTGGAGGTGGATGTTGTGGTGTAAGGATCATAAACTCCAGACATTTTATCCG  19677
               ||||||||||||||||||||||||||||||||||||||||||||||||||||||||||||
AH2012  19663  TGTAAAATGTGGAGGTGGATGTTGTGGTGTAAGGATCATAAACTCCAGACATTTTATCCG  19722

125_10  19678  CAACTTCAGGCCAGTGAATGGAAGTGTGGTTATTCCATGCCTTCTATTTACAAGATACAA  19737
               ||||||||||||||||||||||||||||||||||||||||||||||||||||||||||||
AH2012  19723  CAACTTCAGGCCAGTGAATGGAAGTGTGGTTATTCCATGCCTTCTATTTACAAGATACAA  19782

125_10  19738  CGTATGTGTTTAGAACCTTGCAATCTCTACAACTATGGTGCTGGTATTAAGTTACCTGAT  19797
               ||||||||||||||||||||||||||||||||||||||||||||||||||||||||||||
AH2012  19783  CGTATGTGTTTAGAACCTTGCAATCTCTACAACTATGGTGCTGGTATTAAGTTACCTGAT  19842

125_10  19798  GGCATTATGTTTAACGTAGTTAAATACACACAGCTTTGTCAATATCTCAATAGCACCACA  19857
               ||||||||||||||||||||||||||||||||||||||||||||||||||||||||||||
AH2012  19843  GGCATTATGTTTAACGTAGTTAAATACACACAGCTTTGTCAATATCTCAATAGCACCACA  19902

125_10  19858  ATGTGTGTACCCCATCACATGCGTGTGCTACATCTTGGTGCTGGCTCCGACAAGGGTGTT  19917
               ||||||||||||||||||||||||||||||||||||||||||||||||||||||||||||
AH2012  19903  ATGTGTGTACCCCATCACATGCGTGTGCTACATCTTGGTGCTGGCTCCGACAAGGGTGTT  19962

125_10  19918  GCACCTGGCACGGCTGTCTTACGACGTTGGTTGCCACTGGATGCCATTATAGTTGACAAT  19977
               ||||||||||||||||||||||||||||||||||||||||||||||||||||||||||||
AH2012  19963  GCACCTGGCACGGCTGTCTTACGACGTTGGTTGCCACTGGATGCCATTATAGTTGACAAT  20022

125_10  19978  GATAGTGTGGATTACGTTAGCGATGCTGATTATAGTGTTACAGGAGATTGCTCTACCTTA  20037
               ||||||||||||||||||||||||||||||||||||||||||||||||||||||||||||
AH2012  20023  GATAGTGTGGATTACGTTAGCGATGCTGATTATAGTGTTACAGGAGATTGCTCTACCTTA  20082

125_10  20038  TACCTGTCAGATAAGTTTGATTTAGTTATATCTGATATGTATGATGGTAAGATTAAAAGT  20097
               ||||||||||||||||||||||||||||||||||||||||||||||||||||||||||||
AH2012  20083  TACCTGTCAGATAAGTTTGATTTAGTTATATCTGATATGTATGATGGTAAGATTAAAAGT  20142

125_10  20098  TGTGATGGGGAGAACGTGTCTAAAGAAGGCTTCTTTCCCTATATTAATGGTGTCATCACC  20157
               ||||||||||||||||||||||||||||||||||||||||||||||||||||||||||||
AH2012  20143  TGTGATGGGGAGAACGTGTCTAAAGAAGGCTTCTTTCCCTATATTAATGGTGTCATCACC  20202

125_10  20158  GA-AAAGTTGGCACTTGGTGGTACTGTAGCTATTAAGGTGACGGAGTTTAGTTGGAATAA  20216
               || ||||||||||||||||||||||||||||||||||||||||||| |||||||||||||
AH2012  20203  GACAAAGTTGGCACTTGGTGGTACTGTAGCTATTAAGGTGACGGAGCTTAGTTGGAATAA  20262

125_10  20217  GAAGTTGTATGAACTCATTCAGAGGTTTGAGTATTGGACAATGTTCTGTACCAGTGTTAA  20276
               ||||||||||||||||||||||| ||||||||||||||||||||||||||||||||||||
AH2012  20263  GAAGTTGTATGAACTCATTCAGAAGTTTGAGTATTGGACAATGTTCTGTACCAGTGTTAA  20322

125_10  20277  CACGTCATCGTCAGAGGCATTCTTAATTGGTGTTCACTATTTAGGTGATTTTGCAAGTGG  20336
               ||||||||||||||||||||||||||||||||||||||||||||||||||||||||||||
AH2012  20323  CACGTCATCGTCAGAGGCATTCTTAATTGGTGTTCACTATTTAGGTGATTTTGCAAGTGG  20382

125_10  20337  CGCTGTGATTGACGGCAACACTATGCATGCCAATTATATCTTCTGGCGTAATTCCACAAT  20396
               ||||||||||||||||||||||||||||||||||||||||||||||||||||||||||||
AH2012  20383  CGCTGTGATTGACGGCAACACTATGCATGCCAATTATATCTTCTGGCGTAATTCCACAAT  20442
```

FIG. 1 (cont'd)

```
125_10  20397  TATGACTATGTCTTACAATAGTGTACTTGATTTAAGCAAGTTCAATTGTAAGCATAAGGC  20456
               ||||||||||||||||||||||||||||||||||||||||||||||||||||||||||||
AH2012  20443  TATGACTATGTCTTACAATAGTGTACTTGATTTAAGCAAGTTCAATTGTAAGCATAAGGC  20502

125_10  20457  TACAGTTGTCATTAATTTAAAAGATTCATCCATTAGTGATGTTGTGTTAGGTTTGTTGAA  20516
               ||||||||||||||||||||||||||||||||||||||||||||||||||||||||||||
AH2012  20503  TACAGTTGTCATTAATTTAAAAGATTCATCCATTAGTGATGTTGTGTTAGGTTTGTTGAA  20562

125_10  20517  GAATGGTAAGTTGCTAGTGCGTAATAATGACGCCATTTGTGGTTTTTCTAATCATTTGGT  20576
               ||||||||||||||||||||||||||||||||||||||||||||||||||||||||||||
AH2012  20563  GAATGGTAAGTTGCTAGTGCGTAATAATGACGCCATTTGTGGTTTTTCTAATCATTTGGT  20622

125_10  20577  CAACGTAAACAAATGAAGTCTTTAACCTACTTCTGGTTGTTCTTACCAGTACTTTCAACA  20636
               ||||||||||||||||||||||||||||||||||||||||||||||||||||||||||||
AH2012  20623  CAACGTAAACAAATGAAGTCTTTAACCTACTTCTGGTTGTTCTTACCAGTACTTTCAACA  20682

125_10  20637  CTTAGCCTACCACAAGATGTCACCAGGTGCTCAGCTAACACTAATTTTAGGCGGTTCTTT  20696
               ||||||||||||||||||||||||||||||||||||||||||||||||||||||||||||
AH2012  20683  CTTAGCCTACCACAAGATGTCACCAGGTGCTCAGCTAACACTAATTTTAGGCGGTTCTTT  20742

125_10  20697  TCAAAATTTAATGTTCAGGCGCCTGCAGTTGTTGTACTGGGCGGTTATCTACCTATTGGT  20756
               ||||||||||||||||||||||||||||||||||||||||||||||||||||||||||||
AH2012  20743  TCAAAATTTAATGTTCAGGCGCCTGCAGTTGTTGTACTGGGCGGTTATCTACCTATTGGT  20802

125_10  20757  GAAAACCAGGGTGTCAATTCAACTTGGTACTGTGCTGGCCAACATCCAACTGCTAGTGGC  20816
               ||||||||||||||||||||||||||||||||||||||||||||||||||||||||||||
AH2012  20803  GAAAACCAGGGTGTCAATTCAACTTGGTACTGTGCTGGCCAACATCCAACTGCTAGTGGC  20862

125_10  20817  GTTCATGGTATCTTTGTTAGCCATATTAGAGGTGGTCATGGCTTTGAGATTGGCATTTCG  20876
               ||||||||||||||||||||||||||||||||||||||||||||||||||||||||||||
AH2012  20863  GTTCATGGTATCTTTGTTAGCCATATTAGAGGTGGTCATGGCTTTGAGATTGGCATTTCG  20662

125_10  20877  CAAGAGCCTTTTGACCCTAGTGGTTACCAGCTTTATTTACATAAGGCTACTAACGGTAAC  20936
               ||||||||||||||||||||||||||||||||||||||||||||||||||||||||||||
AH2012  20663  CAAGAGCCTTTTGACCCTAGTGGTTACCAGCTTTATTTACATAAGGCTACTAACGGTAAC  20982

125_10  20937  ACTAATGCTACTGCGCGACTGCGCATTTGCCAGTTTCCTAGCATTAAAACATTGGGCCCC  20996
               ||||||||||||||||||||||||||||||||||||||||||||||||||||||||||||
AH2012  20983  ACTAATGCTACTGCGCGACTGCGCATTTGCCAGTTTCCTAGCATTAAAACATTGGGCCCC  2662

125_10  20997  ACTGCTAATAATGATGTTACAATAGGTCGTAATTGCCTATTTAACAAAGCCATCCCAGCT  21056
               |||||||||||||||||||||| |||||||||||||||||||||||||||||||||||||
AH2012  2663  ACTGCTAATAATGATGTTACAACAGGTCGTAATTGCCTATTTAACAAAGCCATCCCAGCT  21102

125_10  21057  CATATGAGTGAACATAGTGTTGTCGGCATAACATGGGATAATGATCGTGTCACTGTCTTT  21116
               ||||||||||||||||||||||||||||||||||||||||||||||||||||||||||||
AH2012  21103  CATATGAGTGAACATAGTGTTGTCGGCATAACATGGGATAATGATCGTGTCACTGTCTTT  21162

125_10  21117  TCTGACAAGATCTATTATTTTTATTTTAAAAATGATTGGTCCCGTGTTGCGACAAAGTGT  21176
               ||||||||||||||||||||||||||||||||||||||||||||||||||||||||||||
AH2012  21163  TCTGACAAGATCTATTATTTTTATTTTAAAAATGATTGGTCCCGTGTTGCGACAAAGTGT  21222

125_10  21177  TACAACAGTGGAGGTTGTGCTATGCAATATGTTTACGAACCCACCTATTACATGCTTAAT  21236
               ||||||||||||||||||||||||||||||||||||||||||||||||||||||||||||
AH2012  21223  TACAACAGTGGAGGTTGTGCTATGCAATATGTTTACGAACCCACCTATTACATGCTTAAT  21282

125_10  21237  GTTACTAGTGCTGGTGAGGATGGTATTTCTTATCAACCCTGTACAGCTAATTGCATTGGT  21296
               ||||||||||||||||||||||||||||||||||||||||||||||||||||||||||||
AH2012  21283  GTTACTAGTGCTGGTGAGGATGGTATTTCTTATCAACCCTGTACAGCTAATTGCATTGGT  21342

125_10  21297  TATGCTGCCAATGTATTTGCTACTGAGCCCAATGGCCACATACCAGAAGGTTTTAGTTTT  21356
               ||||||||||||||||||||||||||||||||||||||||||||||||||||||||||||
AH2012  21343  TATGCTGCCAATGTATTTGCTACTGAGCCCAATGGCCACATACCAGAAGGTTTTAGTTTT  21402
```

FIG. 1 (cont'd)

```
125_10  21357  AATAATTGGTTTCTTTTGTCCAATGATTCCACTTTGGTGCATGGTAAGGTGGTTTCCAAC  21416
               ||||||||||||||||||||||||||||||||||||||||||||||||||||||||||||
AH2012  21403  AATAATTGGTTTCTTTTGTCCAATGATTCCACTTTGGTGCATGGTAAGGTGGTTTCCAAC  21462

125_10  21417  CAACCATTGTTGGTCAATTGTCTTTTGGCCATTCCTAAGATTTATGGACTAGGCCAATTT  21476
               ||||||||||||||||||||||||||||||||||||||||||||||||||||||||||||
AH2012  21463  CAACCATTGTTGGTCAATTGTCTTTTGGCCATTCCTAAGATTTATGGACTAGGCCAATTT  21522

125_10  21477  TTCTCCTTTAATCAAACGATCGATGGTGTTTGTAATGGAGCTGCTGTGCAGCGTGCACCA  21536
               ||||||||||||||||||||||||||||||||||||||||||||||||||||||||||||
AH2012  21523  TTCTCCTTTAATCAAACGATCGATGGTGTTTGTAATGGAGCTGCTGTGCAGCGTGCACCA  21582

125_10  21537  GAGGCTCTGAGGTTTAATATTAATGACACCTCTGTCATTCTTGCTGAAGGCTCAATTGTA  21596
               ||||||||||||||||||||||||||||||||||||||||||||||||||||||||||||
AH2012  21583  GAGGCTCTGAGGTTTAATATTAATGACACCTCTGTCATTCTTGCTGAAGGCTCAATTGTA  21642

125_10  21597  CTTCATACTGCTTTAGGAACAAATTTTTCTTTTGTTTGCAGTAATTCCCCAAATCCTCAC  21656
               |||||||||||||||||||||||||||||||||||||||||||||||| |||||||||||
AH2012  21643  CTTCATACTGCTTTAGGAACAAATTTTTCTTTTGTTTGCAGTAATTCCTCAAATCCTCAC  21702

125_10  21657  TTAGCCACCTTCGCCATACCTCTGGGTGCTACCCAAGTACCTTATTATTGTTTTCTTAAA  21716
               ||||||||||||||||||||| ||||||||||||||||||| ||||||||||||||||||
AH2012  21703  TTAGCCACCTTCGCCATACCTTTGGGTGCTACCCAAGTACCCTATTATTGTTTTCTTAAA  21762

125_10  21717  GTGGATACTTACAACTCCACTGTTTATAAATTTTTGGCTGTTTTACCTCCTACCGTCAGG  21776
               |||||||||||||||||||||||||||||||| ||||||||||||||||| |||||||||
AH2012  21763  GTGGATACTTACAACTCCACTGTTTATAAATTCTTGGCTGTTTTACCTCCAACCGTCAGG  21822

125_10  21777  GAAATTGTCATCACCAAGTATGGTGATGTTTATGTCAATGGGTTTGGATACTTGCATCTC  21836
               ||||||||||||||||||||||||||||||||||||||||||||||| ||| ||||||||
AH2012  21823  GAAATTGTCATCACCAAGTATGGTGATGTTTATGTCAATGGGTTTGGCTATTTGCATCTC  21882

125_10  21837  GGTTTGTTGGATGCTGTCACAATTAATTTCACTGGTCATGGCACTGACGATGATGTTTCT  21896
               ||||||||||| ||||||||||||||||||||||||||||||||||||||||| ||||| 
AH2012  21883  GGTTTGTTGGACGCTGTCACAATTAATTTCACTGGTCATGGCACTGACGATGACGTTTCA  21942

125_10  21897  GGTTTTTGGACCATAGCATCGACTAATTTTGTTGATGCACTCATCGAAGTTCAAGGAACC  21956
               ||||| ||||||||||||||||||||||||||||||||||| ||||||||||||||||| 
AH2012  21943  GGTTTCTGGACCATAGCATCGACTAATTTTGTTGATGCACTTATCGAAGTTCAAGGAACT  22002

125_10  21957  GCCATTCAGCGTATTCTTTATTGTGATGATCCTGTTAGCCAACTCAAGTGTTCTCAGGTT  22016
               ||||||||||||||||||||||||||||||||||||||||||||||||||||||||||||
AH2012  22003  GCCATTCAGCGTATTCTTTATTGTGATGATCCTGTTAGCCAACTCAAGTGTTCTCAGGTT  22062

125_10  22017  GCTTTTGACCTTGACGATGGTTTTTACCCTATTTCTTCTAGAAACCTTCTGAGTCATGAA  22076
               ||||||||||||||||||||||| ||||||||||||||||||||||||  |||||||||||
AH2012  22063  GCTTTTGACCTTGACGATGGTTTCTACCCTATTTCTTCTAGAAACCTCTTGAGTCATGAA  22122

125_10  22077  CAGCCAATTTCTTTTGTTACTCTGCCATCATTTAATGATCATTCTTTTGTTAACATTACT  22136
               ||||||||||||||||||||| ||||||||||||||||||||||||||||||||||||||
AH2012  22123  CAGCCAATTTCTTTTGTTACTTTGCCATCATTTAATGATCATTCTTTTGTTAACATTACT  22182

125_10  22137  GTATCTGCTTCCTTTGGTGGTCATAGTGGTGCCAACCTTATTGCATCTGACACTACTATC  22196
               || ||||| |||||||||||||||||||||||||||||||||||||||||||||||||||
AH2012  22183  GTCTCTGCGTCCTTTGGTGGTCATAGTGGTGCCAACCTTATTGCATCTGACACTACTATC  22242

125_10  22197  AATGGGTTTAGTTCTTTCTGTGTTGACACTAGACAATTTACCATTTCACTGTTTTATAAC  22256
               ||||||||||||||||||||||||||||||||||||||||||||||||||||||||||||
AH2012  22243  AATGGGTTTAGTTCTTTCTGTGTTGACACTAGACAATTTACCATTTCACTGTTTTATAAC  22302

125_10  22257  GTTACAAACAGTTATGGTTATGTGTCTAAATCACAGGACAGTAATTGCCCTTTCACCTTG  22316
               |||||||||||||||||||||||||||||| |||||||||||||||||||||||||||||
AH2012  22303  GTTACAAACAGTTATGGTTATGTGTCTAACTCACAGGACAGTAATTGCCCTTTCACCTTG  22362
```

FIG. 1 (cont'd)

```
125_10  22317  CAATCTGTTAATGATTACCTGTCTTTTAGCAAATTTTGTGTTTCCACCAGCCTTTTGGCT  22376
               ||||||||||||||||||||||||||||| ||||||||||||||||||||||||||||||
AH2012  22363  CAATCTGTTAATGATTACCTGTCTTTTAGTAAATTTTGTGTTTCCACCAGCCTTTTGGCT  22422

125_10  22377  AGTGCCTGTACCATAGATCTTTTTGGTTACCCTGAGTTTGGTAGTGGTGTTAAGTTTACG  22436
               ||||||||||||||||||||||||||||||||||| ||||||||||||||||||||||||
AH2012  22423  AGTGCCTGTACCATAGATCTTTTTGGTTACCCTGATTTTGGTAGTGGTGTTAAGTTTACG  22482

125_10  22437  TCCCTTTACTTTCAATTCACAAAGGGTGAGTTGATTACTGGCACGACTAAACCACTTGAA  22496
               ||||||||||||||||||||||||||||||||||||||||||||| ||||||||||||||
AH2012  22483  TCCCTTTACTTTCAATTCACAAAGGGTGAGTTGATTACTGGCACGCCTAAACCACTTGAA  22542

125_10  22497  GGTGTCACGGACGTTTCTTTTATGACTCTGGATGTGTGTACCAAGTATACTATCTATGGC  22556
               ||||||||||||||||||||||||||||||||||||||||||||||||||||||||||||
AH2012  22543  GGTGTCACGGACGTTTCTTTTATGACTCTGGATGTGTGTACCAAGTATACTATCTATGGC  22602

125_10  22557  TTTAAAGGTGAGGGTATCATTACCCTTACAAATTCTAGCTTTTTGGCAGGTGTTTATTAC  22616
               ||||||||||||||||||||||||||||||||||||||||||||||||||||||||||||
AH2012  22603  TTTAAAGGTGAGGGTATCATTACCCTTACAAATTCTAGCTTTTTGGCAGGTGTTTATTAC  22662

125_10  22617  ACATCTGTTTCTGGACAGTTGTTAGCCTTTAAGAATGTCACTAGTGGTGCTGTTTATTCT  22676
               ||||||| ||||||||||||||||||||||||||||||||||||||||||||||||||||
AH2012  22663  ACATCTGATTCTGGACAGTTGTTAGCCTTTAAGAATGTCACTAGTGGTGCTGTTTATTCT  22722

125_10  22677  GTTACGCCATGTTCTTTTTCAGAGCAGGCTGCATATGTTGATGATGATATAGTGGGTGTT  22736
               ||||||||||||||||||||||||||||||||||||||||||||||||||||||||||||
AH2012  22723  GTTACGCCATGTTCTTTTTCAGAGCAGGCTGCATATGTTGATGATGATATAGTGGGTGTT  22782

125_10  22737  ATTTCTAGTTTGTCTAGCTCCACTTTTAACAGTACTAGGGAGTTGCCTGGTTTCTTCTAC  22796
               ||||||||||||||||  ||||||||||||||||||||||||||||||||||||||||||
AH2012  22783  ATTTCTAGTTTGTCTAATTCCACTTTTAACAGTACTAGGGAGTTGCCTGGTTTCTTCTAC  22842

125_10  22797  CATTCTAATGATGGCTCTAATTGTACAGAGCCTGTGTTGGTGTATAGTAACATAGGTGTT  22856
               ||||||||||||||||||||||||||||||||||||||||||||||||||||||||||||
AH2012  22843  CATTCTAATGATGGCTCTAATTGTACAGAGCCTGTGTTGGTGTATAGTAACATAGGTGTT  22902

125_10  22857  TGTAAATCTGGCAGTATTGGCTACGTCCCATCTCAGTCTGGCCAAGTCAAGATTGCACCC  22916
               ||||||||||||||||||||||||||||||||||||||||||||||||||||||||||||
AH2012  22903  TGTAAATCTGGCAGTATTGGCTACGTCCCATCTCAGTCTGGCCAAGTCAAGATTGCACCC  22962

125_10  22917  ACGGTTACTGGGAATATTAGTATTCCCACCAACTTTAGTATGAGTATTAGGACAGAATAT  22976
               ||||||||||||||||||||||||||||||||||||||||||||||||||||||||||||
AH2012  22963  ACGGTTACTGGGAATATTAGTATTCCCACCAACTTTAGTATGAGTATTAGGACAGAATAT  23022

125_10  22977  TTACAGCTTTACAACACGCCTGTTAGTGTTGATTGTGCCACATATGTTTGTAATGGTAAC  23036
               ||||||||||||||||||||||||||||||||||||||||||||||||||||||||||||
AH2012  23023  TTACAGCTTTACAACACGCCTGTTAGTGTTGATTGTGCCACATATGTTTGTAATGGTAAC  23082

125_10  23037  TCTCGTTGTAAACAATTACTCACCCAGTACACTGCAGCATGTAAGACCATAGAGTCAGCA  23096
               ||||||||||||||||||||||||||||||||||||||||||||||||||||||||||||
AH2012  23083  TCTCGTTGTAAACAATTACTCACCCAGTACACTGCAGCATGTAAGACCATAGAGTCAGCA  23142

125_10  23097  TTACRACTCAGCGCTAGGCTTGAGTCTGTTGAAGTTAACTCTATGCTTACTATTTCTGAA  23156
               |||| |||||||||||||||||||||||||||||||||||||||||||||||||||||||
AH2012  23143  TTACAACTCAGCGCTAGGCTTGAGTCTGTTGAAGTTAACTCTATGCTTACTATTTCTGAA  23202

125_10  23157  GAGGCTCTACAGTTAGCTACCATTAGTTCGTTTAATGGTGATGGATATAATTTTACTAAT  23216
               ||||||||||||||||||||||| ||||||||||||||||||||||||||||||||||||
AH2012  23203  GAGGCTCTACAGTTAGCTACCATCAGTTCGTTTAATGGTGATGGATATAATTTTACTAAT  23262

125_10  23217  GTGCTGGGTGTTTCTGTGTATGATCCTGCAAGGGGCAGGGTGGTACAAAAAAGGTCTTTT  23276
               |||||||||||||||||||||||||||||||| |||||||||||||||||||||||||||
AH2012  23263  GTGCTGGGTGTTTCTGTGTATGATCCTGCAAGTGGCAGGGTGGTACAAAAAAGGTCTTTT  23322
```

FIG. 1 (cont'd)

```
125_10  23277  ATTGAAGACCTGCTTTTTAATAAAGTGGTTACTAATGGCCTTGGTACTGTTGATGAAGAC  23336
               ||||||||||||||||||||||||||||||||||||||||||||||||||||||||||||
AH2012  23323  ATTGAAGACCTGCTTTTTAATAAAGTGGTTACTAATGGCCTTGGTACTGTTGATGAAGAC  23382

125_10  23337  TATAAGCGCTGTTCTAATGGTCGCTCTGTGGCAGATCTAGTCTGTGCACAGTATTACTCT  23396
               ||||||||||||||||||||||||||||||||||||||||||||||||||||||||||||
AH2012  23383  TATAAGCGCTGTTCTAATGGTCGCTCTGTGGCAGATCTAGTCTGTGCACAGTATTACTCT  23442

125_10  23397  GGTGTCATGGTACTACCTGGTGTTGTTGACGCTGAGAAGCTTCACATGTATAGTGCGTCT  23456
               ||||||||||||||||||||||||||||||||||||||||||||||||||||||||||||
AH2012  23443  GGTGTCATGGTACTACCTGGTGTTGTTGACGCTGAGAAGCTTCACATGTATAGTGCGTCT  23502

125_10  23457  CTCATCGGTGGTATGGTGCTAGGAGGTTTTACTTCTGCAGCGGCATTGCCTTTTAGCTAT  23516
               ||||||||||||||||||||||||||||||||||||||||||||||||||||||||||||
AH2012  23503  CTCATCGGTGGTATGGTGCTAGGAGGTTTTACTTCTGCAGCGGCATTGCCTTTTAGCTAT  23562

125_10  23517  GCTGTTCAAGCTAGACTCAATTATCTTGCTCTACAGACGGATGTTCTACAGCGGAACCAG  23576
               ||||||||||||||||||||||||||||||||||||||||||||||||||||||||||||
AH2012  23563  GCTGTTCAAGCTAGACTCAATTATCTTGCTCTACAGACGGATGTTCTACAGCGGAACCAG  23622

125_10  23577  CAATTGCTTGCTGAGTCTTTTAACTCTGCTATTGGTAATATAACTTCAGCCTTTGAGAGT  23636
               ||||||||||||||||||||||||||||||||||||||||||||||||||||||||||||
AH2012  23623  CAATTGCTTGCTGAGTCTTTTAACTCTGCTATTGGTAATATAACTTCAGCCTTTGAGAGT  23682

125_10  23637  GTTAAAGAGGCTATTAGTCAAACTTCCAAGGGTTTGAACACTGTGGCTCATGCGCTTACT  23696
               ||||||||||||||||||||||||||||||||||||||||||||||||||||||||||||
AH2012  23683  GTTAAAGAGGCTATTAGTCAAACTTCCAAGGGTTTGAACACTGTGGCTCATGCGCTTACT  23742

125_10  23697  AAGGTTCAAGAGGTTGTTAACTCGCAGGGTGCAGCTTTGACTCAACTTACCGTACAGCTG  23756
               ||||||||||||||||||||||||||||||||||||||||||||||||||||||||||||
AH2012  23743  AAGGTTCAAGAGGTTGTTAACTCGCAGGGTGCAGCTTTGACTCAACTTACCGTACAGCTG  23802

125_10  23757  CAACACAACTTCCAAGCCATTTCTAGTTCTATTGATGACATTTACTCTCGACTGGACATT  23816
               ||||||||||||||||||||||||||||||||||||||||||||| | ||||||||||||
AH2012  23803  CAACACAACTTCCAAGCCATTTCTAGTTCTATTGATGACATTTACACCCGACTGGACATT  23862

125_10  23817  CTTTCAGCCGATGTTCAGGTTGACCGTCTCATCACCGGCAGATTATCAGCACTTAATGCT  23876
               ||||||||||||||||||||||||||||||||||||||||||||||||||||||||||||
AH2012  23863  CTTTCAGCCGATGTTCAGGTTGACCGTCTCATCACCGGCAGATTATCAGCACTTAATGCT  23662

125_10  23877  TTTGTTGCTCAAACCCTCACTAAGTATACTGAGGTTCAGGCTAGCAGGAAGTTAGCACAG  23936
               ||||||||||||||||||||||||||||||||||||||||||||||||||| ||||||||
AH2012  23663  TTTGTTGCTCAAACCCTCACTAAGTATACTGAGGTTCAGGCTAGCAGGAAGCTAGCACAG  23982

125_10  23937  CAAAAGGTTAATGAGTGCGTTAAATCGCAATCCCAGCGTTATGGTTTTTGTGGTGGTGAT  23996
               |||||||||||||||||||||||||||||||| |||||||||||||||||||||||||||
AH2012  23983  CAAAAGGTTAATGAGTGCGTTAAATCGCAATCTCAGCGTTATGGTTTTTGTGGTGGTGAT  24042

125_10  23997  GGCGAGCACATTTTCTCTCTGGTACAGGCAGCACCTCAGGGCCTGCTGTTTTTACATACA  24056
               ||||| ||||||||||||||||||||||||||||||||||||||||||||||||||||||
AH2012  24043  GGCGATCACATTTTCTCTCTGGTACAGGCAGCACCTCAGGGCCTGCTGTTTTTACATACA  24102

125_10  24057  GTACTTGTACCGAGTGATTTTGTAGATGTTATTGCCATCGCTGGCTTATGCGTTAACGAT  24116
               |||||||||||| |||||||||||||||||||||||||||||||||||||||||||||||
AH2012  24103  GTACTTGTACCGGGTGATTTTGTAGATGTTATTGCCATCGCTGGCTTATGCGTTAACGAT  24162

125_10  24117  GAAATTGCCTTGACTCTACGTGAGCCTGGCTTAGTCTTGTTTACGCATGAACTTCAAAAT  24176
               ||||||||||||||||||||||||||||||||||||||||||||||||||||||||||||
AH2012  24163  GAAATTGCCTTGACTCTACGTGAGCCTGGCTTAGTCTTGTTTACGCATGAACTTCAAAAT  24222
```

FIG. 1 (cont'd)

```
125_10  24177  CATACTGCGACGGAATATTTTGTTTCATCGCGACGTATGTTTGAACCTAGAAAACCTACC  24236
               ||||||||||||||||||||||||||||||||||||||||||||||||||||||||||||
AH2012  24223  CATACTGCGACGGAATATTTTGTTTCATCGCGACGTATGTTTGAACCTAGAAAACCTACC  24282

125_10  24237  GTTAGTGATTTTGTTCAAATTGAGAGTTGTGTGGTCACCTATGTCAATTTGACTAGAGAC  24296
               ||||||||||||||||||||||||||||||||||||||||||||||||||||||||||||
AH2012  24283  GTTAGTGATTTTGTTCAAATTGAGAGTTGTGTGGTCACCTATGTCAATTTGACTAGAGAC  24342

125_10  24297  CAACTACCAGATGTAATCCCAGATTACATCGATGTTAACAAAACACTTGATGAGATTTTA  24356
               ||||||||||||||||||||||||||||||||||||||||||||||||||||||||||||
AH2012  24343  CAACTACCAGATGTAATCCCAGATTACATCGATGTTAACAAAACACTTGATGAGATTTTA  24402

125_10  24357  GCTTCTCTGCCCAATAGAACTGGTCCAAGTCTTCCTTTAGATGTTTTTAATGCCACTTAT  24416
               ||||||||||||||||||||||||||||||||||||||||||||||||||||||||||||
AH2012  24403  GCTTCTCTGCCCAATAGAACTGGTCCAAGTCTTCCTTTAGATGTTTTTAATGCCACTTAT  24462

125_10  24417  CTTAATCTCACTGGTGAAATTGCAGATTTAGAGCAGCGTTCAGAGTCTCTCCGTAATACT  24476
               || ||||||||||||||||||||| |||||||||||||||||||||||||||||||||||
AH2012  24463  CTCAATCTCACTGGTGAAATTGCAAATTTAGAGCAGCGTTCAGAGTCTCTCCGTAATACT  24522

125_10  24477  ACAGAGGAGCTCCAAAGTCTTATATATAATATCAACAACACACTAGTTGACCTTGAGTGG  24536
               |||||||||||||||||||||||| |||||||||||||||||||||||||||||||||||
AH2012  24523  ACAGAGGAGCTCCAAAGTCTTATACATAATATCAACAACACACTAGTTGACCTTGAGTGG  24582

125_10  24537  CTCAACCGAGTTGAGACATATATCAAGTGGCCGTGGTGGGTTTGGTTGATTATTTTCATT  24596
               |||||||||||||||||||||||||||||||||||||||||||||||| ||||||| |||
AH2012  24583  CTCAACCGAGTTGAGACATATATCAAGTGGCCGTGGTGGGTTTGGTTGGTTATTTTTATT  24642

125_10  24597  GTTCTCATCTTTGTTGTGTCATTACTAGTGTTCTGCTGCATTTCCACGGGTTGTTGTGGA  24656
               ||||||||||||||||||||||||||||||||||||||||||||||||||||||||||||
AH2012  24643  GTTCTCATCTTTGTTGTGTCATTACTAGTGTTCTGCTGCATTTCCACGGGTTGTTGTGGA  24702

125_10  24657  TGCTGCGGCTGCTGCTGTGCTTGTTTCTCAGGTTGTTGTAGGGGTCCTAGACTTCAACCT  24716
               |||||||||||||||||||||||||| |||||||||||||||||||||||||||||||||
AH2012  24703  TGCTGCGGCTGCTGCTGTGCTTGTTTTTCAGGTTGTTGTAGGGGTCCTAGACTTCAACCT  24762

125_10  24717  TACGAAGTTTTTGAAAAGGTCCACGTGCAGTGATGTTTCTTGGACTTTTTCAATACACGA  24776
               ||||||||||||||||||||||||||||||||||||||||||||||||||||||||||||
AH2012  24763  TACGAAGTTTTTGAAAAGGTCCACGTGCAGTGATGTTTCTTGGACTTTTTCAATACACGA  24822

125_10  24777  TTGACACAGTTGTCAAAGATGTCTCAAAGTCTGCTAACTTGTCTTTGGATGCTGTCCAAG  24836
               ||||||||||||||||||||||||||||||||||||||||||||||||||||||||||||
AH2012  24823  TTGACACAGTTGTCAAAGATGTCTCAAAGTCTGCTAACTTGTCTTTGGATGCTGTCCAAG  24882

125_10  24837  AGTTGGAGCTCAATGTAGTTCCAATTAGACAAGCTTCAAATGTGACGGGTTTTCTTTTCA  24896
               ||||||||||||||||||||||||||||||||||||||||||||||||||||||||||||
AH2012  24883  AGTTGGAGCTCAATGTAGTTCCAATTAGACAAGCTTCAAATGTGACGGGTTTTCTTTTCA  24942

125_10  24897  CCAGTGTTTTTATCTACTTCTTTGCACTGTTTAAAGCGTCTTCTTTGAGGCGCAATTATA  24956
               ||||||||||||||||||||||||||||||||||||||||||||||||||||||||||||
AH2012  24943  CCAGTGTTTTTATCTACTTCTTTGCACTGTTTAAAGCGTCTTCTTTGAGGCGCAATTATA  25002

125_10  24957  TTATGTTGGCAGCGCGTTTTGCTGTCATTGTTCTTTATTGCCCACTTTTATATTATTGTG  25016
               ||||||||||||||||||||||||||||||||||||||||||||||||||||||||||||
AH2012  25003  TTATGTTGGCAGCGCGTTTTGCTGTCATTGTTCTTTATTGCCCACTTTTATATTATTGTG  25062

125_10  25017  GTGCATTTTTAGATGCAACTATTATTTGTTGCACACTTATTCAAAGTCGGTGGCAGGCTT  25076
               ||||||||||||||||||||||||||||||||||||||||          ||||||||||
AH2012  25063  GTGCATTTTTAGATGCAACTATTATTTGTTGCACACTTAT----------TGGCAGGCTT  25112

125_10  25077  TGTTTAGTCTGCTTTTACTCCTGGCGCTATAAAAATGCGCTCTTTATTATTTTTAATACT  25136
               |||||||||||||||||||||||||||||||||||||||||||||||||| |||||||||
AH2012  25113  TGTTTAGTCTGCTTTTACTCCTGGCGCTATAAAAATGCGCTCTTTATTATCTTTAATACT  25172
```

FIG. 1 (cont'd)

```
125_10  25137  ACGACACTTTCTTTCCTCAATGGTAAAGCAGCTTATTATGACGGCAAATCCATTGTGATT  25196
               ||||||||||||||||||||||||||||||||||| ||||||||||||||||||||||||
AH2012  25173  ACGACACTTTCTTTCCTCAATGGTAAAGCAGCTTACTATGACGGCAAATCCATTGTGATT  25232

125_10  25197  TTAGAAGGTGGTGACCATTACATCACTTTTGGCAACTCTTTTGTTGCTTTTGTTAGTAGC  25256
                |||||||||||||| |||||||||||||||| ||||||||||||||||| |||||||||
AH2012  25233  CTAGAAGGTGGTGACTATTACATCACTTTTGGGAACTCTTTTGTTGCTTTCGTTAGTAGC  25266

125_10  25257  ATCGACTTGTATCTAGCTATACGTGGGCGGCAAGAAGCTGACCTACAGCTGTTGCGAACT  25316
               || ||||||||||||||||||||||||||||||||||| |||||||||||||||||||||
AH2012  25293  ATTGACTTGTATCTAGCTATACGTGGGCGGCAAGAAGCCGACCTACAGCTGTTGCGAACT  25352

125_10  25317  GTTGAGCTTCTTGATGGCAAGAAGCTTTATGTCTTTTCGCAACATCAAATTGTTGGCATT  25376
               ||||||||||||||||||||||||||||||||||||||||||||||||||||| ||||||
AH2012  25353  GTTGAGCTTCTTGATGGCAAGAAGCTTTATGTCTTTTCGCAACATCAAATTGTAGGCATT  25412

125_10  25377  ACTAATGCTGCATTTGACTCAATTCAACTAGACGAGTATGCTACAATTAGTGAATGATAA  25436
               ||||||||||||||||||||||||||||||||||||||||||||||||||||||||||||
AH2012  25413  ACTAATGCTGCATTTGACTCAATTCAACTAGACGAGTATGCTACAATTAGTGAATGATAA  25472

125_10  25437  TGGTCTAGTAGTTAATGTTATACTTTGGCTTTTCGTACTCTTTTTCCTGCTTATTATAAG  25496
               ||||||||||||||||||||||||||||||||||||||||||||||||||||||||||||
AH2012  25473  TGGTCTAGTAGTTAATGTTATACTTTGGCTTTTCGTACTCTTTTTCCTGCTTATTATAAG  25532

125_10  25497  CATTACTTTCGTCCAATTGGTTAATCTGTGCTTCACTTGTCACCGGTTGTGTAATAGCGC  25556
               |||||||||||||||| |||||||||||||||||||||||||||||||||||||||||||
AH2012  25533  CATTACTTTCGTCCAACTGGTTAATCTGTGCTTCACTTGTCACCGGTTGTGTAATAGCGC  25566

125_10  25557  AGTTTACACACCTATAGGGCGTTTGTATAGAGTTTATAAGTCTTACATGCAAATAGACCC  25616
               ||||||||||||||||||||||||||||||||||||||||||||||||||||||||||||
AH2012  25593  AGTTTACACACCTATAGGGCGTTTGTATAGAGTTTATAAGTCTTACATGCAAATAGACCC  25652

125_10  25617  CCTCCCTAGTACTGTTATTGACGTATAAACGAAATATGTCTAACGGTTCTATTCCCGTTG  25676
               |||||| |||||||||||||||||||||||||||||||||||||||||||||||||||||
AH2012  25653  CCTCCCCAGTACTGTTATTGACGTATAAACGAAATATGTCTAACGGTTCTATTCCCGTTG  25712

125_10  25677  ATGAGGTGATTCAACACCTTAGAAACTGGAATTTCACATGGAATATCATACTGACGATAC  25736
               ||||||||||||||||||||||||||||||||||||||||||||||||||||||||||||
AH2012  25713  ATGAGGTGATTCAACACCTTAGAAACTGGAATTTCACATGGAATATCATACTGACGATAC  25772

125_10  25737  TACTTGTAGTGCTTCAGTATGGCCATTACAAGTACTCTGCGTTCTTGTATGGTGTCAAGA  25796
               |||| |||||||||||||||||||||||||||||||||||||||||||||||||||||||
AH2012  25773  TACTCGTAGTGCTTCAGTATGGCCATTACAAGTACTCTGCGTTCTTGTATGGTGTCAAGA  25832

125_10  25797  TGGCTATTCTATGGATACTTTGGCCTCTTGTGTTAGCACTGTCACTTTTTGATGCATGGG  25856
               |||||||||||||||||||||||||||||||||||||||||||||||||||| |||||||
AH2012  25833  TGGCTATTCTATGGATACTTTGGCCTCTTGTGTTAGCACTGTCACTTTTTGACGCATGGG  25866

125_10  25857  CTAGCTTTCAGGTCAATTGGGTCTTTTTTGCTTTCAGCATCCTTATGGCTTGCATCACTC  25916
               ||||||||||||||||||||||||||||||||||||||||||||||||||||||||||||
AH2012  25893  CTAGCTTTCAGGTCAATTGGGTCTTTTTTGCTTTCAGCATCCTTATGGCTTGCATCACTC  25952

125_10  25917  TTATGCTGTGGATAATGTACTTTGTCAATAGCATTCGGTTGTGGCGCAGGACACATTCTT  25976
               ||||||||||||||||||||||||||||||||||||||||||||||||||||||||||||
AH2012  25953  TTATGCTGTGGATAATGTACTTTGTCAATAGCATTCGGTTGTGGCGCAGGACACATTCTT  26012

125_10  25977  GGTGGTCTTTCAATCCTGAAACAGACGCGCTTCTCACTACTTCTGTGATGGGCCGACAGG  26036
               ||||||||||||||||||||||||||||||||||||||||||||||||||||||||||||
AH2012  26013  GGTGGTCTTTCAATCCTGAAACAGACGCGCTTCTCACTACTTCTGTGATGGGCCGACAGG  26072
```

FIG. 1 (cont'd)

```
125_10  26037  TCTGCATTCCAGTGCTTGGAGCACCAACTGGTGTAACGCTAACACTCCTTAGTGGTACAT  26096
               ||||||||||||||||||||||||||||||||||||||||||||||||||||||||||||
AH2012  26073  TCTGCATTCCAGTGCTTGGAGCACCAACTGGTGTAACGCTAACACTCCTTAGTGGTACAT  26132

125_10  26097  TGCTTGTAGAGGGCTATAAGGTTGCTACTGGCGTACAGGTAAGTCAATTACCTAATTTCG  26156
               ||||||||||||||||||||||||||||||||||||||||||||||||||||||||||||
AH2012  26133  TGCTTGTAGAGGGCTATAAGGTTGCTACTGGCGTACAGGTAAGTCAATTACCTAATTTCG  26166

125_10  26157  TCACAGTCGCCAAGGCCACTACAACAATTGTCTACGGACGTGTTGGTCGTTCAGTCAATG  26216
               ||||||||||||||||||||||||||||||||||||||||||||||||||||||||||||
AH2012  26193  TCACAGTCGCCAAGGCCACTACAACAATTGTCTACGGACGTGTTGGTCGTTCAGTCAATG  26252

125_10  26217  CTTCATCTGGCACTGGTTGGGCTTTCTATGTCCGGTCCAAACACGGCGACTACTCAGCTG  26276
               ||||||||||||||||||||||||||||||||||||||||||||||||||||||||||||
AH2012  26253  CTTCATCTGGCACTGGTTGGGCTTTCTATGTCCGGTCCAAACACGGCGACTACTCAGCTG  26312

125_10  26277  TGAGTAATCCGAGTTCGGTTCTCACAGATAGTGAGAAAGTGCTTCATTTAGTCTAAACAG  26336
               ||||||||||||||||||||||||||||||||||||||||||||||||||||||||||||
AH2012  26313  TGAGTAATCCGAGTTCGGTTCTCACAGATAGTGAGAAAGTGCTTCATTTAGTCTAAACAG  26372

125_10  26337  AAACTTTATGGCTTCTGTCAGTTTTCAGGATCGTGGCCGCAAACGGGTGCCATTATCCCT  26396
               ||||||||||||||||||||||||||||||||||||||||||||||||||||||||||||
AH2012  26373  AAACTTTATGGCTTCTGTCAGTTTTCAGGATCGTGGCCGCAAACGGGTGCCATTATCCCT  26432

125_10  26397  CTATGCCCCTCTTAGGGTTACTAATGACAAACCCCTTTCTAAGGTACTTGCAAATAATGC  26456
               ||||||||||||||||||||||||||||||||||||||||||||||||||||||||||||
AH2012  26433  CTATGCCCCTCTTAGGGTTACTAATGACAAACCCCTTTCTAAGGTACTTGCAAATAATGC  26466

125_10  26457  TGTACCCACTAATAAAGGAAATAAGGACCAGCAAATTGGATACTGGAATGAGCAAATTCG  26516
               ||||||||||||||||||||||||||||||||||||||||||||||||||||||||||||
AH2012  26493  TGTACCCACTAATAAAGGAAATAAGGACCAGCAAATTGGATACTGGAATGAGCAAATTCG  26552

125_10  26517  CTGGCGCATGCGCCGTGGTGAGCGAATTGAACAACCTTCCAATTGGCATTTCTACTACCT  26576
               ||||||||||||||||||||||||||||||||||||||||||||||||||||||||||||
AH2012  26553  CTGGCGCATGCGCCGTGGTGAGCGAATTGAACAACCTTCCAATTGGCATTTCTACTACCT  26612

125_10  26577  CGGAACAGGACCTCACGCCGACCTCCGCTATAGGACTCGTACTGAGGGTGTTTTCTGGGT  26636
               ||||||||||||||||||||||||||||||||||||||||||||||||||||||||||||
AH2012  26613  CGGAACAGGACCTCACGCCGACCTCCGCTATAGGACTCGTACTGAGGGTGTTTTCTGGGT  26672

125_10  26637  TGCTAAAGAAGGCGCAAAGACTGAACCCACTAACCTGGGTGTCAGAAAGGCGTCTGAAAA  26696
               ||||||||||||||||||||||||||||||||||||||||||||||||||||||||||||
AH2012  26673  TGCTAAAGAAGGCGCAAAGACTGAACCCACTAACCTGGGTGTCAGAAAGGCGTCTGAAAA  26732

125_10  26697  GCCAATTATTCCAAATTTCTCTCAACAGCTTCCCAGCGTAGTTGAGATTGTTGAACCTAA  26756
               ||| || |||||||||||||| ||||||||||||||||||||||||||||||||||||||
AH2012  26733  GCCTATCATTCCAAATTTCTCCCAACAGCTTCCCAGCGTAGTTGAGATTGTTGAACCTAA  26766

125_10  26757  CACACCTCCTACTTCACGTGCAAATTCACGTAGCAGGAGTCGTGGTAATGGCAACAACAG  26816
               ||||||||| ||||||||| ||||||||||||||||||||||||||||||||||||||||
AH2012  26793  CACACCTCCCACTTCACGTTCAAATTCACGTAGCAGGAGTCGTGGTAATGGCAACAACAG  26852

125_10  26817  GTCCAGATCTCCAAGTAACAACAGAGGCAATAACCAGTCCCGCGGTAATTCACAGAATCG  26876
               ||||||||||||||||||||||||||||||||||||||||||||||||||||||||||||
AH2012  26853  GTCCAGATCTCCAAGTAACAACAGAGGCAATAACCAGTCCCGCGGTAATTCACAGAATCG  26912

125_10  26877  TGGAAATAACCAGGGTCGTGGAGCTTCTCAGAACAGAGGAGGCAATAATAATAACAATAA  26936
               |||||||||||||| |||||||||||||||||||||||||||||||||||||||||||||
AH2012  26913  TGGAAATAACCAGGATCGTGGAGCTTCTCAGAACAGAGGAGGCAATAATAATAACAATAA  26972
```

FIG. 1 (cont'd)

```
125_10  26937  CAAGTCTCGTAACCAGTCCAAGAACAGAAACCAGTCAAATGACCGTGGTGGTGTAACATC  26996
               ||||||||||||||||||||||||||||||||||||||||||||||||||||||||||||
AH2012  26973  CAAGTCTCGTAACCAGTCCAAGAACAGAAACCAGTCAAATGACCGTGGTGGTGTAACATC  27032

125_10  26997  ACGCGATGATCTGGTGGCTGCTGTCAAGGATGCCCTTAAATCTTTGGGTATTGGCGAAAA  27056
               ||||||||||||||||||||||||||||||||||||||||||||||||||||||||||||
AH2012  27033  ACGCGATGATCTGGTGGCTGCTGTCAAGGATGCCCTTAAATCTTTGGGTATTGGCGAAAA  27066

125_10  27057  CCCTGACAAGCTTAAGCAACAGCAGAAGCCCAAACAGGAAAGGTCTGACAGCAGCGGCAA  27116
               ||||||||||||||||||||||||||||||||||||||||||||||||||||||||||||
AH2012  27093  CCCTGACAAGCTTAAGCAACAGCAGAAGCCCAAACAGGAAAGGTCTGACAGCAGCGGCAA  27152

125_10  27117  AAATACACCTAAGAAGAACAAATCCAGAGCCACTTCGAAAGAACGTGACCTCAAAGACAT  27176
               ||||||||||||||||||||||||||||||||||||||||||||||||||||||||||||
AH2012  27153  AAATACACCTAAGAAGAACAAATCCAGAGCCACTTCGAAAGAACGTGACCTCAAAGACAT  27212

125_10  27177  CCCAGAGTGGAGGAGAATTCCCAAGGGCGAAAATAGCGTAGCAGCTTGCTTCGGACCCAG  27236
               ||||||||||||||||||||||||||||||||||||||||||||||||||||||||||||
AH2012  27213  CCCAGAGTGGAGGAGAATTCCCAAGGGCGAAAATAGCGTAGCAGCTTGCTTCGGACCCAG  27272

125_10  27237  GGGAGGCTTCAAAAATTTTGGAGATGCGGAATTTGTCGAAAAAGGTGTTGATGCCTCAGG  27296
               ||||||||||||||||||||||||||||||||||||||||||||||||||||||||||||
AH2012  27273  GGGAGGCTTCAAAAATTTTGGAGATGCGGAATTTGTCGAAAAAGGTGTTGATGCCTCAGG  27332

125_10  27297  CTATGCTCAGATCGCCAGTTTAGCACCAAATGTTGCAGCATTGCTCTTTGGTGGTAATGT  27356
               ||||||||||||||||||||||||||||||||||||||||||||||||||||||||||||
AH2012  27333  CTATGCTCAGATCGCCAGTTTAGCACCAAATGTTGCAGCATTGCTCTTTGGTGGTAATGT  27366

125_10  27357  GGCTGTTCGTGAGCTAGCGGACTCTTACGAGATTACATATAATTATAAAATGACTGTGCC  27416
               ||||||||||||||||||||||||||||||||||||||||||||||||||||||||||||
AH2012  27393  GGCTGTTCGTGAGCTAGCGGACTCTTACGAGATTACATATAATTATAAAATGACTGTGCC  27452

125_10  27417  AAAGTCTGATCCAAATGTAGAGCTTCTTGTTTCACAGGTGGATGCATTTAAAACTGGGAA  27476
               ||||||||||||||||||||||||||||||||||||||||||||||||||||||||||||
AH2012  27453  AAAGTCTGATCCAAATGTAGAGCTTCTTGTTTCACAGGTGGATGCATTTAAAACTGGGAA  27512

125_10  27477  TGCAAAACCCCAGAGAAAGAAGGAAAAGAAGAAYAAGCGTGAAACCACGCAGCAGCTGAA  27536
               ||||||||||||||||||||||||||||||||| ||||||||||||||||||||||||||
AH2012  27513  TGCAAAACCCCAGAGAAAGAAGGAAAAGAAGAACAAGCGTGAAACCACGCAGCAGCTGAA  27572

125_10  27537  TGAAGAGGCCATCTACGATGATGTGGGTGTGCCATCTGATGTGACTCATGCCAATTTGGA  27596
               ||||||||||||||||||||||||||||||||||||||||||||||||||||||||||||
AH2012  27573  TGAAGAGGCCATCTACGATGATGTGGGTGTGCCATCTGATGTGACTCATGCCAATTTGGA  27632

125_10  27597  ATGGGACACAGCTGTTGATGGTGGTGACACGGCCGTTGAAATTATCAACGAGATCTTCGA  27656
               ||||||||||||||||||||||||||||||||||||||||||||||||||||||||||||
AH2012  27633  ATGGGACACAGCTGTTGATGGTGGTGACACGGCCGTTGAAATTATCAACGAGATCTTCGA  27666

125_10  27657  CACAGGAAATTAAACAATGTTTGACTGGCTTATCCTGGCTATGTCCCAGGGTAGTGCCAT  27716
               ||||||||| |||||||||||||||||||||||||||||||||||||||||| |||||||
AH2012  27693  CACAGGAAACTAAACAATGTTTGACTGGCTTATCCTGGCTATGTCCCAGGGTGGTGCCAT  27752

125_10  27717  TACACTGTTATTACTGAGTGTTTTTCTAGCGACTTGGCTGCTGGGCTATGGCTTTGCCCT  27776
               ||||||||||||||||||||||||||||| ||||||||||||||||||||||||||||||
AH2012  27753  TACACTGTTATTACTGAGTGTTTTTCTAGTGACTTGGCTGCTGGGCTATGGCTTTGCCCT  27812

125_10  27777  CTAACTAGCGGTCTTGGTCTTGCACACAACGGTAAGCCAGTGGTAATGTCAGTGCAAGAA  27836
               ||||||||||||||||||||||||||||||||||||||||||||||||||||||||||||
AH2012  27813  CTAACTAGCGGTCTTGGTCTTGCACACAACGGTAAGCCAGTGGTAATGTCAGTGCAAGAA  27872

125_10  27837  GGATATTACCATAGCACTGTCATGAGGGGAACGCAGTACCTTTTCATCTAAACCTTTGCA  27896
               ||||||||||||||||||||||||||||||||||||||||||||||| ||||||||||||
AH2012  27873  GGATATTACCATAGCACTGTCATGAGGGGAACGCAGTACCTTTTCAACTAAACCTTTGCA  27932
```

FIG. 1 (cont'd)

```
125_10  27897  CGAGTAATCAAAGATCCGCTTGACGAGCCTATATGGAAGAGCGTGCCAGGTATTTGACTC  27956
               ||||||||||||||||||||||||||||||||||||||||||||||||||||||||||||
AH2012  27933  CGAGTAATCAAAGATCCGCTTGACGAGCCTATATGGAAGAGCGTGCCAGGTATTTGACTC  27966

125_10  27957  AAGGACTGTTAGTAACTGAAGACCTGACGGTGTTGATAT  27995
               |||||||||||||||||||||||||||||||||||||||
AH2012  27993  AAGGACTGTTAGTAACTGAAGACCTGACGGTGTTGATAT  28031
```

FIG. 2

PEDV 1251-125-10 (125-10) near-complete genome (SEQ ID NO:1) aligned to closest North American PEDV G2a strain Colorado 2013 (US_Col) (GenBank Accn #: KF272660) (nucleotides 45 to 28031 of SEQ ID NO:11)

```
125_10  1    GACTCTTGTCTACTCAATTCAACTAAACGAAATTCCTTGTCCTTCCGGCCGCATGTCCAT  60
             ||||||||||||||||||||||||||||||||||  ||||||||||||||||||||||||
US_Col  45   GACTCTTGTCTACTCAATTCAACTAAACGAAATT--TTGTCCTTCCGGCCGCATGTCCAT  102

125_10  61   GCTGCTGGAAGCTGACGTGGAATTTCATTAGGTTTGCTTAAGTAGCCATCGCAAGTGCTG  120
             ||||||||||||||||||||||||||||||||||||||||||||||||||||||||||||
US_Col  103  GCTGCTGGAAGCTGACGTGGAATTTCATTAGGTTTGCTTAAGTAGCCATCGCAAGTGCTG  162

125_10  121  TGCTGTCCTCTAGTTCCTGGTTGGCGTTCCGTCGCCTTCTACATACTAGACAAACAGCCT  180
             ||||||||||||||||||||||||||||||||||||||||||||||||||||||||||||
US_Col  163  TGCTGTCCTCTAGTTCCTGGTTGGCGTTCCGTCGCCTTCTACATACTAGACAAACAGCCT  222

125_10  181  TCCTCCGGTTCCGTCTGGGGGTTGTGTGGATAACTAGTTCCGTCTAGTTTGAAACCAGTA  240
             ||||||||||||||||||||||||||||||||||||||||||||||||||||||| ||||
US_Col  223  TCCTCCGGTTCCGTCTGGGGGTTGTGTGGATAACTAGTTCCGTCTAGTTTGAAACTAGTA  282

125_10  241  ACTGTCGGCTATGGCTAGCAACCATGTTACATTGGCTTTTGCCAATGATGCAGAAATTTC  300
             ||||||||||||||||||||||||||||||||||||||||||||||||||||||||||||
US_Col  283  ACTGTCGGCTATGGCTAGCAACCATGTTACATTGGCTTTTGCCAATGATGCAGAAATTTC  342

125_10  301  AGCTTTTGGCTTTTGCACTGCTAGTGAAGCCGTCTCATACTATTCTGAGGCCGCCGCTAG  360
             ||||||||||||||||||||||||||||||||||||||||||||||||||||||||||||
US_Col  343  AGCTTTTGGCTTTTGCACTGCTAGTGAAGCCGTCTCATACTATTCTGAGGCCGCCGCTAG  402

125_10  361  TGGATTTATGCAATGCCGTTTCGTGTCCTTCGATCTCGCTGACACTGTTGAGGGATTGCT  420
             ||||||||||||||||||||||||||||||||||||||||||||||||||||||||||||
US_Col  403  TGGATTTATGCAATGCCGTTTCGTGTCCTTCGATCTCGCTGACACTGTTGAGGGATTGCT  462

125_10  421  TCCCGAAGACTATGTCATGGTGGTGGTCGGCACTACCAAGCTTAGTGCGTATGTGGACAC  480
             ||||||||||||||||||||||||||||||||||||||||||||||||||||||||||||
US_Col  463  TCCCGAAGACTATGTCATGGTGGTGGTCGGCACTACCAAGCTTAGTGCGTATGTGGACAC  522

125_10  481  TTTTGGTAGCCGCCCCAAAAACATTTGTGGTTGGCTGTTATTTTCTAACTGTAATTACTT  540
             ||||||||||||||||||||||||||||||||||||||||||||||||||||||||||||
US_Col  523  TTTTGGTAGCCGCCCCAAAAACATTTGTGGTTGGCTGTTATTTTCTAACTGTAATTACTT  582

125_10  541  CCTCGAAGAGTTAGAGCTTACTTTTGGTCGTCGTGGTGGTAACATCGTGCCAGTTGACCA  600
             ||||||||||||||||||||||||||||||||||||||||||||||||||||||||||||
US_Col  583  CCTCGAAGAGTTAGAGCTTACTTTTGGTCGTCGTGGTGGTAACATCGTGCCAGTTGACCA  642

125_10  601  ATACATGTGTGGCGCTGACGGTAAACCTGTTCTTCAGGAATCCGAATGGGAGTATACAGA  660
             ||||||||||||||||||||||||||||||||||||||||||||||||||||||||||||
US_Col  643  ATACATGTGTGGCGCTGACGGTAAACCTGTTCTTCAGGAATCCGAATGGGAGTATACAGA  702

125_10  661  TTTCTTTGCTGACTCCGAAGACGGTCAACTCAACATTGCTGGTATCACTTATGTGAAGGC  720
             ||||||||||||||||||||||||||||||||||||||||||||||||||||||||||||
US_Col  703  TTTCTTTGCTGACTCCGAAGACGGTCAACTCAACATTGCTGGTATCACTTATGTGAAGGC  762

125_10  721  CTGGATTGTAGAGCGATCGGATGTCTCTTATGCGAGTCAGAATTTAACATCTATTAAGTC  780
             ||||||||||||||||||||||||||||||||||||||||||||||||||||||||||||
US_Col  763  CTGGATTGTAGAGCGATCGGATGTCTCTTATGCGAGTCAGAATTTAACATCTATTAAGTC  822

125_10  781  TATTACTTACTGTTCAACCTATGAGCATACTTTTCCTGATGGTACTGCCATGAAGGTTGC  840
             ||||||||||||||||||||||||||||||||||||||||||||||||||||||||||||
US_Col  823  TATTACTTACTGTTCAACCTATGAGCATACTTTTCCTGATGGTACTGCCATGAAGGTTGC  882
```

FIG. 2 (cont'd)

```
125_10  841   ACGTACTCCAAAGATTAAGAAGACTGTTGTCTTGTCTGAGCCACTTGCTACTATCTACAG  900
              ||||||||||||||||||||||||||||||||||||||||||||||||||||||||||||
US_Col  883   ACGTACTCCAAAGATTAAGAAGACTGTTGTCTTGTCTGAGCCACTTGCTACTATCTACAG  942

125_10  901   GGAAATTGGTTCTCCTTTTGTGGATAATGGGAGCGATGCTCGTTCTATCATTAAGAGACC  960
              ||||||||||||||||||||||||||||||||||||||||||||||||||||||||||||
US_Col  943   GGAAATTGGTTCTCCTTTTGTGGATAATGGGAGCGATGCTCGTTCTATCATTAAGAGACC  1002

125_10  961   AGTGTTCCTCCACGCTTTTGTTAAGTGTAAGTGTGGTAGTTATCATTGGACTGTTGGTGA  1020
              ||||||||||||||||||||||||||||||||||||||||||||||||||||||||||||
US_Col  1003  AGTGTTCCTCCACGCTTTTGTTAAGTGTAAGTGTGGTAGTTATCATTGGACTGTTGGTGA  1062

125_10  1021  TTGGACTTCCTATGTCTCCACTTGCTGTGGCTTTAAGTGTAAGCCAGTCCTTGTGGCTTC  1080
              ||||||||||||||||||||||||||||||||||||||||||||||||||||||||||||
US_Col  1063  TTGGACTTCCTATGTCTCCACTTGCTGTGGCTTTAAGTGTAAGCCAGTCCTTGTGGCTTC  1122

125_10  1081  ATGCTCTGCTACGCCTGGTTCTGTTGTGGTTACGCGCGCTGGTGCTGGCACTGGTGTTAA  1140
              ||||||||||||||||||||||||||||||||||||||||||||||||||||||||||||
US_Col  1123  ATGCTCTGCTACGCCTGGTTCTGTTGTGGTTACGCGCGCTGGTGCTGGCACTGGTGTTAA  1182

125_10  1141  GTATTACAACAACATGTTCCTGCGCCATGTGGCAGACATTGATGGGTTGGCATTCTGGCG  1200
              ||||||||||||||||||||||||||||||||||||||||||||||||||||||||||||
US_Col  1183  GTATTACAACAACATGTTCCTGCGCCATGTGGCAGACATTGATGGGTTGGCATTCTGGCG  1242

125_10  1201  AATTCTCAAGGTGCAGTCCAAAGACGACCTCGCTTGCTCTGGTAAATTCCTTGAACACCA  1260
              ||||||||||||||||||||||||||||||||||||||||||||||||||||||||||||
US_Col  1243  AATTCTCAAGGTGCAGTCCAAAGACGACCTCGCTTGCTCTGGTAAATTCCTTGAACACCA  1302

125_10  1261  TGAGGAAGGTTTCACAGATCCTTGCTACTTTTTGAATGACTCGAGCATTGCTACTAAGCT  1320
              ||||||||||||||||||||||||||||||||||||||||||||||||||||||||||||
US_Col  1303  TGAGGAAGGTTTCACAGATCCTTGCTACTTTTTGAATGACTCGAGCATTGCTACTAAGCT  1362

125_10  1321  CAAGTTTGACATCCTTAGTGGCAAGTTTTCTGATGAAGTCAAACAAGCTATCTTTGCTGG  1380
              ||||||||||||||||||||||||||||||||||||||||||||||||||||||||||||
US_Col  1363  CAAGTTTGACATCCTTAGTGGCAAGTTTTCTGATGAAGTCAAACAAGCTATCTTTGCTGG  1422

125_10  1381  TCATGTTGTTGTTGGCAGCGCGMTCGTTGACATTGTTGACGATGCACTGGGACAGCCTTG  1440
              |||||||||||||||||||||| |||||||||||||||||||||||||||||||||||||
US_Col  1423  TCATGTTGTTGTTGGCAGCGCGCTCGTTGACATTGTTGACGATGCACTGGGACAGCCTTG  1482

125_10  1441  GTTTATACGTAAGCTTGGTGACCTTGCAAGTGCAGCTTGGGAGCAGCTTAAGGCTGTCGT  1500
              ||||||||||||||||||||||||||||||||||||||||||||||||||||||||||||
US_Col  1483  GTTTATACGTAAGCTTGGTGACCTTGCAAGTGCAGCTTGGGAGCAGCTTAAGGCTGTCGT  1542

125_10  1501  TAGAGGCCTTAACCTCCTGTCTGATGAGGTCGTGCTCTTTGGCAAAAGACTTAGCTGTGC  1560
              ||||||||||||||||||||||||||||||||||||||||||||||||||||||||||||
US_Col  1543  TAGAGGCCTTAACCTCCTGTCTGATGAGGTCGTGCTCTTTGGCAAAAGACTTAGCTGTGC  1602

125_10  1561  CACTCTTAGTATCGTTAACGGTGTTTTTGAGTTCATCGCCGAAGTGCCTGAGAAGTTGGC  1620
              ||||||||||||||||||||||||||||||||||||||||||||||||||||||||||||
US_Col  1603  CACTCTTAGTATCGTTAACGGTGTTTTTGAGTTCATCGCCGAAGTGCCTGAGAAGTTGGC  1662

125_10  1621  TGCGGCTGTTACAGTTTTTGTCAACTTCTTGAATGAGCTTTTTGAGTCTGCCTGTGACTG  1680
              ||||||||||||||||||||||||||||||||||||||||||||||||||||||||||||
US_Col  1663  TGCGGCTGTTACAGTTTTTGTCAACTTCTTGAATGAGCTTTTTGAGTCTGCCTGTGACTG  1722

125_10  1681  CTTAAAGGTCGGAGGTAAAACCTTTAACAAGGTTGGCTCTTATGTTCTTTTTGACAACGC  1740
              ||||||||||||||||||||||||||||||||||||||||||||||||||||||||||||
US_Col  1723  CTTAAAGGTCGGAGGTAAAACCTTTAACAAGGTTGGCTCTTATGTTCTTTTTGACAACGC  1782

125_10  1741  ATTGGTTAAGCTTGTCAAGGCAAAAGTTCGCGGCCCACGACAGGCAGGTGTTTGTGAAGT  1800
              ||||||||||||||||||||||||||||||||||||||||||||||||||||||||||||
US_Col  1783  ATTGGTTAAGCTTGTCAAGGCAAAAGTTCGCGGCCCACGACAGGCAGGTGTTTGTGAAGT  1842
```

FIG. 2 (cont'd)

```
125_10  1801   TCGTTACACAAGCCTTGTTATTGGGAGTACTACCAAGGTGGTTTCCAAGCGCGTTGAAAA  1860
               ||||||||||||||||||||||||||||||||||||||||||||||||||||||||||||
US_Col  1843   TCGTTACACAAGCCTTGTTATTGGGAGTACTACCAAGGTGGTTTCCAAGCGCGTTGAAAA  1902

125_10  1861   TGCCAATGTGAATCTCGTCGTCGTTGACGAGGATGTGACCCTCAACACCACTGGTCGTAC  1660
               ||||||||||||||||||||||||||||||||||||||||||||||||||||||||||||
US_Col  1903   TGCCAATGTGAATCTCGTCGTCGTTGACGAGGATGTGACCCTCAACACCACTGGTCGTAC  1962

125_10  1661   AGTTGTTGTTGACGGACTTGCATTCTTCGAGAGTGACGGGTTTTACAGACATCTTGCTGA  1980
               ||||||||||||||||||||||||||||||||||||||||||||||||||||||||||||
US_Col  1963   AGTTGTTGTTGACGGACTTGCATTCTTCGAGAGTGACGGGTTTTACAGACATCTTGCTGA  2022

125_10  1981   TGCTGACGTTGTCATTGAACATCCTGTTTATAAGTCTGCTTGTGAGCTCAAGCCAGTTTT  2040
               ||||||||||||||||||||||||||||||||||||||||||||||||||||||||||||
US_Col  2023   TGCTGACGTTGTCATTGAACATCCTGTTTATAAGTCTGCTTGTGAGCTCAAGCCAGTTTT  2082

125_10  2041   TGAGTGTGACCCAATACCTGATTTTCCTATGCCTGTGGCCGCTAGTGTTGCAGAGCTTTG  2100
               ||||||||||||||||||||||||||||||||||||||||||||||||||||||||||||
US_Col  2083   TGAGTGTGACCCAATACCTGATTTTCCTATGCCTGTGGCCGCTAGTGTTGCAGAGCTTTG  2142

125_10  2101   TGTGCAAACTGATCTGTTGCTTAAAAATTACAACACTCCTTATAAAACTTACAGCTGCGT  2160
               ||||||||||||||||||||||||||||||||||||||||||||||||||||||||||||
US_Col  2143   TGTGCAAACTGATCTGTTGCTTAAAAATTACAACACTCCTTATAAAACTTACAGCTGCGT  2202

125_10  2161   TGTGAGAGGTGATAAGTGTTGTATCACTTGCACCTTACATTTCACAGCACCAAGTTATAT  2220
               ||||||||||||||||||||||||||||||||||||||||||||||||||||||||||||
US_Col  2203   TGTGAGAGGTGATAAGTGTTGTATCACTTGCACCTTACATTTCACAGCACCAAGTTATAT  2262

125_10  2221   GGAGGCTGCTGCTAATTTTGTAGACCTCTGTACCAAGAACATTGGTACTGCTGGTTTTCA  2280
               ||||||||||||||||||||||||||||||||||||||||||||||||||||||||||||
US_Col  2263   GGAGGCTGCTGCTAATTTTGTAGACCTCTGTACCAAGAACATTGGTACTGCTGGTTTTCA  2322

125_10  2281   TGAGTTTTACATTACGGCCCATGAACAACAGGATCTGCAAGGGTTCGTAACCACTTGTTG  2340
               ||||||||||||||||||||||||||||||||||||||||||||||||||||||||||||
US_Col  2323   TGAGTTTTACATTACGGCCCATGAACAACAGGATCTGCAAGGGTTCGTAACCACTTGTTG  2382

125_10  2341   CACGATGTCAGGTTTTGAGTGTTTTATGCCTATAATCCCACAGTGTCCAGCAGTGCTTGA  2400
               ||||||||||||||||||||||||||||||||||||||||||||||||||||||||||||
US_Col  2383   CACGATGTCAGGTTTTGAGTGTTTTATGCCTATAATCCCACAGTGTCCAGCAGTGCTTGA  2442

125_10  2401   AGAGATTGATGGTGGTAGCATCTGGCGGTCTTTTATCACTGGTCTTAATACAATGTGGGA  2460
               ||||||||||||||||||||||||||||||||||||||||||||||||||||||||||||
US_Col  2443   AGAGATTGATGGTGGTAGCATCTGGCGGTCTTTTATCACTGGTCTTAATACAATGTGGGA  2502

125_10  2461   TTTTTGCAAGCATCTTAAAGTCAGCTTTGGACTAGATGGCATTGTTGTCACTGTAGCACG  2520
               ||||||||||||||||||||||||||||||||||||||||||||||||||||||||||||
US_Col  2503   TTTTTGCAAGCATCTTAAAGTCAGCTTTGGACTAGATGGCATTGTTGTCACTGTAGCACG  2562

125_10  2521   CAAATTTAAACGACTTGGTGCTCTCTTGGCAGAAATGTATAACACTTACCTTTCAACTGT  2580
               ||||||||||||||||||||||||||||||||||||||||||||||||||||||||||||
US_Col  2563   CAAATTTAAACGACTTGGTGCTCTCTTGGCAGAAATGTATAACACTTACCTTTCAACTGT  2622

125_10  2581   GGTGGAAAACTTGGTACTGGCCGGTGTTAGCTTCAAGTATTATGCCACCAGTGTCCCAAA  2640
               ||||||||||||||||||||||||||||||||||||||||||||||||||||||||||||
US_Col  2623   GGTGGAAAACTTGGTACTGGCCGGTGTTAGCTTCAAGTATTATGCCACCAGTGTCCCAAA  2682

125_10  2641   AATTGTTTTGGGCTGTTGTTTTCACAGTGTTAAAAGTGTTCTTGCAAGTGCCTTCCAGAT  2700
               ||||||||||||||||||||||||||||||||||||||||||||||||||||||||||||
US_Col  2683   AATTGTTTTGGGCTGTTGTTTTCACAGTGTTAAAAGTGTTCTTGCAAGTGCCTTCCAGAT  2742

125_10  2701   TCCTGTCCAGGCAGGCGTTGAGAAGTTTAAAGTCTTCCTTAACTGTGTTCACCCTGTTGT  2760
               ||||||||||||||||||||||||||||||||||||||||||||||||||||||||||||
US_Col  2743   TCCTGTCCAGGCAGGCGTTGAGAAGTTTAAAGTCTTCCTTAACTGTGTTCACCCTGTTGT  2802
```

FIG. 2 (cont'd)

```
125_10  2761  ACCACGTGTCATTGAAACTTCTTTTGTGGAATTAGAAGAGACGACATTTAAACCACCAGC  2820
              ||||||||||||||||||||||||||||||||||||||||||||||||||||||||||||
US_Col  2803  ACCACGTGTCATTGAAACTTCTTTTGTGGAATTAGAAGAGACGACATTTAAACCACCAGC  2862

125_10  2821  ACTCAATGGTAGTATTGCTATTGTTGATGGCTTTGCTTTCTATTATGATGGAACACTATA  2880
              ||||||||||||||||||||||||||||||||||||||||||||||||||||||||||||
US_Col  2863  ACTCAATGGTAGTATTGCTATTGTTGATGGCTTTGCTTTCTATTATGATGGAACACTATA  2662

125_10  2881  CTATCCCACCGATGGTAATAGCGTTGTTCCTATCTGCTTTAAGAAGAAAGGTGGTGGTGA  2940
              ||||||||||||||||||||||||||||||||||||||||||||||||||||||||||||
US_Col  2663  CTATCCCACCGATGGTAATAGCGTTGTTCCTATCTGCTTTAAGAAGAAAGGTGGTGGTGA  2982

125_10  2941  TGTCAAATTCTCTGATGAAGTCTCTGTTAAAACCATTGACCCAGTTTATAAGGTCTCCCT  3000
              ||||||||||||||||||||||||||||||||||||||||||||||||||||||||||||
US_Col  2983  TGTCAAATTCTCTGATGAAGTCTCTGTTAAAACCATTGACCCAGTTTATAAGGTCTCCCT  3042

125_10  3001  TGAATTTGAGTTCGAGTCTGAGACTATTATGGCTGTGCTTAATAAGGCTGTTGGTAATTG  3060
              ||||||||||||||||||||||||||||||||||||||||||||||||||||||||||||
US_Col  3043  TGAATTTGAGTTCGAGTCTGAGACTATTATGGCTGTGCTTAATAAGGCTGTTGGTAATTG  3102

125_10  3061  TATCAAGGTTACAGGTGGTTGGGACGATGTTGTTGAGTATATCAATGTTGCCATTGAGGT  3120
              ||||||||||||||||||||||||||||||||||||||||||||||||||||||||||||
US_Col  3103  TATCAAGGTTACAGGTGGTTGGGACGATGTTGTTGAGTATATCAATGTTGCCATTGAGGT  3162

125_10  3121  TCTTAAAGATCACATCGATGTGCCTAAGTACTACATCTATGATGAGGAAGGTGGCACCGA  3180
              ||||||||||||||||||||||||||||||||||||||||||||||||||||||||||||
US_Col  3163  TCTTAAAGATCACATCGATGTGCCTAAGTACTACATCTATGATGAGGAAGGTGGCACCGA  3222

125_10  3181  TCCTAATCTGCCCGTAATGGTTTCTCAGTGGCCGTTGAATGATGACACGATCTCACAGGA  3240
              ||||||||||||||||||||||||||||||||||||||||||||||||||||||||||||
US_Col  3223  TCCTAATCTGCCCGTAATGGTTTCTCAGTGGCCGTTGAATGATGACACGATCTCACAGGA  3282

125_10  3241  TCTGCTTGATGTTGAAGTTGTTACTGATGCGCCAGTTGATTTCGAGGGTGATGAAGTAGA  3300
              ||||||||||||||||||||||||||||||||||||||||||||||||||||||||||||
US_Col  3283  TCTGCTTGATGTTGAAGTTGTTACTGATGCGCCAGTTGATTTCGAGGGTGATGAAGTAGA  3342

125_10  3301  CTCCTCTGACCCTGWTAAGGTGGCAGACGTGGCTAACTCTGAGCCTGAGGATGACGGTCT  3360
              |||||||||||||| |||||||||||||||||||||||||||||||||||||||||||||
US_Col  3343  CTCCTCTGACCCTGATAAGGTGGCAGACGTGGCTAACTCTGAGCCTGAGGATGACGGTCT  3402

125_10  3361  TAATGTAGCTCCTGAAACAAATGTAGAGTCTGAAGTTGAGGAAGTTGCCGCAACCTTGTC  3420
              ||||||||||||||||||||||||||||||||||||||||||||||||||||||||||||
US_Col  3403  TAATGTAGCTCCTGAAACAAATGTAGAGTCTGAAGTTGAGGAAGTTGCCGCAACCTTGTC  3462

125_10  3421  CTTTA---AAGATACACCTTCCACAGTTACTAAGGATCCTTTTGCTTTTGACTTTGCAAG  3477
              |||||   ||||||||||||||||||||||||||||||||||||||||||||||||||||
US_Col  3463  CTTTATTAAAGATACACCTTCCACAGTTACTAAGGATCCTTTTGCTTTTGACTTTGCAAG  3522

125_10  3478  CTATGGAGGACTTAAGGTTTTAAGACAATCTCATAACAACTGCTGGGTTACTTCTACCTT  3537
              ||||||||||||||||||||||||||||||||||||||||||||||||||||||||||||
US_Col  3523  CTATGGAGGACTTAAGGTTTTAAGACAATCTCATAACAACTGCTGGGTTACTTCTACCTT  3582

125_10  3538  GGTGCAGCTACAATTGCTTGGCATCGTTGATGACCCTGCAATGGAGCTTTTTAGTGCTGG  3597
              ||||||||||||||||||||||||||||||||||||||||||||||||||||||||||||
US_Col  3583  GGTGCAGCTACAATTGCTTGGCATCGTTGATGACCCTGCAATGGAGCTTTTTAGTGCTGG  3642

125_10  3598  TAGAGTTGGTCCAATGGTTCGCAAATGCTATGAGTCACAAAAGGCTATCTTGGGATCTTT  3657
              ||||||||||||||||||||||||||||||||||||||||||||||||||||||||||||
US_Col  3643  TAGAGTTGGTCCAATGGTTCGCAAATGCTATGAGTCACAAAAGGCTATCTTGGGATCTTT  3702
```

FIG. 2 (cont'd)

```
125_10  3658  GGGTGATGTGTCGGCTTGCCTAGAGTCTCTGACTAAGGACCTACACACACTTAAGATTAC  3717
              ||||||||||||||||||||||||||||||||||||||||||||||||||||||||||||
US_Col  3703  GGGTGATGTGTCGGCTTGCCTAGAGTCTCTGACTAAGGACCTACACACACTTAAGATTAC  3762

125_10  3718  CTGTTCTGTAGTCTGTGGTTGTGGTACTGGTGAACGTATCTATGATGGTTGTGCTTTTCG  3777
              ||||||||||||||||||||||||||||||||||||||||||||||||||||||||||||
US_Col  3763  CTGTTCTGTAGTCTGTGGTTGTGGTACTGGTGAACGTATCTATGATGGTTGTGCTTTTCG  3822

125_10  3778  TATGACGCCAACTTTGGAACCGTTCCCATATGGTGCTTGTGCTCAGTGTGCTCAAGTTTT  3837
              ||||||||||||||||||||||||||||||||||||||||||||||||||||||||||||
US_Col  3823  TATGACGCCAACTTTGGAACCGTTCCCATATGGTGCTTGTGCTCAGTGTGCTCAAGTTTT  3882

125_10  3838  GATGCACACTTTTAAAAGTATTGTTGGCACCGGCATCTTTTGTCGAGATACTACTGCTCT  3897
              ||||||||||||||||||||||||||||||||||||||||||||||||||||||||||||
US_Col  3883  GATGCACACTTTTAAAAGTATTGTTGGCACCGGCATCTTTTGTCGAGATACTACTGCTCT  3942

125_10  3898  CTCCTTGGATTCTTTGGTTGTAAAACCTCTTTGTGCGGCTGCTTTTATAGGCAAGGATAG  3957
              ||||||||||||||||||||||||||||||||||||||||||||||||||||||||||||
US_Col  3943  CTCCTTGGATTCTTTGGTTGTAAAACCTCTTTGTGCGGCTGCTTTTATAGGCAAGGATAG  4002

125_10  3958  TGGTCATTATGTCACTAACTTTTATGATGCTGCTATGGCTATTGATGGTTATGGTCGTCA  4017
              ||||||||||||||||||||||||||||||||||||||||||||||||||||||||||||
US_Col  4003  TGGTCATTATGTCACTAACTTTTATGATGCTGCTATGGCTATTGATGGTTATGGTCGTCA  4062

125_10  4018  TCAGATAAAGTATGACACACTGAACACTATTTGTGTTAAAGACGTTAATTGGACAGCACC  4077
              ||||||||||||||||||||||||||||||||||||||||||||||||||||||||||||
US_Col  4063  TCAGATAAAGTATGACACACTGAACACTATTTGTGTTAAAGACGTTAATTGGACAGCACC  4122

125_10  4078  TTTTGTCCCAGACGTTGAGCCTGTATTGGAGCCTGTTGTCAAACCTTTCTATTCTTATAA  4137
              ||||||||||||||||||||||||||||||||||||||||||||||||||||||||||||
US_Col  4123  TTTTGTCCCAGACGTTGAGCCTGTATTGGAGCCTGTTGTCAAACCTTTCTATTCTTATAA  4182

125_10  4138  GAATGTTGATTTTTACCAAGGAGATTTTAGTGACCTTGTTAAACTTCCATGTGATTTTGT  4197
              ||||||||||||||||||||||||||||||||||||||||||||||||||||||||||||
US_Col  4183  GAATGTTGATTTTTACCAAGGAGATTTTAGTGACCTTGTTAAACTTCCATGTGATTTTGT  4242

125_10  4198  TGTTAATGCTGCAAATGAGAATTTGTCTCACGGTGGCGGCATAGCAAAGGCCATTGATGT  4257
              ||||||||||||||||||||||||||||||||||||||||||||||||||||||||||||
US_Col  4243  TGTTAATGCTGCAAATGAGAATTTGTCTCACGGTGGCGGCATAGCAAAGGCCATTGATGT  4302

125_10  4258  TTATACCAAGGGCATGTTGCAGAAGTGCTCGAATGATTACATTAAAGCACACGGTCCCAT  4317
              ||||||||||||||||||||||||||||||||||||||||||||||||||||||||||||
US_Col  4303  TTATACCAAGGGCATGTTGCAGAAGTGCTCGAATGATTACATTAAAGCACACGGTCCCAT  4362

125_10  4318  TAAAGTTGGACGTGGTGTCATGTTGGAGGCATTAGGTCTTAAGGTCTTTAATGTTGTTGG  4377
              ||||||||||||||||||||||||||||||||||||||||||||||||||||||||||||
US_Col  4363  TAAAGTTGGACGTGGTGTCATGTTGGAGGCATTAGGTCTTAAGGTCTTTAATGTTGTTGG  4422

125_10  4378  TCCACGTAAGGGTAAGCATGCACCTGAGCTTCTTGTTAAGGCTTATAAGTCCGTTTTTGC  4437
              ||||||||||||||||||||||||||||||||||||||||||||||||||||||||||||
US_Col  4423  TCCACGTAAGGGTAAGCATGCACCTGAGCTTCTTGTTAAGGCTTATAAGTCCGTTTTTGC  4482

125_10  4438  TAATTCAGGTGTTGCTCTTACACCTTTGATTAGTGTTGGAATTTTTAGTGTTCCTTTGGA  4497
              ||||||||||||||||||||||||||||||||||||||||||||||||||||||||||||
US_Col  4483  TAATTCAGGTGTTGCTCTTACACCTTTGATTAGTGTTGGAATTTTTAGTGTTCCTTTGGA  4542

125_10  4498  AGAATCTTTATCTGCTTTTCTTGCATGTGTTGGTGATCGCCACTGTAAGTGCTTTTGTTA  4557
              ||||||||||||||||||||||||||||||||||||||||||||||||||||||||||||
US_Col  4543  AGAATCTTTATCTGCTTTTCTTGCATGTGTTGGTGATCGCCACTGTAAGTGCTTTTGTTA  4602

125_10  4558  TAGTGACAAAGAGCGCGAGGCGATCATTAATTACATGGATGGCTTGGTAGATGCTATTTT  4617
              ||||||||||||||||||||||||||||||||||||||||||||||||||||||||||||
US_Col  4603  TAGTGACAAAGAGCGCGAGGCGATCATTAATTACATGGATGGCTTGGTAGATGCTATTTT  4662
```

FIG. 2 (cont'd)

```
125_10  4618   CAAAGATGCACTTGTTGATACTACTCCTGTCCAGGAAGATGTTCAACAAGTTTCACAAAA  4677
               ||||||||||||||||||||||||||||||||||||||||||||||||||||||||||||
US_Col  4663   CAAAGATGCACTTGTTGATACTACTCCTGTCCAGGAAGATGTTCAACAAGTTTCACAAAA  4722

125_10  4678   ACCAGTTTTGCCTAATTTTGAACCTTTCAGGATTGAAGGTGCTCATGCTTTCTATGAGTG  4737
               ||||||||||||||||||||||||||||||||||||||||||||||||||||||||||||
US_Col  4723   ACCAGTTTTGCCTAATTTTGAACCTTTCAGGATTGAAGGTGCTCATGCTTTCTATGAGTG  4782

125_10  4738   CAACCCTGAAGGTTTGATGTCATTAGGTGCTGACAAGCTGGTGTTGTTTACAAATTCCAA  4797
               ||||||||||||||||||||||||||||||||||||||||||||||||||||||||||||
US_Col  4783   CAACCCTGAAGGTTTGATGTCATTAGGTGCTGACAAGCTGGTGTTGTTTACAAATTCCAA  4842

125_10  4798   TTTGGATTTTTGTAGCGTTGGTAAGTGTCTTAACAATGTGACTGGCGGTGCATTGCTTGA  4857
               ||||||||||||||||||||||||||||||||||||||||||||||||||||||||||||
US_Col  4843   TTTGGATTTTTGTAGCGTTGGTAAGTGTCTTAACAATGTGACTGGCGGTGCATTGCTTGA  4902

125_10  4858   AGCCATAAATGTATTTAAAAAGAGTAACAAAACAGTGCCTGCTGGCAACTGTGTTACTTT  4917
               ||||||||||||||||||||||||||||||||||||||||||||||||||||||||||||
US_Col  4903   AGCCATAAATGTATTTAAAAAGAGTAACAAAACAGTGCCTGCTGGCAACTGTGTTACTTT  4962

125_10  4918   TGAGTGTGCAGATATGATTTCTATTACTATGGTAGTATTGCCATCTGACGGTGATGCTAA  4977
               ||||||||||||||||||||||||||||||||||||||||||||||||||||||||||||
US_Col  4963   TGAGTGTGCAGATATGATTTCTATTACTATGGTAGTATTGCCATCTGACGGTGATGCTAA  5022

125_10  4978   TTATGACAAAAATTATGCACGCGCCGTCGTCAAGGTATCTAAGCTTAAAGGCAAGTTATT  5037
               ||||||||||||||||||||||||||||||||||||||||||||||||||||||||||||
US_Col  5023   TTATGACAAAAATTATGCACGCGCCGTCGTCAAGGTATCTAAGCTTAAAGGCAAGTTATT  5082

125_10  5038   GCTTGCTGTTGGTGATGCCATGTTGTATTCCAAGTTGTCCCACCTCAGCGTGTTAGGTTT  5097
               ||||||||||||||||||||||||||||||||||||||||||||||||||||||||||||
US_Col  5083   GCTTGCTGTTGGTGATGCCATGTTGTATTCCAAGTTGTCCCACCTCAGCGTGTTAGGTTT  5142

125_10  5098   CGTATCCACACCTGATGATGTGGAGCGTTTCTACGCAAATAAGAGTGTGGTTATTAAAGT  5157
               ||||||||||||||||||||||||||||||||||||||||||||||||||||||||||||
US_Col  5143   CGTATCCACACCTGATGATGTGGAGCGTTTCTACGCAAATAAGAGTGTGGTTATTAAAGT  5202

125_10  5158   TACTGAGGATACACGTAGTGTTAAGACTGTTAAAGTAGAATCCACTGTTACTTATGGACA  5217
               ||||||||||||||||||||||||||||||||||||||||||||||||||||||||||||
US_Col  5203   TACTGAGGATACACGTAGTGTTAAGACTGTTAAAGTAGAATCCACTGTTACTTATGGACA  5262

125_10  5218   ACAAATTGGACCTTGTCTTGTTAATGACACCGTTGTCACAGACAACAAACCTGTTGTTGC  5277
               ||||||||||||||||||||||||||||||||||||||||||||||||||||||||||||
US_Col  5263   ACAAATTGGACCTTGTCTTGTTAATGACACCGTTGTCACAGACAACAAACCTGTTGTTGC  5322

125_10  5278   TGATGTTGTAGCTAAGGTTGTACCAAGTGCTAATTGGGATTCACATTATGGTTTTGATAA  5337
               ||||||||||||||||||||||||||||||||||||||||||||||||||||||||||||
US_Col  5323   TGATGTTGTAGCTAAGGTTGTACCAAGTGCTAATTGGGATTCACATTATGGTTTTGATAA  5382

125_10  5338   GGCTGGTGAGTTCCACATGCTAGACCATACTGGGTTTGCCTTTCCTAGTGAAGTTGTTAA  5397
               ||||||||||||||||||||||||||||||||||||||||||||||||||||||||||||
US_Col  5383   GGCTGGTGAGTTCCACATGCTAGACCATACTGGGTTTGCCTTTCCTAGTGAAGTTGTTAA  5442

125_10  5398   CGGTAGGCGTGTGCTTAAAACCACAGATAATAACTGTTGGGTTAATGTTACATGTTTACA  5457
               ||||||||||||||||||||||||||||||||||||||||||||||||||||||||||||
US_Col  5443   CGGTAGGCGTGTGCTTAAAACCACAGATAATAACTGTTGGGTTAATGTTACATGTTTACA  5502

125_10  5458   ATTACAGTTTGCTAGATTTAGGTTCAAGTCAGCAGGTCTACAGGCTATGTGGGAGTCCTA  5517
               ||||||||||||||||||||||||||||||||||||||||||||||||||||||||||||
US_Col  5503   ATTACAGTTTGCTAGATTTAGGTTCAAGTCAGCAGGTCTACAGGCTATGTGGGAGTCCTA  5562
```

FIG. 2 (cont'd)

```
125_10   5518   TTGTACTGGTGATGTTGCTATGTTTGTGCATTGGTTGTACTGGCTTACTGGTGTTGACAA   5577
                ||||||||||||||||||||||||||||||||||||||||||||||||||||||||||||
US_Col   5563   TTGTACTGGTGATGTTGCTATGTTTGTGCATTGGTTGTACTGGCTTACTGGTGTTGACAA   5622

125_10   5578   AGGTCAGCCTAGTGATTCAGAAAATGCACTTAACATGTTGTCTAAGTACATTGTTCCTGC   5637
                ||||||||||||||||||||||||||||||||||||||||||||||||||||||||||||
US_Col   5623   AGGTCAGCCTAGTGATTCAGAAAATGCACTTAACATGTTGTCTAAGTACATTGTTCCTGC   5682

125_10   5638   TGGTTCTGTCACTATTGAACGTGTCACGCATGACGGTTGTTGTTGTAGTAAGCGTGTTGT   5697
                ||||||||||||||||||||||||||||||||||||||||||||||||||||||||||||
US_Col   5683   TGGTTCTGTCACTATTGAACGTGTCACGCATGACGGTTGTTGTTGTAGTAAGCGTGTTGT   5742

125_10   5698   CACTGCACCAGTTGTGAATGCTAGCGTGTTGAAGCTTGGCGTCGAGGATGGTCTTTGTCC   5757
                ||||||||||||||||||||||||||||||||||||||||||||||||||||||||||||
US_Col   5743   CACTGCACCAGTTGTGAATGCTAGCGTGTTGAAGCTTGGCGTCGAGGATGGTCTTTGTCC   5802

125_10   5758   ACATGGTCTTAACTACATTGACAAAGTTGTTGTAGTTAAAGGTACTACAATTGTTGTCAA   5817
                ||||||||||||||||||||||||||||||||||||||||||||||||||||||||||||
US_Col   5803   ACATGGTCTTAACTACATTGACAAAGTTGTTGTAGTTAAAGGTACTACAATTGTTGTCAA   5862

125_10   5818   TGTTGGAAAACCTGTAGTGGCACCATCGCACCTCTTTCTTAAGGGTGTTTCCTACACAAC   5877
                ||||||||||||||||||||||||||||||||||||||||||||||||||||||||||||
US_Col   5863   TGTTGGAAAACCTGTAGTGGCACCATCGCACCTCTTTCTTAAGGGTGTTTCCTACACAAC   5662

125_10   5878   ATTCCTAGATAATGGTAACGGTGTTGCCGGCCATTATACTGTTTTTGATCATGACACTGG   5937
                ||||||||||||||||||||||||||||||||||||||||||||||||||||||||||||
US_Col   5663   ATTCCTAGATAATGGTAACGGTGTTGCCGGCCATTATACTGTTTTTGATCATGACACTGG   5982

125_10   5938   TATGGTGCATGATGGAGATGTTTTTGTACCAGGTGATCTCAATGTGTCTCCTGTTACAAA   5997
                ||||||||||||||||||||||||||||||||||||||||||||||||||||||||||||
US_Col   5983   TATGGTGCATGATGGAGATGTTTTTGTACCAGGTGATCTCAATGTGTCTCCTGTTACAAA   6042

125_10   5998   TGTTGTCGTCTCAGAGCAGACGGCTGTTGTGATTAAAGACCCTGTGAAGAAAGTAGAGTT   6057
                ||||||||||||||||||||||||||||||||||||||||||||||||||||||||||||
US_Col   6043   TGTTGTCGTCTCAGAGCAGACGGCTGTTGTGATTAAAGACCCTGTGAAGAAAGTAGAGTT   6102

125_10   6058   AGACGCTACAAAGCTGTTAGACACTATGAATTATGCATCGGAAAGATTCTTTTCCTTTGG   6117
                ||||||||||||||||||||||||||||||||||||||||||||||||||||||||||||
US_Col   6103   AGACGCTACAAAGCTGTTAGACACTATGAATTATGCATCGGAAAGATTCTTTTCCTTTGG   6162

125_10   6118   TGATTTTATGTCACGTAATTTAATTACAGTGTTTTTGTACATCCTTAGTATTTTGGGTCT   6177
                ||||||||||||||||||||||||||||||||||||||||||||||||||||||||||||
US_Col   6163   TGATTTTATGTCACGTAATTTAATTACAGTGTTTTTGTACATCCTTAGTATTTTGGGTCT   6222

125_10   6178   CTGTTTTAGGGCCTTTCGTAAGAGGGATGTTAAAGTTCTAGCTGGTGTACCCCAACGTAC   6237
                ||||||||||||||||||||||||||||||||||||||||||||||||||||||||||||
US_Col   6223   CTGTTTTAGGGCCTTTCGTAAGAGGGATGTTAAAGTTCTAGCTGGTGTACCCCAACGTAC   6282

125_10   6238   TGGTATTATATTGCGTAAAAGTGTGCGCTATAATGCAAAGGCTTTGGGTGTCTTCTTCAA   6297
                ||||||||||||||||||||||||||||||||||||||||||||||||||||||||||||
US_Col   6283   TGGTATTATATTGCGTAAAAGTGTGCGCTATAATGCAAAGGCTTTGGGTGTCTTCTTCAA   6342

125_10   6298   GCTAAAACTTTATTGGTTCAAAGTTCTTGGTAAGTTTAGTTTGGGTATTTATGCATTGTA   6357
                ||||||||||||||||||||||||||||||||||||||||||||||||||||||||||||
US_Col   6343   GCTAAAACTTTATTGGTTCAAAGTTCTTGGTAAGTTTAGTTTGGGTATTTATGCATTGTA   6402

125_10   6358   TGCATTACTATTCATGACAATACGCTTTACACCTATAGGTGGCCCTGTTTGTGATGATGT   6417
                ||||||||||||||||||||||||||||||||||||||||||||||||||||||||||||
US_Col   6403   TGCATTACTATTCATGACAATACGCTTTACACCTATAGGTGGCCCTGTTTGTGATGATGT   6462

125_10   6418   TGTTGCTGGTTATGCTAATTCTAGTTTTGACAAGAATGAGTATTGCAACAGTGTTATTTG   6477
                ||||||||||||||||||||||||||||||||||||||||||||||||||||||||||||
US_Col   6463   TGTTGCTGGTTATGCTAATTCTAGTTTTGACAAGAATGAGTATTGCAACAGTGTTATTTG   6522
```

FIG. 2 (cont'd)

```
125_10  6478   TAAGGTCTGTCTCTATGGGTACCAGGAACTTTCGGACTTCTCTCACACACAGGTAGTATG   6537
               ||||||||||||||||||||||||||||||||||||||||||||||||||||||||||||
US_Col  6523   TAAGGTCTGTCTCTATGGGTACCAGGAACTTTCGGACTTCTCTCACACACAGGTAGTATG   6582

125_10  6538   GCAACACCTTAGAGACCCATTAATTGGTAATGTGATGCCTTTCTTTTATTTGGCATTTCT   6597
               ||||||||||||||||||||||||||||||||||||||||||||||||||||||||||||
US_Col  6583   GCAACACCTTAGAGACCCATTAATTGGTAATGTGATGCCTTTCTTTTATTTGGCATTTCT   6642

125_10  6598   GGCAATTTTTGGGGGTGTTTATGTAAAGGCTATTACTCTCTATTTTATTTTCCAGTATCT   6657
               ||||||||||||||||||||||||||||||||||||||||||||||||||||||||||||
US_Col  6643   GGCAATTTTTGGGGGTGTTTATGTAAAGGCTATTACTCTCTATTTTATTTTCCAGTATCT   6702

125_10  6658   TAACATACTTGGTGTGTTTTTGGGCCTACAACAGTCCATTTGGTTTTTGCAGCTTGTGCC   6717
               ||||||||||||||||||||||||||||||||||||||||||||||||||||||||||||
US_Col  6703   TAACATACTTGGTGTGTTTTTGGGCCTACAACAGTCCATTTGGTTTTTGCAGCTTGTGCC   6762

125_10  6718   TTTTGATGTCTTTGGTGACGAGATCGTCGTCTTTTTCATCGTTACACGCGTATTGATGTT   6777
               ||||||||||||||||||||||||||||||||||||||||||||||||||||||||||||
US_Col  6763   TTTTGATGTCTTTGGTGACGAGATCGTCGTCTTTTTCATCGTTACACGCGTATTGATGTT   6822

125_10  6778   CCTTAAGCATGTTTTCCTTGGCTGCGATAAGGCATCTTGTGTGGCTTGCTCTAAGAGTGC   6837
               ||||||||||||||||||||||||||||||||||||||||||||||||||||||||||||
US_Col  6823   CCTTAAGCATGTTTTCCTTGGCTGCGATAAGGCATCTTGTGTGGCTTGCTCTAAGAGTGC   6882

125_10  6838   TCGCCTTAAGCGCGTTCCTGTCCAGACTATTTTTCAGGGTACTAGCAAATCCTTCTACGT   6897
               ||||||||||||||||||||||||||||||||||||||||||||||||||||||||||||
US_Col  6883   TCGCCTTAAGCGCGTTCCTGTCCAGACTATTTTTCAGGGTACTAGCAAATCCTTCTACGT   6942

125_10  6898   ACATGCCAATGGTGGTTCTAAGTTCTGTAAGAAGCACAATTTCTTTTGTTTAAATTGTGA   6957
               ||||||||||||||||||||||||||||||||||||||||||||||||||||||||||||
US_Col  6943   ACATGCCAATGGTGGTTCTAAGTTCTGTAAGAAGCACAATTTCTTTTGTTTAAATTGTGA   7002

125_10  6958   TTCTTATGGTCCAGGCTGCACTTTTATTAATGACGTCATTGCAACTGAAGTTGGTAATGT   7017
               ||||||||||||||||||||||||||||||||||||||||||||||||||||||||||||
US_Col  7003   TTCTTATGGTCCAGGCTGCACTTTTATTAATGACGTCATTGCAACTGAAGTTGGTAATGT   7062

125_10  7018   TGTCAAACTTAATGTGCAACCGACAGGTCCTGCCACTATTCTTATTGACAAGGTTGAATT   7077
               ||||||||||||||||||||||||||||||||||||||||||||||||||||||||||||
US_Col  7063   TGTCAAACTTAATGTGCAACCGACAGGTCCTGCCACTATTCTTATTGACAAGGTTGAATT   7122

125_10  7078   CAGTAATGGTTTTTACTATCTTTATAGTGGTGACACATTTTGGAAGTACAACTTTGACAT   7137
               ||||||||||||||||||||||||||||||||||||||||||||||||||||||||||||
US_Col  7123   CAGTAATGGTTTTTACTATCTTTATAGTGGTGACACATTTTGGAAGTACAACTTTGACAT   7182

125_10  7138   AACAGATAACAAATACACTTGCAAAGAGTCACTTAAAAATTGTAGCATAATCACAGACTT   7197
               ||||||||||||||||||||||||||||||||||||||||||||||||||||||||||||
US_Col  7183   AACAGATAACAAATACACTTGCAAAGAGTCACTTAAAAATTGTAGCATAATCACAGACTT   7242

125_10  7198   TATTGTTTTTAACAATAATGGTTCCAATGTAAATCAGGTTAAGAATGCATGTGTGTATTT   7257
               ||||||||||||||||||||||||||||||||||||||||||||||||||||||||||||
US_Col  7243   TATTGTTTTTAACAATAATGGTTCCAATGTAAATCAGGTTAAGAATGCATGTGTGTATTT   7302

125_10  7258   TTCACAGATGCTTTGTAAACCTGTTAAGTTAGTGGACTCAGCGTTGTTGGCCAGTTTGTC   7317
               ||||||||||||||||||||||||||||||||||||||||||||||||||||||||||||
US_Col  7303   TTCACAGATGCTTTGTAAACCTGTTAAGTTAGTGGACTCAGCGTTGTTGGCCAGTTTGTC   7362

125_10  7318   TGTTGATTTTGGTGCAAGCTTACATAGTGCTTTTGTTAGTGTGTTGTCGAATAGTTTTGG   7377
               ||||||||||||||||||||||||||||||||||||||||||||||||||||||||||||
US_Col  7363   TGTTGATTTTGGTGCAAGCTTACATAGTGCTTTTGTTAGTGTGTTGTCGAATAGTTTTGG   7422
```

FIG. 2 (cont'd)

```
125_10  7378  CAAAGACCTGTCAAGTTGTAATGACATGCAGGATTGCAAGAGCACATTGGGTTTTGATGA  7437
              ||||||||||||||||||||||||||||||||||||||||||||||||||||||||||||
US_Col  7423  CAAAGACCTGTCAAGTTGTAATGACATGCAGGATTGCAAGAGCACATTGGGTTTTGATGA  7482

125_10  7438  TGTACCATTGGATACCTTTAATGCTGCTGTTGCTGAGGCTCATCGTTACGATGTCCTCTT  7497
              ||||||||||||||||||||||||||||||||||||||||||||||||||||||||||||
US_Col  7483  TGTACCATTGGATACCTTTAATGCTGCTGTTGCTGAGGCTCATCGTTACGATGTCCTCTT  7542

125_10  7498  GACTGACATGTCGTTCAACAATTTTACCACCAGTTATGCAAAACCAGAGGAAAAACTTCC  7557
              ||||||||||||||||||||||||||||||||||||||||||||||||||||||||||||
US_Col  7543  GACTGACATGTCGTTCAACAATTTTACCACCAGTTATGCAAAACCAGAGGAAAAACTTCC  7602

125_10  7558  CGTCCATGACATTGCCACGTGTATGCGTGTAGGTGCCAAGATTGTTAATCATAACGTTCT  7617
              ||||||||||||||||||||||||||||||||||||||||||||||||||||||||||||
US_Col  7603  CGTCCATGACATTGCCACGTGTATGCGTGTAGGTGCCAAGATTGTTAATCATAACGTTCT  7662

125_10  7618  TGTCAAGGATAGTATACCTGTGGTGTGGCTTGTACGTGATTTCATTGCCCTTTCTGAAGA  7677
              ||||||||||||||||||||||||||||||||||||||||||||||||||||||||||||
US_Col  7663  TGTCAAGGATAGTATACCTGTGGTGTGGCTTGTACGTGATTTCATTGCCCTTTCTGAAGA  7722

125_10  7678  AACTAGGAAGTACATTATTCGTACGACTAAAGTTAAGGGTATAACCTTCATGTTGACCTT  7737
              ||||||||||||||||||||||||||||||||||||||||||||||||||||||||||||
US_Col  7723  AACTAGGAAGTACATTATTCGTACGACTAAAGTTAAGGGTATAACCTTCATGTTGACCTT  7782

125_10  7738  TAATGATTGTCGTATGCATACTACCATACCTACTGTTTGCATTGCAAATAAGAAGGGTGC  7797
              ||||||||||||||||||||||||||||||||||||||||||||||||||||||||||||
US_Col  7783  TAATGATTGTCGTATGCATACTACCATACCTACTGTTTGCATTGCAAATAAGAAGGGTGC  7842

125_10  7798  AGGTCTTCCTAGTTTTTCAAAGGTTAAGAAATTCTTCTGGTTTTTGTGTCTGTTCATAGT  7857
              ||||||||||||||||||||||||||||||||||||||||||||||||||||||||||||
US_Col  7843  AGGTCTTCCTAGTTTTTCAAAGGTTAAGAAATTCTTCTGGTTTTTGTGTCTGTTCATAGT  7902

125_10  7858  TGCTGTTTTCTTTGCACTAAGCTTTTTTGATTTTAGTACTCAGGTTAGCAGTGATAGTGA  7917
              ||||||||||||||||||||||||||||||||||||||||||||||||||||||||||||
US_Col  7903  TGCTGTTTTCTTTGCACTAAGCTTTTTTGATTTTAGTACTCAGGTTAGCAGTGATAGTGA  7962

125_10  7918  TTATGACTTCAAGTATATTGAGAGTGGCCAGTTGAAGACTTTTGACAATCCACTTAGTTG  7977
              ||||||||||||||||||||||||||||||||||||||||||||||||||||||||||||
US_Col  7963  TTATGACTTCAAGTATATTGAGAGTGGCCAGTTGAAGACTTTTGACAATCCACTTAGTTG  8022

125_10  7978  TGTGCATAATGTCTTTAGTAACTTCGACCAGTGGCATGATGCCAAGTTTGGTTTCACCCC  8037
              ||||||||||||||||||||||||||||||||||||||||||||||||||||||||||||
US_Col  8023  TGTGCATAATGTCTTTAGTAACTTCGACCAGTGGCATGATGCCAAGTTTGGTTTCACCCC  8082

125_10  8038  CGTCAACAATCCTAGTTGTCCTATAGTCGTTGGTGTATCAGACGAAGCGCGCACTGTTCC  8097
              ||||||||||||||||||||||||||||||||||||||||||||||||||||||||||||
US_Col  8083  CGTCAACAATCCTAGTTGTCCTATAGTCGTTGGTGTATCAGACGAAGCGCGCACTGTTCC  8142

125_10  8098  AGGTATCCCAGCAGGTGTTTATTTAGCTGGTAAAACACTTGTTTTTGCTATTAACACCAT  8157
              ||||||||||||||||||||||||||||||||||||||||||||||||||||||||||||
US_Col  8143  AGGTATCCCAGCAGGTGTTTATTTAGCTGGTAAAACACTTGTTTTTGCTATTAACACCAT  8202

125_10  8158  TTTTGGTACATCTGGTTTGTGCTTTGATGCTAGTGGCGTTGCTGATAAGGGCGCTTGCAT  8217
              ||||||||||||||||||||||||||||||||||||||||||||||||||||||||||||
US_Col  8203  TTTTGGTACATCTGGTTTGTGCTTTGATGCTAGTGGCGTTGCTGATAAGGGCGCTTGCAT  8262

125_10  8218  TTTTAATTCGGCTTGCACCACATTATCTGGTTTGGGTGGAACTGCTGTCTACTGTTATAA  8277
              ||||||||||||||||||||||||||||||||||||||||||||||||||||||||||||
US_Col  8263  TTTTAATTCGGCTTGCACCACATTATCTGGTTTGGGTGGAACTGCTGTCTACTGTTATAA  8322

125_10  8278  GAATGGTCTAGTTGAAGGTGCTAAACTTTATAGTGAGTTGGCACCTCATAGCTACTATAA  8337
              ||||||||||||||||||||||||||||||||||||||||||||||||||||||||||||
US_Col  8323  GAATGGTCTAGTTGAAGGTGCTAAACTTTATAGTGAGTTGGCACCTCATAGCTACTATAA  8382
```

FIG. 2 (cont'd)

```
125_10  8338  AATGGTAGATGGTAATGCTGTGTCTTTACCTGAAATTATCTCACGCGGCTTTGGCATCCG  8397
              ||||||||||||||||||||||||||||||||||||||||||||||||||||||||||||
US_Col  8383  AATGGTAGATGGTAATGCTGTGTCTTTACCTGAAATTATCTCACGCGGCTTTGGCATCCG  8442

125_10  8398  TACTATCCGTACAAAGGCTATGACCTACTGTCGCGTTGGCCAGTGTGTGCAATCTGCAGA  8457
              ||||||||||||||||||||||||||||||||||||||||||||||||||||||||||||
US_Col  8443  TACTATCCGTACAAAGGCTATGACCTACTGTCGCGTTGGCCAGTGTGTGCAATCTGCAGA  8502

125_10  8458  AGGTGTTTGTTTTGGCGCCGATAGATTCTTTGTCTATAATGCAGAATCTGGTTCTGACTT  8517
              ||||||||||||||||||||||||||||||||||||||||||||||||||||||||||||
US_Col  8503  AGGTGTTTGTTTTGGCGCCGATAGATTCTTTGTCTATAATGCAGAATCTGGTTCTGACTT  8562

125_10  8518  TGTTTGTGGCACAGGGCTCTTTACATTGTTGATGAACGTTATTAGTGTTTTTTCCAAGAC  8577
              ||||||||||||||||||||||||||||||||||||||||||||||||||||||||||||
US_Col  8563  TGTTTGTGGCACAGGGCTCTTTACATTGTTGATGAACGTTATTAGTGTTTTTTCCAAGAC  8622

125_10  8578  AGTACCAGTAACTGTGTTGTCTGGTCAAATACTTTTTAATTGCATTATTGCTTTTGCTGC  8637
              ||||||||||||||||||||||||||||||||||||||||||||||||||||||||||||
US_Col  8623  AGTACCAGTAACTGTGTTGTCTGGTCAAATACTTTTTAATTGCATTATTGCTTTTGCTGC  8682

125_10  8638  TGTTGCGGTGTGTTTCTTATTTACAAAGTTTAAGCGCATGTTCGGTGATATGTCTGTTGG  8697
              ||||||||||||||||||||||||||||||||||||||||||||||||||||||||||||
US_Col  8683  TGTTGCGGTGTGTTTCTTATTTACAAAGTTTAAGCGCATGTTCGGTGATATGTCTGTTGG  8742

125_10  8698  CGTTTTCACTGTCGGTGCTTGTACTTTGTTGAACAATGTTTCCTACATTGTAACACAGAA  8757
              ||||||||||||||||||||||||||||||||||||||||||||||||||||||||||||
US_Col  8743  CGTTTTCACTGTCGGTGCTTGTACTTTGTTGAACAATGTTTCCTACATTGTAACACAGAA  8802

125_10  8758  CACACTTGGCATGTTGGGCTATGCAACTTTGTACTTTTTGTGCACTAAAGGTGTTAGATA  8817
              ||||||||||||||||||||||||||||||||||||||||||||||||||||||||||||
US_Col  8803  CACACTTGGCATGTTGGGCTATGCAACTTTGTACTTTTTGTGCACTAAAGGTGTTAGATA  8862

125_10  8818  TATGTGGATTTGGCATTTGGGATTTTTGATCTCATATATACTTATTGCACCATGGTGGGT  8877
              ||||||||||||||||||||||||||||||||||||||||||||||||||||||||||||
US_Col  8863  TATGTGGATTTGGCATTTGGGATTTTTGATCTCATATATACTTATTGCACCATGGTGGGT  8662

125_10  8878  TTTGATGGTTTATGCCTTTTCAGCCATTTTTGAGTTTATGCCTAACCTTTTTAAGCTTAA  8937
              ||||||||||||||||||||||||||||||||||||||||||||||||||||||||||||
US_Col  8663  TTTGATGGTTTATGCCTTTTCAGCCATTTTTGAGTTTATGCCTAACCTTTTTAAGCTTAA  8982

125_10  8938  GGTTTCAACACAACTTTTTGAGGGTGACAAGTTCGTAGGCTCTTTTGAAAATGCTGCAGC  8997
              ||||||||||||||||||||||||||||||||||||||||||||||||||||||||||||
US_Col  8983  GGTTTCAACACAACTTTTTGAGGGTGACAAGTTCGTAGGCTCTTTTGAAAATGCTGCAGC  9042

125_10  8998  AGGTACATTTGTGCTTGATATGCATGCCTATGAGAGACTTGCCAACTCTATCTCAACTGA  9057
              ||||||||||||||||||||||||||||||||||||||||||||||||||||||||||||
US_Col  9043  AGGTACATTTGTGCTTGATATGCATGCCTATGAGAGACTTGCCAACTCTATCTCAACTGA  9102

125_10  9058  AAAACTGCGTCAGTATGCTAGTACTTACAATAAGTACAAGTATTATTCAGGCAGTGCTTC  9117
              ||||||||||||||||||||||||||||||||||||||||||||||||||||||||||||
US_Col  9103  AAAACTGCGTCAGTATGCTAGTACTTACAATAAGTACAAGTATTATTCAGGCAGTGCTTC  9162

125_10  9118  AGAGGCTGATTACAGGCTTGCTTGTTTTGCCCATTTGGCCAAGGCTATGATGGATTATGC  9177
              ||||||||||||||||||||||||||||||||||||||||||||||||||||||||||||
US_Col  9163  AGAGGCTGATTACAGGCTTGCTTGTTTTGCCCATTTGGCCAAGGCTATGATGGATTATGC  6622

125_10  9178  TTCTAATCACAACGACACGTTATACACACCACCCACTGTGAGTTACAATTCAACTCTACA  6637
              ||||||||||||||||||||||||||||||||||||||||||||||||||||||||||||
US_Col  6623  TTCTAATCACAACGACACGTTATACACACCACCCACTGTGAGTTACAATTCAACTCTACA  6682
```

FIG. 2 (cont'd)

```
125_10  6638   GGCTGGCTTGCGTAAGATGGCACAACCATCTGGTGTTGTTGAGAAGTGCATAGTTCGTGT  6697
               ||||||||||||||||||||||||||||||||||||||||||||||||||||||||||||
US_Col  6683   GGCTGGCTTGCGTAAGATGGCACAACCATCTGGTGTTGTTGAGAAGTGCATAGTTCGTGT  9342

125_10  6698   TTGCTATGGTAATATGGCTCTTAATGGCCTATGGCTTGGTGATACTGTTATCTGCCCACG  9357
               ||||||||||||||||||||||||||||||||||||||||||||||||||||||||||||
US_Col  9343   TTGCTATGGTAATATGGCTCTTAATGGCCTATGGCTTGGTGATACTGTTATCTGCCCACG  9402

125_10  9358   CCATGTTATAGCGTCTAGTACTACTAGCACTATAGATTATGACTATGCCCTTTCTGTTTT  9417
               ||||||||||||||||||||||||||||||||||||||||||||||||||||||||||||
US_Col  9403   CCATGTTATAGCGTCTAGTACTACTAGCACTATAGATTATGACTATGCCCTTTCTGTTTT  9462

125_10  9418   ACGCCTCYACAACTTCTCCATTTCATCTGGTAATGTTTTCCTAGGTGTTGTGGGTGTAAC  9477
               ||||||| ||||||||||||||||||||||||||||||||||||||||||||||||||||
US_Col  9463   ACGCCTCCACAACTTCTCCATTTCATCTGGTAATGTTTTCCTAGGTGTTGTGGGTGTAAC  9522

125_10  9478   CATGCGAGGTGCTTTGTTGCAGATAAAGGTTAATCAAAACAATGTCCACACGCCTAAGTA  9537
               ||||||||||||||||||||||||||||||||||||||||||||||||||||||||||||
US_Col  9523   CATGCGAGGTGCTTTGTTGCAGATAAAGGTTAATCAAAACAATGTCCACACGCCTAAGTA  9582

125_10  9538   CACCTATCGCACAGTTAGACCGGGTGAATCTTTTAATATCTTGGCGTGCTATGATGGTTC  9597
               ||||||||||||||||||||||||||||||||||||||||||||||||||||||||||||
US_Col  9583   CACCTATCGCACAGTTAGACCGGGTGAATCTTTTAATATCTTGGCGTGCTATGATGGTTC  9642

125_10  9598   TGCAGCTGGTGTTTACGGCGTTAACATGCGCTCTAATTACACTATTAGAGGCTCGTTCAT  9657
               ||||||||||||||||||||||||||||||||||||||||||||||||||||||||||||
US_Col  9643   TGCAGCTGGTGTTTACGGCGTTAACATGCGCTCTAATTACACTATTAGAGGCTCGTTCAT  9702

125_10  9658   TAATGGCGCTTGTGGTTCACCTGGTTATAACATTAACAATGGTACCGTTGAGTTTTGCTA  9717
               ||||||||||||||||||||||||||||||||||||||||||||||||||||||||||||
US_Col  9703   TAATGGCGCTTGTGGTTCACCTGGTTATAACATTAACAATGGTACCGTTGAGTTTTGCTA  9762

125_10  9718   TTTACACCAGCTTGAACTTGGTTCAGGCTGTCATGTTGGTAGCGACTTAGATGGTGTTAT  9777
               ||||||||||||||||||||||||||||||||||||||||||||||||||||||||||||
US_Col  9763   TTTACACCAGCTTGAACTTGGTTCAGGCTGTCATGTTGGTAGCGACTTAGATGGTGTTAT  9822

125_10  9778   GTATGGTGGTTATGAGGACCAACCTACTTTGCAAGTTGAAGGCGCTAGTAGTCTGTTTAC  9837
               ||||||||||||||||||||||||||||||||||||||||||||||||||||||||||||
US_Col  9823   GTATGGTGGTTATGAGGACCAACCTACTTTGCAAGTTGAAGGCGCTAGTAGTCTGTTTAC  9882

125_10  9838   AGAGAATGTGTTGGCATTTCTTTATGCAGCACTCATTAATGGTTCTACCTGGTGGCTTAG  9897
               ||||||||||||||||||||||||||||||||||||||||||||||||||||||||||||
US_Col  9883   AGAGAATGTGTTGGCATTTCTTTATGCAGCACTCATTAATGGTTCTACCTGGTGGCTTAG  9942

125_10  9898   TTCTTCTAGGATTGCTGTAGACAGGTTTAATGAGTGGGCTGTTCATAATGGTATGACAAC  9957
               ||||||||||||||||||||||||||||||||||||||||||||||||||||||||||||
US_Col  9943   TTCTTCTAGGATTGCTGTAGACAGGTTTAATGAGTGGGCTGTTCATAATGGTATGACAAC  10002

125_10  9958   AGTAGTTAATACTGATTGCTTTTCTATTCTTGCTGCTAAGACTGGTGTTGATGTACAACG  10017
               ||||||||||||||||||||||||||||||||||||||||||||||||||||||||||||
US_Col  10003  AGTAGTTAATACTGATTGCTTTTCTATTCTTGCTGCTAAGACTGGTGTTGATGTACAACG  10062

125_10  10018  TTTGTTGGCCTCAATCCAGTCTCTGCATAAGAATTTTGGTGGAAAGCAAATTCTTGGCTA  10077
               ||||||||||||||||||||||||||||||||||||||||||||||||||||||||||||
US_Col  10063  TTTGTTGGCCTCAATCCAGTCTCTGCATAAGAATTTTGGTGGAAAGCAAATTCTTGGCTA  10122

125_10  10078  TACCTCGTTGACAGATGAGTTTACTACAGGTGAAGTTATACGTCAAATGTATGGCGTTWA  10137
               |||||||||||||||||||||||||||||||||||||||||||||||||||||||||| |
US_Col  10123  TACCTCGTTGACAGATGAGTTTACTACAGGTGAAGTTATACGTCAAATGTATGGCGTTAA  10182

125_10  10138  TCTTCAGAGTGGTTATGTTTCACGCGCCTGTAGAAATGTCTTGCTGGTTGGTTCTTTTCT  10197
               ||||||||||||||||||||||||||||||||||||||||||||||||||||||||||||
US_Col  10183  TCTTCAGAGTGGTTATGTTTCACGCGCCTGTAGAAATGTCTTGCTGGTTGGTTCTTTTCT  10242
```

FIG. 2 (cont'd)

```
125_10  10198  GACTTTCTTTTGGTCAGAATTAGTTTCCTACACTAAGTTCTTTTGGGTAAATCCTGGTTA  10257
               ||||||||||||||||||||||||||||||||||||||||||||||||||||||||||||
US_Col  10243  GACTTTCTTTTGGTCAGAATTAGTTTCCTACACTAAGTTCTTTTGGGTAAATCCTGGTTA  10302

125_10  10258  TGTCACACCTATGTTTGCGTGTTTGTCATTGCTGTCCTCACTTTTGATGTTCACACTCAA  10317
               ||||||||||||||||||||||||||||||||||||||||||||||||||||||||||||
US_Col  10303  TGTCACACCTATGTTTGCGTGTTTGTCATTGCTGTCCTCACTTTTGATGTTCACACTCAA  10362

125_10  10318  GCATAAGACATTGTTTTTCCAGGTCTTTCTAATACCTGCTCTGATTGTTACATCTTGCAT  10377
               ||||||||||||||||||||||||||||||||||||||||||||||||||||||||||||
US_Col  10363  GCATAAGACATTGTTTTTCCAGGTCTTTCTAATACCTGCTCTGATTGTTACATCTTGCAT  6622

125_10  10378  TAATTTGGCATTTGATGTTGAAGTCTACAACTATTTGGCAGAGCATTTTGATTACCATGT  6637
               ||||||||||||||||||||||||||||||||||||||||||||||||||||||||||||
US_Col  6623   TAATTTGGCATTTGATGTTGAAGTCTACAACTATTTGGCAGAGCATTTTGATTACCATGT  6682

125_10  6638   TTCTCTCATGGGTTTTAATGCACAAGGTCTTGTTAACATCTTTGTCTGCTTTGTTGTTAC  6697
               ||||||||||||||||||||||||||||||||||||||||||||||||||||||||||||
US_Col  6683   TTCTCTCATGGGTTTTAATGCACAAGGTCTTGTTAACATCTTTGTCTGCTTTGTTGTTAC  10542

125_10  6698   CATTTTACACGGCACATACACATGGCGCTTTTTTAACACACCTGTGAGTTCTGTCACTTA  10557
               ||||||||||||||||||||||||||||||||||||||||||||||||||||||||||||
US_Col  10543  CATTTTACACGGCACATACACATGGCGCTTTTTTAACACACCTGTGAGTTCTGTCACTTA  10602

125_10  10558  TGTGGTAGCTTTGCTGACTGCGGCATATAACTATTTTTACGCTAGTGACATTCTTAGTTG  10617
               ||||||||||||||||||||||||||||||||||||||||||||||||||||||||||||
US_Col  10603  TGTGGTAGCTTTGCTGACTGCGGCATATAACTATTTTTACGCTAGTGACATTCTTAGTTG  10662

125_10  10618  TGCTATGACACTATTTGCTAGTGTGACTGGCAACTGGTTCGTTGGTGCTGTTTGTTATAA  10677
               ||||||||||||||||||||||||||||||||||||||||||||||||||||||||||||
US_Col  10663  TGCTATGACACTATTTGCTAGTGTGACTGGCAACTGGTTCGTTGGTGCTGTTTGTTATAA  10722

125_10  10678  AGCTGCTGTTTATATGGCCTTGAGATTTCCTACTTTTGTGGCTATTTTTGGTGATATTAA  10737
               ||||||||||||||||||||||||||||||||||||||||||||||||||||||||||||
US_Col  10723  AGCTGCTGTTTATATGGCCTTGAGATTTCCTACTTTTGTGGCTATTTTTGGTGATATTAA  10782

125_10  10738  GAGTGTTATGTTCTGTTACCTTGTGTTGGGTTATTTTACCTGTTGCTTCTACGGTATTCT  10797
               ||||||||||||||||||||||||||||||||||||||||||||||||||||||||||||
US_Col  10783  GAGTGTTATGTTCTGTTACCTTGTGTTGGGTTATTTTACCTGTTGCTTCTACGGTATTCT  10842

125_10  10798  CTACTGGTTCAACAGGTTTTTTAAGGTTAGTGTAGGTGTCTATGACTATACTGTTAGTGC  10857
               ||||||||||||||||||||||||||||||||||||||||||||||||||||||||||||
US_Col  10843  CTACTGGTTCAACAGGTTTTTTAAGGTTAGTGTAGGTGTCTATGACTATACTGTTAGTGC  10902

125_10  10858  TGCTGAGTTTAAGTATATGGTTGCTAACGGCCTACGTGCACCAACTGGAACACTTGATTC  10917
               ||||||||||||||||||||||||||||||||||||||||||||||||||||||||||||
US_Col  10903  TGCTGAGTTTAAGTATATGGTTGCTAACGGCCTACGTGCACCAACTGGAACACTTGATTC  10962

125_10  10918  ACTACTTCTGTCTGCCAAATTGATTGGTATTGGTGGTGAGCGGAATATTAAGATTTCTTC  10977
               ||||||||||||||||||||||||||||||||||||||||||||||||||||||||||||
US_Col  10963  ACTACTTCTGTCTGCCAAATTGATTGGTATTGGTGGTGAGCGGAATATTAAGATTTCTTC  11022

125_10  10978  CGTTCAGTCTAAACTGACTGATATTAAGTGTAGTAACGTTGTGCTTTTAGGCTGTCTCTC  11037
               ||||||||||||||||||||||||||||||||||||||||||||||||||||||||||||
US_Col  11023  CGTTCAGTCTAAACTGACTGATATTAAGTGTAGTAACGTTGTGCTTTTAGGCTGTCTCTC  11082

125_10  11038  TAGCATGAATGTCTCAGCAAATTCAACAGAATGGGCCTATTGTGTTGACTTGCATAACAA  11097
               ||||||||||||||||||||||||||||||||||||||||||||||||||||||||||||
US_Col  11083  TAGCATGAATGTCTCAGCAAATTCAACAGAATGGGCCTATTGTGTTGACTTGCATAACAA  11142
```

FIG. 2 (cont'd)

```
125_10  11098  GATCAACTTGTGTAATGACCCAGAAAAAGCGCAGGAAATGCTACTTGCTTTGTTGGCATT  11157
               ||||||||||||||||||||||||||||||||||||||||||||||||||||||||||||
US_Col  11143  GATCAACTTGTGTAATGACCCAGAAAAAGCGCAGGAAATGCTACTTGCTTTGTTGGCATT  11202

125_10  11158  TTTCCTTAGTAAGAATAGTGCTTTTGGTTTAGATGACTTATTGGAATCCTATTTTAATGA  11217
               ||||||||||||||||||||||||||||||||||||||||||||||||||||||||||||
US_Col  11203  TTTCCTTAGTAAGAATAGTGCTTTTGGTTTAGATGACTTATTGGAATCCTATTTTAATGA  11262

125_10  11218  CAATAGTATGTTGCAGAGTGTTGCATCTACTTATGTCGGTTTGCCTTCTTATGTCATTTA  11277
               ||||||||||||||||||||||||||||||||||||||||||||||||||||||||||||
US_Col  11263  CAATAGTATGTTGCAGAGTGTTGCATCTACTTATGTCGGTTTGCCTTCTTATGTCATTTA  11322

125_10  11278  TGAAAATGCACGCCAACAGTATGAAGATGCTGTTAATAATGGTTCTCCACCTCAGTTGGT  11337
               ||||||||||||||||||||||||||||||||||||||||||||||||||||||||||||
US_Col  11323  TGAAAATGCACGCCAACAGTATGAAGATGCTGTTAATAATGGTTCTCCACCTCAGTTGGT  11382

125_10  11338  TAAGCAATTGCGCCATGCCATGAATGTAGCAAAGAGCGAATTTGACCGTGAGGCTTCTAC  11397
               ||||||||||||||||||||||||||||||||||||||||||||||||||||||||||||
US_Col  11383  TAAGCAATTGCGCCATGCCATGAATGTAGCAAAGAGCGAATTTGACCGTGAGGCTTCTAC  11442

125_10  11398  TCAGCGTAAGCTTGATAGAATGGCGGAACAGGCTGCAGCACAGATGTACAAAGAGGCACG  11457
               ||||||||||||||||||||||||||||||||||||||||||||||||||||||||||||
US_Col  11443  TCAGCGTAAGCTTGATAGAATGGCGGAACAGGCTGCAGCACAGATGTACAAAGAGGCACG  11502

125_10  11458  AGCAGTTAATAGGAAGTCCAAAGTTGTAAGTGCTATGCATTCACTGCTTTTTGGTATGTT  11517
               ||||||||||||||||||||||||||||||||||||||||||||||||||||||||||||
US_Col  11503  AGCAGTTAATAGGAAGTCCAAAGTTGTAAGTGCTATGCATTCACTGCTTTTTGGTATGTT  11562

125_10  11518  GAGACGTTTGGACATGTCTTCTGTAGACACCATTCTCAACTTGGCAAAGGATGGGGTTGT  11577
               ||||||||||||||||||||||||||||||||||||||||||||||||||||||||||||
US_Col  11563  GAGACGTTTGGACATGTCTTCTGTAGACACCATTCTCAACTTGGCAAAGGATGGGGTTGT  11622

125_10  11578  ACCTCTGTCTGTCATACCGGCAGTCAGTGCTACTAAGCTTAACATTGTTACTTCTGATAT  11637
               ||||||||||||||||||||||||||||||||||||||||||||||||||||||||||||
US_Col  11623  ACCTCTGTCTGTCATACCGGCAGTCAGTGCTACTAAGCTTAACATTGTTACTTCTGATAT  11682

125_10  11638  CGATTCTTATAATCGTATCCAGCGTGAGGGATGTGTCCACTACGCTGGTACCATTTGGAA  11697
               ||||||||||||||||||||||||||||||||||||||||||||||||||||||||||||
US_Col  11683  CGATTCTTATAATCGTATCCAGCGTGAGGGATGTGTCCACTACGCTGGTACCATTTGGAA  11742

125_10  11698  TATAATTGATATCAAGGACAATGATGGCAAGGTGGTACACGTTAAGGAGGTAACCGCACA  11757
               ||||||||||||||||||||||||||||||||||||||||||||||||||||||||||||
US_Col  11743  TATAATTGATATCAAGGACAATGATGGCAAGGTGGTACACGTTAAGGAGGTAACCGCACA  11802

125_10  11758  GAATGCTGAGTCCCTGTCATGGCCCCTGGTCCTTGGGTGTGAGCGTATTGTCAAGCTCCA  11817
               ||||||||||||||||||||||||||||||||||||||||||||||||||||||||||||
US_Col  11803  GAATGCTGAGTCCCTGTCATGGCCCCTGGTCCTTGGGTGTGAGCGTATTGTCAAGCTCCA  11862

125_10  11818  GAATAATGAAATTATTCCTGGTAAGCTGAAGCAGCGCTCCATTAAGGCAGAAGGAGATGG  11877
               ||||||||||||||||||||||||||||||||||||||||||||||||||||||||||||
US_Col  11863  GAATAATGAAATTATTCCTGGTAAGCTGAAGCAGCGCTCCATTAAGGCAGAAGGAGATGG  11662

125_10  11878  CATAGTTGGAGAAGGTAAGGCACTTTACAATAATGAGGGTGGACGTACTTTTATGTATGC  11937
               ||||||||||||||||||||||||||||||||||||||||||||||||||||||||||||
US_Col  11663  CATAGTTGGAGAAGGTAAGGCACTTTACAATAATGAGGGTGGACGTACTTTTATGTATGC  11982

125_10  11938  TTTCATCTCGGACAAACCGGACCTGCGTGTAGTCAAGTGGGAGTTCGATGGTGGTTGTAA  11997
               ||||||||||||||||||||||||||||||||||||||||||||||||||||||||||||
US_Col  11983  TTTCATCTCGGACAAACCGGACCTGCGTGTAGTCAAGTGGGAGTTCGATGGTGGTTGTAA  12042

125_10  11998  CACTATTGAGCTAGAACCACCACGTAAGTTCTTGGTGGATTCTCCTAATGGTGCACAGAT  12057
               ||||||||||||||||||||||||||||||||||||||||||||||||||||||||||||
US_Col  12043  CACTATTGAGCTAGAACCACCACGTAAGTTCTTGGTGGATTCTCCTAATGGTGCACAGAT  12102
```

FIG. 2 (cont'd)

```
125_10  12058  CAAGTATCTCTACTTTGTTCGTAACCTTAACACGTTACGTAGGGGTGCTGTTCTCGGCTA  12117
               ||||||||||||||||||||||||||||||||||||||||||||||||||||||||||||
US_Col  12103  CAAGTATCTCTACTTTGTTCGTAACCTTAACACGTTACGTAGGGGTGCTGTTCTCGGCTA  12162

125_10  12118  CATAGGTGCCACTGTACGCTTGCAGGCTGGTAAACAAACAGAACAGGCTATTAACTCTTC  12177
               ||||||||||||||||||||||||||||||||||||||||||||||||||||||||||||
US_Col  12163  CATAGGTGCCACTGTACGCTTGCAGGCTGGTAAACAAACAGAACAGGCTATTAACTCTTC  12222

125_10  12178  ATTGTTGACACTTTGCGCTTTCGCTGTGGATCCTGCTAAGACCTACATCGATGCTGTCAA  12237
               ||||||||||||||||||||||||||||||||||||||||||||||||||||||||||||
US_Col  12223  ATTGTTGACACTTTGCGCTTTCGCTGTGGATCCTGCTAAGACCTACATCGATGCTGTCAA  12282

125_10  12238  AAGTGGTCACAAACCAGTAGGTAACTGTGTTAAGATGTTGGCCAATGGTTCTGGTAATGG  12297
               ||||||||||||||||||||||||||||||||||||||||||||||||||||||||||||
US_Col  12283  AAGTGGTCACAAACCAGTAGGTAACTGTGTTAAGATGTTGGCCAATGGTTCTGGTAATGG  12342

125_10  12298  ACAAGCTGTTACTAATGGTGTGGAGGCTAGTACTAACCAGGATTCATACGGTGGTGCGTC  12357
               ||||||||||||||||||||||||||||||||||||||||||||||||||||||||||||
US_Col  12343  ACAAGCTGTTACTAATGGTGTGGAGGCTAGTACTAACCAGGATTCATACGGTGGTGCGTC  12402

125_10  12358  CGTGTGTCTATATTGTAGAGCACATGTTGAGCATCCATCTATGGATGGTTTTTGCAGACT  12417
               ||||||||||||||||||||||||||||||||||||||||||||||||||||||||||||
US_Col  12403  CGTGTGTCTATATTGTAGAGCACATGTTGAGCATCCATCTATGGATGGTTTTTGCAGACT  12462

125_10  12418  GAAAGGCAAGTACGTACAGGTTCCACTAGGTACAGTGGATCCTATACGTTTTGTACTTGA  12477
               ||||||||||||||||||||||||||||||||||||||||||||||||||||||||||||
US_Col  12463  GAAAGGCAAGTACGTACAGGTTCCACTAGGTACAGTGGATCCTATACGTTTTGTACTTGA  12522

125_10  12478  GAATGACGTTTGCAAGGTTTGTGGTTGTTGGCTGGCTAATGGCTGCACTTGTGACAGATC  12537
               ||||||||||||||||||||||||||||||||||||||||||||||||||||||||||||
US_Col  12523  GAATGACGTTTGCAAGGTTTGTGGTTGTTGGCTGGCTAATGGCTGCACTTGTGACAGATC  12582

125_10  12538  CATTATGCAAAGCACTGATATGGCTTATTTAAACGAGTACGGGGCTCTAGTGCAGCTCGA  12597
               ||||||||||||||||||||||||||||||||||||||||||||||||||||||||||||
US_Col  12583  CATTATGCAAAGCACTGATATGGCTTATTTAAACGAGTACGGGGCTCTAGTGCAGCTCGA  12642

125_10  12598  CTAGAGCCCTGTAACGGTACTGATACACAACATGTGTATCGTGCTTTTGACATCTACAAC  12657
               |||||||| |||||||||||||||||||||||||||||||||||||||||||||||||||
US_Col  12643  CTAGAGCCMTGTAACGGTACTGATACACAACATGTGTATCGTGCTTTTGACATCTACAAC  12702

125_10  12658  AAGGATGTTGCTTGTCTAGGTAAATTCCTCAAGGTGAACTGTGTTCGCCTGAAGAATTTG  12717
               ||||||||||||||||||||||||||||||||||||||||||||||||||||||||||||
US_Col  12703  AAGGATGTTGCTTGTCTAGGTAAATTCCTCAAGGTGAACTGTGTTCGCCTGAAGAATTTG  12762

125_10  12718  GATAAGCATGATGCATTCTATGTTGTCAAAAGATGTACCAAGTCTGCGATGGAACACGAG  12777
               ||||||||||||||||||||||||||||||||||||||||||||||||||||||||||||
US_Col  12763  GATAAGCATGATGCATTCTATGTTGTCAAAAGATGTACCAAGTCTGCGATGGAACACGAG  12822

125_10  12778  CAATCCATCTATAGCAGACTTGAAAAGTGTGGAGCCGTAGCCGAACACGATTTCTTCACT  12837
               ||||||||||||||||||||||||||||||||||||||||||||||||||||||||||||
US_Col  12823  CAATCCATCTATAGCAGACTTGAAAAGTGTGGAGCCGTAGCCGAACACGATTTCTTCACT  12882

125_10  12838  TGGAAGGATGGTCGTGCCATCTATGGTAACGTTTGTAGAAAGGATCTTACCGAGTATACT  12897
               ||||||||||||||||||||||||||||||||||||||||||||||||||||||||||||
US_Col  12883  TGGAAGGATGGTCGTGCCATCTATGGTAACGTTTGTAGAAAGGATCTTACCGAGTATACT  12942

125_10  12898  ATGATGGATTTGTGTTACGCTTTACGTAACTTTGATGAAAACAATTGCGATGTTCTTAAG  12957
               ||||||||||||||||||||||||||||||||||||||||||||||||||||||||||||
US_Col  12943  ATGATGGATTTGTGTTACGCTTTACGTAACTTTGATGAAAACAATTGCGATGTTCTTAAG  13002
```

FIG. 2 (cont'd)

```
125_10  12958  AGCATTTTAATTAAGGTAGGCGCTTGTGAGGAGTCCTACTTCAATAATAAAGTCTGGTTT  13017
               ||||||||||||||||||||||||||||||||||||||||||||||||||||||||||||
US_Col  13003  AGCATTTTAATTAAGGTAGGCGCTTGTGAGGAGTCCTACTTCAATAATAAAGTCTGGTTT  13062

125_10  13018  GACCCTGTTGAAAATGAAGACATTCATCGTGTCTATGCATTGTTAGGTACCATTGTTTCA  13077
               ||||||||||||||||||||||||||||||||||||||||||||||||||||||||||||
US_Col  13063  GACCCTGTTGAAAATGAAGACATTCATCGTGTCTATGCATTGTTAGGTACCATTGTTTCA  13122

125_10  13078  CGTGCTATGCTTAAATGCGTTAAGTTCTGTGATGCAATGGTTGAACAAGGTATAGTTGGT  13137
               ||||||||||||||||||||||||||||||||||||||||||||||||||||||||||||
US_Col  13123  CGTGCTATGCTTAAATGCGTTAAGTTCTGTGATGCAATGGTTGAACAAGGTATAGTTGGT  13182

125_10  13138  GTTGTCACATTAGATAATCAGGATCTTAATGGTGATTTTTATGATTTTGGTGATTTTACT  13197
               ||||||||||||||||||||||||||||||||||||||||||||||||||||||||||||
US_Col  13183  GTTGTCACATTAGATAATCAGGATCTTAATGGTGATTTTTATGATTTTGGTGATTTTACT  13242

125_10  13198  TGTAGCATCAAGGGAATGGGTATACCCATTTGCACATCATATTACTCTTATATGATGCCT  13257
               ||||||||||||||||||||||||||||||||||||||||||||||||||||||||||||
US_Col  13243  TGTAGCATCAAGGGAATGGGTATACCCATTTGCACATCATATTACTCTTATATGATGCCT  13302

125_10  13258  GTTATGGGTATGACTAATTGCCTTGCTAGTGAGTGTTTTGTTAAGAGTGATATATTTGGT  13317
               ||||||||||||||||||||||||||||||||||||||||||||||||||||||||||||
US_Col  13303  GTTATGGGTATGACTAATTGCCTTGCTAGTGAGTGTTTTGTTAAGAGTGATATATTTGGT  13362

125_10  13318  GAGGATTTCAAGTCATATGACCTGCTGGAATATGATTTCACGGAGCATAAGACAGCACTC  13377
               ||||||||||||||||||||||||||||||||||||||||||||||||||||||||||||
US_Col  13363  GAGGATTTCAAGTCATATGACCTGCTGGAATATGATTTCACGGAGCATAAGACAGCACTC  13422

125_10  13378  TTCAACAAGTATTTCAAGTATTGGGGACTGCAATACCACCCTAACTGTGTGGACTGCAGT  13437
               ||||||||||||||||||||||||||||||||||||||||||||||||||||||||||||
US_Col  13423  TTCAACAAGTATTTCAAGTATTGGGGACTGCAATACCACCCTAACTGTGTGGACTGCAGT  13482

125_10  13438  GATGAGCAGTGCATAGTTCACTGTGCCAACTTCAATACGTTGTTTTCCACTACTATACCT  13497
               ||||||||||||||||||||||||||||||||||||||||||||||||||||||||||||
US_Col  13483  GATGAGCAGTGCATAGTTCACTGTGCCAACTTCAATACGTTGTTTTCCACTACTATACCT  13542

125_10  13498  ATTACGGCATTTGGACCTTTGTGTCGCAAGTGTTGGATTGATGGTGTTCCACTGGTAACT  13557
               ||||||||||||||||||||||||||||||||||||||||||||||||||||||||||||
US_Col  13543  ATTACGGCATTTGGACCTTTGTGTCGCAAGTGTTGGATTGATGGTGTTCCACTGGTAACT  13602

125_10  13558  ACAGCTGGTTATCATTTTAAACAGTTAGGTATAGTTTGGAACAATGACCTCAACTTACAC  13617
               ||||||||||||||||||||||||||||||||||||||||||||||||||||||||||||
US_Col  13603  ACAGCTGGTTATCATTTTAAACAGTTAGGTATAGTTTGGAACAATGACCTCAACTTACAC  13662

125_10  13618  TCTAGCAGGCTCTCTATTAACGAATTACTCCAGTTTTGTAGTGATCCTGCATTGCTTATA  13677
               ||||||||||||||||||||||||||||||||||||||||||||||||||||||||||||
US_Col  13663  TCTAGCAGGCTCTCTATTAACGAATTACTCCAGTTTTGTAGTGATCCTGCATTGCTTATA  13722

125_10  13678  GCATCATCACCAGCCCTTGTTGATCAGCGTACTGTTTGCTTTTCAGTTGCAGCGCTAGGT  13737
               ||||||||||||||||||||||||||||||||||||||||||||||||||||||||||||
US_Col  13723  GCATCATCACCAGCCCTTGTTGATCAGCGTACTGTTTGCTTTTCAGTTGCAGCGCTAGGT  13782

125_10  13738  ACAGGTATGACTAACCAGACTGTTAAACCTGGCCATTTCAATAAGGAGTTTTATGACTTC  13797
               ||||||||||||||||||||||||||||||||||||||||||||||||||||||||||||
US_Col  13783  ACAGGTATGACTAACCAGACTGTTAAACCTGGCCATTTCAATAAGGAGTTTTATGACTTC  13842

125_10  13798  TTACTTGAGCAAGGTTTCTTTTCTGAGGGCTCTGAGCTTACTTTAAAGCACTTCTTCTTT  13857
               ||||||||||||||||||||||||||||||||||||||||||||||||||||||||||||
US_Col  13843  TTACTTGAGCAAGGTTTCTTTTCTGAGGGCTCTGAGCTTACTTTAAAGCACTTCTTCTTT  13902

125_10  13858  GCACAGAAGGGTGATGCAGCTGTTAAGGATTTTGACTACTATAGGTATAATAGACCTACT  13917
               ||||||||||||||||||||||||||||||||||||||||||||||||||||||||||||
US_Col  13903  GCACAGAAGGGTGATGCAGCTGTTAAGGATTTTGACTACTATAGGTATAATAGACCTACT  13962
```

FIG. 2 (cont'd)

```
125_10  13918  GTTCTGGACATTTGCCAAGCTCGCGTCGTGTATCAAATAGTGCAACGCTATTTTGATATT  13977
               ||||||||||||||||||||||||||||||||||||||||||||||||||||||||||||
US_Col  13963  GTTCTGGACATTTGCCAAGCTCGCGTCGTGTATCAAATAGTGCAACGCTATTTTGATATT  14022

125_10  13978  TACGAAGGTGGTTGTATCACTGCTAAAGAGGTGGTTGTTACAAACCTTAACAAGAGCGCA  14037
               ||||||||||||||||||||||||||||||||||||||||||||||||||||||||||||
US_Col  14023  TACGAAGGTGGTTGTATCACTGCTAAAGAGGTGGTTGTTACAAACCTTAACAAGAGCGCA  14082

125_10  14038  GGTTATCCTTTGAACAAGTTTGGTAAAGCTGGTCTTTACTATGAGTCTTTATCCTATGAG  14097
               ||||||||||||||||||||||||||||||||||||||||||||||||||||||||||||
US_Col  14083  GGTTATCCTTTGAACAAGTTTGGTAAAGCTGGTCTTTACTATGAGTCTTTATCCTATGAG  14142

125_10  14098  GAACAGGATGAACTTTATGCTTATACTAAGCGTAACATCCTGCCCACTATGACACAGCTC  14157
               ||||||||||||||||||||||||||||||||||||||||||||||||||||||||||||
US_Col  14143  GAACAGGATGAACTTTATGCTTATACTAAGCGTAACATCCTGCCCACTATGACACAGCTC  14202

125_10  14158  AACCTTAAATATGCTATAAGTGGCAAAGAACGTGCACGCACAGTGGGTGGTGTTTCGCTT  14217
               ||||||||||||||||||||||||||||||||||||||||||||||||||||||||||||
US_Col  14203  AACCTTAAATATGCTATAAGTGGCAAAGAACGTGCACGCACAGTGGGTGGTGTTTCGCTT  14262


125_10  14218  TTGTCAACCATGACTACTCGGCAGTATCATCAGAAACACCTTAAGTCCATAGTTAATACT  14277
               ||||||||||||||||||||||||||||||||||||||||||||||||||||||||||||
US_Col  14263  TTGTCAACCATGACTACTCGGCAGTATCATCAGAAACACCTTAAGTCCATAGTTAATACT  14322

125_10  14278  AGGGGCGCTTCGGTTGTTATTGGTACTACTAAGTTTTATGGTGGTTGGGACAATATGCTT  14337
               ||||||||||||||||||||||||||||||||||||||||||||||||||||||||||||
US_Col  14323  AGGGGCGCTTCGGTTGTTATTGGTACTACTAAGTTTTATGGTGGTTGGGACAATATGCTT  14382

125_10  14338  AAGAACCTTATTGATGGTGTTGAAAATCCGTGTCTTATGGGTTGGGACTACCCAAAGTGC  14397
               ||||||||||||||||||||||||||||||||||||||||||||||||||||||||||||
US_Col  14383  AAGAACCTTATTGATGGTGTTGAAAATCCGTGTCTTATGGGTTGGGACTACCCAAAGTGC  14442

125_10  14398  GACAGAGCACTGCCCAATRTGATACGTATGATTTCAGCCATGATTTTAGGCTCTAAGCAC  14457
               |||||||||||||||||| |||||||||||||||||||||||||||||||||||||||||
US_Col  14443  GACAGAGCACTGCCCAATATGATACGTATGATTTCAGCCATGATTTTAGGCTCTAAGCAC  14502

125_10  14458  ACCACATGCTGCAGTTCCACTGACCGCTTTTTCAGGTTGTGCAATGAATTGGCTCAAGTC  14517
               ||||||||||||||||||||||||||||||||||||||||||||||||||||||||||||
US_Col  14503  ACCACATGCTGCAGTTCCACTGACCGCTTTTTCAGGTTGTGCAATGAATTGGCTCAAGTC  14562

125_10  14518  CTTACTGAGGTTGTTTATTCTAATGGAGGTTTTTATTTGAAGCCAGGTGGTACTACCTCT  14577
               ||||||||||||||||||||||||||||||||||||||||||||||||||||||||||||
US_Col  14563  CTTACTGAGGTTGTTTATTCTAATGGAGGTTTTTATTTGAAGCCAGGTGGTACTACCTCT  14622

125_10  14578  GGTGATGCAACCACCGCATATGCAAACTCAGTTTTTAATATCTTCCAAGCAGTAAGTGCC  14637
               ||||||||||||||||||||||||||||||||||||||||||||||||||||||||||||
US_Col  14623  GGTGATGCAACCACCGCATATGCAAACTCAGTTTTTAATATCTTCCAAGCAGTAAGTGCC  14682

125_10  14638  AATGTTAACAAACTTCTTAGTGTTGACAGCAATGTCTGTCATAATTTAGAAGTTAAGCAA  14697
               ||||||||||||||||||||||||||||||||||||||||||||||||||||||||||||
US_Col  14683  AATGTTAACAAACTTCTTAGTGTTGACAGCAATGTCTGTCATAATTTAGAAGTTAAGCAA  14742

125_10  14698  TTGCAGCGTAAGCTTTATGAGTGCTGTTATAGATCAACTACCGTCGATGACCAGTTCGTC  14757
               ||||||||||||||||||||||||||||||||||||||||||||||||||||||||||||
US_Col  14743  TTGCAGCGTAAGCTTTATGAGTGCTGTTATAGATCAACTACCGTCGATGACCAGTTCGTC  14802

125_10  14758  GTTGAGTATTATGGTTACTTGCGTAAACATTTTTCAATGATGATTCTTTCTGATGATGGC  14817
               ||||||||||||||||||||||||||||||||||||||||||||||||||||||||||||
US_Col  14803  GTTGAGTATTATGGTTACTTGCGTAAACATTTTTCAATGATGATTCTTTCTGATGATGGC  14862
```

FIG. 2 (cont'd)

```
125_10  14818  GTTGTTTGTTATAACAATGACTATGCATCACTTGGTTATGTCGCTGATCTTAACGCATTC  14877
               ||||||||||||||||||||||||||||||||||||||||||||||||||||||||||||
US_Col  14863  GTTGTTTGTTATAACAATGACTATGCATCACTTGGTTATGTCGCTGATCTTAACGCATTC  14662

125_10  14878  AAGGCTGTTTTGTATTACCAGAACAATGTCTTCATGAGCGCCTCTAAATGTTGGATCGAG  14937
               ||||||||||||||||||||||||||||||||||||||||||||||||||||||||||||
US_Col  14663  AAGGCTGTTTTGTATTACCAGAACAATGTCTTCATGAGCGCCTCTAAATGTTGGATCGAG  14982

125_10  14938  CCTGACATTAATAAAGGTCCTCATGAATTTTGCTCGCAGCATACTATGCAGATTGTCGAT  14997
               ||||||||||||||||||||||||||||||||||||||||||||||||||||||||||||
US_Col  14983  CCTGACATTAATAAAGGTCCTCATGAATTTTGCTCGCAGCATACTATGCAGATTGTCGAT  15042

125_10  14998  AAAGATGGTACTTATTACCTTCCTTACCCTGATCCTTCAAGAATTCTCTCTGCAGGTGTG  15057
               ||||||||||||||||||||||||||||||||||||||||||||||||||||||||||||
US_Col  15043  AAAGATGGTACTTATTACCTTCCTTACCCTGATCCTTCAAGAATTCTCTCTGCAGGTGTG  15102

125_10  15058  TTTGTTGATGACGTTGTTAAAACTGATGCAGTTGTATTGCTTGAACGTTATGTGTCATTG  15117
               ||||||||||||||||||||||||||||||||||||||||||||||||||||||||||||
US_Col  15103  TTTGTTGATGACGTTGTTAAAACTGATGCAGTTGTATTGCTTGAACGTTATGTGTCATTG  15162

125_10  15118  GCTATAGATGCCTACCCGTTATCTAAGCATGAAAACCCTGAATATAAGAAGGTGTTTTAT  15177
               ||||||||||||||||||||||||||||||||||||||||||||||||||||||||||||
US_Col  15163  GCTATAGATGCCTACCCGTTATCTAAGCATGAAAACCCTGAATATAAGAAGGTGTTTTAT  15222

125_10  15178  GTGCTTTTGGATTGGGTTAAGCATCTGTACAAAACTCTTAATGCTGGTGTGTTAGAGTCT  15237
               ||||||||||||||||||||||||||||||||||||||||||||||||||||||||||||
US_Col  15223  GTGCTTTTGGATTGGGTTAAGCATCTGTACAAAACTCTTAATGCTGGTGTGTTAGAGTCT  15282

125_10  15238  TTTTCTGTCACACTTTTGGAAGATTCTACTGCTAAATTCTGGGATGAGAGCTTTTATGCC  15297
               ||||||||||||||||||||||||||||||||||||||||||||||||||||||||||||
US_Col  15283  TTTTCTGTCACACTTTTGGAAGATTCTACTGCTAAATTCTGGGATGAGAGCTTTTATGCC  15342

125_10  15298  AACATGTATGAGAAATCTGCAGTTTTACAATCTGCAGGGCTTTGTGTTGTTTGTGGCTCT  15357
               ||||||||||||||||||||||||||||||||||||||||||||||||||||||||||||
US_Col  15343  AACATGTATGAGAAATCTGCAGTTTTACAATCTGCAGGGCTTTGTGTTGTTTGTGGCTCT  15402

125_10  15358  CAAACTGTTTTACGTTGTGGTGATTGTCTACGGCGTCCTATGCTTTGTACTAAGTGTGCT  15417
               ||||||||||||||||||||||||||||||||||||||||||||||||||||||||||||
US_Col  15403  CAAACTGTTTTACGTTGTGGTGATTGTCTACGGCGTCCTATGCTTTGTACTAAGTGTGCT  15462

125_10  15418  TATGATCATGTCATTGGAACAACTCACAAGTTCATTTTGGCCATCACTCCATATGTGTGT  15477
               ||||||||||||||||||||||||||||||||||||||||||||||||||||||||||||
US_Col  15463  TATGATCATGTCATTGGAACAACTCACAAGTTCATTTTGGCCATCACTCCATATGTGTGT  15522

125_10  15478  TGTGCTTCAGATTGTGGTGTCAATGATGTAACTAAGCTCTACTTAGGTGGTCTTAGTTAT  15537
               ||||||||||||||||||||||||||||||||||||||||||||||||||||||||||||
US_Col  15523  TGTGCTTCAGATTGTGGTGTCAATGATGTAACTAAGCTCTACTTAGGTGGTCTTAGTTAT  15582

125_10  15538  TGGTGTCATGACCACAAGCCACGTCTTGCATTCCCGTTGTGCTCTGCTGGTAATGTTTTT  15597
               ||||||||||||||||||||||||||||||||||||||||||||||||||||||||||||
US_Col  15583  TGGTGTCATGACCACAAGCCACGTCTTGCATTCCCGTTGTGCTCTGCTGGTAATGTTTTT  15642

125_10  15598  GGCTTGTACAAAAATTCTGCTACCGGCTCACCCGATGTTGAAGACTTTAATCGCATTGCT  15657
               ||||||||||||||||||||||||||||||||||||||||||||||||||||||||||||
US_Col  15643  GGCTTGTACAAAAATTCTGCTACCGGCTCACCCGATGTTGAAGACTTTAATCGCATTGCT  15702

125_10  15658  ACATCCGATTGGACTGATGTTTCTGACTACAGGTTGGCAAATGATGTCAAGGACTCATTG  15717
               ||||||||||||||||||||||||||||||||||||||||||||||||||||||||||||
US_Col  15703  ACATCCGATTGGACTGATGTTTCTGACTACAGGTTGGCAAATGATGTCAAGGACTCATTG  15762

125_10  15718  CGTCTGTTTGCAGCGGAAACTATCAAGGCCAAGGAGGAGAGCGTTAAGTCATCCTATGCT  15777
               ||||||||||||||||||||||||||||||||||||||||||||||||||||||||||||
US_Col  15763  CGTCTGTTTGCAGCGGAAACTATCAAGGCCAAGGAGGAGAGCGTTAAGTCATCCTATGCT  15822
```

FIG. 2 (cont'd)

```
125_10  15778  TGTGCAACACTACATGAGGTTGTAGGACCTAAAGAGTTGTTGCTCAAATGGGAAGTCGGC  15837
               ||||||||||||||||||||||||||||||||||||||||||||||||||||||||||||
US_Col  15823  TGTGCAACACTACATGAGGTTGTAGGACCTAAAGAGTTGTTGCTCAAATGGGAAGTCGGC  15882

125_10  15838  AGACCCAAACCACCCCTTAATAGAAATTCGGTTTTCACTTGTTATCATATAACGAAGAAC  15897
               ||||||||||||||||||||||||||||||||||||||||||||||||||||||||||||
US_Col  15883  AGACCCAAACCACCCCTTAATAGAAATTCGGTTTTCACTTGTTATCATATAACGAAGAAC  15942

125_10  15898  ACCAAATTTCAAATCGGTGAGTTTGTGTTTGAGAAGGCAGAATATGATAATGATGCTGTA  15957
               ||||||||||||||||||||||||||||||||||||||||||||||||||||||||||||
US_Col  15943  ACCAAATTTCAAATCGGTGAGTTTGTGTTTGAGAAGGCAGAATATGATAATGATGCTGTA  16002

125_10  15958  ACATATAAAACTACCGCCACAACAAAACTTGTTCCTGGCATGGTTTTTGTGCTTACCTCA  16017
               ||||||||||||||||||||||||||||||||||||||||||||||||||||||||||||
US_Col  16003  ACATATAAAACTACCGCCACAACAAAACTTGTTCCTGGCATGGTTTTTGTGCTTACCTCA  16062

125_10  16018  CATAATGTTCAGCCATTGCGCGCACCGACCATTGCTAATCAAGAACGTTATTCCACTATA  16077
               ||||||||||||||||||||||||||||||||||||||||||||||||||||||||||||
US_Col  16063  CATAATGTTCAGCCATTGCGCGCACCGACCATTGCTAATCAAGAACGTTATTCCACTATA  16122

125_10  16078  CATAAGTTGCATCCTGCTTTTAACATACCTGAAGCTTATTCTAGCTTAGTGCCCTATTAC  16137
               ||||||||||||||||||||||||||||||||||||||||||||||||||||||||||||
US_Col  16123  CATAAGTTGCATCCTGCTTTTAACATACCTGAAGCTTATTCTAGCTTAGTGCCCTATTAC  16182

125_10  16138  CAATTGATTGGTAAGCAGAAGATTACAACTATTCAGGGACCTCCCGGTAGTGGTAAATCT  16197
               ||||||||||||||||||||||||||||||||||||||||||||||||||||||||||||
US_Col  16183  CAATTGATTGGTAAGCAGAAGATTACAACTATTCAGGGACCTCCCGGTAGTGGTAAATCT  16242

125_10  16198  CACTGTGTTATAGGGCTAGGTTTGTACTATCCAGGTGCACGTATAGTGTTTACAGCTTGT  16257
               ||||||||||||||||||||||||||||||||||||||||||||||||||||||||||||
US_Col  16243  CACTGTGTTATAGGGCTAGGTTTGTACTATCCAGGTGCACGTATAGTGTTTACAGCTTGT  16302

125_10  16258  TCTCATGCAGCGGTCGATTCACTTTGTGTGAAAGCTTCCACTGCTTATAGCAATGACAAA  16317
               ||||||||||||||||||||||||||||||||||||||||||||||||||||||||||||
US_Col  16303  TCTCATGCAGCGGTCGATTCACTTTGTGTGAAAGCTTCCACTGCTTATAGCAATGACAAA  16362

125_10  16318  TGTTCACGCATCATACCACAGCGCGCTCGTGTTGAGTGTTATGATGGTTTCAAGTCTAAT  16377
               ||||||||||||||||||||||||||||||||||||||||||||||||||||||||||||
US_Col  16363  TGTTCACGCATCATACCACAGCGCGCTCGTGTTGAGTGTTATGATGGTTTCAAGTCTAAT  16422

125_10  16378  AATACTAGTGCTCAGTACCTTTTCTCTACTGTCAATGCTTTGCCAGAGTGCAATGCGGAC  16437
               ||||||||||||||||||||||||||||||||||||||||||||||||||||||||||||
US_Col  16423  AATACTAGTGCTCAGTACCTTTTCTCTACTGTCAATGCTTTGCCAGAGTGCAATGCGGAC  16482

125_10  16438  ATTGTTGTGGTGGATGAGGTCTCTATGTGCACTAATTATGACTTGTCTGTCATAAATCAG  16497
               ||||||||||||||||||||||||||||||||||||||||||||||||||||||||||||
US_Col  16483  ATTGTTGTGGTGGATGAGGTCTCTATGTGCACTAATTATGACTTGTCTGTCATAAATCAG  16542

125_10  16498  CGCATCAGCTATAGGCATGTAGTCTATGTTGGTGACCCTCAACAGCTGCCTGCACCACGT  16557
               ||||||||||||||||||||||||||||||||||||||||||||||||||||||||||||
US_Col  16543  CGCATCAGCTATAGGCATGTAGTCTATGTTGGTGACCCTCAACAGCTGCCTGCACCACGT  16602

125_10  16558  GTTATGATTTCACGTGGTACTTTGGAACCAAAGGACTACAACGTTGTCACTCAACGCATG  16617
               ||||||||||||||||||||||||||||||||||||||||||||||||||||||||||||
US_Col  16603  GTTATGATTTCACGTGGTACTTTGGAACCAAAGGACTACAACGTTGTCACTCAACGCATG  16662

125_10  16618  TGTGCCCTTAAGCCTGATGTTTTCTTGCACAAGTGTTATCGCTGTCCTGCTGAGATAGTG  16677
               ||||||||||||||||||||||||||||||||||||||||||||||||||||||||||||
US_Col  16663  TGTGCCCTTAAGCCTGATGTTTTCTTGCACAAGTGTTATCGCTGTCCTGCTGAGATAGTG  16722
```

FIG. 2 (cont'd)

```
125_10  16678  CGTACTGTGTCTGAGATGGTCTATGAAAACCAATTCATTCCTGTGCACCCAGATAGCAAG  16737
               ||||||||||||||||||||||||||||||||||||||||||||||||||||||||||||
US_Col  16723  CGTACTGTGTCTGAGATGGTCTATGAAAACCAATTCATTCCTGTGCACCCAGATAGCAAG  16782

125_10  16738  CAGTGTTTTAAAATCTTTTGCAAGGGTAATGTTCAGGTTGATAATGGTTCAAGCATTAAT  16797
               ||||||||||||||||||||||||||||||||||||||||||||||||||||||||||||
US_Col  16783  CAGTGTTTTAAAATCTTTTGCAAGGGTAATGTTCAGGTTGATAATGGTTCAAGCATTAAT  16842

125_10  16798  CGCAGGCAATTGGATGTTGTGCGTATGTTTTTGGCTAAAAATCCTAGGTGGTCAAAGGCT  16857
               ||||||||||||||||||||||||||||||||||||||||||||||||||||||||||||
US_Col  16843  CGCAGGCAATTGGATGTTGTGCGTATGTTTTTGGCTAAAAATCCTAGGTGGTCAAAGGCT  16902

125_10  16858  GTTTTTATTTCTCCTTATAACAGCCAGAATTATGTTGCCAGCCGCATGCTAGGTCTACAA  16917
               ||||||||||||||||||||||||||||||||||||||||||||||||||||||||||||
US_Col  16903  GTTTTTATTTCTCCTTATAACAGCCAGAATTATGTTGCCAGCCGCATGCTAGGTCTACAA  16962

125_10  16918  ATTCAGACAGTTGACTCATCCCAGGGTAGTGAGTATGACTATGTCATTTACACACAAACT  16977
               ||||||||||||||||||||||||||||||||||||||||||||||||||||||||||||
US_Col  16963  ATTCAGACAGTTGACTCATCCCAGGGTAGTGAGTATGACTATGTCATTTACACACAAACT  17022

125_10  16978  TCAGATACTGCCCATGCCTGTAATGTTAACAGGTTTAATGTTGCCATCACAAGGGCCAAG  17037
               ||||||||||||||||||||||||||||||||||||||||||||||||||||||||||||
US_Col  17023  TCAGATACTGCCCATGCCTGTAATGTTAACAGGTTTAATGTTGCCATCACAAGGGCCAAG  17082

125_10  17038  AAAGGCATATTATGTATAATGTGCGATAGGTCCCTTTTTGATGTGCTTAAATTCTTTGAG  17097
               ||||||||||||||||||||||||||||||||||||||||||||||||||||||||||||
US_Col  17083  AAAGGCATATTATGTATAATGTGCGATAGGTCCCTTTTTGATGTGCTTAAATTCTTTGAG  17142

125_10  17098  CTTAAATTGTCTGATTTGCAGGCTAATGAGGGTTGTGGTCTTTTTAAAGACTGTAGCAGA  17157
               ||||||||||||||||||||||||||||||||||||||||||||||||||||||||||||
US_Col  17143  CTTAAATTGTCTGATTTGCAGGCTAATGAGGGTTGTGGTCTTTTTAAAGACTGTAGCAGA  17202

125_10  17158  GGTGATGATCTGTTGCCACCATCTCACGCTAACACCTTCATGTCTTTAGCGGACAATTTT  17217
               ||||||||||||||||||||||||||||||||||||||||||||||||||||||||||||
US_Col  17203  GGTGATGATCTGTTGCCACCATCTCACGCTAACACCTTCATGTCTTTAGCGGACAATTTT  17262

125_10  17218  AAGACTGATCAAGATCTTGCTGTTCAAATAGGTGTTAATGGACCCATTAAATATGAGCAT  17277
               ||||||||||||||||||||||||||||||||||||||||||||||||||||||||||||
US_Col  17263  AAGACTGATCAAGATCTTGCTGTTCAAATAGGTGTTAATGGACCCATTAAATATGAGCAT  17322

125_10  17278  GTTATCTCGTTTATGGGTTTCCGTTTTGATATCAACATACCCAACCATCATACTCTCTTT  17337
               ||||||||||||||||||||||||||||||||||||||||||||||||||||||||||||
US_Col  17323  GTTATCTCGTTTATGGGTTTCCGTTTTGATATCAACATACCCAACCATCATACTCTCTTT  17382

125_10  17338  TGCACACGCGACTTTGCCATGCGCAATGTTAGAGGTTGGTTAGGCTTTGACGTTGAAGGA  17397
               ||||||||||||||||||||||||||||||||||||||||||||||||||||||||||||
US_Col  17383  TGCACACGCGACTTTGCCATGCGCAATGTTAGAGGTTGGTTAGGCTTTGACGTTGAAGGA  17442

125_10  17398  GCACATGTTGTTGGCTCTAACGTCGGTACAAATGTCCCATTGCAATTAGGGTTTTCTAAC  17457
               ||||||||||||||||||||||||||||||||||||||||||||||||||||||||||||
US_Col  17443  GCACATGTTGTTGGCTCTAACGTCGGTACAAATGTCCCATTGCAATTAGGGTTTTCTAAC  17502

125_10  17458  GGTGTTGATTTTGTTGTCAGACCTGAAGGTTGCGTTGTAACAGAGTCTGGTGACTACATT  17517
               ||||||||||||||||||||||||||||||||||||||||||||||||||||||||||||
US_Col  17503  GGTGTTGATTTTGTTGTCAGACCTGAAGGTTGCGTTGTAACAGAGTCTGGTGACTACATT  17562

125_10  17518  AAACCCGTCAGAGCTCGTGCTCCACCAGGGGAACAATTCGCACACCTTTTGCCTTTACTT  17577
               ||||||||||||||||||||||||||||||||||||||||||||||||||||||||||||
US_Col  17563  AAACCCGTCAGAGCTCGTGCTCCACCAGGGGAACAATTCGCACACCTTTTGCCTTTACTT  17622

125_10  17578  AAACGCGGCCAACCATGGGATGTTGTCCGCAAACGTATAGTGCAGATGTGTAGTGACTAC  17637
               ||||||||||||||||||||||||||||||||||||||||||||||||||||||||||||
US_Col  17623  AAACGCGGCCAACCATGGGATGTTGTCCGCAAACGTATAGTGCAGATGTGTAGTGACTAC  17682
```

FIG. 2 (cont'd)

```
125_10  17638  CTGGCCAACCTATCAGACATACTAATTTTTGTGTTGTGGGCTGGTGGTTTGGAGTTGACA  17697
               ||||||||||||||||||||||||||||||||||||||||||||||||||||||||||||
US_Col  17683  CTGGCCAACCTATCAGACATACTAATTTTTGTGTTGTGGGCTGGTGGTTTGGAGTTGACA  17742

125_10  17698  ACTATGCGTTATTTTGTCAAGATTGGACCAAGTAAGAGTTGTGATTGTGGTAAGGTTGCT  17757
               ||||||||||||||||||||||||||||||||||||||||||||||||||||||||||||
US_Col  17743  ACTATGCGTTATTTTGTCAAGATTGGACCAAGTAAGAGTTGTGATTGTGGTAAGGTTGCT  17802

125_10  17758  ACTTGTTACAATAGTGCGCTGCATACGTACTGTTGTTTCAAACATGCCCTTGGTTGTGAT  17817
               ||||||||||||||||||||||||||||||||||||||||||||||||||||||||||||
US_Col  17803  ACTTGTTACAATAGTGCGCTGCATACGTACTGTTGTTTCAAACATGCCCTTGGTTGTGAT  17862

125_10  17818  TATCTGTATAACCCATACTGTATTGATATACAGCAGTGGGGATACAAGGGATCACTTAGC  17877
               ||||||||||||||||||||||||||||||||||||||||||||||||||||||||||||
US_Col  17863  TATCTGTATAACCCATACTGTATTGATATACAGCAGTGGGGATACAAGGGATCACTTAGC  17662

125_10  17878  CTTAACCACCATGAGCATTGTAATGTACATAGAAACGAGCATGTGGCTTCTGGTGATGCC  17937
               ||||||||||||||||||||||||||||||||||||||||||||||||||||||||||||
US_Col  17663  CTTAACCACCATGAGCATTGTAATGTACATAGAAACGAGCATGTGGCTTCTGGTGATGCC  17982

125_10  17938  ATAATGACTCGCTGTCTGGCCATACATGATTGCTTTGTCAAGAACGTTGACTGGTCCATC  17997
               ||||||||||||||||||||||||||||||||||||||||||||||||||||||||||||
US_Col  17983  ATAATGACTCGCTGTCTGGCCATACATGATTGCTTTGTCAAGAACGTTGACTGGTCCATC  18042

125_10  17998  ACATACCCATTTATTGGTAATGAGGCTGTTATTAATAAGAGCGGCCGAATTGTGCAATCA  18057
               ||||||||||||||||||||||||||||||||||||||||||||||||||||||||||||
US_Col  18043  ACATACCCATTTATTGGTAATGAGGCTGTTATTAATAAGAGCGGCCGAATTGTGCAATCA  18102

125_10  18058  CACACTATGCGGTCAGTTCTTAAGTTATACAATCCGAAAGCCATATATGATATTGGCAAT  18117
               ||||||||||||||||||||||||||||||||||||||||||||||||||||||||||||
US_Col  18103  CACACTATGCGGTCAGTTCTTAAGTTATACAATCCGAAAGCCATATATGATATTGGCAAT  18162

125_10  18118  CCTAAGGGCATTAGATGTGCCGTAACGGATGCTAAGTGGTTTTGCTTTGACAAGAATCCT  18177
               ||||||||||||||||||||||||||||||||||||||||||||||||||||||||||||
US_Col  18163  CCTAAGGGCATTAGATGTGCCGTAACGGATGCTAAGTGGTTTTGCTTTGACAAGAATCCT  18222

125_10  18178  AYTAATTCTAATGTCAAGACATTGGAGTATGACTATATAACACATGGCCAATTTGATGGG  18237
               | ||||||||||||||||||||||||||||||||||||||||||||||||||||||||||
US_Col  18223  ACTAATTCTAATGTCAAGACATTGGAGTATGACTATATAACACATGGCCAATTTGATGGG  18282

125_10  18238  TTGTGCTTGTTTTGGAATTGCAATGTAGACATGTATCCAGAATTTTCTGTGGTCTGTCGT  18297
               ||||||||||||||||||||||||||||||||||||||||||||||||||||||||||||
US_Col  18283  TTGTGCTTGTTTTGGAATTGCAATGTAGACATGTATCCAGAATTTTCTGTGGTCTGTCGT  18342

125_10  18298  TTTGATACTCGCTGTAGGTCACCACTCAACTTGGAGGGTTGTAATGGTGGTTCACTGTAT  18357
               ||||||||||||||||||||||||||||||||||||||||||||||||||||||||||||
US_Col  18343  TTTGATACTCGCTGTAGGTCACCACTCAACTTGGAGGGTTGTAATGGTGGTTCACTGTAT  18402

125_10  18358  GTTAATAATCATGCATTCCATACACCGGCTTTTGACAAGCGTGCTTTTGCTAAGTTGAAG  18417
               ||||||||||||||||||||||||||||||||||||||||||||||||||||||||||||
US_Col  18403  GTTAATAATCATGCATTCCATACACCGGCTTTTGACAAGCGTGCTTTTGCTAAGTTGAAG  18462

125_10  18418  CCAATGCCATTTTTCTTTTATGATGATACTGAGTGTGACAAGTTACAGGACTCCATAAAC  18477
               ||||||||||||||||||||||||||||||||||||||||||||||||||||||||||||
US_Col  18463  CCAATGCCATTTTTCTTTTATGATGATACTGAGTGTGACAAGTTACAGGACTCCATAAAC  18522

125_10  18478  TATGTTCCTCTTAGGGCTAGTAACTGCATTACTAAATGTAATGTTGGTGGTGCTGTCTGT  18537
               ||||||||||||||||||||||||||||||||||||||||||||||||||||||||||||
US_Col  18523  TATGTTCCTCTTAGGGCTAGTAACTGCATTACTAAATGTAATGTTGGTGGTGCTGTCTGT  18582
```

FIG. 2 (cont'd)

```
125_10   18538  AGTAAGCATTGTGCTATGTATCATAGCTATGTTAATGCTTACAACACTTTTACGTCGGCG  18597
                ||||||||||||||||||||||||||||||||||||||||||||||||||||||||||||
US_Col   18583  AGTAAGCATTGTGCTATGTATCATAGCTATGTTAATGCTTACAACACTTTTACGTCGGCG  18642

125_10   18598  GGCTTTACTATTTGGGTGCCTACTTCGTTTGACACCTATAATCTGTGGCAGACATTTAGT  18657
                ||||||||||||||||||||||||||||||||||||||||||||||||||||||||||||
US_Col   18643  GGCTTTACTATTTGGGTGCCTACTTCGTTTGACACCTATAATCTGTGGCAGACATTTAGT  18702

125_10   18658  AACAATTTGCAAGGTCTTGAGAACATTGCTTTCAATGTCGTAAAGAAAGGATCTTTTGTT  18717
                ||||||||||||||||||||||||||||||||||||||||||||||||||||||||||||
US_Col   18703  AACAATTTGCAAGGTCTTGAGAACATTGCTTTCAATGTCGTAAAGAAAGGATCTTTTGTT  18762

125_10   18718  GGTGCCGAAGGTGAACTTCCTGTAGCTGTGGTTAATGACAAAGTGCTCGTTAGAGATGGT  18777
                ||||||||||||||||||||||||||||||||||||||||||||||||||||||||||||
US_Col   18763  GGTGCCGAAGGTGAACTTCCTGTAGCTGTGGTTAATGACAAAGTGCTCGTTAGAGATGGT  18822

125_10   18778  ACTGTTGATACTCTTGTTTTTACAAACAAGACATCACTACCCACTAACGTAGCTTTTGAG  18837
                ||||||||||||||||||||||||||||||||||||||||||||||||||||||||||||
US_Col   18823  ACTGTTGATACTCTTGTTTTTACAAACAAGACATCACTACCCACTAACGTAGCTTTTGAG  18882

125_10   18838  TTGTATGCCAAGCGTAAGGTAGGACTCACCCCACCCATTACGATCCTACGTAACTTGGGT  18897
                ||||||||||||||||||||||||||||||||||||||||||||||||||||||||||||
US_Col   18883  TTGTATGCCAAGCGTAAGGTAGGACTCACCCCACCCATTACGATCCTACGTAACTTGGGT  18942

125_10   18898  GTAGTTTGTACATCTAAGTGTGTCATTTGGGACTATGAAGCCGAACGTCCACTTACTACT  18957
                ||||||||||||||||||||||||||||||||||||||||||||||||||||||||||||
US_Col   18943  GTAGTTTGTACATCTAAGTGTGTCATTTGGGACTATGAAGCCGAACGTCCACTTACTACT  19002

125_10   18958  TTTACAAAGGATGTTTGTAAATATACCGACTTTGAGGGTGACGTCTGTACACTCTTTGAT  19017
                ||||||||||||||||||||||||||||||||||||||||||||||||||||||||||||
US_Col   19003  TTTACAAAGGATGTTTGTAAATATACCGACTTTGAGGGTGACGTCTGTACACTCTTTGAT  19062

125_10   19018  AACAGCATTGTTGGTTCATTAGAGCGATTCTCCATGACCCAAAATGCTGTGCTTATGTCA  19077
                ||||||||||||||||||||||||||||||||||||||||||||||||||||||||||||
US_Col   19063  AACAGCATTGTTGGTTCATTAGAGCGATTCTCCATGACCCAAAATGCTGTGCTTATGTCA  19122

125_10   19078  CTTACAGCTGTTAAAAAGCTTAYTGGCATAAAGTTAACTTATGGTTATCTTAATGGTGTC  19137
                |||||||||||||||||||||| |||||||||||||||||||||||||||||||||||||
US_Col   19123  CTTACAGCTGTTAAAAAGCTTACTGGCATAAAGTTAACTTATGGTTATCTTAATGGTGTC  19182

125_10   19138  CCAGTTAACACACATGAAGATAAACCTTTTACTTGGTATATTTACACTAGGAAGAACGGC  19197
                ||||||||||||||||||||||||||||||||||||||||||||||||||||||||||||
US_Col   19183  CCAGTTAACACACATGAAGATAAACCTTTTACTTGGTATATTTACACTAGGAAGAACGGC  16642

125_10   19198  AAGTTCGAGGACCATCCTGATGGCTATTTTACCCAAGGTAGAACAACCGCTGATTTTAGC  16657
                ||||||||||||||||||||||||||||||||||||||||||||||||||||||||||||
US_Col   16643  AAGTTCGAGGACCATCCTGATGGCTATTTTACCCAAGGTAGAACAACCGCTGATTTTAGC  19302

125_10   16658  CCTCGTAGCGACATGGAAAAGGACTTCCTAAGTATGGATATGGGTCTGTTTATTAACAAG  19317
                ||||||||||||||||||||||||||||||||||||||||||||||||||||||||||||
US_Col   19303  CCTCGTAGCGACATGGAAAAGGACTTCCTAAGTATGGATATGGGTCTGTTTATTAACAAG  19362

125_10   19318  TACGGACTTGAAGATTACGGCTTTGAGCACGTTGTGTATGGTGATGTTTCAAAAACCACC  19377
                ||||||||||||||||||||||||||||||||||||||||||||||||||||||||||||
US_Col   19363  TACGGACTTGAAGATTACGGCTTTGAGCACGTTGTGTATGGTGATGTTTCAAAAACCACC  19422

125_10   19378  CTTGGTGGTTTGCATCTACTAATTTCGCAGGTGCGTCTGGCCTGTATGGGTGTGCTCAAA  19437
                ||||||||||||||||||||||||||||||||||||||||||||||||||||||||||||
US_Col   19423  CTTGGTGGTTTGCATCTACTAATTTCGCAGGTGCGTCTGGCCTGTATGGGTGTGCTCAAA  19482

125_10   19438  ATAGACGAGTTTGTGTCTAGTAATGATAGCACGTTAAAGTCTTGTACTGTTACATATGCT  19497
                ||||||||||||||||||||||||||||||||||||||||||||||||||||||||||||
US_Col   19483  ATAGACGAGTTTGTGTCTAGTAATGATAGCACGTTAAAGTCTTGTACTGTTACATATGCT  19542
```

FIG. 2 (cont'd)

```
125_10  19498  GATAACCCTAGTAGTAAGATGGTTTGTACGTATATGGATCTCCTGCTTGACGATTTTGTC  19557
               ||||||||||||||||||||||||||||||||||||||||||||||||||||||||||||
US_Col  19543  GATAACCCTAGTAGTAAGATGGTTTGTACGTATATGGATCTCCTGCTTGACGATTTTGTC  19602

125_10  19558  AGCATTCTTAAATCTTTGGATTTGGGCGTTGTATCTAAAGTTCATGAAGTTATGGTCGAT  19617
               ||||||||||||||||||||||||||||||||||||||||||||||||||||||||||||
US_Col  19603  AGCATTCTTAAATCTTTGGATTTGGGCGTTGTATCTAAAGTTCATGAAGTTATGGTCGAT  19662

125_10  19618  TGTAAAATGTGGAGGTGGATGTTGTGGTGTAAGGATCATAAACTCCAGACATTTTATCCG  19677
               ||||||||||||||||||||||||||||||||||||||||||||||||||||||||||||
US_Col  19663  TGTAAAATGTGGAGGTGGATGTTGTGGTGTAAGGATCATAAACTCCAGACATTTTATCCG  19722

125_10  19678  CAACTTCAGGCCAGTGAATGGAAGTGTGGTTATTCCATGCCTTCTATTTACAAGATACAA  19737
               ||||||||||||||||||||||||||||||||||||||||||||||||||||||||||||
US_Col  19723  CAACTTCAGGCCAGTGAATGGAAGTGTGGTTATTCCATGCCTTCTATTTACAAGATACAA  19782

125_10  19738  CGTATGTGTTTAGAACCTTGCAATCTCTACAACTATGGTGCTGGTATTAAGTTACCTGAT  19797
               ||||||||||||||||||||||||||||||||||||||||||||||||||||||||||||
US_Col  19783  CGTATGTGTTTAGAACCTTGCAATCTCTACAACTATGGTGCTGGTATTAAGTTACCTGAT  19842

125_10  19798  GGCATTATGTTTAACGTAGTTAAATACACACAGCTTTGTCAATATCTCAATAGCACCACA  19857
               ||||||||||||||||||||||||||||||||||||||||||||||||||||||||||||
US_Col  19843  GGCATTATGTTTAACGTAGTTAAATACACACAGCTTTGTCAATATCTCAATAGCACCACA  19902

125_10  19858  ATGTGTGTACCCCATCACATGCGTGTGCTACATCTTGGTGCTGGCTCCGACAAGGGTGTT  19917
               ||||||||||||||||||||||||||||||||||||||||||||||||||||||||||||
US_Col  19903  ATGTGTGTACCCCATCACATGCGTGTGCTACATCTTGGTGCTGGCTCCGACAAGGGTGTT  19962

125_10  19918  GCACCTGGCACGGCTGTCTTACGACGTTGGTTGCCACTGGATGCCATTATAGTTGACAAT  19977
               ||||||||||||||||||||||||||||||||||||||||||||||||||||||||||||
US_Col  19963  GCACCTGGCACGGCTGTCTTACGACGTTGGTTGCCACTGGATGCCATTATAGTTGACAAT  20022

125_10  19978  GATAGTGTGGATTACGTTAGCGATGCTGATTATAGTGTTACAGGAGATTGCTCTACCTTA  20037
               ||||||||||||||||||||||||||||||||||||||||||||||||||||||||||||
US_Col  20023  GATAGTGTGGATTACGTTAGCGATGCTGATTATAGTGTTACAGGAGATTGCTCTACCTTA  20082

125_10  20038  TACCTGTCAGATAAGTTTGATTTAGTTATATCTGATATGTATGATGGTAAGATTAAAAGT  20097
               ||||||||||||||||||||||||||||||||||||||||||||||||||||||||||||
US_Col  20083  TACCTGTCAGATAAGTTTGATTTAGTTATATCTGATATGTATGATGGTAAGATTAAAAGT  20142

125_10  20098  TGTGATGGGGAGAACGTGTCTAAAGAAGGCTTCTTTCCCTATATTAATGGTGTCATCACC  20157
               ||||||||||||||||||||||||||||||||||||||||||||||||||||||||||||
US_Col  20143  TGTGATGGGGAGAACGTGTCTAAAGAAGGCTTCTTTCCCTATATTAATGGTGTCATCACC  20202

125_10  20158  GAAAAGTTGGCACTTGGTGGTACTGTAGCTATTAAGGTGACGGAGTTTAGTTGGAATAAG  20217
               ||||||||||||||||||||||||||||||||||||||||||||||||||||||||||||
US_Col  20203  GAAAAGTTGGCACTTGGTGGTACTGTAGCTATTAAGGTGACGGAGTTTAGTTGGAATAAG  20262

125_10  20218  AAGTTGTATGAACTCATTCAGAGGTTTGAGTATTGGACAATGTTCTGTACCAGTGTTAAC  20277
               ||||||||||||||||||||||||||||||||||||||||||||||||||||||||||||
US_Col  20263  AAGTTGTATGAACTCATTCAGAGGTTTGAGTATTGGACAATGTTCTGTACCAGTGTTAAC  20322

125_10  20278  ACGTCATCGTCAGAGGCATTCTTAATTGGTGTTCACTATTTAGGTGATTTTGCAAGTGGC  20337
               ||||||||||||||||||||||||||||||||||||||||||||||||||||||||||||
US_Col  20323  ACGTCATCGTCAGAGGCATTCTTAATTGGTGTTCACTATTTAGGTGATTTTGCAAGTGGC  20382

125_10  20338  GCTGTGATTGACGGCAACACTATGCATGCCAATTATATCTTCTGGCGTAATTCCACAATT  20397
               ||||||||||||||||||||||||||||||||||||||||||||||||||||||||||||
US_Col  20383  GCTGTGATTGACGGCAACACTATGCATGCCAATTATATCTTCTGGCGTAATTCCACAATT  20442
```

FIG. 2 (cont'd)

```
125_10  20398  ATGACTATGTCTTACAATAGTGTACTTGATTTAAGCAAGTTCAATTGTAAGCATAAGGCT  20457
               ||||||||||||||||||||||||||||||||||||||||||||||||||||||||||||
US_Col  20443  ATGACTATGTCTTACAATAGTGTACTTGATTTAAGCAAGTTCAATTGTAAGCATAAGGCT  20502

125_10  20458  ACAGTTGTCATTAATTTAAAAGATTCATCCATTAGTGATGTTGTGTTAGGTTTGTTGAAG  20517
               ||||||||||||||||||||||||||||||||||||||||||||||||||||||||||||
US_Col  20503  ACAGTTGTCATTAATTTAAAAGATTCATCCATTAGTGATGTTGTGTTAGGTTTGTTGAAG  20562

125_10  20518  AATGGTAAGTTGCTAGTGCGTAATAATGACGCCATTTGTGGTTTTTCTAATCATTTGGTC  20577
               ||||||||||||||||||||||||||||||||||||||||||||||||||||||||||||
US_Col  20563  AATGGTAAGTTGCTAGTGCGTAATAATGACGCCATTTGTGGTTTTTCTAATCATTTGGTC  20622

125_10  20578  AACGTAAACAAATGAAGTCTTTAACCTACTTCTGGTTGTTCTTACCAGTACTTTCAACAC  20637
               ||||||||||||||||||||||||||||||||||||||||||||||||||||||||||||
US_Col  20623  AACGTAAACAAATGAAGTCTTTAACCTACTTCTGGTTGTTCTTACCAGTACTTTCAACAC  20682

125_10  20638  TTAGCCTACCACAAGATGTCACCAGGTGCTCAGCTAACACTAATTTTAGGCGGTTCTTTT  20697
               ||||||||||||||||||||||||||||||||||||||||||||||||||||||||||||
US_Col  20683  TTAGCCTACCACAAGATGTCACCAGGTGCTCAGCTAACACTAATTTTAGGCGGTTCTTTT  20742

125_10  20698  CAAAATTTAATGTTCAGGCGCCTGCAGTTGTTGTACTGGGCGGTTATCTACCTATTGGTG  20757
               ||||||||||||||||||||||||||||||||||||||||||||||||||||||||||||
US_Col  20743  CAAAATTTAATGTTCAGGCGCCTGCAGTTGTTGTACTGGGCGGTTATCTACCTATTGGTG  20802

125_10  20758  AAAACCAGGGTGTCAATTCAACTTGGTACTGTGCTGGCCAACATCCAACTGCTAGTGGCG  20817
               ||||||||||||||||||||||||||||||||||||||||||||||||||||||||||||
US_Col  20803  AAAACCAGGGTGTCAATTCAACTTGGTACTGTGCTGGCCAACATCCAACTGCTAGTGGCG  20862

125_10  20818  TTCATGGTATCTTTGTTAGCCATATTAGAGGTGGTCATGGCTTTGAGATTGGCATTTCGC  20877
               ||||||||||||||||||||||||||||||||||||||||||||||||||||||||||||
US_Col  20863  TTCATGGTATCTTTGTTAGCCATATTAGAGGTGGTCATGGCTTTGAGATTGGCATTTCGC  20662

125_10  20878  AAGAGCCTTTTGACCCTAGTGGTTACCAGCTTTATTTACATAAGGCTACTAACGGTAACA  20937
               ||||||||||||||||||||||||||||||||||||||||||||||||||||||||||||
US_Col  20663  AAGAGCCTTTTGACCCTAGTGGTTACCAGCTTTATTTACATAAGGCTACTAACGGTAACA  20982

125_10  20938  CTAATGCTACTGCGCGACTGCGCATTTGCCAGTTTCCTAGCATTAAAACATTGGGCCCCA  20997
               ||||||||||||||||||||||||||||||||||||||||||||||||||||||||||||
US_Col  20983  CTAATGCTACTGCGCGACTGCGCATTTGCCAGTTTCCTAGCATTAAAACATTGGGCCCCA  2662

125_10  20998  CTGCTAATAATGATGTTACAATAGGTCGTAATTGCCTATTTAACAAAGCCATCCCAGCTC  21057
               ||||||||||||||||||||| ||||||||||||||||||||||||||||||||||||||
US_Col  2663   CTGCTAATAATGATGTTACAACAGGTCGTAATTGCCTATTTAACAAAGCCATCCCAGCTC  21102

125_10  21058  ATATGAGTGAACATAGTGTTGTCGGCATAACATGGGATAATGATCGTGTCACTGTCTTTT  21117
               ||||||||||||||||||||||||||||||||||||||||||||||||||||||||||||
US_Col  21103  ATATGAGTGAACATAGTGTTGTCGGCATAACATGGGATAATGATCGTGTCACTGTCTTTT  21162

125_10  21118  CTGACAAGATCTATTATTTTTATTTTAAAAATGATTGGTCCCGTGTTGCGACAAAGTGTT  21177
               ||||||||||||||||||||||||||||||||||||||||||||||||||||||||||||
US_Col  21163  CTGACAAGATCTATTATTTTTATTTTAAAAATGATTGGTCCCGTGTTGCGACAAAGTGTT  21222

125_10  21178  ACAACAGTGGAGGTTGTGCTATGCAATATGTTTACGAACCCACCTATTACATGCTTAATG  21237
               ||||||||||||||||||||||||||||||||||||||||||||||||||||||||||||
US_Col  21223  ACAACAGTGGAGGTTGTGCTATGCAATATGTTTACGAACCCACCTATTACATGCTTAATG  21282

125_10  21238  TTACTAGTGCTGGTGAGGATGGTATTTCTTATCAACCCTGTACAGCTAATTGCATTGGTT  21297
               ||||||||||||||||||||||||||||||||||||||||||||||||||||||||||||
US_Col  21283  TTACTAGTGCTGGTGAGGATGGTATTTCTTATCAACCCTGTACAGCTAATTGCATTGGTT  21342

125_10  21298  ATGCTGCCAATGTATTTGCTACTGAGCCCAATGGCCACATACCAGAAGGTTTTAGTTTTA  21357
               ||||||||||||||||||||||||||||||||||||||||||||||||||||||||||||
US_Col  21343  ATGCTGCCAATGTATTTGCTACTGAGCCCAATGGCCACATACCAGAAGGTTTTAGTTTTA  21402
```

FIG. 2 (cont'd)

```
125_10  21358  ATAATTGGTTTCTTTTGTCCAATGATTCCACTTTGGTGCATGGTAAGGTGGTTTCCAACC  21417
               ||||||||||||||||||||||||||||||||||||||||||||||||||||||||||||
US_Col  21403  ATAATTGGTTTCTTTTGTCCAATGATTCCACTTTGGTGCATGGTAAGGTGGTTTCCAACC  21462

125_10  21418  AACCATTGTTGGTCAATTGTCTTTTGGCCATTCCTAAGATTTATGGACTAGGCCAATTTT  21477
               ||||||||||||||||||||||||||||||||||||||||||||||||||||||||||||
US_Col  21463  AACCATTGTTGGTCAATTGTCTTTTGGCCATTCCTAAGATTTATGGACTAGGCCAATTTT  21522

125_10  21478  TCTCCTTTAATCAAACGATCGATGGTGTTTGTAATGGAGCTGCTGTGCAGCGTGCACCAG  21537
               ||||||||||||||||||||||||||||||||||||||||||||||||||||||||||||
US_Col  21523  TCTCCTTTAATCAAACGATCGATGGTGTTTGTAATGGAGCTGCTGTGCAGCGTGCACCAG  21582

125_10  21538  AGGCTCTGAGGTTTAATATTAATGACACCTCTGTCATTCTTGCTGAAGGCTCAATTGTAC  21597
               ||||||||||||||||||||||||||||||||||||||||||||||||||||||||||||
US_Col  21583  AGGCTCTGAGGTTTAATATTAATGACACCTCTGTCATTCTTGCTGAAGGCTCAATTGTAC  21642

125_10  21598  TTCATACTGCTTTAGGAACAAATTTTTCTTTTGTTTGCAGTAATTCCCCAAATCCTCACT  21657
               ||||||||||||||||||||||||||||||||||||||||||||||| ||||||||||||
US_Col  21643  TTCATACTGCTTTAGGAACAAATTTTTCTTTTGTTTGCAGTAATTCCTCAAATCCTCACT  21702

125_10  21658  TAGCCACCTTCGCCATACCTCTGGGTGCTACCCAAGTACCTTATTATTGTTTTCTTAAAG  21717
               ||||||||||||||||||||||||||||||||||||||||||||||||||||||||||||
US_Col  21703  TAGCCACCTTCGCCATACCTCTGGGTGCTACCCAAGTACCTTATTATTGTTTTCTTAAAG  21762

125_10  21718  TGGATACTTACAACTCCACTGTTTATAAATTTTTGGCTGTTTTACCTCCTACCGTCAGGG  21777
               ||||||||||||||||||||||||||||||||||||||||||||||||||||||||||||
US_Col  21763  TGGATACTTACAACTCCACTGTTTATAAATTTTTGGCTGTTTTACCTCCTACCGTCAGGG  21822

125_10  21778  AAATTGTCATCACCAAGTATGGTGATGTTTATGTCAATGGGTTTGGATACTTGCATCTCG  21837
               ||||||||||||||||||||||||||||||||||||||||||||||||||||||||||||
US_Col  21823  AAATTGTCATCACCAAGTATGGTGATGTTTATGTCAATGGGTTTGGATACTTGCATCTCG  21882

125_10  21838  GTTTGTTGGATGCTGTCACAATTAATTTCACTGGTCATGGCACTGACGATGATGTTTCTG  21897
               ||||||||||||||||||||||||||||||||||||||||||||||||||||||||||||
US_Col  21883  GTTTGTTGGATGCTGTCACAATTAATTTCACTGGTCATGGCACTGACGATGATGTTTCTG  21942

125_10  21898  GTTTTTGGACCATAGCATCGACTAATTTTGTTGATGCACTCATCGAAGTTCAAGGAACCG  21957
               ||||||||||||||||||||||||||||||||||||||||||||||||||||||||||||
US_Col  21943  GTTTTTGGACCATAGCATCGACTAATTTTGTTGATGCACTCATCGAAGTTCAAGGAACCG  22002

125_10  21958  CCATTCAGCGTATTCTTTATTGTGATGATCCTGTTAGCCAACTCAAGTGTTCTCAGGTTG  22017
               ||||||||||||||||||||||||||||||||||||||||||||||||||||||||||||
US_Col  22003  CCATTCAGCGTATTCTTTATTGTGATGATCCTGTTAGCCAACTCAAGTGTTCTCAGGTTG  22062

125_10  22018  CTTTTGACCTTGACGATGGTTTTTACCCTATTTCTTCTAGAAACCTTCTGAGTCATGAAC  22077
               ||||||||||||||||||||||||||||||||||||||||||||||||||||||||||||
US_Col  22063  CTTTTGACCTTGACGATGGTTTTTACCCTATTTCTTCTAGAAACCTTCTGAGTCATGAAC  22122

125_10  22078  AGCCAATTTCTTTTGTTACTCTGCCATCATTTAATGATCATTCTTTTGTTAACATTACTG  22137
               ||||||||||||||||||||||||||||||||||||||||||||||||||||||||||||
US_Col  22123  AGCCAATTTCTTTTGTTACTCTGCCATCATTTAATGATCATTCTTTTGTTAACATTACTG  22182

125_10  22138  TATCTGCTTCCTTTGGTGGTCATAGTGGTGCCAACCTTATTGCATCTGACACTACTATCA  22197
               ||||||||||||||||||||||||||||||||||||||||||||||||||||||||||||
US_Col  22183  TATCTGCTTCCTTTGGTGGTCATAGTGGTGCCAACCTTATTGCATCTGACACTACTATCA  22242

125_10  22198  ATGGGTTTAGTTCTTTCTGTGTTGACACTAGACAATTTACCATTTCACTGTTTTATAACG  22257
               ||||||||||||||||||||||||||||||||||||||||||||||||||||||||||||
US_Col  22243  ATGGGTTTAGTTCTTTCTGTGTTGACACTAGACAATTTACCATTTCACTGTTTTATAACG  22302
```

FIG. 2 (cont'd)

```
125_10  22258  TTACAAACAGTTATGGTTATGTGTCTAAATCACAGGACAGTAATTGCCCTTTCACCTTGC  22317
               ||||||||||||||||||||||||||||||||||||||||||||||||||||||||||||
US_Col  22303  TTACAAACAGTTATGGTTATGTGTCTAAATCACAGGACAGTAATTGCCCTTTCACCTTGC  22362

125_10  22318  AATCTGTTAATGATTACCTGTCTTTTAGCAAATTTTGTGTTTCCACCAGCCTTTTGGCTA  22377
               ||||||||||||||||||||||||||||||||||||||||||||||||||||||||||||
US_Col  22363  AATCTGTTAATGATTACCTGTCTTTTAGCAAATTTTGTGTTTCCACCAGCCTTTTGGCTA  22422

125_10  22378  GTGCCTGTACCATAGATCTTTTTGGTTACCCTGAGTTTGGTAGTGGTGTTAAGTTTACGT  22437
               ||||||||||||||||||||||||||||||||||||||||||||||||||||||||||||
US_Col  22423  GTGCCTGTACCATAGATCTTTTTGGTTACCCTGAGTTTGGTAGTGGTGTTAAGTTTACGT  22482

125_10  22438  CCCTTTACTTTCAATTCACAAAGGGTGAGTTGATTACTGGCACGACTAAACCACTTGAAG  22497
               |||||||||||||||||||||||||||||||||||||||||||| |||||||||||||||
US_Col  22483  CCCTTTACTTTCAATTCACAAAGGGTGAGTTGATTACTGGCACGCCTAAACCACTTGAAG  22542

125_10  22498  GTGTCACGGACGTTTCTTTTATGACTCTGGATGTGTGTACCAAGTATACTATCTATGGCT  22557
               ||||||||||||||||||||||||||||||||||||||||||||||||||||||||||||
US_Col  22543  GTGTCACGGACGTTTCTTTTATGACTCTGGATGTGTGTACCAAGTATACTATCTATGGCT  22602

125_10  22558  TTAAAGGTGAGGGTATCATTACCCTTACAAATTCTAGCTTTTTGGCAGGTGTTTATTACA  22617
               ||||||||||||||||||||||||||||||||||||||||||||||||||||||||||||
US_Col  22603  TTAAAGGTGAGGGTATCATTACCCTTACAAATTCTAGCTTTTTGGCAGGTGTTTATTACA  22662

125_10  22618  CATCTGTTTCTGGACAGTTGTTAGCCTTTAAGAATGTCACTAGTGGTGCTGTTTATTCTG  22677
               |||||| |||||||||||||||||||||||||||||||||||||||||||||||||||||
US_Col  22663  CATCTGATTCTGGACAGTTGTTAGCCTTTAAGAATGTCACTAGTGGTGCTGTTTATTCTG  22722

125_10  22678  TTACGCCATGTTCTTTTTCAGAGCAGGCTGCATATGTTGATGATGATATAGTGGGTGTTA  22737
               ||||||||||||||||||||||||||||||||||||||||||||||||||||||||||||
US_Col  22723  TTACGCCATGTTCTTTTTCAGAGCAGGCTGCATATGTTGATGATGATATAGTGGGTGTTA  22782

125_10  22738  TTTCTAGTTTGTCTAGCTCCACTTTTAACAGTACTAGGGAGTTGCCTGGTTTCTTCTACC  22797
               ||||||||||||||||||||||||||||||||||||||||||||||||||||||||||||
US_Col  22783  TTTCTAGTTTGTCTAGCTCCACTTTTAACAGTACTAGGGAGTTGCCTGGTTTCTTCTACC  22842

125_10  22798  ATTCTAATGATGGCTCTAATTGTACAGAGCCTGTGTTGGTGTATAGTAACATAGGTGTTT  22857
               ||||||||||||||||||||||||||||||||||||||||||||||||||||||||||||
US_Col  22843  ATTCTAATGATGGCTCTAATTGTACAGAGCCTGTGTTGGTGTATAGTAACATAGGTGTTT  22902

125_10  22858  GTAAATCTGGCAGTATTGGCTACGTCCCATCTCAGTCTGGCCAAGTCAAGATTGCACCCA  22917
               ||||||||||||||||||||||||||||||||||||||||||||||||||||||||||||
US_Col  22903  GTAAATCTGGCAGTATTGGCTACGTCCCATCTCAGTCTGGCCAAGTCAAGATTGCACCCA  22962

125_10  22918  CGGTTACTGGGAATATTAGTATTCCCACCAACTTTAGTATGAGTATTAGGACAGAATATT  22977
               ||||||||||||||||||||||||||||||||||||||||||||||||||||||||||||
US_Col  22963  CGGTTACTGGGAATATTAGTATTCCCACCAACTTTAGTATGAGTATTAGGACAGAATATT  23022

125_10  22978  TACAGCTTTACAACACGCCTGTTAGTGTTGATTGTGCCACATATGTTTGTAATGGTAACT  23037
               ||||||||||||||||||||||||||||||||||||||||||||||||||||||||||||
US_Col  23023  TACAGCTTTACAACACGCCTGTTAGTGTTGATTGTGCCACATATGTTTGTAATGGTAACT  23082

125_10  23038  CTCGTTGTAAACAATTACTCACCCAGTACACTGCAGCATGTAAGACCATAGAGTCAGCAT  23097
               ||||||||||||||||||||||||||||||||||||||||||||||||||||||||||||
US_Col  23083  CTCGTTGTAAACAATTACTCACCCAGTACACTGCAGCATGTAAGACCATAGAGTCAGCAT  23142

125_10  23098  TACGACTCAGCGCTAGGCTTGAGTCTGTTGAAGTTAACTCTATGCTTACTATTTCTGAAG  23157
               ||| ||||||||||||||||||||||||||||||||||||||||||||||||||||||||
US_Col  23143  TACAACTCAGCGCTAGGCTTGAGTCTGTTGAAGTTAACTCTATGCTTACTATTTCTGAAG  23202

125_10  23158  AGGCTCTACAGTTAGCTACCATTAGTTCGTTTAATGGTGATGGATATAATTTTACTAATG  23217
               ||||||||||||||||||||||||||||||||||||||||||||||||||||||||||||
US_Col  23203  AGGCTCTACAGTTAGCTACCATTAGTTCGTTTAATGGTGATGGATATAATTTTACTAATG  23262
```

FIG. 2 (cont'd)

```
125_10  23218  TGCTGGGTGTTTCTGTGTATGATCCTGCAAGGGGCAGGGTGGTACAAAAAAGGTCTTTTA  23277
               ||||||||||||||||||||||||||||||| ||||||||||||||||||||||||||||
US_Col  23263  TGCTGGGTGTTTCTGTGTATGATCCTGCAAGTGGCAGGGTGGTACAAAAAAGGTCTTTTA  23322

125_10  23278  TTGAAGACCTGCTTTTTAATAAAGTGGTTACTAATGGCCTTGGTACTGTTGATGAAGACT  23337
               ||||||||||||||||||||||||||||||||||||||||||||||||||||||||||||
US_Col  23323  TTGAAGACCTGCTTTTTAATAAAGTGGTTACTAATGGCCTTGGTACTGTTGATGAAGACT  23382

125_10  23338  ATAAGCGCTGTTCTAATGGTCGCTCTGTGGCAGATCTAGTCTGTGCACAGTATTACTCTG  23397
               ||||||||||||||||||||||||||||||||||||||||||||||||||||||||||||
US_Col  23383  ATAAGCGCTGTTCTAATGGTCGCTCTGTGGCAGATCTAGTCTGTGCACAGTATTACTCTG  23442

125_10  23398  GTGTCATGGTACTACCTGGTGTTGTTGACGCTGAGAAGCTTCACATGTATAGTGCGTCTC  23457
               ||||||||||||||||||||||||||||||||||||||||||||||||||||||||||||
US_Col  23443  GTGTCATGGTACTACCTGGTGTTGTTGACGCTGAGAAGCTTCACATGTATAGTGCGTCTC  23502

125_10  23458  TCATCGGTGGTATGGTGCTAGGAGGTTTTACTTCTGCAGCGGCATTGCCTTTTAGCTATG  23517
               ||||||||||||||||||||||||||||||||||||||||||||||||||||||||||||
US_Col  23503  TCATCGGTGGTATGGTGCTAGGAGGTTTTACTTCTGCAGCGGCATTGCCTTTTAGCTATG  23562

125_10  23518  CTGTTCAAGCTAGACTCAATTATCTTGCTCTACAGACGGATGTTCTACAGCGGAACCAGC  23577
               ||||||||||||||||||||||||||||||||||||||||||||||||||||||||||||
US_Col  23563  CTGTTCAAGCTAGACTCAATTATCTTGCTCTACAGACGGATGTTCTACAGCGGAACCAGC  23622

125_10  23578  AATTGCTTGCTGAGTCTTTTAACTCTGCTATTGGTAATATAACTTCAGCCTTTGAGAGTG  23637
               ||||||||||||||||||||||||||||||||||||||||||||||||||||||||||||
US_Col  23623  AATTGCTTGCTGAGTCTTTTAACTCTGCTATTGGTAATATAACTTCAGCCTTTGAGAGTG  23682

125_10  23638  TTAAAGAGGCTATTAGTCAAACTTCCAAGGGTTTGAACACTGTGGCTCATGCGCTTACTA  23697
               ||||||||||||||||||||||||||||||||||||||||||||||||||||||||||||
US_Col  23683  TTAAAGAGGCTATTAGTCAAACTTCCAAGGGTTTGAACACTGTGGCTCATGCGCTTACTA  23742

125_10  23698  AGGTTCAAGAGGTTGTTAACTCGCAGGGTGCAGCTTTGACTCAACTTACCGTACAGCTGC  23757
               ||||||||||||||||||||||||||||||||||||||||||||||||||||||||||||
US_Col  23743  AGGTTCAAGAGGTTGTTAACTCGCAGGGTGCAGCTTTGACTCAACTTACCGTACAGCTGC  23802

125_10  23758  AACACAACTTCCAAGCCATTTCTAGTTCTATTGATGACATTTACTCTCGACTGGACATTC  23817
               ||||||||||||||||||||||||||||||||||||||||||||||||||||||||||||
US_Col  23803  AACACAACTTCCAAGCCATTTCTAGTTCTATTGATGACATTTACTCTCGACTGGACATTC  23862

125_10  23818  TTTCAGCCGATGTTCAGGTTGACCGTCTCATCACCGGCAGATTATCAGCACTTAATGCTT  23877
               ||||||||||||||||||||||||||||||||||||||||||||||||||||||||||||
US_Col  23863  TTTCAGCCGATGTTCAGGTTGACCGTCTCATCACCGGCAGATTATCAGCACTTAATGCTT  23662

125_10  23878  TTGTTGCTCAAACCCTCACTAAGTATACTGAGGTTCAGGCTAGCAGGAAGTTAGCACAGC  23937
               ||||||||||||||||||||||||||||||||||||||||||||||||||||||||||||
US_Col  23663  TTGTTGCTCAAACCCTCACTAAGTATACTGAGGTTCAGGCTAGCAGGAAGTTAGCACAGC  23982

125_10  23938  AAAAGGTTAATGAGTGCGTTAAATCGCAATCCCAGCGTTATGGTTTTTGTGGTGGTGATG  23997
               ||||||||||||||||||||||||||||||| ||||||||||||||||||||||||||||
US_Col  23983  AAAAGGTTAATGAGTGCGTTAAATCGCAATCTCAGCGTTATGGTTTTTGTGGTGGTGATG  24042

125_10  23998  GCGAGCACATTTTCTCTCTGGTACAGGCAGCACCTCAGGGCCTGCTGTTTTTACATACAG  24057
               ||||||||||||||||||||||||||||||||||||||||||||||||||||||||||||
US_Col  24043  GCGAGCACATTTTCTCTCTGGTACAGGCAGCACCTCAGGGCCTGCTGTTTTTACATACAG  24102

125_10  24058  TACTTGTACCGAGTGATTTTGTAGATGTTATTGCCATCGCTGGCTTATGCGTTAACGATG  24117
               ||||||||||||||||||||||||||||||||||||||||||||||||||||||||||||
US_Col  24103  TACTTGTACCGAGTGATTTTGTAGATGTTATTGCCATCGCTGGCTTATGCGTTAACGATG  24162

125_10  24118  AAATTGCCTTGACTCTACGTGAGCCTGGCTTAGTCTTGTTTACGCATGAACTTCAAAATC  24177
               ||||||||||||||||||||||||||||||||||||||||||||||||||||||||||||
US_Col  24163  AAATTGCCTTGACTCTACGTGAGCCTGGCTTAGTCTTGTTTACGCATGAACTTCAAAATC  24222
```

FIG. 2 (cont'd)

```
125_10  24178  ATACTGCGACGGAATATTTTGTTTCATCGCGACGTATGTTTGAACCTAGAAAACCTACCG  24237
               ||||||||||||||||||||||||||||||||||||||||||||||||||||||||||||
US_Col  24223  ATACTGCGACGGAATATTTTGTTTCATCGCGACGTATGTTTGAACCTAGAAAACCTACCG  24282

125_10  24238  TTAGTGATTTTGTTCAAATTGAGAGTTGTGTGGTCACCTATGTCAATTTGACTAGAGACC  24297
               ||||||||||||||||||||||||||||||||||||||||||||||||||||||||||||
US_Col  24283  TTAGTGATTTTGTTCAAATTGAGAGTTGTGTGGTCACCTATGTCAATTTGACTAGAGACC  24342

125_10  24298  AACTACCAGATGTAATCCCAGATTACATCGATGTTAACAAAACACTTGATGAGATTTTAG  24357
               ||||||||||||||||||||||||||||||||||||||||||||||||||||||||||||
US_Col  24343  AACTACCAGATGTAATCCCAGATTACATCGATGTTAACAAAACACTTGATGAGATTTTAG  24402

125_10  24358  CTTCTCTGCCCAATAGAACTGGTCCAAGTCTTCCTTTAGATGTTTTTAATGCCACTTATC  24417
               ||||||||||||||||||||||||||||||||||||||||||||||||||||||||||||
US_Col  24403  CTTCTCTGCCCAATAGAACTGGTCCAAGTCTTCCTTTAGATGTTTTTAATGCCACTTATC  24462

125_10  24418  TTAATCTCACTGGTGAAATTGCAGATTTAGAGCAGCGTTCAGAGTCTCTCCGTAATACTA  24477
               ||||||||||||||||||||||||||||||||||||||||||||||||||||||||||||
US_Col  24463  TTAATCTCACTGGTGAAATTGCAGATTTAGAGCAGCGTTCAGAGTCTCTCCGTAATACTA  24522

125_10  24478  CAGAGGAGCTCCAAAGTCTTATATATAATATCAACAACACACTAGTTGACCTTGAGTGGC  24537
               ||||||||||||||||||||||||||||||||||||||||||||||||||||||||||||
US_Col  24523  CAGAGGAGCTCCAAAGTCTTATATATAATATCAACAACACACTAGTTGACCTTGAGTGGC  24582

125_10  24538  TCAACCGAGTTGAGACATATATCAAGTGGCCGTGGTGGGTTTGGTTGATTATTTTCATTG  24597
               ||||||||||||||||||||||||||||||||||||||||||||||||||||||||||||
US_Col  24583  TCAACCGAGTTGAGACATATATCAAGTGGCCGTGGTGGGTTTGGTTGATTATTTTCATTG  24642

125_10  24598  TTCTCATCTTTGTTGTGTCATTACTAGTGTTCTGCTGCATTTCCACGGGTTGTTGTGGAT  24657
               ||||||||||||||||||||||||||||||||||||||||||||||||||||||||||||
US_Col  24643  TTCTCATCTTTGTTGTGTCATTACTAGTGTTCTGCTGCATTTCCACGGGTTGTTGTGGAT  24702

125_10  24658  GCTGCGGCTGCTGCTGTGCTTGTTTCTCAGGTTGTTGTAGGGGTCCTAGACTTCAACCTT  24717
               ||||||||||||||||||||||||||||||||||||||||||||||||||||||||||||
US_Col  24703  GCTGCGGCTGCTGCTGTGCTTGTTTCTCAGGTTGTTGTAGGGGTCCTAGACTTCAACCTT  24762

125_10  24718  ACGAAGTTTTTGAAAAGGTCCACGTGCAGTGATGTTTCTTGGACTTTTTCAATACACGAT  24777
               ||||||||||||||||||||||||||||||||||||||||||||||||||||||||||||
US_Col  24763  ACGAAGTTTTTGAAAAGGTCCACGTGCAGTGATGTTTCTTGGACTTTTTCAATACACGAT  24822

125_10  24778  TGACACAGTTGTCAAAGATGTCTCAAAGTCTGCTAACTTGTCTTTGGATGCTGTCCAAGA  24837
               ||||||||||||||||||||||||||||||||||||||||||||||||||||||||||||
US_Col  24823  TGACACAGTTGTCAAAGATGTCTCAAAGTCTGCTAACTTGTCTTTGGATGCTGTCCAAGA  24882

125_10  24838  GTTGGAGCTCAATGTAGTTCCAATTAGACAAGCTTCAAATGTGACGGGTTTTCTTTTCAC  24897
               ||||||||||||||||||||||||||||||||||||||||||||||||||||||||||||
US_Col  24883  GTTGGAGCTCAATGTAGTTCCAATTAGACAAGCTTCAAATGTGACGGGTTTTCTTTTCAC  24942

125_10  24898  CAGTGTTTTTATCTACTTCTTTGCACTGTTTAAAGCGTCTTCTTTGAGGCGCAATTATAT  24957
               ||||||||||||||||||||||||||||||||||||||||||||||||||||||||||||
US_Col  24943  CAGTGTTTTTATCTACTTCTTTGCACTGTTTAAAGCGTCTTCTTTGAGGCGCAATTATAT  25002

125_10  24958  TATGTTGGCAGCGCGTTTTGCTGTCATTGTTCTTTATTGCCCACTTTTATATTATTGTGG  25017
               ||||||||||||||||||||||||||||||||||||||||||||||||||||||||||||
US_Col  25003  TATGTTGGCAGCGCGTTTTGCTGTCATTGTTCTTTATTGCCCACTTTTATATTATTGTGG  25062

125_10  25018  TGCATTTTTAGATGCAACTATTATTTGTTGCACACTTATTCAAAGTCGGTGGCAGGCTTT  25077
               |||||||||||||||||||||||||||||||||||||||          |||||||||||
US_Col  25063  TGCATTTTTAGATGCAACTATTATTTGTTGCACACTTAT----------TGGCAGGCTTT  25112
```

FIG. 2 (cont'd)

```
125_10  25078  GTTTAGTCTGCTTTTACTCCTGGCGCTATAAAAATGCGCTCTTTATTATTTTTAATACTA  25137
               ||||||||||||||||||||||||||||||||||||||||||||||||||||||||||||
US_Col  25113  GTTTAGTCTGCTTTTACTCCTGGCGCTATAAAAATGCGCTCTTTATTATTTTTAATACTA  25172

125_10  25138  CGACACTTTCTTTCCTCAATGGTAAAGCAGCTTATTATGACGGCAAATCCATTGTGATTT  25197
               ||||||||||||||||||||||||||||||||||||||||||||||||||||||||||||
US_Col  25173  CGACACTTTCTTTCCTCAATGGTAAAGCAGCTTATTATGACGGCAAATCCATTGTGATTT  25232

125_10  25198  TAGAAGGTGGTGACCATTACATCACTTTTGGCAACTCTTTTGTTGCTTTTGTTAGTAGCA  25257
               |||||||||||||||||||||||||||||||||||||| |||||||||||||||||||||
US_Col  25233  TAGAAGGTGGTGACCATTACATCACTTTTGGCAACTCTCTTGTTGCTTTTGTTAGTAGCA  25266

125_10  25258  TCGACTTGTATCTAGCTATACGTGGGCGGCAAGAAGCTGACCTACAGCTGTTGCGAACTG  25317
               ||||||||||||||||||||||||||||||||||||||||||||||||||||||||||||
US_Col  25293  TCGACTTGTATCTAGCTATACGTGGGCGGCAAGAAGCTGACCTACAGCTGTTGCGAACTG  25352

125_10  25318  TTGAGCTTCTTGATGGCAAGAAGCTTTATGTCTTTTCGCAACATCAAATTGTTGGCATTA  25377
               ||||||||||||||||||||||||||||||||||||||||||||||||||||||||||||
US_Col  25353  TTGAGCTTCTTGATGGCAAGAAGCTTTATGTCTTTTCGCAACATCAAATTGTTGGCATTA  25412

125_10  25378  CTAATGCTGCATTTGACTCAATTCAACTAGACGAGTATGCTACAATTAGTGAATGATAAT  25437
               ||||||||||||||||||||||||||||||||||||||||||||||||||||||||||||
US_Col  25413  CTAATGCTGCATTTGACTCAATTCAACTAGACGAGTATGCTACAATTAGTGAATGATAAT  25472

125_10  25438  GGTCTAGTAGTTAATGTTATACTTTGGCTTTTCGTACTCTTTTTCCTGCTTATTATAAGC  25497
               ||||||||||||||||||||||||||||||||||||||||||||||||||||||||||||
US_Col  25473  GGTCTAGTAGTTAATGTTATACTTTGGCTTTTCGTACTCTTTTTCCTGCTTATTATAAGC  25532

125_10  25498  ATTACTTTCGTCCAATTGGTTAATCTGTGCTTCACTTGTCACCGGTTGTGTAATAGCGCA  25557
               ||||||||||||||||||||||||||||||||||||||||||||||||||||||||||||
US_Col  25533  ATTACTTTCGTCCAATTGGTTAATCTGTGCTTCACTTGTCACCGGTTGTGTAATAGCGCA  25566

125_10  25558  GTTTACACACCTATAGGGCGTTTGTATAGAGTTTATAAGTCTTACATGCAAATAGACCCC  25617
               ||||||||||||||||||||||||||||||||||||||||||||||||||||||||||||
US_Col  25593  GTTTACACACCTATAGGGCGTTTGTATAGAGTTTATAAGTCTTACATGCAAATAGACCCC  25652

125_10  25618  CTCCCTAGTACTGTTATTGACGTATAAACGAAATATGTCTAACGGTTCTATTCCCGTTGA  25677
               ||||||||||||||||||||||||||||||||||||||||||||||||||||||||||||
US_Col  25653  CTCCCTAGTACTGTTATTGACGTATAAACGAAATATGTCTAACGGTTCTATTCCCGTTGA  25712

125_10  25678  TGAGGTGATTCAACACCTTAGAAACTGGAATTTCACATGGAATATCATACTGACGATACT  25737
               ||||||||||||||||||||||||||||||||||||||||||||||||||||||||||||
US_Col  25713  TGAGGTGATTCAACACCTTAGAAACTGGAATTTCACATGGAATATCATACTGACGATACT  25772

125_10  25738  ACTTGTAGTGCTTCAGTATGGCCATTACAAGTACTCTGCGTTCTTGTATGGTGTCAAGAT  25797
               ||||||||||||||||||||||||||||||||||||||||||||||||||||||||||||
US_Col  25773  ACTTGTAGTGCTTCAGTATGGCCATTACAAGTACTCTGCGTTCTTGTATGGTGTCAAGAT  25832

125_10  25798  GGCTATTCTATGGATACTTTGGCCTCTTGTGTTAGCACTGTCACTTTTTGATGCATGGGC  25857
               ||||||||||||||||||||||||||||||||||||||||||||||||||||||||||||
US_Col  25833  GGCTATTCTATGGATACTTTGGCCTCTTGTGTTAGCACTGTCACTTTTTGATGCATGGGC  25866

125_10  25858  TAGCTTTCAGGTCAATTGGGTCTTTTTTGCTTTCAGCATCCTTATGGCTTGCATCACTCT  25917
               ||||||||||||||||||||||||||||||||||||||||||||||||||||||||||||
US_Col  25893  TAGCTTTCAGGTCAATTGGGTCTTTTTTGCTTTCAGCATCCTTATGGCTTGCATCACTCT  25952

125_10  25918  TATGCTGTGGATAATGTACTTTGTCAATAGCATTCGGTTGTGGCGCAGGACACATTCTTG  25977
               ||||||||||||||||||||||||||||||||||||||||||||||||||||||||||||
US_Col  25953  TATGCTGTGGATAATGTACTTTGTCAATAGCATTCGGTTGTGGCGCAGGACACATTCTTG  26012

125_10  25978  GTGGTCTTTCAATCCTGAAACAGACGCGCTTCTCACTACTTCTGTGATGGGCCGACAGGT  26037
               ||||||||||||||||||||||||||||||||||||||||||||||||||||||||||||
US_Col  26013  GTGGTCTTTCAATCCTGAAACAGACGCGCTTCTCACTACTTCTGTGATGGGCCGACAGGT  26072
```

FIG. 2 (cont'd)

```
125_10  26038  CTGCATTCCAGTGCTTGGAGCACCAACTGGTGTAACGCTAACACTCCTTAGTGGTACATT  26097
               ||||||||||||||||||||||||||||||||||||||||||||||||||||||||||||
US_Col  26073  CTGCATTCCAGTGCTTGGAGCACCAACTGGTGTAACGCTAACACTCCTTAGTGGTACATT  26132

125_10  26098  GCTTGTAGAGGGCTATAAGGTTGCTACTGGCGTACAGGTAAGTCAATTACCTAATTTCGT  26157
               ||||||||||||||||||||||||||||||||||||||||||||||||||||||||||||
US_Col  26133  GCTTGTAGAGGGCTATAAGGTTGCTACTGGCGTACAGGTAAGTCAATTACCTAATTTCGT  26166

125_10  26158  CACAGTCGCCAAGGCCACTACAACAATTGTCTACGGACGTGTTGGTCGTTCAGTCAATGC  26217
               ||||||||||||||||||||||||||||||||||||||||||||||||||||||||||||
US_Col  26193  CACAGTCGCCAAGGCCACTACAACAATTGTCTACGGACGTGTTGGTCGTTCAGTCAATGC  26252

125_10  26218  TTCATCTGGCACTGGTTGGGCTTTCTATGTCCGGTCCAAACACGGCGACTACTCAGCTGT  26277
               ||||||||||||||||||||||||||||||||||||||||||||||||||||||||||||
US_Col  26253  TTCATCTGGCACTGGTTGGGCTTTCTATGTCCGGTCCAAACACGGCGACTACTCAGCTGT  26312

125_10  26278  GAGTAATCCGAGTTCGGTTCTCACAGATAGTGAGAAAGTGCTTCATTTAGTCTAAACAGA  26337
               ||||||||||||||||||||||||||||||||||||||||||||||||||||||||||||
US_Col  26313  GAGTAATCCGAGTTCGGTTCTCACAGATAGTGAGAAAGTGCTTCATTTAGTCTAAACAGA  26372

125_10  26338  AACTTTATGGCTTCTGTCAGTTTTCAGGATCGTGGCCGCAAACGGGTGCCATTATCCCTC  26397
               ||||||||||||||||||||||||||||||||||||||||||||||||||||||||||||
US_Col  26373  AACTTTATGGCTTCTGTCAGTTTTCAGGATCGTGGCCGCAAACGGGTGCCATTATCCCTC  26432

125_10  26398  TATGCCCCTCTTAGGGTTACTAATGACAAACCCCTTTCTAAGGTACTTGCAAATAATGCT  26457
               ||||||||||||||||||||||||||||||||||||||||||||||||||||||||||||
US_Col  26433  TATGCCCCTCTTAGGGTTACTAATGACAAACCCCTTTCTAAGGTACTTGCAAATAATGCT  26466

125_10  26458  GTACCCACTAATAAAGGAAATAAGGACCAGCAAATTGGATACTGGAATGAGCAAATTCGC  26517
               ||||||||||||||||||||||||||||||||||||||||||||||||||||||||||||
US_Col  26493  GTACCCACTAATAAAGGAAATAAGGACCAGCAAATTGGATACTGGAATGAGCAAATTCGC  26552

125_10  26518  TGGCGCATGCGCCGTGGTGAGCGAATTGAACAACCTTCCAATTGGCATTTCTACTACCTC  26577
               ||||||||||||||||||||||||||||||||||||||||||||||||||||||||||||
US_Col  26553  TGGCGCATGCGCCGTGGTGAGCGAATTGAACAACCTTCCAATTGGCATTTCTACTACCTC  26612

125_10  26578  GGAACAGGACCTCACGCCGACCTCCGCTATAGGACTCGTACTGAGGGTGTTTTCTGGGTT  26637
               ||||||||||||||||||||||||||||||||||||||||||||||||||||||||||||
US_Col  26613  GGAACAGGACCTCACGCCGACCTCCGCTATAGGACTCGTACTGAGGGTGTTTTCTGGGTT  26672

125_10  26638  GCTAAAGAAGGCGCAAAGACTGAACCCACTAACCTGGGTGTCAGAAAGGCGTCTGAAAAG  26697
               ||||||||||||||||||||||||||||||||||||||||||||||||||||||||||||
US_Col  26673  GCTAAAGAAGGCGCAAAGACTGAACCCACTAACCTGGGTGTCAGAAAGGCGTCTGAAAAG  26732

125_10  26698  CCAATTATTCCAAATTTCTCTCAACAGCTTCCCAGCGTAGTTGAGATTGTTGAACCTAAC  26757
               ||||||||||||||||||||||||||||||||||||||||||||||||||||||||||||
US_Col  26733  CCAATTATTCCAAATTTCTCTCAACAGCTTCCCAGCGTAGTTGAGATTGTTGAACCTAAC  26766

125_10  26758  ACACCTCCTACTTCACGTGCAAATTCACGTAGCAGGAGTCGTGGTAATGGCAACAACAGG  26817
               ||||||||||||||||||||||||||||||||||||||||||||||||||||||||||||
US_Col  26793  ACACCTCCTACTTCACGTGCAAATTCACGTAGCAGGAGTCGTGGTAATGGCAACAACAGG  26852

125_10  26818  TCCAGATCTCCAAGTAACAACAGAGGCAATAACCAGTCCCGCGGTAATTCACAGAATCGT  26877
               ||||||||||||||||||||||||||||||||||||||||||||||||||||||||||||
US_Col  26853  TCCAGATCTCCAAGTAACAACAGAGGCAATAACCAGTCCCGCGGTAATTCACAGAATCGT  26912

125_10  26878  GGAAATAACCAGGGTCGTGGAGCTTCTCAGAACAGAGGAGGCAATAATAATAACAATAAC  26937
               ||||||||||||||||||||||||||||||||||||||||||||||||||||||||||||
US_Col  26913  GGAAATAACCAGGGTCGTGGAGCTTCTCAGAACAGAGGAGGCAATAATAATAACAATAAC  26972
```

FIG. 2 (cont'd)

```
125_10  26938  AAGTCTCGTAACCAGTCCAAGAACAGAAACCAGTCAAATGACCGTGGTGGTGTAACATCA  26997
               ||||||||||||||||||||||||||||||||||||||||||||||||||||||||||||
US_Col  26973  AAGTCTCGTAACCAGTCCAAGAACAGAAACCAGTCAAATGACCGTGGTGGTGTAACATCA  27032

125_10  26998  CGCGATGATCTGGTGGCTGCTGTCAAGGATGCCCTTAAATCTTTGGGTATTGGCGAAAAC  27057
               ||||||||||||||||||||||||||||||||||||||||||||||||||||||||||||
US_Col  27033  CGCGATGATCTGGTGGCTGCTGTCAAGGATGCCCTTAAATCTTTGGGTATTGGCGAAAAC  27066

125_10  27058  CCTGACAAGCTTAAGCAACAGCAGAAGCCCAAACAGGAAAGGTCTGACAGCAGCGGCAAA  27117
               ||||||||||||||||||||||||||||||||||||||||||||||||||||||||||||
US_Col  27093  CCTGACAAGCTTAAGCAACAGCAGAAGCCCAAACAGGAAAGGTCTGACAGCAGCGGCAAA  27152

125_10  27118  AATACACCTAAGAAGAACAAATCCAGAGCCACTTCGAAAGAACGTGACCTCAAAGACATC  27177
               ||||||||||||||||||||||||||||||||||||||||||||||||||||||||||||
US_Col  27153  AATACACCTAAGAAGAACAAATCCAGAGCCACTTCGAAAGAACGTGACCTCAAAGACATC  27212

125_10  27178  CCAGAGTGGAGGAGAATTCCCAAGGGCGAAAATAGCGTAGCAGCTTGCTTCGGACCCAGG  27237
               ||||||||||||||||||||||||||||||||||||||||||||||||||||||||||||
US_Col  27213  CCAGAGTGGAGGAGAATTCCCAAGGGCGAAAATAGCGTAGCAGCTTGCTTCGGACCCAGG  27272

125_10  27238  GGAGGCTTCAAAAATTTTGGAGATGCGGAATTTGTCGAAAAAGGTGTTGATGCCTCAGGC  27297
               ||||||||||||||||||||||||||||||||||||||||||||||||||||||||||||
US_Col  27273  GGAGGCTTCAAAAATTTTGGAGATGCGGAATTTGTCGAAAAAGGTGTTGATGCCTCAGGC  27332

125_10  27298  TATGCTCAGATCGCCAGTTTAGCACCAAATGTTGCAGCATTGCTCTTTGGTGGTAATGTG  27357
               ||||||||||||||||||||||||||||||||||||||||||||||||||||||||||||
US_Col  27333  TATGCTCAGATCGCCAGTTTAGCACCAAATGTTGCAGCATTGCTCTTTGGTGGTAATGTG  27366

125_10  27358  GCTGTTCGTGAGCTAGCGGACTCTTACGAGATTACATATAATTATAAAATGACTGTGCCA  27417
               ||||||||||||||||||||||||||||||||||||||||||||||||||||||||||||
US_Col  27393  GCTGTTCGTGAGCTAGCGGACTCTTACGAGATTACATATAATTATAAAATGACTGTGCCA  27452

125_10  27418  AAGTCTGATCCAAATGTAGAGCTTCTTGTTTCACAGGTGGATGCATTTAAAACTGGGAAT  27477
               ||||||||||||||||||||||||||||||||||||||||||||||||||||||||||||
US_Col  27453  AAGTCTGATCCAAATGTAGAGCTTCTTGTTTCACAGGTGGATGCATTTAAAACTGGGAAT  27512

125_10  27478  GCAAAACCCCAGAGAAAGAAGGAAAAGAAGAAYAAGCGTGAAACCACGCAGCAGCTGAAT  27537
               |||||||||||||||||||||||||||||||| |||||||||||||||||||||||||||
US_Col  27513  GCAAAACCCCAGAGAAAGAAGGAAAAGAAGAACAAGCGTGAAACCACGCAGCAGCTGAAT  27572

125_10  27538  GAAGAGGCCATCTACGATGATGTGGGTGTGCCATCTGATGTGACTCATGCCAATTTGGAA  27597
               ||||||||||||||||||||||||||||||||||||||||||||||||||||||||||||
US_Col  27573  GAAGAGGCCATCTACGATGATGTGGGTGTGCCATCTGATGTGACTCATGCCAATTTGGAA  27632

125_10  27598  TGGGACACAGCTGTTGATGGTGGTGACACGGCCGTTGAAATTATCAACGAGATCTTCGAC  27657
               ||||||||||||||||||||||||||||||||||||||||||||||||||||||||||||
US_Col  27633  TGGGACACAGCTGTTGATGGTGGTGACACGGCCGTTGAAATTATCAACGAGATCTTCGAC  27666

125_10  27658  ACAGGAAATTAAACAATGTTTGACTGGCTTATCCTGGCTATGTCCCAGGGTAGTGCCATT  27717
               ||||||||||||||||||||||||||||||||||||||||||||||||||||||||||||
US_Col  27693  ACAGGAAATTAAACAATGTTTGACTGGCTTATCCTGGCTATGTCCCAGGGTAGTGCCATT  27752

125_10  27718  ACACTGTTATTACTGAGTGTTTTTCTAGCGACTTGGCTGCTGGGCTATGGCTTTGCCCTC  27777
               ||||||||||||||||||||||||||||||||||||||||||||||||||||||||||||
US_Col  27753  ACACTGTTATTACTGAGTGTTTTTCTAGCGACTTGGCTGCTGGGCTATGGCTTTGCCCTC  27812

125_10  27778  TAACTAGCGGTCTTGGTCTTGCACACAACGGTAAGCCAGTGGTAATGTCAGTGCAAGAAG  27837
               ||||||||||||||||||||||||||||||||||||||||||||||||||||||||||||
US_Col  27813  TAACTAGCGGTCTTGGTCTTGCACACAACGGTAAGCCAGTGGTAATGTCAGTGCAAGAAG  27872
```

FIG. 2 (cont'd)

```
125_10  27838  GATATTACCATAGCACTGTCATGAGGGGAACGCAGTACCTTTTCATCTAAACCTTTGCAC  27897
               ||||||||||||||||||||||||||||||||||||||||||||||||||||||||||||
US_Col  27873  GATATTACCATAGCACTGTCATGAGGGGAACGCAGTACCTTTTCATCTAAACCTTTGCAC  27932

125_10  27898  GAGTAATCAAAGATCCGCTTGACGAGCCTATATGGAAGAGCGTGCCAGGTATTTGACTCA  27957
               ||||||||||||||||||||||||||||||||||||||||||||||||||||||||||||
US_Col  27933  GAGTAATCAAAGATCCGCTTGACGAGCCTATATGGAAGAGCGTGCCAGGTATTTGACTCA  27966

125_10  27958  AGGACTGTTAGTAACTGAAGACCTGACGGTGTTGATAT  27995
               ||||||||||||||||||||||||||||||||||||||
US_Col  27993  AGGACTGTTAGTAACTGAAGACCTGACGGTGTTGATAT  28030
```

FIG. 3

PEDV 1251-125-10 (125-10) spike protein (SEQ ID NO:14) aligned to closest Spike protein amino acid sequence from North American PEDV G2a Colorado strain (GenBank Accession No: AGO58664)(SEQ ID NO:12)

```
125-10  1      MKSLTYFWLFLPVLSTLSLPQDVTRCSANTNFRRFFSKFNVQAPAVVVLGGYLPIGENQG  180
               MKSLTYFWLFLPVLSTLSLPQDVTRCSANTNFRRFFSKFNVQAPAVVVLGGYLPIGENQG
US_Col  1      MKSLTYFWLFLPVLSTLSLPQDVTRCSANTNFRRFFSKFNVQAPAVVVLGGYLPIGENQG  60

125-10  181    VNSTWYCAGQHPTASGVHGIFVSHIRGGHGFEIGISQEPFDPSGYQLYLHKATNGNTNAT  360
               VNSTWYCAGQHPTASGVHGIFVSHIRGGHGFEIGISQEPFDPSGYQLYLHKATNGNTNAT
US_Col  61     VNSTWYCAGQHPTASGVHGIFVSHIRGGHGFEIGISQEPFDPSGYQLYLHKATNGNTNAT  120

125-10  361    ARLRICQFPSIKTLGPTANNDVTIGRNCLFNKAIPAHMSEHSVVGITWDNDRVTVFSDKI  540
               ARLRICQFPSIKTLGPTANNDVT GRNCLFNKAIPAHMSEHSVVGITWDNDRVTVFSDKI
US_Col  121    ARLRICQFPSIKTLGPTANNDVTTGRNCLFNKAIPAHMSEHSVVGITWDNDRVTVFSDKI  180

125-10  541    YYFYFKNDWSRVATKCYNSGGCAMQYVYEPTYYMLNVTSAGEDGISYQPCTANCIGYAAN  720
               YYFYFKNDWSRVATKCYNSGGCAMQYVYEPTYYMLNVTSAGEDGISYQPCTANCIGYAAN
US_Col  181    YYFYFKNDWSRVATKCYNSGGCAMQYVYEPTYYMLNVTSAGEDGISYQPCTANCIGYAAN  240

125-10  721    VFATEPNGHIPEGFSFNNWFLLSNDSTLVHGKVVSNQPLLVNCLLAIPKIYGLGQFFSFN  900
               VFATEPNGHIPEGFSFNNWFLLSNDSTLVHGKVVSNQPLLVNCLLAIPKIYGLGQFFSFN
US_Col  241    VFATEPNGHIPEGFSFNNWFLLSNDSTLVHGKVVSNQPLLVNCLLAIPKIYGLGQFFSFN  300

125-10  901    QTIDGVCNGAAVQRAPEALRFNINDTSVILAEGSIVLHTALGTNFSFVCSNSPNPHLATF  1080
               QTIDGVCNGAAVQRAPEALRFNINDTSVILAEGSIVLHTALGTNFSFVCSNS NPHLATF
US_Col  301    QTIDGVCNGAAVQRAPEALRFNINDTSVILAEGSIVLHTALGTNFSFVCSNSSNPHLATF  360

125-10  1081   AIPLGATQVPYYCFLKVDTYNSTVYKFLAVLPPTVREIVITKYGDVYVNGFGYLHLGLLD  1260
               AIPLGATQVPYYCFLKVDTYNSTVYKFLAVLPPTVREIVITKYGDVYVNGFGYLHLGLLD
US_Col  361    AIPLGATQVPYYCFLKVDTYNSTVYKFLAVLPPTVREIVITKYGDVYVNGFGYLHLGLLD  420

125-10  1261   AVTINFTGHGTDDDVSGFWTIASTNFVDALIEVQGTAIQRILYCDDPVSQLKCSQVAFDL  1440
               AVTINFTGHGTDDDVSGFWTIASTNFVDALIEVQGTAIQRILYCDDPVSQLKCSQVAFDL
US_Col  421    AVTINFTGHGTDDDVSGFWTIASTNFVDALIEVQGTAIQRILYCDDPVSQLKCSQVAFDL  480

125-10  1441   DDGFYPISSRNLLSHEQPISFVTLPSFNDHSFVNITVSASFGGHSGANLIASDTTINGFS  1620
               DDGFYPISSRNLLSHEQPISFVTLPSFNDHSFVNITVSASFGGHSGANLIASDTTINGFS
US_Col  481    DDGFYPISSRNLLSHEQPISFVTLPSFNDHSFVNITVSASFGGHSGANLIASDTTINGFS  540

125-10  1621   SFCVDTRQFTISLFYNVTNSYGYVSKSQDSNCPFTLQSVNDYLSFSKFCVSTSLLASACT  1800
               SFCVDTRQFTISLFYNVTNSYGYVSKSQDSNCPFTLQSVNDYLSFSKFCVSTSLLASACT
US_Col  541    SFCVDTRQFTISLFYNVTNSYGYVSKSQDSNCPFTLQSVNDYLSFSKFCVSTSLLASACT  600

125-10  1801   IDLFGYPEFGSGVKFTSLYFQFTKGELITGTTKPLEGVTDVSFMTLDVCTKYTIYGFKGE  1980
               IDLFGYPEFGSGVKFTSLYFQFTKGELITGT KPLEGVTDVSFMTLDVCTKYTIYGFKGE
US_Col  601    IDLFGYPEFGSGVKFTSLYFQFTKGELITGTPKPLEGVTDVSFMTLDVCTKYTIYGFKGE  660

125-10  1981   GIITLTNSSFLAGVYYTSVSGQLLAFKNVTSGAVYSVTPCSFSEQAAYVDDDIVGVISSL  2160
               GIITLTNSSFLAGVYYTS SGQLLAFKNVTSGAVYSVTPCSFSEQAAYVDDDIVGVISSL
US_Col  661    GIITLTNSSFLAGVYYTSDSGQLLAFKNVTSGAVYSVTPCSFSEQAAYVDDDIVGVISSL  720
```

FIG. 3 (cont'd)

```
125-10  2161  SSSTFNSTRELPGFFYHSNDGSNCTEPVLVYSNIGVCKSGSIGYVPSQSGQVKIAPTVTG  2340
              SSSTFNSTRELPGFFYHSNDGSNCTEPVLVYSNIGVCKSGSIGYVPSQSGQVKIAPTVTG
US_Col  721   SSSTFNSTRELPGFFYHSNDGSNCTEPVLVYSNIGVCKSGSIGYVPSQSGQVKIAPTVTG  780

125-10  2341  NISIPTNFSMSIRTEYLQLYNTPVSVDCATYVCNGNSRCKQLLTQYTAACKTIESALXLS  2520
              NISIPTNFSMSIRTEYLQLYNTPVSVDCATYVCNGNSRCKQLLTQYTAACKTIESAL LS
US_Col  781   NISIPTNFSMSIRTEYLQLYNTPVSVDCATYVCNGNSRCKQLLTQYTAACKTIESALQLS  840

125-10  2521  ARLESVEVNSMLTISEEALQLATISSFNGDGYNFTNVLGVSVYDPARGRVVQKRSFIEDL  2700
              ARLESVEVNSMLTISEEALQLATISSFNGDGYNFTNVLGVSVYDPA GRVVQKRSFIEDL
US_Col  841   ARLESVEVNSMLTISEEALQLATISSFNGDGYNFTNVLGVSVYDPASGRVVQKRSFIEDL  900

125-10  2701  LFNKVVTNGLGTVDEDYKRCSNGRSVADLVCAQYYSGVMVLPGVVDAEKLHMYSASLIGG  2880
              LFNKVVTNGLGTVDEDYKRCSNGRSVADLVCAQYYSGVMVLPGVVDAEKLHMYSASLIGG
US_Col  901   LFNKVVTNGLGTVDEDYKRCSNGRSVADLVCAQYYSGVMVLPGVVDAEKLHMYSASLIGG  960

125-10  2881  MVLGGFTSAAALPFSYAVQARLNYLALQTDVLQRNQQLLAESFNSAIGNITSAFESVKEA  3060
              MVLGGFTSAAALPFSYAVQARLNYLALQTDVLQRNQQLLAESFNSAIGNITSAFESVKEA
US_Col  961   MVLGGFTSAAALPFSYAVQARLNYLALQTDVLQRNQQLLAESFNSAIGNITSAFESVKEA  1020

125-10  3061  ISQTSKGLNTVAHALTKVQEVVNSQGAALTQLTVQLQHNFQAISSSIDDIYSRLDILSAD  3240
              ISQTSKGLNTVAHALTKVQEVVNSQGAALTQLTVQLQHNFQAISSSIDDIYSRLDILSAD
US_Col  1021  ISQTSKGLNTVAHALTKVQEVVNSQGAALTQLTVQLQHNFQAISSSIDDIYSRLDILSAD  1080

125-10  3241  VQVDRLITGRLSALNAFVAQTLTKYTEVQASRKLAQQKVNECVKSQSQRYGFCGGDGEHI  3420
              VQVDRLITGRLSALNAFVAQTLTKYTEVQASRKLAQQKVNECVKSQSQRYGFCGGDGEHI
US_Col  1081  VQVDRLITGRLSALNAFVAQTLTKYTEVQASRKLAQQKVNECVKSQSQRYGFCGGDGEHI  1140

125-10  3421  FSLVQAAPQGLLFLHTVLVPSDFVDVIAIAGLCVNDEIALTLREPGLVLFTHELQNHTAT  3600
              FSLVQAAPQGLLFLHTVLVPSDFVDVIAIAGLCVNDEIALTLREPGLVLFTHELQNHTAT
US_Col  1141  FSLVQAAPQGLLFLHTVLVPSDFVDVIAIAGLCVNDEIALTLREPGLVLFTHELQNHTAT  1200

125-10  3601  EYFVSSRRMFEPRKPTVSDFVQIESCVVTYVNLTRDQLPDVIPDYIDVNKTLDEILASLP  3780
              EYFVSSRRMFEPRKPTVSDFVQIESCVVTYVNLTRDQLPDVIPDYIDVNKTLDEILASLP
US_Col  1201  EYFVSSRRMFEPRKPTVSDFVQIESCVVTYVNLTRDQLPDVIPDYIDVNKTLDEILASLP  1260

125-10  3781  NRTGPSLPLDVFNATYLNLTGEIADLEQRSESLRNTTEELQSLIYNINNTLVDLEWLNRV  3960
              NRTGPSLPLDVFNATYLNLTGEIADLEQRSESLRNTTEELQSLIYNINNTLVDLEWLNRV
US_Col  1261  NRTGPSLPLDVFNATYLNLTGEIADLEQRSESLRNTTEELQSLIYNINNTLVDLEWLNRV  1320

125-10  3961  ETYIKWPWWVWLIIFIVLIFVVSLLVFCCISTGCCGCCGCCCACFSGCCRGPRLQPYEVF  4140
              ETYIKWPWWVWLIIFIVLIFVVSLLVFCCISTGCCGCCGCCCACFSGCCRGPRLQPYEVF
US_Col  1321  ETYIKWPWWVWLIIFIVLIFVVSLLVFCCISTGCCGCCGCCCACFSGCCRGPRLQPYEVF  1380

125-10  4141  EKVHVQ  4158
              EKVHVQ
US_Col  1381  EKVHVQ  1386
```

Group least square mean ± standard error anti-PEDV-IgG S:P ratios for D-1, 14, 28 and 49.

Group least square mean ± standard error anti-PEDV-IgA S:P ratios for D-1, 14, 28 and 49.

SEQUENCE LISTING

```
<160> NUMBER OF SEQ ID NOS: 20

<210> SEQ ID NO 1
<211> LENGTH: 27995
<212> TYPE: DNA
<213> ORGANISM: Porcine epidemic diarrhea virus

<400> SEQUENCE: 1

gactcttgtc tactcaattc aactaaacga aattccttgt ccttccggcc gcatgtccat      60

gctgctggaa gctgacgtgg aatttcatta ggtttgctta agtagccatc gcaagtgctg     120

tgctgtcctc tagttcctgg ttggcgttcc gtcgccttct acatactaga caaacagcct     180

tcctccggtt ccgtctgggg gttgtgtgga taactagttc cgtctagttt gaaaccagta     240

actgtcggct atggctagca accatgttac attggctttt gccaatgatg cagaaatttc     300

agcttttggc ttttgcactg ctagtgaagc cgtctcatac tattctgagg ccgccgctag     360
```

-continued

```
tggatttatg caatgccgtt tcgtgtcctt cgatctcgct gacactgttg agggattgct    420
tcccgaagac tatgtcatgg tggtggtcgg cactaccaag cttagtgcgt atgtggacac    480
ttttggtagc cgccccaaaa acatttgtgg ttggctgtta ttttctaact gtaattactt    540
cctcgaagag ttagagctta cttttggtcg tcgtggtggt aacatcgtgc cagttgacca    600
atacatgtgt ggcgctgacg gtaaacctgt tcttcaggaa tccgaatggg agtatacaga    660
tttctttgct gactccgaag acggtcaact caacattgct ggtatcactt atgtgaaggc    720
ctggattgta gagcgatcgg atgtctctta tgcgagtcag aatttaacat ctattaagtc    780
tattacttac tgttcaacct atgagcatac ttttcctgat ggtactgcca tgaaggttgc    840
acgtactcca aagattaaga agactgttgt cttgtctgag ccacttgcta ctatctacag    900
ggaaattggt tctccttttg tggataatgg gagcgatgct cgttctatca ttaagagacc    960
agtgttcctc cacgcttttg ttaagtgtaa gtgtggtagt tatcattgga ctgttggtga   1020
ttggacttcc tatgtctcca cttgctgtgg ctttaagtgt aagccagtcc ttgtggcttc   1080
atgctctgct acgcctggtt ctgttgtggt tacgcgcgct ggtgctggca ctggtgttaa   1140
gtattacaac aacatgttcc tgcgccatgt ggcagacatt gatgggttgg cattctggcg   1200
aattctcaag gtgcagtcca aagacgacct cgcttgctct ggtaaattcc ttgaacacca   1260
tgaggaaggt ttcacagatc cttgctactt tttgaatgac tcgagcattg ctactaagct   1320
caagtttgac atccttagtg gcaagttttc tgatgaagtc aaacaagcta tctttgctgg   1380
tcatgttgtt gttggcagcg cgmtcgttga cattgttgac gatgcactgg gacagccttg   1440
gtttatacgt aagcttggtg accttgcaag tgcagcttgg gagcagctta aggctgtcgt   1500
tagaggcctt aacctcctgt ctgatgaggt cgtgctcttt ggcaaaagac ttagctgtgc   1560
cactcttagt atcgttaacg gtgtttttga gttcatcgcc gaagtgcctg agaagttggc   1620
tgcggctgtt acagtttttg tcaacttctt gaatgagctt tttgagtctg cctgtgactg   1680
cttaaaggtc ggaggtaaaa cctttaacaa ggttggctct tatgttcttt ttgacaacgc   1740
attggttaag cttgtcaagg caaaagttcg cggcccacga caggcaggtg tttgtgaagt   1800
tcgttacaca agccttgtta ttgggagtac taccaaggtg gtttccaagc gcgttgaaaa   1860
tgccaatgtg aatctcgtcg tcgttgacga ggatgtgacc ctcaacacca ctggtcgtac   1920
agttgttgtt gacggacttg cattcttcga gagtgacggg ttttacagac atcttgctga   1980
tgctgacgtt gtcattgaac atcctgttta taagtctgct tgtgagctca agccagtttt   2040
tgagtgtgac ccaatacctg attttcctat gcctgtggcc gctagtgttg cagagctttg   2100
tgtgcaaact gatctgttgc ttaaaaatta caacactcct tataaaactt acagctgcgt   2160
tgtgagaggt gataagtgtt gtatcacttg caccttacat ttcacagcac caagttatat   2220
ggaggctgct gctaattttg tagacctctg taccaagaac attggtactg ctggttttca   2280
tgagttttac attacggccc atgaacaaca ggatctgcaa gggttcgtaa ccacttgttg   2340
cacgatgtca ggttttgagt gttttatgcc tataatccca cagtgtccag cagtgcttga   2400
agagattgat ggtggtagca tctggcggtc ttttatcact ggtcttaata caatgtggga   2460
tttttgcaag catcttaaag tcagctttgg actagatggc attgttgtca ctgtagcacg   2520
caaatttaaa cgacttggtg ctctcttggc agaaatgtat aacacttacc tttcaactgt   2580
ggtggaaaac ttggtactgg ccggtgttag cttcaagtat tatgccacca gtgtcccaaa   2640
aattgttttg ggctgttgtt ttcacagtgt taaaagtgtt cttgcaagtg ccttccagat   2700
tcctgtccag gcaggcgttg agaagtttaa agtcttcctt aactgtgttc accctgttgt   2760
```

accacgtgtc attgaaactt cttttgtgga attagaagag acgacattta aaccaccagc 2820
actcaatggt agtattgcta ttgttgatgg ctttgctttc tattatgatg gaacactata 2880
ctatcccacc gatggtaata gcgttgttcc tatctgcttt aagaagaaag gtggtggtga 2940
tgtcaaattc tctgatgaag tctctgttaa aaccattgac ccagtttata aggtctccct 3000
tgaatttgag ttcgagtctg agactattat ggctgtgctt aataaggctg ttggtaattg 3060
tatcaaggtt acaggtggtt gggacgatgt tgttgagtat atcaatgttg ccattgaggt 3120
tcttaaagat cacatcgatg tgcctaagta ctacatctat gatgaggaag gtggcaccga 3180
tcctaatctg cccgtaatgg tttctcagtg gccgttgaat gatgacacga tctcacagga 3240
tctgcttgat gttgaagttg ttactgatgc gccagttgat ttcgagggtg atgaagtaga 3300
ctcctctgac cctgwtaagg tggcagacgt ggctaactct gagcctgagg atgacggtct 3360
taatgtagct cctgaaacaa atgtagagtc tgaagttgag gaagttgccg caaccttgtc 3420
ctttaaagat acaccttcca cagttactaa ggatcctttt gcttttgact ttgcaagcta 3480
tggaggactt aaggttttaa gacaatctca taacaactgc tgggttactt ctaccttggt 3540
gcagctacaa ttgcttggca tcgttgatga ccctgcaatg gagcttttta gtgctggtag 3600
agttggtcca atggttcgca aatgctatga gtcacaaaag gctatcttgg gatctttggg 3660
tgatgtgtcg gcttgcctag agtctctgac taaggaccta cacacactta agattacctg 3720
ttctgtagtc tgtggttgtg gtactggtga acgtatctat gatggttgtg cttttcgtat 3780
gacgccaact ttggaaccgt tcccatatgg tgcttgtgct cagtgtgctc aagttttgat 3840
gcacactttt aaaagtattg ttggcaccgg catcttttgt cgagatacta ctgctctctc 3900
cttggattct ttggttgtaa aacctctttg tgcggctgct tttataggca aggatagtgg 3960
tcattatgtc actaactttt atgatgctgc tatggctatt gatggttatg gtcgtcatca 4020
gataaagtat gacacactga acactatttg tgttaaagac gttaattgga cagcaccttt 4080
tgtcccagac gttgagcctg tattggagcc tgttgtcaaa cctttctatt cttataagaa 4140
tgttgatttt taccaaggag attttagtga ccttgttaaa cttccatgtg attttgttgt 4200
taatgctgca aatgagaatt tgtctcacgg tggcggcata gcaaaggcca ttgatgttta 4260
taccaagggc atgttgcaga agtgctcgaa tgattacatt aaagcacacg gtcccattaa 4320
agttggacgt ggtgtcatgt tggaggcatt aggtcttaag gtctttaatg ttgttggtcc 4380
acgtaagggt aagcatgcac ctgagcttct tgttaaggct tataagtccg tttttgctaa 4440
ttcaggtgtt gctcttacac ctttgattag tgttggaatt tttagtgttc ctttggaaga 4500
atctttatct gcttttcttg catgtgttgg tgatcgccac tgtaagtgct tttgttatag 4560
tgacaaagag cgcgaggcga tcattaatta catggatggc ttggtagatg ctattttcaa 4620
agatgcactt gttgatacta ctcctgtcca ggaagatgtt caacaagttt cacaaaaacc 4680
agttttgcct aattttgaac ctttcaggat tgaaggtgct catgctttct atgagtgcaa 4740
ccctgaaggt ttgatgtcat taggtgctga caagctggtg ttgtttacaa attccaattt 4800
ggatttttgt agcgttggta agtgtcttaa caatgtgact ggcggtgcat tgcttgaagc 4860
cataaatgta tttaaaaaga gtaacaaaac agtgcctgct ggcaactgtg ttacttttga 4920
gtgtgcagat atgatttcta ttactatggt agtattgcca tctgacggtg atgctaatta 4980
tgacaaaaat tatgcacgcg ccgtcgtcaa ggtatctaag cttaaaggca agttattgct 5040
tgctgttggt gatgccatgt tgtattccaa gttgtcccac ctcagcgtgt taggtttcgt 5100

-continued

```
atccacacct gatgatgtgg agcgtttcta cgcaaataag agtgtggtta ttaaagttac   5160
tgaggataca cgtagtgtta agactgttaa agtagaatcc actgttactt atggacaaca   5220
aattggacct tgtcttgtta atgacaccgt tgtcacagac aacaaacctg ttgttgctga   5280
tgttgtagct aaggttgtac caagtgctaa ttgggattca cattatggtt ttgataaggc   5340
tggtgagttc cacatgctag accatactgg gtttgccttt cctagtgaag ttgttaacgg   5400
taggcgtgtg cttaaaacca cagataataa ctgttgggtt aatgttacat gtttacaatt   5460
acagtttgct agatttaggt tcaagtcagc aggtctacag gctatgtggg agtcctattg   5520
tactggtgat gttgctatgt ttgtgcattg gttgtactgg cttactggtg ttgacaaagg   5580
tcagcctagt gattcagaaa atgcacttaa catgttgtct aagtacattg ttcctgctgg   5640
ttctgtcact attgaacgtg tcacgcatga cggttgttgt tgtagtaagc gtgttgtcac   5700
tgcaccagtt gtgaatgcta gcgtgttgaa gcttggcgtc gaggatggtc tttgtccaca   5760
tggtcttaac tacattgaca aagttgttgt agttaaaggt actacaattg ttgtcaatgt   5820
tggaaaacct gtagtggcac catcgcacct ctttcttaag ggtgtttcct acacaacatt   5880
cctagataat ggtaacggtg ttgccggcca ttatactgtt tttgatcatg acactggtat   5940
ggtgcatgat ggagatgttt ttgtaccagg tgatctcaat gtgtctcctg ttacaaatgt   6000
tgtcgtctca gagcagacgg ctgttgtgat taaagaccct gtgaagaaag tagagttaga   6060
cgctacaaag ctgttagaca ctatgaatta tgcatcggaa agattctttt cctttggtga   6120
ttttatgtca cgtaatttaa ttacagtgtt tttgtacatc cttagtattt tgggtctctg   6180
ttttagggcc tttcgtaaga gggatgttaa agttctagct ggtgtacccc aacgtactgg   6240
tattatattg cgtaaaagtg tgcgctataa tgcaaaggct ttgggtgtct tcttcaagct   6300
aaaactttat tggttcaaag ttcttggtaa gtttagtttg ggtatttatg cattgtatgc   6360
attactattc atgacaatac gctttacacc tataggtggc cctgtttgtg atgatgttgt   6420
tgctggttat gctaattcta gttttgacaa gaatgagtat tgcaacagtg ttatttgtaa   6480
ggtctgtctc tatgggtacc aggaactttc ggacttctct cacacacagg tagtatggca   6540
acaccttaga gacccattaa ttggtaatgt gatgcctttc ttttatttgg catttctggc   6600
aatttttggg ggtgtttatg taaaggctat tactctctat tttattttcc agtatcttaa   6660
catacttggt gtgtttttgg gcctacaaca gtccatttgg tttttgcagc ttgtgccttt   6720
tgatgtcttt ggtgacgaga tcgtcgtctt tttcatcgtt acacgcgtat tgatgttcct   6780
taagcatgtt ttccttggct gcgataaggc atcttgtgtg gcttgctcta agagtgctcg   6840
ccttaagcgc gttcctgtcc agactatttt tcagggtact agcaaatcct tctacgtaca   6900
tgccaatggt ggttctaagt tctgtaagaa gcacaatttc ttttgtttaa attgtgattc   6960
ttatggtcca ggctgcactt ttattaatga cgtcattgca actgaagttg gtaatgttgt   7020
caaacttaat gtgcaaccga caggtcctgc cactattctt attgacaagg ttgaattcag   7080
taatggtttt tactatcttt atagtggtga cacattttgg aagtacaact ttgacataac   7140
agataacaaa tacacttgca aagagtcact taaaaattgt agcataatca cagactttat   7200
tgtttttaac aataatggtt ccaatgtaaa tcaggttaag aatgcatgtg tgtatttttc   7260
acagatgctt tgtaaacctg ttaagttagt ggactcagcg ttgttggcca gtttgtctgt   7320
tgattttggt gcaagcttac atagtgcttt tgttagtgtg ttgtcgaata gttttggcaa   7380
agacctgtca agttgtaatg acatgcagga ttgcaagagc acattgggtt ttgatgatgt   7440
accattggat acctttaatg ctgctgttgc tgaggctcat cgttacgatg tcctcttgac   7500
```

tgacatgtcg ttcaacaatt ttaccaccag ttatgcaaaa ccagaggaaa aacttcccgt 7560
ccatgacatt gccacgtgta tgcgtgtagg tgccaagatt gttaatcata acgttcttgt 7620
caaggatagt atacctgtgg tgtggcttgt acgtgatttc attgcccttt ctgaagaaac 7680
taggaagtac attattcgta cgactaaagt taagggtata accttcatgt tgacctttaa 7740
tgattgtcgt atgcatacta ccatacctac tgtttgcatt gcaaataaga agggtgcagg 7800
tcttcctagt tttcaaagg ttaagaaatt cttctggttt ttgtgtctgt tcatagttgc 7860
tgttttcttt gcactaagct tttttgattt tagtactcag gttagcagtg atagtgatta 7920
tgacttcaag tatattgaga gtggccagtt gaagactttt gacaatccac ttagttgtgt 7980
gcataatgtc tttagtaact tcgaccagtg gcatgatgcc aagtttggtt tcacccccgt 8040
caacaatcct agttgtccta tagtcgttgg tgtatcagac gaagcgcgca ctgttccagg 8100
tatcccagca ggtgtttatt tagctggtaa aacacttgtt tttgctatta acaccatttt 8160
tggtacatct ggtttgtgct ttgatgctag tggcgttgct gataagggcg cttgcatttt 8220
taattcggct tgcaccacat tatctggttt gggtggaact gctgtctact gttataagaa 8280
tggtctagtt gaaggtgcta aactttatag tgagttggca cctcatagct actataaaat 8340
ggtagatggt aatgctgtgt ctttacctga aattatctca cgcggctttg gcatccgtac 8400
tatccgtaca aaggctatga cctactgtcg cgttggccag tgtgtgcaat ctgcagaagg 8460
tgtttgtttt ggcgccgata gattctttgt ctataatgca gaatctggtt ctgactttgt 8520
ttgtggcaca gggctcttta cattgttgat gaacgttatt agtgtttttt ccaagacagt 8580
accagtaact gtgttgtctg gtcaaatact ttttaattgc attattgctt ttgctgctgt 8640
tgcggtgtgt ttcttattta caaagtttaa gcgcatgttc ggtgatatgt ctgttggcgt 8700
tttcactgtc ggtgcttgta ctttgttgaa caatgtttcc tacattgtaa cacagaacac 8760
acttggcatg ttgggctatg caactttgta ctttttgtgc actaaaggtg ttagatatat 8820
gtggatttgg catttgggat ttttgatctc atatatactt attgcaccat ggtgggtttt 8880
gatggtttat gccttttcag ccatttttga gtttatgcct aacctttta agcttaaggt 8940 ttcaacacaa ctttttgagg gtgacaagtt cgtaggctct tttgaaaatg ctgcagcagg 9000
tacatttgtg cttgatatgc atgcctatga gagacttgcc aactctatct caactgaaaa 9060
actgcgtcag tatgctagta cttacaataa gtacaagtat tattcaggca gtgcttcaga 9120
ggctgattac aggcttgctt gttttgccca tttggccaag gctatgatgg attatgcttc 9180
taatcacaac gacacgttat acacaccacc cactgtgagt tacaattcaa ctctacaggc 9240
tggcttgcgt aagatggcac aaccatctgg tgttgttgag aagtgcatag ttcgtgtttg 9300
ctatggtaat atggctctta atggcctatg gcttggtgat actgttatct gcccacgcca 9360
tgttatagcg tctagtacta ctagcactat agattatgac tatgcccttt ctgttttacg 9420
cctcyacaac ttctccattt catctggtaa tgttttccta ggtgttgtgg gtgtaaccat 9480
gcgaggtgct ttgttgcaga taaaggttaa tcaaaacaat gtccacacgc ctaagtacac 9540
ctatcgcaca gttagaccgg gtgaatcttt taatatcttg gcgtgctatg atggttctgc 9600
agctggtgtt tacggcgtta acatgcgctc taattacact attagaggct cgttcattaa 9660
tggcgcttgt ggttcacctg gttataacat taacaatggt accgttgagt tttgctattt 9720
acaccagctt gaacttggtt caggctgtca tgttggtagc gacttagatg gtgttatgta 9780
tggtggttat gaggaccaac ctactttgca agttgaaggc gctagtagtc tgtttacaga 9840

-continued

```
gaatgtgttg gcatttcttt atgcagcact cattaatggt tctacctggt ggcttagttc   9900
ttctaggatt gctgtagaca ggtttaatga gtgggctgtt cataatggta tgacaacagt   9960
agttaatact gattgctttt ctattcttgc tgctaagact ggtgttgatg tacaacgttt  10020
gttggcctca atccagtctc tgcataagaa ttttggtgga aagcaaattc ttggctatac  10080
ctcgttgaca gatgagttta ctacaggtga agttatacgt caaatgtatg gcgttwatct  10140
tcagagtggt tatgtttcac gcgcctgtag aaatgtcttg ctggttggtt cttttctgac  10200
tttcttttgg tcagaattag tttcctacac taagttcttt tgggtaaatc ctggttatgt  10260
cacacctatg tttgcgtgtt tgtcattgct gtcctcactt ttgatgttca cactcaagca  10320
taagacattg tttttccagg tctttctaat acctgctctg attgttacat cttgcattaa  10380
tttggcattt gatgttgaag tctacaacta tttggcagag cattttgatt accatgtttc  10440
tctcatgggt tttaatgcac aaggtcttgt taacatcttt gtctgctttg ttgttaccat  10500
tttacacggc acatacacat ggcgcttttt taacacacct gtgagttctg tcacttatgt  10560
ggtagctttg ctgactgcgg catataacta tttttacgct agtgacattc ttagttgtgc  10620
tatgacacta tttgctagtg tgactggcaa ctggttcgtt ggtgctgttt gttataaagc  10680
tgctgtttat atggccttga gatttcctac ttttgtggct atttttggtg atattaagag  10740
tgttatgttc tgttaccttg tgttgggtta ttttacctgt tgcttctacg gtattctcta  10800
ctggttcaac aggtttttta aggttagtgt aggtgtctat gactatactg ttagtgctgc  10860
tgagtttaag tatatggttg ctaacggcct acgtgcacca actggaacac ttgattcact  10920
acttctgtct gccaaattga ttggtattgg tggtgagcgg aatattaaga tttcttccgt  10980
tcagtctaaa ctgactgata ttaagtgtag taacgttgtg cttttaggct gtctctctag  11040
catgaatgtc tcagcaaatt caacagaatg ggcctattgt gttgacttgc ataacaagat  11100
caacttgtgt aatgacccag aaaaagcgca ggaaatgcta cttgctttgt tggcattttt  11160
ccttagtaag aatagtgctt ttggtttaga tgacttattg gaatcctatt ttaatgacaa  11220
tagtatgttg cagagtgttg catctactta tgtcggtttg ccttcttatg tcatttatga  11280
aaatgcacgc caacagtatg aagatgctgt taataatggt tctccacctc agttggttaa  11340
gcaattgcgc catgccatga atgtagcaaa gagcgaattt gaccgtgagg cttctactca  11400
gcgtaagctt gatagaatgg cggaacaggc tgcagcacag atgtacaaag aggcacgagc  11460
agttaatagg aagtccaaag ttgtaagtgc tatgcattca ctgctttttg gtatgttgag  11520
acgtttggac atgtcttctg tagacaccat tctcaacttg gcaaaggatg gggttgtacc  11580
tctgtctgtc ataccggcag tcagtgctac taagcttaac attgttactt ctgatatcga  11640
ttcttataat cgtatccagc gtgagggatg tgtccactac gctggtacca tttggaatat  11700
aattgatatc aaggacaatg atggcaaggt ggtacacgtt aaggaggtaa ccgcacagaa  11760
tgctgagtcc ctgtcatggc ccctggtcct tgggtgtgag cgtattgtca agctccagaa  11820
taatgaaatt attcctggta agctgaagca gcgctccatt aaggcagaag gagatggcat  11880
agttggagaa ggtaaggcac tttacaataa tgagggtgga cgtactttta tgtatgcttt  11940
catctcggac aaaccggacc tgcgtgtagt caagtgggag ttcgatggtg gttgtaacac  12000
tattgagcta gaaccaccac gtaagttctt ggtggattct cctaatggtg cacagatcaa  12060
gtatctctac tttgttcgta accttaacac gttacgtagg ggtgctgttc tcggctacat  12120
aggtgccact gtacgcttgc aggctggtaa acaaacagaa caggctatta actcttcatt  12180
gttgacactt tgcgctttcg ctgtggatcc tgctaagacc tacatcgatg ctgtcaaaag  12240
```

```
tggtcacaaa ccagtaggta actgtgttaa gatgttggcc aatggttctg gtaatggaca  12300
agctgttact aatggtgtgg aggctagtac taaccaggat tcatacggtg gtgcgtccgt  12360
gtgtctatat tgtagagcac atgttgagca tccatctatg gatggttttt gcagactgaa  12420
aggcaagtac gtacaggttc cactaggtac agtggatcct atacgttttg tacttgagaa  12480
tgacgtttgc aaggtttgtg gttgttggct ggctaatggc tgcacttgtg acagatccat  12540
tatgcaaagc actgatatgg cttatttaaa cgagtacggg gctctagtgc agctcgacta  12600
gagccctgta acggtactga tacacaacat gtgtatcgtg cttttgacat ctacaacaag  12660
gatgttgctt gtctaggtaa attcctcaag gtgaactgtg ttcgcctgaa gaatttggat  12720
aagcatgatg cattctatgt tgtcaaaaga tgtaccaagt ctgcgatgga acacgagcaa  12780
tccatctata gcagacttga aaagtgtgga gccgtagccg aacacgattt cttcacttgg  12840
aaggatggtc gtgccatcta tggtaacgtt tgtagaaagg atcttaccga gtatactatg  12900
atggatttgt gttacgcttt acgtaacttt gatgaaaaca attgcgatgt tcttaagagc  12960
attttaatta aggtaggcgc ttgtgaggag tcctacttca ataataaagt ctggtttgac  13020
cctgttgaaa atgaagacat tcatcgtgtc tatgcattgt taggtaccat tgtttcacgt  13080
gctatgctta aatgcgttaa gttctgtgat gcaatggttg aacaaggtat agttggtgtt  13140
gtcacattag ataatcagga tcttaatggt gatttttatg attttggtga ttttacttgt  13200
agcatcaagg gaatgggtat acccatttgc acatcatatt actcttatat gatgcctgtt  13260
atgggtatga ctaattgcct tgctagtgag tgttttgtta agagtgatat atttggtgag  13320
gatttcaagt catatgacct gctggaatat gatttcacgg agcataagac agcactcttc  13380
aacaagtatt tcaagtattg gggactgcaa taccacccta actgtgtgga ctgcagtgat  13440
gagcagtgca tagttcactg tgccaacttc aatacgttgt tttccactac tatacctatt  13500
acggcatttg gacctttgtg tcgcaagtgt tggattgatg gtgttccact ggtaactaca  13560
gctggttatc attttaaaca gttaggtata gtttggaaca atgacctcaa cttacactct  13620
agcaggctct ctattaacga attactccag ttttgtagtg atcctgcatt gcttatagca  13680
tcatcaccag cccttgttga tcagcgtact gtttgctttt cagttgcagc gctaggtaca  13740
ggtatgacta accagactgt taaacctggc catttcaata aggagtttta tgacttctta  13800
cttgagcaag gtttcttttc tgagggctct gagcttactt taaagcactt cttctttgca  13860
cagaagggtg atgcagctgt taaggatttt gactactata ggtataatag acctactgtt  13920
ctggacattt gccaagctcg cgtcgtgtat caaatagtgc aacgctattt tgatatttac  13980
gaaggtggtt gtatcactgc taaagaggtg gttgttacaa accttaacaa gagcgcaggt  14040
tatcctttga acaagtttgg taaagctggt ctttactatg agtctttatc ctatgaggaa  14100
caggatgaac tttatgctta tactaagcgt aacatcctgc ccactatgac acagctcaac  14160
cttaaatatg ctataagtgg caaagaacgt gcacgcacag tgggtggtgt ttcgcttttg  14220
tcaaccatga ctactcggca gtatcatcag aaacacctta agtccatagt taatactagg  14280
ggcgcttcgg ttgttattgg tactactaag ttttatggtg gttgggacaa tatgcttaag  14340
aaccttattg atggtgttga aaatccgtgt cttatgggtt gggactaccc aaagtgcgac  14400
agagcactgc ccaatrtgat acgtatgatt tcagccatga ttttaggctc taagcacacc  14460
acatgctgca gttccactga ccgctttttc aggttgtgca atgaattggc tcaagtcctt  14520
actgaggttg tttattctaa tggaggtttt tatttgaagc caggtggtac tacctctggt  14580
```

-continued

```
gatgcaacca ccgcatatgc aaactcagtt tttaatatct tccaagcagt aagtgccaat  14640
gttaacaaac ttcttagtgt tgacagcaat gtctgtcata atttagaagt taagcaattg  14700
cagcgtaagc tttatgagtg ctgttataga tcaactaccg tcgatgacca gttcgtcgtt  14760
gagtattatg gttacttgcg taaacatttt tcaatgatga ttctttctga tgatggcgtt  14820
gtttgttata acaatgacta tgcatcactt ggttatgtcg ctgatcttaa cgcattcaag  14880
gctgttttgt attaccagaa caatgtcttc atgagcgcct ctaaatgttg gatcgagcct  14940
gacattaata aaggtcctca tgaattttgc tcgcagcata ctatgcagat tgtcgataaa  15000
gatggtactt attaccttcc ttaccctgat ccttcaagaa ttctctctgc aggtgtgttt  15060
gttgatgacg ttgttaaaac tgatgcagtt gtattgcttg aacgttatgt gtcattggct  15120
atagatgcct acccgttatc taagcatgaa aaccctgaat ataagaaggt gttttatgtg  15180
cttttggatt gggttaagca tctgtacaaa actcttaatg ctggtgtgtt agagtctttt  15240
tctgtcacac ttttggaaga ttctactgct aaattctggg atgagagctt ttatgccaac  15300
atgtatgaga aatctgcagt tttacaatct gcagggcttt gtgttgtttg tggctctcaa  15360
actgttttac gttgtggtga ttgtctacgg cgtcctatgc tttgtactaa gtgtgcttat  15420
gatcatgtca ttggaacaac tcacaagttc attttggcca tcactccata tgtgtgttgt  15480
gcttcagatt gtggtgtcaa tgatgtaact aagctctact taggtggtct tagttattgg  15540
tgtcatgacc acaagccacg tcttgcattc ccgttgtgct ctgctggtaa tgtttttggc  15600
ttgtacaaaa attctgctac cggctcaccc gatgttgaag actttaatcg cattgctaca  15660
tccgattgga ctgatgtttc tgactacagg ttggcaaatg atgtcaagga ctcattgcgt  15720
ctgtttgcag cggaaactat caaggccaag gaggagagcg ttaagtcatc ctatgcttgt  15780
gcaacactac atgaggttgt aggacctaaa gagttgttgc tcaaatggga agtcggcaga  15840
cccaaaccac cccttaatag aaattcggtt ttcacttgtt atcatataac gaagaacacc  15900
aaatttcaaa tcggtgagtt tgtgtttgag aaggcagaat atgataatga tgctgtaaca  15960
tataaaacta ccgccacaac aaaacttgtt cctggcatgg tttttgtgct tacctcacat  16020
aatgttcagc cattgcgcgc accgaccatt gctaatcaag aacgttattc cactatacat  16080
aagttgcatc ctgcttttaa catacctgaa gcttattcta gcttagtgcc ctattaccaa  16140
ttgattggta agcagaagat tacaactatt cagggacctc ccggtagtgg taaatctcac  16200
tgtgttatag ggctaggttt gtactatcca ggtgcacgta tagtgtttac agcttgttct  16260
catgcagcgg tcgattcact ttgtgtgaaa gcttccactg cttatagcaa tgacaaatgt  16320
tcacgcatca taccacagcg cgctcgtgtt gagtgttatg atggtttcaa gtctaataat  16380
actagtgctc agtacctttt ctctactgtc aatgctttgc cagagtgcaa tgcggacatt  16440
gttgtggtgg atgaggtctc tatgtgcact aattatgact tgtctgtcat aaatcagcgc  16500
atcagctata ggcatgtagt ctatgttggt gaccctcaac agctgcctgc accacgtgtt  16560
atgatttcac gtggtacttt ggaaccaaag gactacaacg ttgtcactca acgcatgtgt  16620
gcccttaagc ctgatgtttt cttgcacaag tgttatcgct gtcctgctga gatagtgcgt  16680
actgtgtctg agatggtcta tgaaaaccaa ttcattcctg tgcacccaga tagcaagcag  16740
tgttttaaaa tcttttgcaa gggtaatgtt caggttgata atggttcaag cattaatcgc  16800
aggcaattgg atgttgtgcg tatgtttttg gctaaaaatc ctaggtggtc aaaggctgtt  16860
tttatttctc cttataacag ccagaattat gttgccagcc gcatgctagg tctacaaatt  16920
cagacagttg actcatccca gggtagtgag tatgactatg tcatttacac acaaacttca  16980
```

```
gatactgccc atgcctgtaa tgttaacagg tttaatgttg ccatcacaag ggccaagaaa  17040
ggcatattat gtataatgtg cgataggtcc ctttttgatg tgcttaaatt ctttgagctt  17100
aaattgtctg atttgcaggc taatgagggt tgtggtcttt ttaaagactg tagcagaggt  17160
gatgatctgt tgccaccatc tcacgctaac accttcatgt ctttagcgga caattttaag  17220
actgatcaag atcttgctgt tcaaataggt gttaatggac ccattaaata tgagcatgtt  17280
atctcgttta tgggtttccg ttttgatatc aacataccca accatcatac tctcttttgc  17340
acacgcgact ttgccatgcg caatgttaga ggttggttag gctttgacgt tgaaggagca  17400
catgttgttg gctctaacgt cggtacaaat gtcccattgc aattagggtt ttctaacggt  17460
gttgattttg ttgtcagacc tgaaggttgc gttgtaacag agtctggtga ctacattaaa  17520
cccgtcagag ctcgtgctcc accaggggaa caattcgcac acctttttgcc tttacttaaa  17580
cgcggccaac catgggatgt tgtccgcaaa cgtatagtgc agatgtgtag tgactacctg  17640
gccaacctat cagacatact aatttttgtg ttgtgggctg gtggtttgga gttgacaact  17700
atgcgttatt ttgtcaagat tggaccaagt aagagttgtg attgtggtaa ggttgctact  17760
tgttacaata gtgcgctgca tacgtactgt tgtttcaaac atgcccttgg ttgtgattat  17820
ctgtataacc catactgtat tgatatacag cagtggggat acaagggatc acttagcctt  17880
aaccaccatg agcattgtaa tgtacataga aacgagcatg tggcttctgg tgatgccata  17940
atgactcgct gtctggccat acatgattgc tttgtcaaga acgttgactg gtccatcaca  18000
tacccattta ttggtaatga ggctgttatt aataagagcg gccgaattgt gcaatcacac  18060
actatgcggt cagttcttaa gttatacaat ccgaaagcca tatatgatat tggcaatcct  18120
aagggcatta gatgtgccgt aacggatgct aagtggtttt gctttgacaa gaatcctayt  18180
aattctaatg tcaagacatt ggagtatgac tatataacac atggccaatt tgatgggttg  18240
tgcttgtttt ggaattgcaa tgtagacatg tatccagaat tttctgtggt ctgtcgtttt  18300
gatactcgct gtaggtcacc actcaacttg gagggttgta atggtggttc actgtatgtt  18360
aataatcatg cattccatac accggctttt gacaagcgtg cttttgctaa gttgaagcca  18420
atgccatttt tcttttatga tgatactgag tgtgacaagt tacaggactc cataaactat  18480
gttcctctta gggctagtaa ctgcattact aaatgtaatg ttggtggtgc tgtctgtagt  18540
aagcattgtg ctatgtatca tagctatgtt aatgcttaca acacttttac gtcggcgggc  18600
tttactattt gggtgcctac ttcgtttgac acctataatc tgtggcagac atttagtaac  18660
aatttgcaag gtcttgagaa cattgctttc aatgtcgtaa agaaaggatc ttttgttggt  18720
gccgaaggtg aacttcctgt agctgtggtt aatgacaaag tgctcgttag agatggtact  18780
gttgatactc ttgtttttac aaacaagaca tcactaccca ctaacgtagc ttttgagttg  18840
tatgccaagc gtaaggtagg actcacccca cccattacga tcctacgtaa cttgggtgta  18900
gtttgtacat ctaagtgtgt catttgggac tatgaagccg aacgtccact tactactttt  18960
acaaaggatg tttgtaaata taccgacttt gagggtgacg tctgtacact ctttgataac  19020
agcattgttg gttcattaga gcgattctcc atgacccaaa atgctgtgct tatgtcactt  19080
acagctgtta aaaagcttay tggcataaag ttaacttatg gttatcttaa tggtgtccca  19140
gttaacacac atgaagataa accttttact tggtatattt acactaggaa gaacggcaag  19200
ttcgaggacc atcctgatgg ctattttacc caaggtagaa caaccgctga ttttagccct  19260
cgtagcgaca tggaaaagga cttcctaagt atggatatgg gtctgtttat taacaagtac  19320
```

-continued ggacttgaag attacggctt tgagcacgtt gtgtatggtg atgtttcaaa aaccaccctt 19380
ggtggtttgc atctactaat ttcgcaggtg cgtctggcct gtatgggtgt gctcaaaata 19440
gacgagtttg tgtctagtaa tgatagcacg ttaaagtctt gtactgttac atatgctgat 19500
aaccctagta gtaagatggt ttgtacgtat atggatctcc tgcttgacga ttttgtcagc 19560
attcttaaat ctttggattt gggcgttgta tctaaagttc atgaagttat ggtcgattgt 19620
aaaatgtgga ggtggatgtt gtggtgtaag gatcataaac tccagacatt ttatccgcaa 19680
cttcaggcca gtgaatggaa gtgtggttat tccatgcctt ctatttacaa gatacaacgt 19740
atgtgtttag aaccttgcaa tctctacaac tatggtgctg gtattaagtt acctgatggc 19800
attatgttta acgtagttaa atacacacag ctttgtcaat atctcaatag caccacaatg 19860
tgtgtacccc atcacatgcg tgtgctacat cttggtgctg gctccgacaa gggtgttgca 19920
cctggcacgg ctgtcttacg acgttggttg ccactggatg ccattatagt tgacaatgat 19980
agtgtggatt acgttagcga tgctgattat agtgttacag gagattgctc taccttatac 20040
ctgtcagata agtttgattt agttatatct gatatgtatg atggtaagat taaaagttgt 20100
gatggggaga acgtgtctaa agaaggcttc tttccctata ttaatggtgt catcaccgaa 20160
aagttggcac ttggtggtac tgtagctatt aaggtgacgg agtttagttg gaataagaag 20220
ttgtatgaac tcattcagag gtttgagtat tggacaatgt tctgtaccag tgttaacacg 20280
tcatcgtcag aggcattctt aattggtgtt cactatttag gtgattttgc aagtggcgct 20340
gtgattgacg gcaacactat gcatgccaat tatatcttct ggcgtaattc cacaattatg 20400
actatgtctt acaatagtgt acttgattta agcaagttca attgtaagca taaggctaca 20460
gttgtcatta atttaaaaga ttcatccatt agtgatgttg tgttaggttt gttgaagaat 20520
ggtaagttgc tagtgcgtaa taatgacgcc atttgtggtt tttctaatca tttggtcaac 20580
gtaaacaaat gaagtcttta acctacttct ggttgttctt accagtactt tcaacactta 20640
gcctaccaca agatgtcacc aggtgctcag ctaacactaa ttttaggcgg ttcttttcaa 20700
aatttaatgt tcaggcgcct gcagttgttg tactgggcgg ttatctacct attggtgaaa 20760
accagggtgt caattcaact tggtactgtg ctggccaaca tccaactgct agtggcgttc 20820
atggtatctt tgttagccat attagaggtg gtcatggctt tgagattggc atttcgcaag 20880
agccttttga ccctagtggt taccagcttt atttacataa ggctactaac ggtaacacta 20940
atgctactgc gcgactgcgc atttgccagt ttcctagcat taaaacattg ggccccactg 21000
ctaataatga tgttacaata ggtcgtaatt gcctatttaa caaagccatc ccagctcata 21060
tgagtgaaca tagtgttgtc ggcataacat gggataatga tcgtgtcact gtcttttctg 21120
acaagatcta ttatttttat tttaaaaatg attggtcccg tgttgcgaca aagtgttaca 21180
acagtggagg ttgtgctatg caatatgttt acgaacccac ctattacatg cttaatgtta 21240
ctagtgctgg tgaggatggt atttcttatc aaccctgtac agctaattgc attggttatg 21300
ctgccaatgt atttgctact gagcccaatg gccacatacc agaaggtttt agttttaata 21360
attggtttct tttgtccaat gattccactt tggtgcatgg taaggtggtt tccaaccaac 21420
cattgttggt caattgtctt ttggccattc ctaagattta tggactaggc caatttttct 21480
cctttaatca aacgatcgat ggtgtttgta atggagctgc tgtgcagcgt gcaccagagg 21540
ctctgaggtt taatattaat gacacctctg tcattcttgc tgaaggctca attgtacttc 21600
atactgcttt aggaacaaat ttttcttttg tttgcagtaa ttccccaaat cctcacttag 21660
ccaccttcgc catacctctg ggtgctaccc aagtacctta ttattgtttt cttaaagtgg 21720

```
atacttacaa ctccactgtt tataaatttt tggctgtttt acctcctacc gtcagggaaa  21780
ttgtcatcac caagtatggt gatgtttatg tcaatgggtt tggatacttg catctcggtt  21840
tgttggatgc tgtcacaatt aatttcactg gtcatggcac tgacgatgat gtttctggtt  21900
tttggaccat agcatcgact aattttgttg atgcactcat cgaagttcaa ggaaccgcca  21960
ttcagcgtat tctttattgt gatgatcctg ttagccaact caagtgttct caggttgctt  22020
ttgaccttga cgatggtttt taccctattt cttctagaaa ccttctgagt catgaacagc  22080
caatttcttt tgttactctg ccatcattta atgatcattc ttttgttaac attactgtat  22140
ctgcttcctt tggtggtcat agtggtgcca accttattgc atctgacact actatcaatg  22200
ggtttagttc tttctgtgtt gacactagac aatttaccat ttcactgttt tataacgtta  22260
caaacagtta tggttatgtg tctaaatcac aggacagtaa ttgccctttc accttgcaat  22320
ctgttaatga ttacctgtct tttagcaaat tttgtgtttc caccagcctt ttggctagtg  22380
cctgtaccat agatcttttt ggttaccctg agtttggtag tggtgttaag tttacgtccc  22440
tttactttca attcacaaag ggtgagttga ttactggcac gactaaacca cttgaaggtg  22500
tcacggacgt ttcttttatg actctggatg tgtgtaccaa gtatactatc tatggcttta  22560
aaggtgaggg tatcattacc cttacaaatt ctagcttttt ggcaggtgtt tattacacat  22620
ctgtttctgg acagttgtta gcctttaaga atgtcactag tggtgctgtt tattctgtta  22680
cgccatgttc tttttcagag caggctgcat atgttgatga tgatatagtg ggtgttattt  22740
ctagtttgtc tagctccact tttaacagta ctagggagtt gcctggtttc ttctaccatt  22800
ctaatgatgg ctctaattgt acagagcctg tgttggtgta tagtaacata ggtgtttgta  22860
aatctggcag tattggctac gtcccatctc agtctggcca agtcaagatt gcacccacgg  22920
ttactgggaa tattagtatt cccaccaact ttagtatgag tattaggaca gaatatttac  22980
agctttacaa cacgcctgtt agtgttgatt gtgccacata tgtttgtaat ggtaactctc  23040
gttgtaaaca attactcacc cagtacactg cagcatgtaa gaccatagag tcagcattac  23100
ractcagcgc taggcttgag tctgttgaag ttaactctat gcttactatt tctgaagagg  23160
ctctacagtt agctaccatt agttcgttta atggtgatgg atataatttt actaatgtgc  23220
tgggtgtttc tgtgtatgat cctgcaaggg gcagggtggt acaaaaaagg tcttttattg  23280
aagacctgct ttttaataaa gtggttacta atggccttgg tactgttgat gaagactata  23340
agcgctgttc taatggtcgc tctgtggcag atctagtctg tgcacagtat tactctggtg  23400
tcatggtact acctggtgtt gttgacgctg agaagcttca catgtatagt gcgtctctca  23460
tcggtggtat ggtgctagga ggttttactt ctgcagcggc attgcctttt agctatgctg  23520
ttcaagctag actcaattat cttgctctac agacggatgt tctacagcgg aaccagcaat  23580
tgcttgctga gtcttttaac tctgctattg gtaatataac ttcagccttt gagagtgtta  23640
aagaggctat tagtcaaact tccaagggtt tgaacactgt ggctcatgcg cttactaagg  23700
ttcaagaggt tgttaactcg cagggtgcag ctttgactca acttaccgta cagctgcaac  23760
acaacttcca agccatttct agttctattg atgacattta ctctcgactg gacattcttt  23820
cagccgatgt tcaggttgac cgtctcatca ccggcagatt atcagcactt aatgcttttg  23880
ttgctcaaac cctcactaag tatactgagg ttcaggctag caggaagtta gcacagcaaa  23940
aggttaatga gtgcgttaaa tcgcaatccc agcgttatgg tttttgtggt ggtgatggcg  24000
agcacatttt ctctctggta caggcagcac ctcagggcct gctgttttta catacagtac  24060
```

-continued ttgtaccgag tgattttgta gatgttattg ccatcgctgg cttatgcgtt aacgatgaaa 24120
ttgccttgac tctacgtgag cctggcttag tcttgtttac gcatgaactt caaaatcata 24180
ctgcgacgga atattttgtt tcatcgcgac gtatgtttga acctagaaaa cctaccgtta 24240
gtgattttgt tcaaattgag agttgtgtgg tcacctatgt caatttgact agagaccaac 24300
taccagatgt aatcccagat tacatcgatg ttaacaaaac acttgatgag attttagctt 24360
ctctgcccaa tagaactggt ccaagtcttc ctttagatgt ttttaatgcc acttatctta 24420
atctcactgg tgaaattgca gatttagagc agcgttcaga gtctctccgt aatactacag 24480
aggagctcca aagtcttata tataatatca acaacacact agttgacctt gagtggctca 24540
accgagttga gacatatatc aagtggccgt ggtgggtttg gttgattatt ttcattgttc 24600
tcatctttgt tgtgtcatta ctagtgttct gctgcatttc cacgggttgt tgtggatgct 24660
gcggctgctg ctgtgcttgt ttctcaggtt gttgtagggg tcctagactt caaccttacg 24720
aagtttttga aaaggtccac gtgcagtgat gtttcttgga ctttttcaat acacgattga 24780
cacagttgtc aaagatgtct caaagtctgc taacttgtct ttggatgctg tccaagagtt 24840
ggagctcaat gtagttccaa ttagacaagc ttcaaatgtg acgggttttc ttttcaccag 24900
tgtttttatc tacttctttg cactgtttaa agcgtcttct ttgaggcgca attatattat 24960
gttggcagcg cgttttgctg tcattgttct ttattgccca cttttatatt attgtggtgc 25020
atttttagat gcaactatta tttgttgcac acttattcaa agtcggtggc aggctttgtt 25080
tagtctgctt ttactcctgg cgctataaaa atgcgctctt tattattttt aatactacga 25140
cactttcttt cctcaatggt aaagcagctt attatgacgg caaatccatt gtgattttag 25200
aaggtggtga ccattacatc acttttggca actcttttgt tgcttttgtt agtagcatcg 25260
acttgtatct agctatacgt gggcggcaag aagctgacct acagctgttg cgaactgttg 25320
agcttcttga tggcaagaag ctttatgtct tttcgcaaca tcaaattgtt ggcattacta 25380
atgctgcatt tgactcaatt caactagacg agtatgctac aattagtgaa tgataatggt 25440
ctagtagtta atgttatact ttggcttttc gtactctttt tcctgcttat tataagcatt 25500
actttcgtcc aattggttaa tctgtgcttc acttgtcacc ggttgtgtaa tagcgcagtt 25560
tacacaccta tagggcgttt gtatagagtt tataagtctt acatgcaaat agaccccctc 25620
cctagtactg ttattgacgt ataaacgaaa tatgtctaac ggttctattc ccgttgatga 25680
ggtgattcaa caccttagaa actggaattt cacatggaat atcatactga cgatactact 25740
tgtagtgctt cagtatggcc attacaagta ctctgcgttc ttgtatggtg tcaagatggc 25800
tattctatgg atactttggc ctcttgtgtt agcactgtca ctttttgatg catgggctag 25860
ctttcaggtc aattgggtct tttttgcttt cagcatcctt atggcttgca tcactcttat 25920
gctgtggata atgtactttg tcaatagcat tcggttgtgg cgcaggacac attcttggtg 25980
gtctttcaat cctgaaacag acgcgcttct cactacttct gtgatgggcc gacaggtctg 26040
cattccagtg cttggagcac caactggtgt aacgctaaca ctccttagtg gtacattgct 26100
tgtagagggc tataaggttg ctactggcgt acaggtaagt caattaccta atttcgtcac 26160
agtcgccaag gccactacaa caattgtcta cggacgtgtt ggtcgttcag tcaatgcttc 26220
atctggcact ggttgggctt tctatgtccg gtccaaacac ggcgactact cagctgtgag 26280
taatccgagt tcggttctca cagatagtga gaaagtgctt catttagtct aaacagaaac 26340
tttatggctt ctgtcagttt tcaggatcgt ggccgcaaac gggtgccatt atccctctat 26400
gcccctctta gggttactaa tgacaaaccc ctttctaagg tacttgcaaa taatgctgta 26460

```
cccactaata aaggaaataa ggaccagcaa attggatact ggaatgagca aattcgctgg  26520

cgcatgcgcc gtggtgagcg aattgaacaa ccttccaatt ggcatttcta ctacctcgga  26580

acaggacctc acgccgacct ccgctatagg actcgtactg agggtgtttt ctgggttgct  26640

aaagaaggcg caaagactga acccactaac ctgggtgtca gaaaggcgtc tgaaaagcca  26700

attattccaa atttctctca acagcttccc agcgtagttg agattgttga acctaacaca  26760

cctcctactt cacgtgcaaa ttcacgtagc aggagtcgtg gtaatggcaa caacaggtcc  26820

agatctccaa gtaacaacag aggcaataac cagtcccgcg gtaattcaca gaatcgtgga  26880

aataaccagg gtcgtggagc ttctcagaac agaggaggca ataataataa caataacaag  26940

tctcgtaacc agtccaagaa cagaaaccag tcaaatgacc gtggtggtgt aacatcacgc  27000

gatgatctgg tggctgctgt caaggatgcc cttaaatctt tgggtattgg cgaaaaccct  27060

gacaagctta agcaacagca gaagcccaaa caggaaaggt ctgacagcag cggcaaaaat  27120

acacctaaga agaacaaatc cagagccact tcgaaagaac gtgacctcaa agacatccca  27180

gagtggagga gaattcccaa gggcgaaaat agcgtagcag cttgcttcgg acccagggga  27240

ggcttcaaaa attttggaga tgcggaattt gtcgaaaaag gtgttgatgc ctcaggctat  27300

gctcagatcg ccagtttagc accaaatgtt gcagcattgc tctttggtgg taatgtggct  27360

gttcgtgagc tagcggactc ttacgagatt acatataatt ataaaatgac tgtgccaaag  27420

tctgatccaa atgtagagct tcttgtttca caggtggatg catttaaaac tgggaatgca  27480

aaaccccaga gaaagaagga aaagaagaay aagcgtgaaa ccacgcagca gctgaatgaa  27540

gaggccatct acgatgatgt gggtgtgcca tctgatgtga ctcatgccaa tttggaatgg  27600

gacacagctg ttgatggtgg tgacacggcc gttgaaatta tcaacgagat cttcgacaca  27660

ggaaattaaa caatgtttga ctggcttatc ctggctatgt cccagggtag tgccattaca  27720

ctgttattac tgagtgtttt tctagcgact tggctgctgg gctatggctt tgccctctaa  27780

ctagcggtct tggtcttgca cacaacggta agccagtggt aatgtcagtg caagaaggat  27840

attaccatag cactgtcatg aggggaacgc agtacctttt catctaaacc tttgcacgag  27900

taatcaaaga tccgcttgac gagcctatat ggaagagcgt gccaggtatt tgactcaagg  27960

actgttagta actgaagacc tgacggtgtt gatat                             27995
```

```
<210> SEQ ID NO 2
<211> LENGTH: 4159
<212> TYPE: DNA
<213> ORGANISM: Porcine epidemic diarrhea virus

<400> SEQUENCE: 2

atgaagtctt taacctactt ctggttgttc ttaccagtac tttcaacact tagcctacca     60

caagatgtca ccaggtgctc agctaacact aattttaggc ggttcttttc aaaatttaat    120

gttcaggcgc ctgcagttgt tgtactgggc ggttatctac ctattggtga aaaccagggt    180

gtcaattcaa cttggtactg tgctggccaa catccaactg ctagtggcgt tcatggtatc    240

tttgttagcc atattagagg tggtcatggc tttgagattg gcatttcgca agagcctttt    300

gaccctagtg gttaccagct ttatttacat aaggctacta acggtaacac taatgctact    360

gcgcgactgc gcatttgcca gtttcctagc attaaaacat tgggccccac tgctaataat    420

gatgttacaa caggtcgtaa ttgcctattt aacaaagcca tcccagctca tatgagtgaa    480

catagtgttg tcggcataac atgggataat gatcgtgtca ctgtcttttc tgacaagatc    540
```

-continued

```
tattattttt attttaaaaa tgattggtcc cgtgttgcga caaagtgtta caacagtgga    600
ggttgtgcta tgcaatatgt ttacgaaccc acctattaca tgcttaatgt tactagtgct    660
ggtgaggatg gtatttctta tcaaccctgt acagctaatt gcattggtta tgctgccaat    720
gtatttgcta ctgagcccaa tggccacata ccagaaggtt ttagttttaa taattggttt    780
cttttgtcca atgattccac tttggtgcat ggtaaggtgg tttccaacca accattgttg    840
gtcaattgtc ttttggccat tcctaagatt tatggactag gccaattttt ctcctttaat    900
caaacgatcg atggtgtttg taatggagct gctgtgcagc gtgcaccaga ggctctgagg    960
tttaatatta atgacacctc tgtcattctt gctgaaggct caattgtact tcatactgct   1020
ttaggaacaa atttttcttt tgtttgcagt aattcctcaa atcctcactt agccaccttc   1080
gccatacctt tgggtgctac ccaagtaccc tattattgtt ttcttaaagt ggatacttac   1140
aactccactg tttataaatt cttggctgtt ttacctccaa ccgtcaggga aattgtcatc   1200
accaagtatg gtgatgttta tgtcaatggg tttggatact tgcatctcgg tttgttggat   1260
gctgtcacaa ttaatttcac tggtcatggc actgacgatg atgtttctgg tttttggacc   1320
atagcatcga ctaattttgt tgatgcactc atcgaagttc aaggaaccgc cattcagcgt   1380
attctttatt gtgatgatcc tgttagccaa ctcaagtgtt ctcaggttgc ttttgacctt   1440
gacgatggtt tttaccctat ttcttctaga aaccttctga gtcatgaaca gccaatttct   1500
tttgttactc tgccatcatt taatgatcat tcttttgtta acattactgt atctgcttcc   1560
tttggtggtc atagtggtgc caaccttatt gcatctgaca ctactatcaa tgggtttagt   1620
tctttctgtg ttgacactag acaatttacc atttcactgt tttataacgt tacaaacagt   1680
tatggttatg tgtctaaatc acaggacagt aattgccctt tcaccttgca atctgttaat   1740
gattacctgt cttttagcaa attttgtgtt tccaccagcc ttttggctag tgcctgtacc   1800
atagatcttt ttggttaccc tgagtttggt agtggtgtta agtttacgtc cctttacttt   1860
caattcacaa agggtgagtt gattactggc acgcctaaac cacttgaagg tgtcacggac   1920
gtttctttta tgactctgga tgtgtgtacc aagtatacta tctatggctt taaaggtgag   1980
ggtatcatta cccttacaaa ttctagcttt ttggcaggtg tttattacac atctgattct   2040
ggacagttgt tagcctttaa gaatgtcact agtggtgctg tttattctgt tacgccatgt   2100
tctttttcag agcaggctgc atatgttgat gatgatatag tgggtgttat ttctagtttg   2160
tctagctcca cttttaacag tactagggag ttgcctggtt tcttctacca ttctaatgat   2220
ggctctaatt gtacagagcc tgtgttggtg tatagtaaca taggtgtttg taaatctggc   2280
agtattggct acgtcccatc tcagtctggc caagtcaaga ttgcacccac ggttactggg   2340
aatattagta ttcccaccaa ctttagtatg agtattagga cagaatattt acagctttac   2400
aacacgcctg ttagtgttga ttgtgccaca tatgtttgta atggtaactc tcgttgtaaa   2460
caattactca cccagtacac tgcagcatgt aagaccatag agtcagcatt acaactcagc   2520
gctaggcttg agtctgttga agttaactct atgcttacta tttctgaaga ggctctacag   2580
ttagctacca ttagttcgtt taatggtgat ggatataatt ttactaatgt gctgggtgtt   2640
tctgtgtatg atcctgcaag tggcagggtg gtacaaaaaa ggtcttttat tgaagacctg   2700
ctttttaata aagtggttac taatggcctt ggtactgttg atgaagacta taagcgctgt   2760
tctaatggtc gctctgtggc agatctagtc tgtgcacagt attactctgg tgtcatggta   2820
ctacctggtg ttgttgacgc tgagaagctt cacatgtata gtgcgtctct catcggtggt   2880
atggtgctag gaggttttac ttctgcagcg gcattgcctt ttagctatgc tgttcaagct   2940
```

```
agactcaatt atcttgctct acagacggat gttctacagc ggaaccagca attgcttgct   3000

gagtctttta actctgctat tggtaatata acttcagcct ttgagagtgt taaagaggct   3060

attagtcaaa cttccaaggg tttgaacact gtggctcatg cgcttactaa ggttcaagag   3120

gttgttaact cgcagggtgc agctttgact caacttaccg tacagctgca acacaacttc   3180

caagccattt ctagttctat tgatgacatt tactctcgac tggacattct ttcagccgat   3240

gttcaggttg accgtctcat caccggcaga ttatcagcac ttaatgcttt tgttgctcaa   3300

accctcacta agtatactga ggttcaggct agcaggaagt tagcacagca aaaggttaat   3360

gagtgcgtta aatcgcaatc tcagcgttat ggtttttgtg gtggtgatgg cgagcacatt   3420

ttctctctgg tacaggcagc acctcagggc ctgctgtttt tacatacagt acttgtaccg   3480

agtgattttg tagatgttat tgccatcgct ggcttatgcg ttaacgatga aattgccttg   3540

actctacgtg agcctggctt agtcttgttt acgcatgaac ttcaaaatca tactgcgacg   3600

gaatattttg tttcatcgcg acgtatgttt gaacctagaa aacctaccgt tagtgatttt   3660

gttcaaattg agagttgtgt ggtcacctat gtcaatttga ctagagacca actaccagat   3720

gtaatcccag attacatcga tgttaacaaa acacttgatg agattttagc ttctctgccc   3780

aatagaactg gtccaagtct tcctttagat gtttttaatg ccacttatct taatctcact   3840

ggtgaaattg cagatttaga gcagcgttca gagtctctcc gtaatactac agaggagctc   3900

caaagtctta tatataatat caacaacaca ctagttgacc ttgagtggct caaccgagtt   3960

gagacatata tcaagtggcc gtggtgggtt tggttgatta ttttcattgt tctcatcttt   4020

gttgtgtcat tactagtgtt ctgctgcatt tccacgggtt gttgtggatg ctgcggctgc   4080

tgctgtgctt gtttctcagg ttgttgtagg ggtcctagac ttcaacctta cgaagttttt   4140

gaaaaggtcc acgtgcagt                                                 4159
```

<210> SEQ ID NO 3
<211> LENGTH: 1386
<212> TYPE: PRT
<213> ORGANISM: Porcine epidemic diarrhea virus

<400> SEQUENCE: 3

```
Met Lys Ser Leu Thr Tyr Phe Trp Leu Phe Leu Pro Val Leu Ser Thr
1               5                   10                  15

Leu Ser Leu Pro Gln Asp Val Thr Arg Cys Ser Ala Asn Thr Asn Phe
            20                  25                  30

Arg Arg Phe Phe Ser Lys Phe Asn Val Gln Ala Pro Ala Val Val Val
        35                  40                  45

Leu Gly Gly Tyr Leu Pro Ile Gly Glu Asn Gln Gly Val Asn Ser Thr
    50                  55                  60

Trp Tyr Cys Ala Gly Gln His Pro Thr Ala Ser Gly Val His Gly Ile
65                  70                  75                  80

Phe Val Ser His Ile Arg Gly Gly His Gly Phe Glu Ile Gly Ile Ser
                85                  90                  95

Gln Glu Pro Phe Asp Pro Ser Gly Tyr Gln Leu Tyr Leu His Lys Ala
            100                 105                 110

Thr Asn Gly Asn Thr Asn Ala Thr Ala Arg Leu Arg Ile Cys Gln Phe
        115                 120                 125

Pro Ser Ile Lys Thr Leu Gly Pro Thr Ala Asn Asn Asp Val Thr Thr
    130                 135                 140

Gly Arg Asn Cys Leu Phe Asn Lys Ala Ile Pro Ala His Met Ser Glu
```

-continued

```
145                 150                 155                 160

His Ser Val Val Gly Ile Thr Trp Asp Asn Asp Arg Val Thr Val Phe
                165                 170                 175

Ser Asp Lys Ile Tyr Tyr Phe Tyr Phe Lys Asn Asp Trp Ser Arg Val
            180                 185                 190

Ala Thr Lys Cys Tyr Asn Ser Gly Gly Cys Ala Met Gln Tyr Val Tyr
        195                 200                 205

Glu Pro Thr Tyr Tyr Met Leu Asn Val Thr Ser Ala Gly Glu Asp Gly
    210                 215                 220

Ile Ser Tyr Gln Pro Cys Thr Ala Asn Cys Ile Gly Tyr Ala Ala Asn
225                 230                 235                 240

Val Phe Ala Thr Glu Pro Asn Gly His Ile Pro Glu Gly Phe Ser Phe
                245                 250                 255

Asn Asn Trp Phe Leu Leu Ser Asn Asp Ser Thr Leu Val His Gly Lys
            260                 265                 270

Val Val Ser Asn Gln Pro Leu Leu Val Asn Cys Leu Leu Ala Ile Pro
        275                 280                 285

Lys Ile Tyr Gly Leu Gly Gln Phe Phe Ser Phe Asn Gln Thr Ile Asp
    290                 295                 300

Gly Val Cys Asn Gly Ala Ala Val Gln Arg Ala Pro Glu Ala Leu Arg
305                 310                 315                 320

Phe Asn Ile Asn Asp Thr Ser Val Ile Leu Ala Glu Gly Ser Ile Val
                325                 330                 335

Leu His Thr Ala Leu Gly Thr Asn Phe Ser Phe Val Cys Ser Asn Ser
            340                 345                 350

Ser Asn Pro His Leu Ala Thr Phe Ala Ile Pro Leu Gly Ala Thr Gln
        355                 360                 365

Val Pro Tyr Tyr Cys Phe Leu Lys Val Asp Thr Tyr Asn Ser Thr Val
    370                 375                 380

Tyr Lys Phe Leu Ala Val Leu Pro Pro Thr Val Arg Glu Ile Val Ile
385                 390                 395                 400

Thr Lys Tyr Gly Asp Val Tyr Val Asn Gly Phe Gly Tyr Leu His Leu
                405                 410                 415

Gly Leu Leu Asp Ala Val Thr Ile Asn Phe Thr Gly His Gly Thr Asp
            420                 425                 430

Asp Asp Val Ser Gly Phe Trp Thr Ile Ala Ser Thr Asn Phe Val Asp
        435                 440                 445

Ala Leu Ile Glu Val Gln Gly Thr Ala Ile Gln Arg Ile Leu Tyr Cys
    450                 455                 460

Asp Asp Pro Val Ser Gln Leu Lys Cys Ser Gln Val Ala Phe Asp Leu
465                 470                 475                 480

Asp Asp Gly Phe Tyr Pro Ile Ser Ser Arg Asn Leu Leu Ser His Glu
                485                 490                 495

Gln Pro Ile Ser Phe Val Thr Leu Pro Ser Phe Asn Asp His Ser Phe
            500                 505                 510

Val Asn Ile Thr Val Ser Ala Ser Phe Gly Gly His Ser Gly Ala Asn
        515                 520                 525

Leu Ile Ala Ser Asp Thr Thr Ile Asn Gly Phe Ser Ser Phe Cys Val
    530                 535                 540

Asp Thr Arg Gln Phe Thr Ile Ser Leu Phe Tyr Asn Val Thr Asn Ser
545                 550                 555                 560

Tyr Gly Tyr Val Ser Lys Ser Gln Asp Ser Asn Cys Pro Phe Thr Leu
                565                 570                 575
```

-continued

```
Gln Ser Val Asn Asp Tyr Leu Ser Phe Ser Lys Phe Cys Val Ser Thr
            580                 585                 590

Ser Leu Leu Ala Ser Ala Cys Thr Ile Asp Leu Phe Gly Tyr Pro Glu
        595                 600                 605

Phe Gly Ser Gly Val Lys Phe Thr Ser Leu Tyr Phe Gln Phe Thr Lys
    610                 615                 620

Gly Glu Leu Ile Thr Gly Thr Pro Lys Pro Leu Glu Gly Val Thr Asp
625                 630                 635                 640

Val Ser Phe Met Thr Leu Asp Val Cys Thr Lys Tyr Thr Ile Tyr Gly
                645                 650                 655

Phe Lys Gly Glu Gly Ile Ile Thr Leu Thr Asn Ser Ser Phe Leu Ala
            660                 665                 670

Gly Val Tyr Tyr Thr Ser Asp Ser Gly Gln Leu Leu Ala Phe Lys Asn
        675                 680                 685

Val Thr Ser Gly Ala Val Tyr Ser Val Thr Pro Cys Ser Phe Ser Glu
    690                 695                 700

Gln Ala Ala Tyr Val Asp Asp Asp Ile Val Gly Val Ile Ser Ser Leu
705                 710                 715                 720

Ser Ser Ser Thr Phe Asn Ser Thr Arg Glu Leu Pro Gly Phe Phe Tyr
                725                 730                 735

His Ser Asn Asp Gly Ser Asn Cys Thr Glu Pro Val Leu Val Tyr Ser
            740                 745                 750

Asn Ile Gly Val Cys Lys Ser Gly Ser Ile Gly Tyr Val Pro Ser Gln
        755                 760                 765

Ser Gly Gln Val Lys Ile Ala Pro Thr Val Thr Gly Asn Ile Ser Ile
    770                 775                 780

Pro Thr Asn Phe Ser Met Ser Ile Arg Thr Glu Tyr Leu Gln Leu Tyr
785                 790                 795                 800

Asn Thr Pro Val Ser Val Asp Cys Ala Thr Tyr Val Cys Asn Gly Asn
                805                 810                 815

Ser Arg Cys Lys Gln Leu Leu Thr Gln Tyr Thr Ala Ala Cys Lys Thr
            820                 825                 830

Ile Glu Ser Ala Leu Gln Leu Ser Ala Arg Leu Glu Ser Val Glu Val
        835                 840                 845

Asn Ser Met Leu Thr Ile Ser Glu Glu Ala Leu Gln Leu Ala Thr Ile
    850                 855                 860

Ser Ser Phe Asn Gly Asp Gly Tyr Asn Phe Thr Asn Val Leu Gly Val
865                 870                 875                 880

Ser Val Tyr Asp Pro Ala Ser Gly Arg Val Val Gln Lys Arg Ser Phe
                885                 890                 895

Ile Glu Asp Leu Leu Phe Asn Lys Val Val Thr Asn Gly Leu Gly Thr
            900                 905                 910

Val Asp Glu Asp Tyr Lys Arg Cys Ser Asn Gly Arg Ser Val Ala Asp
        915                 920                 925

Leu Val Cys Ala Gln Tyr Tyr Ser Gly Val Met Val Leu Pro Gly Val
    930                 935                 940

Val Asp Ala Glu Lys Leu His Met Tyr Ser Ala Ser Leu Ile Gly Gly
945                 950                 955                 960

Met Val Leu Gly Gly Phe Thr Ser Ala Ala Ala Leu Pro Phe Ser Tyr
                965                 970                 975

Ala Val Gln Ala Arg Leu Asn Tyr Leu Ala Leu Gln Thr Asp Val Leu
            980                 985                 990
```

-continued

```
Gln Arg Asn Gln Gln Leu Leu Ala  Glu Ser Phe Asn Ser  Ala Ile Gly
        995                 1000                 1005

Asn Ile  Thr Ser Ala Phe Glu  Ser Val Lys Glu Ala  Ile Ser Gln
    1010                 1015                 1020

Thr Ser  Lys Gly Leu Asn Thr  Val Ala His Ala Leu  Thr Lys Val
    1025                 1030                 1035

Gln Glu  Val Val Asn Ser Gln  Gly Ala Ala Leu Thr  Gln Leu Thr
    1040                 1045                 1050

Val Gln  Leu Gln His Asn Phe  Gln Ala Ile Ser Ser  Ser Ile Asp
    1055                 1060                 1065

Asp Ile  Tyr Ser Arg Leu Asp  Ile Leu Ser Ala Asp  Val Gln Val
    1070                 1075                 1080

Asp Arg  Leu Ile Thr Gly Arg  Leu Ser Ala Leu Asn  Ala Phe Val
    1085                 1090                 1095

Ala Gln  Thr Leu Thr Lys Tyr  Thr Glu Val Gln Ala  Ser Arg Lys
    1100                 1105                 1110

Leu Ala  Gln Gln Lys Val Asn  Glu Cys Val Lys Ser  Gln Ser Gln
    1115                 1120                 1125

Arg Tyr  Gly Phe Cys Gly Gly  Asp Gly Glu His Ile  Phe Ser Leu
    1130                 1135                 1140

Val Gln  Ala Ala Pro Gln Gly  Leu Leu Phe Leu His  Thr Val Leu
    1145                 1150                 1155

Val Pro  Ser Asp Phe Val Asp  Val Ile Ala Ile Ala  Gly Leu Cys
    1160                 1165                 1170

Val Asn  Asp Glu Ile Ala Leu  Thr Leu Arg Glu Pro  Gly Leu Val
    1175                 1180                 1185

Leu Phe  Thr His Glu Leu Gln  Asn His Thr Ala Thr  Glu Tyr Phe
    1190                 1195                 1200

Val Ser  Ser Arg Arg Met Phe  Glu Pro Arg Lys Pro  Thr Val Ser
    1205                 1210                 1215

Asp Phe  Val Gln Ile Glu Ser  Cys Val Val Thr Tyr  Val Asn Leu
    1220                 1225                 1230

Thr Arg  Asp Gln Leu Pro Asp  Val Ile Pro Asp Tyr  Ile Asp Val
    1235                 1240                 1245

Asn Lys  Thr Leu Asp Glu Ile  Leu Ala Ser Leu Pro  Asn Arg Thr
    1250                 1255                 1260

Gly Pro  Ser Leu Pro Leu Asp  Val Phe Asn Ala Thr  Tyr Leu Asn
    1265                 1270                 1275

Leu Thr  Gly Glu Ile Ala Asp  Leu Glu Gln Arg Ser  Glu Ser Leu
    1280                 1285                 1290

Arg Asn  Thr Thr Glu Glu Leu  Gln Ser Leu Ile Tyr  Asn Ile Asn
    1295                 1300                 1305

Asn Thr  Leu Val Asp Leu Glu  Trp Leu Asn Arg Val  Glu Thr Tyr
    1310                 1315                 1320

Ile Lys  Trp Pro Trp Trp Val  Trp Leu Ile Ile Phe  Ile Val Leu
    1325                 1330                 1335

Ile Phe  Val Val Ser Leu Leu  Val Phe Cys Cys Ile  Ser Thr Gly
    1340                 1345                 1350

Cys Cys  Gly Cys Cys Gly Cys  Cys Cys Ala Cys Phe  Ser Gly Cys
    1355                 1360                 1365

Cys Arg  Gly Pro Arg Leu Gln  Pro Tyr Glu Val Phe  Glu Lys Val
    1370                 1375                 1380

His Val  Gln
```

1385

<210> SEQ ID NO 4
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 4
ggatccatga agtctttaac ctacttctgg ttgttcttac 40

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
gcggccgcac tgcacgtgga ccttttc 27

<210> SEQ ID NO 6
<211> LENGTH: 3912
<212> TYPE: DNA
<213> ORGANISM: Porcine epidemic diarrhea virus

<400> SEQUENCE: 6
gatgtcacca ggtgctcagc taacactaat tttaggcggt tcttttcaaa atttaatgtt 60
caggcgcctg cagttgttgt actgggcggt tatctaccta ttggtgaaaa ccagggtgtc 120
aattcaactt ggtactgtgc tggccaacat ccaactgcta gtggcgttca tggtatcttt 180
gttagccata ttagaggtgg tcatggcttt gagattggca tttcgcaaga gccttttgac 240
cctagtggtt accagcttta tttacataag gctactaacg gtaacactaa tgctactgcg 300
cgactgcgca tttgccagtt tcctagcatt aaaacattgg gccccactgc taataatgat 360
gttacaacag gtcgtaattg cctatttaac aaagccatcc cagctcatat gagtgaacat 420
agtgttgtcg gcataacatg ggataatgat cgtgtcactg tcttttctga caagatctat 480
tatttttatt ttaaaaatga ttggtcccgt gttgcgacaa agtgttacaa cagtggaggt 540
tgtgctatgc aatatgttta cgaacccacc tattacatgc ttaatgttac tagtgctggt 600
gaggatggta tttcttatca accctgtaca gctaattgca ttggttatgc tgccaatgta 660
tttgctactg agcccaatgg ccacatacca gaaggtttta gttttaataa ttggtttctt 720
ttgtccaatg attccacttt ggtgcatggt aaggtggttt ccaaccaacc attgttggtc 780
aattgtcttt tggccattcc taagatttat ggactaggcc aatttttctc ctttaatcaa 840
acgatcgatg gtgtttgtaa tggagctgct gtgcagcgtg caccagaggc tctgaggttt 900
aatattaatg acacctctgt cattcttgct gaaggctcaa ttgtacttca tactgcttta 960
ggaacaaatt tttcttttgt ttgcagtaat tcctcaaatc ctcacttagc caccttcgcc 1020
atacctttgg gtgctaccca agtaccctat tattgttttc ttaaagtgga tacttacaac 1080
tccactgttt ataaattctt ggctgtttta cctccaaccg tcagggaaat tgtcatcacc 1140
aagtatggtg atgtttatgt caatgggttt ggatacttgc atctcggttt gttggatgct 1200
gtcacaatta atttcactgg tcatggcact gacgatgatg tttctggttt ttggaccata 1260
gcatcgacta attttgttga tgcactcatc gaagttcaag gaaccgccat tcagcgtatt 1320

-continued

```
ctttattgtg atgatcctgt tagccaactc aagtgttctc aggttgcttt tgaccttgac   1380
gatggttttt accctatttc ttctagaaac cttctgagtc atgaacagcc aatttctttt   1440
gttactctgc catcatttaa tgatcattct tttgttaaca ttactgtatc tgcttccttt   1500
ggtggtcata gtggtgccaa ccttattgca tctgacacta ctatcaatgg gtttagttct   1560
ttctgtgttg acactagaca atttaccatt tcactgtttt ataacgttac aaacagttat   1620
ggttatgtgt ctaaatcaca ggacagtaat tgccctttca ccttgcaatc tgttaatgat   1680
tacctgtctt ttagcaaatt ttgtgtttcc accagccttt tggctagtgc ctgtaccata   1740
gatctttttg gttaccctga gtttggtagt ggtgttaagt ttacgtccct ttactttcaa   1800
ttcacaaagg gtgagttgat tactggcacg cctaaaccac ttgaaggtgt cacggacgtt   1860
tcttttatga ctctggatgt gtgtaccaag tatactatct atggctttaa aggtgagggt   1920
atcattaccc ttacaaattc tagctttttg gcaggtgttt attacacatc tgattctgga   1980
cagttgttag cctttaagaa tgtcactagt ggtgctgttt attctgttac gccatgttct   2040
ttttcagagc aggctgcata tgttgatgat gatatagtgg gtgttatttc tagtttgtct   2100
agctccactt ttaacagtac tagggagttg cctggtttct tctaccattc taatgatggc   2160
tctaattgta cagagcctgt gttggtgtat agtaacatag gtgtttgtaa atctggcagt   2220
attggctacg tcccatctca gtctggccaa gtcaagattg cacccacggt tactgggaat   2280
attagtattc ccaccaactt tagtatgagt attaggacag aatatttaca gctttacaac   2340
acgcctgtta gtgttgattg tgccacatat gtttgtaatg gtaactctcg ttgtaaacaa   2400
ttactcaccc agtacactgc agcatgtaag accatagagt cagcattaca actcagcgct   2460
aggcttgagt ctgttgaagt taactctatg cttactattt ctgaagaggc tctacagtta   2520
gctaccatta gttcgtttaa tggtgatgga tataatttta ctaatgtgct gggtgtttct   2580
gtgtatgatc ctgcaagtgg cagggtggta caaaaaaggt cttttattga agacctgctt   2640
tttaataaag tggttactaa tggccttggt actgttgatg aagactataa gcgctgttct   2700
aatggtcgct ctgtggcaga tctagtctgt gcacagtatt actctggtgt catggtacta   2760
cctggtgttg ttgacgctga gaagcttcac atgtatagtg cgtctctcat cggtggtatg   2820
gtgctaggag gttttacttc tgcagcggca ttgccttttta gctatgctgt tcaagctaga   2880
ctcaattatc ttgctctaca gacggatgtt ctacagcgga accagcaatt gcttgctgag   2940
tcttttaact ctgctattgg taatataact tcagcctttg agagtgttaa agaggctatt   3000
agtcaaactt ccaagggttt gaacactgtg gctcatgcgc ttactaaggt tcaagaggtt   3060
gttaactcgc agggtgcagc tttgactcaa cttaccgtac agctgcaaca caacttccaa   3120
gccatttcta gttctattga tgacatttac tctcgactgg acattctttc agccgatgtt   3180
caggttgacc gtctcatcac cggcagatta tcagcactta atgcttttgt tgctcaaacc   3240
ctcactaagt atactgaggt tcaggctagc aggaagttag cacagcaaaa ggttaatgag   3300
tgcgttaaat cgcaatctca gcgttatggt ttttgtggtg gtgatggcga gcacattttc   3360
tctctggtac aggcagcacc tcagggcctg ctgtttttac atacagtact tgtaccgagt   3420
gattttgtag atgttattgc catcgctggc ttatgcgtta acgatgaaat tgccttgact   3480
ctacgtgagc ctggcttagt cttgtttacg catgaacttc aaaatcatac tgcgacggaa   3540
tattttgttt catcgcgacg tatgtttgaa cctagaaaac ctaccgttag tgattttgtt   3600
caaattgaga gttgtgtggt cacctatgtc aatttgacta gagaccaact accagatgta   3660
```

atcccagatt acatcgatgt taacaaaaca cttgatgaga ttttagcttc tctgcccaat 3720
agaactggtc caagtcttcc tttagatgtt tttaatgcca cttatcttaa tctcactggt 3780
gaaattgcag atttagagca gcgttcagag tctctccgta atactacaga ggagctccaa 3840
agtcttatat ataatatcaa caacacacta gttgaccttg agtggctcaa ccgagttgag 3900
acatatatca ag 3912

<210> SEQ ID NO 7
<211> LENGTH: 1304
<212> TYPE: PRT
<213> ORGANISM: Porcine epidemic diarrhea virus

<400> SEQUENCE: 7

Asp Val Thr Arg Cys Ser Ala Asn Thr Asn Phe Arg Arg Phe Phe Ser
1 5 10 15

Lys Phe Asn Val Gln Ala Pro Ala Val Val Val Leu Gly Gly Tyr Leu
20 25 30

Pro Ile Gly Glu Asn Gln Gly Val Asn Ser Thr Trp Tyr Cys Ala Gly
35 40 45

Gln His Pro Thr Ala Ser Gly Val His Gly Ile Phe Val Ser His Ile
50 55 60

Arg Gly Gly His Gly Phe Glu Ile Gly Ile Ser Gln Glu Pro Phe Asp
65 70 75 80

Pro Ser Gly Tyr Gln Leu Tyr Leu His Lys Ala Thr Asn Gly Asn Thr
85 90 95

Asn Ala Thr Ala Arg Leu Arg Ile Cys Gln Phe Pro Ser Ile Lys Thr
100 105 110

Leu Gly Pro Thr Ala Asn Asn Asp Val Thr Thr Gly Arg Asn Cys Leu
115 120 125

Phe Asn Lys Ala Ile Pro Ala His Met Ser Glu His Ser Val Val Gly
130 135 140

Ile Thr Trp Asp Asn Asp Arg Val Thr Val Phe Ser Asp Lys Ile Tyr
145 150 155 160

Tyr Phe Tyr Phe Lys Asn Asp Trp Ser Arg Val Ala Thr Lys Cys Tyr
165 170 175

Asn Ser Gly Gly Cys Ala Met Gln Tyr Val Tyr Glu Pro Thr Tyr Tyr
180 185 190

Met Leu Asn Val Thr Ser Ala Gly Glu Asp Gly Ile Ser Tyr Gln Pro
195 200 205

Cys Thr Ala Asn Cys Ile Gly Tyr Ala Ala Asn Val Phe Ala Thr Glu
210 215 220

Pro Asn Gly His Ile Pro Glu Gly Phe Ser Phe Asn Asn Trp Phe Leu
225 230 235 240

Leu Ser Asn Asp Ser Thr Leu Val His Gly Lys Val Val Ser Asn Gln
245 250 255

Pro Leu Leu Val Asn Cys Leu Leu Ala Ile Pro Lys Ile Tyr Gly Leu
260 265 270

Gly Gln Phe Phe Ser Phe Asn Gln Thr Ile Asp Gly Val Cys Asn Gly
275 280 285

Ala Ala Val Gln Arg Ala Pro Glu Ala Leu Arg Phe Asn Ile Asn Asp
290 295 300

Thr Ser Val Ile Leu Ala Glu Gly Ser Ile Val Leu His Thr Ala Leu
305 310 315 320

Gly Thr Asn Phe Ser Phe Val Cys Ser Asn Ser Ser Asn Pro His Leu

-continued

```
                325                 330                 335

Ala Thr Phe Ala Ile Pro Leu Gly Ala Thr Gln Val Pro Tyr Tyr Cys
            340                 345                 350

Phe Leu Lys Val Asp Thr Tyr Asn Ser Thr Val Tyr Lys Phe Leu Ala
        355                 360                 365

Val Leu Pro Pro Thr Val Arg Glu Ile Val Ile Thr Lys Tyr Gly Asp
    370                 375                 380

Val Tyr Val Asn Gly Phe Gly Tyr Leu His Leu Gly Leu Leu Asp Ala
385                 390                 395                 400

Val Thr Ile Asn Phe Thr Gly His Gly Thr Asp Asp Asp Val Ser Gly
                405                 410                 415

Phe Trp Thr Ile Ala Ser Thr Asn Phe Val Asp Ala Leu Ile Glu Val
            420                 425                 430

Gln Gly Thr Ala Ile Gln Arg Ile Leu Tyr Cys Asp Asp Pro Val Ser
        435                 440                 445

Gln Leu Lys Cys Ser Gln Val Ala Phe Asp Leu Asp Asp Gly Phe Tyr
    450                 455                 460

Pro Ile Ser Ser Arg Asn Leu Leu Ser His Glu Gln Pro Ile Ser Phe
465                 470                 475                 480

Val Thr Leu Pro Ser Phe Asn Asp His Ser Phe Val Asn Ile Thr Val
                485                 490                 495

Ser Ala Ser Phe Gly Gly His Ser Gly Ala Asn Leu Ile Ala Ser Asp
            500                 505                 510

Thr Thr Ile Asn Gly Phe Ser Ser Phe Cys Val Asp Thr Arg Gln Phe
        515                 520                 525

Thr Ile Ser Leu Phe Tyr Asn Val Thr Asn Ser Tyr Gly Tyr Val Ser
    530                 535                 540

Lys Ser Gln Asp Ser Asn Cys Pro Phe Thr Leu Gln Ser Val Asn Asp
545                 550                 555                 560

Tyr Leu Ser Phe Ser Lys Phe Cys Val Ser Thr Ser Leu Leu Ala Ser
                565                 570                 575

Ala Cys Thr Ile Asp Leu Phe Gly Tyr Pro Glu Phe Gly Ser Gly Val
            580                 585                 590

Lys Phe Thr Ser Leu Tyr Phe Gln Phe Thr Lys Gly Glu Leu Ile Thr
        595                 600                 605

Gly Thr Pro Lys Pro Leu Glu Gly Val Thr Asp Val Ser Phe Met Thr
    610                 615                 620

Leu Asp Val Cys Thr Lys Tyr Thr Ile Tyr Gly Phe Lys Gly Glu Gly
625                 630                 635                 640

Ile Ile Thr Leu Thr Asn Ser Ser Phe Leu Ala Gly Val Tyr Tyr Thr
                645                 650                 655

Ser Asp Ser Gly Gln Leu Leu Ala Phe Lys Asn Val Thr Ser Gly Ala
            660                 665                 670

Val Tyr Ser Val Thr Pro Cys Ser Phe Ser Glu Gln Ala Ala Tyr Val
        675                 680                 685

Asp Asp Asp Ile Val Gly Val Ile Ser Ser Leu Ser Ser Ser Thr Phe
    690                 695                 700

Asn Ser Thr Arg Glu Leu Pro Gly Phe Phe Tyr His Ser Asn Asp Gly
705                 710                 715                 720

Ser Asn Cys Thr Glu Pro Val Leu Val Tyr Ser Asn Ile Gly Val Cys
                725                 730                 735

Lys Ser Gly Ser Ile Gly Tyr Val Pro Ser Gln Ser Gly Gln Val Lys
            740                 745                 750
```

-continued

```
Ile Ala Pro Thr Val Thr Gly Asn Ile Ser Ile Pro Thr Asn Phe Ser
        755                 760                 765

Met Ser Ile Arg Thr Glu Tyr Leu Gln Leu Tyr Asn Thr Pro Val Ser
    770                 775                 780

Val Asp Cys Ala Thr Tyr Val Cys Asn Gly Asn Ser Arg Cys Lys Gln
785                 790                 795                 800

Leu Leu Thr Gln Tyr Thr Ala Ala Cys Lys Thr Ile Glu Ser Ala Leu
                805                 810                 815

Gln Leu Ser Ala Arg Leu Glu Ser Val Glu Val Asn Ser Met Leu Thr
            820                 825                 830

Ile Ser Glu Glu Ala Leu Gln Leu Ala Thr Ile Ser Ser Phe Asn Gly
        835                 840                 845

Asp Gly Tyr Asn Phe Thr Asn Val Leu Gly Val Ser Val Tyr Asp Pro
    850                 855                 860

Ala Ser Gly Arg Val Val Gln Lys Arg Ser Phe Ile Glu Asp Leu Leu
865                 870                 875                 880

Phe Asn Lys Val Val Thr Asn Gly Leu Gly Thr Val Asp Glu Asp Tyr
                885                 890                 895

Lys Arg Cys Ser Asn Gly Arg Ser Val Ala Asp Leu Val Cys Ala Gln
            900                 905                 910

Tyr Tyr Ser Gly Val Met Val Leu Pro Gly Val Val Asp Ala Glu Lys
        915                 920                 925

Leu His Met Tyr Ser Ala Ser Leu Ile Gly Gly Met Val Leu Gly Gly
    930                 935                 940

Phe Thr Ser Ala Ala Ala Leu Pro Phe Ser Tyr Ala Val Gln Ala Arg
945                 950                 955                 960

Leu Asn Tyr Leu Ala Leu Gln Thr Asp Val Leu Gln Arg Asn Gln Gln
                965                 970                 975

Leu Leu Ala Glu Ser Phe Asn Ser Ala Ile Gly Asn Ile Thr Ser Ala
            980                 985                 990

Phe Glu Ser Val Lys Glu Ala Ile  Ser Gln Thr Ser Lys  Gly Leu Asn
        995                 1000                1005

Thr Val  Ala His Ala Leu Thr  Lys Val Gln Glu Val  Val Asn Ser
    1010                1015                1020

Gln Gly  Ala Ala Leu Thr Gln  Leu Thr Val Gln Leu  Gln His Asn
    1025                1030                1035

Phe Gln  Ala Ile Ser Ser Ser  Ile Asp Asp Ile Tyr  Ser Arg Leu
    1040                1045                1050

Asp Ile  Leu Ser Ala Asp Val  Gln Val Asp Arg Leu  Ile Thr Gly
    1055                1060                1065

Arg Leu  Ser Ala Leu Asn Ala  Phe Val Ala Gln Thr  Leu Thr Lys
    1070                1075                1080

Tyr Thr  Glu Val Gln Ala Ser  Arg Lys Leu Ala Gln  Gln Lys Val
    1085                1090                1095

Asn Glu  Cys Val Lys Ser Gln  Ser Gln Arg Tyr Gly  Phe Cys Gly
    1100                1105                1110

Gly Asp  Gly Glu His Ile Phe  Ser Leu Val Gln Ala  Ala Pro Gln
    1115                1120                1125

Gly Leu  Leu Phe Leu His Thr  Val Leu Val Pro Ser  Asp Phe Val
    1130                1135                1140

Asp Val  Ile Ala Ile Ala Gly  Leu Cys Val Asn Asp  Glu Ile Ala
    1145                1150                1155
```

-continued

```
Leu Thr  Leu Arg Glu Pro Gly  Leu Val Leu Phe Thr  His Glu Leu
    1160                 1165                 1170

Gln Asn  His Thr Ala Thr Glu  Tyr Phe Val Ser Ser  Arg Arg Met
    1175                 1180                 1185

Phe Glu  Pro Arg Lys Pro Thr  Val Ser Asp Phe Val  Gln Ile Glu
    1190                 1195                 1200

Ser Cys  Val Val Thr Tyr Val  Asn Leu Thr Arg Asp  Gln Leu Pro
    1205                 1210                 1215

Asp Val  Ile Pro Asp Tyr Ile  Asp Val Asn Lys Thr  Leu Asp Glu
    1220                 1225                 1230

Ile Leu  Ala Ser Leu Pro Asn  Arg Thr Gly Pro Ser  Leu Pro Leu
    1235                 1240                 1245

Asp Val  Phe Asn Ala Thr Tyr  Leu Asn Leu Thr Gly  Glu Ile Ala
    1250                 1255                 1260

Asp Leu  Glu Gln Arg Ser Glu  Ser Leu Arg Asn Thr  Thr Glu Glu
    1265                 1270                 1275

Leu Gln  Ser Leu Ile Tyr Asn  Ile Asn Asn Thr Leu  Val Asp Leu
    1280                 1285                 1290

Glu Trp  Leu Asn Arg Val Glu  Thr Tyr Ile Lys
    1295                 1300
```

<210> SEQ ID NO 8
<211> LENGTH: 4131
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 8

```
atgaagtgcc ttttgtactt agccttttta ttcattgggg tgaattgcca tcaccatcac     60

catcacgatg tcaccaggtg ctcagctaac actaatttta ggcggttctt ttcaaaattt    120

aatgttcagg cgcctgcagt tgttgtactg ggcggttatc tacctattgg tgaaaaccag    180

ggtgtcaatt caacttggta ctgtgctggc caacatccaa ctgctagtgg cgttcatggt    240

atctttgtta gccatattag aggtggtcat ggctttgaga ttggcatttc gcaagagcct    300

tttgacccta gtggttacca gctttattta cataaggcta ctaacggtaa cactaatgct    360

actgcgcgac tgcgcatttg ccagtttcct agcattaaaa cattgggccc cactgctaat    420

aatgatgtta caacaggtcg taattgccta tttaacaaag ccatcccagc tcatatgagt    480

gaacatagtg ttgtcggcat aacatgggat aatgatcgtg tcactgtctt ttctgacaag    540

atctattatt tttattttaa aaatgattgg tcccgtgttg cgacaaagtg ttacaacagt    600

ggaggttgtg ctatgcaata tgtttacgaa cccacctatt acatgcttaa tgttactagt    660

gctggtgagg atggtatttc ttatcaaccc tgtacagcta attgcattgg ttatgctgcc    720

aatgtatttg ctactgagcc caatggccac ataccagaag gttttagttt taataattgg    780

tttcttttgt ccaatgattc cactttggtg catggtaagg tggtttccaa ccaaccattg    840

ttggtcaatt gtcttttggc cattcctaag atttatggac taggccaatt tttctccttt    900

aatcaaacga tcgatggtgt ttgtaatgga gctgctgtgc agcgtgcacc agaggctctg    960

aggtttaata ttaatgacac ctctgtcatt cttgctgaag gctcaattgt acttcatact   1020

gctttaggaa caaatttttc ttttgtttgc agtaattcct caaatcctca cttagccacc   1080

ttcgccatac ctttgggtgc tacccaagta ccctattatt gttttcttaa agtggatact   1140
```

-continued

```
tacaactcca ctgtttataa attcttggct gttttacctc caaccgtcag ggaaattgtc   1200
atcaccaagt atggtgatgt ttatgtcaat gggtttggat acttgcatct cggtttgttg   1260
gatgctgtca caattaattt cactggtcat ggcactgacg atgatgtttc tggtttttgg   1320
accatagcat cgactaattt tgttgatgca ctcatcgaag ttcaaggaac cgccattcag   1380
cgtattcttt attgtgatga tcctgttagc caactcaagt gttctcaggt tgcttttgac   1440
cttgacgatg gtttttaccc tatttcttct agaaaccttc tgagtcatga acagccaatt   1500
tcttttgtta ctctgccatc atttaatgat cattcttttg ttaacattac tgtatctgct   1560
tcctttggtg gtcatagtgg tgccaacctt attgcatctg acactactat caatgggttt   1620
agttctttct gtgttgacac tagacaattt accatttcac tgttttataa cgttacaaac   1680
agttatggtt atgtgtctaa atcacaggac agtaattgcc ctttcacctt gcaatctgtt   1740
aatgattacc tgtcttttag caaattttgt gtttccacca gccttttggc tagtgcctgt   1800
accatagatc tttttggtta ccctgagttt ggtagtggtg ttaagtttac gtccctttac   1860
tttcaattca caaagggtga gttgattact ggcacgccta aaccacttga aggtgtcacg   1920
gacgtttctt ttatgactct ggatgtgtgt accaagtata ctatctatgg ctttaaaggt   1980
gagggtatca ttacccttac aaattctagc tttttggcag gtgtttatta cacatctgat   2040
tctggacagt tgttagcctt taagaatgtc actagtggtg ctgtttattc tgttacgcca   2100
tgttcttttt cagagcaggc tgcatatgtt gatgatgata tagtgggtgt tatttctagt   2160
ttgtctagct ccacttttaa cagtactagg gagttgcctg gtttcttcta ccattctaat   2220
gatggctcta attgtacaga gcctgtgttg gtgtatagta acataggtgt ttgtaaatct   2280
ggcagtattg gctacgtccc atctcagtct ggccaagtca agattgcacc cacggttact   2340
gggaatatta gtattcccac caactttagt atgagtatta ggacagaata tttacagctt   2400
tacaacacgc ctgttagtgt tgattgtgcc acatatgttt gtaatggtaa ctctcgttgt   2460
aaacaattac tcacccagta cactgcagca tgtaagacca tagagtcagc attacaactc   2520
agcgctaggc ttgagtctgt tgaagttaac tctatgctta ctatttctga agaggctcta   2580
cagttagcta ccattagttc gtttaatggt gatggatata attttactaa tgtgctgggt   2640
gtttctgtgt atgatcctgc aagtggcagg gtggtacaaa aaaggtcttt tattgaagac   2700
ctgcttttta ataaagtggt tactaatggc cttggtactg ttgatgaaga ctataagcgc   2760
tgttctaatg gtcgctctgt ggcagatcta gtctgtgcac agtattactc tggtgtcatg   2820
gtactacctg gtgttgttga cgctgagaag cttcacatgt atagtgcgtc tctcatcggt   2880
ggtatggtgc taggaggttt tacttctgca gcggcattgc cttttagcta tgctgttcaa   2940
gctagactca attatcttgc tctacagacg gatgttctac agcggaacca gcaattgctt   3000
gctgagtctt ttaactctgc tattggtaat ataacttcag cctttgagag tgttaaagag   3060
gctattagtc aaacttccaa gggtttgaac actgtggctc atgcgcttac taaggttcaa   3120
gaggttgtta actcgcaggg tgcagctttg actcaactta ccgtacagct gcaacacaac   3180
ttccaagcca tttctagttc tattgatgac atttactctc gactggacat tctttcagcc   3240
gatgttcagg ttgaccgtct catcaccggc agattatcag cacttaatgc ttttgttgct   3300
caaaccctca ctaagtatac tgaggttcag gctagcagga agttagcaca gcaaaaggtt   3360
aatgagtgcg ttaaatcgca atctcagcgt tatggttttt gtggtggtga tggcgagcac   3420
attttctctc tggtacaggc agcacctcag ggcctgctgt tttacatac agtacttgta   3480
ccgagtgatt ttgtagatgt tattgccatc gctggcttat gcgttaacga tgaaattgcc   3540
```

```
ttgactctac gtgagcctgg cttagtcttg tttacgcatg aacttcaaaa tcatactgcg   3600

acggaatatt ttgtttcatc gcgacgtatg tttgaaccta gaaaacctac cgttagtgat   3660

tttgttcaaa ttgagagttg tgtggtcacc tatgtcaatt tgactagaga ccaactacca   3720

gatgtaatcc cagattacat cgatgttaac aaaacacttg atgagatttt agcttctctg   3780

cccaatagaa ctggtccaag tcttccttta gatgttttta atgccactta tcttaatctc   3840

actggtgaaa ttgcagattt agagcagcgt tcagagtctc tccgtaatac tacagaggag   3900

ctccaaagtc ttatatataa tatcaacaac acactagttg accttgagtg gctcaaccga   3960

gttgagacat atatcaagtg gaaaagctct attgcctctt ttttctttat catagggtta   4020

atcattggac tattcttggt tctccgagtt ggtatccatc tttgcattaa attaaagcac   4080

accaagaaaa gacagattta tacagacata gagatgaacc gacttggaaa g            4131
```

```
<210> SEQ ID NO 9
<211> LENGTH: 1377
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Lys Cys Leu Leu Tyr Leu Ala Phe Leu Phe Ile Gly Val Asn Cys
1               5                   10                  15

His His His His His His Asp Val Thr Arg Cys Ser Ala Asn Thr Asn
            20                  25                  30

Phe Arg Arg Phe Phe Ser Lys Phe Asn Val Gln Ala Pro Ala Val Val
        35                  40                  45

Val Leu Gly Gly Tyr Leu Pro Ile Gly Glu Asn Gln Gly Val Asn Ser
    50                  55                  60

Thr Trp Tyr Cys Ala Gly Gln His Pro Thr Ala Ser Gly Val His Gly
65                  70                  75                  80

Ile Phe Val Ser His Ile Arg Gly Gly His Gly Phe Glu Ile Gly Ile
                85                  90                  95

Ser Gln Glu Pro Phe Asp Pro Ser Gly Tyr Gln Leu Tyr Leu His Lys
            100                 105                 110

Ala Thr Asn Gly Asn Thr Asn Ala Thr Ala Arg Leu Arg Ile Cys Gln
        115                 120                 125

Phe Pro Ser Ile Lys Thr Leu Gly Pro Thr Ala Asn Asn Asp Val Thr
    130                 135                 140

Thr Gly Arg Asn Cys Leu Phe Asn Lys Ala Ile Pro Ala His Met Ser
145                 150                 155                 160

Glu His Ser Val Val Gly Ile Thr Trp Asp Asn Asp Arg Val Thr Val
                165                 170                 175

Phe Ser Asp Lys Ile Tyr Tyr Phe Tyr Phe Lys Asn Asp Trp Ser Arg
            180                 185                 190

Val Ala Thr Lys Cys Tyr Asn Ser Gly Gly Cys Ala Met Gln Tyr Val
        195                 200                 205

Tyr Glu Pro Thr Tyr Tyr Met Leu Asn Val Thr Ser Ala Gly Glu Asp
    210                 215                 220

Gly Ile Ser Tyr Gln Pro Cys Thr Ala Asn Cys Ile Gly Tyr Ala Ala
225                 230                 235                 240

Asn Val Phe Ala Thr Glu Pro Asn Gly His Ile Pro Glu Gly Phe Ser
                245                 250                 255
```

-continued

```
Phe Asn Asn Trp Phe Leu Leu Ser Asn Asp Ser Thr Leu Val His Gly
            260                 265                 270

Lys Val Val Ser Asn Gln Pro Leu Leu Val Asn Cys Leu Leu Ala Ile
        275                 280                 285

Pro Lys Ile Tyr Gly Leu Gly Gln Phe Phe Ser Phe Asn Gln Thr Ile
    290                 295                 300

Asp Gly Val Cys Asn Gly Ala Ala Val Gln Arg Ala Pro Glu Ala Leu
305                 310                 315                 320

Arg Phe Asn Ile Asn Asp Thr Ser Val Ile Leu Ala Glu Gly Ser Ile
                325                 330                 335

Val Leu His Thr Ala Leu Gly Thr Asn Phe Ser Phe Val Cys Ser Asn
            340                 345                 350

Ser Ser Asn Pro His Leu Ala Thr Phe Ala Ile Pro Leu Gly Ala Thr
        355                 360                 365

Gln Val Pro Tyr Tyr Cys Phe Leu Lys Val Asp Thr Tyr Asn Ser Thr
    370                 375                 380

Val Tyr Lys Phe Leu Ala Val Leu Pro Pro Thr Val Arg Glu Ile Val
385                 390                 395                 400

Ile Thr Lys Tyr Gly Asp Val Tyr Val Asn Gly Phe Gly Tyr Leu His
                405                 410                 415

Leu Gly Leu Leu Asp Ala Val Thr Ile Asn Phe Thr Gly His Gly Thr
            420                 425                 430

Asp Asp Asp Val Ser Gly Phe Trp Thr Ile Ala Ser Thr Asn Phe Val
        435                 440                 445

Asp Ala Leu Ile Glu Val Gln Gly Thr Ala Ile Gln Arg Ile Leu Tyr
    450                 455                 460

Cys Asp Asp Pro Val Ser Gln Leu Lys Cys Ser Gln Val Ala Phe Asp
465                 470                 475                 480

Leu Asp Asp Gly Phe Tyr Pro Ile Ser Ser Arg Asn Leu Leu Ser His
                485                 490                 495

Glu Gln Pro Ile Ser Phe Val Thr Leu Pro Ser Phe Asn Asp His Ser
            500                 505                 510

Phe Val Asn Ile Thr Val Ser Ala Ser Phe Gly Gly His Ser Gly Ala
        515                 520                 525

Asn Leu Ile Ala Ser Asp Thr Thr Ile Asn Gly Phe Ser Ser Phe Cys
    530                 535                 540

Val Asp Thr Arg Gln Phe Thr Ile Ser Leu Phe Tyr Asn Val Thr Asn
545                 550                 555                 560

Ser Tyr Gly Tyr Val Ser Lys Ser Gln Asp Ser Asn Cys Pro Phe Thr
                565                 570                 575

Leu Gln Ser Val Asn Asp Tyr Leu Ser Phe Ser Lys Phe Cys Val Ser
            580                 585                 590

Thr Ser Leu Leu Ala Ser Ala Cys Thr Ile Asp Leu Phe Gly Tyr Pro
        595                 600                 605

Glu Phe Gly Ser Gly Val Lys Phe Thr Ser Leu Tyr Phe Gln Phe Thr
    610                 615                 620

Lys Gly Glu Leu Ile Thr Gly Thr Pro Lys Pro Leu Glu Gly Val Thr
625                 630                 635                 640

Asp Val Ser Phe Met Thr Leu Asp Val Cys Thr Lys Tyr Thr Ile Tyr
                645                 650                 655

Gly Phe Lys Gly Glu Gly Ile Ile Thr Leu Thr Asn Ser Ser Phe Leu
            660                 665                 670
```

```
Ala Gly Val Tyr Tyr Thr Ser Asp Ser Gly Gln Leu Leu Ala Phe Lys
        675                 680                 685

Asn Val Thr Ser Gly Ala Val Tyr Ser Val Thr Pro Cys Ser Phe Ser
    690                 695                 700

Glu Gln Ala Ala Tyr Val Asp Asp Asp Ile Val Gly Val Ile Ser Ser
705                 710                 715                 720

Leu Ser Ser Ser Thr Phe Asn Ser Thr Arg Glu Leu Pro Gly Phe Phe
                725                 730                 735

Tyr His Ser Asn Asp Gly Ser Asn Cys Thr Glu Pro Val Leu Val Tyr
            740                 745                 750

Ser Asn Ile Gly Val Cys Lys Ser Gly Ser Ile Gly Tyr Val Pro Ser
        755                 760                 765

Gln Ser Gly Gln Val Lys Ile Ala Pro Thr Val Thr Gly Asn Ile Ser
    770                 775                 780

Ile Pro Thr Asn Phe Ser Met Ser Ile Arg Thr Glu Tyr Leu Gln Leu
785                 790                 795                 800

Tyr Asn Thr Pro Val Ser Val Asp Cys Ala Thr Tyr Val Cys Asn Gly
                805                 810                 815

Asn Ser Arg Cys Lys Gln Leu Leu Thr Gln Tyr Thr Ala Ala Cys Lys
            820                 825                 830

Thr Ile Glu Ser Ala Leu Gln Leu Ser Ala Arg Leu Glu Ser Val Glu
        835                 840                 845

Val Asn Ser Met Leu Thr Ile Ser Glu Glu Ala Leu Gln Leu Ala Thr
    850                 855                 860

Ile Ser Ser Phe Asn Gly Asp Gly Tyr Asn Phe Thr Asn Val Leu Gly
865                 870                 875                 880

Val Ser Val Tyr Asp Pro Ala Ser Gly Arg Val Val Gln Lys Arg Ser
                885                 890                 895

Phe Ile Glu Asp Leu Leu Phe Asn Lys Val Val Thr Asn Gly Leu Gly
            900                 905                 910

Thr Val Asp Glu Asp Tyr Lys Arg Cys Ser Asn Gly Arg Ser Val Ala
        915                 920                 925

Asp Leu Val Cys Ala Gln Tyr Tyr Ser Gly Val Met Val Leu Pro Gly
    930                 935                 940

Val Val Asp Ala Glu Lys Leu His Met Tyr Ser Ala Ser Leu Ile Gly
945                 950                 955                 960

Gly Met Val Leu Gly Gly Phe Thr Ser Ala Ala Ala Leu Pro Phe Ser
                965                 970                 975

Tyr Ala Val Gln Ala Arg Leu Asn Tyr Leu Ala Leu Gln Thr Asp Val
            980                 985                 990

Leu Gln Arg Asn Gln Gln Leu Leu  Ala Glu Ser Phe Asn  Ser Ala Ile
        995                 1000                 1005

Gly Asn  Ile Thr Ser Ala Phe  Glu Ser Val Lys Glu  Ala Ile Ser
    1010                 1015                 1020

Gln Thr  Ser Lys Gly Leu Asn  Thr Val Ala His Ala  Leu Thr Lys
    1025                 1030                 1035

Val Gln  Glu Val Val Asn Ser  Gln Gly Ala Ala Leu  Thr Gln Leu
    1040                 1045                 1050

Thr Val  Gln Leu Gln His Asn  Phe Gln Ala Ile Ser  Ser Ser Ile
    1055                 1060                 1065

Asp Asp  Ile Tyr Ser Arg Leu  Asp Ile Leu Ser Ala  Asp Val Gln
    1070                 1075                 1080

Val Asp  Arg Leu Ile Thr Gly  Arg Leu Ser Ala Leu  Asn Ala Phe
```

```
    1085                1090                1095

Val Ala  Gln Thr Leu Thr Lys  Tyr Thr Glu Val Gln  Ala Ser Arg
    1100                1105                1110

Lys Leu  Ala Gln Gln Lys Val  Asn Glu Cys Val Lys  Ser Gln Ser
    1115                1120                1125

Gln Arg  Tyr Gly Phe Cys Gly  Gly Asp Gly Glu His  Ile Phe Ser
    1130                1135                1140

Leu Val  Gln Ala Ala Pro Gln  Gly Leu Leu Phe Leu  His Thr Val
    1145                1150                1155

Leu Val  Pro Ser Asp Phe Val  Asp Val Ile Ala Ile  Ala Gly Leu
    1160                1165                1170

Cys Val  Asn Asp Glu Ile Ala  Leu Thr Leu Arg Glu  Pro Gly Leu
    1175                1180                1185

Val Leu  Phe Thr His Glu Leu  Gln Asn His Thr Ala  Thr Glu Tyr
    1190                1195                1200

Phe Val  Ser Ser Arg Arg Met  Phe Glu Pro Arg Lys  Pro Thr Val
    1205                1210                1215

Ser Asp  Phe Val Gln Ile Glu  Ser Cys Val Val Thr  Tyr Val Asn
    1220                1225                1230

Leu Thr  Arg Asp Gln Leu Pro  Asp Val Ile Pro Asp  Tyr Ile Asp
    1235                1240                1245

Val Asn  Lys Thr Leu Asp Glu  Ile Leu Ala Ser Leu  Pro Asn Arg
    1250                1255                1260

Thr Gly  Pro Ser Leu Pro Leu  Asp Val Phe Asn Ala  Thr Tyr Leu
    1265                1270                1275

Asn Leu  Thr Gly Glu Ile Ala  Asp Leu Glu Gln Arg  Ser Glu Ser
    1280                1285                1290

Leu Arg  Asn Thr Thr Glu Glu  Leu Gln Ser Leu Ile  Tyr Asn Ile
    1295                1300                1305

Asn Asn  Thr Leu Val Asp Leu  Glu Trp Leu Asn Arg  Val Glu Thr
    1310                1315                1320

Tyr Ile  Lys Trp Lys Ser Ser  Ile Ala Ser Phe Phe  Phe Ile Ile
    1325                1330                1335

Gly Leu  Ile Ile Gly Leu Phe  Leu Val Leu Arg Val  Gly Ile His
    1340                1345                1350

Leu Cys  Ile Lys Leu Lys His  Thr Lys Lys Arg Gln  Ile Tyr Thr
    1355                1360                1365

Asp Ile  Glu Met Asn Arg Leu  Gly Lys
    1370                1375
```

<210> SEQ ID NO 10
<211> LENGTH: 28039
<212> TYPE: DNA
<213> ORGANISM: Porcine epidemic diarrhea virus

<400> SEQUENCE: 10

```
acttaaaaag attttctatc tacggatagt tagctctttt tctagactct tgtctactca     60

attcaactaa acgaaatttt gtccttccgg ccgcatgtcc atgctgctgg aagctgacgt    120

ggaatttcat taggtttgct taagtagcca tcgcaagtgc tgtgctgtcc tctagttcct    180

ggttggcgtt ccgtcgcctt ctacatacta gacaaacagc cttcctccgg ttccgtctgg    240

gggttgcgtg gataactagt tccgtctagt ttgaaaccag taactgtcgg ctatggctag    300

caaccaagtc acattggctt ttgccaatga tgcagaaatt tcagcttttg gcttttgcac    360
```

```
tgctagtgaa gccgtctcat actattctga ggccgccgct agtggattta tgcaatgccg    420
tttcgtgtcc ttcgatctcg ctgacactgt tgagggattg cttcccgaag actatgtcat    480
ggtggtggtc ggcactacca agcttagtgc gtatgtggac acttttggta gccgccccag    540
aaacatttgt ggttggctgt tattttctaa ctgtaattac ttcctcgaag agttagagct    600
cacttttggt cgtcgtggtg gtaacatcgt gccagttgac caatacatgt gtggcgctga    660
cgggaaacct gttcttcagg aatccgagtg ggagtataca gactttttg ctgactccga    720
agacggtcaa ctcaacattg ctgggatcac ttatgtgaag gcctggattg tagagcgatc    780
ggacgtctct tatgcgagtc agaatttaac atctattaag tctattactt actgttcaac    840
ctatgagcat acttttcctg atggtactgc catgaaggtt gcacgtactc caaagattaa    900
gaagactgtt gtcttgtctg agccacttgc tactatctac agggaaattg gttctccttt    960
tgtggataat gggagcgatg ctcgttctat cattaagaga ccagtgttcc tccacgcttt   1020
tgttaagtgt aagtgtggta gttatcattg gactgttggt gattggactt cctatgtctc   1080
cacttgctgt ggctttaagt gtaagccagt ccttgtggct tcatgctctg ctacgcctgg   1140
ttctgttgtg gttacgcgcg ctggtgctgg cactggtgtt aagtattaca acaacatgtt   1200
cctgcgccat gtggcagaca ttgatgggtt ggcattctgg cgaattctta aggtgcagtc   1260
caaagacgac ctcgcttgct ctggtaaatt ccttgaacac catgaggaag gtttcacaga   1320
tccttgctac tttttgaatg actcgagcat tgctactaag ctcaagtttg acatccttag   1380
tggcaagttt tctgatgaag tcaaacaagc tatctttgct ggtcatgttg ttgttggcag   1440
tgcgctcgtt gacattgttg acgatgcact gggacagcct tggtttatac gtaagcttgg   1500
tgaccttgca agtgcagctt gggagcagct taaggctgtc gttagaggcc ttaacctcct   1560
gtctgatgag gtcgtgctct ttggcaaaag acttagctgt gccactctta gtatcgttaa   1620
cggtgttttt gagtttatcg ccgaagtgcc agagaagttg gctgcggctg ttacagtttt   1680
tgtcaacttc ttgaatgagc tttttgagtc tgcctgtgac tgcttaaagg tcggaggtaa   1740
aacctttaac aaggttggct cctatgtcct ttttgacaac gcattggtta agcttgtcaa   1800
ggcaaaagtt cgcggcccac gacaggcagg tgtttgtgaa gttcgttaca caagccttgt   1860
tattgggagt actaccaagg tggtttccaa gcgcgttgaa aatgccaatg tgaatctcgt   1920
cgtcgttgac gaggatgtga ccctcaacac cactggtcat acagttgttg ttgacggact   1980
tgcattcttc gagagtgacg ggttttacag acatcttgct gatgctgacg ttgtcattga   2040
acatcctgtt tataagtctg cttgtgagct caagccagtt tttgagtgtg atccaatacc   2100
tggttttcct atgcctgtgg ccgctagtgt tgcagagctt tgtgtgcaaa ctgatctgtt   2160
gcttaaaaat tacaacactc cttataaaac ttacagctgc gttgtgagag gtgataagtg   2220
ttgcatcact tgcaccttac atatcacagc accaagttat atggaggatg ctgctaattt   2280
tgtagacctc tgtaccaaga acattggtac tgctggtttt catgagtttt acattacggc   2340
ccatgaacaa caggatctgc aagggttcgt aaccacttgt tgcacgatgt caggttttga   2400
gtgttttatg cctataatcc cacagtgtcc agcagtgctt gaagagattg atggtggtag   2460
catctggcgg tcttttatca ctggtcttaa tacaatgtgg gatttttgca agcatcttaa   2520
agtcagcttt ggactagatg gcattgttgt cactgtagca cgcaaattta aacgacttgg   2580
tgctctcttg gcagaaatgt ataacactta cctttcaact gtggtggaaa acttggtact   2640
ggccggtgtt agcttcaagt attatgccac cagtgtccca aaaattgttt tgggctgttg   2700
ttttcacagt gttaaaagtg ttcttgcaag tgccttccag attcctgtcc aggcaggcat   2760
```

-continued tgagaagttt aaagtcttcc ttaactgtgt tcaccctgtt gtaccacgcg tcattgaaac 2820
ttcttttgtg gaattagaag agacgacatt taaaccacca gcactcaatg gtagtattgc 2880
tattgttgat ggctttgctt tctattatga tggaacacta tactatccca ccgatggtaa 2940
tagtgttgtg cctatttgtt ttaagaagaa gggtggtggt gatgtcaaat tctctgatga 3000
agtctctgtt agaaccattg acccagttta taaggtctcc cttgaatttg agttcgagtc 3060
tgagactatt atggctgtgc ttaataaggc tgttggtaat cgtatcaagg ttacaggtgg 3120
ttgggacgat gttgttgagt atatcaacgt tgccattgag gttcttaaag atcatatcga 3180
tgtgcctaag tactacatct atgatgagga aggtggcacc gatcctaatc ttcccgtaat 3240
ggtttctcag tggccgttga atgatgacac gatctcacag gatctgcttg atgtggaagt 3300
tgttactgat gcaccaattg atttcgaggg tgatgaagta gactcctctg accctgataa 3360
ggtggcagat gtggctaact ctgagcctga ggatgatggt cctaatgtag ctcctgaaac 3420
aaatgtagag tctgaagttg aggaagttgc cgcaaccttg tcttttatta aagatacacc 3480
ttccacagtt actaaggatc cttttgcttt tgactttgca agctatggag gacttaaggt 3540
tttaagacaa tctcataaca actgctgggt tacttctacc ttggtgcagc tacaattgct 3600
tggcatcgtt gatgaccctg caatggagct tttagtgct ggtagagttg gtccaatggt 3660
tcgcaaatgc tatgagtcac aaaaggctat cttgggatct ttgggtgatg tgtcggcttg 3720
cctagagtct ctgactaagg acctacacac acttaagatt acctgttctg tagtctgtgg 3780
ttgtggtact ggtgaacgta tctatgaggg ttgtgctttt cgtatgacgc caactttgga 3840
accgttccca tatggtgctt gtgctcagtg tgctcaagtt ttgatgcaca cttttaaaag 3900
tattgttggc accggcatct tttgtcgaga tactactgct ctctccttgg attctttggt 3960
tgtaaaacct ctttgtgcgg ctgcttttat aggcaaggat agtggtcatt atgtcactaa 4020
cttttatgat gctgctatgg ctattgatgg ttatggtcgt catcagataa agtatgacac 4080
actgaacact atttgtgtta aagacgttaa ttggacagca ccttttgtcc cagacgttga 4140
gcctgtattg gagcctgttg tcaaaccttt ctattcttat aagaatgttg atttttacca 4200
aggagatttt agtgaccttg ttaaacttcc atgtgatttt gttgttaatg ctgcaaatga 4260
gaatttgtct cacggtggcg gcatagcaaa ggccattgat gtttatacca agggcatgtt 4320
gcagaagtgc tcgaatgatt acattaaagc acacggtccc attaaagttg gacgtggtgt 4380
catgttggag gcattaggtc ttaaggtctt taatgttgtt ggtccacgta agggtaagca 4440
tgcacctgag cttcttgtta aggcttataa gtccgttttt gctaattcag gtgttgctct 4500
tacacctttg attagtgttg gaatttttag tgttcctttg gaagaatctt tatctgcttt 4560
tcttgcatgt gttggtgatc gccactgtaa gtgcttttgt tatagtgaca aagagcgcga 4620
ggcgatcatt aattacatgg atggcttggt agatgctatt ttcaaagatg cgcttgttga 4680
tactactcct gtccaggaag atgttcaaca agtttcacaa aaaccagttt tgcctaattt 4740
tgaacctttc aggattgaag gtgctcatgc tttctatgag tgcaaccctg aaggtttgat 4800
gtcattaggt gctgacaagc tggtgttgtt tacaaattcc aatttggatt tttgtagcgt 4860
tggtaagtgt cttaacaatg tgaccggcgg tgcattgctt gaagccataa atgtatttaa 4920
aaagagtaac aaaacagtgc ctgctggcaa ctgtgttact tttgagtgtg cagacatgat 4980
ttctattact atggtagtat tgccatctga tggtgatgct aattatgaca aaaattatgc 5040
acgcgccgtc gtcaaggtat ctaagcttaa aggcaagtta ttgcttgctg ttggtgatgc 5100

-continued

```
cacgttgtat tccaagttgt cccacctcag cgtggtaggt ttcgtatcca cacctgatga   5160
tgtggagcgt ttctacgcaa ataagagtgt ggttattaaa gtcactgagg atacacgtag   5220
tgttaaggct gttaaagtag aatccactgt tacttatgga caacaaattg gaccttgtct   5280
tgttaatgac accgttgtca cagacaacaa acctgttgtt gctgatgttg tagctaaggt   5340
tgtaccaagt gctaattggg attcacatta tggttttgat aaggctggtg agttccacat   5400
gctagaccat actgggtttg cctttcctag tgaagttgtt aacggtaggc gtgtgcttaa   5460
aaccacagat aataactgtt gggttaatgt tacatgttta caattacagt ttgctagatt   5520
taggttcaag tcagcaggtc tacaggctat gtgggagtcc tattgtactg gtgatgttgc   5580
tatgtttgtg cattggttgt actggcttac tggtgttgac aaaggtcagc ctagtgattc   5640
agaaaatgca cttaacatgt tgtccaagta cattgtttct gctggttctg tcactattga   5700
acgtgtcacg catgacggct gttgttgtag taagcgtgtt gtcactgcac cagttgtgaa   5760
tgctagcgta ttgaagcttg gcgtcgagga tggtctttgt ccacatggtc ttaactacat   5820
tgacaaagtt gttgtagtca aaggtactac aattgttgtc aatgttggaa aacctgtagt   5880
ggcaccatca cacctctttc ttaagggtgt ttcttacaca acattcctag ataatggtaa   5940
cggtgttgtc ggccattata ctgtttttga tcatgacact ggtatggtgc atgatggaga   6000
tgcttttgta ccgggtgatc tcaatgtatc tcctgttaca aatgttgtcg tctcagagca   6060
gacggctgtt gtgattaaag accctgtgaa gaaagtagag ttagacgcta caaagctgtt   6120
agacactatg aattatgcat cggaaagatt cttttccttt ggtgatttta tgtcacgtaa   6180
tttaattaca gtgtttttgt acatccttag tattttgggt ctctgtttta gggcctttcg   6240
taagagggat gttaaagttc tagctggtgt accccaacgt actggtatta tattgcgtaa   6300
aagtgtgcgc tataatgcaa aggctttggg tgtcttcttc aagctaaaac tttattggtt   6360
caaagttctt ggtaagttta gtttgggtat ttatgcattg tatgcattac tattcatgac   6420
aatacgcttt acacctatag gtggccctgt ttgtgatgat gttgttgctg gttatgctaa   6480
ttctagtttt gacaagaatg agtattgcaa cagtgttatt tgtaaggtct gtctctatgg   6540
gtaccaggaa ctttcggact tctctcacac acaggtagta tggcaacacc ttagagaccc   6600
attaattggt aatgtgatgc ctttctttta tttggcattt ctggcaattt ttggggggtgt  6660
ttatgtaaag gctattactc tctattttat tttccagtat cttaacattc ttggtgtgtt   6720
tttgggccta caacagtcca tttggttttt gcagcttgtg ccttttgatg tctttggtga   6780
cgagatcgtc gtctttttca tcgttacacg cgtattgatg ttccttaagc atgttttcct   6840
tggctgcgat aaggcatctt gtgtggcttg ctctaagagt gctcgcctta agcgcgttcc   6900
tgtccagact atttttcagg gtactagcaa atccttctac gtacatgcca atggtggttc   6960
taagttctgt aagaagcaca atttcttttg tttaaattgt gattcttatg gtccaggctg   7020
cacttttatt aatgacgtca ttgcaactga agttggtaat gttgtcaaac ttaatgtgca   7080
accgacaggt cctgccacta ttcttattga caaggttgaa ttcagtaatg gtttttacta   7140
tctttatagt ggtgacacat tttggaagta caactttgac ataacagata acaaatacac   7200
ttgcaaagag tcacttaaaa attgtagcat aatcacagac tttattgttt ttaacaataa   7260
tggttccaat gtaaatcagg ttaagaatgc atgtgtgtat tttttcacaga tgctttgtaa   7320
acctgttaag ttagtggact cagcgttgtt ggccagtttg tctgttgatt ttggtgcaag   7380
cttacatagt gcttttgtta gtgtgttgtc gaatagtttt ggcaaagacc tgtcaagttg   7440
taatgacatg caggattgca agagcacatt gggttttgat gatgtaccat tggatacctt   7500
```

taatgctgct gttgctgagg ctcatcgtta cgatgtcctc ttgactgaca tgtcgttcaa 7560
caattttacc accagttatg caaaaccaga ggaaaaactt cccgtccatg acattgccac 7620
gtgtatgcgt gtaggtgcca agattgttaa tcataacgtt cttgtcaagg atagtatacc 7680
tgtggtgtgg cttgtacgtg atttcattgc cctttcggaa gaaactagga agtacattat 7740
tcgtacgact aaagttaagg gtataacctt catgttgacc tttaatgatt gtcgtatgca 7800
tactaccata cctactgttt gcattgcaaa taagaagggt gcaggtcttc ctagtttttc 7860
aaaggttaag aaattcttct ggtttttgtg tctgttcata gttgctgttt tctttgcact 7920
aagctttctt gattttagta ctcaggttag cagtgatagc gattatgact tcaagtatat 7980
tgagagtggc cagttgaaga cttttgacaa tccacttagt tgtgtgcata atgtctttag 8040
taacttcgac cagtggcatg atgccaagtt tggtttcacc cccgtcaaca atcctagttg 8100
tcctatagtc gttggtgtgt cagacgaagc gcgcactgtt ccaggtatcc cagcaggtgt 8160
ttatttagct ggtaaaacac ttgtttttgc tattaacacc atttttggta catctggttt 8220
gtgctttgat gctagtggcg ttgctgataa gggcgcttgc atttttaatt cggcttgcac 8280
cacattatct ggtttgggtg gaactgctgt ctactgttat aagaatggtc tagttgaagg 8340
tgctaaactt tatagtgagt tggcacctca tagctactat aaaatggtag atggtaatgc 8400
tgtgtcttta cctgaaatta tctcacgcgg ctttggcatc cgtactatcc gtacaaaggc 8460
tatgacctac tgtcgcgttg gccagtgtgt gcaatctgca gaaggtgttt gttttggcgc 8520
cgatagattc tttgtctata atgcagaatc tggttctgac tttgtttgtg gcacagggct 8580
ctttacattg ttgatgaacg ttattagtgt tttttccaag acagtaccag taactgtgtt 8640
gtctggtcaa atacttttta attgcattat tgcttttgct gctgttgcgg tgtgtttctt 8700
atttacaaag tttaagcgca tgttcggtga tatgtctgtt ggcgttttca ctgtcggtgc 8760
ttgtactttg ttgaacaatg tttcctacat tgtaacacag aacacacttg gcatgttggg 8820
ctatgcaact ttgtactttt tgtgcactaa aggtgttaga tatatgtgga tttggcattt 8880
gggatttttg atctcatata tacttattgc accatggtgg gttttgatgg tttatgcctt 8940
ttcagccatt tttgagttta tgcctaacct ttttaagctt aaggtttcaa cacaactttt 9000
tgagggtgac aagttcgtag gctcttttga aaatgctgca gcaggtacat ttgtgcttga 9060
tatgcatgcc tatgagagac ttgccaactc tatctcaact gaaaaactgc gtcagtatgc 9120
tagtacttac aataagtaca agtattattc aggcagtgct tcagaggctg attacaggct 9180
tgcttgtttt gcccatttgg ccaaggctat gatggattat gcttctaatc acaacgacac 9240
gttatacaca ccacccactg tgagttacaa ttcaactcta caggctggct tgcgtaagat 9300
ggcacaacca tctggtgttg ttgagaagtg catagttcgt gtttgctatg gtaatatggc 9360
tcttaatggc ctatggcttg gtgatactgt tatctgccca cgccatgtta tagcgtctag 9420
tactactagc actatagatt atgactatgc cctttctgtt ttacgcctcc acaacttctc 9480
catttcatct ggtaatgttt tcctaggtgt tgtgggtgta accatgcgag gtgctttgtt 9540
gcagataaag gttaatcaaa acaatgtcca cacgcctaag tacacctatc gcacagttag 9600
accgggtgaa tcttttaata tcttggcgtg ctatgatggt tctgcagctg gtgtttacgg 9660
cgttaacatg cgctctaatt acactattag aggctcgttc attaatggcg cttgtggttc 9720
acctggttat aacattaaca atggtaccgt tgagttttgc tatttacacc agcttgaact 9780
tggttcaggc tgtcatgttg gtagcgactt agatggtgtt atgtatggtg gttatgagga 9840

-continued

```
ccaacctact ttgcaagttg aaggcgctag tagtctgttt acagagaatg tgttggcatt   9900
tctttatgca gcactcatta atggttctac ctggtggctt agttcttcta ggattgctgt   9960
agacaggttt aatgagtggg ctgttcataa tggtatgaca acagtagtta atactgattg  10020
cttttctatt cttgctgcta agactggtgt tgatgtacaa cgtttgttgg cctcaatcca  10080
gtctctgcat aagaatttgg gtggaaagca aattcttggc tatacctcgt tgacagatga  10140
gtttactaca ggtgaagtta tacgtcaaat gtatggcgtt aatcttcaga gtggttatgt  10200
ttcacgcgcc tgtagaaatg tcttgctggt tggttctttt ctgactttct tttggtcaga  10260
attagtttcc tacactaagt tcttttgggt aaatcctggt tatgtcacac ctatgtttgc  10320
gtgtttgtca ttgctgtcct cacttttgat gttcacactc aagcataaga cattgttttt  10380
ccaggtcttt ctaatacctg ctctgattgt tacatcttgc attaatttgg catttgatgt  10440
tgaagtctac aactatttgg cagagcattt tgattaccat gtttctctca tgggttttaa  10500
tgcacaaggt cttgttaaca tctttgtctg ctttgttgtt accattttac acggcacata  10560
cacatggcgc ttttttaaca cacctgtgag ttctgtcact tatgtggtag ctttgctgac  10620
tgcggcatat aactattttt acgctagtga cattcttagt tgtgctatga cactatttgc  10680
tagtgtgact ggcaactggt tcgttggtgc tgtttgttat aaagctgctg tttatatggc  10740
cttgagattt cctacttttg tggctatttt tggtgatatt aagagtgtta tgttctgtta  10800
ccttgtgttg ggttatttta cctgttgctt ctacggtatt ctctactggt tcaacaggtt  10860
ttttaaggtt agtgtaggtg tctatgacta tactgttagt gctgctgagt ttaagtatat  10920
ggttgctaac ggcctacgtg caccaactgg aacacttgat tcactacttc tgtctgccaa  10980
attgattggt attggtggtg agcggaatat taagatttct tccgttcagt ctaaactgac  11040
tgatattaag tgtagtaacg ttgtgctttt aggctgtctc tctagcatga atgtctcagc  11100
aaattcaaca gaatgggcct attgtgttga cttgcataac aagatcaact tgtgtaatga  11160
cccagaaaaa gcgcaggaaa tgctacttgc tttgttggca tttttcctta gtaagaatag  11220
tgcttttggt ttagatgact tattggaatc ctattttaat gacaatagta tgttgcagag  11280
tgttgcatct acttatgtcg gtttgccttc ttatgtcatt tatgaaaatg cacgccaaca  11340
gtatgaagat gctgttaata atggttctcc acctcagttg gttaagcaat tgcgccatgc  11400
catgaatgta gcaaagagcg aatttgaccg tgaggcttct actcagcgta agcttgatag  11460
aatggcggaa caggctgcag cacagatgta caaagaggca agagcagtta ataggaagtc  11520
caaagttgta agtgctatgc attcactgct tttggtatg ttgagacgtt tggacatgtc  11580
ttctgtagac accattctca acttggcaaa ggatggggtt gtacctctgt ctgtcatacc  11640
ggcagtcagt gctactaagc ttaacattgt tacttctgat atcgattctt ataatcgtat  11700
ccagcgtgag ggatgtgtcc actacgctgg taccatttgg aatataattg atatcaagga  11760
caatgatggc aaggtggtac acgttaagga ggtaaccgca cagaatgctg agtccctgtc  11820
atggcccctg gtccttgggt gtgagcgtat tgtcaagctc cagaataatg aaattattcc  11880
tggtaagctg aagcagcgct ccattaaggc agaaggagat ggcatagttg gagaaggtaa  11940
ggcactttac aataatgagg gtggacgtac ttttatgtat gctttcatct cggacaaacc  12000
ggacctgcgt gtagtcaagt gggagttcga tggtggttgt aacactattg agctagaacc  12060
accacgtaag ttcttggtgg attctcctaa tggtgcacag atcaagtatc tctactttgt  12120
tcgtaacctt aacacgttac gtaggggtgc tgttctcggc tacataggtg ccactgtacg  12180
cttgcaggct ggtaaacaaa cagaacaggc tattaactct tcattgttga cactttgcgc  12240
```

```
tttcgctgtg gatcctgcta agacctacat cgatgctgtc aaaagtggtc acaaaccagt  12300
aggtaactgt gttaagatgt tggccaatgg ttctggtaat ggacaagctg ttactaatgg  12360
tgtggaggct agtactaacc aggattcata cggtggtgcg tccgtgtgtc tatattgtag  12420
agcacatgtt gagcatccat ctatggatgg tttttgcaga ctgaaaggca agtacgtaca  12480
ggttccacta ggtacagtgg atcctatacg ttttgtactt gagaatgacg tttgcaaggt  12540
ttgtggttgt tggctggcta atggctgcac ttgtgacaga tccattatgc aaagcactga  12600
tatggcttat ttaaacgagt acggggctct agtgcagctc gactagagcc ctgtaacggt  12660
actgatacac aacatgtgta tcgtgctttt gacatctaca acaaggatgt tgcttgtcta  12720
ggtaaattcc tcaaggtgaa ctgtgttcgc ctgaagaatt tggataagca tgatgcattc  12780
tatgttgtca aaagatgtac caagtctgcg atggaacacg agcaatccat ctatagcaga  12840
cttgaaaagt gtggagccgt agccgaacac gatttcttca cttggaagga tggtcgtgcc  12900
atctatggta acgtttgtag aaaggatctt accgagtata ctatgatgga tttgtgttac  12960
gctttacgta actttgatga aaacaattgc gatgttctta agagcatttt aattaaggta  13020
ggcgcttgtg aggagtccta cttcaataat aaagtctggt ttgaccctgt tgaaaatgaa  13080
gacattcatc gtgtctatgc attgttaggt accattgttt cacgtgctat gcttaaatgc  13140
gttaagttct gtgatgcaat ggttgaacaa ggtatagttg gtgttgtcac tttagataat  13200
caggatctta atggtgattt ttatgatttt ggtgatttta cttgtagcat caagggaatg  13260
ggtataccca tttgcacatc atattactct tatatgatgc ctgttatggg tatgactaat  13320
tgccttgcta gtgagtgttt tgttaagagt gatatatttg gtgaggattt caagtcatat  13380
gacctgctgg aatatgattt cacggagcat aagacagcac tcttcaacaa gtatttcaag  13440
tattggggac tgcaatacca ccctaactgt gtggactgca gtgatgagca gtgcatagtt  13500
cactgtgcca acttcaatac gttgttttcc actactatac ctattacggc atttggacct  13560
ttgtgtcgca agtgttggat tgatggtgtt ccactggtaa ctacagctgg ttatcatttt  13620
aaacagttag gtatagtttg gaacaatgac ctcaacttac actctagcag gctctctatt  13680
aacgaattac tccagttttg tagtgatcct gcattgctta tagcatcatc accagccctt  13740
gttgatcagc gtactgtttg cttttcagtt gcagcgctag gtacaggtat gactaaccag  13800
actgttaaac ctggccattt caataaggag ttttatgact tcttacttga gcaaggtttc  13860
ttttctgagg gctctgagct tactttaaag cacttcttct ttgcacagaa gggtgatgca  13920
gctgttaagg attttgacta ctataggtat aatagaccta ctgttctgga catttgccaa  13980
gctcgcgtcg tgtatcaaat agtgcaacgc tattttgata tttacgaagg tggttgtatc  14040
actgctaaag aggtggttgt tacaaacctt aacaagagcg caggttatcc tttgaacaag  14100
tttggtaaag ctggtcttta ctatgagtct ttatcctatg aggaacagga tgaactttat  14160
gcttatacta agcgtaacat cctgcccact atgacacagc tcaaccttaa atatgctata  14220
agtggcaaag aacgtgcacg cacagtgggt ggtgtttcgc ttttgtcaac catgactact  14280
cggcagtatc atcagaaaca ccttaagtcc atagttaata ctaggggcgc ttcggttgtt  14340
attggtacta ctaagtttta tggtggttgg gacaatatgc ttaagaacct tattgatggt  14400
gttgaaaatc cgtgtcttat gggttgggac tacccaaagt gcgacagagc actgcccaat  14460
atgatacgta tgatttcagc catgatttta ggctctaagc acaccacatg ctgcagttcc  14520
actgaccgct tttcaggtt gtgcaatgaa ttggctcaag tccttactga ggttgtttat  14580
```

-continued

```
tctaatggag gtttttattt gaagccaggt ggtactacct ctggtgatgc aaccaccgca  14640
tatgcaaact cagtttttaa tatcttccaa gcagtaagtg ccaatgttaa caaacttctt  14700
agtgttgaca gcaatgtctg tcataattta gaagttaagc aattgcagcg taagctttat  14760
gagtgctgtt atagatcaac taccgtcgat gaccagttcg tcgttgagta ttatggttac  14820
ttgcgtaaac atttttcaat gatgattctt tctgatgatg gcgttgtttg ttataacaat  14880
gactatgcat cacttggtta tgtcgctgat cttaacgcat tcaaggctgt tttgtattac  14940
cagaacaatg tcttcatgag cgcctctaaa tgttggatcg agcctgacat taataaaggt  15000
cctcatgaat tttgctcgca gcatactata cagattgtcg ataaagatgg tacttattac  15060
cttccttacc ctgatccttc aagaatcctc tctgcaggtg tgtttgttga tgacgttgtt  15120
aaaactgatg cacttgtatt gcttgaacgt tatgtgtcat tggctataga tgcctacccg  15180
ttatctaagc atgaaaaccc tgaatataag aaggtgtttt atgtgctttt ggattgggtt  15240
aagcatctgt acaaaactct taatgctggt gtgttagagt ctttttctgt cacacttttg  15300
gaagattcta ctgctaaatt ctgggatgag agcttttatg ccaacatgta tgagaaatct  15360
gcagttttac aatctgcagg gctttgtgtt gtttgtggct ctcaaactgt tttacgttgt  15420
ggtgattgtc tacggcgtcc tatgctttgt actaagtgtg cttatgatca tgtcattgga  15480
acaactcaca agttcatttt ggccatcact ccatatgtgt gttgtgcttc agattgtggt  15540
gtcaatgatg taactaagct ctacttaggt ggtcttagtt attggtgtca tgaccacaag  15600
ccacgtcttg cattcccgtt gtgctctgct ggtaatgttt ttggcttgta caaaaattct  15660
gctaccggct cacccgatgt tgaagacttt aatcgcattg ctacatccga ttggactgat  15720
gtttctgact acaggttggc aaatgatgtc aaggactcat tgcgtctgtt tgcagcggaa  15780
actatcaagg ccaaggagga gagcgttaag tcatcctatg cttgtgcaac actacatgat  15840
gttgtaggac ctaaagagtt gttgctcaaa tgggaagtcg gcagacccaa accacccctt  15900
aatagaaatt cggttttcac ttgttatcat ataacgaaga acaccaaatt tcaaatcggt  15960
gagtttgtgt ttgagaaggc agaatatgat aatgatgctg taacatataa aactaccgcc  16020
acaacaaaac ttgttcctgg catggttttt gtgcttacct cacataatgt tcagccattg  16080
cgcgcaccga ccattgctaa tcaagaacgt tattccacta tacataagtt gcatcctgct  16140
tttaacatac ctgaagctta ttctagctta gtgccctatt accaattgat tggtaagcag  16200
aagattacaa ctattcaggg acctcccggt agtggtaaat ctcactgtgt tatagggcta  16260
ggtttgtact atccaggtgc acgtatagtg tttacagctt gttctcatgc agcggtcgat  16320
tcactttgtg tgaaagcctc cactgcttat agcaatgaca aatgttcacg catcatacca  16380
cagcgcgctc gtgttgagtg ttatgatggt ttcaagtcta ataatactag tgctcagtac  16440
cttttctcta ctgtcaatgc tttgccagag tgcaatgcgg acattgttgt ggtggatgag  16500
gtctctatgt gcactaatta tgacttgtct gtcataaatc agcgcatcag ctataggcat  16560
gtagtctatg ttggtgaccc tcaacagctg cctgcaccac gtgttatgat ttcacgtggt  16620
actttggaac caaaggacta caacgttgtc actcaacgca tgtgtgccct taagcctgat  16680
gttttcttgc acaagtgtta tcgctgtcct gctgagatag tgcgtactgt gtctgagatg  16740
gtctatgaaa accaattcat tcctgtgcac ccagatagca agcagtgttt taaaatcttt  16800
tgcaagggta atgttcaggt tgataatggt tcaagcatta atcgcaggca attggatgtt  16860
gtgcgtatgt ttttggctaa aaatcctagg tggtcaaagg ctgtttttat ttctccttat  16920
aacagccaga attatgttgc cagccgcatg ctaggtctac aaattcagac agttgactca  16980
```

tcccagggta gtgagtatga ctatgtcatt tacacacaaa cttcagatac tgcccatgcc 17040
tgtaatgtta acaggtttaa tgttgccatc acaagggcca agaaaggcat attatgtata 17100
atgtgcgata ggtccctttt tgatgtgctt aaattctttg agcttaaatt gtctgatttg 17160
caggctaatg agggttgtgg tctttttaaa gactgtagca gaggtgatga tctgttgcca 17220
ccatctcacg ctaacacctt catgtcttta gcggacaatt ttaagactga tcaagatctt 17280
gctgttcaaa taggtgttaa tggacccatt aaatatgagc atgttatctc gtttatgggt 17340
ttccgttttg atatcaacat acccaaccat catactctct tttgcacacg cgactttgcc 17400
atgcgcaatg ttagaggttg gttaggcttt gacgttgaag gagcacatgt tgttggctct 17460
aacgtcggta caaatgtccc attgcaatta gggttttcta acggtgttga ttttgttgtc 17520
agacctgaag gttgcgttgt aacagagtct ggtgactaca ttaaacccgt cagagctcgt 17580
gctccaccag gggaacaatt cgcacacctt ttgcctttac ttaaacgcgg ccaaccatgg 17640
gatgttgtcc gcaaacgtat agtgcagatg tgtagtgact acctggccaa cctatcagac 17700
atactaattt ttgtgttgtg ggctggtggt ttggagttga caactatgcg ttattttgtc 17760
aagattggac caagtaagag ttgtgattgt ggtaaggttg ctacttgtta caatagtgcg 17820
ctgcatacgt actgttgttt caaacatgcc cttggttgtg attatctgta taacccatac 17880
tgtattgata tacagcagtg gggatacaag ggatcactta gccttaacca ccatgagcat 17940
tgtaatgtac atagaaacga gcatgtggct tctggtgatg ccataatgac tcgctgtctg 18000
gccatacatg attgctttgt caagaacgtt gactggtcca tcacataccc atttattggt 18060
aatgaggctg ttattaataa gagcggccga attgtgcaat cacacactat gcggtcagtt 18120
cttaagttat acaatccgaa agccatatat gatattggca atcctaaggg cattagatgt 18180
gccgtaacgg atgctaagtg gttttgcttt gacaagaatc ctactaattc taatgtcaag 18240
acattggagt atgactatat aacacatggc caatttgatg ggttgtgctt gttttggaat 18300
tgcaatgtag acatgtatcc agaattttct gtggtctgtc gttttgatac tcgctgtagg 18360
tcaccactca acttggaggg ttgtaatggt ggttcactgt atgttaataa tcatgcattc 18420
catacaccgg cttttgacaa gcgtgctttt gctaagttga agccaatgcc atttttcttt 18480
tatgatgata ctgagtgtga caagttacag gactccataa actatgttcc tcttagggct 18540
agtaactgca ttactaaatg taatgttggt ggtgctgtct gtagtaagca ttgtgctatg 18600
tatcatagct atgttaatgc ttacaacact tttacgtcgg cgggctttac tatttgggtg 18660
cctacttcgt ttgacaccta taatctgtgg cagacattta gtaacaattt gcaaggtctt 18720
gagaacattg ctttcaatgt cgtaaagaaa ggatcttttg ttggtgccga aggtgaactt 18780
cctgtagctg tggttaatga caaagtgctc gttagagatg gtactgttga tactcttgtt 18840
tttacaaaca agacatcact acccactaac gtagcttttg agttgtatgc caagcgtaag 18900
gtaggactca ccccacccat tacgatccta cgtaacttgg gtgtagtttg tacatctaag 18960
tgtgtcattt gggactatga agccgaacgt ccacttacta cttttacaaa ggatgtttgt 19020
aaatataccg actttgaggg tgacgtctgt acactctttg ataacagcat tgttggttca 19080
ttagagcgat tctccatgac ccaaaatgct gtgcttatgt cacttacagc tgttaaaaag 19140
cttactggca taaagttaac ttatggttat cttaatggtg tcccagttaa cacacatgaa 19200
gataaacctt ttacttggta tatttacact aggaagaacg gcaagttcga ggaccatcct 19260
gatggctatt ttacccaagg tagaacaacc gctgatttta gccctcgtag cgacatggaa 19320

-continued aaggacttcc taagtatgga tatgggtctg tttattaaca agtacggact tgaagattac 19380
ggctttgagc acgttgtgta tggtgatgtt tcaaaaacca cccttggtgg tttgcatcta 19440
ctaatttcgc aggtgcgtct ggcctgtatg ggtgtgctca aaatagacga gtttgtgtct 19500
agtaatgata gcacgttaaa gtcttgtact gttacatatg ctgataaccc tagtagtaag 19560
atggtttgta cgtatatgga tctcctgctt gacgattttg tcagcattct taaatctttg 19620
gatttgggcg ttgtatctaa agttcatgaa gttatggtcg attgtaaaat gtggaggtgg 19680
atgttgtggt gtaaggatca taaactccag acattttatc cgcaacttca ggccagtgaa 19740
tggaagtgtg gttattccat gccttctatt tacaagatac aacgtatgtg tttagaacct 19800
tgcaatctct acaactatgg tgctggtatt aagttacctg atggcattat gtttaacgta 19860
gttaaataca cacagctttg tcaatatctc aatagcacca caatgtgtgt accccatcac 19920
atgcgtgtgc tacatcttgg tgctggctcc gacaagggtg ttgcacctgg cacggctgtc 19980
ttacgacgtt ggttgccact ggatgccatt atagttgaca atgatagtgt ggattacgtt 20040
agcgatgctg attatagtgt tacaggagat tgctctacct tatacctgtc agataagttt 20100
gatttagtta tatctgatat gtatgatggt aagattaaaa gttgtgatgg ggagaacgtg 20160
tctaaagaag gcttctttcc ctatattaat ggtgtcatca ccgacaaagt tggcacttgg 20220
tggtactgta gctattaagg tgacggagct tagttggaat aagaagttgt atgaactcat 20280
tcagaagttt gagtattgga caatgttctg taccagtgtt aacacgtcat cgtcagaggc 20340
attcttaatt ggtgttcact atttaggtga ttttgcaagt ggcgctgtga ttgacggcaa 20400
cactatgcat gccaattata tcttctggcg taattccaca attatgacta tgtcttacaa 20460
tagtgtactt gatttaagca agttcaattg taagcataag gctacagttg tcattaattt 20520
aaaagattca tccattagtg atgttgtgtt aggtttgttg aagaatggta agttgctagt 20580
gcgtaataat gacgccattt gtggtttttc taatcatttg gtcaacgtaa acaaatgaag 20640
tctttaacct acttctggtt gttcttacca gtactttcaa cacttagcct accacaagat 20700
gtcaccaggt gctcagctaa cactaatttt aggcggttct tttcaaaatt taatgttcag 20760
gcgcctgcag ttgttgtact gggcggttat ctacctattg gtgaaaacca gggtgtcaat 20820
tcaacttggt actgtgctgg ccaacatcca actgctagtg gcgttcatgg tatctttgtt 20880
agccatatta gaggtggtca tggctttgag attggcattt cgcaagagcc ttttgaccct 20940
agtggttacc agctttattt acataaggct actaacggta acactaatgc tactgcgcga 21000
ctgcgcattt gccagtttcc tagcattaaa acattgggcc ccactgctaa taatgatgtt 21060
acaacaggtc gtaattgcct atttaacaaa gccatcccag ctcatatgag tgaacatagt 21120
gttgtcggca taacatggga taatgatcgt gtcactgtct tttctgacaa gatctattat 21180
ttttatttta aaaatgattg gtcccgtgtt gcgacaaagt gttacaacag tggaggttgt 21240
gctatgcaat atgtttacga acccacctat tacatgctta atgttactag tgctggtgag 21300
gatggtattt cttatcaacc ctgtacagct aattgcattg gttatgctgc caatgtattt 21360
gctactgagc ccaatggcca cataccagaa ggttttagtt ttaataattg gtttcttttg 21420
tccaatgatt ccactttggt gcatggtaag gtggtttcca accaaccatt gttggtcaat 21480
tgtcttttgg ccattcctaa gatttatgga ctaggccaat tttctccttt taatcaaacg 21540
atcgatggtg tttgtaatgg agctgctgtg cagcgtgcac cagaggctct gaggtttaat 21600
attaatgaca cctctgtcat tcttgctgaa ggctcaattg tacttcatac tgctttagga 21660
acaaattttt cttttgtttg cagtaattcc tcaaatcctc acttagccac cttcgccata 21720
cctttgggtg ctacccaagt accctattat tgttttctta aagtggatac ttacaactcc 21780
actgtttata aattcttggc tgttttacct ccaaccgtca gggaaattgt catcaccaag 21840
tatggtgatg tttatgtcaa tgggtttggc tatttgcatc tcggtttgtt ggacgctgtc 21900
acaattaatt tcactggtca tggcactgac gatgacgttt caggtttctg gaccatagca 21960
tcgactaatt ttgttgatgc acttatcgaa gttcaaggaa ctgccattca gcgtattctt 22020
tattgtgatg atcctgttag ccaactcaag tgttctcagg ttgcttttga ccttgacgat 22080
ggtttctacc ctatttcttc tagaaacctc ttgagtcatg aacagccaat ttcttttgtt 22140
actttgccat catttaatga tcattctttt gttaacatta ctgtctctgc gtcctttggt 22200
ggtcatagtg gtgccaacct tattgcatct gacactacta tcaatgggtt tagttctttc 22260
tgtgttgaca ctagacaatt taccatttca ctgttttata acgttacaaa cagttatggt 22320
tatgtgtcta actcacagga cagtaattgc cctttcacct tgcaatctgt taatgattac 22380
ctgtctttta gtaaattttg tgtttccacc agccttttgg ctagtgcctg taccatagat 22440
ctttttggtt accctgattt tggtagtggt gttaagttta cgtcccttta ctttcaattc 22500
acaaagggtg agttgattac tggcacgcct aaaccacttg aaggtgtcac ggacgtttct 22560
tttatgactc tggatgtgtg taccaagtat actatctatg gctttaaagg tgagggtatc 22620
attaccctta caaattctag ctttttggca ggtgtttatt acacatctga ttctggacag 22680
ttgttagcct ttaagaatgt cactagtggt gctgtttatt ctgttacgcc atgttctttt 22740
tcagagcagg ctgcatatgt tgatgatgat atagtgggtg ttatttctag tttgtctaat 22800
tccactttta acagtactag ggagttgcct ggtttcttct accattctaa tgatggctct 22860
aattgtacag agcctgtgtt ggtgtatagt aacataggtg tttgtaaatc tggcagtatt 22920
ggctacgtcc catctcagtc tggccaagtc aagattgcac ccacggttac tgggaatatt 22980
agtattccca ccaactttag tatgagtatt aggacagaat atttacagct ttacaacacg 23040
cctgttagtg ttgattgtgc cacatatgtt tgtaatggta actctcgttg taaacaatta 23100
ctcacccagt acactgcagc atgtaagacc atagagtcag cattacaact cagcgctagg 23160
cttgagtctg ttgaagttaa ctctatgctt actatttctg aagaggctct acagttagct 23220
accatcagtt cgtttaatgg tgatggatat aattttacta atgtgctggg tgtttctgtg 23280
tatgatcctg caagtggcag ggtggtacaa aaaaggtctt ttattgaaga cctgcttttt 23340
aataaagtgg ttactaatgg ccttggtact gttgatgaag actataagcg ctgttctaat 23400
ggtcgctctg tggcagatct agtctgtgca cagtattact ctggtgtcat ggtactacct 23460
ggtgttgttg acgctgagaa gcttcacatg tatagtgcgt ctctcatcgg tggtatggtg 23520
ctaggaggtt ttacttctgc agcggcattg ccttttagct atgctgttca agctagactc 23580
aattatcttg ctctacagac ggatgttcta cagcggaacc agcaattgct tgctgagtct 23640
tttaactctg ctattggtaa tataacttca gcctttgaga gtgttaaaga ggctattagt 23700
caaacttcca agggtttgaa cactgtggct catgcgctta ctaaggttca agaggttgtt 23760
aactcgcagg gtgcagcttt gactcaactt accgtacagc tgcaacacaa cttccaagcc 23820
atttctagtt ctattgatga catttacacc cgactggaca ttctttcagc cgatgttcag 23880
gttgaccgtc tcatcaccgg cagattatca gcacttaatg cttttgttgc tcaaaccctc 23940
actaagtata ctgaggttca ggctagcagg aagctagcac agcaaaaggt taatgagtgc 24000
gttaaatcgc aatctcagcg ttatggtttt tgtggtggtg atggcgatca cattttctct 24060
ctggtacagg cagcacctca gggcctgctg tttttacata cagtacttgt accgggtgat 24120
tttgtagatg ttattgccat cgctggctta tgcgttaacg atgaaattgc cttgactcta 24180
cgtgagcctg gcttagtctt gtttacgcat gaacttcaaa atcatactgc gacggaatat 24240
tttgtttcat cgcgacgtat gtttgaacct agaaaaccta ccgttagtga ttttgttcaa 24300
attgagagtt gtgtggtcac ctatgtcaat ttgactagag accaactacc agatgtaatc 24360
ccagattaca tcgatgttaa caaaacactt gatgagattt tagcttctct gcccaataga 24420
actggtccaa gtcttccttt agatgttttt aatgccactt atctcaatct cactggtgaa 24480
attgcaaatt tagagcagcg ttcagagtct ctccgtaata ctacagagga gctccaaagt 24540
cttatacata atatcaacaa cacactagtt gaccttgagt ggctcaaccg agttgagaca 24600
tatatcaagt ggccgtggtg ggtttggttg gttattttta ttgttctcat ctttgttgtg 24660
tcattactag tgttctgctg catttccacg ggttgttgtg gatgctgcgg ctgctgctgt 24720
gcttgttttt caggttgttg taggggtcct agacttcaac cttacgaagt ttttgaaaag 24780
gtccacgtgc agtgatgttt cttggacttt ttcaatacac gattgacaca gttgtcaaag 24840
atgtctcaaa gtctgctaac ttgtctttgg atgctgtcca agagttggag ctcaatgtag 24900
ttccaattag acaagcttca aatgtgacgg gttttctttt caccagtgtt tttatctact 24960
tctttgcact gtttaaagcg tcttctttga ggcgcaatta tattatgttg gcagcgcgtt 25020
ttgctgtcat tgttctttat tgcccacttt tatattattg tggtgcattt ttagatgcaa 25080
ctattatttg ttgcacactt attggcaggc tttgtttagt ctgcttttac tcctggcgct 25140
ataaaaatgc gctctttatt atctttaata ctacgacact ttctttcctc aatggtaaag 25200
cagcttacta tgacggcaaa tccattgtga ttctagaagg tggtgactat tacatcactt 25260
ttgggaactc ttttgttgct ttcgttagta gcattgactt gtatctagct atacgtgggc 25320
ggcaagaagc cgacctacag ctgttgcgaa ctgttgagct tcttgatggc aagaagcttt 25380
atgtcttttc gcaacatcaa attgtaggca ttactaatgc tgcatttgac tcaattcaac 25440
tagacgagta tgctacaatt agtgaatgat aatggtctag tagttaatgt tatactttgg 25500
cttttcgtac tctttttcct gcttattata agcattactt tcgtccaact ggttaatctg 25560
tgcttcactt gtcaccggtt gtgtaatagc gcagtttaca cacctatagg gcgtttgtat 25620
agagtttata agtcttacat gcaaatagac cccctcccca gtactgttat tgacgtataa 25680
acgaaatatg tctaacggtt ctattcccgt tgatgaggtg attcaacacc ttagaaactg 25740
gaatttcaca tggaatatca tactgacgat actactcgta gtgcttcagt atggccatta 25800
caagtactct gcgttcttgt atggtgtcaa gatggctatt ctatggatac tttggcctct 25860
tgtgttagca ctgtcacttt ttgacgcatg ggctagcttt caggtcaatt gggtcttttt 25920
tgctttcagc atccttatgg cttgcatcac tcttatgctg tggataatgt actttgtcaa 25980
tagcattcgg ttgtggcgca ggacacattc ttggtggtct ttcaatcctg aaacagacgc 26040
gcttctcact acttctgtga tgggccgaca ggtctgcatt ccagtgcttg gagcaccaac 26100
tggtgtaacg ctaacactcc ttagtggtac attgcttgta gagggctata aggttgctac 26160
tggcgtacag gtaagtcaat tacctaattt cgtcacagtc gccaaggcca ctacaacaat 26220
tgtctacgga cgtgttggtc gttcagtcaa tgcttcatct ggcactggtt gggctttcta 26280
tgtccggtcc aaacacggcg actactcagc tgtgagtaat ccgagttcgg ttctcacaga 26340
tagtgagaaa gtgcttcatt tagtctaaac agaaacttta tggcttctgt cagttttcag 26400
gatcgtggcc gcaaacgggt gccattatcc ctctatgccc ctcttagggt tactaatgac 26460

```
aaacccettt ctaaggtact tgcaaataat gctgtaccca ctaataaagg aaataaggac  26520
cagcaaattg gatactggaa tgagcaaatt cgctggcgca tgcgccgtgg tgagcgaatt  26580
gaacaacctt ccaattggca tttctactac ctcggaacag gacctcacgc cgacctccgc  26640
tataggactc gtactgaggg tgttttctgg gttgctaaag aaggcgcaaa gactgaaccc  26700
actaacctgg gtgtcagaaa ggcgtctgaa aagcctatca ttccaaattt ctcccaacag  26760
cttcccagcg tagttgagat tgttgaacct aacacacctc ccacttcacg ttcaaattca  26820
cgtagcagga gtcgtggtaa tggcaacaac aggtccagat ctccaagtaa caacagaggc  26880
aataaccagt cccgcggtaa ttcacagaat cgtggaaata accaggatcg tggagcttct  26940
cagaacagag gaggcaataa taataacaat aacaagtctc gtaaccagtc caagaacaga  27000
aaccagtcaa atgaccgtgg tggtgtaaca tcacgcgatg atctggtggc tgctgtcaag  27060
gatgccctta aatctttggg tattggcgaa aaccctgaca agcttaagca acagcagaag  27120
cccaaacagg aaaggtctga cagcagcggc aaaaatacac ctaagaagaa caaatccaga  27180
gccacttcga aagaacgtga cctcaaagac atcccagagt ggaggagaat tcccaagggc  27240
gaaaatagcg tagcagcttg cttcggaccc aggggaggct tcaaaaattt tggagatgcg  27300
gaatttgtcg aaaaaggtgt tgatgcctca ggctatgctc agatcgccag tttagcacca  27360
aatgttgcag cattgctctt tggtggtaat gtggctgttc gtgagctagc ggactcttac  27420
gagattacat ataattataa aatgactgtg ccaaagtctg atccaaatgt agagcttctt  27480
gtttcacagg tggatgcatt taaaactggg aatgcaaaac cccagagaaa gaaggaaaag  27540
aagaacaagc gtgaaaccac gcagcagctg aatgaagagg ccatctacga tgatgtgggt  27600
gtgccatctg atgtgactca tgccaatttg gaatgggaca cagctgttga tggtggtgac  27660
acggccgttg aaattatcaa cgagatcttc gacacaggaa actaaacaat gtttgactgg  27720
cttatcctgg ctatgtccca gggtggtgcc attacactgt tattactgag tgtttttcta  27780
gtgacttggc tgctgggcta tggctttgcc ctctaactag cggtcttggt cttgcacaca  27840
acggtaagcc agtggtaatg tcagtgcaag aaggatatta ccatagcact gtcatgaggg  27900
gaacgcagta ccttttcaac taaacctttg cacgagtaat caaagatccg cttgacgagc  27960
ctatatggaa gagcgtgcca ggtatttgac tcaaggactg ttagtaactg aagacctgac  28020
ggtgttgata tggatacac                                              28039
```

<210> SEQ ID NO 11
<211> LENGTH: 28038
<212> TYPE: DNA
<213> ORGANISM: Porcine epidemic diarrhea virus

<400> SEQUENCE: 11

```
acttaaaaag attttctatc tacggatagt tagctctttt tctagactct tgtctactca     60
attcaactaa acgaaatttt gtccttccgg ccgcatgtcc atgctgctgg aagctgacgt    120
ggaatttcat taggtttgct taagtagcca tcgcaagtgc tgtgctgtcc tctagttcct    180
ggttggcgtt ccgtcgcctt ctacatacta gacaaacagc cttcctccgg ttccgtctgg    240
gggttgtgtg gataactagt tccgtctagt ttgaaactag taactgtcgg ctatggctag    300
caaccatgtt acattggctt ttgccaatga tgcagaaatt tcagcttttg gcttttgcac    360
tgctagtgaa gccgtctcat actattctga ggccgccgct agtggattta tgcaatgccg    420
tttcgtgtcc ttcgatctcg ctgacactgt tgagggattg cttcccgaag actatgtcat    480
```

-continued

```
ggtggtggtc ggcactacca agcttagtgc gtatgtggac acttttggta gccgccccaa    540
aaacatttgt ggttggctgt tattttctaa ctgtaattac ttcctcgaag agttagagct    600
tacttttggt cgtcgtggtg gtaacatcgt gccagttgac caatacatgt gtggcgctga    660
cggtaaacct gttcttcagg aatccgaatg ggagtataca gatttctttg ctgactccga    720
agacggtcaa ctcaacattg ctggtatcac ttatgtgaag gcctggattg tagagcgatc    780
ggatgtctct tatgcgagtc agaatttaac atctattaag tctattactt actgttcaac    840
ctatgagcat acttttcctg atggtactgc catgaaggtt gcacgtactc caaagattaa    900
gaagactgtt gtcttgtctg agccacttgc tactatctac agggaaattg gttctccttt    960
tgtggataat gggagcgatg ctcgttctat cattaagaga ccagtgttcc tccacgcttt   1020
tgttaagtgt aagtgtggta gttatcattg gactgttggt gattggactt cctatgtctc   1080
cacttgctgt ggctttaagt gtaagccagt ccttgtggct tcatgctctg ctacgcctgg   1140
ttctgttgtg gttacgcgcg ctggtgctgg cactggtgtt aagtattaca acaacatgtt   1200
cctgcgccat gtggcagaca ttgatgggtt ggcattctgg cgaattctca aggtgcagtc   1260
caaagacgac ctcgcttgct ctggtaaatt ccttgaacac catgaggaag gtttcacaga   1320
tccttgctac tttttgaatg actcgagcat tgctactaag ctcaagtttg acatccttag   1380
tggcaagttt tctgatgaag tcaaacaagc tatctttgct ggtcatgttg ttgttggcag   1440
cgcgctcgtt gacattgttg acgatgcact gggacagcct tggtttatac gtaagcttgg   1500
tgaccttgca agtgcagctt gggagcagct taaggctgtc gttagaggcc ttaacctcct   1560
gtctgatgag gtcgtgctct ttggcaaaag acttagctgt gccactctta gtatcgttaa   1620
cggtgttttt gagttcatcg ccgaagtgcc tgagaagttg gctgcggctg ttacagtttt   1680
tgtcaacttc ttgaatgagc tttttgagtc tgcctgtgac tgcttaaagg tcggaggtaa   1740
aacctttaac aaggttggct cttatgttct ttttgacaac gcattggtta agcttgtcaa   1800
ggcaaaagtt cgcggcccac gacaggcagg tgtttgtgaa gttcgttaca caagccttgt   1860
tattgggagt actaccaagg tggtttccaa gcgcgttgaa aatgccaatg tgaatctcgt   1920
cgtcgttgac gaggatgtga ccctcaacac cactggtcgt acagttgttg ttgacggact   1980
tgcattcttc gagagtgacg ggttttacag acatcttgct gatgctgacg ttgtcattga   2040
acatcctgtt tataagtctg cttgtgagct caagccagtt tttgagtgtg acccaatacc   2100
tgattttcct atgcctgtgg ccgctagtgt tgcagagctt tgtgtgcaaa ctgatctgtt   2160
gcttaaaaat tacaacactc cttataaaac ttacagctgc gttgtgagag gtgataagtg   2220
ttgtatcact tgcaccttac atttcacagc accaagttat atggaggctg ctgctaattt   2280
tgtagacctc tgtaccaaga acattggtac tgctggtttt catgagtttt acattacggc   2340
ccatgaacaa caggatctgc aagggttcgt aaccacttgt tgcacgatgt caggttttga   2400
gtgttttatg cctataatcc cacagtgtcc agcagtgctt gaagagattg atggtggtag   2460
catctggcgg tcttttatca ctggtcttaa tacaatgtgg gatttttgca agcatcttaa   2520
agtcagcttt ggactagatg gcattgttgt cactgtagca cgcaaattta aacgacttgg   2580
tgctctcttg gcagaaatgt ataacactta cctttcaact gtggtggaaa acttggtact   2640
ggccggtgtt agcttcaagt attatgccac cagtgtccca aaaattgttt tgggctgttg   2700
ttttcacagt gttaaaagtg ttcttgcaag tgccttccag attcctgtcc aggcaggcgt   2760
tgagaagttt aaagtcttcc ttaactgtgt tcaccctgtt gtaccacgtg tcattgaaac   2820
ttcttttgtg gaattagaag agacgacatt taaaccacca gcactcaatg gtagtattgc   2880
```

-continued

```
tattgttgat ggctttgctt tctattatga tggaacacta tactatccca ccgatggtaa   2940
tagcgttgtt cctatctgct ttaagaagaa aggtggtggt gatgtcaaat tctctgatga   3000
agtctctgtt aaaaccattg acccagttta taaggtctcc cttgaatttg agttcgagtc   3060
tgagactatt atggctgtgc ttaataaggc tgttggtaat tgtatcaagg ttacaggtgg   3120
ttgggacgat gttgttgagt atatcaatgt tgccattgag gttcttaaag atcacatcga   3180
tgtgcctaag tactacatct atgatgagga aggtggcacc gatcctaatc tgcccgtaat   3240
ggtttctcag tggccgttga atgatgacac gatctcacag gatctgcttg atgttgaagt   3300
tgttactgat gcgccagttg atttcgaggg tgatgaagta gactcctctg accctgataa   3360
ggtggcagac gtggctaact ctgagcctga ggatgacggt cttaatgtag ctcctgaaac   3420
aaatgtagag tctgaagttg aggaagttgc cgcaaccttg tcctttatta aagatacacc   3480
ttccacagtt actaaggatc cttttgcttt tgactttgca agctatggag gacttaaggt   3540
tttaagacaa tctcataaca actgctgggt tacttctacc ttggtgcagc tacaattgct   3600
tggcatcgtt gatgaccctg caatggagct ttttagtgct ggtagagttg gtccaatggt   3660
tcgcaaatgc tatgagtcac aaaaggctat cttgggatct ttgggtgatg tgtcggcttg   3720
cctagagtct ctgactaagg acctacacac acttaagatt acctgttctg tagtctgtgg   3780
ttgtggtact ggtgaacgta tctatgatgg ttgtgctttt cgtatgacgc caactttgga   3840
accgttccca tatggtgctt gtgctcagtg tgctcaagtt ttgatgcaca cttttaaaag   3900
tattgttggc accggcatct tttgtcgaga tactactgct ctctccttgg attctttggt   3960
tgtaaaacct ctttgtgcgg ctgcttttat aggcaaggat agtggtcatt atgtcactaa   4020
cttttatgat gctgctatgg ctattgatgg ttatggtcgt catcagataa agtatgacac   4080
actgaacact atttgtgtta aagacgttaa ttggacagca ccttttgtcc cagacgttga   4140
gcctgtattg gagcctgttg tcaaaccttt ctattcttat aagaatgttg atttttacca   4200
aggagatttt agtgaccttg ttaaacttcc atgtgatttt gttgttaatg ctgcaaatga   4260
gaatttgtct cacggtggcg gcatagcaaa ggccattgat gtttatacca agggcatgtt   4320
gcagaagtgc tcgaatgatt acattaaagc acacggtccc attaaagttg gacgtggtgt   4380
catgttggag gcattaggtc ttaaggtctt taatgttgtt ggtccacgta agggtaagca   4440
tgcacctgag cttcttgtta aggcttataa gtccgttttt gctaattcag gtgttgctct   4500
tacacctttg attagtgttg gaatttttag tgttcctttg gaagaatctt tatctgcttt   4560
tcttgcatgt gttggtgatc gccactgtaa gtgcttttgt tatagtgaca aagagcgcga   4620
ggcgatcatt aattacatgg atggcttggt agatgctatt ttcaaagatg cacttgttga   4680
tactactcct gtccaggaag atgttcaaca agtttcacaa aaaccagttt tgcctaattt   4740
tgaacctttc aggattgaag gtgctcatgc tttctatgag tgcaaccctg aaggtttgat   4800
gtcattaggt gctgacaagc tggtgttgtt tacaaattcc aatttggatt tttgtagcgt   4860
tggtaagtgt cttaacaatg tgactggcgg tgcattgctt gaagccataa atgtatttaa   4920
aaagagtaac aaaacagtgc ctgctggcaa ctgtgttact tttgagtgtg cagatatgat   4980
ttctattact atggtagtat tgccatctga cggtgatgct aattatgaca aaaattatgc   5040
acgcgccgtc gtcaaggtat ctaagcttaa aggcaagtta ttgcttgctg ttggtgatgc   5100
catgttgtat tccaagttgt cccacctcag cgtgttaggt ttcgtatcca cacctgatga   5160
tgtggagcgt ttctacgcaa ataagagtgt ggttattaaa gttactgagg atacacgtag   5220
```

```
tgttaagact gttaaagtag aatccactgt tacttatgga caacaaattg gaccttgtct   5280
tgttaatgac accgttgtca cagacaacaa acctgttgtt gctgatgttg tagctaaggt   5340
tgtaccaagt gctaattggg attcacatta tggttttgat aaggctggtg agttccacat   5400
gctagaccat actgggtttg cctttcctag tgaagttgtt aacggtaggc gtgtgcttaa   5460
aaccacagat aataactgtt gggttaatgt tacatgttta caattacagt ttgctagatt   5520
taggttcaag tcagcaggtc tacaggctat gtgggagtcc tattgtactg gtgatgttgc   5580
tatgtttgtg cattggttgt actggcttac tggtgttgac aaaggtcagc ctagtgattc   5640
agaaaatgca cttaacatgt tgtctaagta cattgttcct gctggttctg tcactattga   5700
acgtgtcacg catgacggtt gttgttgtag taagcgtgtt gtcactgcac cagttgtgaa   5760
tgctagcgtg ttgaagcttg gcgtcgagga tggtctttgt ccacatggtc ttaactacat   5820
tgacaaagtt gttgtagtta aaggtactac aattgttgtc aatgttggaa aacctgtagt   5880
ggcaccatcg cacctctttc ttaagggtgt ttcctacaca acattcctag ataatggtaa   5940
cggtgttgcc ggccattata ctgtttttga tcatgacact ggtatggtgc atgatggaga   6000
tgtttttgta ccaggtgatc tcaatgtgtc tcctgttaca aatgttgtcg tctcagagca   6060
gacggctgtt gtgattaaag accctgtgaa gaaagtagag ttagacgcta caaagctgtt   6120
agacactatg aattatgcat cggaaagatt cttttccttt ggtgatttta tgtcacgtaa   6180
tttaattaca gtgtttttgt acatccttag tattttgggt ctctgtttta gggcctttcg   6240
taagagggat gttaaagttc tagctggtgt accccaacgt actggtatta tattgcgtaa   6300
aagtgtgcgc tataatgcaa aggctttggg tgtcttcttc aagctaaaac tttattggtt   6360
caaagttctt ggtaagttta gtttgggtat ttatgcattg tatgcattac tattcatgac   6420
aatacgcttt acacctatag gtggccctgt ttgtgatgat gttgttgctg gttatgctaa   6480
ttctagtttt gacaagaatg agtattgcaa cagtgttatt tgtaaggtct gtctctatgg   6540
gtaccaggaa ctttcggact tctctcacac acaggtagta tggcaacacc ttagagaccc   6600
attaattggt aatgtgatgc ctttctttta tttggcattt ctggcaattt ttgggggtgt   6660
ttatgtaaag gctattactc tctattttat tttccagtat cttaacatac ttggtgtgtt   6720
tttgggccta caacagtcca tttggttttt gcagcttgtg ccttttgatg tctttggtga   6780
cgagatcgtc gtctttttca tcgttacacg cgtattgatg ttccttaagc atgttttcct   6840
tggctgcgat aaggcatctt gtgtggcttg ctctaagagt gctcgcctta agcgcgttcc   6900
tgtccagact atttttcagg gtactagcaa atccttctac gtacatgcca atggtggttc   6960
taagttctgt aagaagcaca atttcttttg tttaaattgt gattcttatg gtccaggctg   7020
cacttttatt aatgacgtca ttgcaactga agttggtaat gttgtcaaac ttaatgtgca   7080
accgacaggt cctgccacta ttcttattga caaggttgaa ttcagtaatg gtttttacta   7140
tctttatagt ggtgacacat tttggaagta caactttgac ataacagata acaaatacac   7200
ttgcaaagag tcacttaaaa attgtagcat aatcacagac tttattgttt ttaacaataa   7260
tggttccaat gtaaatcagg ttaagaatgc atgtgtgtat ttttcacaga tgctttgtaa   7320
acctgttaag ttagtggact cagcgttgtt ggccagtttg tctgttgatt ttggtgcaag   7380
cttacatagt gcttttgtta gtgtgttgtc gaatagtttt ggcaaagacc tgtcaagttg   7440
taatgacatg caggattgca agagcacatt gggttttgat gatgtaccat tggatacctt   7500
taatgctgct gttgctgagg ctcatcgtta cgatgtcctc ttgactgaca tgtcgttcaa   7560
caattttacc accagttatg caaaaccaga ggaaaaactt cccgtccatg acattgccac   7620
```

-continued

```
gtgtatgcgt gtaggtgcca agattgttaa tcataacgtt cttgtcaagg atagtatacc   7680
tgtggtgtgg cttgtacgtg atttcattgc cctttctgaa gaaactagga agtacattat   7740
tcgtacgact aaagttaagg gtataacctt catgttgacc tttaatgatt gtcgtatgca   7800
tactaccata cctactgttt gcattgcaaa taagaagggt gcaggtcttc ctagtttttc   7860
aaaggttaag aaattcttct ggtttttgtg tctgttcata gttgctgttt tctttgcact   7920
aagctttttt gattttagta ctcaggttag cagtgatagt gattatgact tcaagtatat   7980
tgagagtggc cagttgaaga cttttgacaa tccacttagt tgtgtgcata atgtctttag   8040
taacttcgac cagtggcatg atgccaagtt tggtttcacc cccgtcaaca atcctagttg   8100
tcctatagtc gttggtgtat cagacgaagc gcgcactgtt ccaggtatcc cagcaggtgt   8160
ttatttagct ggtaaaacac ttgtttttgc tattaacacc atttttggta catctggttt   8220
gtgctttgat gctagtggcg ttgctgataa gggcgcttgc atttttaatt cggcttgcac   8280
cacattatct ggtttgggtg gaactgctgt ctactgttat aagaatggtc tagttgaagg   8340
tgctaaactt tatagtgagt tggcacctca tagctactat aaaatggtag atggtaatgc   8400
tgtgtcttta cctgaaatta tctcacgcgg ctttggcatc cgtactatcc gtacaaaggc   8460
tatgacctac tgtcgcgttg gccagtgtgt gcaatctgca gaaggtgttt gttttggcgc   8520
cgatagattc tttgtctata atgcagaatc tggttctgac tttgtttgtg gcacagggct   8580
ctttacattg ttgatgaacg ttattagtgt tttttccaag acagtaccag taactgtgtt   8640
gtctggtcaa atacttttta attgcattat tgcttttgct gctgttgcgg tgtgtttctt   8700
atttacaaag tttaagcgca tgttcggtga tatgtctgtt ggcgttttca ctgtcggtgc   8760
ttgtactttg ttgaacaatg tttcctacat tgtaacacag aacacacttg gcatgttggg   8820
ctatgcaact ttgtactttt tgtgcactaa aggtgttaga tatatgtgga tttggcattt   8880
gggatttttg atctcatata tacttattgc accatggtgg gttttgatgg tttatgcctt   8940
ttcagccatt tttgagttta tgcctaacct ttttaagctt aaggtttcaa cacaactttt   9000
tgagggtgac aagttcgtag gctcttttga aaatgctgca gcaggtacat ttgtgcttga   9060
tatgcatgcc tatgagagac ttgccaactc tatctcaact gaaaaactgc gtcagtatgc   9120
tagtacttac aataagtaca agtattattc aggcagtgct tcagaggctg attacaggct   9180
tgcttgtttt gcccatttgg ccaaggctat gatggattat gcttctaatc acaacgacac   9240
gttatacaca ccacccactg tgagttacaa ttcaactcta caggctggct tgcgtaagat   9300
ggcacaacca tctggtgttg ttgagaagtg catagttcgt gtttgctatg gtaatatggc   9360
tcttaatggc ctatggcttg gtgatactgt tatctgccca cgccatgtta tagcgtctag   9420
tactactagc actatagatt atgactatgc cctttctgtt ttacgcctcc acaacttctc   9480
catttcatct ggtaatgttt tcctaggtgt tgtgggtgta accatgcgag gtgctttgtt   9540
gcagataaag gttaatcaaa acaatgtcca cacgcctaag tacacctatc gcacagttag   9600
accgggtgaa tcttttaata tcttggcgtg ctatgatggt tctgcagctg gtgtttacgg   9660
cgttaacatg cgctctaatt acactattag aggctcgttc attaatggcg cttgtggttc   9720
acctggttat aacattaaca atggtaccgt tgagttttgc tatttacacc agcttgaact   9780
tggttcaggc tgtcatgttg gtagcgactt agatggtgtt atgtatggtg gttatgagga   9840
ccaacctact ttgcaagttg aaggcgctag tagtctgttt acagagaatg tgttggcatt   9900
tctttatgca gcactcatta atggttctac ctggtggctt agttcttcta ggattgctgt   9960
```

```
agacaggttt aatgagtggg ctgttcataa tggtatgaca acagtagtta atactgattg  10020
cttttctatt cttgctgcta agactggtgt tgatgtacaa cgtttgttgg cctcaatcca  10080
gtctctgcat aagaattttg gtggaaagca aattcttggc tatacctcgt tgacagatga  10140
gtttactaca ggtgaagtta tacgtcaaat gtatggcgtt aatcttcaga gtggttatgt  10200
ttcacgcgcc tgtagaaatg tcttgctggt tggttctttt ctgactttct tttggtcaga  10260
attagtttcc tacactaagt tcttttgggt aaatcctggt tatgtcacac ctatgtttgc  10320
gtgtttgtca ttgctgtcct cacttttgat gttcacactc aagcataaga cattgttttt  10380
ccaggtcttt ctaatacctg ctctgattgt tacatcttgc attaatttgg catttgatgt  10440
tgaagtctac aactatttgg cagagcattt tgattaccat gtttctctca tgggttttaa  10500
tgcacaaggt cttgttaaca tctttgtctg ctttgttgtt accattttac acggcacata  10560
cacatggcgc ttttttaaca cacctgtgag ttctgtcact tatgtggtag ctttgctgac  10620
tgcggcatat aactattttt acgctagtga cattcttagt tgtgctatga cactatttgc  10680
tagtgtgact ggcaactggt tcgttggtgc tgtttgttat aaagctgctg tttatatggc  10740
cttgagattt cctacttttg tggctatttt tggtgatatt aagagtgtta tgttctgtta  10800
ccttgtgttg ggttatttta cctgttgctt ctacggtatt ctctactggt tcaacaggtt  10860
ttttaaggtt agtgtaggtg tctatgacta tactgttagt gctgctgagt ttaagtatat  10920
ggttgctaac ggcctacgtg caccaactgg aacacttgat tcactacttc tgtctgccaa  10980
attgattggt attggtggtg agcggaatat taagatttct tccgttcagt ctaaactgac  11040
tgatattaag tgtagtaacg ttgtgctttt aggctgtctc tctagcatga atgtctcagc  11100
aaattcaaca gaatgggcct attgtgttga cttgcataac aagatcaact tgtgtaatga  11160
cccagaaaaa gcgcaggaaa tgctacttgc tttgttggca tttttcctta gtaagaatag  11220
tgcttttggt ttagatgact tattggaatc ctattttaat gacaatagta tgttgcagag  11280
tgttgcatct acttatgtcg gtttgccttc ttatgtcatt tatgaaaatg cacgccaaca  11340
gtatgaagat gctgttaata atggttctcc acctcagttg gttaagcaat tgcgccatgc  11400
catgaatgta gcaaagagcg aatttgaccg tgaggcttct actcagcgta agcttgatag  11460
aatggcggaa caggctgcag cacagatgta caaagaggca cgagcagtta ataggaagtc  11520
caaagttgta agtgctatgc attcactgct tttggtatg ttgagacgtt tggacatgtc  11580
ttctgtagac accattctca acttggcaaa ggatggggtt gtacctctgt ctgtcatacc  11640
ggcagtcagt gctactaagc ttaacattgt tacttctgat atcgattctt ataatcgtat  11700
ccagcgtgag ggatgtgtcc actacgctgg taccatttgg aatataattg atatcaagga  11760
caatgatggc aaggtggtac acgttaagga ggtaaccgca cagaatgctg agtccctgtc  11820
atggcccctg gtccttgggt gtgagcgtat tgtcaagctc cagaataatg aaattattcc  11880
tggtaagctg aagcagcgct ccattaaggc agaaggagat ggcatagttg gagaaggtaa  11940
ggcactttac aataatgagg gtggacgtac ttttatgtat gctttcatct cggacaaacc  12000
ggacctgcgt gtagtcaagt gggagttcga tggtggttgt aacactattg agctagaacc  12060
accacgtaag ttcttggtgg attctcctaa tggtgcacag atcaagtatc tctactttgt  12120
tcgtaacctt aacacgttac gtaggggtgc tgttctcggc tacataggtg ccactgtacg  12180
cttgcaggct ggtaaacaaa cagaacaggc tattaactct tcattgttga cactttgcgc  12240
tttcgctgtg gatcctgcta agacctacat cgatgctgtc aaaagtggtc acaaaccagt  12300
aggtaactgt gttaagatgt tggccaatgg ttctggtaat ggacaagctg ttactaatgg  12360
```

```
tgtggaggct agtactaacc aggattcata cggtggtgcg tccgtgtgtc tatattgtag  12420
agcacatgtt gagcatccat ctatggatgg tttttgcaga ctgaaaggca agtacgtaca  12480
ggttccacta ggtacagtgg atcctatacg ttttgtactt gagaatgacg tttgcaaggt  12540
ttgtggttgt tggctggcta atggctgcac ttgtgacaga tccattatgc aaagcactga  12600
tatggcttat ttaaacgagt acggggctct agtgcagctc gactagagcc mtgtaacggt  12660
actgatacac aacatgtgta tcgtgctttt gacatctaca acaaggatgt tgcttgtcta  12720
ggtaaattcc tcaaggtgaa ctgtgttcgc ctgaagaatt tggataagca tgatgcattc  12780
tatgttgtca aaagatgtac caagtctgcg atggaacacg agcaatccat ctatagcaga  12840
cttgaaaagt gtggagccgt agccgaacac gatttcttca cttggaagga tggtcgtgcc  12900
atctatggta acgtttgtag aaaggatctt accgagtata ctatgatgga tttgtgttac  12960
gctttacgta actttgatga aaacaattgc gatgttctta agagcatttt aattaaggta  13020
ggcgcttgtg aggagtccta cttcaataat aaagtctggt ttgaccctgt tgaaaatgaa  13080
gacattcatc gtgtctatgc attgttaggt accattgttt cacgtgctat gcttaaatgc  13140
gttaagttct gtgatgcaat ggttgaacaa ggtatagttg gtgttgtcac attagataat  13200
caggatctta atggtgattt ttatgatttt ggtgatttta cttgtagcat caagggaatg  13260
ggtataccca tttgcacatc atattactct tatatgatgc ctgttatggg tatgactaat  13320
tgccttgcta gtgagtgttt tgttaagagt gatatatttg gtgaggattt caagtcatat  13380
gacctgctgg aatatgattt cacggagcat aagacagcac tcttcaacaa gtatttcaag  13440
tattggggac tgcaatacca ccctaactgt gtggactgca gtgatgagca gtgcatagtt  13500
cactgtgcca acttcaatac gttgttttcc actactatac ctattacggc atttggacct  13560
ttgtgtcgca agtgttggat tgatggtgtt ccactggtaa ctacagctgg ttatcatttt  13620
aaacagttag gtatagtttg gaacaatgac ctcaacttac actctagcag gctctctatt  13680
aacgaattac tccagttttg tagtgatcct gcattgctta tagcatcatc accagcccctt  13740
gttgatcagc gtactgtttg cttttcagtt gcagcgctag gtacaggtat gactaaccag  13800
actgttaaac ctggccattt caataaggag ttttatgact tcttacttga gcaaggtttc  13860
ttttctgagg gctctgagct tactttaaag cacttcttct ttgcacagaa gggtgatgca  13920
gctgttaagg attttgacta ctataggtat aatagaccta ctgttctgga catttgccaa  13980
gctcgcgtcg tgtatcaaat agtgcaacgc tattttgata tttacgaagg tggttgtatc  14040
actgctaaag aggtggttgt tacaaacctt aacaagagcg caggttatcc tttgaacaag  14100
tttggtaaag ctggtcttta ctatgagtct ttatcctatg aggaacagga tgaactttat  14160
gcttatacta agcgtaacat cctgcccact atgacacagc tcaaccttaa atatgctata  14220
agtggcaaag aacgtgcacg cacagtgggt ggtgtttcgc ttttgtcaac catgactact  14280
cggcagtatc atcagaaaca ccttaagtcc atagttaata ctaggggcgc ttcggttgtt  14340
attggtacta ctaagtttta tggtggttgg gacaatatgc ttaagaacct tattgatggt  14400
gttgaaaatc cgtgtcttat gggttgggac tacccaaagt gcgacagagc actgcccaat  14460
atgatacgta tgatttcagc catgatttta ggctctaagc acaccacatg ctgcagttcc  14520
actgaccgct tttcaggtt gtgcaatgaa ttggctcaag tccttactga ggttgtttat  14580
tctaatggag gtttttattt gaagccaggt ggtactacct ctggtgatgc aaccaccgca  14640
tatgcaaact cagtttttaa tatcttccaa gcagtaagtg ccaatgttaa caaacttctt  14700
```

-continued

```
agtgttgaca gcaatgtctg tcataattta gaagttaagc aattgcagcg taagctttat  14760
gagtgctgtt atagatcaac taccgtcgat gaccagttcg tcgttgagta ttatggttac  14820
ttgcgtaaac atttttcaat gatgattctt tctgatgatg gcgttgtttg ttataacaat  14880
gactatgcat cacttggtta tgtcgctgat cttaacgcat tcaaggctgt tttgtattac  14940
cagaacaatg tcttcatgag cgcctctaaa tgttggatcg agcctgacat taataaaggt  15000
cctcatgaat tttgctcgca gcatactatg cagattgtcg ataaagatgg tacttattac  15060
cttccttacc ctgatccttc aagaattctc tctgcaggtg tgtttgttga tgacgttgtt  15120
aaaactgatg cagttgtatt gcttgaacgt tatgtgtcat tggctataga tgcctacccg  15180
ttatctaagc atgaaaaccc tgaatataag aaggtgtttt atgtgctttt ggattgggtt  15240
aagcatctgt acaaaactct taatgctggt gtgttagagt ctttttctgt cacacttttg  15300
gaagattcta ctgctaaatt ctgggatgag agcttttatg ccaacatgta tgagaaatct  15360
gcagttttac aatctgcagg gctttgtgtt gtttgtggct ctcaaactgt tttacgttgt  15420
ggtgattgtc tacggcgtcc tatgctttgt actaagtgtg cttatgatca tgtcattgga  15480
acaactcaca agttcatttt ggccatcact ccatatgtgt gttgtgcttc agattgtggt  15540
gtcaatgatg taactaagct ctacttaggt ggtcttagtt attggtgtca tgaccacaag  15600
ccacgtcttg cattcccgtt gtgctctgct ggtaatgttt ttggcttgta caaaaattct  15660
gctaccggct cacccgatgt tgaagacttt aatcgcattg ctacatccga ttggactgat  15720
gtttctgact acaggttggc aaatgatgtc aaggactcat tgcgtctgtt tgcagcggaa  15780
actatcaagg ccaaggagga gagcgttaag tcatcctatg cttgtgcaac actacatgag  15840
gttgtaggac ctaaagagtt gttgctcaaa tgggaagtcg gcagacccaa accacccctt  15900
aatagaaatt cggttttcac ttgttatcat ataacgaaga acaccaaatt tcaaatcggt  15960
gagtttgtgt ttgagaaggc agaatatgat aatgatgctg taacatataa aactaccgcc  16020
acaacaaaac ttgttcctgg catggttttt gtgcttacct cacataatgt tcagccattg  16080
cgcgcaccga ccattgctaa tcaagaacgt tattccacta tacataagtt gcatcctgct  16140
tttaacatac ctgaagctta ttctagctta gtgccctatt accaattgat tggtaagcag  16200
aagattacaa ctattcaggg acctcccggt agtggtaaat ctcactgtgt tatagggcta  16260
ggtttgtact atccaggtgc acgtatagtg tttacagctt gttctcatgc agcggtcgat  16320
tcactttgtg tgaaagcttc cactgcttat agcaatgaca aatgttcacg catcatacca  16380
cagcgcgctc gtgttgagtg ttatgatggt ttcaagtcta ataatactag tgctcagtac  16440
cttttctcta ctgtcaatgc tttgccagag tgcaatgcgg acattgttgt ggtggatgag  16500
gtctctatgt gcactaatta tgacttgtct gtcataaatc agcgcatcag ctataggcat  16560
gtagtctatg ttggtgaccc tcaacagctg cctgcaccac gtgttatgat ttcacgtggt  16620
actttggaac caaaggacta caacgttgtc actcaacgca tgtgtgccct taagcctgat  16680
gttttcttgc acaagtgtta tcgctgtcct gctgagatag tgcgtactgt gtctgagatg  16740
gtctatgaaa accaattcat tcctgtgcac ccagatagca agcagtgttt taaaatcttt  16800
tgcaagggta atgttcaggt tgataatggt tcaagcatta atcgcaggca attggatgtt  16860
gtgcgtatgt ttttggctaa aaatcctagg tggtcaaagg ctgtttttat ttctccttat  16920
aacagccaga attatgttgc cagccgcatg ctaggtctac aaattcagac agttgactca  16980
tcccagggta gtgagtatga ctatgtcatt tacacacaaa cttcagatac tgcccatgcc  17040
tgtaatgtta acaggtttaa tgttgccatc acaagggcca agaaaggcat attatgtata  17100
```

```
atgtgcgata ggtccctttt tgatgtgctt aaattctttg agcttaaatt gtctgatttg  17160
caggctaatg agggttgtgg tctttttaaa gactgtagca gaggtgatga tctgttgcca  17220
ccatctcacg ctaacacctt catgtcttta gcggacaatt ttaagactga tcaagatctt  17280
gctgttcaaa taggtgttaa tggacccatt aaatatgagc atgttatctc gtttatgggt  17340
ttccgttttg atatcaacat acccaaccat catactctct tttgcacacg cgactttgcc  17400
atgcgcaatg ttagaggttg gttaggcttt gacgttgaag gagcacatgt tgttggctct  17460
aacgtcggta caaatgtccc attgcaatta gggttttcta acggtgttga ttttgttgtc  17520
agacctgaag gttgcgttgt aacagagtct ggtgactaca ttaaacccgt cagagctcgt  17580
gctccaccag gggaacaatt cgcacacctt ttgcctttac ttaaacgcgg ccaaccatgg  17640
gatgttgtcc gcaaacgtat agtgcagatg tgtagtgact acctggccaa cctatcagac  17700
atactaattt ttgtgttgtg ggctggtggt ttggagttga caactatgcg ttattttgtc  17760
aagattggac caagtaagag ttgtgattgt ggtaaggttg ctacttgtta caatagtgcg  17820
ctgcatacgt actgttgttt caaacatgcc cttggttgtg attatctgta taacccatac  17880
tgtattgata tacagcagtg ggatacaagg ggatcactta gccttaacca ccatgagcat  17940
tgtaatgtac atagaaacga gcatgtggct tctggtgatg ccataatgac tcgctgtctg  18000
gccatacatg attgctttgt caagaacgtt gactggtcca tcacataccc atttattggt  18060
aatgaggctg ttattaataa gagcggccga attgtgcaat cacacactat gcggtcagtt  18120
cttaagttat acaatccgaa agccatatat gatattggca atcctaaggg cattagatgt  18180
gccgtaacgg atgctaagtg gttttgcttt gacaagaatc ctactaattc taatgtcaag  18240
acattggagt atgactatat aacacatggc caatttgatg ggttgtgctt gttttggaat  18300
tgcaatgtag acatgtatcc agaattttct gtggtctgtc gttttgatac tcgctgtagg  18360
tcaccactca acttggaggg ttgtaatggt ggttcactgt atgttaataa tcatgcattc  18420
catacaccgg cttttgacaa gcgtgctttt gctaagttga agccaatgcc atttttcttt  18480
tatgatgata ctgagtgtga caagttacag gactccataa actatgttcc tcttagggct  18540
agtaactgca ttactaaatg taatgttggt ggtgctgtct gtagtaagca ttgtgctatg  18600
tatcatagct atgttaatgc ttacaacact tttacgtcgg cgggctttac tatttgggtg  18660
cctacttcgt ttgacaccta taatctgtgg cagacattta gtaacaattt gcaaggtctt  18720
gagaacattg ctttcaatgt cgtaaagaaa ggatcttttg ttggtgccga aggtgaactt  18780
cctgtagctg tggttaatga caaagtgctc gttagagatg gtactgttga tactcttgtt  18840
tttacaaaca agacatcact acccactaac gtagcttttg agttgtatgc caagcgtaag  18900
gtaggactca ccccacccat tacgatccta cgtaacttgg gtgtagtttg tacatctaag  18960
tgtgtcattt gggactatga agccgaacgt ccacttacta cttttacaaa ggatgtttgt  19020
aaatataccg actttgaggg tgacgtctgt acactctttg ataacagcat tgttggttca  19080
ttagagcgat tctccatgac ccaaaatgct gtgcttatgt cacttacagc tgttaaaaag  19140
cttactggca taaagttaac ttatggttat cttaatggtg tcccagttaa cacacatgaa  19200
gataaacctt ttacttggta tatttacact aggaagaacg gcaagttcga ggaccatcct  19260
gatggctatt ttacccaagg tagaacaacc gctgatttta gccctcgtag cgacatggaa  19320
aaggacttcc taagtatgga tatgggtctg tttattaaca agtacggact tgaagattac  19380
ggctttgagc acgttgtgta tggtgatgtt tcaaaaacca cccttggtgg tttgcatcta  19440
```

```
ctaatttcgc aggtgcgtct ggcctgtatg ggtgtgctca aaatagacga gtttgtgtct  19500
agtaatgata gcacgttaaa gtcttgtact gttacatatg ctgataaccc tagtagtaag  19560
atggtttgta cgtatatgga tctcctgctt gacgattttg tcagcattct taaatctttg  19620
gatttgggcg ttgtatctaa agttcatgaa gttatggtcg attgtaaaat gtggaggtgg  19680
atgttgtggt gtaaggatca taaactccag acattttatc cgcaacttca ggccagtgaa  19740
tggaagtgtg gttattccat gccttctatt tacaagatac aacgtatgtg tttagaacct  19800
tgcaatctct acaactatgg tgctggtatt aagttacctg atggcattat gtttaacgta  19860
gttaaataca cacagctttg tcaatatctc aatagcacca caatgtgtgt accccatcac  19920
atgcgtgtgc tacatcttgg tgctggctcc gacaagggtg ttgcacctgg cacggctgtc  19980
ttacgacgtt ggttgccact ggatgccatt atagttgaca atgatagtgt ggattacgtt  20040
agcgatgctg attatagtgt tacaggagat tgctctacct tatacctgtc agataagttt  20100
gatttagtta tatctgatat gtatgatggt aagattaaaa gttgtgatgg ggagaacgtg  20160
tctaaagaag gcttctttcc ctatattaat ggtgtcatca ccgaaaagtt ggcacttggt  20220
ggtactgtag ctattaaggt gacggagttt agttggaata agaagttgta tgaactcatt  20280
cagaggtttg agtattggac aatgttctgt accagtgtta acacgtcatc gtcagaggca  20340
ttcttaattg gtgttcacta tttaggtgat tttgcaagtg gcgctgtgat tgacggcaac  20400
actatgcatg ccaattatat cttctggcgt aattccacaa ttatgactat gtcttacaat  20460
agtgtacttg atttaagcaa gttcaattgt aagcataagg ctacagttgt cattaattta  20520
aaagattcat ccattagtga tgttgtgtta ggtttgttga agaatggtaa gttgctagtg  20580
cgtaataatg acgccatttg tggtttttct aatcatttgg tcaacgtaaa caaatgaagt  20640
ctttaaccta cttctggttg ttcttaccag tactttcaac acttagccta ccacaagatg  20700
tcaccaggtg ctcagctaac actaatttta ggcggttctt ttcaaaattt aatgttcagg  20760
cgcctgcagt tgttgtactg ggcggttatc tacctattgg tgaaaaccag ggtgtcaatt  20820
caacttggta ctgtgctggc caacatccaa ctgctagtgg cgttcatggt atctttgtta  20880
gccatattag aggtggtcat ggctttgaga ttggcatttc gcaagagcct tttgacccta  20940
gtggttacca gctttattta cataaggcta ctaacggtaa cactaatgct actgcgcgac  21000
tgcgcatttg ccagtttcct agcattaaaa cattgggccc cactgctaat aatgatgtta  21060
caacaggtcg taattgccta tttaacaaag ccatcccagc tcatatgagt gaacatagtg  21120
ttgtcggcat aacatgggat aatgatcgtg tcactgtctt ttctgacaag atctattatt  21180
tttattttaa aaatgattgg tcccgtgttg cgacaaagtg ttacaacagt ggaggttgtg  21240
ctatgcaata tgtttacgaa cccacctatt acatgcttaa tgttactagt gctggtgagg  21300
atggtatttc ttatcaaccc tgtacagcta attgcattgg ttatgctgcc aatgtatttg  21360
ctactgagcc caatggccac ataccagaag gttttagttt taataattgg tttcttttgt  21420
ccaatgattc cactttggtg catggtaagg tggtttccaa ccaaccattg ttggtcaatt  21480
gtcttttggc cattcctaag atttatggac taggccaatt tttctccttt aatcaaacga  21540
tcgatggtgt ttgtaatgga gctgctgtgc agcgtgcacc agaggctctg aggtttaata  21600
ttaatgacac ctctgtcatt cttgctgaag gctcaattgt acttcatact gctttaggaa  21660
caaatttttc ttttgtttgc agtaattcct caaatcctca cttagccacc ttcgccatac  21720
ctctgggtgc tacccaagta ccttattatt gttttcttaa agtggatact tacaactcca  21780
ctgtttataa atttttggct gttttacctc ctaccgtcag ggaaattgtc atcaccaagt  21840
```

atggtgatgt ttatgtcaat gggtttggat acttgcatct cggtttgttg gatgctgtca 21900
caattaattt cactggtcat ggcactgacg atgatgtttc tggtttttgg accatagcat 21960
cgactaattt tgttgatgca ctcatcgaag ttcaaggaac cgccattcag cgtattcttt 22020
attgtgatga tcctgttagc caactcaagt gttctcaggt tgcttttgac cttgacgatg 22080
gtttttaccc tatttcttct agaaaccttc tgagtcatga acagccaatt tcttttgtta 22140
ctctgccatc atttaatgat cattcttttg ttaacattac tgtatctgct tcctttggtg 22200
gtcatagtgg tgccaacctt attgcatctg acactactat caatgggttt agttctttct 22260
gtgttgacac tagacaattt accatttcac tgttttataa cgttacaaac agttatggtt 22320
atgtgtctaa atcacaggac agtaattgcc ctttcacctt gcaatctgtt aatgattacc 22380
tgtcttttag caaattttgt gtttccacca gccttttggc tagtgcctgt accatagatc 22440
tttttggtta ccctgagttt ggtagtggtg ttaagtttac gtccctttac tttcaattca 22500
caaagggtga gttgattact ggcacgccta aaccacttga aggtgtcacg gacgtttctt 22560
ttatgactct ggatgtgtgt accaagtata ctatctatgg ctttaaaggt gagggtatca 22620
ttacccttac aaattctagc tttttggcag gtgtttatta cacatctgat tctggacagt 22680
tgttagcctt taagaatgtc actagtggtg ctgtttattc tgttacgcca tgttcttttt 22740
cagagcaggc tgcatatgtt gatgatgata tagtgggtgt tatttctagt ttgtctagct 22800
ccacttttaa cagtactagg gagttgcctg gtttcttcta ccattctaat gatggctcta 22860
attgtacaga gcctgtgttg gtgtatagta acataggtgt ttgtaaatct ggcagtattg 22920
gctacgtccc atctcagtct ggccaagtca agattgcacc cacggttact gggaatatta 22980
gtattcccac caactttagt atgagtatta ggacagaata tttacagctt tacaacacgc 23040
ctgttagtgt tgattgtgcc acatatgttt gtaatggtaa ctctcgttgt aaacaattac 23100
tcacccagta cactgcagca tgtaagacca tagagtcagc attacaactc agcgctaggc 23160
ttgagtctgt tgaagttaac tctatgctta ctatttctga agaggctcta cagttagcta 23220
ccattagttc gtttaatggt gatggatata attttactaa tgtgctgggt gtttctgtgt 23280
atgatcctgc aagtggcagg gtggtacaaa aaaggtcttt tattgaagac ctgcttttta 23340
ataaagtggt tactaatggc cttggtactg ttgatgaaga ctataagcgc tgttctaatg 23400
gtcgctctgt ggcagatcta gtctgtgcac agtattactc tggtgtcatg gtactacctg 23460
gtgttgttga cgctgagaag cttcacatgt atagtgcgtc tctcatcggt ggtatggtgc 23520
taggaggttt tacttctgca gcggcattgc cttttagcta tgctgttcaa gctagactca 23580
attatcttgc tctacagacg gatgttctac agcggaacca gcaattgctt gctgagtctt 23640
ttaactctgc tattggtaat ataacttcag cctttgagag tgttaaagag gctattagtc 23700
aaacttccaa gggtttgaac actgtggctc atgcgcttac taaggttcaa gaggttgtta 23760
actcgcaggg tgcagctttg actcaactta ccgtacagct gcaacacaac ttccaagcca 23820
tttctagttc tattgatgac atttactctc gactggacat tctttcagcc gatgttcagg 23880
ttgaccgtct catcaccggc agattatcag cacttaatgc ttttgttgct caaaccctca 23940
ctaagtatac tgaggttcag gctagcagga agttagcaca gcaaaaggtt aatgagtgcg 24000
ttaaatcgca atctcagcgt tatggttttt gtggtggtga tggcgagcac attttctctc 24060
tggtacaggc agcacctcag ggcctgctgt ttttacatac agtacttgta ccgagtgatt 24120
ttgtagatgt tattgccatc gctggcttat gcgttaacga tgaaattgcc ttgactctac 24180
gtgagcctgg cttagtcttg tttacgcatg aacttcaaaa tcatactgcg acggaatatt 24240
ttgtttcatc gcgacgtatg tttgaaccta gaaaacctac cgttagtgat tttgttcaaa 24300
ttgagagttg tgtggtcacc tatgtcaatt tgactagaga ccaactacca gatgtaatcc 24360
cagattacat cgatgttaac aaaacacttg atgagatttt agcttctctg cccaatagaa 24420
ctggtccaag tcttccttta gatgttttta atgccactta tcttaatctc actggtgaaa 24480
ttgcagattt agagcagcgt tcagagtctc tccgtaatac tacagaggag ctccaaagtc 24540
ttatatataa tatcaacaac acactagttg accttgagtg gctcaaccga gttgagacat 24600
atatcaagtg gccgtggtgg gtttggttga ttattttcat tgttctcatc tttgttgtgt 24660
cattactagt gttctgctgc atttccacgg gttgttgtgg atgctgcggc tgctgctgtg 24720
cttgtttctc aggttgttgt aggggtccta gacttcaacc ttacgaagtt tttgaaaagg 24780
tccacgtgca gtgatgtttc ttggactttt tcaatacacg attgacacag ttgtcaaaga 24840
tgtctcaaag tctgctaact tgtctttgga tgctgtccaa gagttggagc tcaatgtagt 24900
tccaattaga caagcttcaa atgtgacggg ttttcttttc accagtgttt ttatctactt 24960
ctttgcactg tttaaagcgt cttctttgag gcgcaattat attatgttgg cagcgcgttt 25020
tgctgtcatt gttctttatt gcccactttt atattattgt ggtgcatttt tagatgcaac 25080
tattatttgt tgcacactta ttggcaggct ttgtttagtc tgcttttact cctggcgcta 25140
taaaaatgcg ctctttatta tttttaatac tacgacactt tctttcctca atggtaaagc 25200
agcttattat gacggcaaat ccattgtgat tttagaaggt ggtgaccatt acatcacttt 25260
tggcaactct cttgttgctt ttgttagtag catcgacttg tatctagcta tacgtgggcg 25320
gcaagaagct gacctacagc tgttgcgaac tgttgagctt cttgatggca agaagcttta 25380
tgtcttttcg caacatcaaa ttgttggcat tactaatgct gcatttgact caattcaact 25440
agacgagtat gctacaatta gtgaatgata atggtctagt agttaatgtt atactttggc 25500
ttttcgtact ctttttcctg cttattataa gcattacttt cgtccaattg gttaatctgt 25560
gcttcacttg tcaccggttg tgtaatagcg cagtttacac acctataggg cgtttgtata 25620
gagtttataa gtcttacatg caaatagacc ccctccctag tactgttatt gacgtataaa 25680
cgaaatatgt ctaacggttc tattcccgtt gatgaggtga ttcaacacct tagaaactgg 25740
aatttcacat ggaatatcat actgacgata ctacttgtag tgcttcagta tggccattac 25800
aagtactctg cgttcttgta tggtgtcaag atggctattc tatggatact ttggcctctt 25860
gtgttagcac tgtcactttt tgatgcatgg gctagctttc aggtcaattg ggtctttttt 25920
gctttcagca tccttatggc ttgcatcact cttatgctgt ggataatgta ctttgtcaat 25980
agcattcggt tgtggcgcag gacacattct tggtggtctt tcaatcctga aacagacgcg 26040
cttctcacta cttctgtgat gggccgacag gtctgcattc cagtgcttgg agcaccaact 26100
ggtgtaacgc taacactcct tagtggtaca ttgcttgtag agggctataa ggttgctact 26160
ggcgtacagg taagtcaatt acctaatttc gtcacagtcg ccaaggccac tacaacaatt 26220
gtctacggac gtgttggtcg ttcagtcaat gcttcatctg gcactggttg ggctttctat 26280
gtccggtcca aacacggcga ctactcagct gtgagtaatc cgagttcggt tctcacagat 26340
agtgagaaag tgcttcattt agtctaaaca gaaactttat ggcttctgtc agttttcagg 26400
atcgtggccg caaacgggtg ccattatccc tctatgcccc tcttagggtt actaatgaca 26460
aacccctttc taaggtactt gcaaataatg ctgtacccac taataaagga aataaggacc 26520
agcaaattgg atactggaat gagcaaattc gctggcgcat gcgccgtggt gagcgaattg 26580
aacaaccttc caattggcat ttctactacc tcggaacagg acctcacgcc gacctccgct 26640
ataggactcg tactgagggt gttttctggg ttgctaaaga aggcgcaaag actgaaccca 26700
ctaacctggg tgtcagaaag gcgtctgaaa agccaattat tccaaatttc tctcaacagc 26760
ttcccagcgt agttgagatt gttgaaccta acacacctcc tacttcacgt gcaaattcac 26820
gtagcaggag tcgtggtaat ggcaacaaca ggtccagatc tccaagtaac aacagaggca 26880
ataaccagtc ccgcggtaat tcacagaatc gtggaaataa ccagggtcgt ggagcttctc 26940
agaacagagg aggcaataat aataacaata acaagtctcg taaccagtcc aagaacagaa 27000
accagtcaaa tgaccgtggt ggtgtaacat cacgcgatga tctggtggct gctgtcaagg 27060
atgcccttaa atctttgggt attggcgaaa accctgacaa gcttaagcaa cagcagaagc 27120
ccaaacagga aaggtctgac agcagcggca aaaatacacc taagaagaac aaatccagag 27180
ccacttcgaa agaacgtgac ctcaaagaca tcccagagtg gaggagaatt cccaagggcg 27240
aaaatagcgt agcagcttgc ttcggaccca ggggaggctt caaaaatttt ggagatgcgg 27300
aatttgtcga aaaaggtgtt gatgcctcag gctatgctca gatcgccagt ttagcaccaa 27360
atgttgcagc attgctcttt ggtggtaatg tggctgttcg tgagctagcg gactcttacg 27420
agattacata taattataaa atgactgtgc caaagtctga tccaaatgta gagcttcttg 27480
tttcacaggt ggatgcattt aaaactggga atgcaaaacc ccagagaaag aaggaaaaga 27540
agaacaagcg tgaaaccacg cagcagctga atgaagaggc catctacgat gatgtgggtg 27600
tgccatctga tgtgactcat gccaatttgg aatgggacac agctgttgat ggtggtgaca 27660
cggccgttga aattatcaac gagatcttcg acacaggaaa ttaaacaatg tttgactggc 27720
ttatcctggc tatgtcccag ggtagtgcca ttacactgtt attactgagt gtttttctag 27780
cgacttggct gctgggctat ggctttgccc tctaactagc ggtcttggtc ttgcacacaa 27840
cggtaagcca gtggtaatgt cagtgcaaga aggatattac catagcactg tcatgagggg 27900
aacgcagtac cttttcatct aaacctttgc acgagtaatc aaagatccgc ttgacgagcc 27960
tatatggaag agcgtgccag gtatttgact caaggactgt tagtaactga agacctgacg 28020
gtgttgatat ggatacac 28038

<210> SEQ ID NO 12
<211> LENGTH: 1386
<212> TYPE: PRT
<213> ORGANISM: Porcine epidemic diarrhea virus

<400> SEQUENCE: 12

Met Lys Ser Leu Thr Tyr Phe Trp Leu Phe Leu Pro Val Leu Ser Thr
1               5                   10                  15

Leu Ser Leu Pro Gln Asp Val Thr Arg Cys Ser Ala Asn Thr Asn Phe
            20                  25                  30

Arg Arg Phe Phe Ser Lys Phe Asn Val Gln Ala Pro Ala Val Val Val
        35                  40                  45

Leu Gly Gly Tyr Leu Pro Ile Gly Glu Asn Gln Gly Val Asn Ser Thr
    50                  55                  60

Trp Tyr Cys Ala Gly Gln His Pro Thr Ala Ser Gly Val His Gly Ile
65                  70                  75                  80

Phe Val Ser His Ile Arg Gly Gly His Gly Phe Glu Ile Gly Ile Ser
                85                  90                  95

Gln Glu Pro Phe Asp Pro Ser Gly Tyr Gln Leu Tyr Leu His Lys Ala
            100                 105                 110

```
Thr Asn Gly Asn Thr Asn Ala Thr Ala Arg Leu Arg Ile Cys Gln Phe
        115                 120                 125

Pro Ser Ile Lys Thr Leu Gly Pro Thr Ala Asn Asn Asp Val Thr Thr
    130                 135                 140

Gly Arg Asn Cys Leu Phe Asn Lys Ala Ile Pro Ala His Met Ser Glu
145                 150                 155                 160

His Ser Val Val Gly Ile Thr Trp Asp Asn Asp Arg Val Thr Val Phe
                165                 170                 175

Ser Asp Lys Ile Tyr Tyr Phe Tyr Phe Lys Asn Asp Trp Ser Arg Val
            180                 185                 190

Ala Thr Lys Cys Tyr Asn Ser Gly Gly Cys Ala Met Gln Tyr Val Tyr
        195                 200                 205

Glu Pro Thr Tyr Tyr Met Leu Asn Val Thr Ser Ala Gly Glu Asp Gly
    210                 215                 220

Ile Ser Tyr Gln Pro Cys Thr Ala Asn Cys Ile Gly Tyr Ala Ala Asn
225                 230                 235                 240

Val Phe Ala Thr Glu Pro Asn Gly His Ile Pro Glu Gly Phe Ser Phe
                245                 250                 255

Asn Asn Trp Phe Leu Leu Ser Asn Asp Ser Thr Leu Val His Gly Lys
            260                 265                 270

Val Val Ser Asn Gln Pro Leu Leu Val Asn Cys Leu Leu Ala Ile Pro
        275                 280                 285

Lys Ile Tyr Gly Leu Gly Gln Phe Phe Ser Phe Asn Gln Thr Ile Asp
    290                 295                 300

Gly Val Cys Asn Gly Ala Ala Val Gln Arg Ala Pro Glu Ala Leu Arg
305                 310                 315                 320

Phe Asn Ile Asn Asp Thr Ser Val Ile Leu Ala Glu Gly Ser Ile Val
                325                 330                 335

Leu His Thr Ala Leu Gly Thr Asn Phe Ser Phe Val Cys Ser Asn Ser
            340                 345                 350

Ser Asn Pro His Leu Ala Thr Phe Ala Ile Pro Leu Gly Ala Thr Gln
        355                 360                 365

Val Pro Tyr Tyr Cys Phe Leu Lys Val Asp Thr Tyr Asn Ser Thr Val
    370                 375                 380

Tyr Lys Phe Leu Ala Val Leu Pro Pro Thr Val Arg Glu Ile Val Ile
385                 390                 395                 400

Thr Lys Tyr Gly Asp Val Tyr Val Asn Gly Phe Gly Tyr Leu His Leu
                405                 410                 415

Gly Leu Leu Asp Ala Val Thr Ile Asn Phe Thr Gly His Gly Thr Asp
            420                 425                 430

Asp Asp Val Ser Gly Phe Trp Thr Ile Ala Ser Thr Asn Phe Val Asp
        435                 440                 445

Ala Leu Ile Glu Val Gln Gly Thr Ala Ile Gln Arg Ile Leu Tyr Cys
    450                 455                 460

Asp Asp Pro Val Ser Gln Leu Lys Cys Ser Gln Val Ala Phe Asp Leu
465                 470                 475                 480

Asp Asp Gly Phe Tyr Pro Ile Ser Ser Arg Asn Leu Leu Ser His Glu
                485                 490                 495

Gln Pro Ile Ser Phe Val Thr Leu Pro Ser Phe Asn Asp His Ser Phe
            500                 505                 510

Val Asn Ile Thr Val Ser Ala Ser Phe Gly Gly His Ser Gly Ala Asn
        515                 520                 525
```

-continued

```
Leu Ile Ala Ser Asp Thr Thr Ile Asn Gly Phe Ser Ser Phe Cys Val
    530                 535                 540

Asp Thr Arg Gln Phe Thr Ile Ser Leu Phe Tyr Asn Val Thr Asn Ser
545                 550                 555                 560

Tyr Gly Tyr Val Ser Lys Ser Gln Asp Ser Asn Cys Pro Phe Thr Leu
                565                 570                 575

Gln Ser Val Asn Asp Tyr Leu Ser Phe Ser Lys Phe Cys Val Ser Thr
            580                 585                 590

Ser Leu Leu Ala Ser Ala Cys Thr Ile Asp Leu Phe Gly Tyr Pro Glu
        595                 600                 605

Phe Gly Ser Gly Val Lys Phe Thr Ser Leu Tyr Phe Gln Phe Thr Lys
    610                 615                 620

Gly Glu Leu Ile Thr Gly Thr Pro Lys Pro Leu Glu Gly Val Thr Asp
625                 630                 635                 640

Val Ser Phe Met Thr Leu Asp Val Cys Thr Lys Tyr Thr Ile Tyr Gly
                645                 650                 655

Phe Lys Gly Glu Gly Ile Ile Thr Leu Thr Asn Ser Ser Phe Leu Ala
            660                 665                 670

Gly Val Tyr Tyr Thr Ser Asp Ser Gly Gln Leu Leu Ala Phe Lys Asn
        675                 680                 685

Val Thr Ser Gly Ala Val Tyr Ser Val Thr Pro Cys Ser Phe Ser Glu
    690                 695                 700

Gln Ala Ala Tyr Val Asp Asp Asp Ile Val Gly Val Ile Ser Ser Leu
705                 710                 715                 720

Ser Ser Ser Thr Phe Asn Ser Thr Arg Glu Leu Pro Gly Phe Phe Tyr
                725                 730                 735

His Ser Asn Asp Gly Ser Asn Cys Thr Glu Pro Val Leu Val Tyr Ser
            740                 745                 750

Asn Ile Gly Val Cys Lys Ser Gly Ser Ile Gly Tyr Val Pro Ser Gln
        755                 760                 765

Ser Gly Gln Val Lys Ile Ala Pro Thr Val Thr Gly Asn Ile Ser Ile
    770                 775                 780

Pro Thr Asn Phe Ser Met Ser Ile Arg Thr Glu Tyr Leu Gln Leu Tyr
785                 790                 795                 800

Asn Thr Pro Val Ser Val Asp Cys Ala Thr Tyr Val Cys Asn Gly Asn
                805                 810                 815

Ser Arg Cys Lys Gln Leu Leu Thr Gln Tyr Thr Ala Ala Cys Lys Thr
            820                 825                 830

Ile Glu Ser Ala Leu Gln Leu Ser Ala Arg Leu Glu Ser Val Glu Val
        835                 840                 845

Asn Ser Met Leu Thr Ile Ser Glu Glu Ala Leu Gln Leu Ala Thr Ile
    850                 855                 860

Ser Ser Phe Asn Gly Asp Gly Tyr Asn Phe Thr Asn Val Leu Gly Val
865                 870                 875                 880

Ser Val Tyr Asp Pro Ala Ser Gly Arg Val Val Gln Lys Arg Ser Phe
                885                 890                 895

Ile Glu Asp Leu Leu Phe Asn Lys Val Val Thr Asn Gly Leu Gly Thr
            900                 905                 910

Val Asp Glu Asp Tyr Lys Arg Cys Ser Asn Gly Arg Ser Val Ala Asp
        915                 920                 925

Leu Val Cys Ala Gln Tyr Tyr Ser Gly Val Met Val Leu Pro Gly Val
    930                 935                 940

Val Asp Ala Glu Lys Leu His Met Tyr Ser Ala Ser Leu Ile Gly Gly
```

-continued

```
945                 950                 955                 960

Met Val Leu Gly Gly Phe Thr Ser Ala Ala Ala Leu Pro Phe Ser Tyr
                965                 970                 975

Ala Val Gln Ala Arg Leu Asn Tyr Leu Ala Leu Gln Thr Asp Val Leu
            980                 985                 990

Gln Arg Asn Gln Gln Leu Leu Ala  Glu Ser Phe Asn Ser  Ala Ile Gly
        995                 1000                1005

Asn Ile  Thr Ser Ala Phe Glu  Ser Val Lys Glu Ala  Ile Ser Gln
    1010                 1015                 1020

Thr Ser  Lys Gly Leu Asn Thr  Val Ala His Ala Leu  Thr Lys Val
    1025                 1030                 1035

Gln Glu  Val Val Asn Ser Gln  Gly Ala Ala Leu Thr  Gln Leu Thr
    1040                 1045                 1050

Val Gln  Leu Gln His Asn Phe  Gln Ala Ile Ser Ser  Ser Ile Asp
    1055                 1060                 1065

Asp Ile  Tyr Ser Arg Leu Asp  Ile Leu Ser Ala Asp  Val Gln Val
    1070                 1075                 1080

Asp Arg  Leu Ile Thr Gly Arg  Leu Ser Ala Leu Asn  Ala Phe Val
    1085                 1090                 1095

Ala Gln  Thr Leu Thr Lys Tyr  Thr Glu Val Gln Ala  Ser Arg Lys
    1100                 1105                 1110

Leu Ala  Gln Gln Lys Val Asn  Glu Cys Val Lys Ser  Gln Ser Gln
    1115                 1120                 1125

Arg Tyr  Gly Phe Cys Gly Gly  Asp Gly Glu His Ile  Phe Ser Leu
    1130                 1135                 1140

Val Gln  Ala Ala Pro Gln Gly  Leu Leu Phe Leu His  Thr Val Leu
    1145                 1150                 1155

Val Pro  Ser Asp Phe Val Asp  Val Ile Ala Ile Ala  Gly Leu Cys
    1160                 1165                 1170

Val Asn  Asp Glu Ile Ala Leu  Thr Leu Arg Glu Pro  Gly Leu Val
    1175                 1180                 1185

Leu Phe  Thr His Glu Leu Gln  Asn His Thr Ala Thr  Glu Tyr Phe
    1190                 1195                 1200

Val Ser  Ser Arg Arg Met Phe  Glu Pro Arg Lys Pro  Thr Val Ser
    1205                 1210                 1215

Asp Phe  Val Gln Ile Glu Ser  Cys Val Val Thr Tyr  Val Asn Leu
    1220                 1225                 1230

Thr Arg  Asp Gln Leu Pro Asp  Val Ile Pro Asp Tyr  Ile Asp Val
    1235                 1240                 1245

Asn Lys  Thr Leu Asp Glu Ile  Leu Ala Ser Leu Pro  Asn Arg Thr
    1250                 1255                 1260

Gly Pro  Ser Leu Pro Leu Asp  Val Phe Asn Ala Thr  Tyr Leu Asn
    1265                 1270                 1275

Leu Thr  Gly Glu Ile Ala Asp  Leu Glu Gln Arg Ser  Glu Ser Leu
    1280                 1285                 1290

Arg Asn  Thr Thr Glu Glu Leu  Gln Ser Leu Ile Tyr  Asn Ile Asn
    1295                 1300                 1305

Asn Thr  Leu Val Asp Leu Glu  Trp Leu Asn Arg Val  Glu Thr Tyr
    1310                 1315                 1320

Ile Lys  Trp Pro Trp Trp Val  Trp Leu Ile Ile Phe  Ile Val Leu
    1325                 1330                 1335

Ile Phe  Val Val Ser Leu Leu  Val Phe Cys Cys Ile  Ser Thr Gly
    1340                 1345                 1350
```

Cys Cys Gly Cys Cys Gly Cys Cys Cys Ala Cys Phe Ser Gly Cys
1355 1360 1365

Cys Arg Gly Pro Arg Leu Gln Pro Tyr Glu Val Phe Glu Lys Val
1370 1375 1380

His Val Gln
1385

<210> SEQ ID NO 13
<211> LENGTH: 4161
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 13
atgaagtctt taacctactt ctggttgttc ttaccagtac tttcaacact tagcctacca 60
caagatgtca ccaggtgctc agctaacact aattttaggc ggttcttttc aaaatttaat 120
gttcaggcgc ctgcagttgt tgtactgggc ggttatctac ctattggtga aaaccagggt 180
gtcaattcaa cttggtactg tgctggccaa catccaactg ctagtggcgt tcatggtatc 240
tttgttagcc atattagagg tggtcatggc tttgagattg gcatttcgca agagcctttt 300
gaccctagtg gttaccagct ttatttacat aaggctacta acggtaacac taatgctact 360
gcgcgactgc gcatttgcca gtttcctagc attaaaacat tgggccccac tgctaataat 420
gatgttacaa taggtcgtaa ttgcctattt aacaaagcca tcccagctca tatgagtgaa 480
catagtgttg tcggcataac atgggataat gatcgtgtca ctgtcttttc tgacaagatc 540
tattattttt attttaaaaa tgattggtcc cgtgttgcga caaagtgtta caacagtgga 600
ggttgtgcta tgcaatatgt ttacgaaccc acctattaca tgcttaatgt tactagtgct 660
ggtgaggatg gtatttctta tcaaccctgt acagctaatt gcattggtta tgctgccaat 720
gtatttgcta ctgagcccaa tggccacata ccagaaggtt ttagttttaa taattggttt 780
cttttgtcca atgattccac tttggtgcat ggtaaggtgg tttccaacca accattgttg 840
gtcaattgtc ttttggccat tcctaagatt tatggactag gccaattttt ctcctttaat 900
caaacgatcg atggtgtttg taatggagct gctgtgcagc gtgcaccaga ggctctgagg 960
tttaatatta atgacacctc tgtcattctt gctgaaggct caattgtact tcatactgct 1020
ttaggaacaa atttttcttt tgtttgcagt aattccccaa atcctcactt agccaccttc 1080
gccatacctc tgggtgctac ccaagtacct tattattgtt ttcttaaagt ggatacttac 1140
aactccactg tttataaatt tttggctgtt ttacctccta ccgtcaggga aattgtcatc 1200
accaagtatg gtgatgttta tgtcaatggg tttggatact tgcatctcgg tttgttggat 1260
gctgtcacaa ttaatttcac tggtcatggc actgacgatg atgtttctgg tttttggacc 1320
atagcatcga ctaattttgt tgatgcactc atcgaagttc aaggaaccgc cattcagcgt 1380
attctttatt gtgatgatcc tgttagccaa ctcaagtgtt ctcaggttgc ttttgacctt 1440
gacgatggtt tttaccctat ttcttctaga aaccttctga gtcatgaaca gccaatttct 1500
tttgttactc tgccatcatt taatgatcat tcttttgtta acattactgt atctgcttcc 1560
tttggtggtc atagtggtgc caaccttatt gcatctgaca ctactatcaa tgggtttagt 1620
tctttctgtg ttgacactag acaatttacc atttcactgt tttataacgt tacaaacagt 1680
tatggttatg tgtctaaatc acaggacagt aattgccctt tcaccttgca atctgttaat 1740

-continued

```
gattacctgt cttttagcaa attttgtgtt tccaccagcc ttttggctag tgcctgtacc   1800
atagatcttt ttggttaccc tgagtttggt agtggtgtta agtttacgtc cctttacttt   1860
caattcacaa agggtgagtt gattactggc acgactaaac cacttgaagg tgtcacggac   1920
gtttctttta tgactctgga tgtgtgtacc aagtatacta tctatggctt taaaggtgag   1980
ggtatcatta cccttacaaa ttctagcttt ttggcaggtg tttattacac atctgtttct   2040
ggacagttgt tagcctttaa gaatgtcact agtggtgctg tttattctgt tacgccatgt   2100
tctttttcag agcaggctgc atatgttgat gatgatatag tgggtgttat ttctagtttg   2160
tctagctcca cttttaacag tactagggag ttgcctggtt tcttctacca ttctaatgat   2220
ggctctaatt gtacagagcc tgtgttggtg tatagtaaca taggtgtttg taaatctggc   2280
agtattggct acgtcccatc tcagtctggc caagtcaaga ttgcacccac ggttactggg   2340
aatattagta ttcccaccaa ctttagtatg agtattagga cagaatattt acagctttac   2400
aacacgcctg ttagtgttga ttgtgccaca tatgtttgta atggtaactc tcgttgtaaa   2460
caattactca cccagtacac tgcagcatgt aagaccatag agtcagcatt acractcagc   2520
gctaggcttg agtctgttga agttaactct atgcttacta tttctgaaga ggctctacag   2580
ttagctacca ttagttcgtt taatggtgat ggatataatt ttactaatgt gctgggtgtt   2640
tctgtgtatg atcctgcaag gggcagggtg gtacaaaaaa ggtcttttat tgaagacctg   2700
ctttttaata aagtggttac taatggcctt ggtactgttg atgaagacta taagcgctgt   2760
tctaatggtc gctctgtggc agatctagtc tgtgcacagt attactctgg tgtcatggta   2820
ctacctggtg ttgttgacgc tgagaagctt cacatgtata gtgcgtctct catcggtggt   2880
atggtgctag gaggttttac ttctgcagcg gcattgcctt ttagctatgc tgttcaagct   2940
agactcaatt atcttgctct acagacggat gttctacagc ggaaccagca attgcttgct   3000
gagtctttta actctgctat tggtaatata acttcagcct ttgagagtgt taaagaggct   3060
attagtcaaa cttccaaggg tttgaacact gtggctcatg cgcttactaa ggttcaagag   3120
gttgttaact cgcagggtgc agctttgact caacttaccg tacagctgca acacaacttc   3180
caagccattt ctagttctat tgatgacatt tactctcgac tggacattct ttcagccgat   3240
gttcaggttg accgtctcat caccggcaga ttatcagcac ttaatgcttt tgttgctcaa   3300
accctcacta agtatactga ggttcaggct agcaggaagt tagcacagca aaaggttaat   3360
gagtgcgtta aatcgcaatc ccagcgttat ggtttttgtg gtggtgatgg cgagcacatt   3420
ttctctctgg tacaggcagc acctcagggc ctgctgtttt tacatacagt acttgtaccg   3480
agtgattttg tagatgttat tgccatcgct ggcttatgcg ttaacgatga aattgccttg   3540
actctacgtg agcctggctt agtcttgttt acgcatgaac ttcaaaatca tactgcgacg   3600
gaatattttg tttcatcgcg acgtatgttt gaacctagaa aacctaccgt tagtgatttt   3660
gttcaaattg agagttgtgt ggtcacctat gtcaatttga ctagagacca actaccagat   3720
gtaatcccag attacatcga tgttaacaaa acacttgatg agattttagc ttctctgccc   3780
aatagaactg gtccaagtct tcctttagat gtttttaatg ccacttatct taatctcact   3840
ggtgaaattg cagatttaga gcagcgttca gagtctctcc gtaatactac agaggagctc   3900
caaagtctta tatataatat caacaacaca ctagttgacc ttgagtggct caaccgagtt   3960
gagacatata tcaagtggcc gtggtgggtt tggttgatta ttttcattgt tctcatcttt   4020
gttgtgtcat tactagtgtt ctgctgcatt tccacgggtt gttgtggatg ctgcggctgc   4080
tgctgtgctt gtttctcagg ttgttgtagg ggtcctagac ttcaacctta cgaagttttt   4140
```

gaaaaggtcc acgtgcagtg a 4161

<210> SEQ ID NO 14
<211> LENGTH: 1386
<212> TYPE: PRT
<213> ORGANISM: Porcine epidemic diarrhea virus
<220> FEATURE:
<221> NAME/KEY: MOD_RES
<222> LOCATION: (838)..(838)
<223> OTHER INFORMATION: Any amino acid

<400> SEQUENCE: 14

Met Lys Ser Leu Thr Tyr Phe Trp Leu Phe Leu Pro Val Leu Ser Thr
1               5                   10                  15

Leu Ser Leu Pro Gln Asp Val Thr Arg Cys Ser Ala Asn Thr Asn Phe
            20                  25                  30

Arg Arg Phe Phe Ser Lys Phe Asn Val Gln Ala Pro Ala Val Val Val
        35                  40                  45

Leu Gly Gly Tyr Leu Pro Ile Gly Glu Asn Gln Gly Val Asn Ser Thr
    50                  55                  60

Trp Tyr Cys Ala Gly Gln His Pro Thr Ala Ser Gly Val His Gly Ile
65                  70                  75                  80

Phe Val Ser His Ile Arg Gly Gly His Gly Phe Glu Ile Gly Ile Ser
                85                  90                  95

Gln Glu Pro Phe Asp Pro Ser Gly Tyr Gln Leu Tyr Leu His Lys Ala
            100                 105                 110

Thr Asn Gly Asn Thr Asn Ala Thr Ala Arg Leu Arg Ile Cys Gln Phe
        115                 120                 125

Pro Ser Ile Lys Thr Leu Gly Pro Thr Ala Asn Asn Asp Val Thr Ile
    130                 135                 140

Gly Arg Asn Cys Leu Phe Asn Lys Ala Ile Pro Ala His Met Ser Glu
145                 150                 155                 160

His Ser Val Val Gly Ile Thr Trp Asp Asn Asp Arg Val Thr Val Phe
                165                 170                 175

Ser Asp Lys Ile Tyr Tyr Phe Tyr Phe Lys Asn Asp Trp Ser Arg Val
            180                 185                 190

Ala Thr Lys Cys Tyr Asn Ser Gly Gly Cys Ala Met Gln Tyr Val Tyr
        195                 200                 205

Glu Pro Thr Tyr Tyr Met Leu Asn Val Thr Ser Ala Gly Glu Asp Gly
    210                 215                 220

Ile Ser Tyr Gln Pro Cys Thr Ala Asn Cys Ile Gly Tyr Ala Ala Asn
225                 230                 235                 240

Val Phe Ala Thr Glu Pro Asn Gly His Ile Pro Glu Gly Phe Ser Phe
                245                 250                 255

Asn Asn Trp Phe Leu Leu Ser Asn Asp Ser Thr Leu Val His Gly Lys
            260                 265                 270

Val Val Ser Asn Gln Pro Leu Leu Val Asn Cys Leu Leu Ala Ile Pro
        275                 280                 285

Lys Ile Tyr Gly Leu Gly Gln Phe Phe Ser Phe Asn Gln Thr Ile Asp
    290                 295                 300

Gly Val Cys Asn Gly Ala Ala Val Gln Arg Ala Pro Glu Ala Leu Arg
305                 310                 315                 320

Phe Asn Ile Asn Asp Thr Ser Val Ile Leu Ala Glu Gly Ser Ile Val
                325                 330                 335

Leu His Thr Ala Leu Gly Thr Asn Phe Ser Phe Val Cys Ser Asn Ser

```
            340                 345                 350

Pro Asn Pro His Leu Ala Thr Phe Ala Ile Pro Leu Gly Ala Thr Gln
        355                 360                 365

Val Pro Tyr Tyr Cys Phe Leu Lys Val Asp Thr Tyr Asn Ser Thr Val
    370                 375                 380

Tyr Lys Phe Leu Ala Val Leu Pro Pro Thr Val Arg Glu Ile Val Ile
385                 390                 395                 400

Thr Lys Tyr Gly Asp Val Tyr Val Asn Gly Phe Gly Tyr Leu His Leu
                405                 410                 415

Gly Leu Leu Asp Ala Val Thr Ile Asn Phe Thr Gly His Gly Thr Asp
            420                 425                 430

Asp Asp Val Ser Gly Phe Trp Thr Ile Ala Ser Thr Asn Phe Val Asp
        435                 440                 445

Ala Leu Ile Glu Val Gln Gly Thr Ala Ile Gln Arg Ile Leu Tyr Cys
    450                 455                 460

Asp Asp Pro Val Ser Gln Leu Lys Cys Ser Gln Val Ala Phe Asp Leu
465                 470                 475                 480

Asp Asp Gly Phe Tyr Pro Ile Ser Ser Arg Asn Leu Leu Ser His Glu
                485                 490                 495

Gln Pro Ile Ser Phe Val Thr Leu Pro Ser Phe Asn Asp His Ser Phe
            500                 505                 510

Val Asn Ile Thr Val Ser Ala Ser Phe Gly Gly His Ser Gly Ala Asn
        515                 520                 525

Leu Ile Ala Ser Asp Thr Thr Ile Asn Gly Phe Ser Ser Phe Cys Val
    530                 535                 540

Asp Thr Arg Gln Phe Thr Ile Ser Leu Phe Tyr Asn Val Thr Asn Ser
545                 550                 555                 560

Tyr Gly Tyr Val Ser Lys Ser Gln Asp Ser Asn Cys Pro Phe Thr Leu
                565                 570                 575

Gln Ser Val Asn Asp Tyr Leu Ser Phe Ser Lys Phe Cys Val Ser Thr
            580                 585                 590

Ser Leu Leu Ala Ser Ala Cys Thr Ile Asp Leu Phe Gly Tyr Pro Glu
        595                 600                 605

Phe Gly Ser Gly Val Lys Phe Thr Ser Leu Tyr Phe Gln Phe Thr Lys
    610                 615                 620

Gly Glu Leu Ile Thr Gly Thr Thr Lys Pro Leu Glu Gly Val Thr Asp
625                 630                 635                 640

Val Ser Phe Met Thr Leu Asp Val Cys Thr Lys Tyr Thr Ile Tyr Gly
                645                 650                 655

Phe Lys Gly Glu Gly Ile Ile Thr Leu Thr Asn Ser Ser Phe Leu Ala
            660                 665                 670

Gly Val Tyr Tyr Thr Ser Val Ser Gly Gln Leu Leu Ala Phe Lys Asn
        675                 680                 685

Val Thr Ser Gly Ala Val Tyr Ser Val Thr Pro Cys Ser Phe Ser Glu
    690                 695                 700

Gln Ala Ala Tyr Val Asp Asp Asp Ile Val Gly Val Ile Ser Ser Leu
705                 710                 715                 720

Ser Ser Ser Thr Phe Asn Ser Thr Arg Glu Leu Pro Gly Phe Phe Tyr
                725                 730                 735

His Ser Asn Asp Gly Ser Asn Cys Thr Glu Pro Val Leu Val Tyr Ser
            740                 745                 750

Asn Ile Gly Val Cys Lys Ser Gly Ser Ile Gly Tyr Val Pro Ser Gln
        755                 760                 765
```

-continued

```
Ser Gly Gln Val Lys Ile Ala Pro Thr Val Thr Gly Asn Ile Ser Ile
    770                 775                 780

Pro Thr Asn Phe Ser Met Ser Ile Arg Thr Glu Tyr Leu Gln Leu Tyr
785                 790                 795                 800

Asn Thr Pro Val Ser Val Asp Cys Ala Thr Tyr Val Cys Asn Gly Asn
                805                 810                 815

Ser Arg Cys Lys Gln Leu Leu Thr Gln Tyr Thr Ala Ala Cys Lys Thr
            820                 825                 830

Ile Glu Ser Ala Leu Xaa Leu Ser Ala Arg Leu Glu Ser Val Glu Val
        835                 840                 845

Asn Ser Met Leu Thr Ile Ser Glu Glu Ala Leu Gln Leu Ala Thr Ile
    850                 855                 860

Ser Ser Phe Asn Gly Asp Gly Tyr Asn Phe Thr Asn Val Leu Gly Val
865                 870                 875                 880

Ser Val Tyr Asp Pro Ala Arg Gly Arg Val Val Gln Lys Arg Ser Phe
                885                 890                 895

Ile Glu Asp Leu Leu Phe Asn Lys Val Val Thr Asn Gly Leu Gly Thr
            900                 905                 910

Val Asp Glu Asp Tyr Lys Arg Cys Ser Asn Gly Arg Ser Val Ala Asp
        915                 920                 925

Leu Val Cys Ala Gln Tyr Tyr Ser Gly Val Met Val Leu Pro Gly Val
    930                 935                 940

Val Asp Ala Glu Lys Leu His Met Tyr Ser Ala Ser Leu Ile Gly Gly
945                 950                 955                 960

Met Val Leu Gly Gly Phe Thr Ser Ala Ala Ala Leu Pro Phe Ser Tyr
                965                 970                 975

Ala Val Gln Ala Arg Leu Asn Tyr Leu Ala Leu Gln Thr Asp Val Leu
            980                 985                 990

Gln Arg Asn Gln Gln Leu Leu Ala  Glu Ser Phe Asn Ser  Ala Ile Gly
        995                 1000                 1005

Asn Ile  Thr Ser Ala Phe Glu  Ser Val Lys Glu Ala  Ile Ser Gln
    1010                 1015                 1020

Thr Ser  Lys Gly Leu Asn Thr  Val Ala His Ala Leu  Thr Lys Val
    1025                 1030                 1035

Gln Glu  Val Val Asn Ser Gln  Gly Ala Ala Leu Thr  Gln Leu Thr
    1040                 1045                 1050

Val Gln  Leu Gln His Asn Phe  Gln Ala Ile Ser Ser  Ser Ile Asp
    1055                 1060                 1065

Asp Ile  Tyr Ser Arg Leu Asp  Ile Leu Ser Ala Asp  Val Gln Val
    1070                 1075                 1080

Asp Arg  Leu Ile Thr Gly Arg  Leu Ser Ala Leu Asn  Ala Phe Val
    1085                 1090                 1095

Ala Gln  Thr Leu Thr Lys Tyr  Thr Glu Val Gln Ala  Ser Arg Lys
    1100                 1105                 1110

Leu Ala  Gln Gln Lys Val Asn  Glu Cys Val Lys Ser  Gln Ser Gln
    1115                 1120                 1125

Arg Tyr  Gly Phe Cys Gly Gly  Asp Gly Glu His Ile  Phe Ser Leu
    1130                 1135                 1140

Val Gln  Ala Ala Pro Gln Gly  Leu Leu Phe Leu His  Thr Val Leu
    1145                 1150                 1155

Val Pro  Ser Asp Phe Val Asp  Val Ile Ala Ile Ala  Gly Leu Cys
    1160                 1165                 1170
```

```
Val Asn  Asp Glu Ile Ala Leu  Thr Leu Arg Glu Pro  Gly Leu Val
    1175                 1180                 1185

Leu Phe  Thr His Glu Leu Gln  Asn His Thr Ala Thr  Glu Tyr Phe
    1190                 1195                 1200

Val Ser  Ser Arg Arg Met Phe  Glu Pro Arg Lys Pro  Thr Val Ser
    1205                 1210                 1215

Asp Phe  Val Gln Ile Glu Ser  Cys Val Val Thr Tyr  Val Asn Leu
    1220                 1225                 1230

Thr Arg  Asp Gln Leu Pro Asp  Val Ile Pro Asp Tyr  Ile Asp Val
    1235                 1240                 1245

Asn Lys  Thr Leu Asp Glu Ile  Leu Ala Ser Leu Pro  Asn Arg Thr
    1250                 1255                 1260

Gly Pro  Ser Leu Pro Leu Asp  Val Phe Asn Ala Thr  Tyr Leu Asn
    1265                 1270                 1275

Leu Thr  Gly Glu Ile Ala Asp  Leu Glu Gln Arg Ser  Glu Ser Leu
    1280                 1285                 1290

Arg Asn  Thr Thr Glu Glu Leu  Gln Ser Leu Ile Tyr  Asn Ile Asn
    1295                 1300                 1305

Asn Thr  Leu Val Asp Leu Glu  Trp Leu Asn Arg Val  Glu Thr Tyr
    1310                 1315                 1320

Ile Lys  Trp Pro Trp Trp Val  Trp Leu Ile Ile Phe  Ile Val Leu
    1325                 1330                 1335

Ile Phe  Val Val Ser Leu Leu  Val Phe Cys Cys Ile  Ser Thr Gly
    1340                 1345                 1350

Cys Cys  Gly Cys Cys Gly Cys  Cys Cys Ala Cys Phe  Ser Gly Cys
    1355                 1360                 1365

Cys Arg  Gly Pro Arg Leu Gln  Pro Tyr Glu Val Phe  Glu Lys Val
    1370                 1375                 1380

His Val  Gln
    1385
```

<210> SEQ ID NO 15
<211> LENGTH: 27995
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 15

```
gacucuuguc uacucaauuc aacuaaacga aauuccuugu ccuuccggcc gcauguccau     60

gcugcuggaa gcugacgugg aauuucauua gguuugcuua aguagccauc gcaagugcug    120

ugcuguccuc uaguuccugg uuggcguucc gucgccuucu acauacuaga caaacagccu    180

uccuccgguu ccgucugggg guugugugga uaacuaguuc cgucuaguuu gaaaccagua    240

acugucggcu auggcuagca accauguuac auuggcuuuu gccaaugaug cagaaauuuc    300

agcuuuuggc uuuugcacug cuagugaagc cgucucauac uauucugagg ccgccgcuag    360

uggauuuaug caaugccguu ucguguccuu cgaucucgcu gacacuguug agggauugcu    420

ucccgaagac uaugucaugg ugguggucgg cacuaccaag cuuagugcgu auguggacac    480

uuuugguagc cgccccaaaa acauuuugug uuggcuguua uuuucuaacu guaauuacuu    540

ccucgaagag uuagagcuua cuuuuggucg ucgugguggu aacaucgugc caguugacca    600

auacaugugu ggcgcugacg guaaaccugu ucuucaggaa uccgaauggg aguauacaga    660

uuucuuugcu gacuccgaag acggucaacu caacauugcu gguaucacuu augugaaggc    720
```

```
cuggauugua gagcgaucgg augucucuua ugcgagucag aauuuaacau cuauuaaguc    780
uauuacuuac uguucaaccu augagcauac uuuuccugau gguacugcca ugaagguugc    840
acguacucca aagauuaaga agacuguugu cuugucugag ccacuugcua cuaucuacag    900
ggaaauuggu ucuccuuuug uggauaaugg gagcgaugcu cguucuauca uuaagagacc    960
aguguuccuc cacgcuuuug uuaaguguaa guguggguagu uaucauugga cuguuggguga   1020
uuggacuucc uaugucucca cuugcugugg cuuuaagugu aagccagucc uuguggcuuc   1080
augcucugcu acgccugguu cuguuguggu uacgcgcgcu ggugcuggca cuggguguuaa   1140
guauuacaac aacauguucc ugcgccaugu ggcagacauu gaugggguugg cauucuggcg   1200
aauucucaag gugcagucca aagacgaccu cgcuugcucu gguaaauucc uugaacacca   1260
ugaggaaggu uucacagauc cuugcuacuu uuugaaugac ucgagcauug cuacuaagcu   1320
caaguuugac auccuuagug gcaaguuuuc ugaugaaguc aaacaagcua ucuuugcugg   1380
ucauguuguu guuggcagcg cgmucguuga cauuguugac gaugcacugg gacagccuug   1440
guuuauacgu aagcuuggug accuugcaag ugcagcuugg gagcagcuua aggcugucgu   1500
uagaggccuu aaccuccugu cugaugaggu cgugcucuuu ggcaaaagac uuagcugugc   1560
cacucuuagu aucguuaacg guguuuuuga guucaucgcc gaagugccug agaaguuggc   1620
ugcggcuguu acaguuuuug ucaacuucuu gaaugagcuu uuugagucug ccugugacug   1680
cuuaaagguc ggagguaaaa ccuuuaacaa gguuggcucu uauguucuuu uugacaacgc   1740
auugguuaag cuugucaagg caaaaguucg cggcccacga caggcaggug uuugugaagu   1800
ucguuacaca agccuuguua uugggaguac uaccaaggug guuuccaagc gcguugaaaa   1860
ugccaaugug aaucucgucg ucguugacga ggaugugacc cucaacacca cuggucguac   1920
aguuguuguu gacggacuug cauucuucga gagugacggg uuuuacagac aucuugcuga   1980
ugcugacguu gucauugaac auccuguuua uaagucugcu ugugagcuca agccaguuuu   2040
ugagugugac ccaauaccug auuuuccuau gccuguggcc gcuaguguug cagagcuuug   2100
ugugcaaacu gaucuguugc uuaaaaauua caacacuccu uauaaaacuu acagcugcgu   2160
ugugagaggu gauaaguguu guaucacuug caccuuacau uucacagcac caaguuauau   2220
ggaggcugcu gcuaauuuug uagaccucug uaccaagaac auugguacug cugguuuuca   2280
ugaguuuuac auuacggccc augaacaaca ggaucugcaa ggguucguaa ccacuuguug   2340
cacgauguca gguuuugagu guuuuaugcc uauaaauccca caguguccag cagugcuuga   2400
agagauugau gguggguagca ucuggcgguc uuuuaucacu ggucuuaaua caaugugggga   2460
uuuuugcaag caucuuaaag ucagcuuugg acuagauggc auuguuguca cuguagcacg   2520
caaauuuaaa cgacuuggug cucucuuggc agaaauguau aacacuuacc uuucaacugu   2580
gguggaaaac uugguacugg ccggguguuag cuucaaguau uaugccacca gugucccaaa   2640
aauuguuuug ggcuguuguu uucacagugu uaaaagugguu cuugcaagug ccuuccagau   2700
uccuguccag gcaggcguug agaaguuuaa agucuuccuu aacuguguuc acccuguugu   2760
accacguguc auugaaacuu cuuuugugga auuagaagag acgacauuua aaccaccagc   2820
acucaauggu aguauugcua uuguugaugg cuuugcuuuc uauuaugaug gaacacuaua   2880
cuaucccacc gaugguaaua gcguuguucc uaucugcuuu aagaagaaag gugguggguga   2940
ugucaaauuc ucugaugaag ucucuguuaa aaccauugac ccaguuuaua aggucucccu   3000
ugaauuugag uucgagucug agacuauuau ggcugugcuu aauaaggcug uugguaauug   3060
```

-continued

```
uaucaagguu acaggugguu gggacgaugu uguugaguau aucaauguug ccauugaggu   3120
ucuuaaagau cacaucgaug ugccuaagua cuacaucuau gaugaggaag guggcaccga   3180
uccuaaucug cccguaaugg uuucucagug gccguugaau gaugacacga ucucacagga   3240
ucugcuugau guugaaguug uuacugaugc gccaguugau uucgagggug augaaguaga   3300
cuccucugac ccugwuaagg uggcagacgu ggcuaacucu gagccugagg augacggucu   3360
uaauguagcu ccugaaacaa auguagaguc ugaaguugag gaaguugccg caaccuuguc   3420
cuuuaaagau acaccuucca caguuacuaa ggauccuuuu gcuuuugacu uugcaagcua   3480
uggaggacuu aagguuuuaa gacaaucuca uaacaacugc uggguuacuu cuaccuuggu   3540
gcagcuacaa uugcuuggca ucguugauga cccugcaaug gagcuuuuua gugcugguag   3600
aguuggucca augguucgca aaugcuauga gucacaaaag gcuaucuugg gaucuuuggg   3660
ugauguguucg gcuugccuag agucucugac uaaggaccua cacacacuua agauuaccug   3720
uucuguaguc ugugguugug guacugguga acguaucuau gaugguugug cuuuucguau   3780
gacgccaacu uuggaaccgu ucccauaugg ugcuugugcu cagugugcuc aaguuuugau   3840
gcacacuuuu aaaaguauug uuggcaccgg caucuuuugu cgagauacua cugcucucuc   3900
cuuggauucu uugguuguaa aaccucuuug ugcggcugcu uuuauaggca aggauagugg   3960
ucauuauguc acuaacuuuu augaugcugc uauggcuauu gaugguuaug gucgucauca   4020
gauaaaguau gacacacuga acacuauuug uguuaaagac guuaauugga cagcaccuuu   4080
ugucccagac guugagccug uauuggagcc uguugucaaa ccuuucuauu cuuauaagaa   4140
uguugauuuu uaccaaggag auuuuaguga ccuuguuaaa cuuccaugug auuuuguugu   4200
uaaugcugca aaugagaauu ugucucacgg uggcggcaua gcaaaggcca uugauguuua   4260
uaccaagggc auguugcaga agugcucgaa ugauuacauu aaagcacacg gucccauuaa   4320
aguuggacgu ggugucaugu uggaggcauu aggucuuaag gucuuuaaug uuguuggucc   4380
acguaagggu aagcaugcac cugagcuucu uguuaaggcu uauaaguccg uuuuugcuaa   4440
uucaggugu gcucuuacac cuuugauuag uguuggaauu uuuaguguuc cuuuggaaga   4500
aucuuuaucu gcuuuucuug caugugguugg ugaucgccac uguaagugcu uuuguuauag   4560
ugacaaagag cgcgaggcga ucauuaauua cauggauggc uugguagaug cuauuuucaa   4620
agaugcacuu guugauacua cuccugucca ggaagauguu caacaaguuu cacaaaaacc   4680
aguuuugccu aauuuugaac cuuucaggau ugaaggugcu caugcuuucu augagugcaa   4740
cccugaaggu uugaugucau uaggugcuga caagcuggug uuguuuacaa auuccaauuu   4800
ggauuuuugu agcguuggua agugucuuaa caaugugacu ggcggugcau ugcuugaagc   4860
cauaaaugua uuuaaaaaga guaacaaaac agugccugcu ggcaacugug uuacuuuuga   4920
gugugcagau augauuucua uuacuauggu aguauugcca ucugacggug augcuaauua   4980
ugacaaaaau uaugcacgcg ccgucgucaa gguaucuaag cuuaaaggca aguuauugcu   5040
ugcuguuggu gaugccaugu uguauuccaa guugucccac cucagcgugu uagguuucgu   5100
auccacaccu gaugaugugg agcguuucua cgcaaauaag agugugguua uuaaaguuac   5160
ugaggauaca cguaguguua agacuguuaa aguagaaucc acuguuacuu auggacaaca   5220
aauuggaccu ugucuuguua augacaccgu ugucacagac aacaaaccug uuguugcuga   5280
uguuguagcu aagguuguac caagugcuaa uugggauuca cauuaugguu uugauaaggc   5340
uggugaguuc cacaugcuag accauacugg guuugccuuu ccuagugaag uuguuaacgg   5400
uaggcgugug cuuaaaacca cagauaauaa cuguugggguu aauguuacau guuuacaauu   5460
```

-continued

```
acaguuugcu agauuuaggu ucaagucagc aggucuacag gcuauguggg aguccuauug   5520
uacuggugau guugcuaugu uugugcauug guuguacugg cuuacuggug uugacaaagg   5580
ucagccuagu gauucagaaa augcacuuaa cauguugucu aaguacauug uuccugcugg   5640
uucugucacu auugaacgug ucacgcauga cgguuguugu uguaguaagc guguugucac   5700
ugcaccaguu gugaaugcua gcguguugaa gcuuggcguc gaggaugguc uuuguccaca   5760
uggucuuaac uacauugaca aaguuguugu aguuaaaggu acuacaauug uugucaaugu   5820
uggaaaaccu guaguggcac caucgcaccu cuuucuuaag gguguuuccu acacaacauu   5880
ccuagauaau gguaacggug uugccggcca uuauacuguu uuugaucaug acacugguau   5940
ggugcaugau ggagauguuu uuguaccagg ugaucucaau gugucuccug uuacaaaugu   6000
ugucgucuca gagcagacgg cuguugugau uaaagacccu gugaagaaag uagaguuaga   6060
cgcuacaaag cuguuagaca cuaugaauua ugcaucggaa agauucuuuu ccuuugguga   6120
uuuuauguca cguaauuuaa uuacaguguu uuuguacauc cuuaguauuu ugggucucug   6180
uuuuagggcc uuucguaaga gggauguuaa aguucuagcu gguguacccc aacguacugg   6240
uauuauauug cguaaaagug ugcgcuauaa ugcaaaggcu uugggugucu ucuucaagcu   6300
aaaacuuuau ugguucaaag uucuugguaa guuuaguuug gguauuuaug cauuguaugc   6360
auuacuauuc augacaauac gcuuuacacc uauaggugc ccuguuugug augauguugu   6420
ugcugguuau gcuaauucua guuuugacaa gaaugaguau ugcaacagug uuauuuguaa   6480
ggucugucuc uaugguacc aggaacuuuc ggacuucucu cacacacagg uaguauggca   6540
acaccuuaga gacccauuaa uugguaaugu gaugccuuuc uuuuauuugg cauuucuggc   6600
aauuuuuggg gguguuuaug uaaaggcuau uacucucuau uuuauuuucc aguaucuuaa   6660
cauacuuggu guguuuuugg gccuacaaca guccauuugg uuuuugcagc uugugccuuu   6720
ugaugucuuu ggugacgaga ucgucgucuu uuucaucguu acacgcguau ugauguuccu   6780
uaagcauguu uuccuuggcu gcgauaaggc aucuugugug gcuugcucua agagugcucg   6840
ccuuaagcgc guuccugucc agacuauuuu ucaggguacu agcaaauccu ucuacguaca   6900
ugccaauggu gguucuaagu ucuguaagaa gcacaauuuc uuuuguuuaa auugugauuc   6960
uuauggucca ggcugcacuu uuauuaauga cgucauugca acugaaguug guaauguugu   7020
caaacuuaau gugcaaccga cagguccugc cacuauucuu auugacaagg uugaauucag   7080
uaaugguuuu uacuaucuuu auagugguga cacauuuugg aaguacaacu uugacauaac   7140
agauaacaaa uacacuugca aagagucacu uaaaaaauugu agcauaauca cagacuuuau   7200
uguuuuuaac aauaaugguu ccaauguaaa ucagguuaag aaugcaugug uguauuuuuc   7260
acagaugcuu uguaaaccug uuaaguuagu ggacucagcg uuguuggcca guuugucugu   7320
ugauuuuggu gcaagcuuac auagugcuuu uguuagugug uugucgaaua guuuuggcaa   7380
agaccuguca aguuguaaug acaugcagga uugcaagagc acauuggguu uugaugaugu   7440
accauuggau accuuuaaug cugcuguugc ugaggcucau cguuacgaug uccucuugac   7500
ugacaugucg uucaacaauu uuaccaccag uuaugcaaaa ccagaggaaa aacuucccgu   7560
ccaugacauu gccacgugua ugcguguagg ugccaagauu guuaaucaua acguucuugu   7620
caaggauagu auaccugugg uguggcuugu acgugauuuc auugcccuuu cugaagaaac   7680
uaggaaguac auuauucgua cgacuaaagu uaaggguaua accuucaugu ugaccuuuaa   7740
ugauugucgu augcauacua ccauaccuac uguuugcauu gcaaauaaga agggugcagg   7800
```

ucuuccuagu uuuucaaagg uuaagaaauu cuucugguuu uugugucugu ucauaguugc 7860
uguuuucuuu gcacuaagcu uuuuugauuu uaguacucag guuagcagug auagugauua 7920
ugacuucaag uauauugaga guggccaguu gaagacuuuu gacaauccac uuaguugugu 7980
gcauaauguc uuuaguaacu ucgaccagug gcaugaugcc aaguuugguu ucaccccgu 8040 caacaauccu aguuguccua uagucguugg uguaucagac gaagcgcgca cuguuccagg 8100
uaucccagca gguguuuauu uagcugguaa aacacuuguu uuugcuauua acaccauuuu 8160
ugguacaucu gguuugugcu uugaugcuag uggcguugcu gauaagggcg cuugcauuuu 8220
uaauucggcu ugcaccacau uaucugguuu ggguggaacu gcugucuacu guuauaagaa 8280
uggucuaguu gaaggugcua aacuuuauag ugaguuggca ccucauagcu acuauaaaau 8340
gguagauggu aaugcugugu cuuuaccuga aauuaucuca cgcggcuuug gcauccguac 8400
uauccguaca aaggcuauga ccuacugucg cguuggccag ugugugcaau cugcagaagg 8460
uguuuguuuu ggcgccgaua gauucuuugu cuauaaugca gaaucugguu cugacuuugu 8520
uuguggcaca gggcucuuua cauuguugau gaacguuauu aguguuuuuu ccaagacagu 8580
accaguaacu guguugucug gucaaauacu uuuuaauugc auuauugcuu uugcugcugu 8640
ugcggugugu uucuuauuua caaaguuuaa gcgcauguuc ggugauaugu cuguuggcgu 8700
uuucacuguc ggugcuugua cuuuguugaa caauguuucc uacauuguaa cacagaacac 8760
acuuggcaug uugggcuaug caacuuugua cuuuuugugc acuaaaggug uuagauauau 8820
guggauuugg cauuugggau uuuugaucuc auauauacuu auugcaccau ggugggguuu 8880
gaugguuuau gccuuuucag ccauuuuuga guuuaugccu aaccuuuuua agcuuaaggu 8940
uucaacacaa cuuuuugagg gugacaaguu cguaggcucu uuugaaaaug cugcagcagg 9000
uacauuugug cuugauaugc augccuauga gagacuugcc aacucuaucu caacugaaaa 9060
acugcgucag uaugcuagua cuuacaauaa guacaaguau uauucaggca gugcuucaga 9120
ggcugauuac aggcuugcuu guuuugccca uuuggccaag gcuaugaugg auuaugcuuc 9180
uaaucacaac gacacguuau acacaccacc cacugugagu uacaauucaa cucuacaggc 9240
uggcuugcgu aagauggcac aaccaucugg uguuguugag aagugcauag uucguguuug 9300
cuaugguaau auggcucuua auggccuaug gcuuggugau acuguuaucu gcccacgcca 9360
uguuauagcg ucuaguacua cuagcacuau agauuaugac uaugcccuuu cuguuuuacg 9420
ccucyacaac uucuccauuu caucugguaa uguuuuccua gguguugugg guguaaccau 9480
gcgaggugcu uuguugcaga uaaagguuaa ucaaaacaau guccacacgc cuaaguacac 9540
cuaucgcaca guuagaccgg gugaaucuuu uaauaucuug gcgugcuaug augguucugc 9600
agcugguguu uacggcguua acaugcgcuc uaauuacacu auuagaggcu cguucauuaa 9660
uggcgcuugu gguucaccug guuauaacau uaacaauggu accguugagu uuugcuauuu 9720
acaccagcuu gaacuugguu caggcuguca uguugguagc gacuuagaug guguuaugua 9780
uggugguuau gaggaccaac cuacuuugca aguugaaggc gcuaguaguc uguuuacaga 9840
gaauguguug gcauuucuuu augcagcacu cauuaauggu ucuaccuggu ggcuuaguuc 9900
uucuaggauu gcuguagaca gguuuaauga gugggcuguu cauaauggua ugacaacagu 9960
aguuaauacu gauugcuuuu cuauucuugc ugcuaagacu gguguugaug uacaacguuu 10020
guuggccuca auccagucuc ugcauaagaa uuuuggugga aagcaaauuc uuggcuauac 10080
cucguugaca gaugaguuua cuacagguga aguuauacgu caaauguaug gcguuwaucu 10140
ucagaguggu uauguuucac gcgccuguag aaaugucuug cugguugguu cuuuucugac 10200
uuucuuuugg ucagaauuag uuuccuacac uaaguucuuu uggguaaauc cugguuaugu 10260
cacaccuaug uuugcguguu ugucauugcu guccucacuu uugauguuca cacucaagca 10320
uaagacauug uuuuuccagg ucuuucuaau accugcucug auuguuacau cuugcauuaa 10380
uuuggcauuu gauguugaag ucuacaacua uuuggcagag cauuuugauu accauguuuc 10440
ucucaugggu uuuaaugcac aaggucuugu uaacaucuuu gucugcuuug uuguuaccau 10500
uuuacacggc acauacacau ggcgcuuuuu uaacacaccu gugaguucug ucacuuaugu 10560
gguagcuuug cugacugcgg cauauaacua uuuuuacgcu agugacauuc uuaguugugc 10620
uaugacacua uuugcuagug ugacuggcaa cugguucguu ggugcuguuu guuauaaagc 10680
ugcuguuuau auggccuuga gauuuccuac uuuuguggcu auuuuuggug auauuaagag 10740
uguuauguuc uguuaccuug uguuggguua uuuuaccugu ugcuucuacg guauucucua 10800
cugguucaac agguuuuuua agguuagugu aggugucuau gacuauacug uuagugcugc 10860
ugaguuuaag uauaugguug cuaacggccu acgugcacca acuggaacac uugauucacu 10920
acuucugucu gccaaauuga uugguauugg uggugagcgg aauauuaaga uuucuuccgu 10980
ucagucuaaa cugacugaua uuaagugaag uaacguugug cuuuuaggcu gucucucuag 11040
caugaauguc ucagcaaauu caacagaaug ggccuauugu guugacuugc auaacaagau 11100
caacuugugu aaugacccag aaaaagcgca ggaaaugcua cuugcuuugu uggcauuuuu 11160
ccuuaguaag aauagugcuu uugguuuaga ugacuuauug gaauccuauu uuaaugacaa 11220
uaguauguug cagaguguug caucuacuua ugucgguuug ccuucuuaug ucauuuauga 11280
aaaugcacgc caacaguaug aagaugcugu uaauaauggu ucuccaccuc aguugguuaa 11340
gcaauugcgc caugccauga auguagcaaa gagcgaauuu gaccgugagg cuucuacuca 11400
gcguaagcuu gauagaaugg cggaacaggc ugcagcacag auguacaaag aggcacgagc 11460
aguuaauagg aaguccaaag uuuguaagugc uaugcauuca cugcuuuuug guauguugag 11520
acguuuggac augucuucug uagacaccau ucucaacuug gcaaaggaug ggguuguacc 11580
ucugucuguc auaccggcag ucagugcuac uaagcuuaac auuguuacuu cugauaucga 11640
uucuuauaau cguauccagc gugagggaug uguccacuac gcugguacca uuuggaauau 11700
aauugauauc aaggacaaug auggcaaggu gguacacguu aaggagguaa ccgcacagaa 11760
ugcugagucc cugucauggc cccuggnccu ugggugugag cguauuguca agcuccagaa 11820
uaaugaaauu auuccuggua agcugaagca gcgcuccauu aaggcagaag gagauggcau 11880
aguuggagaa gguaaggcac uuuacaauaa ugagggugga cguacuuuua uguaugcuuu 11940
caucucggac aaaccggacc ugcguguagu caagugggag uucgauggug guuguaacac 12000
uauugagcua gaaccaccac guaaguucuu gguggauucu ccuaauggug cacagaucaa 12060
guaucucuac uuuguucgua accuuaacac guuacguagg ggugcuguuc ucggcuacau 12120
aggugccacu guacgcuugc aggcugguaa acaaacagaa caggcuauua acucuucauu 12180
guugacacuu ugcgcuuucg cuguggaucc ugcuaagacc uacaucgaug cugucaaaag 12240
uggucacaaa ccaguaggua acuguguuaa gauguuggcc aaugguucug guaauggaca 12300
agcuguuacu aauggugugg aggcuaguac uaaccaggau ucauacggug gugcguccgu 12360
gugucuauau uguagagcac auguugagca uccaucuaug gaugguuuuu gcagacugaa 12420
aggcaaguac guacagguuc cacuagguac aguggauccu auacguuuug uacuugagaa 12480
ugacguuugc aagguuugug guuguuggcu ggcuaauggc ugcacuugug acagauccau 12540

-continued

```
uaugcaaagc acugauaugg cuuauuuaaa cgaguacggg gcucuagugc agcucgacua  12600
gagcccugua acgguacuga uacacaacau guguaucgug cuuuugacau cuacaacaag  12660
gauguugcuu gucuagguaa auuccucaag gugaacugug uucgccugaa gaauuuggau  12720
aagcaugaug cauucuaugu ugucaaaaga uguaccaagu cugcgaugga acacgagcaa  12780
uccaucuaua gcagacuuga aaagugugga gccguagccg aacacgauuu cuucacuugg  12840
aaggaugguc gugccaucua ugguaacguu uguagaaagg aucuuaccga guauacuaug  12900
auggauuugu guuacgcuuu acguaacuuu gaugaaaaca auugcgaugu ucuuaagagc  12960
auuuuaauua agguaggcgc uugugaggag uccuacuuca auaauaaagu cugguuugac  13020
ccuguugaaa augaagacau ucaucguguc uaugcauugu uagguaccau uguuucacgu  13080
gcuaugcuua aaugcguuaa guucugugau gcaaugguug aacaagguau aguuggugau  13140
gucacauuag auaaucagga ucuuaauggu gauuuuuaug auuuugguga uuuuacuugu  13200
agcaucaagg gaaugguuau acccauuugc acaucauauu acucuuauau gaugccuguu  13260
augguuauga cuaauugccu ugcuagugag uguuuuguua agagugauau auuuggugag  13320
gauuucaagu cauaugaccu gcuggaauau gauuucacgg agcauaagac agcacucuuc  13380
aacaaguauu ucaaguauug gggacugcaa uaccacccua acugugugga cugcagugau  13440
gagcagugca uaguucacug ugccaacuuc aauacguugu uuuccacuac uauaccuauu  13500
acggcauuug gaccuuugug ucgcaagugu uggauugaug guguuccacu gguaacuaca  13560
gcugguuauc auuuuaaaca guuagguaua guuuggaaca augaccucaa cuuacacucu  13620
agcaggcucu cuauuaacga auuacuccag uuuuguagug auccugcauu gcuuauagca  13680
ucaucaccag cccuuguuga ucagcguacu guuugcuuuu caguugcagc gcuagguaca  13740
gguaugacua accagacugu uaaaccuggc cauuucaaua aggaguuuua ugacuucuua  13800
cuugagcaag guuucuuuuc ugagggcucu gagcuuacuu uaaagcacuu cuucuuugca  13860
cagaagggug augcagcugu uaaggauuuu gacuacuaua gguauaauag accuacuguu  13920
cuggacauuu gccaagcucg cgucguguau caaauagugc aacgcuauuu ugauauuuac  13980
gaagguguu guaucacugc uaaagaggug guuguuacaa accuuaacaa gagcgcaggu  14040
uauccuuuga acaaguuugg uaaagcuggu cuuuacuaug agucuuuauc cuaugaggaa  14100
caggaugaac uuuaugcuua uacuaagcgu aacauccugc ccacuaugac acagcucaac  14160
cuuaaauaug cuauaagugg caaagaacgu gcacgcacag ugggugguguu uucgcuuuug  14220
ucaaccauga cuacucggca guaucaucag aaacaccuua aguccauagu uaauacuagg  14280
ggcgcuucgg uuguuauugg uacuacuaag uuuuauggug guugggacaa uaugcuuaag  14340
aaccuuauug augguguuga aaauccgugu cuuaugggguu gggacuaccc aaagugcgac  14400
agagcacugc ccaaurugau acguaugauu ucagccauga uuuuaggcuc uaagcacacc  14460
acaugcugca guuccacuga ccgcuuuuuc agguugugca augaauuggc ucaaguccuu  14520
acugagguug uuuauucuaa uggagguuuu uauuugaagc cagguggguac uaccucuggu  14580
gaugcaacca ccgcauaugc aaacucaguu uuuaauaucu uccaagcagu aagugccaau  14640
guuaacaaac uucuuagugu ugacagcaau gucugucaua auuuagaagu uaagcaauug  14700
cagcguaagc uuuaugagug cuguuauaga ucaacuaccg ucgaugacca guucgucguu  14760
gaguauuaug guuacuugcg uaaacauuuu ucaaugauga uucuuucuga ugauggcguu  14820
guuuguuaua acaaugacua ugcaucacuu gguuaugucg cugaucuuaa cgcauucaag  14880
gcuguuuugu auuaccagaa caaugucuuc augagcgccu cuaaaauguug gaucgagccu  14940
```

gacauuaaua aagguccuca ugaauuuugc ucgcagcaua cuaugcagau ugucgauaaa 15000
gaugguacuu auuaccuucc uuacccugau ccuucaagaa uucucucugc aggugugguuu 15060 guugaugacg uuguuaaaac ugaugcaguu guauugcuug aacguuaugu gucauuggcu 15120
auagaugccu acccguuauc uaagcaugaa aacccugaau auaagaaggu guuuuaugug 15180
cuuuuggauu ggguuaagca ucuguacaaa acucuuaaug cuggugugu u agagucuuuu 15240 ucugucacac uuuuggaaga uucuacugcu aaauucuggg augagagcuu uuaugccaac 15300
auguaugaga aaucugcagu uuuacaaucu gcagggcuuu guguuguuug uggcucucaa 15360
acuguuuuac guuguggugu a uugucuacgg cguccuaugc uuuguacuaa gugugcuuau 15420
gaucauguca uuggaacaac ucacaaguuc auuuuggcca ucacuccaua ugugguguugu 15480 gcuucagauu gugguguca a ugauguaacu aagcucuacu uagguggucu uaguuauugg 15540
ugucaugacc acaagccacg ucuugcauuc ccguugugcu cugcugguaa uguuuuuggc 15600
uuguacaaaa auucugcuac cggcucaccc gauguugaag acuuuaaucg cauugcuaca 15660
uccgauugga cugauguuuc ugacuacagg uuggcaaaug augucaagga cucauugcgu 15720
cuguuugcag cggaaacuau caaggccaag gaggagagcg uuaagucauc cuaugcuugu 15780
gcaacacuac augagguugu aggaccuaaa gaguuguugc ucaaauggga agucggcaga 15840
cccaaaccac cccuuaauag aaauucgguu uucacuuguu aucauauaac gaagaacacc 15900
aaauuucaaa ucggugaguu uguguuugag aaggcagaau augauaauga ugcuguaaca 15960
uauaaaacua ccgccacaac aaaacuuguu ccuggcaugg uuuuugugcu uaccucacau 16020
aauguucagc cauugcgcgc accgaccauu gcuaaucaag aacguuauuc cacuauacau 16080
aaguugcauc cugcuuuuaa cauaccugaa gcuuauucua gcuuagugcc cuauuaccaa 16140
uugauuggua agcagaagau uacaacuauu cagggaccuc ccgguagugg uaaaucucac 16200
uguguuauag ggcuagguuu guacuaucca ggugcacgua uaguguuuac agcuuguucu 16260
caugcagcgg ucgauucacu uugugugaaa gcuuccacug cuuauagcaa ugacaaaugu 16320
ucacgcauca uaccacagcg cgcucguguu gaguguuaug augguuucaa gucuaauaau 16380
acuagugcuc aguaccuuuu cucuacuguc aaugcuuugc cagagugcaa ugcggacauu 16440 guugugguugg augaggucuc uaugugcacu aauuaugacu ugucugucau aaaucagcgc 16500
aucagcuaua ggcauguagu cuauguuggu gacccucaac agcugccugc accacguguu 16560
augauuucac gugguacuuu ggaaccaaag gacuacaacg uugucacuca acgcaugugu 16620
gcccuuaagc cugauguuuu cuugcacaag uguuaucgcu guccugcuga gauaguugcgu 16680 acugugucug agauggucua ugaaaaccaa uucauuccug ugcacccaga uagcaagcag 16740
uguuuuaaaa ucuuuugcaa ggguaauguu cagguugaua augguucaag cauuaaucgc 16800
aggcaauugg auguugugcg uauguuuuug gcuaaaaauc cuagguggguc aaaggcuguu 16860 uuuauuucuc cuuauaacag ccagaauuau guugccagcc gcaugcuagg ucuacaaauu 16920
cagacaguug acucauccca ggguagugag uaugacuaug ucauuuacac acaaacuuca 16980
gauacugccc augccuguaa uguuaacagg uuuaauguug ccaucacaag ggccaagaaa 17040
ggcauauuau guauaaugug cgauaggucc cuuuuugaug ugcuuaaauu cuuugagcuu 17100
aaauugucug auuugcaggc uaaugagggu uguggucuuu uuaaagacug uagcagaggu 17160
gaugaucugu ugccaccauc ucacgcuaac accuucaugu cuuuagcgga caauuuuaag 17220
acugaucaag aucuugcugu ucaaauaggu guuaauggac ccauuaaaua ugagcauguu 17280
aucucguuua uggguuuccg uuuugauauc aacauaccca accaucauac ucucuuuugc 17340
acacgcgacu uugccaugcg caauguuaga gguugguuag gcuuugacgu ugaaggagca 17400
cauguuguug gcucuaacgu cgguacaaau gucccauugc aauuaggguu uucuaacggu 17460
guugauuuug uugucagacc ugaagguugc guuguaacag agucugguga cuacauuaaa 17520
cccgucagag cucgugcucc accaggggaa caauucgcac accuuuugcc uuuacuuaaa 17580
cgcggccaac caugggaugu uguccgcaaa cguauagugc agauguguag ugacuaccug 17640
gccaaccuau cagacauacu aauuuuugug uugugggcug gugguuugga guugacaacu 17700
augcguuauu uugucaagau uggaccaagu aagaguugug auugugguaa gguugcuacu 17760
uguuacaaua gugcgcugca uacguacugu uguuucaaac augcccuugg uugugauuau 17820
cuguauaacc cauacuguau ugauauacag caguggggau acaagggauc acuuagccuu 17880
aaccaccaug agcauuguaa uguacauaga aacgagcaug uggcuucugg ugaugccaua 17940
augacucgcu gucuggccau acaugauugc uuugucaaga acguugacug guccaucaca 18000
uacccauuua uugguaauga ggcuguuauu aauaagagcg gccgaauugu gcaaucacac 18060
acuaugcggu caguucuuaa guuauacaau ccgaaagcca uauaugauau uggcaauccu 18120
aagggcauua gaugugccgu aacggaugcu aagugguuuu gcuuugacaa gaauccuayu 18180
aauucuaaug ucaagacauu ggaguaugac uauauaacac auggccaauu ugauggguug 18240
ugcuuguuuu ggaauugcaa uguagacaug uauccagaau uuucuguggu cugucguuuu 18300
gauacucgcu guaggucacc acucaacuug gaggguugua augguggu uc acuguauguu 18360 aauaaaucaug cauuccauac accggcuuuu gacaagcgug cuuuugcuaa guugaagcca 18420
augccauuuu ucuuuuauga ugauacugag ugugacaagu uacaggacuc cauaaacuau 18480
guuccucuua gggcuaguaa cugcauuacu aaauguaaug uuggugugc ugucuguagu 18540 aagcauugug cuauguauca uagcuauguu aaugcuuaca acacuuuuac gucggcgggc 18600
uuuacuauuu gggugccuac uucguuugac accuauaauc uguggcagac auuuaguaac 18660
aauuugcaag gucuugagaa cauugcuuuc aaugucguaa agaaaggauc uuuuguuggu 18720
gccgaaggug aacuuccugu agcugugguu aaugacaaag ugcucguuag agaugguacu 18780
guugauacuc uuguuuuuac aaacaagaca ucacuaccca cuaacguagc uuuugaguug 18840
uaugccaagc guaagguagg acucacccca cccauuacga ucccuacguaa cuugggugua 18900 guuuguacau cuaagugugu cauuugggac uaugaagccg aacguccacu uacuacuuuu 18960
acaaaggaug uuuguaaaua uaccgacuuu gagggugacg ucuguacacu cuuugauaac 19020
agcauuguug guucauuaga gcgauucucc augacccaaa augcugugcu uaugucacuu 19080
acagcuguua aaaagcuuay uggcauaaag uuaacuuaug guuaucuuaa ugguguccca 19140
guuaacacac augaagauaa accuuuuacu ugguauauuu acacuaggaa gaacggcaag 19200
uucgaggacc auccugaugg cuauuuuacc caagguagaa caaccgcuga uuuuagcccu 19260
cguagcgaca uggaaaagga cuucccuaagu auggauaugg gucuguuuau uaacaaguac 19320
ggacuugaag auuacggcuu ugagcacguu guguauggug auguuucaaa aaccacccuu 19380
ggugguuugc aucuacuaau uucgcaggug cgucuggccu guaugggugu gcucaaaaua 19440
gacgaguuug ugucuaguaa ugauagcacg uuaaagucuu guacuguuac auaugcugau 19500
aacccuagua guaagauggu uuguacguau auggaucucc ugcuugacga uuuugucagc 19560
auucuuaaau cuuuggauuu gggcguugua ucuaaaguuc augaaguuau ggucgauugu 19620
aaaaugugga gguggauguu gugguguaag gaucauaaac uccagacauu uuauccgcaa 19680
cuucaggcca gugaauggaa gugugguuau uccaugccuu cuauuuacaa gauacaacgu 19740
auguguuuag aaccuugcaa ucucuacaac uauggugcug guauuaaguu accugauggc 19800
auuauguuua acguaguuaa auacacacag cuuugucaau aucucaauag caccacaaug 19860
uguguacccc aucacaugcg ugugcuacau cuuggugcug gcuccgacaa ggguguugca 19920
ccuggcacgg cugucuuacg acguugguug ccacuggaug ccauuauagu ugacaaugau 19980
aguguggauu acguuagcga ugcugauuau aguguuacag gagauugcuc uaccuuauac 20040
cugucagaua aguuugauuu aguuauaucu gauauguaug augguaagau uaaaaguugu 20100
gauggggaga acgugucuaa agaaggcuuc uuucccuaua uuaauggugu caucaccgaa 20160
aaguuggcac uuggugguac uguagcuauu aaggugacgg aguuuaguug gaauaagaag 20220
uuguaugaac ucauucagag guuugaguau uggacaaugu ucuguaccag uguuaacacg 20280
ucaucgucag aggcauucuu aauuggugu cacuauuuag gugauuuugc aaguggcgcu 20340
gugauugacg gcaacacuau gcaugccaau uauaucuucu ggcguaauuc cacaauuaug 20400
acuaugucuu acaauagugu acuugauuua agcaaguuca auuguaagca uaaggcuaca 20460
guugucauua auuuaaaaga uucauccauu agugauguug uguuagguuu guugaagaau 20520
gguaaguugc uagugcguaa uaaugacgcc auuuguggu uuucuaauca uuuggucaac 20580
guaaacaaau gaagucuuua accuacuucu gguuguucuu accaguacuu ucaacacuua 20640
gccuaccaca agaugucacc aggugcucag cuaacacuaa uuuuaggcgg uucuuuucaa 20700
aauuuaaugu ucaggcgccu gcaguuguug uacugggcgg uuaucuaccu auuggugaaa 20760
accagggugu caauucaacu ugguacugug cuggccaaca uccaacugcu aguggcguuc 20820
augguaucuu uguuagccau auuagaggug gucauggcuu ugagauuggc auuucgcaag 20880
agccuuuuga cccuaguggu uaccagcuuu auuuacauaa ggcuacuaac gguaacacua 20940
augcuacugc gcgacugcgc auuugccagu uuccuagcau uaaaacauug ggccccacug 21000
cuaauaauga uguuacaaua ggucguaauu gccuauuuaa caaagccauc ccagcucaua 21060
ugagugaaca uaguguuguc ggcauaacau gggauaauga ucgugucacu gucuuuucug 21120
acaagaucua uuauuuuuau uuuaaaaaug auugguccg uguugcgaca aaguguuaca 21180
acaguggagg uugugcuaug caauauguuu acgaacccac cuauuacaug cuuaauguua 21240
cuagugcugg ugaggauggu auuucuuauc aacccuguac agcuaauugc auugguuaug 21300
cugccaaugu auuugcuacu gagcccaaug gccacauacc agaagguuuu aguuuuaaua 21360
auugguuucu uuuguccaau gauuccacuu uggugcaugg uaagguguu uccaaccaac 21420 cauuguuggu caauugucuu uuggccauuc cuaagauuua uggacuaggc caauuuuucu 21480
ccuuuaauca aacgaucgau gguguuugua auggagcugc ugugcagcgu gcaccagagg 21540
cucugagguu uaauauuaau gacaccucug ucauucuugc ugaaggcuca auuguacuuc 21600
auacugcuuu aggaacaaau uuuucuuuug uuugcaguaa uuccccaaau ccucacuuag 21660
ccaccuucgc cauaccucug ggugcuaccc aaguaccuua uuauuguuuu cuuaaagugg 21720
auacuuacaa cuccacuguu uauaaauuuu uggcuguuuu accuccuacc gucagggaaa 21780
uugucaucac caaguauggu gauguuuaug ucaauggguu uggauacuug caucucgguu 21840
uguuggaugc ugucacaauu aauuucacug gucauggcac ugacgaugau guuucugguu 21900
uuuggaccau agcaucgacu aauuuuguug augcacucau cgaaguucaa ggaaccgcca 21960
uucagcguau ucuuuauugu gaugauccug uuagccaacu caaguguucu cagguugcuu 22020
uugaccuuga cgaugguuuu uacccuauuu cuucuagaaa ccuucugagu caugaacagc 22080
caauuucuuu uguuacucug ccaucauuua augaucauuc uuuuguuaac auuacuguau 22140
cugcuuccuu ugguggucau aguggugcca accuuauugc aucugacacu acuaucaaug 22200
gguuuaguuc uuucuguguu gacacuagac aauuuaccau uucacuguuu uauaacguua 22260
caaacaguua ugguuaugug ucuaaaucac aggacaguaa uugcccuuuc accuugcaau 22320
cuguuaauga uuaccugucu uuuagcaaau uuuguguuuc caccagccuu uuggcuagug 22380
ccuguaccau agaucuuuuu gguuacccug aguuugguag ugguguuaag uuuacguccc 22440
uuuacuuuca auucacaaag ggugaguuga uuacuggcac gacuaaacca cuugaaggug 22500
ucacggacgu uucuuuuaug acucuggaug uguguaccaa guauacuauc uauggcuuua 22560
aaggugaggg uaucauuacc cuuacaaauu cuagcuuuuu ggcagguguu uauuacacau 22620
cuguuucugg acaguuguua gccuuuaaga augucacuag uggugcuguu uauucuguua 22680
cgccauguuc uuuuucagag caggcugcau auguugauga ugauauagug gguguuauuu 22740
cuaguuuguc uagcuccacu uuuaacagua cuagggaguu gccugguuuc uucuaccauu 22800
cuaaugaugg cucuaauugu acagagccug uguuggugua uaguaacaua gguguuugua 22860
aaucuggcag uauuggcuac gucccaucuc agucuggcca agucaagauu gcacccacgg 22920
uuacugggaa uauuaguauu cccaccaacu uuaguaugag uauuaggaca gaauauuuac 22980
agcuuuacaa cacgccuguu aguguugauu gugccacaua uguuuguaau gguaacucuc 23040
guuguaaaca auuacucacc caguacacug cagcauguaa gaccauagag ucagcauuac 23100
racucagcgc uaggcuugag ucuguugaag uuaacucuau gcuuacuauu ucugaagagg 23160
cucuacaguu agcuaccauu aguucguuua augugaugg auauaauuuu acuaaugugc 23220
ugggguguuuc uguguaugau ccugcaaggg gcaggguggu acaaaaaagg ucuuuuauug 23280
aagaccugcu uuuuaauaaa gugguuacua auggccuugg uacuguugau gaagacuaua 23340
agcgcuguuc uaauggucgc ucuguggcag aucuagucug ugcacaguau uacucuggug 23400
ucaugguacu accuggugu guugacgcug agaagcuuca cauguauagu gcgucucuca 23460
ucgguggguau ggugcuagga gguuuuacuu cugcagcggc auugccuuuu agcuaugcug 23520
uucaagcuag acucaauuau cuugcucuac agacggaugu ucuacagcgg aaccagcaau 23580
ugcuugcuga gucuuuuaac ucugcuauug guaauauaac uucagccuuu gagaguguua 23640
aagaggcuau uagucaaacu uccaaggguu ugaacacugu ggcucaugcg cuuacuaagg 23700
uucaagaggu uguuaacucg cagggugcag cuuugacuca acuuaccgua cagcugcaac 23760
acaacuucca agccauuucu aguucuauug augacauuua cucucgacug gacauucuuu 23820
cagccgaugu ucagguugac cgucucauca ccggcagauu aucagcacuu aaugcuuuug 23880
uugcucaaac ccucacuaag uauacugagg uucaggcuag caggaaguua gcacagcaaa 23940
agguuaauga gugcguuaaa ucgcaauccc agcguuaugg uuuuuguggu ggugauggcg 24000
agcacauuuu cucucuggua caggcagcac cucagggccu gcuguuuuua cauacaguac 24060
uuguaccgag ugauuuugua gauguuauug ccaucgcugg cuuaugcguu aacgaugaaa 24120
uugccuugac ucuacgugag ccuggcuuag ucuuguuuac gcaugaacuu caaaaucaua 24180
cugcgacgga auauuuuguu ucaucgcgac guauguuuga accuagaaaa ccuaccguua 24240
gugauuuugu ucaaauugag aguugugugg ucaccuaugu caauuugacu agagaccaac 24300
uaccagaugu aaucccagau uacaucgaug uuaacaaaac acuugaugag auuuuagcuu 24360
cucugcccaa uagaacuggu ccaagucuuc cuuuagaugu uuuuaaugcc acuuaucuua 24420
aucucacugg ugaaauugca gauuuagagc agcguucaga gucucuccgu aauacuacag 24480
aggagcucca aagucuuaua uauaauauca acaacacacu aguugaccuu gaguggcuca 24540
accgaguuga gacauauauc aaguggccgu gguggguuug guugauuauu uucauuguuc 24600
ucaucuuugu ugugucauua cuaguguucu gcugcauuuc cacggguugu uguggaugcu 24660
gcggcugcug cugugcuugu uucucagguu guuguagggg uccuagacuu caaccuuacg 24720
aaguuuuuga aaagguccac gugcagugau guuucuugga cuuuuucaau acacgauuga 24780
cacaguuguc aaagaugucu caaagucugc uaacuugucu uuggaugcug uccaagaguu 24840
ggagcucaau guaguuccaa uuagacaagc uucaaaugug acggguuuuc uuuucaccag 24900
uguuuuuauc uacuucuuug cacuguuuaa agcgucuucu uugaggcgca auuauauuau 24960
guuggcagcg cguuuugcug ucauuguucu uuauugccca cuuuuauauu auuguggugc 25020
auuuuuagau gcaacuauua uuuguugcac acuuauucaa agucggugge aggcuuuguu 25080 uagucugcuu uuacuccugg cgcuauaaaa augcgcucuu uauuauuuuu aauacuacga 25140
cacuuucuuu ccucaauggu aaagcagcuu auuaugacgg caaauccauu gugauuuuag 25200
aaggugguga ccauuacauc acuuuuggca acucuuuugu ugcuuuuguu aguagcaucg 25260
acuuguaucu agcuauacgu gggcggcaag aagcugaccu acagcuguug cgaacuguug 25320
agcuucuuga uggcaagaag cuuuaugucu uuucgcaaca ucaaauuguu ggcauuacua 25380
augcugcauu ugacucaauu caacuagacg aguaugcuac aauuagugaa ugauaauggu 25440
cuaguaguua auguuauacu uuggcuuuuc guacucuuuu uccugcuuau uauaagcauu 25500
acuuucgucc aauugguuaa ucugugcuuc acuugucacc gguuguguaa uagcgcaguu 25560
uacacaccua uagggcguuu guauagaguu uauaagucuu acaugcaaau agacccccuc 25620
ccuaguacug uuauugacgu auaaacgaaa uaugucuaac gguucuauuc ccguugauga 25680
ggugauucaa caccuuagaa acuggaauuu cacauggaau aucauacuga cgauacuacu 25740
uguagugcuu caguauggcc auuacaagua cucugcguuc uuguauggug ucaagauggc 25800
uauucuaugg auacuuuggc cucuuguguu agcacuguca cuuuuugaug caugggcuag 25860
cuuucagguc aauugggucu uuuuugcuuu cagcauccuu auggcuugca ucacucuuau 25920
gcuguggaua auguacuuug ucaauagcau ucgguugugg cgcaggacac auucuuggug 25980
gucuuucaau ccugaaacag acgcgcuucu cacuacuucu gugaugggcc gacaggucug 26040
cauuccagug cuuggagcac caacuggugu aacgcuaaca cuccuuagug guacauugcu 26100
uguagagggc uauaagguug cuacuggcgu acagguaagu caauuaccua auuucgucac 26160
agucgccaag gccacuacaa caauugucua cggacguguu ggucguucag ucaaugcuuc 26220
aucuggcacu gguugggcuu ucuauguccg guccaaacac ggcgacuacu cagcugugag 26280
uaauccgagu ucgguucuca cagauaguga gaaagugcuu cauuuagucu aaacagaaac 26340
uuuauggcuu cugucaguuu ucaggaucgu ggccgcaaac gggugccauu aucccucuau 26400
gccccucuua ggguuacuaa ugacaaaccc cuuucuaagg uacuugcaaa uaaugcugua 26460
cccacuaaua aaggaaauaa ggaccagcaa auuggauacu ggaaugagca aauucgcugg 26520
cgcaugcgcc guggugagcg aauugaacaa ccuuccaauu ggcauuucua cuaccucgga 26580
acaggaccuc acgccgaccu ccgcuauagg acucguacug agggguguuu cuggguugcu 26640
aaagaaggcg caaagacuga acccacuaac cuggguguca gaaaggcguc ugaaaagcca 26700
auuauuccaa auuucucuca acagcuuccc agcguaguug agauuguuga accuaacaca 26760

```
ccuccuacuu cacgugcaaa uucacguagc aggagucgug guaauggcaa caacaggucc  26820

agaucuccaa guaacaacag aggcaauaac cagucccgcg guaauucaca gaaucgugga  26880

aauaaccagg gucguggagc uucucagaac agaggaggca auaauaauaa caauaacaag  26940

ucucguaacc aguccaagaa cagaaaccag ucaaaugacc gugguggugu aacaucacgc  27000

gaugaucugg uggcugcugu caaggaugcc cuuaaaucuu uggguauugg cgaaaacccu  27060

gacaagcuua agcaacagca gaagcccaaa caggaaaggu cugacagcag cggcaaaaau  27120

acaccuaaga agaacaaauc cagagccacu ucgaaagaac gugaccucaa agacauccca  27180

gaguggagga gaauucccaa gggcgaaaau agcguagcag cuugcuucgg acccagggga  27240

ggcuucaaaa auuuuggaga ugcggaauuu gucgaaaaag guguugaugc cucaggcuau  27300

gcucagaucg ccaguuuagc accaaauguu gcagcauugc ucuuuggugg uaauguggcu  27360

guucgugagc uagcggacuc uuacgagauu acauauaauu auaaaaugac ugugccaaag  27420

ucugauccaa auguagagcu ucuuguuuca cagguggaug cauuuaaaac ugggaaugca  27480

aaaccccaga gaaagaagga aaagaagaay aagcgugaaa ccacgcagca gcugaaugaa  27540

gaggccaucu acgaugaugu gggugugcca ucugauguga cucaugccaa uuuggaaugg  27600

gacacagcug uugauggugg ugacacggcc guugaaauua ucaacgagau cuucgacaca  27660

ggaaauuaaa caauguuuga cuggcuuauc cuggcuaugu cccaggguag ugccauuaca  27720

cuguuauuac ugaguguuuu ucuagcgacu uggcugcugg gcuauggcuu ugcccucuaa  27780

cuagcggucu uggucuugca cacaacggua agccaguggu aaugucagug caagaaggau  27840

auuaccauag cacugucaug aggggaacgc aguaccuuuu caucuaaacc uuugcacgag  27900

uaaucaaaga uccgcuugac gagccuauau ggaagagcgu gccagguauu ugacucaagg  27960

acuguuagua acugaagacc ugacggugu gauau                             27995
```

<210> SEQ ID NO 16
<211> LENGTH: 29
<212> TYPE: DNA
<213> ORGANISM: Artificial Sequence
<220> FEATURE:
<223> OTHER INFORMATION: Description of Artificial Sequence: Synthetic probe

<400> SEQUENCE: 16

```
acagagcctg tgttggtgta tagtaacat                                    29
```

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 17

```
tatagtgggt gttatttcta gtt                                          23
```

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 18

-continued

```
gccaatactg ccagatttac a                                                21


<210> SEQ ID NO 19
<211> LENGTH: 170
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

tgatgatata gtgggtgtta tttctagttt gtctagctcc acttttaaca gtactaggga      60

gttgcctggt ttcttctacc attctaatga tggctctaat tgtacagagc ctgtgttggt     120

gtatagtaac ataggtgttt gtaaatctgg cagtattggc tatgtcccat                170


<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Pro Arg Leu Gln Pro Tyr
1               5
```

PORCINE EPIDEMIC DIARRHEA VIRUS VACCINE

SEQUENCE LISTING

This application contains a sequence listing in accordance with 37 C.F.R. 1.821-1.825. The sequence listing accompanying this application is hereby incorporated by reference in its entirety.

BACKGROUND OF THE INVENTION

Field of the Invention

The present invention relates to a porcine epidemic diarrhea virus (PEDV) vaccine specific to the isolates currently endemic in the United States which are capable of reducing clinical signs of disease caused by PEDV. Due to the high mortality (up to 100%) in less than 10 day old piglets, the disease is of economic concern to the U.S. swine industry.

Description of the Related Art

The porcine epidemic diarrhea virus is an enveloped, positive-sense single-stranded RNA virus that causes acute diarrhea, vomiting, and dehydration in pigs. It was first identified in Europe but has become increasingly problematic in many Asian countries, including Korea, China, Japan, the Philippines, and Thailand. In April of 2013, PEDV emerged in U.S. swine in the Midwest, swiftly spreading across the country. By October 2013, PEDV was detected in swine herds in 18 States. The economic impact of PEDV infection has already been substantial. North American isolates of PEDV have been identified (Huang, et al. 2013; Stevenson et al. 2013), however no fully licensed vaccine is commercially available in the United States. Accordingly, there is a continuing need to develop vaccines capable of protecting pigs against disease associated with PEDV. It would be advantageous to develop a vaccine that is effective against emerging North American PEDV strains which could be administered via a mucosal route (oral or intranasal) as well as via parenteral methods (e.g., intramuscularly, subcutaneously or intravenously).

PEDV is a member of the subfamily Coronavirinae of genus *Alphacoronavirus* (Bridgen et al. 1993) and was first identified in England in 1971 and later in other countries, such as Belgium, China, Hungary, Italy, Japan, Korea, and Thailand (Oldham J. 1972; Pensaert and De Bouck P. 1978; Chen et al. 2008; Nagy et al. 1996; Martelli et al. 2008; Takahashi et al. 1983; Chae et al. 2000; and Puranaveja et al. 2009). Other members of this family include Porcine Respiratory Coronavirus (PRCV), Hemagglutinating Encephalomyelitis Coronavirus (PHE), and Transmissible Gastroenteritis Virus (TGEV). Although PEDV and TGEV viruses are related and the clinical signs are very similar, there is no immune cross-protection.

PEDV is an enveloped virus possessing approximately a 28 kb, positive-sense, single stranded RNA genome, with a 5' cap and a 3' polyadenylated tail. (Pensaert and De Bouck P. 1978). The genome comprises a 5' untranslated region (UTR), a 3' UTR, and at least seven open reading frames (ORFs) that encode four structural proteins (spike (S), envelope (E), membrane (M), and nucleocapsid (N)) and three non-structural proteins (replicases 1a and 1b and ORF3); these are arranged on the genome in the order 5'-replicase (1a/1b)-S-ORF3-E-M-N-3' (Oldham J. 1972; and Bridgen et al. 1993). The first three emergent North American PEDV genomic sequences characterized, Minnesota MN (GenBank: KF468752.1), Iowa IA1 (GenBank: KF468753.1), and Iowa IA2 (GenBank: KF468754.1), have the same size of 28,038 nucleotides (nt), excluding the polyadenosine tail and share the genome organization with the prototype PEDV CV777 strain (GenBank: AF353511.1). These three North American PEDV sequences shared 99.8 to 99.9% nucleotide identities. In particular, strains MN and IA2 had only 11 nucleotide differences across the entire genome.

The PEDV S protein is a type I glycoprotein composed of 1,383 amino acids (aa). The S protein can be divided into S1 (1-789 aa) and S2 (790-1,383 aa) domains based on its homology with S protein of other coronaviruses (Chang et al; 2002; Cruz et al, 1994; Godet, et al 1994; Jackwood et al. 2001; Sturman and Holmes; 1984; and Sun et al. 2008). The S protein in coronaviruses is a surface antigen, where it plays a role in regulating interactions with host cell receptor glycoproteins to mediate viral entry, and stimulating induction of neutralizing antibodies in the natural host. Thus the S glycoprotein is a primary target for the development of effective vaccines against PEDV.

The PEDV M protein is the most abundant envelope component playing an important role in the viral assembly process and also induces antibodies that neutralize the virus. Likewise the PEDV N protein, which binds to virion RNA providing a structural basis for the nucleocapsid, may also be important for induction of cell-mediated immunity (Saif, L. 1993).

The only accessory gene in PEDV is ORF3. While accessory genes are generally maintained in field strains, alteration of ORF3 is thought to influence virulence; cell culture adaptation has been used to alter the ORF3 gene in order to reduce virulence (Song et al. 2003). In fact, through investigation of the ORF3 gene, researchers have charted the emergence of new genogroups of PEDV in immunized swine herds in China since 2006. Phylogenic studies of these strains and the geographical reemergence of PEDV in China have demonstrated that those field strains causing devastating enteric disease differ genetically in ORF3 from the European strains and vaccine strains (Park et al. 2011).

It is well know that different strains of PEDV do exist with varying levels of virulence. During the 1980s and 1990s, PEDV was prevalent throughout Europe, in countries such as Belgium, England, Germany, France, the Netherlands, and Switzerland. The frequency of reported cases in Europe subsequently tapered off and/or the disease caused by PEDV was not of sufficient economic importance to start commercial development of a vaccine (Song and Park 2012). While outbreaks of PEDV have been documented in China since the 1980s, variant strains of PEDV emerging since 2010 associated with large-scale outbreaks of diarrhea have been more acute and severe. Thus the trial of vaccine development was mainly accomplished in Asian countries (Song and Park 2012). Variants emerging since 2010 have been reported as having 80-90% morbidity and 50-90% mortality in suckling piglets (Bi et al. 2012; Pan et al. 2012; and Li et al. 1012). Recent evidence suggests that the emerging virulent forms of PEDV in China may be a result of evolution of the live vaccine strains (Chen et al. 2010).

As an enteric disease affecting the pig's intestine, PEDV spreads via fecal-oral exposure. Contaminated trucks and equipment are frequent sources of infection to naïve animals. The clinical signs of PEDV infection are similar to transmissible gastroenteritis virus (TGEV) infection (Pijpers et al. 1993). In pigs three weeks of age and younger, clinical signs (including acute watery, diarrhea, vomiting, and dehydration) can be seen as soon as 24 hours after PEDV infection leading to 100% mortality can appear. PEDV-infected feeder and grower pigs, as well as sows and boars, can develop diarrhea and vomiting. The animals can also show signs of anorexia and can be lethargic. The full impact on older pigs is yet to be determined, but reduced feed efficiency, additional days to market, and the susceptibility of infected animals to secondary infections is likely. For sows, reduced body condition may negatively impact reproductive performance. Reports have indicated that there are signs that PEDV could become endemic in North American herds, resulting in persistent diarrhea and other challenges.

The gross and histological changes in the gut of animals infected with PEDV are similar in the United States as those observed in China; essentially the virus destroys the villi of a pig's intestine so that there is a failure to absorb nutrients. Huang et al. 2012 reported that animals succumbing to the disease in the Minnesota and Iowa outbreaks had gross pathological lesions confined to the small intestine and that the small intestine was characterized by thin translucent walls distended with yellow fluid. Histological evaluations revealed regions of small intestines with villus blunting and fusion and minimal lymphoblastic infiltration of the villi of the lamia propria.

Huang et al. 2013 characterized three different strains of PEDV from outgoing outbreaks in the United States—one from Minnesota and two from Iowa, designated MN (GenBank accession No: KF468752) and IA1 (GenBank accession No: KF468753) and IA2 (GenBank accession No: KF48754), respectively. Huang's phylogenic survey grouped PEDV strains as falling into two distinct genogroups, designated genogroup 1 (G1) and genogroup 2 (G2). The significant changes in the N-terminal domain (NTD) of the spike gene differentiated genogroup 1 and 2. Huang et al. 2013 suggests that the second deletion region (DR2) in the N-terminal domain (NTD) appears to have a higher degree of antigenic change than DR1, suggesting that the emerging North American strains may be less "antigenically" related to the G1a vaccine strains.

Genogroup 1 includes at least three clusters 1a, 1b, and R. Subgroup 1a includes the early European, Chinese, and Korean isolates, e.g., prototype CV777 strain (Belgium, 1978, GenBank: AF353511.1) and strains LZC (Gansu, China, 2006; GenBank: EF185992) and SM98 (Korea, 1998; GenBank: GU937797.1). Subgroup 1b contains five strains—one from South Korea (the DR13 attenuated vaccine strain, GenBank: JQ023162.1) and the others from China linked by the common "genetic signature" 8-aa deletion in nsp3 and the large ORF3 deletion at the C terminus. Group "R" is associated with recombinants of the other genogroups. However, the newly emergent PEDV strains, including those arising in China since 2010 and in North America since 2013, belong to genogroup G2a. The Chinese strain AH2012 (GenBank accession no: KC210145) and the North American strains share several unique nucleotides changes and are clustered together in genogroup 2a. Nucleotide identity to AH2012 for strains MN and IA2 was 99.6% and for strain IA1 was 99.5%. Researchers have speculated that an AH2012-like virus was possibly transmitted to the eastern China regions and then transported to the United States and is most likely the closest ancestor to the North American strains. Members of the genogroup 2a share only approximately 96.9% similarity to the prototype PEDV strain CV777 of genogroup 1a (Bridgen, et al. 1993; Huang et al. 2013; GenBank: AF353511.1). As such, the attenuated PEDV vaccines based on the historical CV777-derived G1a strains or DR13-derived G1b strains may be antigenically less related to the newly emergent Chinese and North American G2a PEDV strains and therefore may be poor vaccine candidates.

A closely related North American isolate US/Colorado/2013 (GenBank Accession No: KF272920.1) has also been reported by Marthaler et al, 2013. Like the North American isolates above, the complete PEDV genome of CO/13 has a nucleotide identity of 96.5 to 99.5% with other complete PEDV genomes available in GenBank, with the highest nucleotide identity (99.5%) with Chinese strain AH2012 (GenBank Accession No. KC210145). It is a member of the 2a genogroup. Comparison of the complete genome of CO/13 to that of PEDV reference strain CV777, demonstrates that CO/13 contains a 1-nt insertion (at position 48) and deletions of 5 nucleotides in the 5' UTR (at positions 73 and 83 to 86). This North American virus exhibits increased divergence within 51 at genomic positions 20,696 and 21,125 sharing only 82% nucleotide identity with several insertions/deletions.

Several PEDV vaccines, which differ in their genomic sequence, mode of delivery, and efficacy, have been developed. A cell culture adaptation of the European CV777 strain has been used in Asian countries where the PEDV outbreaks have been severe. These have been in use since the 1990s.

In the early 1980s Japanese researchers isolated a causative PED virus strain 83P-5 from the diarrhea of an infected pig. Kusanagi et al. 1989 isolated and adapted the strain in Vero cells. An attenuated virus vaccine of cell culture adapted PEDV (P-5V) (83P-5) has been used in Japan in sows since 1997. The $100^{th}$-passaged 83P-5 strain was licensed for use as an attenuated PEDV vaccine in Japan by Nisseiken Co., Ltd. (Sato et al. 2011). It has been reported that adaptation and attenuation of the 83P-5 strain showed mutations in the extra-cellular portion of the S protein with sequence similarity to that of the attenuated DR13 strain (Sato et al. 2011; See Strain 83P-5 Spike gene sequence at $100^{th}$ passage, GenBank: AB548621.1). Although this later Japanese vaccine is considered efficacious, not all sows were able to pass immunity to their piglets (Usami et al. 1998). The Japanese strains and the European strains are members of genogroup G1a or G1b. As discussed above these attenuated vaccine strains are less related to the divergent North American strains than the newly emergent Chinese strains of genogroup 2a.

Oral vaccination with an attenuated Korean PEDV strain, DR13 (passage level 100) (GenBank: JQ023162.1), a member of genogroup G1b, has been shown to be efficacious as a vaccine. The viral strain was licensed and used as an oral vaccine in South Korea since 2004, and registered and commercialized in the Philippines in 2011 (Song and Park 2012). However, it has been reported that attenuated DR13 does not significantly alter the duration of virus shedding in challenged piglets—an indication that immune protection is incomplete. Moreover, oral immunization with highly attenuated PEDV only conferred protection at very high doses of vaccine (Song and Park 2012).

Other known vaccines include SUISHOT® PT-100 (ChoongAng Vaccine Laboratories, South Korea) a combination killed PEDV and TGEV vaccine, and SUISHOT® PED a killed PEDV vaccine. The strain and subtypes offered through ChoonAng Vaccine Laboratories are unknown. Also Komipharm International Co., another South Korean company, offers a series of killed, live, and combination vaccines marketed under the tradename PRO-VAC® which include the PEDV strain SM98P of genogroup G1a. Qilu Animal Health Products Factory of China, also markets a combination killed vaccine in China containing PEDV and TGEV whose strain and subtypes are unknown.

Therefore, what is needed is a PEDV vaccine specific to the isolates currently endemic in North America which is capable of reducing the clinical signs of disease caused by PEDV, and inducing protective immunity in immunized animals, including the reduction of viral shedding in immunized animals.

SUMMARY OF THE INVENTION

The present invention provides immunogenic compositions, vaccines, and related methods that overcome deficiencies in the art. The present invention relates to immunogenic compositions which include inactivated/killed and/or recombinant forms of an enveloped (+) single-stranded RNA virus, porcine epidemic diarrhea virus, or PEDV. In particular, the application provides a vaccine for protecting pigs against diseases associated with North American isolates of PEDV. The present PEDV isolate BI1251-125-10 (herein referred to as "125-10") (SEQ ID NO:1 and SEQ ID NO:15) is a virulent North American RNA virus strain with a genetic profile similar to those of other North American PEDVs reported of genogroup 2a.

Immunogenic compositions and vaccines of the invention comprise inactivated/killed PEDV (e.g., chemically inactivated PEDV isolate 125-10 (SEQ ID NO:1 and SEQ ID NO:15)) and typically also includes an adjuvant. The vaccine may also include other components, such as preservative(s), antimicrobial agents, stabilizer(s), for example a stabilizer that can increase the shelf-life of the vaccine, emulsions, and antigens against other porcine pathogens.

Immunogenic compositions and vaccines of the invention comprise a Spike antigen, expressed in one non-limiting example in insect cells via a recombinant baculovirus expressing a modified PEDV Spike protein (e.g., modified Spike nucleic acid sequence (SEQ ID NO:8) encoding amino acid sequence (SEQ ID NO: 9)) and typically also includes an adjuvant. The vaccine may also include other components, such as preservative(s), stabilizer(s) and antigens against other porcine pathogens.

A preferred spike nucleic acid sequence suitable for use in the invention is a polynucleotide encoding a Spike polypeptide, said polynucleotide having at least at least 80%, 81%, 82%, 83%, 84%, 85%, 86%, 87%, 88%, or 89%, more preferably at least 90%, 91%, 92%, 93%, or 94%, and most preferably at least 95%, 96%, 96.1%, 96.2%, 96.3%, 96.4%, 96.5%, 96.6%, 96.7%, 96.8%, 96.9%, 97%, 97.1%, 97.2%, 97.3%, 97.4%, 97.5%, 97.6%, 97.7%, 97.8%, 97.9%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%. 99.99% sequence identity to SEQ ID NO: 2, 6, 8, and/or 13. "As used herein, it is in particular understood that the term "sequence identity to SEQ ID NO:X" or "identical SEQ ID NO:X", respectively, is equivalent to the term "sequence identity with the sequence of SEQ ID NO:X over the length of SEQ ID NO: X" or "identical to the sequence of SEQ ID NO:X over the length of SEQ ID NO: X", respectively, wherein in this context "X" is any integer selected from 1, 2, 6, 8, 13, and 15."

A preferred spike polypeptide suitable for use in the invention is the polypeptide having the sequence set out in SEQ ID NO:3, 7, 9 and/or 14 having at least 80% homology with SEQ ID NO:3, 7, 9 and/or 14, for example at least 85% homology with SEQ ID NO:3, 7, 9 and/or 14, such as a least 85% homology with SEQ ID NO:3, 7, 9 and/or 14, such as at least 90% homology with SEQ ID NO:3, 7, 9 and/or 14, for example at least 95%, at least 98% or at least 99% homology with SEQ ID NO:3, 7, 9 and/or 14.

The terms "vaccine" and "immunogenic composition" are defined herein in a broad sense to refer to any type of biological agent in an administrable form capable of stimulating an immune response in an animal inoculated with the vaccine. Vaccines in general may be based on either the virus itself (e.g., killed/inactivated or attenuated) or an immunogenic (antigenic) component of the virus. In one embodiment of the invention, the vaccine (immunogenic composition) preferably includes the viral agent in a killed/inactivated form or an antigenic portion of the virus presented as a sub-unit vaccine. Herein, the term "protection" when used in reference to a vaccine refers to the amelioration (either partial or complete) of any of the symptoms associated with the disease or condition in question. Thus, protection of pigs from PEDV by the present vaccines generally results in a diminishing of virus shedding and/or one or more of the clinical symptoms associated with infection by PEDV (e.g., acute watery diarrhea, acute vomiting, dehydration, anorexia, lethargy, depression, and high mortality in pigs less than 10 days old).

Those of skill in the art will understand that the compositions used herein may incorporate known injectable, physiologically acceptable sterile solutions. For preparing a ready-to-use solution for parenteral injection or infusion, aqueous isotonic solutions, e.g. saline or plasma protein solutions, are readily available. In addition, the immunogenic and vaccine compositions of the present invention can include veterinary-acceptable carriers, diluents, isotonic agents, stabilizers, or adjuvants.

Methods of the invention include, but are not limited to, a method of provoking an immune response against a PEDV infection in a subject comprising the step of administering to the subject an immunogenic composition comprising an inactivated/killed PEDV, attenuated PEDV, and/or Spike antigen. Preferably, the immune response is provoked against more than one serotype, or strain of PEDV. Compositions of the invention may be used to prevent a PEDV infection. Preferably, such immune response reduces the incidence of or severity of one or more clinical signs associated with or caused by the infection with one or more PEDV serotypes.

Herein, suitable subjects and subjects in need to which compositions of the invention may be administered include animals in need of prophylactic treatment for a viral associated infection, disease, or condition. Animals in which the immune response is stimulated by use of compositions or methods of the invention include livestock, such as swine, bovines, poultry (e.g., chickens, ducks, geese, or turkeys) goats, and sheep, and domestic animals, such as mice, rabbits, dogs, cats, and horses. Preferred animals include porcine, murids, equids, lagomorphs, and bovids. Most preferably, an immune response is stimulated in pigs.

The invention also provides a method of reducing the incidence of or severity of one or more clinical signs associated with or caused by PEDV infection, comprising the step of administering an immunogenic composition of the invention that comprises inactivated/killed PEDV vaccine and/or in combination with a Spike antigen as provided herewith and preferably a carrier molecule, such that the incidence of or the severity of a clinical sign of the PEDV infection is reduced by at least 10%, preferably at least 20%, even more preferred at least 30%, even more preferred at least 50%, even more preferred at least 70%, most preferred 100% relative to a subject that has not received the immunogenic composition as provided herewith. Such clinical signs include watery diarrhea, vomiting, and dehydration. Any of these clinical signs may result from an infection with PEDV having the genogroup of 2a or any other PEDV genogroup including G1a, G1b, or G2b In one embodiment, the present immunogenic compositions include a chemically inactivated form of PEDV. Vaccines which include chemically inactivated PEDV (SEQ ID NO:1 or SEQ ID NO:15) virus are particularly desirable. A variety of chemical inactivating agents known to those skilled in the art may be employed to inactivate the virus. Ethylenimine and related derivatives, such as binary ethylenimine ("BEI") and acetylethylenimine, are examples of suitable chemical inactivating agents for use in inactivating the PED virus. Other chemical inactivating agents, e.g., beta-propiolactone or aldehydes (such as formaldehyde and glutaraldehyde), can also be used to inactivate the virus.

The present immunogenic compositions and/or vaccines generally include an adjuvant which desirably may have bioadhesive properties, particularly where the virus is designed to be capable of intranasal administration. Examples of suitable adjuvants include cross-linked olefinically unsaturated carboxylic acid polymers, such as cross-linked acrylic acid polymers. As used herein the term "cross-linked acrylic acid polymer" refers to polymer and copolymers formed from a monomer mixture which includes acrylic acid as the predominant monomer in the mixture. Examples of suitable cross-linked acrylic acid polymers include those commercially available under the tradenames CARBOPOL® 934P and CARBOPOL® 971 (available from B.F. Goodrich Co., Cleveland, Ohio). One particularly suitable adjuvant for use in the present vaccines is a cross-linked acrylic acid polymer having a Brookfield viscosity of no more than about 20,000 cPs (as measured at 20 rpm as a 1.0 wt. % aqueous solution at pH 7.5). Where a bioadhesive adjuvant is desired, it may be advantageous to utilize an adjuvant which has a bioadhesive property of at least about 50 dynes/cm2 as measured between two pieces of freshly excised rabbit stomach tissue (as determined by the procedure described in U.S. Pat. No. 4,615,697).

The present invention also relates to a method of immunizing a subject, comprising administering to a subject any of the immunogenic compositions as described herein.

The term "immunizing" relates to an active immunization by the administration of an immunogenic composition to a subject to be immunized, thereby causing an immunological response against the antigen included in such immunogenic composition.

Preferably, immunization results in lessening of the incidence of the particular PEDV infection in a herd or in the reduction in the severity of clinical signs caused by or associated with the particular PEDV infection.

Further, the immunization of a subject in need with the immunogenic compositions as provided herewith, results in preventing infection of a subject by PEDV infection. Even more preferably, immunization results in an effective, long-lasting, immunological-response against PEDV infection. It will be understood that the said period of time will last more than 2 months, preferably more than 3 months, more preferably more than 4 months, more preferably more than 5 months, more preferably more than 6 months. It is to be understood that immunization may not be effective in all subjects immunized.

Preferably, a herd of subjects is envisaged in this context which normally, i.e. without immunization, would develop clinical signs normally caused by or associated with a PEDV infection. Whether the subjects of a herd are effectively immunized can be determined without further ado by the person skilled in the art. Preferably, the immunization shall be effective if clinical signs in at least 20%, at least 30%, at least 40%, at least 50%, at least 60%, at least 70%, at least 80%, at least 90%, still more preferably in at least 95% and most preferably in 100% of the subjects of a given herd are lessened in incidence or severity by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, still more preferably by at least 90%, still more preferably by at least 95% and most preferably by 100% in comparison to subjects that are either not immunized or immunized with an immunogenic composition that was available prior to the present invention but subsequently infected by the particular PEDV.

Methods for preventing clinical signs caused by PEDV in a subject in need, or methods of protecting pigs against diseases associated with PEDV include administering an immunogenic composition and/or vaccine containing inactivated/killed PEDV and/or Spike antigen to the pigs. The vaccine can be administered using a variety of methods including intranasal, oral and/or parenteral (e.g., intramuscular) administration. In one embodiment of the method, for example, the inactivated PEDV containing vaccine is administered intramuscularly one or more times (e.g., at intervals of 2-4 weeks). In another embodiment of the method, for example, the inactivated PEDV containing vaccine is administered orally one or more times (e.g., at intervals of 2-4 weeks). In an alternative embodiment oral administration can be followed by and/or precede administration of the vaccine at least once, intramuscularly (e.g., 2-4 weeks after and/or before the parenteral administration of vaccine). Ideally, all pigs in a given herd are vaccinated at the prescribed intervals in order to protect against the spread of symptoms of the disease.

A method of producing an inactivated/killed PEDV vaccine is also provided. The method typically includes inoculating simian cells with PED virus, e.g., with PED virus SEQ ID NO:1 or SEQ ID NO:15. The inoculated simian cells are incubated, generally at least until CPE is observed (commonly after 24 to 120 hours at 37° C.), and then the PED virus is harvested from the incubated cells (e.g., by decanting and filtering the culture fluids). The harvested virus-containing fluids can be treated with a chemical inactivating agent, such as binary ethylenimine, to form inactivated/killed PED virus. Typically, the inactivated virus is further processed, e.g., by concentration and blending with other components, to produce a commercial formulation. For example, the fluids containing the inactivated virus may be concentrated and blended with an adjuvant and/or antigen(s) to one or more other porcine pathogens.

A method of producing a recombinantly expressed Spike antigen vaccine generated in insect cells via a recombinant baculovirus expressing a modified PEDV Spike protein is also provided. The method in one exemplary embodiment includes cloning the PEDV Spike coding sequence (SEQ ID NO:7) modified to remove the PEDV Spike signal peptide, transmembrane domain, and c-terminal domain into a vector (VSVG-PEDVS-VSVG DNA Sequence (SEQ ID NO:8)) and co-transfect Sf9 insect cells. For the inactivated recombinant PEDV material, PEDV baculoviral harvest was inactivated for 24 hours using 5 mM BEI, clarified and 0.45 μm filtered. Typically, the inactivated virus is further processed, e.g., by concentration and blending with other components, to produce a commercial formulation. For example, the fluids containing the inactivated virus may be concentrated and blended with an adjuvant and/or antigen(s) to one or more other porcine pathogens.

The present application is also directed to a kit which includes in combination, (1) a dispenser capable of administering a vaccine to a pig; and (2) a chemically inactivated PEDV and/or recombinant Spike antigen containing vaccine capable of protecting against diseases associated with PEDV. The kit may include a dispenser which is capable of dispensing its contents as droplets, e.g., as aerosol, atomized spray and/or liquid droplets, and a form of the vaccine which is capable of protecting against diseases associated with PEDV, for example when administered intranasally and/or intramuscularly.

Throughout this application, the text refers to various embodiments of the present compositions and/or related methods. The various embodiments described are meant to provide a variety of illustrative examples and should not be construed as descriptions of alternative species. Rather, it should be noted that the descriptions of various embodiments provided herein may be of overlapping scope. The embodiments discussed herein are merely illustrative and are not meant to limit the scope of the present invention.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1 DNA Alignment of PEDV 1251-125-10 (125-10) genome (SEQ ID NO:1) and closest Chinese PEDV strain AH2012 (GenBank Accession No: KC210145) (SEQ ID NO:10).

FIG. 2 DNA Alignment of PEDV 1251-125-10 (125-10) genome (SEQ ID NO:1) and closest North American PEDV strain Colorado 2013 (GenBank Accession No: KF272920) (SEQ ID NO:11).

FIG. 3 Amino Acid Sequence Alignment of PEDV 1251-125-10 (125-10) spike protein (SEQ ID NO:14) aligned and closest GenBank sequence corresponding to North American Colorado strain (GenBank Accession No: AGO58924) (SEQ ID NO:12).

DETAILED DESCRIPTION

Figure 4:
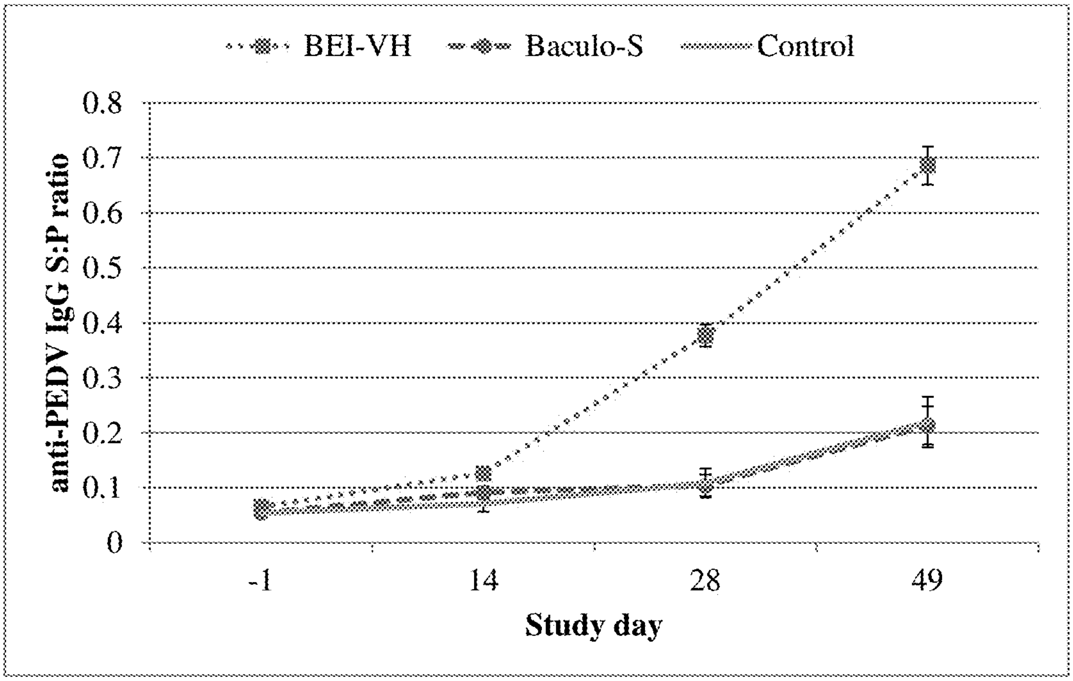
FIG. 4 Graphical representation of Anti-PEDV-IgG ELISA data (Group least square mean±standard error anti-PEDV-IgG S:P ratios for D-1, 14, 28 and 49).
Figure 5:
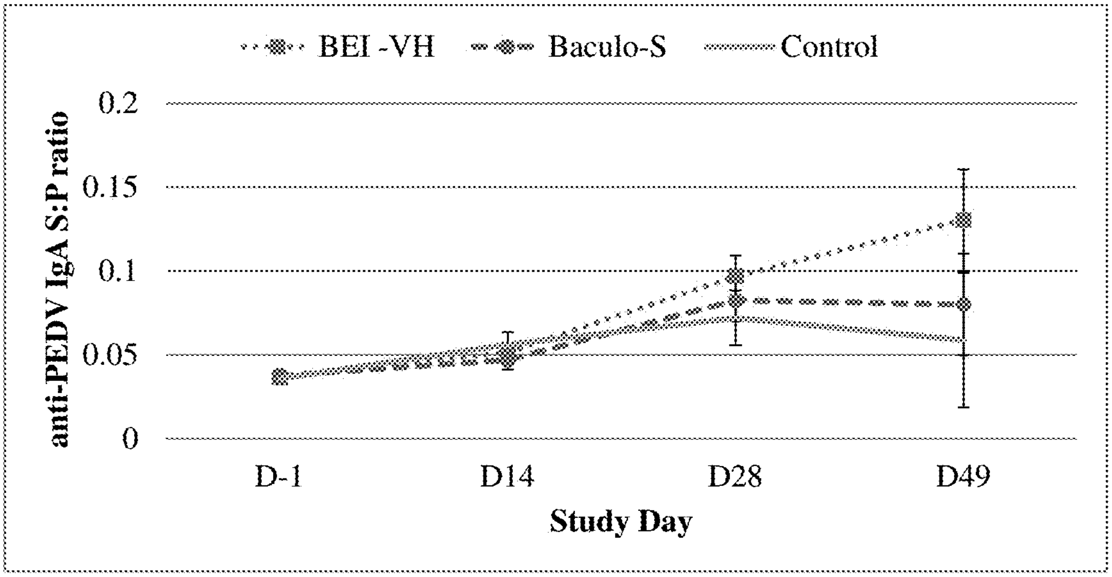
FIG. 5 Graphical representation of Anti-PEDV-IgA ELISA data (Group least square mean±standard error anti-PEDV-IgA S:P ratios for D-1, 14, 28 and 49).

The invention provides immunogenic compositions including inactivated/killed, forms of PEDV and/or recombinantly expressed PEDV-Spike antigen. The vaccines are designed for protecting swine against diseases associated with PEDV. The vaccines typically include a chemically inactivated form of PEDV and those which include chemically inactivated/killed PEDV virus are particularly desirable. In another embodiment the vaccines include a recombinant expressed Spike antigen generated, for example, in insect cells via a recombinant baculovirus expressing a modified PEDV Spike protein.

One embodiment of the invention can be a vaccine comprising one or more antigens of PEDV genotype 2a. In a preferred embodiment PEDV is of North American origin. More preferably, the PEDV of North American genotype is any PEDV encoded by SEQ ID NO:1, or comprising the sequence of SEQ ID NO:1, and/or comprises the RNA equivalent of SEQ ID NO:1; which sequence is at least 99% identical with the SEQ ID NO:1, and/or is at least 99% identical with the RNA equivalent of SEQ ID. NO:1; which spike protein is encoded by nucleic acid sequences of SEQ ID NO:2, 6, 8, or 13; which spike protein is encoded by a nucleic acid sequence that is at least 90% identical with the SEQ ID NO:2, 6, 8, or 13; that is encoded by SEQ ID NO:15; or which sequence is at least 99% identical SEQ ID NO:15.

In other embodiments of the invention, the vaccine is a recombinant vaccine or a killed vaccine. In exemplary embodiments of the invention, PEDV is chemically inactivated, for example, by treatment with a chemical inactivating agent which includes a compound selected from the group consisting of ethylenimine, binary ethylenimine, acetylethylenimine and mixtures thereof. In a preferred embodiment, PEDV is chemically inactivated by treatment with binary ethylenimine.

In yet other embodiments of the invention, the vaccine further comprises an adjuvant. In a preferred embodiment, the adjuvant is an EMULSIGEN® based oil-in-water emulsion.

In one embodiment of the invention, the vaccine is recombinant vaccine. In a preferred embodiment, such a recombinant vaccine comprises one or more immunogenic components selected from the group consisting of an isolated nucleic acid encoding an antigen of PEDV spike protein, wherein the recombinant Spike polypeptide has at least 90% homology with SEQ ID NO:3, 7, 9 or 14; a vector comprising the isolated nucleic acid of a); the recombinant PEDV Spike protein encoded by the nucleic acid of a); and/or any combination thereof. Optionally, such a recombinant vaccine comprises a pharmaceutical acceptable carrier and/or excipient. In one embodiment the excipient is one or more adjuvants. Preferably, the adjuvant is an EMULSIGEN® oil-in-water emulsion-based adjuvant.

In yet another aspect of the invention, the recombinant vaccine further comprises one or more additional antigens, for example, the additional antigen can be structural protein M, E, or N of a PEDV.

In another embodiment, the recombinant vaccine comprises an immunogenic component that can be an isolated nucleic acid, a vector, a recombinant PEDV Spike protein, and/or a combination of at least two of the later.

Embodiments of the invention also include methods of preventing clinical signs and/or for protecting a pig against diseases associated with PEDV, comprising administering to such pig any of the killed/inactivated and/or recombinant vaccines described herein. For example the administered vaccine comprises one or more antigens of PEDV of genotype 2a. In a preferred embodiment PEDV is of North American origin. More preferably, PEDV) of North American genotype is any PEDV encoded by or comprising the sequence of SEQ ID NO:1; which sequence is at least 99% identical with the SEQ ID NO:1; which spike protein is encoded by nucleic acid sequences of SEQ ID NO:2, 6, 8, or 13; and/or which spike protein is encoded by a nucleic acid sequence at least 90% identical with the SEQ ID NO:2, 6, 8, or 13.

In another embodiment the method includes administration of a vaccine comprising one or more immunogenic components selected from the group consisting of a PEDV that is encoded by SEQ ID NO:1, or comprising the sequence of SEQ ID NO:1, and/or comprises the RNA equivalent (SEQ ID NO:16); which sequence is at least 99% identical with the SEQ ID NO:1, and/or is at least 99% identical with the RNA equivalent (SEQ ID NO:15); which spike protein is encoded by nucleic acid sequences of SEQ ID NO:2, 6, 8, or 13; which spike protein is encoded by a nucleic acid sequence that is at least 90% identical with the SEQ ID NO:2, 6, 8, or 13; that is encoded by SEQ ID NO:15; or which sequence is at least 99% identical SEQ ID NO:15.

In another embodiment the method includes administration of a vaccine comprising one or more immunogenic components selected from the group consisting of an isolated nucleic acid encoding an antigen of PEDV spike protein, wherein the recombinant Spike polypeptide has at least 90% homology with SEQ ID NO:3, 7, 9 or 14; a vector comprising the isolated nucleic acid of a); the recombinant PEDV Spike protein encoded by the nucleic acid of a); and any combination thereof.

Yet another embodiment of the invention includes a kit for vaccinating a pig against diseases associated with PEDV comprising: a dispenser capable of administering a vaccine to a pig; and a PEDV vaccine as described herein.

An embodiment of the invention includes a method of producing a porcine epidemic diarrhea vaccine according to claim 5 comprising: (a) inoculating simian cells with PEDV; (b) incubating the inoculated simian cells; (c) harvesting PEDV from the incubated cells; and (d) treating the harvested cells with a chemical inactivating agent, preferably with a compound selected from the group consisting of ethylenimine, binary ethylenimine, acetylethylenimine or a mixture thereof to form inactivated PEDV vaccine. In a preferred embodiment, the method comprises a (PEDV comprising a sequence that is encoded by SEQ ID NO:1, or comprising the sequence of SEQ ID NO:1, and/or comprises the RNA equivalent of SEQ ID NO:1; which sequence is at least 99% identical with the SEQ ID NO:1, and/or is at least 99% identical with the RNA equivalent of SEQ ID. NO:1; which spike protein is encoded by nucleic acid sequences of SEQ ID NO:2, 6, 8, or 13; which spike protein is encoded by a nucleic acid sequence that is at least 90% identical with the SEQ ID NO:2, 6, 8, or 13; that is encoded by SEQ ID NO:15; or which sequence is at least 99% identical SEQ ID NO:15.

In one embodiment, the method includes PEDV of genogroup 2a comprising SEQ ID NO:1 and or SEQ ID NO:15. In alternative embodiments of the method, the inoculated simian cells are Vero cells. In a preferred embodiment of the method the chemical inactivating agent includes binary ethylenimine. The method can further comprise adding an adjuvant to the PEDV vaccine, preferably, the adjuvant is an EMULSIGEN® oil-in-water emulsion-based adjuvant.

Another embodiment of the invention includes a method of producing a recombinant vaccine comprising: expressing one or more antigens of PEDV in a host cell; and harvesting one or more antigens from PEDV-expressing cells. In one such embodiment the method can include one or more antigens comprising an isolated nucleic acid encoding an antigen of PEDV spike protein, wherein the recombinant Spike polypeptide has at least 90% homology with SEQ ID NO:3, 7, 9 or 14; a vector comprising the isolated nucleic acid of a); the recombinant PEDV Spike protein encoded by the nucleic acid of a); and any combination thereof. In one exemplary embodiment, one or more antigens of PEDV are expressed by a recombinant baculovirus vector. The method can include one or more antigens of PEDV expressed in insect cells. One embodiment further comprises the addition of an adjuvant to the PEDV vaccine, preferably wherein the adjuvant is an EMULSIGEN® oil-in-water emulsion-based adjuvant.

In more general terms, a variety of chemical inactivating agents known to those skilled in the art may be employed to inactivate the virus. Ethylenimine and related derivatives, such as binary ethylenimine (BEI) and acetylethylenimine, are examples of suitable chemical inactivating agents for use in inactivating the PED virus. Other chemical inactivating agents, e.g., beta-propiolactone, aldehydes (such as formaldehyde) and/or detergents (e.g., Tween® detergent, Triton® X, or alkyl trimethylammonium salts) can also be used to inactivate the virus. The inactivation can be performed using standard methods known to those of skill in the art. Samples can be taken at periodic time intervals and assayed for residual live virus. Monitoring of cytopathic effect on an appropriate cell line and/or fluorescent staining with an appropriate specific monoclonal or polyclonal antibody can be used to detect the presence of residual live virus.

Inactivation with BEI can be accomplished by combining a stock BEI solution (e.g., a solution formed by adding 0.1-0.2 M 2-bromo-ethylamine hydrobromide to 0.1-0.2 N aqueous NaOH) with viral fluids to a final concentration of about 1-5 mM BEI. Inactivation is commonly performed by holding the BEI-virus mixture at 35-40° C. (e.g., 37° C.) with constant mixing for 24-72 hours. Virus inactivation can be halted by the addition of sodium thiosulfate solution to a final concentration in excess of the BEI concentration (e.g., addition of sodium thiosulfate at 17% of the volume of BEI to neutralize excess BEI) followed by mixing.

The present immunogenic compositions usually include an adjuvant and, if desired, one or more emulsifiers such as Tween® detergent incorporated with the inactivated/killed PEDV. Suitable adjuvants include, for example, vitamin E acetate solubilisate, aluminum hydroxide, aluminum phosphate or aluminum oxide, (mineral) oil emulsions, non-ionic detergents, squalene and saponins. Other adjuvants which may be used include an oil based adjuvants such as Freund's complete adjuvant (FCA), and Freund's incomplete adjuvant (FIA). It has been found that cross-linked olefinically unsaturated carboxylic acid polymers, such as CARBOPOL® 971 polymer, are particularly suitable adjuvants for use in the present inactivated PEDV immunogenic compositions.

Examples for suitable oil-in water emulsions are EMULSIGEN® based adjuvants, such as EMULSIGEN® (an oil-in-water emulsion), EMULSIGEN-D® (an oil-in-water) with dimethyldioctadecylammonium bromide (DDA)), EMULSIGEN-P® (an oil-in-water) with a proprietary immunostimulant), EMULSIGEN-75® (a double adjuvant comprised of an oil-in-water) with a cross-linked polymer), and EMULSIGEN®-BCL (an oil-in-water emulsion that is free of animal origin components). (MVP Technologies, Inc. Omaha, Nebr., USA). Pharmaceutical/vaccine compositions that comprise inactivated PEDV or recombinant PEDV proteins, have been effectively adjuvanted with oil-in water emulsions, preferably with such EMULSIGEN®-based adjuvants, more preferably with EMULSIGEN® (an oil-in-water emulsion that is free of animal origin components) and EMULSIGEN®-BCL (an oil-in-water emulsion that is free of animal origin components).

It is generally advantageous to formulate the present compositions in dosage unit form for ease of administration and uniformity of dosage. Dosage unit form as used herein refers to physically discrete units suited as unitary dosages for the mammalian subjects to the treated; each unit containing a predetermined quantity of the active material calculated to produce the desired therapeutic effect in association with the required pharmaceutical carrier. The specification for the dosage unit forms of inactivated/killed PEDV, and/or recombinantly expressed PEDV antigen are dictated by and depend on among other factors (a) the unique characteristics of the active material and the particular therapeutic effect to be achieved; (b) the limitations inherent in the art of compounding such active material for the treatment of disease; and (c) the manner of intended administration of the dosage unit form.

The principal active ingredient is typically compounded for convenient and effective administration in effective amounts with a suitable pharmaceutically acceptable carrier in dosage unit form as disclosed herein. A unit dosage form can, for example, contain the PEDV antigen in amounts ranging from 1 to about 5 relative potency units ("RPUs"). This amount of the antigen is generally present in from about 1 to about 25/ml of carrier. In the case of compositions containing supplementary active ingredients, the dosages are determined by reference to the usual dose and manner of administration of the supplementary active ingredients.

The present vaccines typically include inactivated PEDV formulated with a pharmaceutically acceptable carrier. The pharmaceutical forms suitable for injectable use commonly include sterile aqueous solutions (where water soluble) or dispersions and sterile powders for the extemporaneous preparation of sterile injectable solutions or dispersion. The formulation should desirably be sterile and fluid to the extent that easy syringability exists. The dosage form should be stable under the conditions of manufacture and storage and typically is preserved against the contaminating action of microorganisms such as bacteria and fungi. The carrier can be a solvent or dispersion medium containing, for example, water, ethanol, polyol (for example, glycerol, propylene glycol, liquid polyethylene glycol, and the like), suitable mixtures thereof and vegetable oils. One possible carrier is a physiological salt solution. The proper fluidity of the solution can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabenes, chlorobutanol, phenol, sorbic acid, thimerosal (sodium ethylmercuri-thiosalicylate), deomycin, gentamicin and the like. In many cases it may be preferable to include isotonic agents, for example, sugars or sodium chloride. Prolonged absorption of the injectable compositions, if desired, can be brought about by the use in the compositions of agents delaying absorption, for example, aluminum monostearate and gelatin.

Sterile injectable solutions may be prepared by incorporating the inactivated virus in the desired amount in an appropriate solvent with various other ingredients as enumerated above, as required, followed by filtered sterilization. Generally, dispersions can be prepared by incorporating the various active ingredients into a sterile vehicle which contains the basic dispersion medium and the required other ingredients from those enumerated above. In the case of sterile powders for the preparation of sterile injectable solutions, the preferred methods of preparation are vacuum-drying and the freeze-drying technique which yield a powder of the active ingredient plus any additional desired ingredient from a previously sterile-filtered solution thereof.

It may also be advantageous to add a stabilizer to the present compositions to improve the stability of inactivated virus. Suitable stabilizers include, for example, glycerol/EDTA, carbohydrates (such as sorbitol, mannitol, trehalose, starch, sucrose, dextran or glucose), proteins (such as albumin or casein) and protein degradation products (e.g., partially hydrolyzed gelatin). If desired, the formulation may be buffered by methods known in the art, using reagents such as alkali metal phosphates, e.g., sodium hydrogen phosphate, sodium dihydrogen phosphate, potassium hydrogen phosphate and/or potassium dihydrogen phosphate. Other solvents, such as ethanol or propylene glycol, can be used to increase solubility of ingredients in the vaccine formulation and/or the stability of the solution. Further additives which can be used in the present formulation include conventional antioxidants and conventional chelating agents, such as ethylenediamine tetraacetic acid (EDTA).

The compositions and methods of the present invention may be illustrated by the following examples, which are presented to illustrate the present invention and to assist in teaching one of ordinary skill how to make and use the same. These examples are not intended in any way to narrow or otherwise limit the scope of the present invention.

The practice of the present invention will employ, unless otherwise indicated, conventional techniques of molecular biology, microbiology, recombinant DNA technology, protein chemistry and immunology, which are within the skill of the art. Such techniques are explained fully in the literature. See, e.g., Sambrook, Fritsch & Maniatis, Molecular Cloning: A Laboratory Manual, Vols. I, II and III, Second Edition (1989); DNA Cloning, Vols. I and II (D. N. Glover ed. 1985); Oligonucleotide Synthesis (M. J. Gait ed. 1984); Nucleic Acid Hybridization (B. D. Hames & S. J. Higgins eds. 1984); Animal Cell Culture (R. K. Freshney ed. 1986); Immobilized Cells and Enzymes (IRL press, 1986); Perbal, B., A Practical Guide to Molecular Cloning (1984); the series, Methods In Enzymology (S. Colowick and N. Kaplan eds., Academic Press, Inc.); Protein purification methods—a practical approach (E. L. V. Harris and S. Angal, eds., IRL Press at Oxford University Press); and Handbook of Experimental Immunology, Vols. I-IV (D. M. Weir and C. C. Blackwell eds., 1986, Blackwell Scientific Publications).

It is to be understood that this invention is not limited to particular DNA, RNA, polypeptide sequences, or process parameters as such may, of course, vary. It is also to be understood that the terminology used herein is for the purpose of describing particular embodiments of the invention only, and is not intended to be limiting. It must be noted that, as used in this specification and the appended claims, the singular forms "a", "an" and "the" include plural referents unless the content clearly dictates otherwise. Thus, for example, reference to "an antigen" includes a mixture of two or more antigens; reference to "an excipient" includes mixtures of two or more excipients, and the like.

Definitions

Unless defined otherwise, all technical and scientific terms used herein have the same meaning as is commonly understood by one of skill in the art to which this invention belongs at the time of filing. The meaning and scope of terms should be clear; however, in the event of any latent ambiguity, definitions provided herein take precedent over any dictionary or extrinsic definition. Further, unless otherwise required by context, singular terms shall include pluralities and plural terms shall include the singular. Herein, the use of "or" means "and/or" unless stated otherwise. Furthermore, the use of the term "including", as well as other forms such as "includes" and "included" is not limiting. All patents and publications referred to herein are incorporated by reference herein.

"Protection against disease", "protective immunity", "functional immunity" and similar phrases, means a response against a disease or condition generated by administration of one or more therapeutic compositions of the invention, or a combination thereof, that results in fewer deleterious effects than would be expected in a non-immunized subject that has been exposed to disease or infection. That is, the severity of the deleterious effects of the infection are lessened in a vaccinated subject. Infection may be reduced, slowed, or possibly fully prevented, in a vaccinated subject. Herein, where complete prevention of infection is meant, it is specifically stated. If complete prevention is not stated then the term includes partial prevention.

Herein, "reduction of the incidence and/or severity of clinical signs" or "reduction of clinical symptoms" means, but is not limited to, reducing the number of infected subjects in a group, reducing or eliminating the number of subjects exhibiting clinical signs of infection, or reducing the severity of any clinical signs that are present in one or more subjects, in comparison to wild-type infection. For example, it should refer to any reduction of pathogen load, pathogen shedding, reduction in pathogen transmission, or reduction of any clinical sign symptomatic of PEDV. Preferably these clinical signs are reduced in one or more subjects receiving the therapeutic composition of the present invention by at least 10% in comparison to subjects not receiving the composition and that become infected. More preferably clinical signs are reduced in subjects receiving a composition of the present invention by at least 20%, preferably by at least 30%, more preferably by at least 40%, and even more preferably by at least 50%.

The term "increased protection" herein means, but is not limited to, a statistically significant reduction of one or more clinical symptoms which are associated with infection by an infectious agent, preferably PEDV, respectively, in a vaccinated group of subjects vs. a non-vaccinated control group of subjects. The term "statistically significant reduction of clinical symptoms" means, but is not limited to, the frequency in the incidence of at least one clinical symptom in the vaccinated group of subjects is at least 10%, preferably 20%, more preferably 30%, even more preferably 50%, and even more preferably 70% lower than in the non-vaccinated control group after the challenge with the infectious agent.

"Long-lasting protection" shall refer to "improved efficacy" that persists for at least 3 weeks, but more preferably at least 3 months, still more preferably at least 6 months. In the case of livestock, it is most preferred that the long lasting protection shall persist until the average age at which animals are marketed for meat.

An "immunogenic or immunological composition" refers to a composition of matter that comprises at least one porcine epidemic diarrhea virus, or immunogenic portion thereof, that elicits an immunological response in the host of a cellular or antibody-mediated immune response to the composition. In a preferred embodiment of the present invention, an immunogenic composition induces an immune response and, more preferably, confers protective immunity against one or more of the clinical signs of a PEDV infection.

The immunogenic composition as used herein also refers to a composition that comprises any of the PEDV Spike proteins described herein. According to a further embodiment, such immunogenic composition further comprises at least a portion of a viral vector expressing said PEDV Spike protein, preferably of a recombinant baculovirus. Moreover, the immunogenic composition can comprise i) any of the PEDV proteins described above, preferably in concentrations described above, ii) at least a portion of the viral vector expressing said PEDV Spike protein, preferably of a recombinant baculovirus, and iii) a portion of the cell culture supernatant.

Thus according to one aspect, the present invention relates to a method for reducing the percentage of PEDV infections in a herd of pigs comprising the step administering to said pig(s) an effective amount of PEDV Spike antigen or an immunogenic composition comprising PEDV antigen, wherein the PEDV antigen is recombinant PEDV Spike antigen, preferably a baculovirus expressed PEDV Spike protein. Preferably those recombinant or baculovirus expressed PEDV Spike having the sequence as described herein.

An "immune response" or "immunological response" means, but is not limited to, the development of a cellular and/or antibody-mediated immune response to the composition or vaccine of interest. Usually, an immune or immunological response includes, but is not limited to, one or more of the following effects: the production or activation of antibodies, B cells, helper T cells, suppressor T cells, and/or cytotoxic T cells, directed specifically to an antigen or antigens included in the composition or vaccine of interest. Preferably, the host will display either a therapeutic or a protective immunological (memory) response such that resistance to new infection will be enhanced and/or the clinical severity of the disease reduced. Such protection will be demonstrated by either a reduction in number of symptoms, severity of symptoms, or the lack of one or more of the symptoms associated with the infection of the pathogen, a delay in the of onset of viremia, reduced viral persistence, a reduction in the overall viral load and/or a reduction of viral excretion.

As used herein, "a pharmaceutical- or veterinary-acceptable carrier" includes any and all solvents, dispersion media, coatings, adjuvants, stabilizing agents, diluents, preservatives, antibacterial and antifungal agents, isotonic agents, adsorption delaying agents, and the like. In some preferred embodiments, and especially those that include lyophilized immunogenic compositions, stabilizing agents for use in the present invention include stabilizers for lyophilization or freeze-drying.

In some embodiments, the immunogenic composition of the present invention contains an adjuvant. "Adjuvants" as used herein, can include aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion.

The emulsion can be based in particular on light liquid paraffin oil (European Pharmacopea type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al. The Theory and Practical Application of Adjuvants (Ed. Stewart-Tull, D. E. S.), John Wiley and Sons, NY, pp 51-94 (1995) and Todd et al. Vaccine 15:564-570 (1997). Exemplary adjuvants are the SPT emulsion described on page 147 of "Vaccine Design, The Subunit and Adjuvant Approach" edited by M. Powell and M. Newman, Plenum Press, 1995, and the emulsion MF59 described on page 183 of this same book.

Examples for suitable oil-in water emulsions are EMULSIGEN® based adjuvants, such as EMULSIGEN® (an oil-in-water emulsion o/w), EMULSIGEN-D® (an oil-in-water (o/w) with dimethyldioctadecylammonium bromide (DDA)), EMULSIGEN-P® (an oil-in-water (o/w) with a proprietary immunostimulant), EMULSIGEN-75® (a double adjuvant comprised of an oil-in-water (o/w) with a cross-linked polymer), and EMULSIGEN®-BCL (an oil-in-water emulsion that is free of animal origin components). (MVP Laboratories, Inc. Omaha, Nebr., USA). Pharmaceutical/vaccine compositions that comprise inactivated PEDV or recombinant PEDV proteins, have been effectively adjuvanted with oil-in water emulsions, preferably with such EMULSIGEN®-based adjuvants, more preferably with EMULSIGEN® (an oil-in-water emulsion o/w) and/or EMULSIGEN®-BCL (an oil-in-water emulsion that is free of animal origin components).

Examples of suitable adsorbent aluminum hydroxide gels for use in veterinary vaccines include REHYDRAGEL®, REHYDRAGEL-CG®; REHYDRAGEL-LV; REHYDRAGEL-HPA; REHYDRAPHOS (General Chemical, Berkeley Heights, N.J., USA)?

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name CARBOPOL® (also known as polyacrylic acid); (BF Goodrich, Ohio, USA) are particularly appropriate. They are cross-linked with an allyl sucrose or with allyl pentaerythritol. Among then, there may be mentioned CARBOPOL® 974P (also known as polyacrylic acid), CARBOPOL® 934P (also known as polyacrylic acid) and CARBOPOL® 971P (also known as polyacrylic acid). Most preferred is the use of CARBOPOL® 971P (also known as polyacrylic acid). Among the copolymers of maleic anhydride and alkenyl derivative, the copolymers EMA (Monsanto) which are copolymers of maleic anhydride and ethylene. The dissolution of these polymers in water leads to an acid solution that will be neutralized, preferably to physiological pH, in order to give the adjuvant solution into which the immunogenic, immunological or vaccine composition itself will be incorporated.

Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from *E. coli* (recombinant or otherwise), cholera toxin, or muramyl dipeptide among many others.

It is expected that an adjuvant can be added in an amount of about 100 μg to about 10 mg per dose, preferably in an amount of about 100 μg to about 10 mg per dose, more preferably in an amount of about 500 μg to about 5 mg per dose, even more preferably in an amount of about 750 μg to about 2.5 mg per dose, and most preferably in an amount of about 1 mg per dose. Alternatively, the adjuvant may be at a concentration of about 0.01 to 50%, preferably at a concentration of about 2% to 30%, more preferably at a concentration of about 5% to 25%, still more preferably at a concentration of about 7% to 22%, and most preferably at a concentration of 10% to 20% by volume of the final product.

"Diluents" can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

"Isolated" means altered "by the hand of man" from its natural state, i.e., if it occurs in nature, it has been changed or removed from its original environment, or both. For example, a polynucleotide or polypeptide naturally present in a living organism is not "isolated," but the same polynucleotide or polypeptide separated from the coexisting materials of its natural state is "isolated", as the term is employed herein.

"Safety" refers to the absence of adverse consequences in a vaccinated animal following vaccination, including but not limited to: potential reversion of a viral-based vaccine to virulence, clinically significant side effects such as persistent, systemic illness or unacceptable inflammation at the site of vaccine administration.

The terms "vaccination" or "vaccinating" or variants thereof, as used herein means, but is not limited to, a process which includes the administration of an immunogenic composition of the invention that, when administered to an animal, elicits, or is able to elicit—directly or indirectly—, an immune response in the animal against PEDV.

"Mortality", in the context of the present invention, refers to death caused by PEDV infection, and includes the situation where the infection is so severe that an animal is euthanized to prevent suffering and provide a humane ending to its life.

Herein, "effective dose" means, but is not limited to, an amount of antigen that elicits, or is able to elicit, an immune response that yields a reduction of clinical symptoms in an animal to which the antigen is administered.

As used herein, the term "effective amount" means, in the context of a composition, an amount of an immunogenic composition capable of inducing an immune response that reduces the incidence of or lessens the severity of infection or incident of disease in an animal. Particularly, an effective amount refers to colony forming units (CFU) per dose. Alternatively, in the context of a therapy, the term "effective amount" refers to the amount of a therapy which is sufficient to reduce or ameliorate the severity or duration of a disease or disorder, or one or more symptoms thereof, prevent the advancement of a disease or disorder, cause the regression of a disease or disorder, prevent the recurrence, development, onset, or progression of one or more symptoms associated with a disease or disorder, or enhance or improve the prophylaxis or treatment of another therapy or therapeutic agent.

"Sequence Identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al. Nucleic Acids Research, 12(1):387 (1984)), BLASTP, BLASTN and FASTA (Altschul, S. F. et al. J. Molec. Biol., 215:403-410 (1990). The BLAST programs are publicly available from NCBI and other sources (BLAST Manual, Altschul, S. et al. NCVI NLM NIH Bethesda, Md. 20894, Altschul, S. F. et al. J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 85%, preferably 90%, even more preferably 95% "sequence identity" to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, even more preferably 95% identity relative to the reference nucleotide sequence, up to 15%, preferably 10%, even more preferably 5% of the nucleotides in the reference sequence may be deleted or substituted with another nucleotide, or a number of nucleotides up to 15%, preferably 10%, even more preferably 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 85%, preferably 90%, even more preferably 95% sequence identity to a reference amino acid sequence, it is intended that the given amino acid sequence of the polypeptide is identical to the reference sequence except that the given polypeptide sequence may include up to 15, preferably up to 10, even more preferably up to 5 amino acid alterations per each 100 amino acids of the reference amino acid sequence. In other words, to obtain a given polypeptide sequence having at least 85%, preferably 90%, even more preferably 95% sequence identity with a reference amino acid sequence, up to 15%, preferably up to 10%, even more preferably up to 5% of the amino acid residues in the reference sequence may be deleted or substituted with another amino acid, or a number of amino acids up to 15%, preferably up to 10%, even more preferably up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence homology.

A "conservative substitution" refers to the substitution of an amino acid residue or with another amino acid residue having similar characteristics or properties including size, hydrophobicity, etc., such that the overall functionality does not change significantly.

"Sequence homology", as used herein, refers to a method of determining the relatedness of two sequences discounting conservative substitutions. To determine sequence homology, two or more sequences are optimally aligned, and gaps are introduced if necessary. In other words, to obtain a polypeptide having 95% sequence homology with a reference sequence, 85%, preferably 90%, even more preferably 95% of the amino acid residues in the reference sequence must match or comprise a conservative substitution with another amino acid, or a number of amino acids up to 15%, preferably up to 10%, even more preferably up to 5% of the total amino acid residues, not including conservative substitutions, in the reference sequence may be inserted into the reference sequence. Preferably the homolog sequence comprises at least a stretch of 50, even more preferred of 100, even more preferred of 250, even more preferred of 500 amino acids.

The terms "sequence identity" or "percent identity" are used interchangeably herein. For the purpose of this invention, it is defined here that in order to determine the percent identity of two amino acid sequences or two nucleic acid sequences, the sequences are aligned for optimal comparison purposes (e.g., gaps can be introduced in the sequence of a first amino acid or nucleic acid for optimal alignment with a second amino or nucleic acid sequence). The amino acid or nucleotide residues at corresponding amino acid or nucleotide positions are then compared. When a position in the first sequence is occupied by the same amino acid or nucleotide residue as the corresponding position in the second sequence, then the molecules are identical at that position. The percent identity between the two sequences is a function of the number of identical positions shared by the sequences (i.e., % identity=number of identical positions/total number of positions (i.e. overlapping positions)×100).

Preferably, the two sequences are the same length. When sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity."

A sequence comparison may be carried out over the entire lengths of the two sequences being compared or over fragment of the two sequences. Typically, the comparison will be carried out over the full length of the two sequences being compared. However, sequence identity may be carried out over a region of, for example, twenty, fifty, one hundred or more contiguous amino acid residues.

The skilled person will be aware of the fact that several different computer programs are available to determine the homology between two sequences. For instance, a comparison of sequences and determination of percent identity between two sequences can be accomplished using a mathematical algorithm. In a preferred embodiment, the percent identity between two amino acid or nucleic acid sequences is determined using the Needleman and Wunsch (J. Mol. Biol. (48): 444-453 (1970)) algorithm which has been incorporated into the GAP program in the Accelrys GCG software package (available at http://www.accelrys.com/products/gcg/), using either a Blosum 62 matrix or a PAM250 matrix, and a gap weight of 16, 14, 12, 10, 8, 6, or 4 and a length weight of 1, 2, 3, 4, 5, or 6. The skilled person will appreciate that all these different parameters will yield slightly different results but that the overall percentage identity of two sequences is not significantly altered when using different algorithms.

The protein sequences or nucleic acid sequences of the present invention can further be used as a "query sequence" to perform a search against public databases to, for example, to identify other family members or related sequences. Such searches can be performed using the BLASTN and BLASTP programs (version 2.0) of Altschul, et al. (1990) J. Mol. Biol. 215:403-10. BLAST protein searches can be performed with the BLASTP program, score=50, wordlength=3 to obtain amino acid sequences homologous to protein molecules of the invention. To obtain gapped alignments for comparison purposes, Gapped BLAST can be utilized as described in Altschul et al. (1997) Nucleic Acids Res. 25(17): 3389-3402. When utilizing BLAST and Gapped BLAST programs, the default parameters of the respective programs (e.g., BLASTP and BLASTN) can be used. See the homepage of the National Center for Biotechnology Information at http://www.ncbi.nlm.nih.gov/.

The claimed PEDV of the invention shall also encompass variants of the PEDV isolate 1251-125-10 ("125-10") and variants of sub-fragments thereof. Such variants have essentially the same immunological properties as characteristic of the Oklahoma strain (SEQ ID NO 1 and 15). The term "having essentially the same immunological properties" encompass (but is not restricted to) that said variants are essentially effective in treating or preventing the clinical signs caused by PEDV as described below or in improving the efficacy parameters as described below.

The term "variant" with respect to sequence SEQ ID NO:1, 2, 3, 6, 7, 8, 9, 14 and 15 (e.g., a polypeptide or nucleic acid sequence) is intended to mean substantially similar sequences. For nucleotide sequences comprising an open reading frame, variants include those sequences that, because of the degeneracy of the genetic code, encode the identical amino acid sequence of the native protein. Variant nucleotide sequences also include synthetically derived nucleotide sequences, such as those generated, for example, by using site-directed mutagenesis and for open reading frames, encode the native protein, as well as those that encode a polypeptide having amino acid substitutions relative to the native protein for the purposes of codon optimization. Generally, nucleotide sequence variants of the invention will have at least at least 80%, 81%, 82%, 83%, 84%, 85%, 86%, 87%, 88%, or 89%, more preferably at least 90%, 91%, 92%, 93%, or 94%, and most preferably at least 95%, 96%, 96.1%, 96.2%, 96.3%, 96.4%, 96.5%, 96.6%, 96.7%, 96.8%, 96.9%, 97%, 97.1%, 97.2%, 97.3%, 97.4%, 97.5%, 97.6%, 97.7%, 97.8%, 97.9%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%. 99.99% sequence identity compared to a reference sequence using one of the alignment programs described using standard parameters.

The term "genogroup" as it is known in the art refers to related viruses within a genus; which may be further subdivided into genetic clusters. Identified genogroups of PEDV include group G1, comprising subgroups G1a, G1b, R (attenuated/adapted); and G2, comprising subgroups G2a, and G2b. Members of the G2a genogroup include the Chinese strain AH2012 (GenBank accession no: KC210145) and the North American strains, sharing several unique nucleotides changes. Strains MN and IA2 had 99.6% and strain IA1 had 99.5% nucleotide identity with AH2012, respectively. Researchers have speculated that an AH2012-like virus was possibly transmitted to the eastern China regions and then transported to the United States and is the most likely closest ancestor to the North American strains. Members of the genogroup 2a share only approximately 96.9% similarity to the prototype PEDV strain CV777 of genogroup 1a (Bridgen, et al. 1993; Huang et al. 2013; GenBank: AF353511.1). As such, the attenuated PEDV vaccines based on the historical CV777-derived G1a strains or DR13-derived G1b strains may be antigenically less related to the newly emergent Chinese and North American G2a PEDV strains.

A closely related North American isolate US/Colorado/2013 (GenBank Accession No: KF272920.1) has also been reported by Marthaler et al. 2013. Like the North American isolates above the complete PEDV genome of CO/13 has a nucleotide identity of 96.5 to 99.5% with other complete PEDV genomes available in GenBank, with the highest nucleotide identity (99.5%) with Chinese strain AH2012 (GenBank Accession No. KC210145). Chinese strain AH2012 is a member of the 2a genogroup. Comparison of the complete genome of North American isolate CO/13 to that of PEDV reference strain CV777, shows that CO/13 contains a 1-nucleotide insertion (at position 48) and deletions of 5 nucleotides in the 5' UTR (at positions 73 and 83 to 86), while the spike gene contains insertions of 16 nucleotides (positions 20804, 20810 to 20820, 20843, and 21053 to 21055) and deletions of 7 nucleotides (positions 20853 and 21118 to 21124).

The term "PEDV of North American origin" means a PEDV isolate comprising SEQ ID NO:1 and/or SEQ ID NO:15, and/or any PEDV isolates having at least 99% sequence identity to SEQ ID NO:1, and/or is at least 99% identical with the RNA equivalent of SEQ ID. NO:1, and/or a PEDV isolate in which a Spike protein is encoded by SEQ ID NO:13, and/or any PEDV isolate in which a Spike protein has at least 98% sequence identity to SEQ ID:13, and/or any PEDV isolate in which the expressed Spike protein has at least 90% homology with SEQ ID NO:14.

The term "clade" as it is known in the art refers to a group consisting of an ancestor and all its descendants, a single "branch" in a phylogenetic tree. The ancestor may be, as an example an individual, a population or a species. A genogroup can include multiple clades, for example AH2012 is in a different clade than the North American isolates.

According to a further embodiment, the present invention also relates to a vector that comprises any of such nucleic acid molecules as described herein. In other words, the present invention relates to a vector, that includes the coding sequence of any such Spike, M, E, N PEDV protein, or part thereof. Preferably, said vector is an expression vector, which allows the expression of any such Spike, M, E, and/or N PEDV protein or part of the protein. Vectors according to the invention are those which are suitable for the transfection or infection of bacterial, yeast or animal cells, in vitro or in vivo.

Vectors and methods for making and/or using vectors (or recombinants) for expression can be by or analogous to the methods disclosed in: U.S. Pat. Nos. 4,603,112, 4,769,330, 5,174,993, 5,505,941, 5,338,683, 5,494,807, 4,722,848, 5,942,235, 5,364,773, 5,762,938, 5,770,212, 5,942,235, 382, 425, PCT publications WO 94/16716, WO 96/39491, WO 95/30018; Paoletti, "Applications of pox virus vectors to vaccination: An update, "PNAS USA 93: 11349-11353, October 1996; Moss, "Genetically engineered poxviruses for recombinant gene expression, vaccination, and safety," PNAS USA 93: 11341-11348, October 1996; Smith et al., U.S. Pat. No. 4,745,051 (recombinant baculovirus); Richardson, C. D. (Editor), Methods in Molecular Biology 39, "Baculovirus Expression Protocols" (1995 Humana Press Inc.); Smith et al., "Production of Human Beta Interferon in Insect Cells Infected with a Baculovirus Expression Vector", Molecular and Cellular Biology, December, 1983, Vol. 3, No. 12, p. 2156-2165; Pennock et al., "Strong and Regulated Expression of *Escherichia coli* B-Galactosidase in Infect Cells with a Baculovirus vector, "Molecular and Cellular Biology March 1984, Vol. 4, No. 3, p. 406; EPAO 370 573; U.S. application No. 920,197, filed Oct. 16, 1986; EP Patent publication No. 265785; U.S. Pat. No. 4,769,331 (recombinant herpesvirus); Roizman, "The function of herpes simplex virus genes: A primer for genetic engineering of novel vectors," PNAS USA 93:11307-11312, October 1996; Andreansky et al., "The application of genetically engineered herpes simplex viruses to the treatment of experimental brain tumors," PNAS USA 93: 11313-11318, October 1996; Robertson et al., "Epstein-Barr virus vectors for gene delivery to B lymphocytes", PNAS USA 93: 11334-11340, October 1996; Frolov et al., "Alphavirus-based expression vectors: Strategies and applications," PNAS USA 93: 11371-11377, October 1996; Kitson et al., J. Virol. 65, 3068-3075, 1991; U.S. Pat. Nos. 5,591,439, 5,552,143; WO 98/00166; allowed U.S. application Ser. Nos. 08/675, 556, and 08/675,566 both filed Jul. 3, 1996 (recombinant adenovirus); Grunhaus et al., 1992, "Adenovirus as cloning vectors," Seminars in Virology (Vol. 3) p. 237-52, 1993; Ballay et al. EMBO Journal, vol. 4, p. 3861-65, Graham, Tibtech 8, 85-87, April, 1990; Prevec et al., J. Gen Virol. 70, 42434; PCT WO 91/11525; Felgner et al. (1994), J. Biol. Chem. 269, 2550-2561, Science, 259: 1745-49, 1993; and McClements et al., "Immunization with DNA vaccines encoding glycoprotein D or glycoprotein B, alone or in combination, induces protective immunity in animal models of herpes simplex virus-2 disease", PNAS USA 93: 11414-11420, October 1996; and U.S. Pat. Nos. 5,591,639, 5,589, 466, and 5,580,859, as well as WO 90/11092, WO93/19183, WO94/21797, WO95/11307, WO95/20660; Tang et al., Nature, and Furth et al., Analytical Biochemistry, relating to DNA expression vectors, inter alia. See also WO 98/33510; Ju et al., Diabetologia, 41: 736-739, 1998 (lentiviral expression system); Sanford et al., U.S. Pat. No. 4,945,050; Fischbach et al. (Intracel); WO 90/01543; Robinson et al., Seminars in Immunology vol. 9, pp. 271-283 (1997), (DNA vector systems); Szoka et al., U.S. Pat. No. 4,394,448 (method of inserting DNA into living cells); McCormick et al., U.S. Pat. No. 5,677,178 (use of cytopathic viruses); and U.S. Pat. No. 5,928,913 (vectors for gene delivery); as well as other documents cited herein.

Preferred viral vectors include baculovirus such as BaculoGold (BD Biosciences Pharmingen, San Diego, Calif.), in particular provided that the production cells are insect cells. Although the baculovirus expression system is preferred, it is understood by those of skill in the art that other expression systems will work for purposes of the present invention, namely the expression of HG into the supernatant of a cell culture. Such other expression systems may require the use of a signal sequence in order to cause H5 expression into the media.

Effective Dose:

The compounds described herein can be administered to a subject at therapeutically effective doses to prevent PEDV-associated diseases. The dosage will depend upon the host receiving the vaccine as well as factors such as the size, weight, and age of the host.

The precise amount of immunogenic composition of the invention to be employed in a formulation will depend on the route of administration and the nature of the subject (e.g., age, size, stage/level of disease), and should be decided according to the judgment of the practitioner and each subject's circumstances according to standard clinical techniques. An effective immunizing amount is that amount sufficient to treat or prevent a PEDV infectious disease in a subject.

Immunogenicity of a composition can be determined by monitoring the immune response of test subjects following immunization with the composition by use of any immunoassay known in the art. Generation of a humoral (antibody) response and/or cell-mediated immunity may be taken as an indication of an immune response. Test subjects may include animals such as pigs, mice, hamsters, dogs, cats, rabbits, cows, horses, sheep, poultry (e.g. chickens, ducks, geese, and turkeys), and humans.

The immune response of the test subjects can be analyzed by various approaches such as: the reactivity of the resultant immune serum to the immunogenic conjugate, as assayed by known techniques, e.g., enzyme linked immunosorbent assay (ELISA), immunoblots, immunoprecipitations, virus neutralization, etc.; or, by protection of immunized hosts from infection by the pathogen and/or attenuation of symptoms due to infection by the pathogen in immunized hosts as determined by any method known in the art, for assaying the levels of an infectious disease agent, e.g., the viral levels (for example, by culturing of a sample from the subject), or other technique known in the art. The levels of the infectious disease agent may also be determined by measuring the levels of the antigen against which the immunoglobulin was directed. A decrease in the levels of the infectious disease agent or an amelioration of the symptoms of the infectious disease indicates that the composition is effective.

The therapeutics of the invention can be tested in vitro for the desired therapeutic or prophylactic activity, prior to in vivo use in animals. For example, in vitro assays that can be used to determine whether administration of a specific therapeutic is indicated include in vitro cell culture assays in which appropriate cells from a cell line or cells cultured from a subject having a particular disease or disorder are exposed to or otherwise administered a therapeutic, and the effect of the therapeutic on the cells is observed.

Alternatively, the therapeutic may be assayed by contacting the therapeutic to cells (either cultured from a subject or from a cultured cell line) that are susceptible to infection by the infectious disease agent but that are not infected with the infectious disease agent, exposing the cells to the infectious disease agent, and then determining whether the infection rate of cells contacted with the therapeutic was lower than the infection rate of cells not contacted with the therapeutic. Infection of cells with an infectious disease agent may be assayed by any method known in the art.

In addition, the therapeutic can be assessed by measuring the level of the molecule against which the antibody is directed in the animal model or human subject at suitable time intervals before, during, or after therapy. Any change or absence of change in the amount of the molecule can be identified and correlated with the effect of the treatment on the subject. The level of the molecule can be determined by any method known in the art.

After vaccination of an animal to PEDV using the methods and compositions of the present invention, any binding assay known in the art can be used to assess the binding between the resulting antibody and the particular molecule. These assays may also be performed to select antibodies that exhibit a higher affinity or specificity for the particular antigen.

Administration to a Subject:

Preferred routes of administration include but are not limited to intranasal, oral, intradermal, and intramuscular. The skilled artisan will recognize that compositions of the invention may also be administered in one, two or more doses, as well as, by other routes of administration. For example, such other routes include subcutaneously, intracutaneously, intravenously, intravascularly, intraarterially, intraperitnoeally, intrathecally, intratracheally, intracutaneously, intracardially, intralobally, intramedullarly, intrapulmonarily, and intravaginally. Depending on the desired duration and effectiveness of the treatment, the compositions according to the invention may be administered once or several times, also intermittently, for instance on a daily basis for several days, weeks or months and in different dosages.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1: Isolation and Production of Inactivated PEDV Strain

To produce the porcine epidemic diarrhea virus vaccine, killed virus, a master seed culture of a PEDV (isolate) was first produced. From this master seed, a culture of PEDV was grown and then inactivated. The inactivated virus culture was then mixed with an adjuvant in order to produce the porcine epidemic diarrhea virus vaccine. The following method was used to produce the porcine epidemic diarrhea virus vaccine.

Animals or tissues from animals exhibiting extreme diarrhea were acquired in 2013. Homogenates from mucosal scrapings were generated from these animals filtered through a 0.2 micron syringe filter and the filtrate was used to inoculate African Green Monkey kidney cells (VERO). Virus was grown in the presence of PEDV maintenance media containing modified MEM, porcine trypsin, tryptose phosphate broth, yeast extract and HEPES buffer. Virus growth was evaluated and visualized by checking for characteristic syncytia formation and fusion of cell monolayer. CPE positive material was subjected to sequencing using Illumina-based MiSeq technology.

In order to produce the PEDV master seed virus culture ("PEDV MSV"), porcine epidemic diarrhea virus strain (isolate) (PEDV isolate) was isolated in BI VERO cells and passed a total nineteen times in BI VERO cells and then virus was grown in 2013 EU VERO cells till passage 30. The $30^{th}$ passage of the virus was diluted and put down as the master seed virus designated PEDV KV-1251-125-10-OK.

From the master seed virus, a culture of PEDV (KV-1251-125-10-OK, to be referred to herein as "125-10") was produced by infecting 2013 EU VERO cells with PEDV KV-1251-125-10-OK MSV in PEDV maintenance media containing modified Minimal Essential Media, porcine trypsin (10 μg/ml), tryptose phosphate broth (0.3%), yeast extract (0.02%) and 1M HEPES buffer (2.5%) The 2013 EU VERO cells were typically infected with the PEDV (125-10) MSV at a minimum dose of $10^4$ $TCID_{50}/850\ cm^2$ roller bottle. Such cultures can be grown in sterile disposable roller bottles or on microcarrier beads. The culture was incubated at 36° C.±2° C. for 24 to 48 hours until cytopathic effect ("CPE") was observed. Typically, characteristic syncytia can be seen within 12 hours of infection, syncytia expand and cell monolayer fuses from 24-48 hours followed by sloughing of cells. During incubation, the culture was monitored for PEDV induced CPE to ensure a pure PEDV strain. If atypical CPE was observed or any macroscopic or microscopic evidence of contamination existed, the culture was discarded. Pure virus culture was aseptically harvested into sterile polypropylene carboys. Virus was freeze thawed to release cell associated virions and was clarified by centrifugation or by filtration through filters of 0.45 microns followed by 0.2 microns. Bulk virus harvest fluids were tested to ensure the absence of mycoplasma prior to inactivation. Harvested fluids which were not immediately inactivated were stored at −70° C. or below.

The volume of harvested fluids is determined and the temperature of the fluids is brought to 36±2° C. A 0.4 M solution of 2-bromoethyleneamine (BEA) is mixed with a stock solution of 0.3 N NaOH to generate a binary ethyleneimine (BEI) stock solution which is then added to the harvest fluids to give a final concentration of BEI of 5 mM. The fluids are stirred continuously for a minimum of 24 hours. A 1.0 M sodium thiosulfate solution to give a final minimum concentration of 5 mM is added to neutralize any residual BEI. The inactivated fluids can be stored at −70±3° C. for long term storage or at 4±3° C. for short term.

After treatment with BEI, the culture was tested for its ability to induce CPE typical of PEDV to ensure inactivation of the virus. This task was accomplished by passing the BEI treated viral fluids over Vero cells and checking the Vero cells for any viral infection. The BEI treated culture fluids were typically stored at −70° C. or below until the inactivation assay had been completed.

The inactivated virus was formulated as an adjuvanted vaccine by thoroughly blending the inactivated PEDV culture with adjuvant EMULSIGEN®-BCL at a 20% inclusion rate to form a bulk serial. The bulk serial was maintained at 2-8° C. until being transferred into vials containing either one or ten doses (@2.0 ml per dose).

Example 2: Genome Sequence Analysis of PEDV Isolate 1251-125-10 "125-10"

Sample Preparation and Analysis:

Prior to extraction virus tissue culture supernatants were pre-treated with a cocktail of DNase and RNase to remove residual host cell genomic nucleic acids. Viral genomic RNA was then extracted from the nuclease-treated samples using the Qiagen viral RNA extraction kit (Cat #52906). Post extraction, samples were again treated with DNase to further enrich for viral genomic RNA. Subsequently, viral genomic RNA was converted to double stranded cDNA (ds cDNA) through randomly primed reverse transcription and Klenow fragment treatment. The ds cDNA products were then used to generate a library for Illumina MiSeq-based sequencing using the NextEraXT library preparation kit (Cat # FC-131-1024). Each sample was barcoded with unique tags on both the 5'- and 3'-ends to minimize the chances of bioinformatic mis-binning. This library was run on the MiSeq using the 500-cycle kit (Cat # MS-102-2003) and data was analyzed using a combination of NextGene (version 2.3.4) and Sequencher software (version 5.1). High quality sequences were selected as those containing a median Q-score of greater than 25 and trimmed with a cut-off of no more than three uncalled bases at 3'-end or 3-consecutive bases with Q-score measuring less than 16. The sequences were then assembled de novo using criteria of 85% or greater match over a 35 bp stretch to generate a putative PEDV full genome for each strain. The putative complete genome sequence for each was then verified by template-based alignment to verify single nucleotide polymorphisms (SNP) or variable small insertions/deletions.

For sample 1251-125-10, a total of 570,253 sequences were generated with an average length of 136 bp after trimming of low quality data. Of those sequences; 484,247 (84.9%) assembled into a single contig 27,995 bp long which through BLASTn analysis revealed strong identity to the single-stranded RNA alphacoronavirus PEDV. A total of 11 positions exhibited polymorphism at either a single nucleotide or a small insertion/deletion, these positions are listed in Table 1.

TABLE 1

Polymorphic Residues in Isolate 1251-125-10 "125-10"

| Position | Residue Frequencies | Gene |
|---|---|---|
| 3,315 | T (51%)<br>A (49%) | ORF1A/B |
| 3,423-3,426 | DEL (50%)<br>TTA (50%) | ORF1A/B |
| 9,425 | C (64%)<br>T (36%) | ORF1A/B |
| 10,136 | T (52%)<br>A (48%) | ORF1A/B |
| 14,416 | A (69%)<br>G (31%) | ORF1A/B |
| 18,179 | C (73%)<br>T (27%) | ORF1A/B |
| 19,100 | C (73%)<br>T (27%) | ORF1A/B |
| 23,101 | G (63%)<br>A (37%) | Spike |
| 25,057 | T (59%)<br>10bp INS<br>(41%) | Spike |
| 25,165-25,169 | TTATG<br>(74%)<br>DEL (26%) | ORF3 |
| 27,510 | C (73%)<br>T (27%) | ORF3 |

The putative complete/near-complete PEDV genome of 1251-125-10 (SEQ ID NO:1) was aligned to the closest Chinese AH2012 (GenBank Accession No: KC210145) and North American Colorado 2013 isolate (GenBank Accession No: AGO58924) of PEDV (See FIG. 1 and FIG. 2). The identities to both isolates exceed 99.2% indicating very close relation to both strains, both in genogroup 2a.

Next, the immunogenic spike protein sequence was examined for protein identity/similarity to the larger GenBank repository of PEDV spike proteins. Again, the closest GenBank isolate submitted was derived from the North American Colorado 2013 strain deposited by the University of Minnesota Veterinary diagnostic laboratory (GenBank Accession No: AGO58924) exhibiting over 99.5% identity (1380/1386 identical amino acids) (FIG. 3). Of the 6 amino acid changes, 1 was due to the polymorphism at position 23,101 which would encode either CGA (Arg) in the majority or CAA (Gln) in minority at position 838. The North American Colorado 2013 strain contains a Gln at this position.

Example 3: Method of Monitoring Inactivation of Viruses

Each lot of PEDV virus or pool is tested for inactivation by passage in VERO cells. Seventy five $cm^2$ of 24 hour cell culture are inoculated with 2.0 mL of inactivated PEDV fluids and maintained at 36±3° C. for 48 hours. One flask of VERO cells remains uninoculated. For positive virus controls one culture of VERO cells is inoculated with a positive control PEDV. At the end of the incubation period, the cell monolayers are examined for CPE typical of PEDV. The material is frozen and thawed three times and then 2 ml of each material is inoculated onto one day old VERO cells. The culture should be maintained at 37±2° C. for 48 hours. Following the second passage, a third passage is performed. After incubation and passage, the absence of virus-infected cells in the BEI treated viral fluids as determined by lack of immunofluorescence staining constitutes a satisfactory inactivation test. The control cells inoculated with the positive control virus shall show CPE typical of PEDV and the uninoculated flask shall show no evidence of PEDV CPE.

Example 4: Construction of a Recombinant Baculoviruses Coding for and Expressing PEDV Spike Antigens The BaculoDisplay-Spike antigen was generated in insect cells via a recombinant baculovirus expressing a modified PEDV Spike protein. Briefly, the nucleic acid sequence (SEQ ID NO:2) encoding the PEDV Spike protein (SEQ ID NO:3) was cloned from a diagnostic sample using specific primers (Forward primer: SEQ ID NO:4 and Reverse primer: SEQ ID NO:5). The cloned PEDV Spike coding sequence was modified to remove the PEDV Spike signal peptide, transmembrane domain, and c-terminal domain (SEQ ID NO:6). These domains were replaced with the equivalent domains from the Vesicular stomatitis virus G protein (VSVG) by overlap extension PCR. The VSVG-PEDVS-VSVG coding sequence (SEQ ID NO:8) was transferred into a baculovirus transfer vector (pVL1393) using complementary restriction sites. The pVL1393 vector containing the VSVG-PEDV-VSVG Spike coding sequence expressing the modified Spike protein (SEQ ID NO:9) was used to co-transfect Sf9 insect cells along with FlashBAC ULTRA baculovirus DNA. Recombinant baculovirus were amplified and checked for PEDV Spike protein expression by IFA and Western blot using PEDV-specific serum. The PEDV Spike protein was shown to co-pellet with the baculovirus particles after a 100,000 g centrifugation step, suggesting that it was associated with the baculovirus.

Example 5: Preparation of Pharmaceutical Compositions (Vaccines) Comprising PEDV Spike Antigens For the inactivated PEDV material, PEDV viral harvest was inactivated for a minimum of 24 hours using 5 mM BEI, clarified and 0.45 μm filtered.

After neutralization various adjuvants were added and the following vaccine/pharmaceutical compositions were generated.

Example 6: Inoculation of Pigs with Inactivated PEDV and Baculovirus Spike Vaccine and Assessment of the Serological Response The purpose of the study was to demonstrate immunogenicity of an inactivated PEDV virus for protection of vaccinated pigs. The vaccine used in the study included inactivated PED virus and a BaculoDisplay-Spike (Baculo-S) protein construct. Both the inactivated PEDV vaccine and the BaculoDisplay-Spike (Baculo-S) protein vaccines were adjuvanted with EMULISGEN®-BCL. A previous challenge study had shown a strong positive correlation between clinical protection and the IgA and IgG responses detected in the blood 21 days following challenge with PEDV (De Arriba et al. 2002). Therefore, the serological response of each of the prototype vaccines was assessed by IgG and IgA ELISA analysis. In addition, a virus neutralizing assay was done on the sera.

Experimental Design:

Experiments were designed to evaluate the serological response to two prototype PEDV vaccines.

Eighteen pigs (28±7 days of age at D-1) were randomized into three treatment groups (See Table 2) and housed in a single room for the duration of the study. The animals were intramuscularly vaccinated on D0, 14 and 28 with either a placebo or one of the two PEDV prototype vaccines. Pigs were monitored for clinical signs daily from D0 through D49. Rectal temperatures and injection sites were monitored to evaluate the vaccines' safety from D0-D4, D14-18, and D28-D32. Fecal, oral and nasal swabs and serum were taken from the piglets on D-1, 3, 14, 17, 28, 31 and 49. The serum samples taken on D-1, 14, 28 and 49 were screened by ELISA for anti-PEDV-IgG and by FFN assay for the presence of neutralizing antibodies. Fecal samples and serum collected on D-1, D3, 17 and 31 were evaluated by PCR to confirm that neither prototype was able to replicate in the pig. Fecal samples from D14, 28 and 49 were stored at −70° C. for potential future evaluation. On D49, animals were humanely euthanized and necropsied.

TABLE 2

Summary of experimental design

| Group (name) | n | Vaccine | Volume/ Dose |
|---|---|---|---|
| 1 (BEI-VH) | 7 | BEI inactivated PEDV viral harvest adjuvanted with EMULSIGEN ®-BCL (20% v/v) | 2 ml/5.6 log $TCID_{50}$ |
| 2 (Baculo-S) | 7 | BaculoDisplay-Spike protein adjuvanted with EMULSIGEN ®-BCL(20% v/v) | 1 ml/ 866 μg/ml total protein |
| 3 (Control) | 4 | Placebo | 2 ml |

Prototype Vaccines:

Tables 4a and b describe the prototype vaccines. For the placebo treatment, 2 ml of Production PBS was administered. The BaculoDisplay-Spike antigen was generated in insect cells via a recombinant baculovirus expressing a modified PEDV Spike protein. Briefly, the coding sequence for the PEDV Spike protein was cloned from a diagnostic sample using specific primers. The cloned PEDV Spike coding sequence was modified to remove the PEDV Spike signal peptide, transmembrane domain, and c-terminal domain (SEQ ID NO:7). These domains were replaced with the equivalent domains from the Vesicular stomatitis virus G protein (VSVG) by overlap extension PCR (SEQ ID NO:8). The VSVG-PEDVS-VSVG coding sequence was transferred into a baculovirus transfer vector (pVL1393) using complementary restriction sites. The pVL1393 vector containing the VSVG-PEDV-VSVG Spike coding sequence was used to co-transfect Sf9 insect cells along with FlashBAC ULTRA baculovirus DNA. Recombinant baculovirus were amplified and checked for PEDV Spike expression by IFA and Western blot using PEDV-specific serum. The PEDV Spike protein was shown to co-pellet with the baculovirus particles after a 100,000 g centrifugation step, suggesting that it was associated with the baculovirus. For the inactivated PEDV material, PEDV viral harvest was inactivated for 24 hours using 5 mM BEI, clarified and 0.45 μm filtered.

TABLE 4a

Summary of PEDV prototype vaccine material - Inactivated viral harvest

| | |
|---|---|
| Material: | 0.45 μm filtered, BEI inactivated porcine epidemic disease virus p7 on BI-Vero (production grade trypsin); 5.3 log $TCID_{50}$/ml |
| Testing of vaccine material | BEI inactivated material was passed once in BI-Veros at various dilutions. Lack of viral growth was confirmed by IFA using anti-PEDV polyclonal sera. Sterility of the formulated vaccine was |

TABLE 4a-continued

| Summary of PEDV prototype vaccine material - Inactivated viral harvest | |
|---|---|
| | determined by inoculating a blood agar plate and a MacConkey agar plate with 50 μl of material. Plates were incubated aerobically and anaerobically for 48 hrs. No growth was noted following incubation. The sterility testing was done for each of the prepared vaccine batches (D0, D14 and D28). |
| Formulation: | 42 ml of BEI inactivated material was divided into three 14 ml aliquots. One aliquot was thawed in a 37° C. waterbath on D0, 14 and 28. On each of the vaccination days, 3.5 ml of EMULSIGEN ®-BCL (MVP) was added to 14 ml of inactivated material slowly over 1 minute while stirring. The mixture was stirred for 10 min, transferred to a vaccine bottle, than stored at 4° C. |

TABLE 4b

| Summary of the PEDV prototype vaccine material - BaculoDisplay-Spike | |
|---|---|
| Material: | BaculoFBU/PEDVS p2 |
| Testing of vaccine material | Sterility of the formulated vaccine was determined by inoculating a blood agar plate and a MacConkey agar plate with 50 μl of material. Plates were incubated aerobically and anaerobically for 48 hrs. No growth was noted following incubation. The sterility testing was done for each of the prepared vaccine batches (D0, D14 and D28). |
| Formulation: | 27 ml of BaculoDisplay-Spike protein was divided into three 9 ml aliquots and stored at 4° C. On D0, 14 and 28, 2.0 ml of EMULSIGEN ®-BCL (MVP) was added to 8.0 ml of material slowly over 1 minute while stirring. Mixture was stirred for 10 min then stored at 4° C. |

PEDv Vaccination:

On D0, 14 and 28, the Investigator or designee administered the vaccine material to all pigs. Each pig received 2 ml of the BEI inactivated PEDV vaccine, 1 ml of the BaculoDisplay-Spike prototype or 2 ml of the placebo intramuscularly using a sterile needle and syringe appropriate for their age. On D0 and D28, the vaccine was given in the right neck musculature and on D14 it was given in the left neck musculature.

Tissue Collection:

Pigs were evaluated for macroscopic lesions. Abnormalities were recorded on the necropsy form. Fresh samples of small intestine and colon and fixed sections of lung, heart, spleen, kidney, small intestine, colon and liver were collected. Fresh samples were stored at BIVI-Ames at −70° C. for a minimum of six months after the completion of the study. Fixed sections were stored at BIVI-Ames at room temperature for a minimum of six months after the completion of the study.

Viral Assays:

PEDV RT-PCR: Samples were screened by RT-PCR as described in Table 3. The quantitative one-step RT-PCR kit (ISCRIPT™ One-Step RT-PCR kit for probes; BioRad, cat no. 170-8895) was used for the assay. Sequence information for the primers, probe and ultramer are as follows: PEDV-qPCR-probe, 5'-6-FAM/ACAGAGCCTGTGTTGGTG-TATAGTAACAT-3'BHQ_1 (SEQ ID NO: 16); PEDV-qPCR-F, 5'-TATAGTGGGTGTTATTTCTAGTT-3' (SEQ ID NO: 17); PEDV-qPCR-R, 5'-GCCAATACTGCCAGATT-TACA-3'(SEQ ID NO: 18), PEDV-ultramer, 5'-TGATGA-TATAGTGGGTGTTATTTCTAGTTTGTCTAGCTC-CACTTTTAACAGTACTAGG GAGTTGCCTGGTTTCT-TCTACCATTCTAATGATGGCTCTAATTGTACAGAGC-CTGTGT TGGTGTATAGTAACATAGGTGTTTG-TAAATCTGGCAGTATTGGCTATGTCCCAT-3' (SEQ ID NO: 19). Real-time RT-PCR was carried out in a 25 μl reaction containing 2 μl of extracted total nucleic acid, 0.75 μl of probe (4 μM), 0.5 μl of each primer (10 μM), 12.5 μl of 2× RT-PCR mix, 0.5 μl ISCRIPT™ reverse transcriptase and 8.25 μl of DEPC-treated water. The reaction took place using a CFX96 real-time PCR detection system (BioRad) under the following conditions: initial reverse transcription at 50° C. for 30 min, followed by initial denaturation at 95° C. for 5 min, 40 cycles of denaturation at 95° C. for 15 s and annealing and extension at 57° C. for 30 s. The optical data were analyzed using CFX Manager software (version 2.1, BioRad). For each determination, the threshold lines were automatically calculated using the regression setting for cycle threshold (Ct) determination mode. Baseline subtraction was done automatically using the baseline subtracted mode. Curves with baseline end values of less than 10 were manually corrected. Samples were run in single reactions and quantitative amounts were determined using an ultramer-based standard curve and reported as genomic copies per microliter (gc/μl). Samples with no detection following 40 cycles were considered negative.

Anti-PEDV-IgG ELISA:

Samples were screened by ELISA as described in Table 3. For the assay, plates were coated with 4 ng/μl of PEDV-1251-125-2 for one hour at 37° C. Following washing, wells were coated with 100 μl of a 1:100 diluted serum sample (for the IgG a assay) and incubated for one hour at 37° C. Following washing, wells were blocked with 0.05% non-fat milk and incubated for one hour at 37° C. Following washing, wells were coated with 100 μl of a 1:10,000 dilution of horse-radish peroxidase (HRP)-conjugated-goat-anti-swine-IgG and incubated for one hour at 37° C. Following washing, the plate was developed with 3,5,3',5'-tetramethylbenzidine for 5 minutes and the reaction was stopped with 2 M $H_2SO_4$ before optical density (OD) measurement at 450 nm. Samples were run in duplicate wells and results are reported as the average sample to positive (S:P) ratio. As no cut-off values for positive versus negative interpretation have been generated for either of the ELISA assays, samples with S:P ratios greater than the sum of two standard deviations higher plus the highest control group mean were considered positive (S:P ratio>0.28 or >0.16 for the IgG assay).

PEDV Fluorescent Focus Assay:

The PEDV FFN assay was run consisted of a duplicate serum dilution series screened in a 96-well plate format by a virus neutralization assay using a cell culture adapted PEDV stain. Titers were reported as the greatest serum dilution showing a 90% reduction of fluorescent foci in comparison to the negative control. For each sample, duplicate well titers were averaged.

Statistical Analysis of Data:

Data analysis was performed using JMP 9.0.3 (SAS Institute, Inc., Cary, N.C., USA) by the Monitor. For all analysis, a p-value less than 0.05 was considered significant. For repeated measures of data (serology), a multiple analysis of variance was performed using time as the repeated variable in the model. If a significant p-value was noted, a one-way ANOVA was performed using group as the independent factor; separate analyses were done for each day. If a significant p-value was noted; pair-wise differences between group means were evaluated using Wilcoxon adjusted pairwise comparisons.

Serology:

PEDV Fluorescent focus neutralization (FFN) assay: See Table 5 for individual animal results. All animals in the BEI-VH group showed four-fold increases in neutralizing titers, while only two of seven animals in Group 2 had a similar response. The control animals had no detectable neutralizing titers.

TABLE 5

PEDV Fluorescent focus neutralization assay results for study D-1, 14, 28 and 49. Highlighted cells indicate titers greater than 0.

| Animal | PEDV | Study day | | | |
|---|---|---|---|---|---|
| no. | group | -1 | 14 | 28 | 49 |
| 131 | BEI-VH | 0 | 0 | 80 | 120 |
| 132 | | 0 | 0 | 60 | 80 |
| 134 | | 0 | 0 | 40 | 80 |
| 142 | | 0 | 0 | 160 | 80 |
| 143 | | 0 | 0 | 80 | 160 |
| 146 | | 0 | 0 | 30 | 60 |
| 148 | | 0 | 0 | 40 | 160 |
| 133 | Baculo-S | 0 | 0 | 20 | 0 |
| 135 | | 0 | 0 | 0 | 0 |
| 136 | | 0 | 0 | 0 | 0 |
| 139 | | 0 | 0 | 0 | 0 |
| 141 | | 0 | 0 | 0 | 0 |
| 144 | | 0 | 0 | 0 | 40 |
| 145 | | 0 | 0 | 0 | 120 |
| 137 | Control | 0 | 0 | 0 | 0 |
| 138 | | 0 | 0 | 0 | 0 |
| 140 | | 0 | 0 | 0 | 0 |
| 147 | | 0 | 0 | 0 | 0 |

Anti-PEDV-IgG ELISA:

Sample to positive (S:P) ratios for individual animals are listed in Table 6 below. All animals in Group 1 (BEI-VH) had a detectable IgG response by D28 that was at least two standard deviations higher in comparison to mean S:P ratios of the control group. In contrast, only two animals in Group 2 (Baculo-S) had detectable IgG responses and only after receiving three doses of the vaccine. Group least square mean S:P ratios±standard error are presented in FIG. 4. By D28, animals in Group 1 (BEI-VH) had significantly higher S:P ratios in comparison to Group 2 and Group 3 ($p<0.01$, Wilcoxon adjusted pairwise comparisons).

TABLE 6

Individual anti-PEDV-IgG S:P ratios for D-1, 14, 28 and 49. Highlighted values indicate S:P ratios at least two standard deviations greater than the mean S:P ratios of the control group on D49.

| Animal | PEDV | Study days | | | |
|---|---|---|---|---|---|
| no. | group | D-1 | D14 | D28 | D49 |
| 131 | BEI-VH | 0.078995 | 0.119838 | 0.452301 | 0.93054393 |
| 132 | | 0.085278 | 0.126571 | 0.317992 | 0.58200837 |

TABLE 6-continued

Individual anti-PEDV-IgG S:P ratios for D-1, 14, 28 and 49. Highlighted values indicate S:P ratios at least two standard deviations greater than the mean S:P ratios of the control group on D49.

| Animal | PEDV | Study days | | | |
|---|---|---|---|---|---|
| no. | group | D-1 | D14 | D28 | D49 |
| 134 | | 0.069569 | 0.183124 | 0.328033 | 0.65230126 |
| 142 | | 0.057002 | 0.094704 | 0.392887 | 0.62552301 |
| 143 | | 0.049372 | 0.150808 | 0.351464 | 0.59874477 |
| 146 | | 0.048923 | 0.079443 | 0.296653 | 0.65104603 |
| 148 | | 0.069569 | 0.130162 | 0.498326 | 0.75774059 |
| 133 | Baculo-S | 0.066427 | 0.093806 | 0.086611 | 0.13807531 |
| 135 | | 0.058348 | 0.109964 | 0.156904 | 0.28410042 |
| 136 | | 0.04623 | 0.09605 | 0.094142 | 0.18995816 |
| 139 | | 0.054309 | 0.067325 | 0.093305 | 0.18158996 |
| 141 | | 0.051167 | 0.061041 | 0.079916 | 0.14937238 |
| 144 | | 0.061041 | 0.14632 | 0.138075 | 0.34644351 |
| 145 | | 0.042639 | 0.064183 | 0.079916 | 0.20292887 |
| 137 | Control | 0.05386 | 0.071364 | 0.135146 | 0.21464435 |
| 138 | | 0.050269 | 0.062837 | 0.082427 | 0.21631799 |
| 140 | | 0.048923 | 0.060144 | 0.089121 | 0.18661088 |
| 147 | | 0.064632 | 0.090664 | 0.127615 | 0.25941423 |

PEDV Viremia/Shedding:

To assess the potential for shedding and viremia following vaccination, serum and fecal samples were screened by RT-PCR for the presence of PEDV RNA on the fourth day following each vaccination (D3, D18 and D31). No PEDV RNA was detected in any of the samples.

Conclusions:

Based on the combined serological data (IgG and FFN) of the above study, three doses of the PEDV Spike protein expressed by the BacuoloDisplay method given at 866 μg per dose and adjuvanted with EMULSIGEN®-BCL was not able to generate a consistent serological response. In this case, the lack of response indicates that the vaccine was either not sufficiently immunogenic (i.e. protein was not delivered in sufficient quantity or a non-suitable adjuvant was used) or that the confirmation of the recombinant Spike protein was not similar to the wildtype virus.

Conversely, the anti-PEDV IgG and FFN serological data does suggest that two or three doses of the BEI inactivated PEDV viral harvest given at 5.6 log/dose and adjuvanted with EMULSIGEN®-BCL was able to consistently elicit a serological response in naïve swine. However, the average anti-PEDV-IgG S:P ratio in vaccinated animals was lower in comparison to animals administered feedback material. Specifically, the average anti-PEDV-IgG S:P ratio (±standard deviation) in 45 animals from one herd administered feedback material prior to sampling was found to be 0.90±0.20 in comparison to 0.69±0.12 in vaccinated animals (data not shown). In addition, via personal communications with Dr. Eric Nelson, FFN titers in five of seven of the vaccinated animals in this study were below titers typically seen following feedback administration.

Example 7: Efficacy BEI Inactivated PEDV (Three Dose, Various Adjuvants)

(Study 2013131)—Troy Kaiser

The following study evaluated whether a vaccination with three 2-mL does of a killed PEDV vaccine could elicit an immune response when administered to pigs three weeks of age at 14 day intervals. The primary outcome was serology tested by fluorescent focus neutralization (FFN).

Study groups included: T01=PBS (n=10); T02=6.04 log $TCID_{50}$/ml BEI PEDV+20% EMULSIGEN®-BCL (n=18); T03=6.04 log $TCID_{50}$/ml BEI PEDV+10% EMULSIGEN-D® (n=20); T04=6.04 log $TCID_{50}$/ml BEI PEDV+15% REHYDRAGEL®; T05=6.04 log $TCID_{50}$/ml BEI PEDV+5% S:P oil (n=20).

TABLE 7

| Vaccine Formulations and Controls | | |
|---|---|---|
| | Treatment | Description |
| T01 | Negative Control (NC) | Phosphate Buffered Saline (1x) |
| T02 | Experimental Vaccine (EV) | PEDv at 6.04 $log_{10}$ $TCID_{50}$/mL inactivated with binary ethyleneimine, adjuvanted with 20% EMULSIGEN ®-BCL |
| T03 | Experimental Vaccine (EV) | PEDv at 6.04 $log_{10}$ $TCID_{50}$/mL inactivated with binary ethyleneimine, adjuvanted with 10% EMULSIGEN-D ® |
| T04 | Experimental Vaccine (EV) | PEDv at 6.04 $log_{10}$ $TCID_{50}$/mL inactivated with binary ethyleneimine, adjuvanted with 15% REHYDRAGEL ® |
| T05 | Experimental Vaccine (EV) | PEDv at 6.04 $log_{10}$ $TCID_{50}$/mL inactivated with binary ethyleneimine, adjuvanted with 5% S:P oil |

On D0, pigs were administered the 2-mL treatment intramuscularly in the right neck. A second treatment was administered on D14 in the left neck, and a third treatment was administered on D28 in the right neck for all groups. Blood samples were collected on D-1, D13, D27, D42, and D49. Serum was tested for PEDV neutralizing antibodies using FFN.

Serology:

Seroconversion occurred in 11.2% of pigs after two vaccinations and 55.6% of pigs when vaccinated three times with PEDV vaccine adjuvanted with 20% EMULSIGEN® BCL (T02; Table 8). The geometric mean titer for seropositive pigs≥1:20 for all treatment groups are presented below in Table 8. The frequency distribution of titers by treatment group of all pigs is presented in Table 9.

TABLE 8

| Proportion of seropositive pigs and geometric mean titer by group for pigs responding serologically | | |
|---|---|---|
| Group | Pigs with ≥1:20 Response | Geometric Mean Titer |
| T01 | 0/10 (0%) | Not applicable |
| T02 | 10/18 (55.6%) | 1:45.9 |
| T03 | 6/20 (30%) | 1:44.8 |
| T04 | 2/20 (10%) | 1:40.0 |
| T05 | 2/20 (10%) | 1:56.6 |

Conclusions:

Seroconversion occurred in 11.2% of T02 pigs after two doses and seroconversion occurred in 55.6% of pigs when vaccinated three times with the experimental vaccine formulated with 6.04 log 10 TCID50/mL PEDv inactivated with binary ethyleneimine and adjuvanted with 20% EMULSIGEN® BCL. The data collected from this study indicate that this experimental vaccine elicited an immune response that supports a claim of reasonable expectation of efficacy.

Example 8: Efficacy of Baculovirus Vaccines (Two Dose, Various Adjuvants)

(Study 2014236) Kara Claxton

The following study evaluated the serological response to vaccination with two 2-mL does of a killed Porcine Epidemic Diarrhea Virus (PEDv) Vaccine, or a baculovirus construct vaccine, as measured after administration of either vaccine to pigs at three weeks of age. The primary outcome was serology tested by fluorescent focus neutralization (FFN) for serum samples collected following vaccination in the treated pigs.

The study groups included: T01=PBS (n=10); T02=6.93 log $TCID_{50}$/ml BEI PEDV+20% EMULSIGEN®-BCL (n=20); T03=Baculovirus with PEDV Spike Ag (n=9); 6× Concentrated Baculovirus with PEDV Spike Ag (n=10); Trypsin Baculovirus with PEDV Spike Ag (n=10); and Killed Positive Control vaccine conditionally licensed (POS CON) (n=10). On D0, pigs were administered the 2-mL treatment intramuscularly in the right neck. A second treatment was administered on D14 in the left neck for T01-T05 and on D21 for T06.

TABLE 10

| Vaccine Formulation and Controls | | |
|---|---|---|
| | Treatment | Description |
| T01 | Negative Control (NC) | Saline (PBS 1x) |
| T02 | Experimental Vaccine (EV) | Porcine epidemic diarrhea virus at 6.93 $log_{10}$ $TCID_{50}$/mL PEDv inactivated with BEI, adjuvanted with 20% Emulsigen BCL. |
| T03 | EV | Recombinant baculovirus with PEDv Spike glycoprotein displayed in the viral envelope.* |
| T04 | EV | Recombinant baculovirus with PEDv Spike glycoprotein displayed in the viral envelope.* The clarified inactivated material was concentrated ~6X prior to formulation. |
| T05 | EV | Recombinant baculovirus with PEDv Spike glycoprotein displayed in the viral envelope.* Recombinant PEDv Spike-Display Baculovirus |

TABLE 9

| Frequency distribution of titers by group | | | | | | | | |
|---|---|---|---|---|---|---|---|---|
| | | PEDv Neutralizing Antibodies* | | | | | | |
| Group | n | <1:20 | 1:20 | 1:28 | 1:40 | 1:80 | 1:113 | 1:160 |
| T01 | 10 | 10 (100%) | 0 (0.0%) | 0 (0.0%) | 0 (0.0%) | 0 (0.0%) | 0 (0.0%) | 0 (0.0%) |
| T02 | 18 | 8 (44.4%) | 2 (11.1%) | 1 (5.6%) | 4 (22.2%) | 1 (5.6%) | 1 (5.6%) | 1 (5.6%) |
| T03 | 20 | 14 (70.0%) | 1 (5.0%) | 1 (5.0%) | 2 (10.0%) | 1 (5.0%) | 1 (5.0%) | 0 (0.0%) |
| T04 | 20 | 18 (90.0%) | 1 (5.0%) | 0 (0.0%) | 0 (0.0%) | 1 (5.0%) | 0 (0.0%) | 0 (0.0%) |
| T05 | 20 | 18 (90.0%) | 0 (0.0%) | 0 (0.0%) | 1 (5.0%) | 1 (5.0%) | 0 (0.0%) | 0 (0.0%) |

*Maximum titer on D42 or D49

TABLE 10-continued

| Vaccine Formulation and Controls | | |
|---|---|---|
| Treatment | | Description |
| | | was produced in insect cells with 10 μg/mL trypsin added during infection. |
| T06 | Positive Control (PC) | iPED+ (Harris vaccine - Conditionally Licensed) |

BEI = binary ethyleneimine

*The PEDV Spike signal sequence and C-terminal tail were replaced with the baculovirus gp64 equivalent.

Recombinant PEDv Spike-Display Baculovirus was produced in insect cells. Infected cultures were harvested and clarified by centrifugation and 0.2-μm filtration. Clarified harvest material was inactivated with 5 mM BEI for 72 hours at 37° C. then clarified by centrifugation and 0.2-μm filtration.

Serology:

Seroconversion post-vaccination (D28 & D35) occurred in 20% of pigs vaccinated with PEDv vaccine adjuvanted with 20% EMULSIGEN® BCL (T02; [0171]1) and 60% of pigs vaccinated with trypsin-grown PEDV SPIKE-baculovirus (T05; [0171]1). The geometric mean titer for seropositive pigs≥1:20 for all treatment groups are presented below in Table 11. The frequency distribution of titers by treatment group of all pigs is presented in Table 12.

TABLE 11

| Proportion of seropositive pigs and geometric mean titer by group for pigs responding serologically | | |
|---|---|---|
| Group | Pigs with ≥1:20 Response | Geometric Mean Titer |
| T01 | 0/10 (0%) | Not applicable |
| T02 | 4/20 (20%) | 1:30.7 |
| T03 | 0/9 (0%) | Not applicable |
| T04 | 0/10 (0%) | Not applicable |
| T05 | 6/10 (60%) | 1:35.5 |
| T06 | 7/10 (70%) | 1:41.9 |

TABLE 12

| Frequency distribution of titers by group | | | | | | | | | |
|---|---|---|---|---|---|---|---|---|---|
| | | PEDv Neutralizing Antibodies* | | | | | | | |
| Group | n | <1:20 | 1:20 | 1:28 | 1:40 | 1:57 | 1:80 | 1:113 | 1:160 |
| T01 | 10 | 10 (100%) | 0 (0.0%) | 0 (0.0%) | 0 (0.0%) | 0 (0.0%) | 0 (0.0%) | 0 (0.0%) | 0 (0.0%) |
| T02 | 20 | 16 (80%) | 1 (5%) | 2 (10%) | 0 (0.0%) | 1 (5%) | 0 (0.0%) | 0 (0.0%) | 0 (0.0%) |
| T03 | 9 | 9 (100%) | 0 (0.0%) | 0 (0.0%) | 0 (0.0%) | 0 (0.0%) | 0 (0.0%) | 0 (0.0%) | 0 (0.0%) |
| T04 | 10 | 10 (100%) | 0 (0.0%) | 0 (0.0%) | 0 (0.0%) | 0 (0.0%) | 0 (0.0%) | 0 (0.0%) | 0 (0.0%) |
| T05 | 10 | 4 (40%) | 2 (20%) | 2 (20%) | 1 (10%) | 0 (0.0%) | 0 (0.0%) | 0 (0.0%) | 1 (10%) |
| T06 | 10 | 3 (30%) | 2 (20%) | 2 (20%) | 0 (0.0%) | 0 (0.0%) | 2 (20%) | 1 (10%) | 0 (0.0%) |

Conclusion:

Seroconversion occurred in 20% of T02 pigs after two administrations of the experimental vaccine formulated with 6.93 $\log_{10}$ $TCID_{50}$/mL PEDV inactivated with BEI and adjuvanted with 20% EMULISGEN® BCL. Seroconversion occurred in 60% of T05 pigs after two administrations of the experimental recombinant trypsin grown-baculovirus vaccine formulated with PEDV Spike glycoprotein.

Example 9: Efficacy Study

POC Efficacy (Study 2014030)—Abby Patterson

The below study was designed to assess the efficacy of killed vaccine and other prototype vaccines in sows. The primary outcome parameter is piglet mortality following challenge with porcine epidemic diarrhea virus (PEDV). The secondary outcome parameter was dam serology. Other parameters measured included: clinical signs (including ISL) in sows following vaccination; PEDV shedding in sows following vaccination (via qRT-PCR); clinical signs in piglets; and PEDV serology in piglets At four and two weeks pre-farrow (D0 and D14), each gestating dam was administered 2 mL of one of the following treatments by three routes (intramuscular, intranasal and oral): T01 (negative control, NC) phosphate buffered saline; T02 (BEI-VH) adjuvanted with 20% EMULSIGEN® BCL; T03 (strict control, SC) served as non-vaccinated/non-challenged control. Eight animals were used per group, excluding T06 which had four animals. On D35 or D36, pigs were challenged orally with 1 mL of 2.0 log 10 TCID50/mL PEDV viral harvest. Clinical signs (vomiting and diarrhea) in dams and pigs were observed daily during the challenge phase. Serum was collected from dams at four- and two-weeks pre-farrow (D0 and D14), the day prior to piglet challenge (D34 or D35) and the day of off-test (D57).

On D0 and D14, the PEDV prototype vaccines were administered to the sows. At each vaccination, the sows received a total of 6 mL of vaccine where 2 mL were administered by intramuscular, intranasal and oral route. For the intramuscular administration route, a 2 mL injection was given into the musculature of the neck below the ear. The side of the neck for administration was alternated for the initial and booster vaccination. For the oral administration route, 2 ml were delivered over the caudal oropharynx using an 8 Fr polypropylene catheter (2.7 mm diameter by 254 mm length) attached to a syringe. For the intranasal route, 1 ml was injected into each nare using a 4.5 inch catheter attached to a syringe.

TABLE 13

| Experimental Vaccine and Control Product | | | |
|---|---|---|---|
| Treatment | Group | Serial # | Description |
| T01 | NC | 2842-182-D | 1X Phosphate Buffered Saline; Gibco catalog no. 10010-023; Lot no. 1510272 |
| T02 | BEI-VH | 2842-182-E | KV-1251-125-10-OK, 0.2 μm filtered, passage MSV + 5, 6.04 log $TCID_{50}$/mL. Viral harvest was inactivated with 5 mM BEI for 72 hr at 37° C. For formulation, Emulsigen BCL (MVP lot no. 17006, |

TABLE 13-continued

| Experimental Vaccine and Control Product | | |
|---|---|---|
| Treatment Group | Serial # | Description |
| | | manufacture date Feb. 11, 2011) was added at a 20% inclusion rate. |

TABLE 14

| Challenge Material | |
|---|---|
| PEDV Challenge Strain: | Isolate id. 1251-140-4; passage 5 |
| Challenge preparation: | Propagated in Vero cells |
| Dose of Challenge material: | 1 mL at 2.0 $log_{10}$ $TCID_{50}$/mL |
| Testing of Challenge Material: | Challenge virus was titrated prior to administration on 2013 EU Vero cells (5.03 TCID50/ml) and diluted to 2 log $TCID_{50}$/mL. |
| Method of Administration: | Oral administration (by syringe) with pigs manually restrained. |

Vaccine Efficacy:

Pig mortality: Pig mortality following challenge with a virulent PEDV isolate was the primary outcome parameter used to assess vaccine efficacy. A summary of mortality by group during the challenge period is listed below. With 55% mortality and all litters affected in T01 (NC), the challenge was considered sufficiently virulent. In comparison to T01 (NC), T02 (BEI-VH) demonstrated a numerical reduction in pig mortality with a PF (95% CI) of 0.20 (−0.550, 0.586). The reduction was not statistically significant as the 95% CI (−0.550, 0.586) included zero.

Extra-binomial variation was evident in this study, resulting in a wide confidence interval for T02 (BEI-VH) PF when utilizing the underlying binomial distribution. Mortality varied greatly among litters within a group, including ranging from 0% to 100% for T02 (BEI-VH).

An intestinal sample or intestinal content was taken at the time necropsy and tested by qRT-PCR to detect PEDV antigen. Of samples tested from animals during the time of peak mortality, PEDV was detected in 55.5% of samples.

TABLE 15

| Group | Proportion Mortality Estimate | Standard Error | Prevented Fraction* | 95% Confidence interval | Median Mortality | Minimum %/ Maximum % |
|---|---|---|---|---|---|---|
| NC | 0.55 | 0.11 | . | . | 52.78 | 12.50/100.00 |
| BEI-VH | 0.44 | 0.10 | 0.20 | (−0.550, 0.586) | 34.29 | 0.00/100.00 |

*Based on T01 (NC) proportion affected.
**NC = Not Calculated. Confidence Interval possible for T02 (BEI-VH) based on study design Sow Serology:

Fluorescent Focus Neutralizing (FFN) assay: The FFN assay was used to assess the dam virus neutralizing response following vaccination and challenge. Geometric mean titers listed by group are presented below for days on which blood was collected from sows.

Following two doses of vaccine, 2/8 (25%) of sows in T02 (BEI-VH) had detectable levels of neutralizing antibody. Detectable levels of neutralizing antibody were not observed in any of the other groups.

Following lateral exposure to PEDV, all sows in exposed treatment groups had detectable levels of neutralizing antibody. Animals in T03 (SC) group remained seronegative throughout the trial. The geometric mean titer on D57 (approximately 21 days post-exposure) indicated that vaccination resulted in numerically higher titers in comparison to T01 (NC). Sows in T02 (BEI-VH) group had a GMT of 613, which is an approximately three-fold higher titer in comparison to the GMT of 200 for sows in T01 (NC) (p=0.005). As multiple samples in T02 (BEI-VH) group had detectable neutralizing antibodies at the highest dilution tested (1:640), these results likely represent a conservative estimate of the differences between groups.

TABLE 16

| | | Geometric Mean Titer* Study Day** | | | |
|---|---|---|---|---|---|
| Treatment | Group | D0 | D14 | D34 or D35 | D57 |
| T01 | NC | <20 | <20 | <20 | 200 |
| T02 | BEI-VH | <20 | <20 | 15 | 613 |
| T03 | SC | <20 | <20 | <20 | <20 |

Where all values were <20, geometric mean titer is presented as <20. Otherwise, values of <20 were set to 10 for GMT calculation
**D57 GMT for T01 (NC) and T02 (BEI-VH) are back-transformed Least-Squares Means S1-Based ELISA Data:

An S1-based ELISA was used to assess the dam's response to the PEDV-spike protein following vaccination and challenge. Assay results for colostrum, milk and serum are listed by group for days on which samples were collected.

At the time of pig challenge, sows in T02 (BEI-VH) had significantly higher geometric mean titer in serum as compared to sows in T01 (NC) (p=0.0005). Following exposure to PEDV, a larger significant difference was noted between the two groups (p<0.0001).

Significant differences in geometric mean titers of anti-PEDV IgA in colostrum and in milk were not observed between T02 (BEI-VH) and T04 (NC).

TABLE 17

| | | Geometric Mean Titer* Study Day | | | |
|---|---|---|---|---|---|
| Treatment | Group | D27 through D32: Colostrum | D34 or D35: Serum | D57: Serum | D57: Milk |
| T01 | NC | 0.186 | 0.098 | 0.504 | 0.220 |
| T02 | BEI-VH | 0.139 | 0.256 | 1.499 | 0.244 |
| T03 | SC | 0.134 | 0.125 | 0.164 | 0.088 |

*GMT for T01 (NC) and T02 (BEI-VH) are back-transformed Least-Squares Means

Pig Serology:

Serum was collected at the time of necropsy from pigs to evaluate the presence of neutralizing antibodies. The table below presents the geometric mean FFN titers of positive pigs by group. The table also includes the frequency of detection expressed as the number of pigs with a GMT greater than or equal to 20 over the number of animals tested. Testing was performed on all available samples. Samples from numerous pigs were unable to be obtained due to the time difference between death and necropsy.

Descriptive statistics for FFN titers by mortality status (Died: Yes/No) and group (Overall) are listed below. Overall, a similar proportion of pigs in the vaccinated groups seroconverted (or had maternal antibodies) regardless of time of necropsy. However, in T01 (NC), a higher percentage of pigs that died prior to off test had titers (88%) in comparison to pigs that lived for the duration of the study (43%).

When looking at the overall pig titers by group, the proportion mortality estimate was inversely related to the overall group FFN percentage for T02 (BEI-VH).

TABLE 18

| Group | Pigs (Died = yes) | Pigs (Died = no) | Overall | Proportion Mortality Estimate |
|---|---|---|---|---|
| NC | 55 (28/32; 88%) | 33 (9/21; 43%) | 63 (37/53; 59%) | 0.55 |
| BEI-VH | 44 (23/42; 55%) | 50 (9/16; 56%) | 64 (32/58; 55%) | 0.44 |

*GMT (no. animals titer ≥20/total pigs tested; percentage); note that serum was not obtained from all pigs Clinical Observations Following Challenge:

Pig fecal scores: Descriptive statistics for the duration of abnormal fecal observations in pigs, by group and mortality status (Died: Yes/No), are listed below. Overall, the median duration of abnormal fecal scores in pigs with the same mortality status was similar among groups. In animals that died or were euthanized, there was a numerically shorter median duration of abnormal fecal scores. This trend was most evident in T01 (NC) pigs and is likely secondary to the fact that the majority of these animals died within the first week following challenge.

TABLE 19

| | | Duration (days) abnormal fecal score | | | | |
|---|---|---|---|---|---|---|
| Died | Group | # pigs | Median | Minimum | Maximum | Std Dev |
| No | NC | 32 | 5.5 | 3.5 | 7.0 | 0.8 |
| | BEI-VH | 42 | 6.0 | 4.5 | 8.5 | 0.8 |
| Yes | NC | 39 | 2.3 | 0.5 | 6.0 | 1.3 |
| | BEI-VH | 33 | 4.3 | 2.0 | 6.0 | 1.4 |

The severity of fecal scores in pigs is summarized in the frequency table below. In all treatment groups a high portion of pigs (>91%) presented with a fecal score of 2 during at least one observation following challenge.

TABLE 20

| | Maximum Fecal Score | | | |
|---|---|---|---|---|
| Group | 0 | 1 | 2 | Total |
| NC | 1<br>1.41 | 5<br>7.04 | 65<br>91.55 | 71 |
| BEI-VH | 1<br>1.33 | 0<br>0.00 | 74<br>98.67 | 75 |
| Total | 2 | 5 | 139 | 146 |

Conclusions:

A 20% reduction in pig mortality was observed in T02 (BEI-VH) as compared to T01 (NC) group. Three routes of administration were attempted in this study. Although 3 routes were used, there is no expectation that routes other than IM contributed to the efficacy of T02 (BEI-VH) based on the adjuvant and vaccine formulation. Overall the inactivated PEDV adjuvanted with 20% EMULSIGEN-BCL® vaccine with a minimum pre-inactivation titer of 6.04 log $TCID_{50}$/ml appears to induce better immune responses in the piglets and sows. The preferred vaccination schedule is IM route of administration for piglets 3 weeks of age or older, three 2 ml doses at 2-week intervals. Clinical signs in sows following vaccination were not observed in T02 (BEI-VH) and were limited in the other treatment groups. The use of vaccination did not appear to affect the percentage of pigs born live (data not shown).

Dam serology was evaluated as a secondary parameter by two separate assays (focus fluorescent neutralization, S1-based ELISA). Both assays indicated a significant increase in titer in T02 (BEI-VH) following vaccination and exposure as compared to T01 (NC). Due to known limitations of the FFN assay, samples were also tested by an S1-based ELISA. This ELISA was chosen as the S1 domain of the spike protein is expected to contain neutralizing epitopes.

Following lateral exposure to PEDV, all animals in exposed treatment groups had detectable levels of neutralizing antibody. Sows in T02 (BEI-VH) had approximately three-fold higher titers in comparison to the T01 (NC) animals. This is evidence that use of the vaccine stimulated an initial primary response and resulted in a greater secondary response following exposure to the challenge virus. As multiple samples in T02 (BEI-VH) group had detectable neutralizing antibodies at the highest dilution tested (1:640), these results likely represent a conservative estimate of the differences between groups.

TABLE 21

| Pig mortality and sow serological data are summarized below. | | | | | |
|---|---|---|---|---|---|
| Treatment | Group | FFN (Sow serum, D21) | IgG ELISA (Sow serum, D21) | Pig Mortality (%) | Prevented Fraction (pig mortality) |
| T01 | NC | 200 | 0.504 | 55% | . |
| T02 | BEI-VH | 613 | 1.499 | 44% | 0.20 |
| T03 | SC | <20 | 0.164 | NA | NA |

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the following claims.

The following references, to the extent that they provide exemplary procedural or other details supplementary to those set forth herein, are specifically incorporated herein by reference.

1. Bridgen A, Duarte M, Tobler K, Laude H, Ackermann M. 1993. Sequence determination of the nucleocapsid protein gene of the porcine epidemic diarrhoea virus confirms that this virus is a coronavirus related to human coronavirus 229E and porcine transmissible gastroenteritis virus. J. Gen. Virol. 74 (Pt 9):1795-1804.
2. Duarte M, Gelfi J, Lambert P, Rasschaert D, Laude H. 1993. Genome organization of porcine epidemic diarrhoea virus. Adv. Exp. Med. Biol. 342:55-60
3. Tobler K, Bridgen A, Ackermann M. 1993. Sequence analysis of the nucleocapsid protein gene of porcine epidemic diarrhoea virus. Adv. Exp. Med. Biol. 342:49-54.
4. Oldham J. 1972. Letter to the editor. Pig Farming 1972 (October suppl):72-73.
5. Pensaert M B, de Bouck P. 1978. A new coronavirus-like particle associated with diarrhea in swine. Arch. Virol. 58:243-247.
6. Chen J F, Sun D B, Wang C B, Shi H Y, Cui X C, Liu S W, Qiu H J, Feng L. 2008. Molecular characterization and phylogenetic analysis of membrane protein genes of porcine epidemic diarrhea virus isolates in China. Virus Genes 36:355-364.
7. Nagy B, Nagy G, Meder M, Mocsári E. 1996. Enterotoxigenic *Escherichia coli*, rotavirus, porcine epidemic diarrhoea virus, adenovirus and calici-like virus in porcine postweaning diarrhoea in Hungary. Acta Vet. Hung. 44:9-19.
8. Martelli P, Lavazza A, Nigrelli A D, Merialdi G, Alborali L G, Pensaert M B. 2008. Epidemic of diarrhoea caused by porcine epidemic diarrhoea virus in Italy. Vet. Rec. 162:307-310.
9. Takahashi K, Okada K, Ohshima K. 1983. An outbreak of swine diarrhea of a new-type associated with coronavirus-like particles in Japan. Nippon Juigaku Zasshi 45:829-832.
10. Chae C, Kim O, Choi C, Min K, Cho W S, Kim J, Tai J H. 2000. Prevalence of porcine epidemic diarrhoea virus and transmissible gastroenteritis virus infection in Korean pigs. Vet. Rec. 147:606-608
11. Puranaveja S, Poolperm P, Lertwatcharasarakul P, Kesdaengsakonwut S, Boonsoongnern A, Urairong K, Kitikoon P, Choojai P, Kedkovid R, Teankum K, Thanawongnuwech R. 2009. Chinese-like strain of porcine epidemic diarrhea virus, Thailand. Emerg. Infect. Dis. 15:1112-1115.
12. Stevenson G W, Hoang H, Schwartz K J, Burrough E R, Sun D, Madson D, Cooper V L, Pillatzki A, Gauger P, Schmitt B J, Koster L G, Killian M L, Yoon K J. 2013. Emergence of porcine epidemic diarrhea virus in the United States: clinical signs, lesions, and viral genomic sequences. J. Vet. Diagn. Invest. 25:649-654.
13. Kim S H, Kim I J, Pyo H M, Tark D S, Song J Y, Hyun B H. 2007. Multiplex real-time RT-PCR for the simultaneous detection and quantification of transmissible gastroenteritis virus and porcine epidemic diarrhea virus. J. Virol. Methods 146:172-177.
14. Hofmann M, Wyler R. 1988. Propagation of the virus of porcine epidemic diarrhea in cell culture. J. Clin. Microbiol. 26:2235-2239.
15. Marthaler D, Jiang Y, Otterson T, Goyal S, Rossow K, Collins J. 2013. Complete genome sequence of porcine epidemic diarrhea virus strain USA/Colorado/2013 from the United States. Genome Announc. 1 (4):e00555-13.10.1128/genomeA.00555-13
16. Song D, Park B. 2012. Porcine epidemic diarrhoea virus: a comprehensive review of molecular epidemiology, diagnosis, and vaccines. Virus Genes 44:167-175.
17. Huang Y W, Dickerman A W, Piñeyro P, Li L, Fang L, Kiehne R, Opriessnig T, Meng X J. 2013. Origin, evolution, and genotyping of emergent porcine epidemic diarrhea virus strains in the United States. mBio 4(5):e00737-13.
18. Bi J, Zeng S, Xiao S, Chen H, Fang L. 2012. Complete genome sequence of porcine epidemic diarrhea virus strain AJ1102 isolated from a suckling piglet with acute diarrhea in China. J. Virol. 86:10910-10911.
19. Chen J, Wang C, Shi H, Qiu H J, Liu S, Shi D, Zhang X, Feng L. 2011. Complete genome sequence of a Chinese virulent porcine epidemic diarrhea virus strain. J. Virol. 85:11538-11539.
20. Chen J, Liu X, Shi D, Shi H, Zhang X, Feng L. 2012. Complete genome sequence of a porcine epidemic diarrhea virus variant. J. Virol. 86:3408.10.1128/JVI. 07150-11
21. Fan H, Zhang J, Ye Y, Tong T, Xie K, Liao M. 2012. Complete genome sequence of a novel porcine epidemic diarrhea virus in south China. J. Virol. 86:10248-10249.
22. Gao Y, Kou Q, Ge X, Zhou L, Guo X, Yang H. 2013. Phylogenetic analysis of porcine epidemic diarrhea virus field strains prevailing recently in China. Arch. Virol. 158:711-715.
23. Li B, Liu H, He K, Guo R, Ni Y, Du L, Wen L, Zhang X, Yu Z, Zhou J, Mao A, Lv L, Hu Y, Yu Y, Zhu H, Wang X. 2013. Complete genome sequence of a recombinant porcine epidemic diarrhea virus strain from eastern China. Genome Announc. 1(2):e00105-13.10.1128/genomeA.00105-13
24. Luo Y, Zhang J, Deng X, Ye Y, Liao M, Fan H. 2012. Complete genome sequence of a highly prevalent isolate of porcine epidemic diarrhea virus in south China. J. Virol. 86:9551-9551.
25. Wang X M, Niu B B, Yan H, Gao D S, Huo J Y, Chen L, Chang H T, Wang C Q, Zhao J. 2013. Complete genome sequence of a variant porcine epidemic diarrhea virus strain isolated in central China. Genome Announc. 1(1):e00243-12.10.1128/genomeA.00243-12
26. Wei Z Y, Lu W H, Li Z L, Mo J Y, Zeng X D, Zeng Z L, Sun B L, Chen F, Xie Q M, Bee Y Z, Ma J-Y. 2012. Complete genome sequence of novel porcine epidemic diarrhea virus strain GD-1 in China. J. Virol. 86:13824-13825.
27. Zhao M, Sun Z, Zhang Y, Wang G, Wang H, Yang F, Tian F, Jiang S. 2012. Complete genome sequence of a Vero cell-adapted isolate of porcine epidemic diarrhea virus in eastern China. J. Virol. 86:13858-13859.
28. S. H. Chang, J. L. Bae, T. J. Kang, J. Kim, G. H. Chung, C. W. Lim, H. Laude, M. S. Yang, Y. S. Jang. 2002. Identification of the epitope region capable of inducing neutralizing antibodies against the porcine epidemic diarrhea virus. Mol. Cells 14, 295-299.

29. D. J. Cruz, C. J. Kim, H. J. Shin. 2008. The GPRLQPY motif (SEQ ID NO: 20) located at the carboxy-terminal of the spike protein induces antibodies that neutralize Porcine epidemic diarrhea virus. Virus Res. 132, 192-196.
30. M. Godet, J. Grosclaude, B. Delmas, H. Laude. 1994. Major receptor-binding and neutralization determinants are located within the same domain of the transmissible gastroenteritis virus (coronavirus) spike protein. J. Virol. 68, 8008-8016.
31. M. W. Jackwood, D. A. Hilt, S. A. Callison, C. W. Lee, H. Plaza, E. Wade. 2001. Spike glycoprotein cleavage recognition site analysis of infectious bronchitis virus. Avian Dis. 45, 366-372.
32. L. S. Sturman, K. V. Holmes. 1984 Proteolytic cleavage of peplomeric glycoprotein E2 of MHV yields two 90K subunits and activates cell fusion. Adv. Exp. Med. Biol. 173, 25-35.
33. D. Sun, L. Feng, H. Shi, J. Chen, X. Cui, H. Chen, S. Liu, Y. Tong, Y. Wang, G. Tong. 2008. Identification of two novel B cell epitopes on porcine epidemic diarrhea virus spike protein. Vet. Microbiol. 131, 73-81.
34. S. J. Park, H. J. Moon, J. S. Yang, C. S. Lee, D. S. Song, B. K. Kang, B. K. Park. 2007. Sequence analysis of the partial spike glycoprotein gene of porcine epidemic diarrhea viruses isolated in Korea. Virus Genes 35, 321-332.
35. L. J. Saif. 1993. Coronavirus immunogens. Vet. Microbiol. 285-297.
36. S. J. Park, H. K. Kim, D. S. Song, H. J. Moon, B. K. Park. 2011 Molecular characterization and phylogenetic analysis of porcine epidemic diarrhea virus (PEDV) field isolates in Korea. Arch. Virol. 156, 577-585.
37. D. S. Song, J. S. Yang, J. S. Oh, J. H. Han, B. K. Park. Differentiation of a Vero cell adapted porcine epidemic diarrhea virus from Korean field strains by restriction fragment length polymorphism analysis of ORF 3. 2003. Vaccine 21, 1833-1842.
38. D. S. Song, J. S., B. K. Park. 2012 Porcine epidemic diarrhoea virus: a comprehensive review of molecular epidemiology, diagnosis, and vaccines. Virus Genes 44, 167-175.
39. J. F. Chen, D. B. Sun, C. B. Wang, H. Y. Shi, X. C. Cui, S. W. Liu, H. J. Qiu, L. Feng. 2008. Molecular characterization and phylogenetic analysis of membrane protein genes of porcine epidemic diarrhea virus isolates in China. Virus Genes 36, 355-364.
40. L. Yuan, S. Y. Kang, L. A. Ward, T. L. To, L. J. Saif. 1998 Antibody-secreting cell responses and protective immunity assessed in gnotobiotic pigs inoculated orally or intramuscularly with inactivated human rotavirus. J. Virol. 72, 330-338.
41. C. H. Kweon, B. J. Kwon, J. G. Lee, G. O. Kwon, Y. B. Kang. 1999. Derivation of attenuated porcine epidemic diarrhea virus (PEDV) as vaccine candidate. Vaccine 17, 2546-2553.
42. Y. Usami, O. Yamaguchi, K. Kumanomido, Y. Matsumura. 1998. Antibody response of pregnant sows to porcine epidemic diarrhea virus live vaccine and maternally-derived antibodies of the piglets. J. Jpn. Vet. Med. Assoc. 51, 652-655.
43. L. A. Ward, L. Yuan, B. I. Rosen, T. L. To, L. J. Saif. 1996. Development of mucosal and systemic lymphoproliferative responses and protective immunity to human group A rotaviruses in a gnotobiotic pig model. Clin. Diagn. Lab. Immunol. 3, 342-350.
44. A. Pijpers, A. P. van Nieuwstadt, C. Terpstra, J. H. Verheijden. 1993. Porcine epidemic diarrhoea virus as a cause of persistent diarrhoea in a herd of breeding and finishing pigs. Vet. Rec. 132, 129-131.
45. T. Sato, Takeyama, N., Katsumata, A., Tuchiya, K., Kodama, T., Kusanagi, K. 2011. Mutations in the spike gene of porcine epidemic diarrhea virus associated with growth adaptation in vitro and attenuation of virulence in vivo. Virus Genes, 43, 1, 72.
46. Park, S. J., Kim, H. K., Song, D. S., An, D. J. and Park, B. K. 2012. Complete genome sequences of a Korean virulent porcine epidemic diarrhea virus and its attenuated counterpart J. Virol. 86 (10), 5964.
47. Kusanagi K, Kuwahara H, Katoh T, Nunoya T, Ishikawa Y, Samejima T, Tajima M. 1992. Isolation and serial propagation of porcine epidemic diarrhea virus in cell cultures and partial characterization of the isolate. J Vet Med Sci. 1992 April; 54(2):313-8.
48. Hofmann M, Wyler R. 1988. Propagation of the virus of porcine epidemic diarrhea in cell culture. J Clin Microbiol. November; 26(11):2235-9.
49. de Arriba M L, Carvajal A, Pozo J, Rubio P. 2002. Mucosal and Systemic Isotype-specific Antibody Responses and Protection in Conventional Pigs Exposed to Virulent or Attenuated Porcine Epidemic Diarrhoea Virus. Vet Immunol Immunopathol. 85(1-2): p. 85-97.

What is claimed is:

1. An immunogenic composition comprising a recombinant spike antigen of porcine epidemic diarrhea virus (PEDV) having a heterologous C-terminal domain and a heterologous transmembrane domain, and an oil-in-water emulsion as an adjuvant, wherein the porcine epidemic diarrhea virus (PEDV) is a PEDV of North American origin and a. wherein the spike antigen is encoded by a nucleic acid sequence that is at least 95% identical with SEQ ID NO: 8 over the length of SEQ ID NO: 8.

2. The immunogenic composition of claim 1, wherein the recombinant antigen comprises one or more immunogenic components selected from the group consisting of:

a. an isolated nucleic acid encoding an antigen of porcine epidemic diarrhea virus (PEDV) spike protein, wherein the antigen has at least 95% homology with SEQ ID NO:3, 7, 9 or 14, b. a recombinant vector comprising the isolated nucleic acid of a), c. the recombinant PEDV Spike protein encoded by the nucleic acid of a), and d. any combination thereof.

3. The immunogenic composition of claim 2, wherein such immunogenic composition comprises a pharmaceutical acceptable carrier and/or an excipient.

4. The immunogenic composition of claim 1, wherein the oil-in-water emulsion is an EMULSIGEN® oil-in-water emulsion-based adjuvant.

5. The immunogenic composition of claim 2, wherein an immunogenic component is the isolated nucleic acid.

6. The immunogenic composition of claim 2, wherein an immunogenic component is the recombinant vector.

7. The immunogenic composition of claim 2, wherein an immunogenic component is the recombinant porcine epidemic diarrhea virus (PEDV) Spike protein.

8. The immunogenic composition of claim 2, wherein an immunogenic component is a combination.

9. The immunogenic composition of claim 2, further comprising at least one additional antigen associated with a pathogen other than porcine epidemic diarrhea virus.

10. A kit for inducing an immunogenic response in a pig against porcine epidemic diarrhea virus (PEDV) comprising:

a. a dispenser capable of administering an immunogenic composition to a pig; and b. the immunogenic composition according to claim 2.

11. A method of producing an immunogenic composition comprising:

a. expressing an antigen of porcine epidemic diarrhea virus (PEDV) comprising the recombinant antigen of claim 2 in a host cell, b. harvesting the antigen of porcine epidemic diarrhea virus (PEDV) cells, and c. adding an oil-in-water emulsion-based adjuvant to the porcine epidemic diarrhea virus (PEDV) antigen of step b).

12. The method of claim 11, wherein the PEDV antigen comprises:

a. an isolated nucleic acid encoding an antigen of porcine epidemic diarrhea virus (PEDV) spike protein, wherein the recombinant Spike polypeptide has at least 95% homology with SEQ ID NO:3, 7, 9 or 14, b. a recombinant vector comprising the isolated nucleic acid of a), c. the recombinant PEDV Spike protein encoded by the nucleic acid of a), and d. any combination thereof.

13. The method of claim 11, wherein the antigen of porcine epidemic diarrhea virus (PEDV) is expressed by a recombinant baculovirus vector.

14. The method of claim 13, wherein the antigen of porcine epidemic diarrhea virus (PEDV) is expressed in insect cells.

15. The method of claim 11, wherein the oil-in-water emulsion-based adjuvant is an EMULSIGEN® oil-in-water emulsion-based adjuvant.

16. A method for protecting a pig against diseases associated with porcine epidemic diarrhea virus (PEDV), comprising administering to such pig the vaccine of claim 1.

* * * * *